US012747252B2

(12) United States Patent
Chovatia et al.

(10) Patent No.: US 12,747,252 B2
(45) Date of Patent: Sep. 29, 2026

(54) OREXIN RECEPTOR AGONISTS AND USES THEREOF

(71) Applicant: Jazz Pharmaceuticals Ireland Limited, Dublin (IE)

(72) Inventors: Prafulkumar Chovatia, Abingdon (GB); Claudia Beato, Abingdon (GB); Gilles Ouvry, Abingdon (GB); Davide Marinelli, Verona (IT)

(73) Assignee: Jazz Pharmaceuticals Ireland Limited, Dublin (IE)

( * ) Notice: Subject to any disclaimer, the term of this patent is extended or adjusted under 35 U.S.C. 154(b) by 383 days.

(21) Appl. No.: 18/558,245

(22) PCT Filed: May 3, 2022

(86) PCT No.: PCT/EP2022/061851

§ 371 (c)(1),
(2) Date: Oct. 31, 2023

(87) PCT Pub. No.: WO2022/233872

PCT Pub. Date: Nov. 10, 2022

(65) Prior Publication Data

US 2024/0254143 A1 Aug. 1, 2024

Related U.S. Application Data

(60) Provisional application No. 63/183,321, filed on May 3, 2021.

(51) Int. Cl.

| | |
|---|---|
| ***C07D 498/10*** | (2006.01) |
| ***C07D 471/10*** | (2006.01) |
| ***C07D 513/10*** | (2006.01) |
| ***C07D 515/10*** | (2006.01) |

(52) U.S. Cl.

CPC ......... *C07D 498/10* (2013.01); *C07D 471/10* (2013.01); *C07D 513/10* (2013.01); *C07D 515/10* (2013.01)

(58) Field of Classification Search

CPC .. C07D 498/10; C07D 471/10; C07D 513/10; C07D 515/10

USPC .................................................... 514/210.18

See application file for complete search history.

(56) References Cited

U.S. PATENT DOCUMENTS

| | | | |
|---|---|---|---|
| 6,465,478 | B1 | 10/2002 | Ito et al. |
| 2012/0101110 | A1 | 4/2012 | Badiger et al. |
| 2017/0226137 | A1 | 8/2017 | Fujimoto et al. |
| 2024/0360081 | A1 | 10/2024 | Marinelli |
| 2025/0320227 | A1 | 10/2025 | Beato |

FOREIGN PATENT DOCUMENTS

| | | | |
|---|---|---|---|
| CN | 1099035 | A | 2/1995 |
| WO | WO-1994020500 | A1 | 9/1994 |
| WO | WO-2007000246 | A1 | 1/2007 |
| WO | WO-2011076747 | A1 | 6/2011 |
| WO | WO-2012101487 | A1 | 8/2012 |
| WO | WO-2013119639 | A1 | 8/2013 |
| WO | WO-2017135306 | A1 | 8/2017 |
| WO | WO-2018175474 | A1 | 9/2018 |
| WO | WO-2018208985 | A2 | 11/2018 |
| WO | WO-2019191327 | A1 | 10/2019 |
| WO | WO-2020004537 | A1 | 1/2020 |
| WO | WO-2020167701 | A1 | 8/2020 |
| WO | WO-2020167706 | A1 | 8/2020 |
| WO | WO-2021106975 | A1 | 6/2021 |
| WO | WO-2021108628 | A1 | 6/2021 |
| WO | WO-2022109117 | A1 | 5/2022 |
| WO | WO-2022140316 | A1 | 6/2022 |
| WO | WO-2022232025 | A1 | 11/2022 |
| WO | WO-2022251302 | A1 | 12/2022 |
| WO | WO-2022269049 | A1 | 12/2022 |
| WO | WO-2023167925 | A1 | 9/2023 |
| WO | WO-2023232966 | A1 | 12/2023 |
| WO | WO-2024112899 | A1 | 5/2024 |
| WO | WO-2024160822 | A1 | 8/2024 |

OTHER PUBLICATIONS

Co-pending U.S. Appl. No. 18/571,860, inventor MArinelli; Davide, filed on Dec. 19, 2023.

International Search Report and Written Opinion of the International Searching Authority for International Application No. PCT/EP2022/061851 dated Aug. 12, 2022, 11 pages.

International Search Report and Written Opinion of the International Searching Authority for International Application No. PCT/EP2022/067376 dated Nov. 3, 2022, 10 pages.

(Continued)

*Primary Examiner* — Kahsay Habte

(74) *Attorney, Agent, or Firm* — COOLEY LLP

(57) ABSTRACT

Provided herein are compounds of Formula (I), or pharmaceutically acceptable salt thereof, wherein n, m, $A_1$, $A_2$, $A_3$, $A_4$, $A_5$, $A_6$, $L_1$, $L_2$, $R_1$, $R_2$, $R_3$, Y and Z are defined herein. Also provided herein are pharmaceutical compositions comprising a compound N of Formula (I) or pharmaceutically acceptable salt thereof, and methods of using a compound of Formula (I) or pharmaceutically acceptable salt thereof, e.g., in the treatment of a disease or disorder that is treatable by administration of an Orexin agonist.

20 Claims, No Drawings

(56) References Cited

OTHER PUBLICATIONS

International Search Report and Written Opinion of the International Searching Authority for International Application No. PCT/EP2023/064735 dated Jul. 28, 2023, 15 pages.
Hernández-Ibáñez et al., "Stereoselective synthesis of 5-(1-aminoalkyl)-2-pyrrolidones and 1,7-diazaspiro[4.5]decane-2,8-diones from chiral N-tert-butanesulfinyl imines and ethyl 4-nitrobutanoate," Tetrahedron, vol. 76, Issue 3, Jan. 17, 2020, 130842, 9 pages.
International Search Report and Written Opinion of the International Searching Authority for International Application No. PCT/EP2024/052241 dated Apr. 3, 2024, 9 pages.

OREXIN RECEPTOR AGONISTS AND USES THEREOF

CROSS-REFERENCE TO RELATED APPLICATIONS

This application is a U.S. National Stage Application under 35 U.S.C. § 371 of International Application No. PCT/EP2022/061851, filed May 3, 2022, which claims priority U.S. Provisional Application No. 63/183,321, filed on May 3, 2021, the contents of which is hereby incorporated by reference in their entireties for all purposes.

BACKGROUND

Orexin is a neuropeptide specifically produced in particular neurons located sparsely in the lateral hypothalamus and its surrounding area. Orexin consists of two subtypes, orexin A and orexin B. Both orexin A (OX-A) and orexin B (OX-B) are endogenous ligands of the orexin receptors, which are mainly present in the brain. Two orexin receptors have been cloned and characterized in mammals. They belong to the super family of G-protein coupled receptors: the orexin-1 receptor (OX or OX1R) is partially selective for OX-A and the orexin-2 receptor (OX2 or OX2R) is capable of binding OX-A as well as OX-B with similar affinity. The physiological actions in which orexins are presumed to participate are thought to be expressed via one or both of OX1 receptor and OX2 receptor as the two subtypes of orexin receptors.

Orexins regulate states of sleep and wakefulness making the orexin system a target for potential therapeutic approaches to treat sleep disorders. Orexins are found to stimulate food consumption in rats suggesting a physiological role for these peptides as mediators in the central feedback mechanism that regulates feeding behavior. Orexins have also been indicated as playing a role in arousal, emotion, energy homeostasis, reward, learning and memory.

There is a need for compounds that modulate orexin receptors, as well as compositions and methods for treating a disease or disorder that is treatable by administration of an Orexin agonist.

SUMMARY

The present disclosure is directed to compounds that are agonists of the orexin-2 receptor as well as pharmaceutical compositions thereof and uses thereof in treating a disease or disorder that is treatable by administration of an Orexin agonist.

In one aspect, the present disclosure provides a compound of Formula (I):

(I)

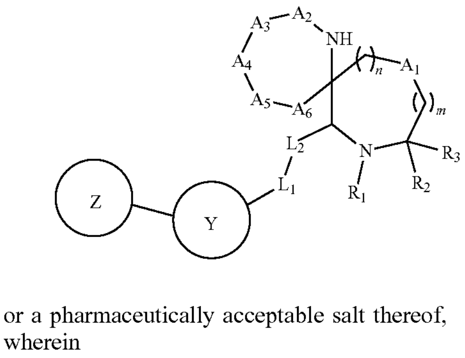

or a pharmaceutically acceptable salt thereof, wherein n and m are independently 0 or 1;

$A_1$ is —O—, —$CR_4R_5$—, —$NR_6$—, —S— or a bond;

$A_2$ is —C(O)— or —$S(O)_2$—;

$A_3$ and $A_4$, are independently —O—, —$CR_4R_5$—, —$NR_6$, —S—, a bond; or $A_3$ and $A_4$ together are —$C(R_4)$═$C(R_5)$—;

$A_5$ and $A_6$ are independently —O—, —$CR_4R_5$—, —$NR_6$, —S— or a bond; with the proviso that ring that includes $A_2$, $A_3$, $A_4$, $A_5$ and $A_6$ does not contain —O—O—, —$NR_6$—$NR_6$— or —O—$NR_6$—;

$L_1$ is —O—, —$CR_4R_5$— or a bond;

$L_2$ is —$CR_4R_5$;

$R_1$ is a alkyl, cycloalkyl, heterocyclyl, aryl, heteroaryl, —(C═O)alkyl, —(C═O)cycloalkyl, —(C═O)heterocyclyl, —(C═O)aryl, —(C═O)heteroaryl, —(C═O)—O-alkyl, —(C═O)—O-cycloalkyl, —(C═O)—O-heterocyclyl, —(C═O)—O-aryl, —(C═O)—O-heteroaryl, —$S(O)_2$-alkyl, —$S(O)_2$-cycloalkyl, —$S(O)_2$-heterocyclyl, —$S(O)_2$-aryl, —$S(O)_2$-heteroaryl, —(C═O)$NR_7R_8$, or $R_1$ and $R_2$ together with the atom to which they are attached form a heterocycle or heteroaryl;

$R_2$ and $R_3$ are independently hydrogen, halogen, alkyl, cycloalkyl, heterocyclyl, or $R_2$ and $R_3$ together with the atom to which they are attached form a carbocycle or heterocycle;

$R_4$ and $R_5$ are independently hydrogen, alkyl, cycloalkyl, heterocyclyl, alkoxy, —O-cycloalkyl, —O-heterocyclyl, halogen, or $R_4$ and $R_5$ together with the atom to which they are attached to form a carbocycle or heterocycle;

$R_6$ is hydrogen, alkyl, cycloalkyl, heterocyclyl, aryl, heteroaryl, —(C═O)alkyl, —(C═O) cycloalkyl, —(C═O)heterocyclyl, —(C═O)aryl, —(C═O)heteroaryl, —(C═O)—O-alkyl, —(C═O)—O-cycloalkyl, —(C═O)—O-heterocyclyl, —(C═O)—O-aryl, —(C═O)—O-heteroaryl, —$S(O)_2$-alkyl, —$S(O)_2$-cycloalkyl, —$S(O)_2$-heterocyclyl, —$S(O)_2$-aryl, —$S(O)_2$-heteroaryl, or —(C═O)$NR_7R_8$, $R_7$ and $R_8$ are independently hydrogen, alkyl, cycloalkyl, heterocyclyl, aryl or heteroaryl, or $R_7$ and $R_8$ together with the atom to which they are attached to form a heterocycle;

Y is cycloalkyl, heterocyclyl, heteroaryl or aryl; and

Z is absent, heteroaryl or aryl.

In some embodiments, the present disclosure provides a compound of Formula (II):

(II)

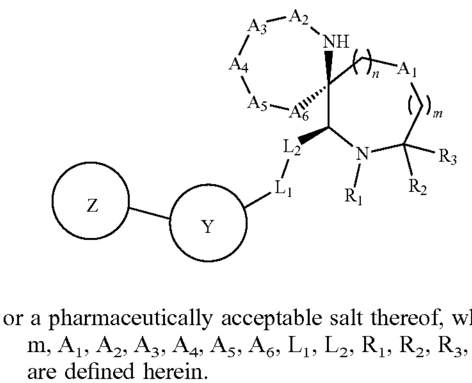

or a pharmaceutically acceptable salt thereof, wherein n, m, $A_1$, $A_2$, $A_3$, $A_4$, $A_5$, $A_6$, $L_1$, $L_2$, $R_1$, $R_2$, $R_3$, Y and Z are defined herein.

In some embodiments, the present disclosure provides a compound of Formula (III):

(III)

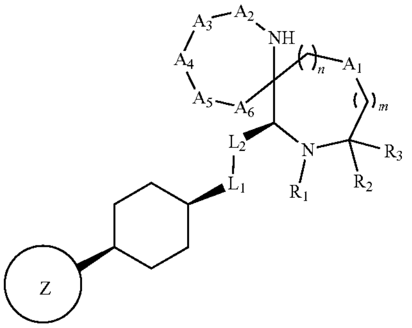

or a pharmaceutically acceptable salt thereof, wherein n, m, $A_1$, $A_2$, $A_3$, $A_4$, $A_5$, $A_6$, $L_1$, $L_2$, $R_1$, $R_2$, $R_3$, and Z are defined herein.

In some embodiments, the present disclosure provides a compound of Formula (IV):

(IV)

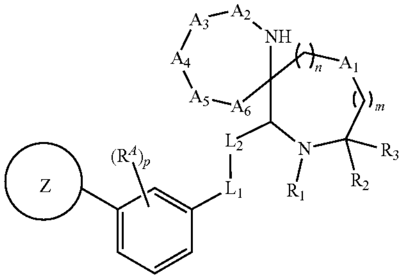

or a pharmaceutically acceptable salt thereof, wherein n, m, p, $A_1$, $A_2$, $A_3$, $A_4$, $A_5$, $A_6$, $L_1$, $L_2$, $R_1$, $R_2$, $R_3$, $R^A$, and Z are defined herein.

In some embodiments, the present disclosure provides a compound of Formula (V-A):

(V-A)

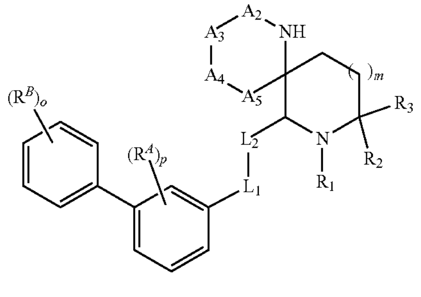

or a pharmaceutically acceptable salt thereof, wherein p, o, m, $A_2$, $A_3$, $A_4$, $A_5$, $L_1$, $L_2$, $R_1$, $R_2$, $R_3$, $R^A$, and $R^B$ are defined herein.

In some embodiments, the present disclosure provides a compound of Formula (V-B):

(V-B)

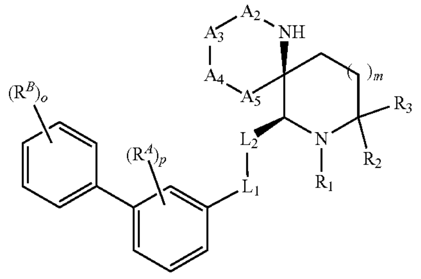

or a pharmaceutically acceptable salt thereof, wherein p, o, m, $A_2$, $A_3$, $A_4$, $A_5$, $L_1$, $L_2$, $R_1$, $R_2$, $R_3$, $R^A$, and $R^B$ are defined herein.

In some embodiments, the present disclosure provides a compound of Formula (V-C):

(V-C)

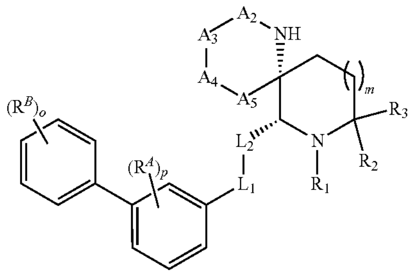

or a pharmaceutically acceptable salt thereof, wherein p, o, m, $A_2$, $A_3$, $A_4$, $A_5$, $L_1$, $L_2$, $R_1$, $R_2$, $R_3$, $R^A$, and $R^B$ are defined herein.

In some embodiments, the present disclosure provides a compound of Formula (VI-A):

(VI-A)

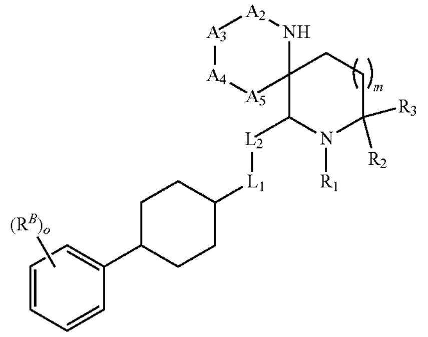

or a pharmaceutically acceptable salt thereof, wherein o, m, $A_2$, $A_3$, $A_4$, $A_5$, $L_1$, $L_2$, $R_1$, $R_2$, $R_3$, and $R^B$ are defined herein.

In some embodiments, the present disclosure provides a compound of Formula (VI-B):

(VI-B)

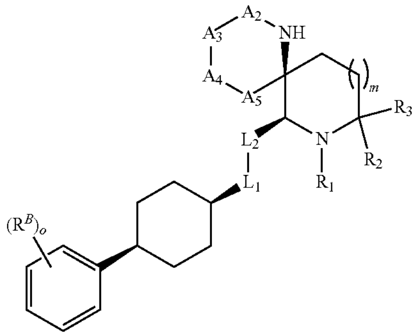

or a pharmaceutically acceptable salt thereof, wherein o, m, $A_2$, $A_3$, $A_4$, $A_5$, $L_1$, $L_2$, $R_1$, $R_2$, $R_3$, and $R^B$ are defined herein.

In some embodiments, the present disclosure provides a compound of Formula (VI-C):

(VI-C)

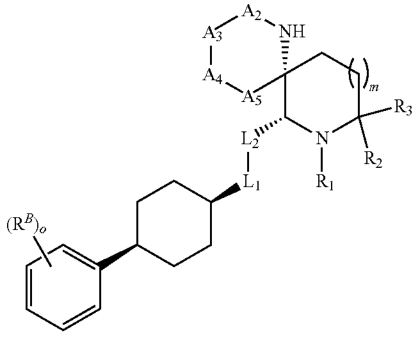

or a pharmaceutically acceptable salt thereof, wherein o, m, $A_2$, $A_3$, $A_4$, $A_5$, $L_1$, $L_2$, $R_1$, $R_2$, $R_3$, and $R^B$ are defined herein.

DETAILED DESCRIPTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The terms "administer," "administering" or "administration" as used herein refer to administering a compound or pharmaceutically acceptable salt of the compound or a composition or formulation comprising the compound or pharmaceutically acceptable salt of the compound to a patient.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

The term "treating" as used herein with regard to a patient, refers to improving at least one symptom of the patient's disorder. Treating can be improving, or at least partially ameliorating a disorder or an associated symptom of a disorder.

The terms "effective amount" and "therapeutically effective amount" are used interchangeably in this disclosure and refer to an amount of a compound, or a salt thereof, (or pharmaceutical composition containing the compound or salt) that, when administered to a patient, is capable of performing the intended result. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

The term "carrier" or "vehicle" as used interchangeably herein encompasses carriers, excipients, adjuvants, and diluents or a combination of any of the foregoing, meaning a material, composition or vehicle, such as a liquid or solid filler, diluent, excipient, solvent or encapsulating material involved in carrying or transporting a pharmaceutical agent from one organ, or portion of the body, to another organ or portion of the body. In addition to the adjuvants, excipients and diluents known to one skilled in the art, the carrier includes nanoparticles of organic and inorganic nature.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_1$-6, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain having from two to twelve carbon atoms and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to an unsaturated, straight or branched divalent hydrocarbon chain radical having one or more olefins and from two to twelve carbon atoms. Non-limiting examples of $C_2$-$C_{12}$ alkenylene include ethenylene, propenylene, n-butenylene, and the like. The alkenylene chain is attached to the rest of the molecule through a single bond and to a radical group (e.g., those described herein) through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to an unsaturated, straight or branched divalent hydrocarbon chain radical having one or more alkynes and from two to twelve carbon atoms. Non-limiting examples of $C_2$-$C_{12}$ alkynylene include ethynylene, propynylene, n-butynylene, and the like. The alkynylene chain is attached to the rest of the molecule through a single bond and to a radical group (e.g., those described herein) through a single bond. The points of attachment of the alkynylene chain to the rest of the molecule and to the radical group can be through any two carbons within the chain having a suitable valency. Unless stated otherwise specifically in the specification, an alkynylene chain can be optionally substituted.

"Alkoxy" refers to a group of the formula —$OR_a$ where $R_a$ is an alkyl, alkenyl or alkynyl as defined above containing one to twelve carbon atoms. Unless stated otherwise specifically in the specification, an alkoxy group can be optionally substituted.

"Aryl" refers to a hydrocarbon ring system comprising hydrogen, 6 to 18 carbon atoms and at least one aromatic ring, and which is attached to the rest of the molecule by a single bond. For purposes of this disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the "aryl" can be optionally substituted.

"Aralkyl" or "arylalkyl" refers to a radical of the formula —$R_b$—$R_c$ where $R_b$ is an alkylene group as defined above and $R_c$ is one or more aryl radicals as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Carbocyclic rings include aryls and cycloalkyl, cycloalkenyl, and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon consisting solely of carbon and hydrogen atoms, which can include fused, bridged, or spirocyclic ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyls include, for example, cyclopentenyl, cyclohexenyl, cycloheptenyl, cycloctenyl, and the like. Polycyclic cycloalkenyls include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl include, for example, cycloheptynyl, cyclooctynyl, and the like. Unless otherwise stated specifically in the specification, a cycloalkynyl group can be optionally substituted.

As used herein, the term "halo" refers to fluoro, chloro, bromo, or iodo.

"Haloalkyl" refers to an alkyl, as defined above, that is substituted by one or more halo radicals, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclyl or heterocyclic rings include heteroaryls, heterocyclylalkyls, heterocyclylalkenyls, and hetercyclylalkynyls. Unless stated otherwise specifically in the specification, the heterocyclyl can be a monocyclic, bicyclic, tricyclic or tetracyclic ring system, which can include fused, bridged, or spirocyclic ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heteroaryl" refers to a 5- to 20-membered ring system comprising hydrogen atoms, one to nineteen carbon atoms, one to six heteroatoms selected from the group consisting of nitrogen, oxygen and sulfur, at least one aromatic ring, and which is attached to the rest of the molecule by a single bond. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"Heterocyclylalkyl" refers to a radical of the formula —$R_b$—$R_e$ where $R_b$ is an alkylene, alkenylene, or alkynylene group as defined above and $R_e$ is a heterocyclyl radical as defined above. Unless stated otherwise specifically in the specification, a heterocyclylalkyl group can be optionally substituted.

The term "substituted" used herein means any of the groups described herein (e.g., alkyl, alkenyl, alkynyl, alkoxy, aryl, aralkyl, carbocyclyl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol "

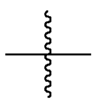

" (hereinafter can be referred to as "a point of attachment bond") denotes a bond that is a point of attachment between two chemical entities, one of which is depicted as being attached to the point of attachment bond and the other of which is not depicted as being attached to the point of attachment bond. For example, "

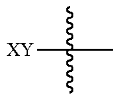

" indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or "

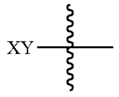

" infers that when $R^3$ is "XY", the point of attachment bond is the same bond as the bond by which $R^3$ is depicted as being bonded to CM.

Compounds

The present disclosure provides compounds that are agonists of the orexin type 2 receptor as well as pharmaceutical compositions thereof and uses thereof in treating various diseases and disorders.

In one aspect, the present disclosure provides a compound of Formula (I):

(I)

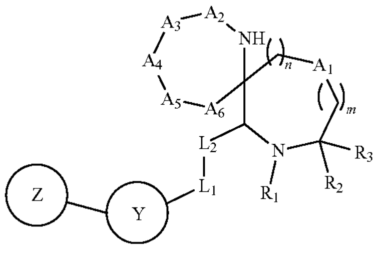

or a pharmaceutically acceptable salt thereof, wherein n and m are independently 0 or 1;

$A_1$ is —O—, —$CR_4R_5$—, —$NR_6$—, —S— or a bond;

$A_2$ is —C(O)— or —$S(O)_2$—;

$A_3$ and $A_4$, are independently —O—, —$CR_4R_5$—, —$NR_6$, —S—, a bond; or $A_3$ and $A_4$ together are —$C(R_4)=C(R_5)$—;

$A_5$ and $A_6$ are independently —O—, —$CR_4R_5$—, —$NR_6$, —S— or a bond; with the proviso that a ring that includes $A_2$, $A_3$, $A_4$, $A_5$ and $A_6$ does not contain —O—O—, —$NR_6$—$NR_6$— or —O—$NR_6$—;

$L_1$ is —O—, —$CR_4R_5$— or a bond;

$L_2$ is —$CR_4R_5$;

$R_1$ is a alkyl, cycloalkyl, heterocyclyl, aryl, heteroaryl, —(C=O)alkyl, —(C=O)cycloalkyl, —(C=O)heterocyclyl, —(C=O)aryl, —(C=O)heteroaryl, —(C=O)—O-alkyl, —(C=O)—O-cycloalkyl, —(C=O)—O-heterocyclyl, —(C=O)—O-aryl, —(C=O)—O-heteroaryl, —$S(O)_2$-alkyl, —$S(O)_2$-cycloalkyl, —$S(O)_2$-heterocyclyl, —$S(O)_2$-aryl, —S(O)

$_2$-heteroaryl, —(C═O)NR$_7$R$_8$, or R$_1$ and R$_2$ together with the atom to which they are attached form a heterocycle or heteroaryl;

R$_2$ and R$_3$ are independently hydrogen, halogen, alkyl, cycloalkyl, heterocyclyl, or R$_2$ and R$_3$ together with the atom to which they are attached form a carbocycle or heterocycle;

R$_4$ and R$_5$ are independently hydrogen, alkyl, cycloalkyl, heterocyclyl, alkoxy, —O-cycloalkyl, —O-heterocyclyl, halogen, or R$_4$ and R$_5$ together with the atom to which they are attached to form a carbocycle or heterocycle;

R$_6$ is hydrogen, alkyl, cycloalkyl, heterocyclyl, aryl, heteroaryl, —(C═O)alkyl, —(C═O) cycloalkyl, —(C═O)heterocyclyl, —(C═O)aryl, —(C═O)heteroaryl, —(C═O)—O-alkyl, —(C═O)—O-cycloalkyl, —(C═O)—O-heterocyclyl, —(C═O)—O-aryl, —(C═O)—O-heteroaryl, —S(O)$_2$-alkyl, —S(O)$_2$-cycloalkyl, —S(O)$_2$-heterocyclyl, —S(O)$_2$-aryl, —S(O)$_2$-heteroaryl —(C═O)NR$_7$R$_8$, R$_7$ and R$_8$ are independently hydrogen, alkyl, cycloalkyl, heterocyclyl, aryl or heteroaryl, or R$_7$ and R$_8$ together with the atom to which they are attached to form a heterocycle;

Y is cycloalkyl, heterocyclyl, heteroaryl or aryl; and

Z is absent, heteroaryl or aryl.

In some embodiments, is the present disclosure provides a compound of Formula (II), (II)

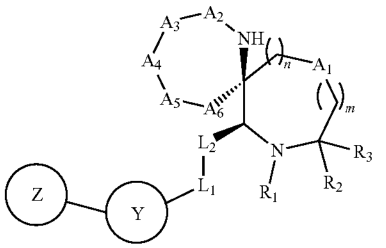

or a pharmaceutically acceptable salt thereof, wherein n, m, A$_1$, A$_2$, A$_3$, A$_4$, A$_5$, A$_6$, L$_1$, L$_2$, R$_1$, R$_2$, R$_3$, Y and Z are defined herein.

In some embodiments, the compound of Formula (I) is a compound of the Formula:

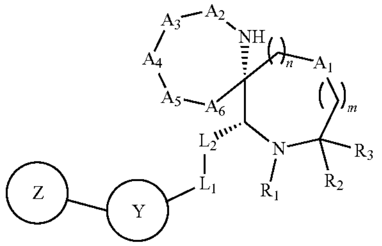

or a pharmaceutically acceptable salt thereof, wherein n, m, A$_1$, A$_2$, A$_3$, A$_4$, A$_5$, A$_6$, L$_1$, L$_2$, R$_1$. R$_2$, R$_3$, Y and Z are defined herein.

In some embodiments, the compound of Formula (I) is a compound of the Formula:

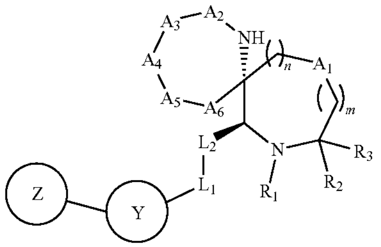

or a pharmaceutically acceptable salt thereof, wherein n, m, A$_1$, A$_2$, A$_3$. A$_4$, A$_5$, A$_6$, L$_1$, L$_2$, R$_1$. R$_2$, R$_3$, Y and Z are defined herein.

In some embodiments, the compound of Formula (I) is a compound of the Formula:

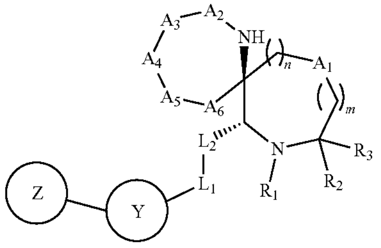

or a pharmaceutically acceptable salt thereof, wherein n, m, A$_1$, A$_2$, A$_3$, A$_4$, A$_5$, A$_6$, L$_1$, L$_2$, R$_1$. R$_2$, R$_3$, Y and Z are defined herein.

In some embodiments, the present disclosure provides a compound of Formula (III), (III)

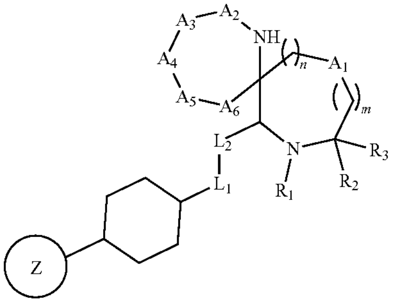

or a pharmaceutically acceptable salt thereof, wherein n, m, A$_1$, A$_2$, A$_3$, A$_4$, A$_5$, A$_6$, L$_1$, L$_2$, R$_1$, R$_2$, R$_3$, and Z are defined herein.

In some embodiments, the present disclosure provides a compound of Formula (III).

(III)

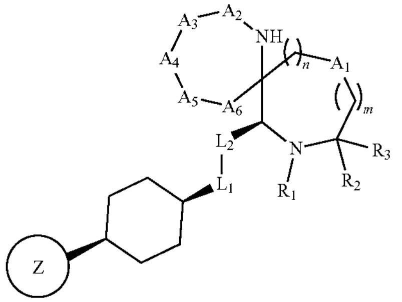

or a pharmaceutically acceptable salt thereof, wherein n, m, $A_1$, $A_2$, $A_3$, $A_4$, $A_5$, $A_6$, $L_1$, $L_2$, $R_1$, $R_2$, $R_3$, and Z are defined herein.

In some embodiments, provided herein is a compound of Formula (IV):

(IV)

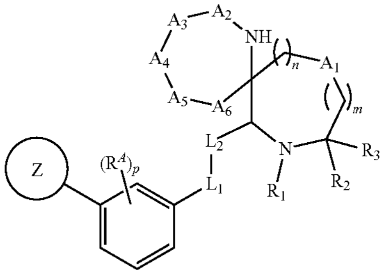

or a pharmaceutically acceptable salt thereof, wherein n, m, p, $A_1$, $A_2$, $A_3$, $A_4$, $A_5$, $A_6$, $L_1$, $L_2$, $R_1$, $R_2$, $R_3$, $R^A$, and Z are defined herein. In some embodiments, provided herein is a compound of Formula (V-A):

(V-A)

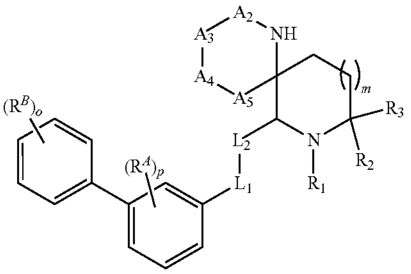

or a pharmaceutically acceptable salt thereof, wherein p, o, m, $A_2$, $A_3$, $A_4$, $A_5$, $L_1$, $L_2$, $R_1$, $R_2$, $R_3$, $R^A$, and $R^B$ are defined herein.

In some embodiments, provided herein is a compound of Formula (V-B):

(V-B)

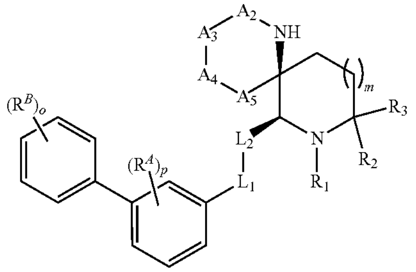

or a pharmaceutically acceptable salt thereof, wherein p, o, m, $A_2$, $A_3$, $A_4$, $A_5$, $L_1$, $L_2$, $R_1$, $R_2$, $R_3$, $R^A$, and $R^B$ are defined herein.

In some embodiments, provided herein is a compound of Formula (V-C):

(V-C)

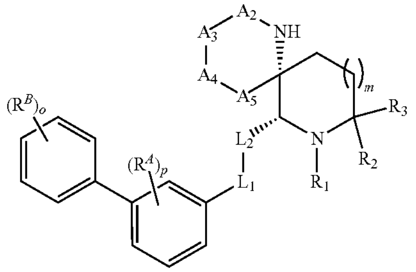

or a pharmaceutically acceptable salt thereof, wherein p, o, m, $A_2$, $A_3$, $A_4$, $A_5$, $L_1$, $L_2$, $R_1$, $R_2$, $R_3$, $R^A$, and $R^B$ are defined herein.

In some embodiments, provided herein is a compound of Formula (VI-A):

(VI-A)

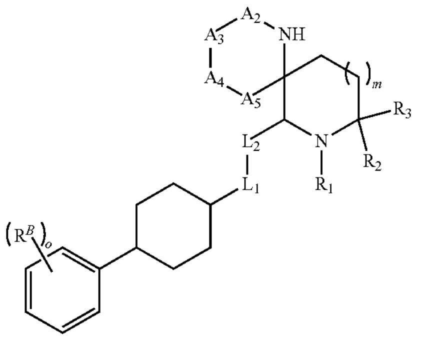

or a pharmaceutically acceptable salt thereof, wherein o, m, $A_2$, $A_3$, $A_4$, $A_5$, $L_1$, $L_2$, $R_1$, $R_2$, $R_3$, and $R^B$ are defined herein.

In some embodiments, provided herein is a compound of Formula (VI-B):

(VI-B)

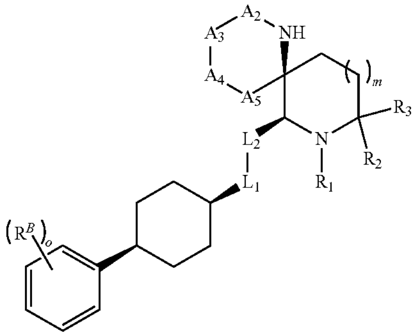

or a pharmaceutically acceptable salt thereof, wherein o, m, $A_2$, $A_3$, $A_4$, $A_5$, $L_1$, $L_2$, $R_1$, $R_2$, $R_3$, and $R^B$ are defined herein.

In some embodiments, provided herein is a compound of Formula (VI-C):

(VI-C)

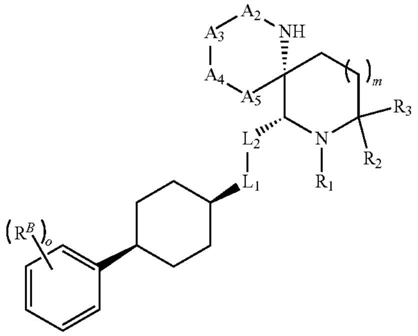

or a pharmaceutically acceptable salt thereof, wherein o, m, $A_2$, $A_3$, $A_4$, $A_5$, $L_1$, $L_2$, $R_1$, $R_2$, $R_3$, and $R^B$ are defined herein.

In some embodiments of the compounds of Formula (I), (II), (III), or (IV), $A_1$ is —O—, —$CR_4R_5$—, —$NR_6$—, —S— or a bond.

In some embodiments of the compounds of Formula (I), (II), (III), or (IV), $A_1$ is —$CR_4R_5$—.

In some embodiments of the compounds of Formula (I), (II), (III), (IV), (V-A), (V-B), (V-C), (VI-A), (VI-B), or (VI-C), $A_2$ is —C(O)— or —$S(O)_2$—.

In some embodiments of the compounds of Formula (I), (II), (III), (IV), (V-A), (V-B), (V-C), (VI-A), (VI-B), or (VI-C), $A_2$ is —C(O)—.

In some embodiments of the compounds of Formula (I), (II), (III), (IV), (V-A), (V-B), (V-C), (VI-A), (VI-B), or (VI-C), $A_2$ is —$S(O)_2$—.

In some embodiments of the compounds of Formula (I), (II), (III), (IV), (V-A), (V-B), (V-C), (VI-A), (VI-B), or (VI-C), $A_3$ and $A_4$, are independently —O—, —$CR_4R_5$—, —$NR_6$, —S—, a bond; or $A_3$ and $A_4$ together are —$C(R_4)$=$C(R_5)$—.

In some embodiments of the compounds of Formula (I), (II), (III), (IV), (V-A), (V-B), (V-C), (VI-A), (VI-B), or (VI-C), $A_3$ and $A_4$, are independently —O—, —$CR_4R_5$—, or —$NR_6$.

In some embodiments of the compounds of Formula (I), (II), (III), (IV), (V-A), (V-B), (V-C), (VI-A), (VI-B), or (VI-C), $A_3$ and $A_4$, are independently —O—, or —$CR_4R_5$—.

In some embodiments of the compounds of Formula (I), (II), (III), (IV), (V-A), (V-B), (V-C), (VI-A), (VI-B), or (VI-C), $A_3$ is —O—, —$CR_4R_5$—, or —$NR_6$. In some embodiments, $A_3$ is —O—. In some embodiments, $A_3$ is —$CR_4R_5$—. In some embodiments, $A_3$ is —$NR_6$.

In some embodiments of the compounds of Formula (I), (II), (III), (IV), (V-A), (V-B), (V-C), (VI-A), (VI-B), or (VI-C), $A_4$, is —O—, or —$CR_4R_5$—. In some embodiments, $A_4$ is —O—. In some embodiments, $A_4$ is —$CR_4R_5$—. In some embodiments, $A_4$ is —O—, —$CR_4R_5$—, or —$NR_6$. In embodiments, $A_4$ is —$NR_6$.

In some embodiments of the compounds of Formula (I), (II), (III), (IV), (V-A), (V-B), (V-C), (VI-A), (VI-B), or (VI-C), $A_5$ and $A_6$ are independently —O—, —$CR_4R_5$—, —$NR_6$, —S— or a bond.

In some embodiments of compounds of Formula (I), (II), (III), (IV), (V-A), (V-B), (V-C), (VI-A), (VI-B), or (VI-C), $A_5$ is —$CR_4R_5$— or a bond. In embodiments, $A_5$ is —$CR_4R_5$—. In embodiments, $A_5$ is a bond.

In some embodiments of compounds of Formula (I), (II), (III), or (IV), $A_6$ is a bond.

In some embodiments of the compounds of Formula (I), (II), (III), (IV), (V-A), (V-B), (V-C), (VI-A), (VI-B), or (VI-C), $A_2$ is —C(O)— and $A_3$ is —O—.

In some embodiments of the compounds of Formula (I), (II), (III), (IV), (V-A), (V-B), (V-C), (VI-A), (VI-B), or (VI-C), $A_2$ is —$S(O)_2$— and $A_3$ is —$NR_6$.

In some embodiments of the compounds of Formula (I), (II), (III), (IV), (V-A), (V-B), (V-C), (VI-A), (VI-B), or (VI-C), $A_2$ is —C(O)— and $A_3$ and $A_4$, are independently —O— or —$CR_4R_5$—.

In some embodiments of the compounds of Formula (I), (II), (III), (IV), (V-A), (V-B), (V-C), (VI-A), (VI-B), or (VI-C), a ring that includes $A_2$, $A_3$, $A_4$, $A_5$ and $A_6$ does not contain —O—O—, —$NR_6$—$NR_6$— or —O—$NR_6$—.

In some embodiments of the compounds of Formula (I), (II), (III), or (IV), $A_5$ and $A_6$ are independently —$CR_4R_5$— or a bond. In some embodiments, $A_5$ is —$CR_4R_5$— and $A_6$ is a bond. In some embodiments, $A_5$ and $A_6$ are both a bond.

In some embodiments of the compounds of Formula (I), (II), (III), or (IV), $A_2$, $A_3$, $A_4$, $A_5$, and $A_6$ together with the atoms to which they are attached to form a 5-membered heterocycle.

In some embodiments of the compounds of Formula (I), (II), (III), or (IV), $A_2$, $A_3$, $A_4$, $A_5$, and $A_6$ together with the atoms to which they are attached to form a 6-membered heterocycle.

In some embodiments of the compounds of Formula (I), (II), (III), or (IV), $A_2$, $A_3$, $A_4$, $A_5$, and $A_6$ together with the atoms to which they are attached to form a 7-membered heterocycle.

In some embodiments of the compounds of Formula (I), (II), (III), or (IV), $A_2$, $A_3$, $A_4$, $A_5$, and $A_6$ together with the atoms to which they are attached to form a 6-membered or 7-membered heterocycle.

In some embodiments of the compounds of Formula (I), (II), (III), (IV), (V-A), (V-B), (V-C), (VI-A), (VI-B), and/or (VI-C), $A_2$ is —C(O)— or —$S(O)_2$—;

$A_3$, is —O—, —$CR_4R_5$—, or —$NR_6$—;

$A_4$ is —$CR_4R_5$—; and $A_5$, and $A_6$ are a bond.

In some embodiments of the compounds of Formula (I), (II), (III), (IV), (V-A), (V-B), (V-C), (VI-A), (VI-B), and/or (VI-C):

$A_2$ is —C(O)— or —$S(O)_2$—;

$A_3$ and $A_4$ are independently —O—, —$CR_4R_5$—, or —$NR_6$—;

$A_5$ is —$CR_4R_5$—; and $A_6$ are a bond.

In some embodiments of the compounds of Formula (I), (II), (III), (IV), (V-A), (V-B), (V-C), (VI-A), (VI-B), and/or (VI-C):

$A_2$ is —C(O)— or —$S(O)_2$—;

$A_3$, $A_4$, and $A_6$ are —$CR_4R_5$—; and $A_5$ is —O—.

In some embodiments of the compounds of Formula (I), (II), (III), (IV), (V-A), (V-B), (V-C), (VI-A), (VI-B), or (VI-C), $L_1$ is —O—, —$CR_4R_5$— or a bond. In some embodiments, $L_1$ is a bond. In some embodiments, $L_1$ is —O—.

In some embodiments of the compounds of Formula (I), (II), (III), (IV), (V-A), (V-B), (V-C), (VI-A), (VI-B), or (VI-C), $L_2$ is —$CR_4R_5$. In embodiments, $L_2$ is $CH_2$.

In some embodiments of the compounds of Formula (I), (II), (III), (IV), (V-A), (V-B), (V-C), (VI-A), (VI-B), or (VI-C), $R_1$ is a alkyl, cycloalkyl, heterocyclyl, aryl, heteroaryl, —(C═O)alkyl, —(C═O)cycloalkyl, —(C═O) heterocyclyl, —(C═O)aryl, —(C═O)heteroaryl, —(C═O)—O-alkyl, —(C═O)—O-cycloalkyl, —(C═O)—O-heterocyclyl, —(C═O)—O-aryl, —(C═O)—O-heteroaryl, —$S(O)_2$-alkyl, —$S(O)_2$-cycloalkyl, —$S(O)_2$-heterocyclyl, —$S(O)_2$-aryl, —$S(O)_2$-heteroaryl, —(C═O)$NR_7R_8$, or $R_1$ and $R_2$ together with the atom to which they are attached form a heterocycle or heteroaryl.

In some embodiments of the compounds of Formula (I), (II), (III), (IV), (V-A), (V-B), (V-C), (VI-A), (VI-B), or (VI-C), $R_1$ is aryl, heteroaryl, —(C═O) $C_{1-6}$ alkyl, —(C═O) $C_{3-6}$ cycloalkyl, —(C═O) $C_{4-6}$ saturated heterocyclyl, —(C═O)—O—$C_{1-6}$ alkyl, —(C═O)—O—$C_{3-6}$ cycloalkyl, —(C═O)—O—$C_{4-6}$ saturated heterocyclyl, —$S(O)_2$—$C_{1-6}$ alkyl, —$S(O)_2$—$C_{3-6}$ cycloalkyl, —$S(O)_2$—$C_{4-6}$ heterocyclyl, —(C═O)$NR_7R_8$, or $R_1$ and $R_2$ together with the atom to which they are attached form a 4-7 membered heterocycle or a 5-6-membered heteroaryl.

In some embodiments of the compounds of Formula (T), (II), (ITT), (IV), (V-A), (V-B), (V-C), (VI-A), (VI-B), or (VI-C), $R_1$ is —(C═O) $C_{1-6}$ alkyl, —(C═O) $C_{3-6}$ cycloalkyl, —(C═O) $C_{4-6}$ saturated heterocyclyl, —(C═O)—O—$C_{1-6}$ alkyl, —(C═O)—O—$C_{3-6}$ cycloalkyl, —(C═O)—O—$C_{4-6}$ saturated heterocyclyl, —$S(O)_2$—$C_{1-6}$ alkyl, —$S(O)_2$—$C_{3-6}$ cycloalkyl, —$S(O)_2$—$C_{4-6}$ saturated heterocyclyl, or —(C═O)$NR_7R_8$.

In some embodiments of the compounds of Formula (I), (II), (III), (IV), (V-A), (V-B), (V-C), (VI-A), (VI-B), or (VI-C), $R_1$ is $C_{1-6}$ alkyl, 5 or 6-membered heteroaryl, —(C═O)$NR_7R_8$, —(C═O)—O—$C_{1-6}$ alkyl, —(C═O) $C_{3-6}$ cycloalkyl, —(C═O) $C_{1-6}$ alkyl, —(C═O) $C_{4-6}$ saturated heterocyclyl or —$S(O)_2$—$C_{1-6}$ alkyl; wherein each $C_{1-6}$ alkyl, $C_{3-6}$ cycloalkyl, $C_{4-6}$ saturated heterocyclyl, and heteroaryl is independently optionally substituted with one or more hydroxy, —$C_{1-6}$ alkyl, —O—$C_{1-6}$ alkyl, or fluoro.

In some embodiments of the compounds of Formula (I), (II), (III), (IV), (V-A), (V-B), (V-C), (VI-A), (VI-B), or (VI-C), $R_1$ is —(C═O)$NR_7R_8$, —(C═O)—O—$C_{1-6}$ alkyl, or —(C═O)—O—$C_{4-6}$ saturated heterocyclyl. In some embodiments, $R_1$ is —(C═O)$NR_7R_8$. In some embodiments, $R_1$ is —(C═O)—O—$C_{1-6}$ alkyl. In some embodiments, $R_1$ is —(C═O)—O—$C_{4-6}$ saturated heterocyclyl.

In some embodiments of the compounds of Formula (I), (II), (III), (IV), (V-A), (V-B), (V-C), (VI-A), (VI-B), or (VI-C), $R_1$ is —(C═O)N(H)($C_{1-6}$ alkyl), —(C═O)—O—$C_{1-3}$ alkyl, or —(C═O)—O-cyclopropyl.

In some embodiments of the compounds of Formula (I), (II), (III), (IV), (V-A), (V-B), (V-C), (VI-A), (VI-B), or (VI-C), $R_1$ is —(C═O)N(H)($CH_2CH_3$). In some embodiments, $R_1$ is —(C═O)—O—$CH_3$. In some embodiments, $R_1$ is —(C═O)—O-cyclopropyl.

In some embodiments of the compounds of Formula (I), (II), (III), (IV), (V-A), (V-B), (V-C), (VI-A), (VI-B), or (VI-C), $R_1$ is —(C═O)$NR_7R_8$, —(C═O)—O—$C_{1-6}$ alkyl, —(C═O)-cyclopropyl optionally substituted with one or more fluoro, —(C═O)—$C_{1-6}$ alkyl-OH, —(C═O)—O—$C_{1-6}$ haloalkyl, —$C_{1-6}$ haloalkyl, —(C═O)—$C_{1-6}$ haloalkyl, —(C═O)—$C_{1-3}$ alkyl-O—$C_{1-3}$ alkyl, —(C═O)-cyclobutyl optionally substituted with one or more fluoro, —(C═O)-azetidin-1-yl optionally substituted with one or more fluoro, —(C═O)-bicyclo[1.1.1]pentan-1-yl, pyridyl optionally substituted with —O—$C_{1-3}$ alkyl, tetrazolyl optionally substituted with $C_{1-3}$alkyl, —(C═O)-oxetan-2-yl or —$S(O)_2$—$C_{1-3}$ alkyl.

In some embodiments of the compounds of Formula (I), (II), (III), (IV), (V-A), (V-B), (V-C), (VI-A), (VI-B), or (VI-C), $R_2$ and $R_3$ are independently hydrogen, halogen, alkyl, cycloalkyl, heterocyclyl, or $R_2$ and $R_3$ together with the atom to which they are attached form a carbocycle or heterocycle.

In some embodiments of the compounds of Formula (I), (II), (III), (IV), (V-A), (V-B), (V-C), (VI-A), (VI-B), or (VI-C), $R_2$ and $R_3$ are independently hydrogen, $C_{1-5}$ alkyl, $C_{3-6}$ cycloalkyl, $C_{4-6}$ saturated heterocyclyl, or $R_2$ and $R_3$ together with the atom to which they are attached form a 3-6 membered carbocycle or 4-7 membered saturated heterocycle.

In some embodiments of the compounds of Formula (I), (II), (III), (IV), (V-A), (V-B), (V-C), (VI-A), (VI-B), or (VI-C), $R_2$ and $R_3$ are independently hydrogen, fluorine, $C_{1-5}$ alkyl, $C_{3-6}$ cycloalkyl, $C_{4-6}$ saturated heterocyclyl, or $R_2$ and $R_3$ together with the atom to which they are attached form a 3-6 membered carbocycle or 5-6 membered saturated heterocycle.

In some embodiments of the compounds of Formula (I), (II), (III), (IV), (V-A), (V-B), (V-C), (VI-A), (VI-B), or (VI-C), $R_2$ is independently hydrogen, fluorine, $C_{1-5}$ alkyl, $C_{3-6}$ cycloalkyl, $C_{4-6}$ saturated heterocyclyl, or $R_2$ and $R_3$ together with the atom to which they are attached form a 3-6 membered carbocycle or 5-6 membered saturated heterocycle and $R_3$ is hydrogen.

In some embodiments of the compounds of Formula (I), (II), (III), (IV), (V-A), (V-B), (V-C), (VI-A), (VI-B), or (VI-C), $R_2$ and $R_3$ are independently hydrogen or $C_{1-5}$ alkyl; wherein $C_{1-5}$ alkyl is optionally substituted with one or more fluorine.

In some embodiments of the compounds of Formula (I), (II), (III), (IV), (V-A), (V-B), (V-C), (VI-A), (VI-B), or (VI-C), $R_2$ and $R_3$ are independently hydrogen, $C_{1-3}$ alkyl, or $C_{1-3}$ haloalkyl.

In some embodiments of the compounds of Formula (I), (II), (III), (IV), (V-A), (V-B), (V-C), (VI-A), (VI-B), or (VI-C), $R_2$ is optionally substituted $C_{1-5}$ alkyl and $R_3$ is hydrogen. In embodiments, $R_2$ is optionally substituted (R)-$C_{1-5}$ alkyl and $R_3$ is hydrogen, or in embodiment $R_2$ is optionally substituted (S)-$C_{1-5}$ alkyl and $R_3$ is hydrogen.

In some embodiments of the compounds of Formula (I), (II), (TTT), (IV), (V-A), (V-B), (V-C), (VI-A), (VI-B), or (VI-C), $R_2$ and $R_3$ are both hydrogen.

In some embodiments of the compounds of Formula (I), (II), (III), (IV), (V-A), (V-B), (V-C), (VI-A), (VI-B), or (VI-C), $R_4$ and $R_5$ are independently hydrogen, alkyl, cycloalkyl, heterocyclyl, alkoxy, —O-cycloalkyl, —O-heterocyclyl, halogen, or $R_4$ and $R_5$ together with the atom to which they are attached to form a carbocycle or heterocycle.

In some embodiments of the compounds of Formula (I), (II), (III), (IV), (V-A), (V-B), (V-C), (VI-A), (VI-B), or (VI-C), $R_4$ and $R_5$ are independently hydrogen, $C_{1-5}$ alkyl, $C_{3-6}$ cycloalkyl, $C_{4-6}$ saturated heterocyclyl, $C_{1-6}$ alkoxy, —O—(C═O) $C_{3-6}$ cycloalkyl, —O—$C_{4-6}$ saturated heterocyclyl, fluorine, or $R_4$ and $R_5$ together with the atom to which they are attached to form a 3-6 membered carbocycle or 4-6 membered saturated heterocycle.

In some embodiments of the compounds of Formula (I), (II), (III), (IV), (V-A), (V-B), (V-C), (VI-A), (VI-B), or (VI-C), $R_4$ and $R_5$ are independently hydrogen, halo, or $C_{1-5}$ alkyl.

In some embodiments of the compounds of Formula (I), (II), (III), (IV), (V-A), (V-B), (V-C), (VI-A), (VI-B), or (VI-C), $R_4$ and $R_5$ are both hydrogen.

In some embodiments of the compounds of Formula (I), (II), (III), (IV), (V-A), (V-B), (V-C), (VI-A), (VI-B), or (VI-C), $R_6$ is hydrogen, $C_{1-6}$ alkyl, $C_{3-6}$ cycloalkyl, $C_{4-6}$ saturated heterocyclyl, aryl, heteroaryl, —(C═O)$C_{1-6}$ alkyl, —(C═O)$C_{3-6}$ cycloalkyl, —(C═O)$C_{4-6}$ saturated heterocyclyl, —(C═O)aryl, —(C═O)heteroaryl, —(C═O)—O—$C_{1-6}$ alkyl, —(C═O)—O—$C_{3-6}$ cycloalkyl, —(C═O)—O—$C_{4-6}$ saturated heterocyclyl, —(C═O)—O-aryl, —(C═O)—O-heteroaryl, —$S(O)_2$—$C_{1-6}$ alkyl, —$S(O)_2$—$C_{3-6}$ cycloalkyl, —$S(O)_2$—$C_{4-6}$ saturated heterocyclyl, —$S(O)_2$-aryl, —$S(O)_2$-heteroaryl or —(C═O)$NR_7R_8$.

In some embodiments of the compounds of Formula (I), (II), (III), (IV), (V-A), (V-B), (V-C), (VI-A), (VI-B), or (VI-C), $R_6$ is hydrogen, $C_{1-5}$ alkyl, $C_{3-6}$ cycloalkyl, $C_{4-6}$ saturated heterocyclyl, —(C═O) $C_{1-6}$ alkyl, —(C═O) $C_{3-6}$ cycloalkyl, —(C═O) $C_{4-6}$ saturated heterocyclyl, —(C═O)—O—$C_{1-6}$ alkyl, —(C═O)—O—$C_{3-6}$ cycloalkyl, —(C═O)—O—$C_{4-6}$ saturated heterocyclyl, —$S(O)_2$—$C_{1-6}$ alkyl, —$S(O)_2$—$C_{3-6}$ cycloalkyl, —$S(O)_2$—$C_{4-6}$ heterocyclyl, or —(C═O)$NR_7R_8$.

In some embodiments of the compounds of Formula (I), (II), (III), (IV), (V-A), (V-B), (V-C), (VI-A), (VI-B), or (VI-C), $R_6$ is hydrogen, alkyl, cycloalkyl, heterocyclyl, aryl, or heteroaryl.

In some embodiments of the compounds of Formula (I), (II), (III), (IV), (V-A), (V-B), (V-C), (VI-A), (VI-B), or (VI-C), $R_6$ is —(C═O)alkyl, —(C═O) cycloalkyl, —(C═O)heterocyclyl, —(C═O)aryl, —(C═O)heteroaryl, —(C═O)—O-alkyl, —(C═O)—O-cycloalkyl, —(C═O)—O-heterocyclyl, —(C═O)—O-aryl, —(C═O)—O-heteroaryl, —$S(O)_2$-alkyl, —$S(O)_2$-cycloalkyl, —$S(O)_2$-heterocyclyl, —$S(O)_2$-aryl, —$S(O)_2$-heteroaryl or —(C═O)$NR_7R_8$.

In some embodiments of the compounds of Formula (I), (II), (III), (IV), (V-A), (V-B), (V-C), (VI-A), (VI-B), or (VI-C), $R_6$ is hydrogen or alkyl. In some embodiments, $R_6$ is hydrogen.

In some embodiments of the compounds of Formula (I), (II), (III), (IV), (V-A), (V-B), (V-C), (VI-A), (VI-B), or (VI-C), $R_6$ is hydrogen or $C_{1-5}$ alkyl. In some embodiments, $R_6$ is $C_{1-5}$ alkyl. In embodiments, $R_6$ is $CH_3$.

In some embodiments, $R_7$ and $R_8$ are independently hydrogen, alkyl, cycloalkyl, heterocyclyl, aryl or heteroaryl, or $R_7$ and $R_8$ together with the atom to which they are attached to form a heterocycle.

In some embodiments of the compounds of Formula (I), (II), (III), (IV), (V-A), (V-B), (V-C), (VI-A), (VI-B), or (VI-C), $R_7$ and $R_8$ are independently hydrogen, $C_{1-6}$ alkyl, $C_{3-6}$ cycloalkyl, $C_{4-6}$ heterocyclyl, 5-6-membered heteroaryl, or $R_7$ and $R_8$ together with the atom to which they are attached to form a heterocycle.

In some embodiments of the compounds of Formula (I), (II), (III), (IV), (V-A), (V-B), (V-C), (VI-A), (VI-B), or (VI-C), $R_7$ and $R_8$ are independently hydrogen, and $C_{1-6}$ alkyl. In some embodiments, $R_7$ is hydrogen, and $R_8$ is $C_{1-6}$ alkyl.

In some embodiments of the compounds of Formula (I), (II), (III), (IV), (V-A), (V-B), (V-C), (VI-A), (VI-B), or (VI-C), $R_7$ and $R_8$ are independently hydrogen or $C_{1-6}$ alkyl or $R_7$ and $R_8$ together with the atom to which they are attached to form a saturated heterocycle, wherein the $C_{1-6}$ alkyl, and saturated heterocycle are independently optionally substituted with one or more fluoro or —O—$C_{1-6}$ alkyl.

In some embodiments of the compounds of Formula (I), (II), (III), (IV), (V-A), (V-B), (V-C), (VI-A), (VI-B), or (VI-C), $R_7$ and $R_8$ are independently hydrogen, —$C_{1-6}$ alkyl, —$C_{1-6}$ haloalkyl, —$C_{1-6}$ alkoxy, or $R_7$ and $R_8$ together with the atom to which they are attached to form a saturated 4-membered heterocycle optionally substituted with one or more fluoro.

In some embodiments of the compounds of Formula (I) or (II), Y is cycloalkyl, heterocyclyl, heteroaryl or aryl.

In some embodiments of the compounds of Formula (I) or (II), Y is 3-7 membered monocycloalkyl, 5-8 membered bicyclic cycloalkyl, 4-7 membered saturated heterocyclyl, 5-8 membered bicyclic heterocyclyl, 5-6-membered heteroaryl or phenyl.

In some embodiments of the compounds of Formula (I) or (II), Y is a 3-7 membered monocycloalkyl, 4-7 membered saturated heterocyclyl, or phenyl; wherein the phenyl is optionally substituted with one or more fluoro.

In some embodiments of the compounds of Formula (I) or (II), Y is cyclohexyl, phenyl, or a saturated 6-membered heterocyclyl; wherein the phenyl is optionally substituted with one or more fluoro.

In some embodiments of the compounds of Formula (I) or (II), Y is a 3-7 membered monocycloalkyl. In some embodiments, Y is a 5-8 membered bicyclic cycloalkyl. In some embodiments, Y is a 4-7 membered saturated heterocyclyl. In some embodiments, Y is a 5-8 membered bicyclic heterocyclyl. In some embodiments, Y is a 5-6-membered heteroaryl. In some embodiments, Y is a phenyl.

In some embodiments, Y is optionally substituted with —$(R^A)_p$, wherein $R^A$ and p are defined herein.

In some embodiments of the compounds of Formula (I), (II), (III), or (IV), Z is absent, heteroaryl or aryl. In some embodiments of the compounds of Formula (I), (II), (III), or (IV), Z is heteroaryl or aryl. In some embodiments, Z is absent, 5-10 membered heteroaromatic or phenyl. In some embodiments, Z is a 5-10 membered heteroaromatic or phenyl. In some embodiments, Z is aryl.

In some embodiments of the compounds of Formula (I), (II), (III), or (IV), Z is a 6 membered heteroaromatic or phenyl; wherein the 6 membered heteroaromatic and phenyl are independently optionally substituted with one or more fluoro.

In some embodiments of the compounds of Formula (I), (II), (III), or (IV), Z is:

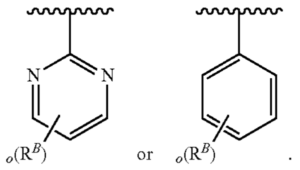

wherein $R^B$ and o are defined herein.

In some embodiments of the compounds of Formula (I), (II), (III), or (IV), Y is cyclohexyl and Z is substituted on the para position (or the 4-position) of Y.

In some embodiments of the compounds of Formula (I), (II), (III), or (IV), Y is phenyl and Z is substituted on the meta position (or the 3-position) of Y.

In some embodiments, Z is optionally substituted with $-(R^B)_o$, wherein $R^B$ and o are defined herein.

In some embodiments of the compounds of Formula (I) or (II), Y is aryl and Z is aryl. In some embodiments, Y and Z are phenyl.

In some embodiments of the compounds of Formula (I) or (II), Y is cyclohexyl and Z is aryl. In some embodiments, Y is cyclohexyl and Z is phenyl.

In some embodiments of the compounds of Formula (I), (II), (III), (IV), (V-A), (V-B), (V-C), (VI-A), (VI-B), and/or (VI-C), n and m are independently 0 or 1. In some embodiments, m and n are 0. In some embodiments, m is 1 and n is 0. In some embodiments, m is 0 and n is 1. In some embodiments, m is 1 and n is 1.

In some embodiments of the compounds of Formula (I), (II), (IV), (V-A) (V-B), or (V-C), p is 0, 1, 2, 3, or 4. In some embodiments, p is 0. In embodiments p is 0 or 1. In embodiments, p is 1.

In some embodiments of the compounds of Formula (I), (II), (III), (IV), (V-A), (V-B), (V-C), (VI-A), (VI-B), or (VI-C), o is 0, 1, 2, 3, or 4. In some embodiments, p is 0. In embodiments, o is 1. In embodiments, o is 2. In embodiments, o is 0, 1, or 2.

In some embodiments of the compounds of Formula (I), (II), (III), (IV), (V-A), (V-B), (V-C), (VI-A), (VI-B), and/or (VI-C), $R^A$ and $R^B$ are independently, for each occurrence, selected from the group consisting of hydroxy, halo, $-NO_2$, $-CN$, $-NR_7R_8$, $-CO_2R_9$, $-OC(O)R_9$, $-COR_9$, $-C(O)NR_7R_8$, $-NR_7C(O)R_8$, $-OC(O)NR_7R_8$, $-NR_7C(O)OR_9$, $-S(O)_wR_9$ (wherein w is 0, 1, or 2), $-OSO_2R_9$, $-SO_3R_9$, $-S(O)_2NR_7R_8$, $-NR_7S(O)_2R_9$, $-NR_7C(O)NR_7R_8$, $-C_{1-6}$ alkyl-$NR_7R_8$, $-C_{1-6}$ alkyl-O$-C_{1-6}$ alkyl, $-C_{1-6}$ alkyl, $C_{1-6}$ alkoxy, $C_{2-6}$ alkenyl, and $C_{2-6}$ alkynyl.

In some embodiments of the compounds of Formula (I), (II), (III), (IV), (V-A), (V-B), (V-C), (VI-A), (VI-B), and/or (VI-C), $R^A$ is halo.

In some embodiments of the compounds of Formula (I), (II), (III), (IV), (V-A), (V-B), (V-C), (VI-A), (VI-B), and/or (VI-C), $R^B$ is halo.

In some embodiments of the compounds of Formula (I), (II), (III), (IV), (V-A), (V-B), (V-C), (VI-A), (VI-B), and/or (VI-C), $R_9$ is independently selected, for each occurrence, from the group consisting of hydrogen, $C_{1-6}$alkyl, $C_{2-6}$alkenyl, $C_{2-6}$alkynyl, aryl, cycloalkyl, heterocyclyl, and heteroaryl.

In some embodiments, the compounds disclosed herein are a racemic mixture. In some embodiments, the compounds disclosed herein are enriched in one enantiomer. In some embodiments, the compounds disclosed herein are enriched are substantially free of the opposite enantiomer. In embodiments, provided herein is the (+)-enantiomer of a compound disclosed herein. In embodiments, provided herein is the (−)-enantiomer of a compound disclosed herein. In some embodiments, the compounds disclosed herein have an enantiomeric excess of about or greater than about 55%, about or greater than about 60%, about or greater than about 65%, about or greater than about 70%, about or greater than about 75%, about or greater than about 80%, about or greater than about 85%, about or greater than about 90%, about or greater than about 91%, about or greater than about 92%, about or greater than about 93%, about or greater than about 94%, about or greater than about 95%, about or greater than about 96%, about or greater than about 97%, about or greater than about 98%, about or greater than about 98.5%, about or greater than about 99%, about or greater than about 99.5%, or more, including all subranges and values therebetween. In embodiments, the compounds disclosed herein are enriched in the (+)-enantiomer. In embodiments, the compounds disclosed herein are enriched in the (−)-enantiomer.

In some embodiments, the compounds of the present disclosure are provided as a mixture of diastereomers. In some embodiments, a diastereomer of a compound of the present disclosure is provided substantially free of other possible diastereomer(s). In some embodiments, the compounds of the present disclosure are designated as "cis-relative" or "trans-relative" as described herein.

The present disclosure includes tautomers of any said compounds.

In some embodiments, provided herein is one or more compounds selected from Table 1 or a pharmaceutically acceptable salt thereof, or a stereoisomer thereof.

In some embodiments, provided herein is one or more compounds selected from Table 1 or a pharmaceutically acceptable salt thereof, or an enantiomer thereof.

In some embodiments, provided herein is one or more compounds selected from Table 1 or a pharmaceutically acceptable salt thereof, or a diastereomer, or mixture of diastereomers thereof.

In some embodiments, provided herein is one or more compounds selected from Table 1 or a pharmaceutically acceptable salt thereof, or a diastereomer, or mixture of diastereomers thereof, or an enantiomer or mixture of enantiomers thereof.

In some embodiments, provided herein is one or more compounds selected from Table 1. In some embodiments, provided herein is one or more compounds selected from Table 2. In embodiments, provided herein is compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90-i, 90, 91, 92, or 93. In embodiments provided herein is compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In some embodiments, provided herein is one or more pharmaceutically acceptable salts of a compound selected from Table 1. In some embodiments, provided herein is one or more pharmaceutically acceptable salts of a compound selected from Table 2. In embodiments, provided herein is a pharmaceutically acceptable salt of compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90-i, 90, 91, 92, or 93. In embodiments, provided herein is a pharmaceutically acceptable salt of compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.
TABLE 1
| Compounds |
|---|
1-A
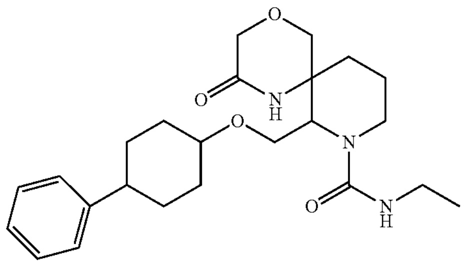 [SMILES: CCNC(=O)N1CCCC2(COCC(=O)N2)C1COC1CCC(c2ccccc2)CC1]
1
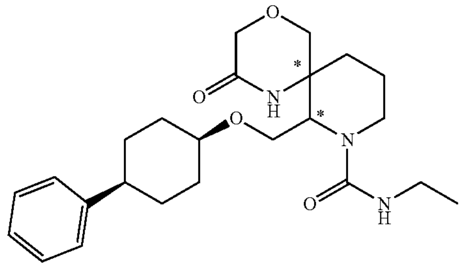
* cis-relative stereochemistry
2
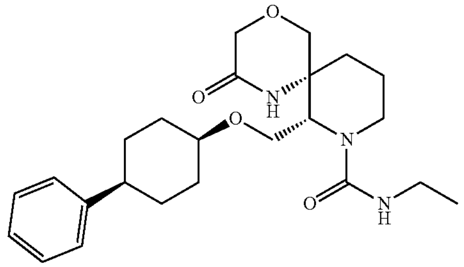 [SMILES: CCNC(=O)N1CCC[C@]2(COCC(=O)N2)[C@H]1CO[C@H]1CC[C@@H](c2ccccc2)CC1]
3
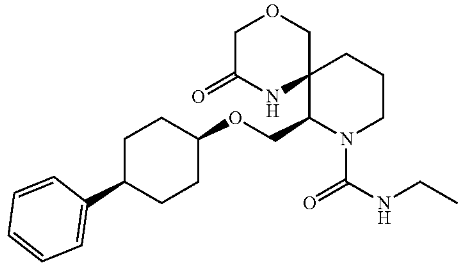 [SMILES: CCNC(=O)N1CCC[C@@]2(COCC(=O)N2)[C@@H]1CO[C@H]1CC[C@@H](c2ccccc2)CC1]
4-A
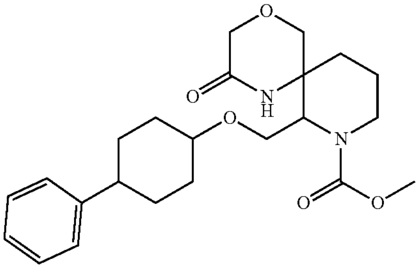 [SMILES: COC(=O)N1CCCC2(COCC(=O)N2)C1COC1CCC(c2ccccc2)CC1]
TABLE 1-continued
| Compounds |
|---|
4
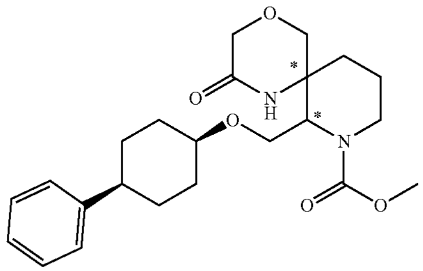
* cis-relative stereochemistry
5
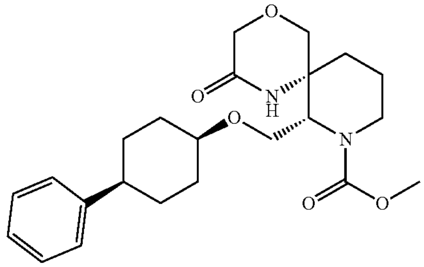 [SMILES: COC(=O)N1CCC[C@]2(COCC(=O)N2)[C@H]1CO[C@H]1CC[C@@H](c2ccccc2)CC1]
6
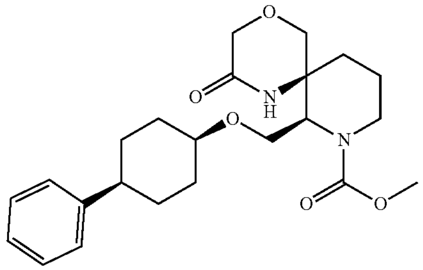 [SMILES: COC(=O)N1CCC[C@@]2(COCC(=O)N2)[C@@H]1CO[C@H]1CC[C@@H](c2ccccc2)CC1]
7-A
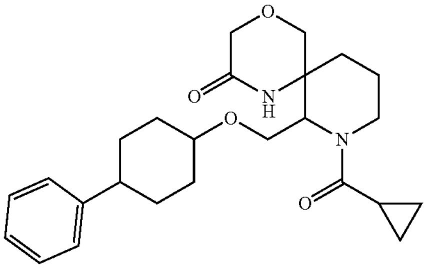 [SMILES: O=C1COCC2(CCCN(C(=O)C3CC3)C2COC2CCC(c3ccccc3)CC2)N1]
7
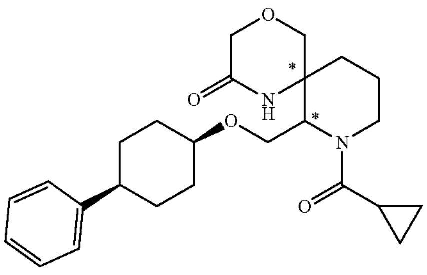
* cis-relative stereochemistry TABLE 1-continued
Compounds
8
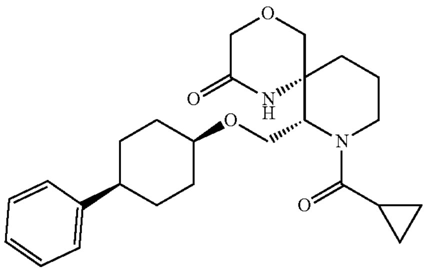 [SMILES: O=C1COC[C@]2(CCCN(C(=O)C3CC3)[C@@H]2CO[C@H]2CC[C@@H](c3ccccc3)CC2)N1]
9
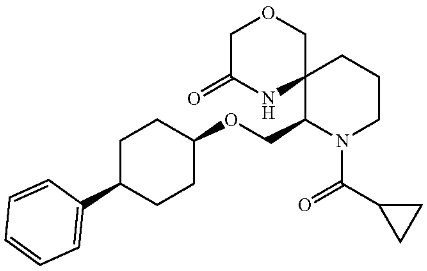 [SMILES: O=C1COC[C@@]2(CCCN(C(=O)C3CC3)[C@H]2CO[C@H]2CC[C@@H](c3ccccc3)CC2)N1]
10-A
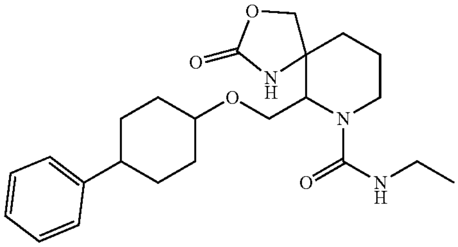 [SMILES: CCNC(=O)N1CCCC2(COC(=O)N2)C1COC1CCC(c2ccccc2)CC1]
10
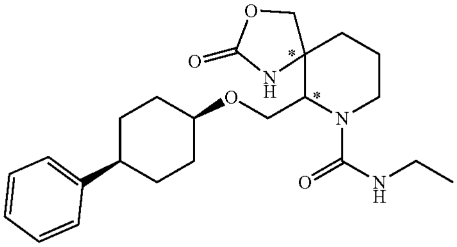
* cis-relative stereochemistry
10-B
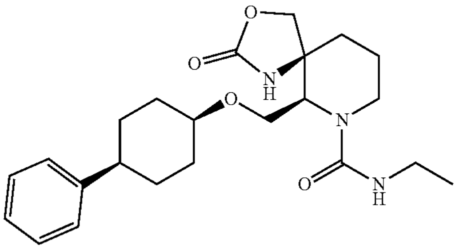 [SMILES: CCNC(=O)N1CCC[C@@]2(COC(=O)N2)[C@@H]1CO[C@H]1CC[C@@H](c2ccccc2)CC1]
10-C
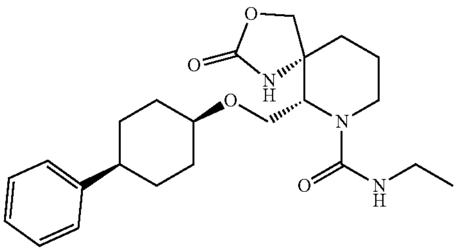 [SMILES: CCNC(=O)N1CCC[C@]2(COC(=O)N2)[C@H]1CO[C@H]1CC[C@@H](c2ccccc2)CC1]
TABLE 1-continued
Compounds
11-A
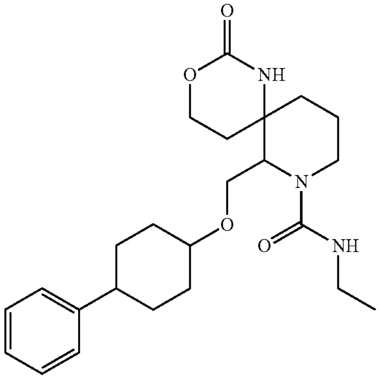 [SMILES: CCNC(=O)N1CCCC2(CCOC(=O)N2)C1COC1CCC(c2ccccc2)CC1]
11
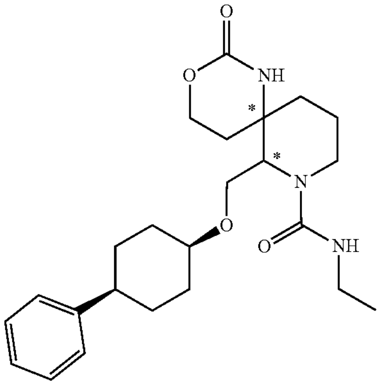
* cis-relative stereochemistry
12
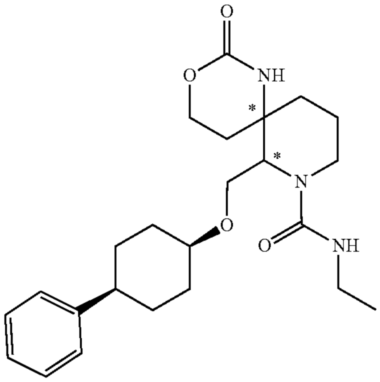
* trans-relative stereochemistry TABLE 1-continued
| Compounds |
|---|
12-B
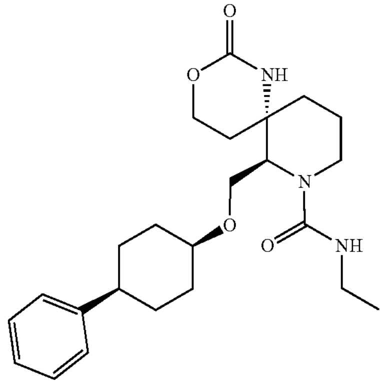 [SMILES: CCNC(=O)N1CCC[C@]2(CCOC(=O)N2)[C@@H]1CO[C@H]1CC[C@@H](c2ccccc2)CC1]
12-C
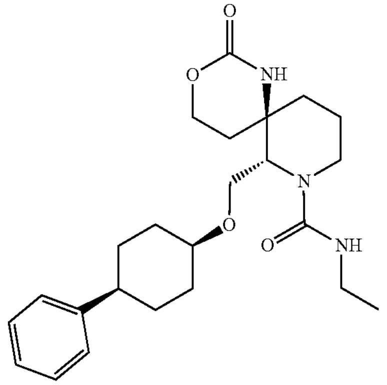 [SMILES: CCNC(=O)N1CCC[C@@]2(CCOC(=O)N2)[C@H]1CO[C@H]1CC[C@@H](c2ccccc2)CC1]
13
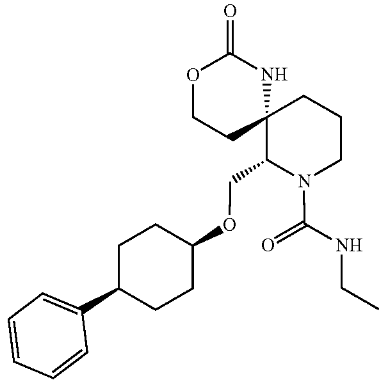 [SMILES: CCNC(=O)N1CCC[C@]2(CCOC(=O)N2)[C@H]1CO[C@H]1CC[C@@H](c2ccccc2)CC1]
14
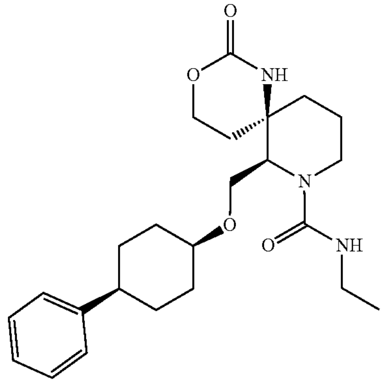 [SMILES: CCNC(=O)N1CCC[C@@]2(CCOC(=O)N2)[C@@H]1CO[C@H]1CC[C@@H](c2ccccc2)CC1]
TABLE 1-continued
| Compounds |
|---|
15-A
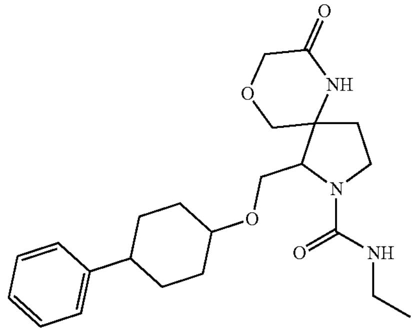 [SMILES: CCNC(=O)N1CCC2(COCC(=O)N2)C1COC1CCC(c2ccccc2)CC1]
15
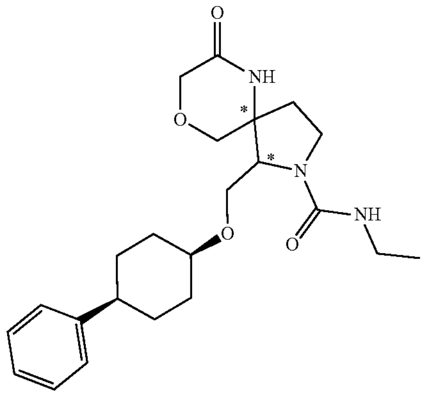
* cis-relative stereochemistry
16
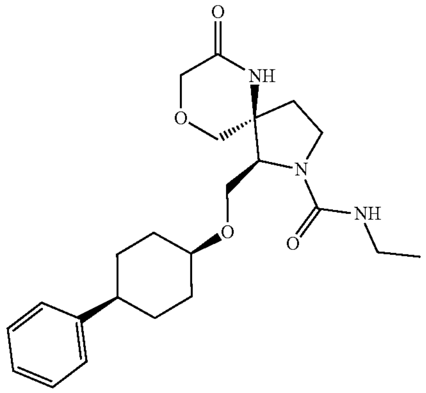 [SMILES: CCNC(=O)N1CC[C@@]2(COCC(=O)N2)[C@@H]1CO[C@H]1CC[C@@H](c2ccccc2)CC1]
17
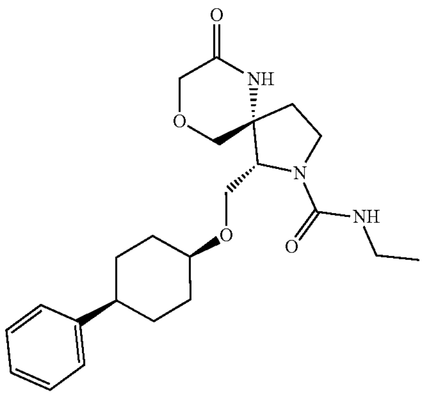 [SMILES: CCNC(=O)N1CC[C@]2(COCC(=O)N2)[C@H]1CO[C@H]1CC[C@@H](c2ccccc2)CC1]

TABLE 1-continued
| Compounds |
|---|
18-A
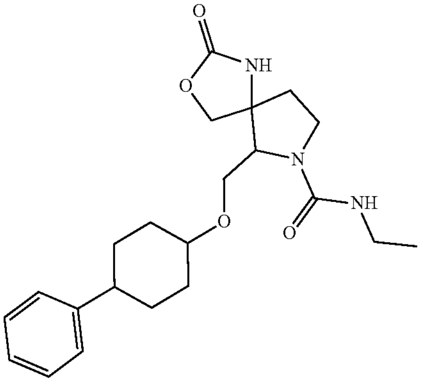 [SMILES: CCNC(=O)N1CCC2(COC(=O)N2)C1COC1CCC(c2ccccc2)CC1]
18
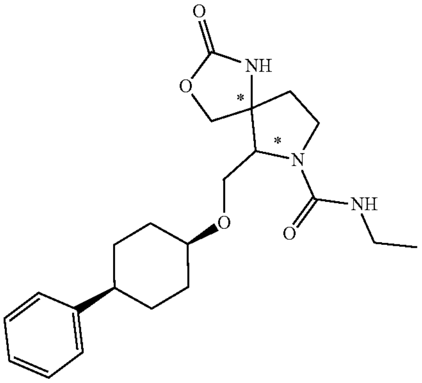
* cis-relative stereochemistry
18-B
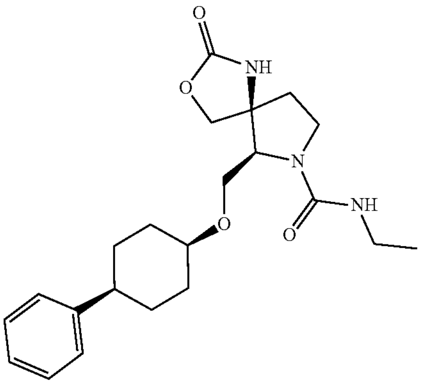 [SMILES: CCNC(=O)N1CC[C@@]2(COC(=O)N2)[C@@H]1CO[C@H]1CC[C@@H](c2ccccc2)CC1]
18-C
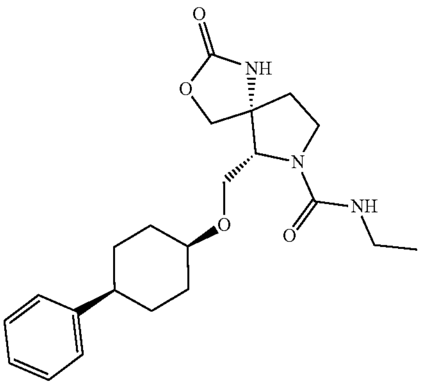 [SMILES: CCNC(=O)N1CC[C@]2(COC(=O)N2)[C@H]1CO[C@H]1CC[C@@H](c2ccccc2)CC1]
TABLE 1-continued
| Compounds |
|---|
19
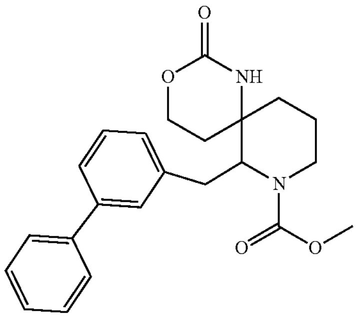 [SMILES: COC(=O)N1CCCC2(CCOC(=O)N2)C1Cc1cccc(-c2ccccc2)c1]
20
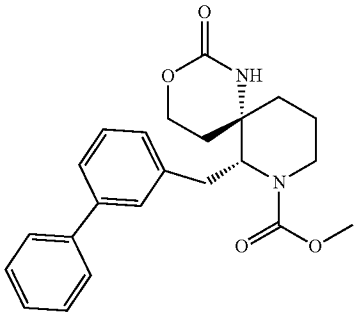 [SMILES: COC(=O)N1CCC[C@]2(CCOC(=O)N2)[C@H]1Cc1cccc(-c2ccccc2)c1]
21
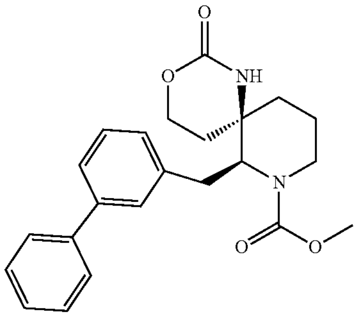 [SMILES: COC(=O)N1CCC[C@@]2(CCOC(=O)N2)[C@@H]1Cc1cccc(-c2ccccc2)c1]
22
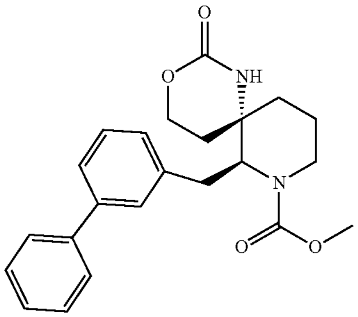 [SMILES: COC(=O)N1CCC[C@]2(CCOC(=O)N2)[C@@H]1Cc1cccc(-c2ccccc2)c1]
23
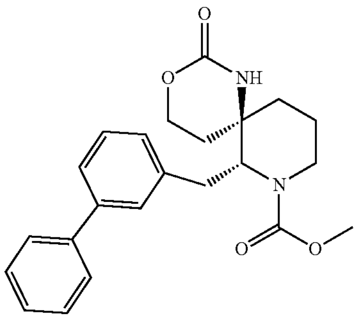 [SMILES: COC(=O)N1CCC[C@@]2(CCOC(=O)N2)[C@H]1Cc1cccc(-c2ccccc2)c1]

TABLE 1-continued
| Compounds |
| --- |
24-A
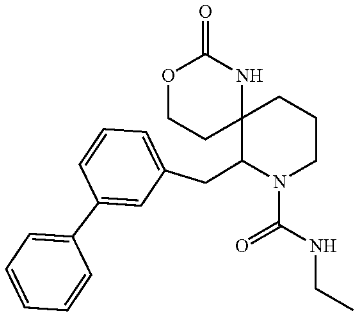 [SMILES: CCNC(=O)N1CCCC2(CCOC(=O)N2)C1Cc1cccc(-c2ccccc2)c1]
24
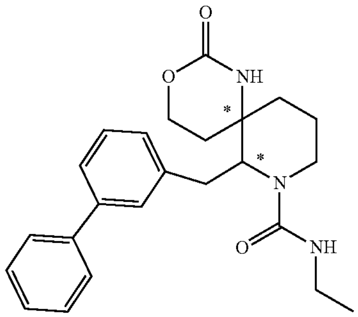
* cis-relative stereochemistry
25
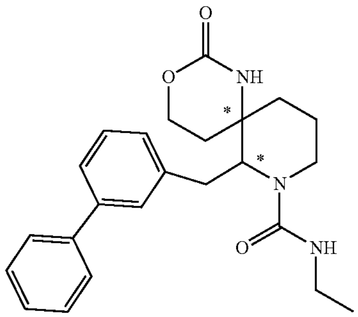
* trans-relative stereochemistry
26
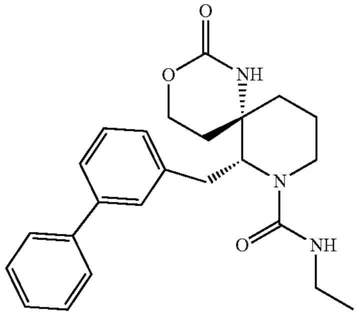 [SMILES: CCNC(=O)N1CCC[C@]2(CCOC(=O)N2)[C@H]1Cc1cccc(-c2ccccc2)c1]
TABLE 1-continued
| Compounds |
| --- |
27
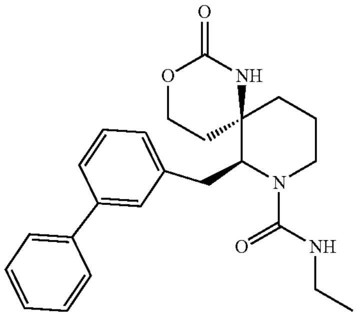 [SMILES: CCNC(=O)N1CCC[C@@]2(CCOC(=O)N2)[C@@H]1Cc1cccc(-c2ccccc2)c1]
25-A
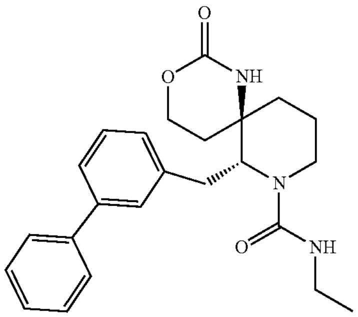 [SMILES: CCNC(=O)N1CCC[C@@]2(CCOC(=O)N2)[C@H]1Cc1cccc(-c2ccccc2)c1]
25-B
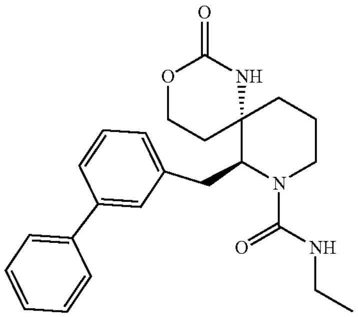 [SMILES: CCNC(=O)N1CCC[C@]2(CCOC(=O)N2)[C@@H]1Cc1cccc(-c2ccccc2)c1]
28
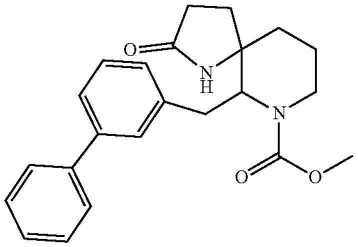 [SMILES: COC(=O)N1CCCC2(CCC(=O)N2)C1Cc1cccc(-c2ccccc2)c1]
29
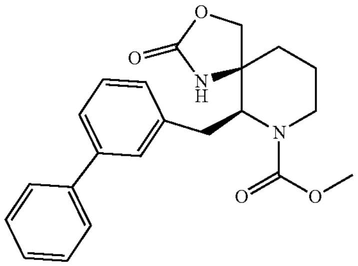 [SMILES: COC(=O)N1CCC[C@@]2(COC(=O)N2)[C@@H]1Cc1cccc(-c2ccccc2)c1]

TABLE 1-continued
| Compounds | |
|---|---|
| 29-B | 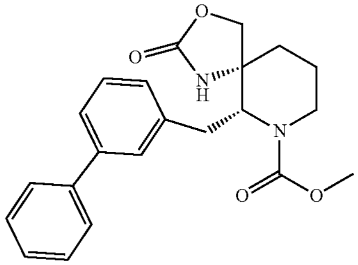 [SMILES: COC(=O)N1CCC[C@]2(COC(=O)N2)[C@H]1Cc1cccc(-c2ccccc2)c1] |
| 30 | 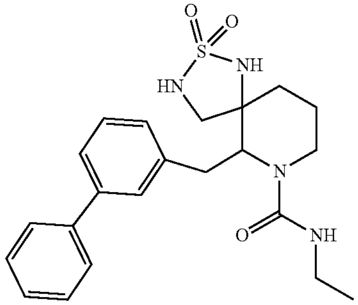 [SMILES: CCNC(=O)N1CCCC2(CNS(=O)(=O)N2)C1Cc1cccc(-c2ccccc2)c1] |
| 31 | 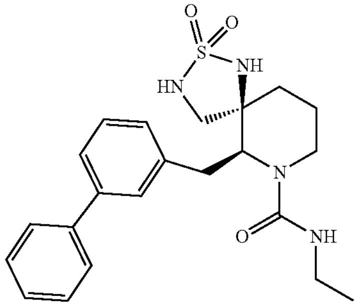 [SMILES: CCNC(=O)N1CCC[C@@]2(CNS(=O)(=O)N2)[C@@H]1Cc1cccc(-c2ccccc2)c1] |
| 32 | 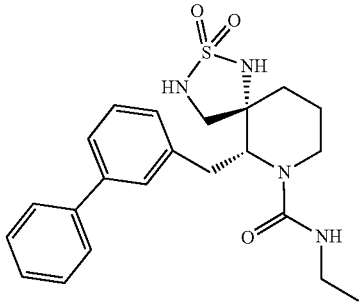 [SMILES: CCNC(=O)N1CCC[C@]2(CNS(=O)(=O)N2)[C@H]1Cc1cccc(-c2ccccc2)c1] |
| 33-A | 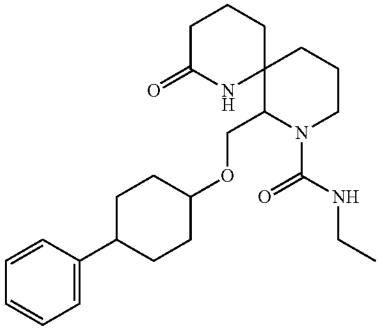 [SMILES: CCNC(=O)N1CCCC2(CCCC(=O)N2)C1COC1CCC(c2ccccc2)CC1] |
TABLE 1-continued
| Compounds | |
|---|---|
| 33 | 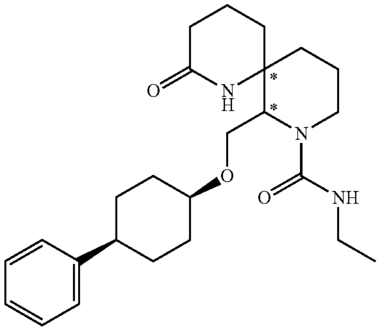 [SMILES: CCNC(=O)N1CCC[C@]2(CCCC(=O)N2)[C@H]1CO[C@H]1CC[C@@H](c2ccccc2)CC1]<br>*cis-relative stereochemistry |
| 34 | 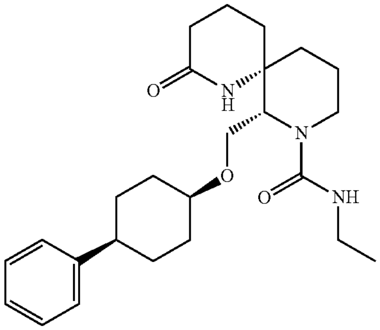 |
| 35 | 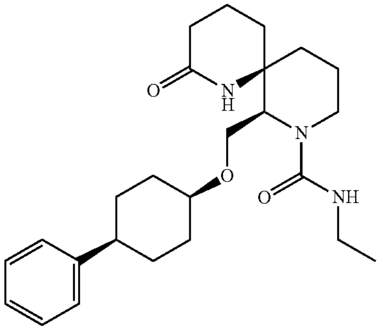 [SMILES: CCNC(=O)N1CCC[C@@]2(CCCC(=O)N2)[C@@H]1CO[C@H]1CC[C@@H](c2ccccc2)CC1] |
| 36-A | 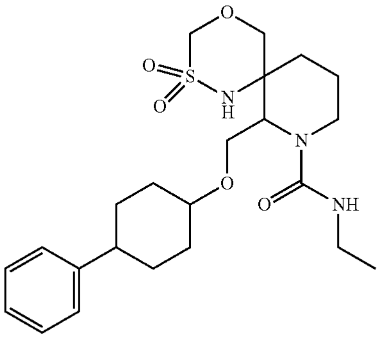 [SMILES: CCNC(=O)N1CCCC2(COCS(=O)(=O)N2)C1COC1CCC(c2ccccc2)CC1] |

TABLE 1-continued
| Compounds |
|---|
36
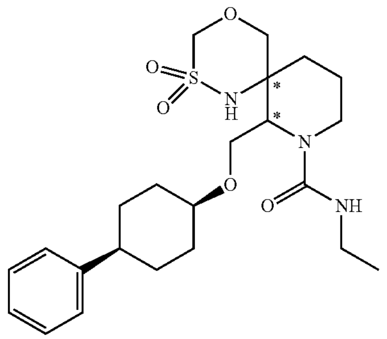
*cis-relative stereochemistry
36-B
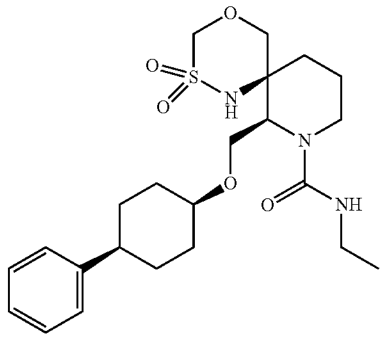 [SMILES: CCNC(=O)N1CCC[C@@]2(COCS(=O)(=O)N2)[C@@H]1CO[C@H]1CC[C@@H](c2ccccc2)CC1]
36-C
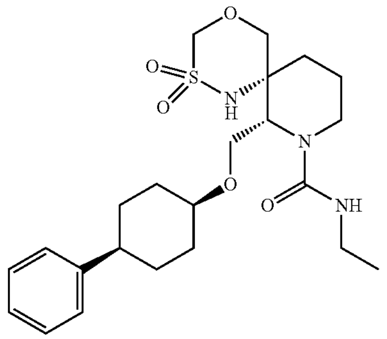 [SMILES: CCNC(=O)N1CCC[C@]2(COCS(=O)(=O)N2)[C@H]1CO[C@H]1CC[C@@H](c2ccccc2)CC1]
37-A
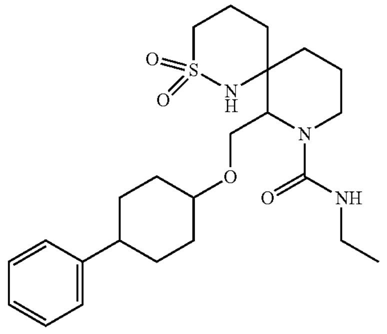 [SMILES: CCNC(=O)N1CCCC2(CCCS(=O)(=O)N2)C1COC1CCC(c2ccccc2)CC1]
TABLE 1-continued
| Compounds |
|---|
37
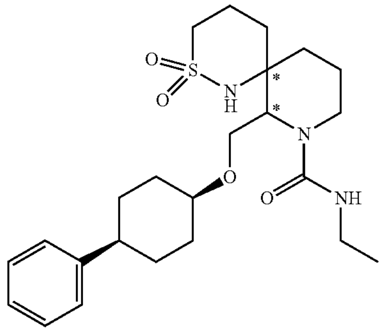 [SMILES: CCNC(=O)N1CCCC2(CCCS(=O)(=O)N2)C1CO[C@H]1CC[C@@H](c2ccccc2)CC1]
37-B
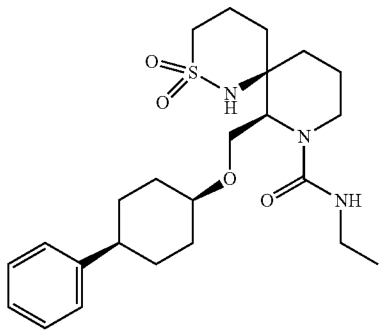 [SMILES: CCNC(=O)N1CCC[C@@]2(CCCS(=O)(=O)N2)[C@@H]1CO[C@H]1CC[C@@H](c2ccccc2)CC1]
37-C
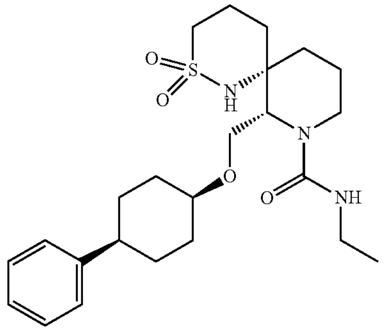 [SMILES: CCNC(=O)N1CCC[C@]2(CCCS(=O)(=O)N2)[C@H]1CO[C@H]1CC[C@@H](c2ccccc2)CC1]
38-A
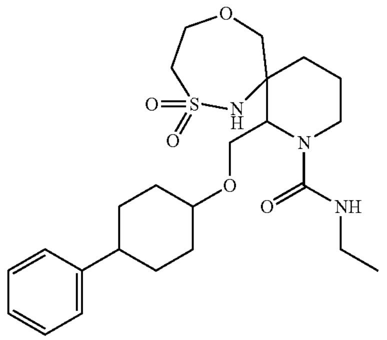 [SMILES: CCNC(=O)N1CCCC2(COCCS(=O)(=O)N2)C1COC1CCC(c2ccccc2)CC1]

TABLE 1-continued
Compounds
38
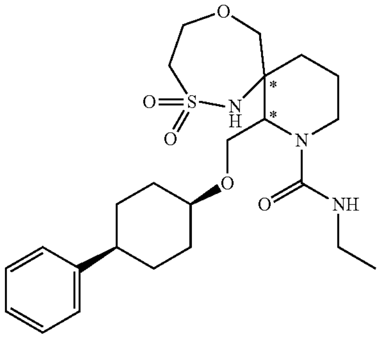
*cis-relative stereochemistry
38-B
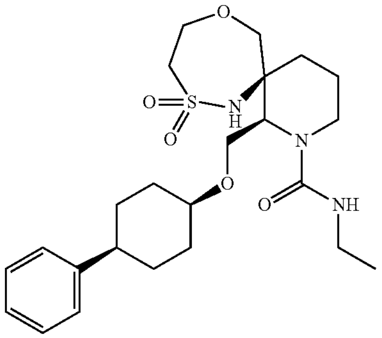 [SMILES: CCNC(=O)N1CCC[C@@]2(COCCS(=O)(=O)N2)[C@@H]1CO[C@H]1CC[C@@H](c2ccccc2)CC1]
38-C
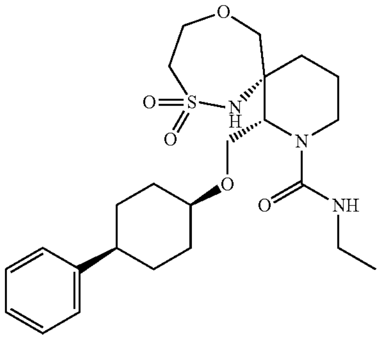 [SMILES: CCNC(=O)N1CCC[C@]2(COCCS(=O)(=O)N2)[C@H]1CO[C@H]1CC[C@@H](c2ccccc2)CC1]
39-A
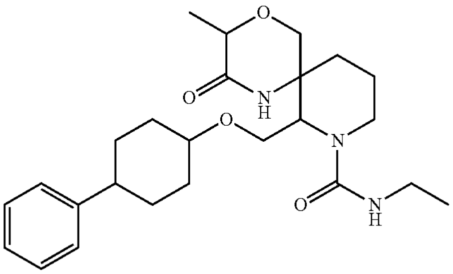 [SMILES: CCNC(=O)N1CCCC2(COC(C)C(=O)N2)C1COC1CCC(c2ccccc2)CC1]
TABLE 1-continued
Compounds
39
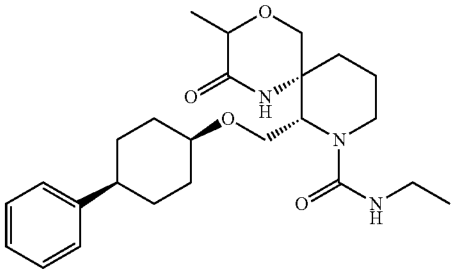
39-B
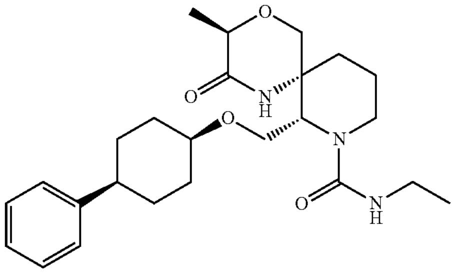 [SMILES: CCNC(=O)N1CCC[C@]2(CO[C@H](C)C(=O)N2)[C@H]1CO[C@H]1CC[C@@H](c2ccccc2)CC1]
39-C
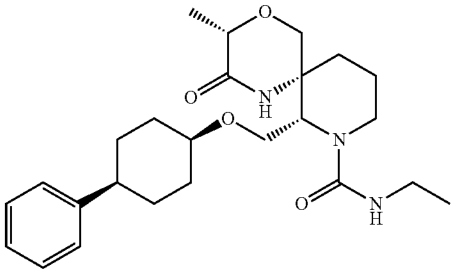 [SMILES: CCNC(=O)N1CCC[C@]2(CO[C@@H](C)C(=O)N2)[C@H]1CO[C@H]1CC[C@@H](c2ccccc2)CC1]
40
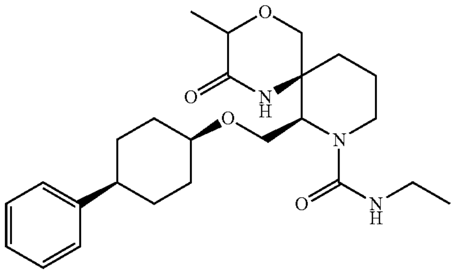
40-B
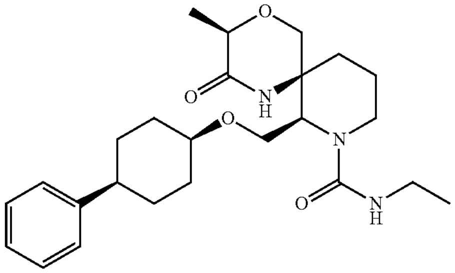 [SMILES: CCNC(=O)N1CCC[C@@]2(CO[C@H](C)C(=O)N2)[C@@H]1CO[C@H]1CC[C@@H](c2ccccc2)CC1]

TABLE 1-continued
Compounds
40-C
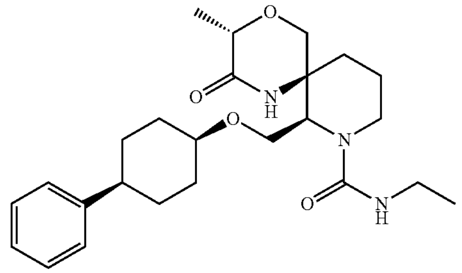 [SMILES: CCNC(=O)N1CCC[C@@]2(CO[C@@H](C)C(=O)N2)[C@@H]1CO[C@H]1CC[C@@H](c2ccccc2)CC1]
41-A
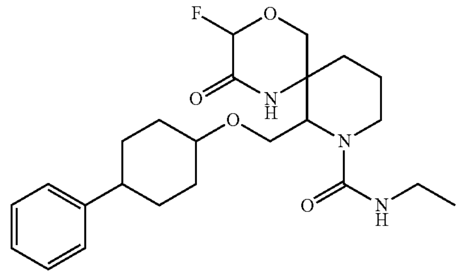 [SMILES: CCNC(=O)N1CCCC2(COC(F)C(=O)N2)C1COC1CCC(c2ccccc2)CC1]
41
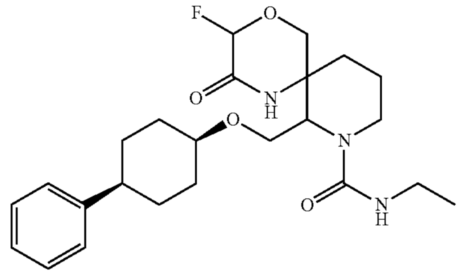
*cis-relative stereochemistry
42
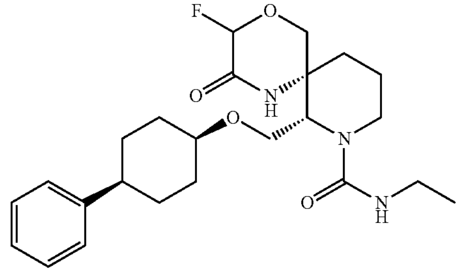
42-B
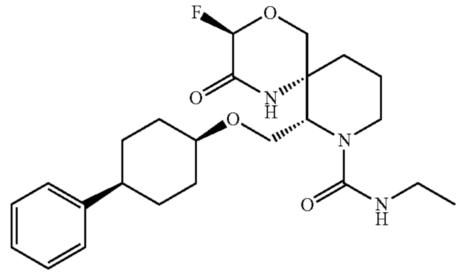 [SMILES: CCNC(=O)N1CCC[C@]2(CO[C@H](F)C(=O)N2)[C@H]1CO[C@H]1CC[C@@H](c2ccccc2)CC1]
TABLE 1-continued
Compounds
42-C
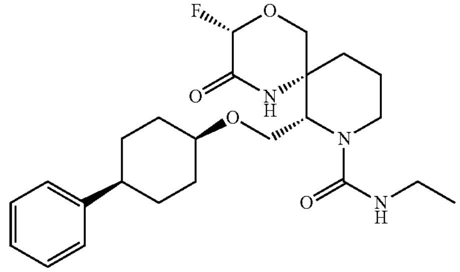
43
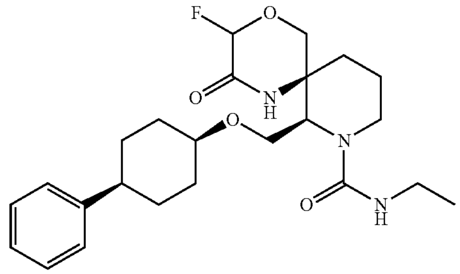
43-B
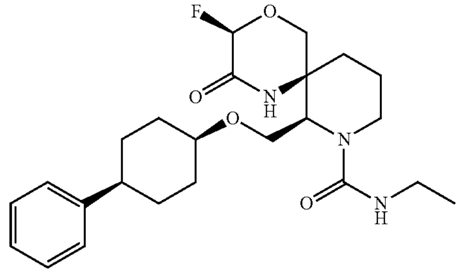 [SMILES: CCNC(=O)N1CCC[C@@]2(CO[C@H](F)C(=O)N2)[C@@H]1CO[C@H]1CC[C@@H](c2ccccc2)CC1]
43-C
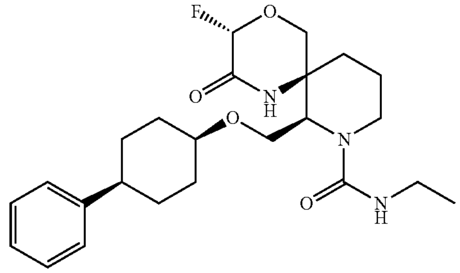 [SMILES: CCNC(=O)N1CCC[C@@]2(CO[C@@H](F)C(=O)N2)[C@@H]1CO[C@H]1CC[C@@H](c2ccccc2)CC1]
44-A
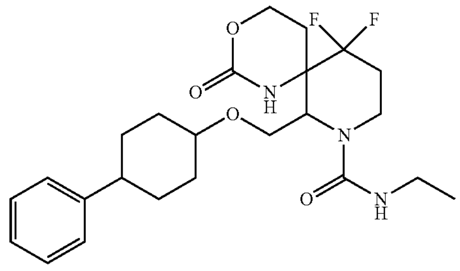 [SMILES: CCNC(=O)N1CCC(F)(F)C2(CCOC(=O)N2)C1COC1CCC(c2ccccc2)CC1]

TABLE 1-continued
| Compounds |
| --- |
44
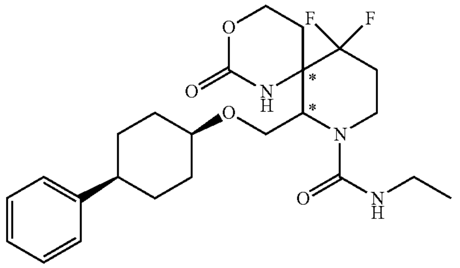
*cis-relative stereochemistry
45
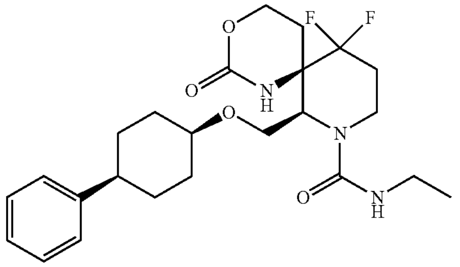 [SMILES: CCNC(=O)N1CCC(F)(F)[C@@]2(CCOC(=O)N2)[C@@H]1CO[C@H]1CC[C@@H](c2ccccc2)CC1]
46
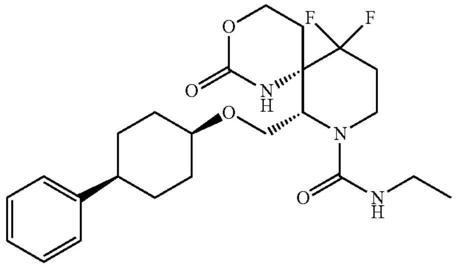 [SMILES: CCNC(=O)N1CCC(F)(F)[C@]2(CCOC(=O)N2)[C@H]1CO[C@H]1CC[C@@H](c2ccccc2)CC1]
47-A
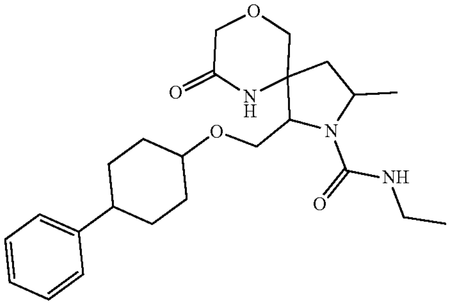 [SMILES: CCNC(=O)N1C(C)CC2(COCC(=O)N2)C1COC1CCC(c2ccccc2)CC1]
47
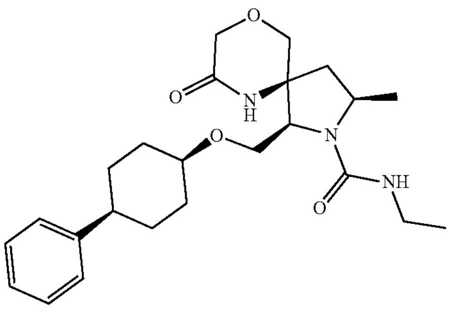 [SMILES: CCNC(=O)N1[C@H](C)C[C@@]2(COCC(=O)N2)[C@@H]1CO[C@H]1CC[C@@H](c2ccccc2)CC1]
TABLE 1-continued
| Compounds |
| --- |
48
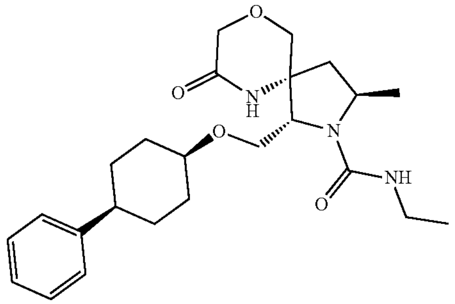 [SMILES: CCNC(=O)N1[C@H](C)C[C@]2(COCC(=O)N2)[C@H]1CO[C@H]1CC[C@@H](c2ccccc2)CC1]
49-A
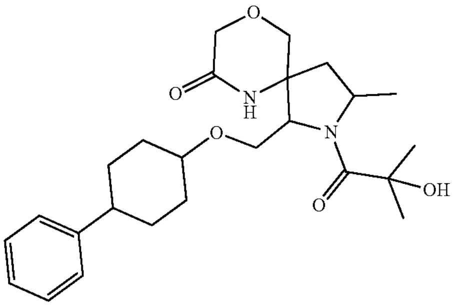 [SMILES: CC1CC2(COCC(=O)N2)C(COC2CCC(c3ccccc3)CC2)N1C(=O)C(C)(C)O]
49
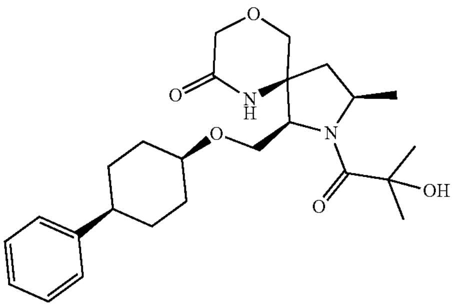 [SMILES: C[C@@H]1C[C@@]2(COCC(=O)N2)[C@H](CO[C@H]2CC[C@@H](c3ccccc3)CC2)N1C(=O)C(C)(C)O]
50-A
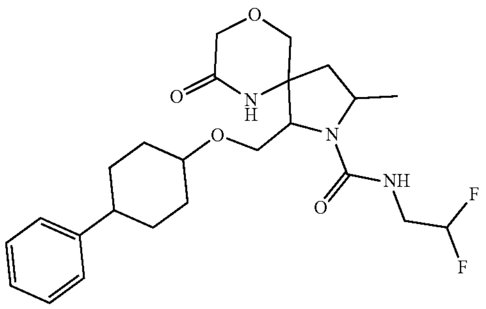 [SMILES: CC1CC2(COCC(=O)N2)C(COC2CCC(c3ccccc3)CC2)N1C(=O)NCC(F)F]
50
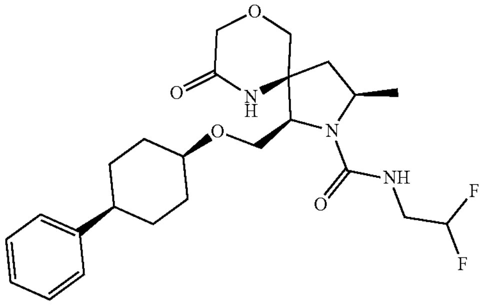 [SMILES: C[C@@H]1C[C@@]2(COCC(=O)N2)[C@H](CO[C@H]2CC[C@@H](c3ccccc3)CC2)N1C(=O)NCC(F)F]

TABLE 1-continued
| Compounds |
|---|
51-A
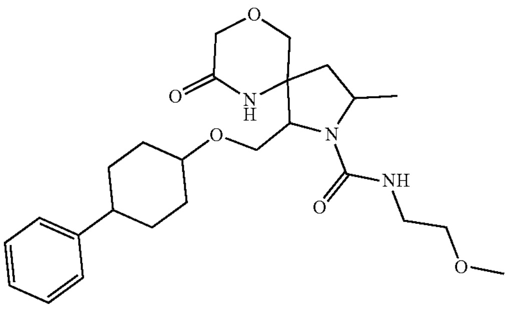 [SMILES: COCCNC(=O)N1C(C)CC2(COCC(=O)N2)C1COC1CCC(c2ccccc2)CC1]
51
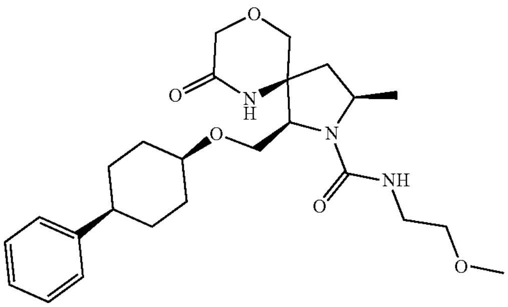 [SMILES: COCCNC(=O)N1[C@H](C)C[C@@]2(COCC(=O)N2)[C@@H]1CO[C@H]1CC[C@@H](c2ccccc2)CC1]
52-A
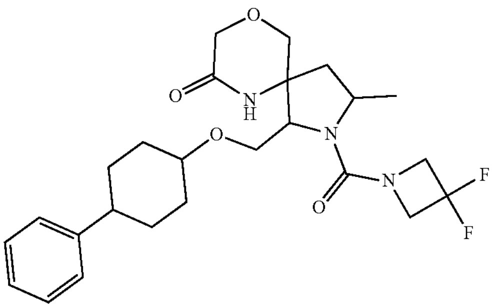 [SMILES: CC1CC2(COCC(=O)N2)C(COC2CCC(c3ccccc3)CC2)N1C(=O)N1CC(F)(F)C1]
52
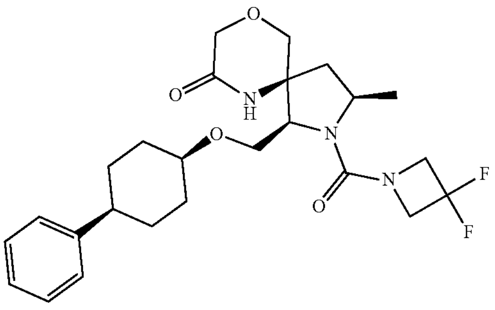 [SMILES: C[C@@H]1C[C@@]2(COCC(=O)N2)[C@H](CO[C@H]2CC[C@@H](c3ccccc3)CC2)N1C(=O)N1CC(F)(F)C1]
TABLE 1-continued
| Compounds |
|---|
53-A
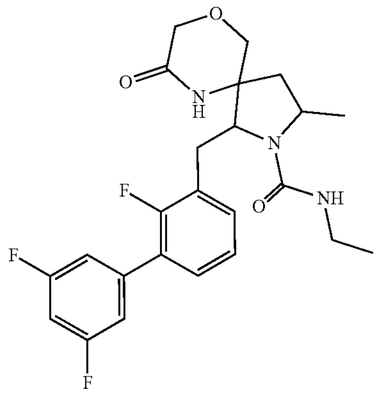 [SMILES: CCNC(=O)N1C(C)CC2(COCC(=O)N2)C1Cc1cccc(-c2cc(F)cc(F)c2)c1F]
53
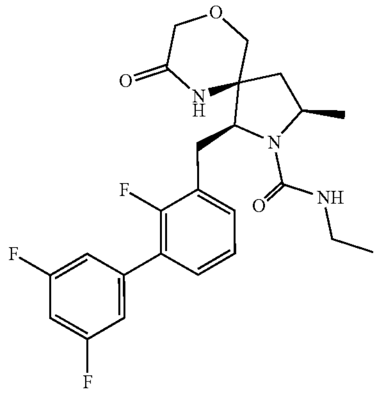 [SMILES: CCNC(=O)N1[C@H](C)C[C@@]2(COCC(=O)N2)[C@@H]1Cc1cccc(-c2cc(F)cc(F)c2)c1F]
54-A
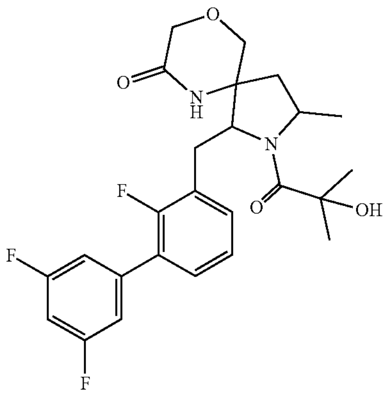 [SMILES: CC1CC2(COCC(=O)N2)C(Cc2cccc(-c3cc(F)cc(F)c3)c2F)N1C(=O)C(C)(C)O]
54
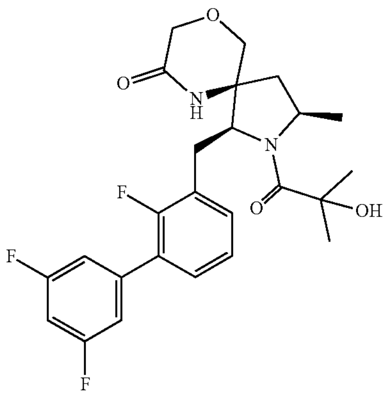 [SMILES: C[C@@H]1C[C@@]2(COCC(=O)N2)[C@H](Cc2cccc(-c3cc(F)cc(F)c3)c2F)N1C(=O)C(C)(C)O]

TABLE 1-continued
| Compounds |
| --- |
55-A
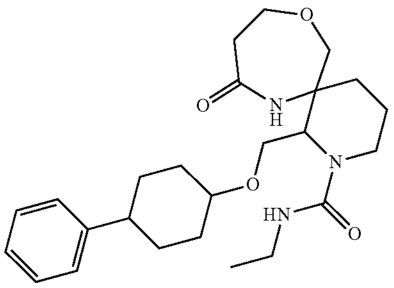 [SMILES: CCNC(=O)N1CCCC2(COCCC(=O)N2)C1COC1CCC(c2ccccc2)CC1]
55
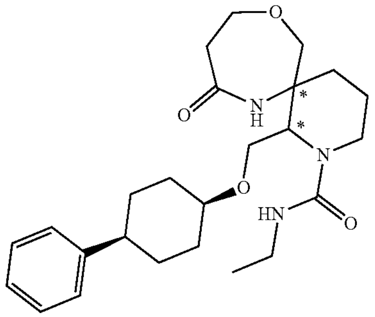
*cis-relative stereochemistry
55-B
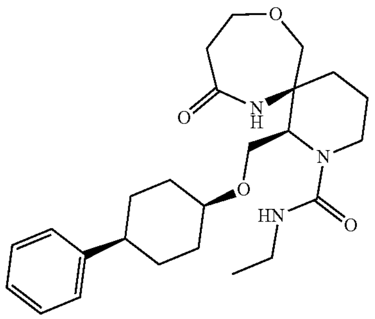 [SMILES: CCNC(=O)N1CCC[C@@]2(COCCC(=O)N2)[C@@H]1CO[C@H]1CC[C@@H](c2ccccc2)CC1]
55-C
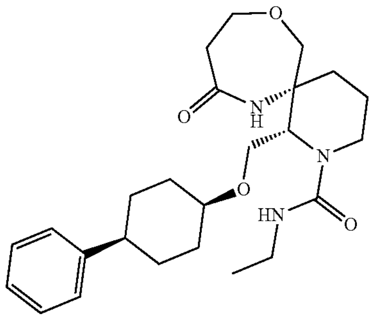 [SMILES: CCNC(=O)N1CCC[C@]2(COCCC(=O)N2)[C@H]1CO[C@H]1CC[C@@H](c2ccccc2)CC1]
TABLE 1-continued
| Compounds |
| --- |
56-A
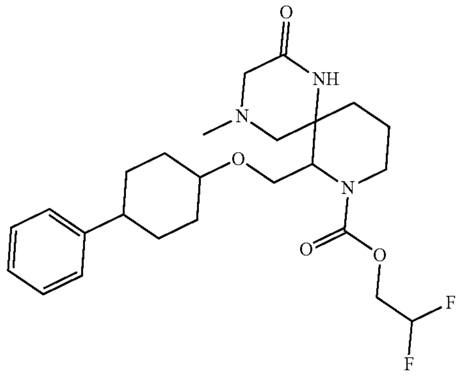
*cis-relative stereochemistry
56
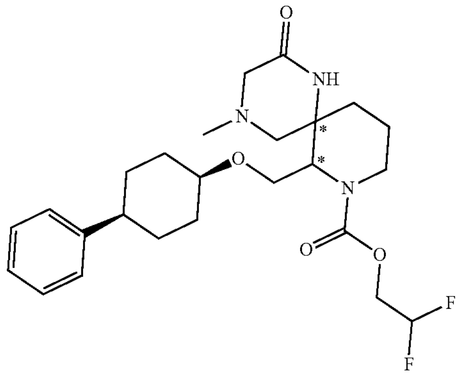
*cis-relative stereochemistry
56-B
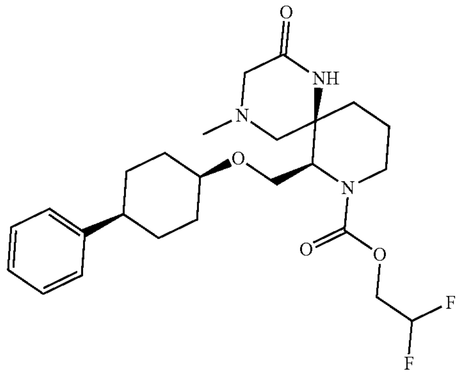 [SMILES: CN1CC(=O)N[C@]2(CCCN(C(=O)OCC(F)F)[C@H]2CO[C@H]2CC[C@@H](c3ccccc3)CC2)C1]
56-C
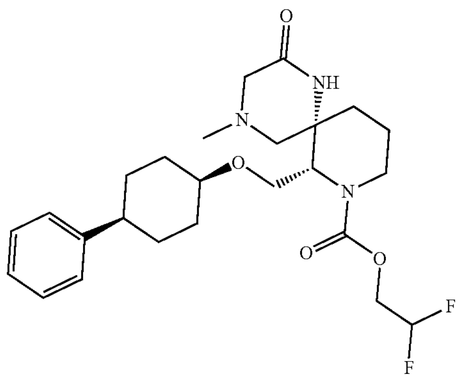 [SMILES: CN1CC(=O)N[C@@]2(CCCN(C(=O)OCC(F)F)[C@@H]2CO[C@H]2CC[C@@H](c3ccccc3)CC2)C1]

TABLE 1-continued
Compounds
57-A
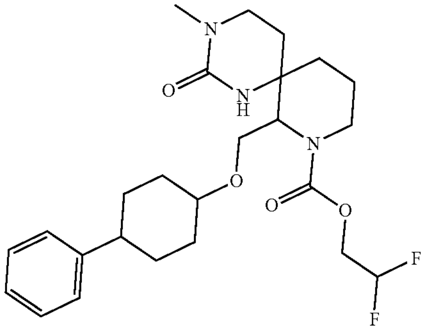 [SMILES: CN1CCC2(CCCN(C(=O)OCC(F)F)C2COC2CCC(c3ccccc3)CC2)NC1=O]
57
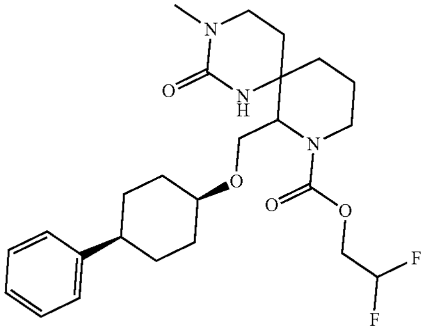 [SMILES: CN1CCC2(CCCN(C(=O)OCC(F)F)C2CO[C@H]2CC[C@@H](c3ccccc3)CC2)NC1=O]
57-B
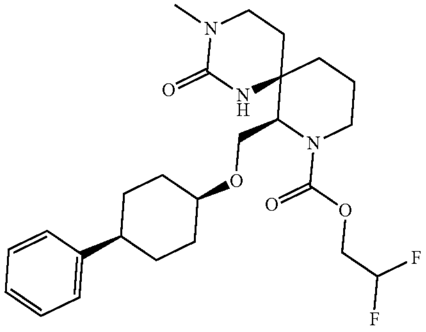 [SMILES: CN1CC[C@@]2(CCCN(C(=O)OCC(F)F)[C@H]2CO[C@H]2CC[C@@H](c3ccccc3)CC2)NC1=O]
57-C
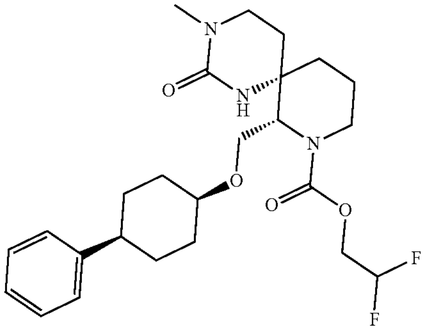 [SMILES: CN1CC[C@]2(CCCN(C(=O)OCC(F)F)[C@@H]2CO[C@H]2CC[C@@H](c3ccccc3)CC2)NC1=O]
58-A
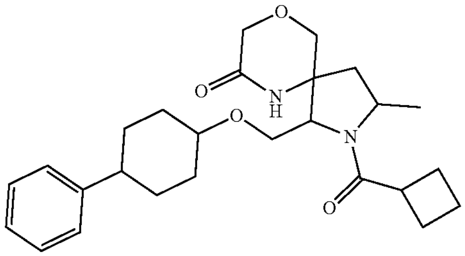 [SMILES: CC1CC2(COCC(=O)N2)C(COC2CCC(c3ccccc3)CC2)N1C(=O)C1CCC1]
TABLE 1-continued
Compounds
58
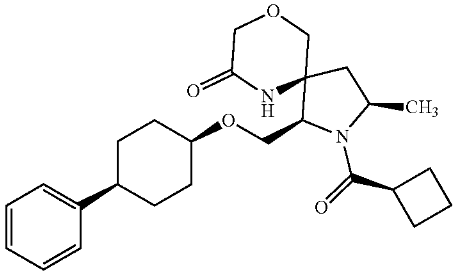
59-A
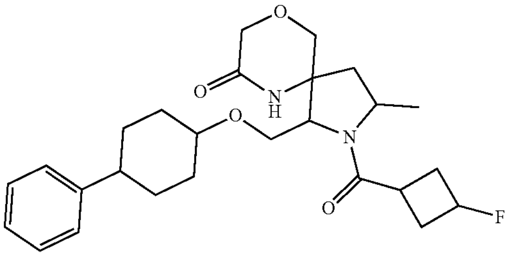 [SMILES: CC1CC2(COCC(=O)N2)C(COC2CCC(c3ccccc3)CC2)N1C(=O)C1CC(F)C1]
59
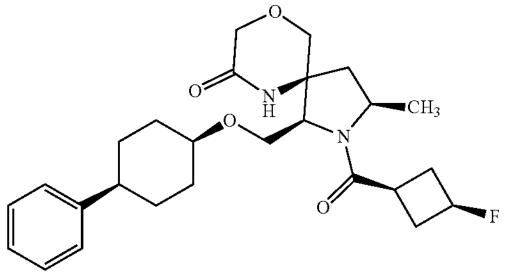 [SMILES: C[C@@H]1C[C@@]2(COCC(=O)N2)[C@H](CO[C@H]2CC[C@@H](c3ccccc3)CC2)N1C(=O)[C@H]1C[C@@H](F)C1]
60-A
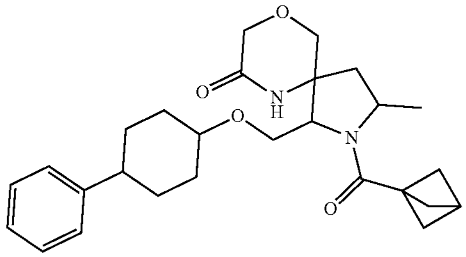 [SMILES: CC1CC2(COCC(=O)N2)C(COC2CCC(c3ccccc3)CC2)N1C(=O)C12CC(C1)C2]
60
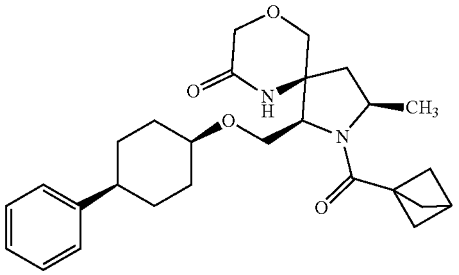 [SMILES: C[C@@H]1C[C@@]2(COCC(=O)N2)[C@H](CO[C@H]2CC[C@@H](c3ccccc3)CC2)N1C(=O)C12CC(C1)C2]

TABLE 1-continued
Compounds
61-A
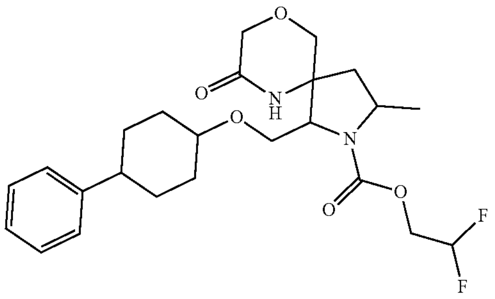 [SMILES: CC1CC2(COCC(=O)N2)C(COC2CCC(c3ccccc3)CC2)N1C(=O)OCC(F)F]
61
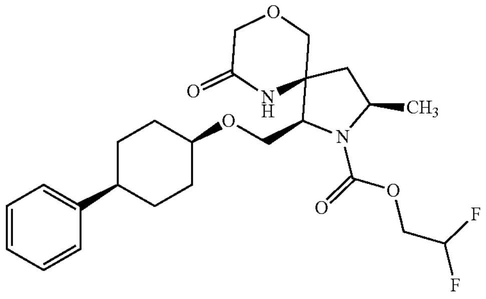 [SMILES: C[C@@H]1C[C@@]2(COCC(=O)N2)[C@H](CO[C@H]2CC[C@@H](c3ccccc3)CC2)N1C(=O)OCC(F)F]
62-A
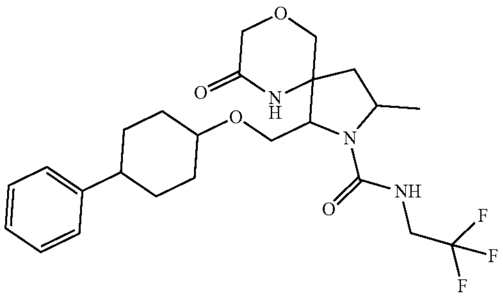 [SMILES: CC1CC2(COCC(=O)N2)C(COC2CCC(c3ccccc3)CC2)N1C(=O)NCC(F)(F)F]
62
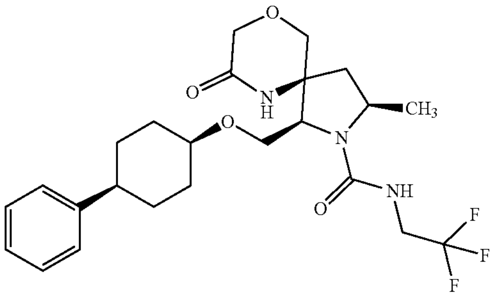 [SMILES: C[C@@H]1C[C@@]2(COCC(=O)N2)[C@H](CO[C@H]2CC[C@@H](c3ccccc3)CC2)N1C(=O)NCC(F)(F)F]
63-A
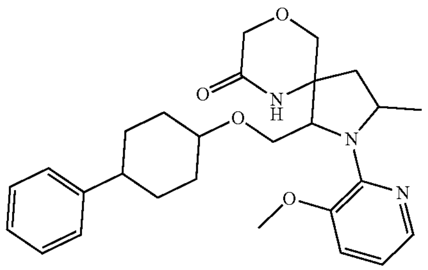 [SMILES: COc1cccnc1N1C(C)CC2(COCC(=O)N2)C1COC1CCC(c2ccccc2)CC1]
TABLE 1-continued
Compounds
63
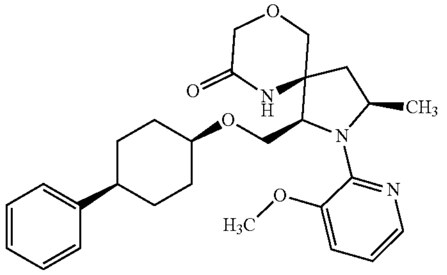 [SMILES: COc1cccnc1N1[C@H](C)C[C@@]2(COCC(=O)N2)[C@@H]1CO[C@H]1CC[C@@H](c2ccccc2)CC1]
64-A
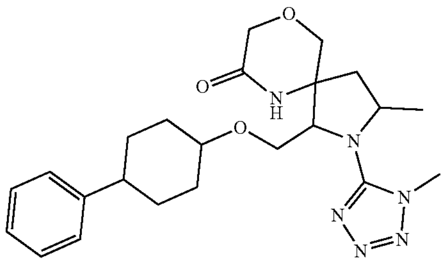 [SMILES: CC1CC2(COCC(=O)N2)C(COC2CCC(c3ccccc3)CC2)N1c1nnnn1C]
64
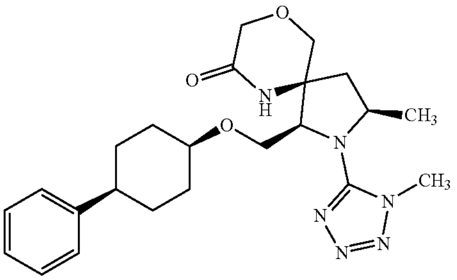 [SMILES: C[C@@H]1C[C@@]2(COCC(=O)N2)[C@H](CO[C@H]2CC[C@@H](c3ccccc3)CC2)N1c1nnnn1C]
65-A
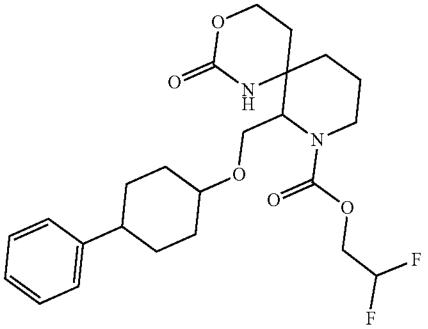 [SMILES: O=C1NC2(CCCN(C(=O)OCC(F)F)C2COC2CCC(c3ccccc3)CC2)CCO1]
65
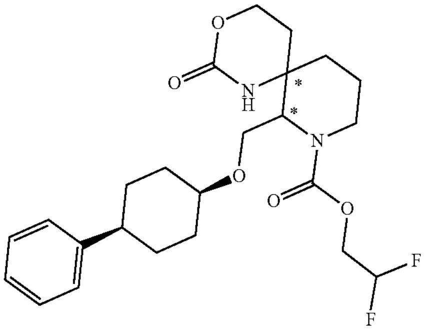
*cis-relative stereochemistry TABLE 1-continued
| Compounds |
|---|
65-B
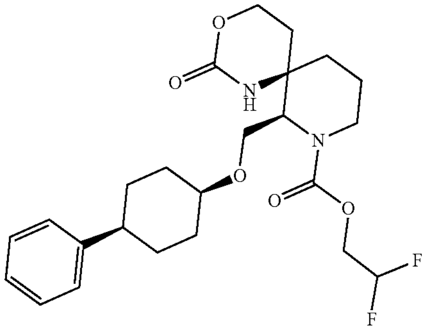 [SMILES: O=C1N[C@]2(CCCN(C(=O)OCC(F)F)[C@H]2CO[C@H]2CC[C@@H](c3ccccc3)CC2)CCO1]
65-C
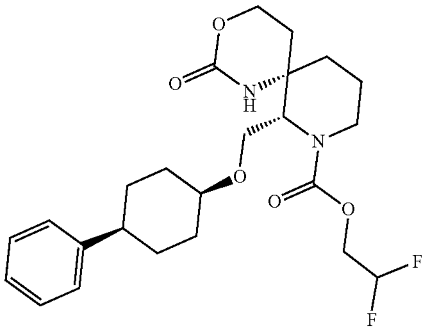 [SMILES: O=C1N[C@@]2(CCCN(C(=O)OCC(F)F)[C@@H]2CO[C@H]2CC[C@@H](c3ccccc3)CC2)CCO1]
66-A
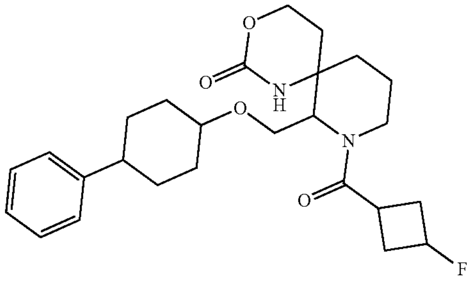 [SMILES: O=C1NC2(CCCN(C(=O)C3CC(F)C3)C2COC2CCC(c3ccccc3)CC2)CCO1]
66
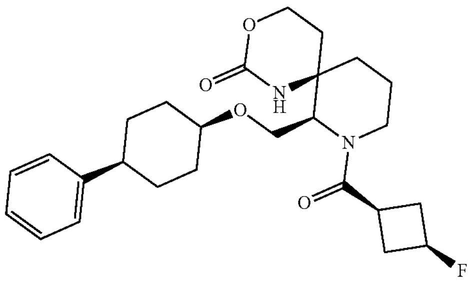 [SMILES: O=C1N[C@]2(CCCN(C(=O)[C@H]3C[C@@H](F)C3)[C@H]2CO[C@H]2CC[C@@H](c3ccccc3)CC2)CCO1]
67
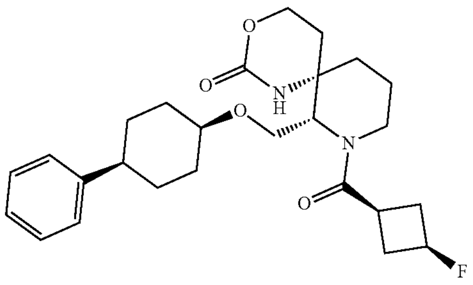 [SMILES: O=C1N[C@@]2(CCCN(C(=O)[C@H]3C[C@@H](F)C3)[C@@H]2CO[C@H]2CC[C@@H](c3ccccc3)CC2)CCO1]
TABLE 1-continued
| Compounds |
|---|
68-A
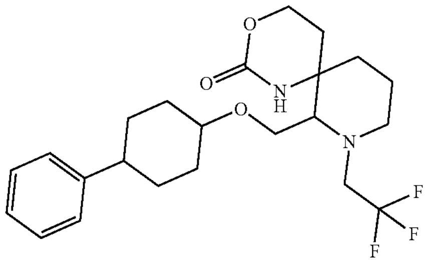 [SMILES: O=C1NC2(CCCN(CC(F)(F)F)C2COC2CCC(c3ccccc3)CC2)CCO1]
68
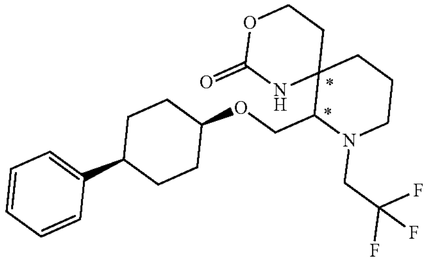
*cis-relative stereochemistry
68-B
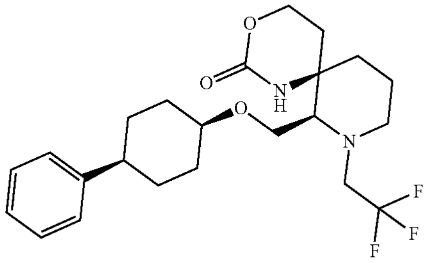 [SMILES: O=C1N[C@]2(CCCN(CC(F)(F)F)[C@H]2CO[C@H]2CC[C@@H](c3ccccc3)CC2)CCO1]
68-C
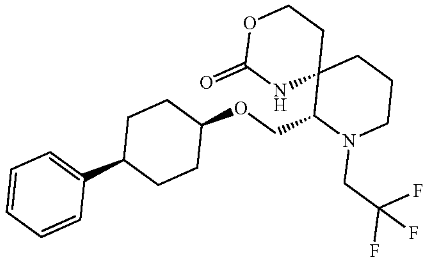 [SMILES: O=C1N[C@@]2(CCCN(CC(F)(F)F)[C@@H]2CO[C@H]2CC[C@@H](c3ccccc3)CC2)CCO1]
69-A
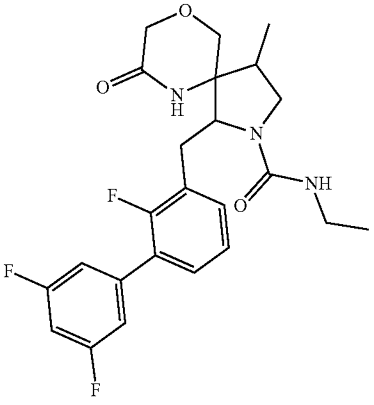 [SMILES: CCNC(=O)N1CC(C)C2(COCC(=O)N2)C1Cc1cccc(-c2cc(F)cc(F)c2)c1F]

TABLE 1-continued
| Compounds |
| --- |
| 69 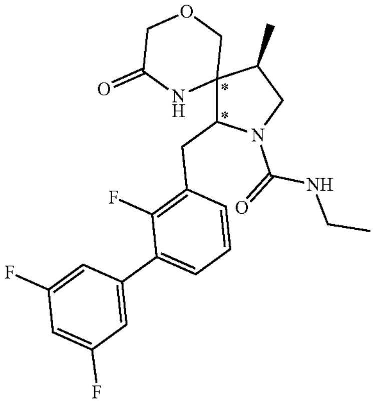 *cis-relative stereochemistry |
| 69-B 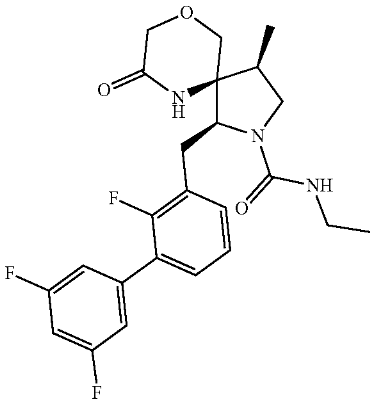 [SMILES: CCNC(=O)N1C[C@H](C)[C@@]2(COCC(=O)N2)[C@@H]1Cc1cccc(-c2cc(F)cc(F)c2)c1F] |
| 69-C 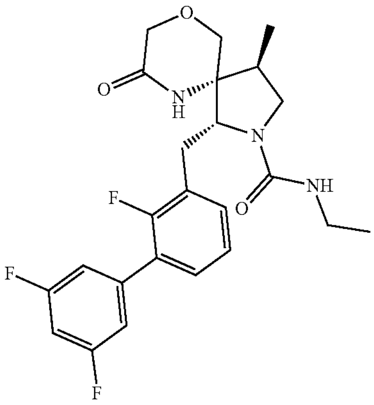 [SMILES: CCNC(=O)N1C[C@H](C)[C@]2(COCC(=O)N2)[C@H]1Cc1cccc(-c2cc(F)cc(F)c2)c1F] |
TABLE 1-continued
| Compounds |
| --- |
| 70 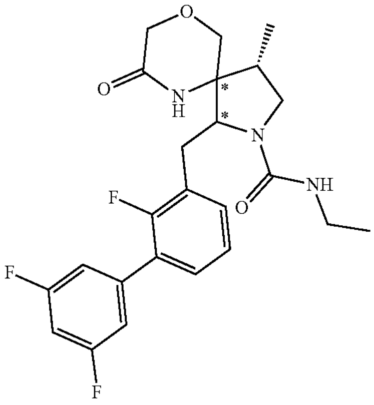 *cis-relative stereochemistry |
| 70-B 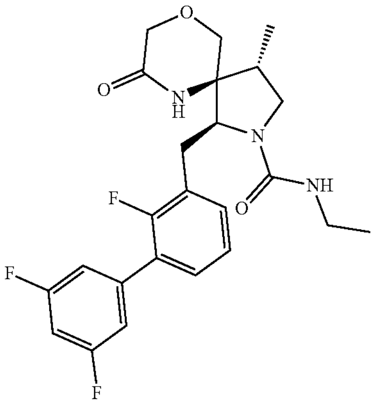 [SMILES: CCNC(=O)N1C[C@@H](C)[C@@]2(COCC(=O)N2)[C@@H]1Cc1cccc(-c2cc(F)cc(F)c2)c1F] |
| 70-C 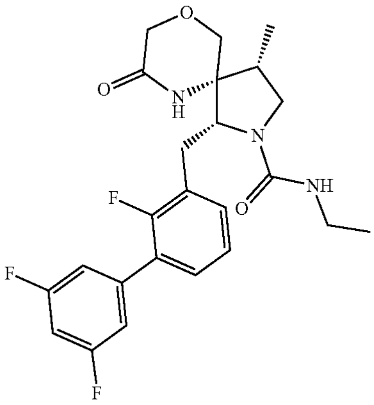 [SMILES: CCNC(=O)N1C[C@@H](C)[C@]2(COCC(=O)N2)[C@H]1Cc1cccc(-c2cc(F)cc(F)c2)c1F] |

TABLE 1-continued
Compounds
71-A
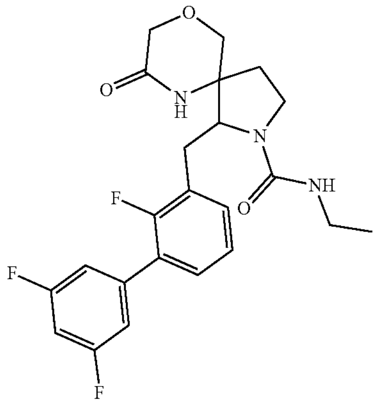 [SMILES: CCNC(=O)N1CCC2(COCC(=O)N2)C1Cc1cccc(-c2cc(F)cc(F)c2)c1F]
71
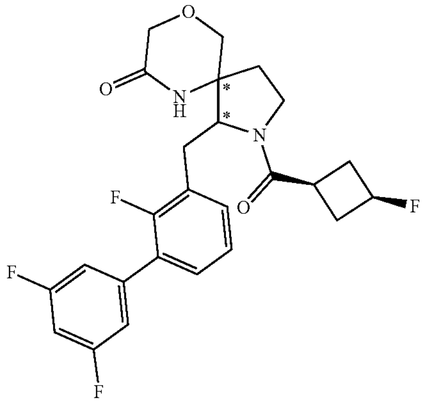
*cis-relative stereochemistry
72
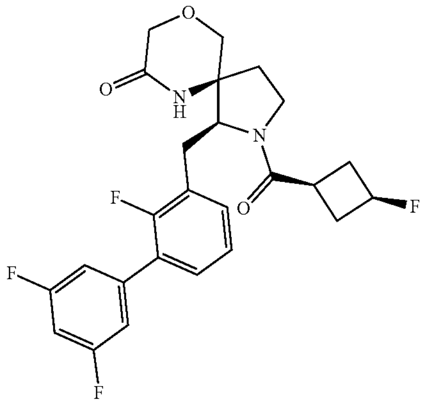 [SMILES: O=C1COC[C@@]2(CCN(C(=O)[C@H]3C[C@@H](F)C3)[C@H]2Cc2cccc(-c3cc(F)cc(F)c3)c2F)N1]
TABLE 1-continued
Compounds
73
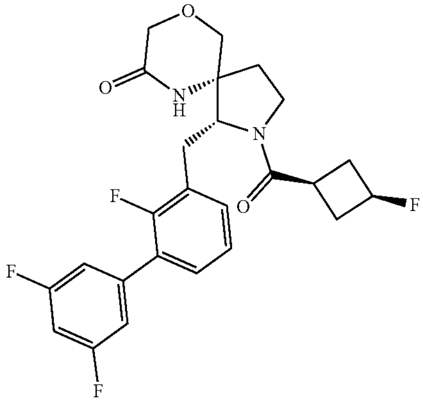 [SMILES: O=C1COC[C@]2(CCN(C(=O)[C@H]3C[C@@H](F)C3)[C@@H]2Cc2cccc(-c3cc(F)cc(F)c3)c2F)N1]
74-A
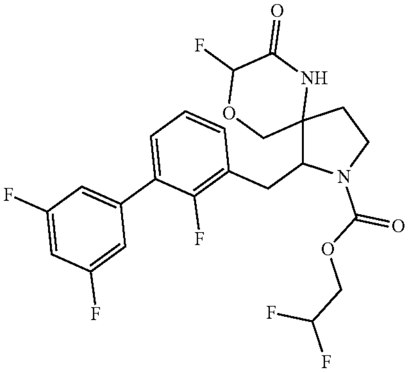 [SMILES: O=C1NC2(CCN(C(=O)OCC(F)F)C2Cc2cccc(-c3cc(F)cc(F)c3)c2F)COC1F]
74
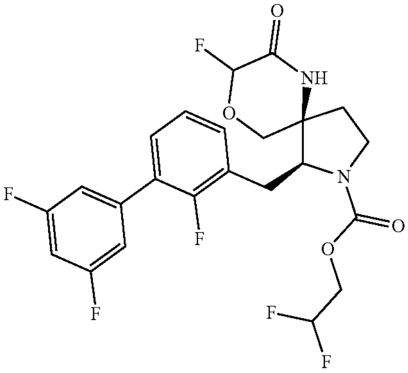
75
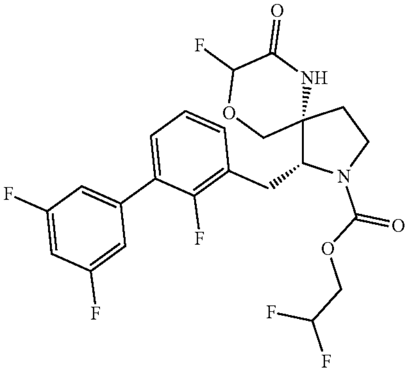

| Compounds |
|---|
| 76-A 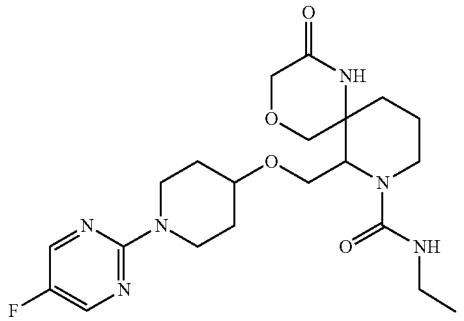 [SMILES: CCNC(=O)N1CCCC2(COCC(=O)N2)C1COC1CCN(c2ncc(F)cn2)CC1] |
| 76 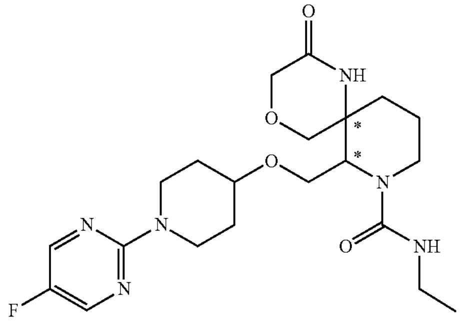 *cis-relative stereochemistry |
| 76-B 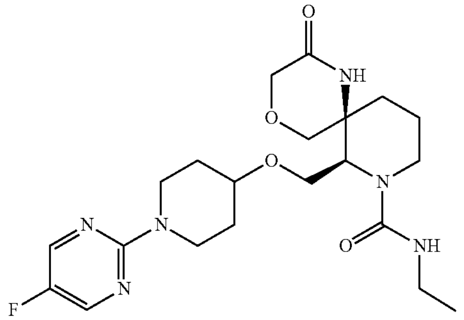 [SMILES: CCNC(=O)N1CCC[C@@]2(COCC(=O)N2)[C@@H]1COC1CCN(c2ncc(F)cn2)CC1] |
| 76-C 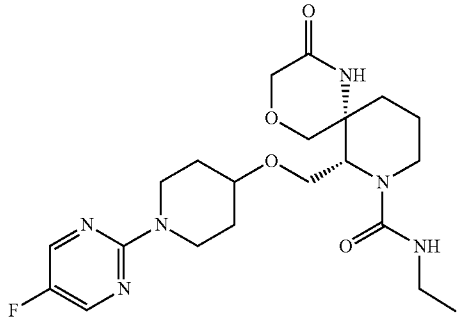 [SMILES: CCNC(=O)N1CCC[C@]2(COCC(=O)N2)[C@H]1COC1CCN(c2ncc(F)cn2)CC1] |
| Compounds |
|---|
| 77-A 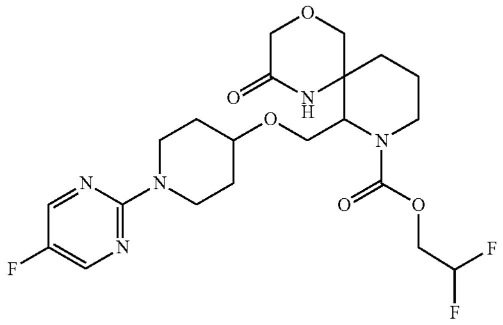 [SMILES: O=C1COCC2(CCCN(C(=O)OCC(F)F)C2COC2CCN(c3ncc(F)cn3)CC2)N1] |
| 77 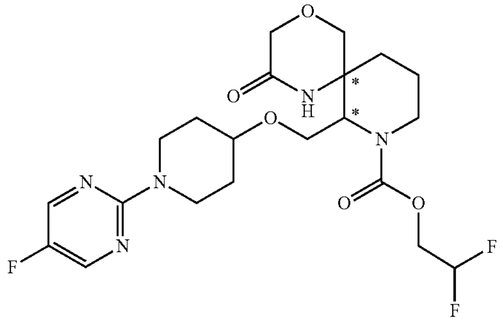 *cis-relative stereochemistry |
| 77-B 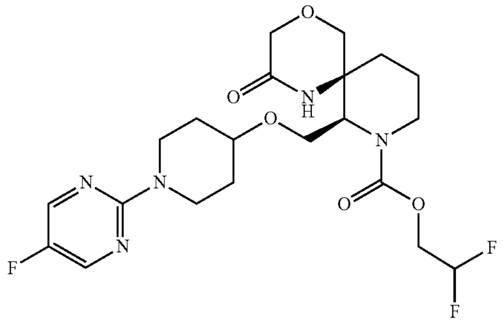 [SMILES: O=C1COC[C@@]2(CCCN(C(=O)OCC(F)F)[C@H]2COC2CCN(c3ncc(F)cn3)CC2)N1] |
| 77-C 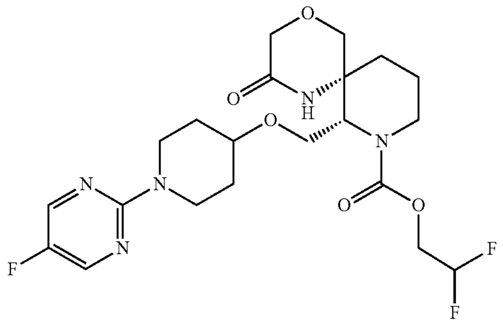 [SMILES: O=C1COC[C@]2(CCCN(C(=O)OCC(F)F)[C@@H]2COC2CCN(c3ncc(F)cn3)CC2)N1] |

TABLE 1-continued
Compounds
78-A
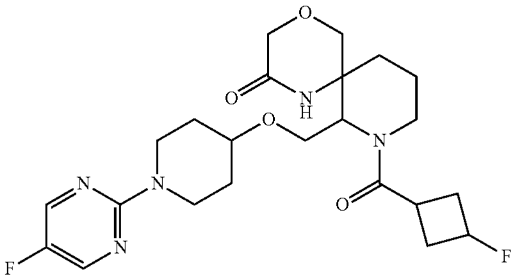 [SMILES: O=C1COCC2(CCCN(C(=O)C3CC(F)C3)C2COC2CCN(c3ncc(F)cn3)CC2)N1]
78
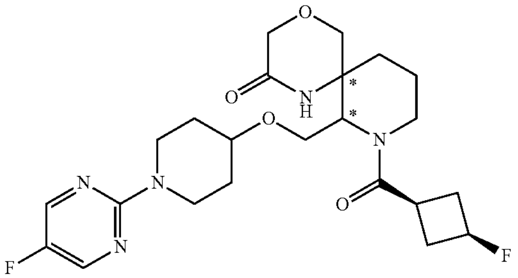
*cis-relative stereochemistry
78-B
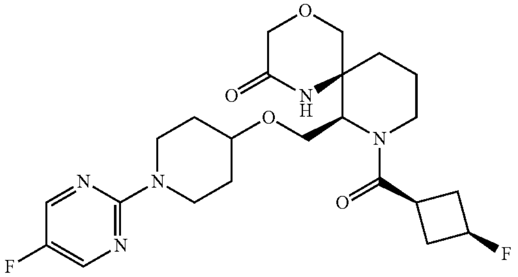 [SMILES: O=C1COC[C@@]2(CCCN(C(=O)[C@H]3C[C@@H](F)C3)[C@H]2COC2CCN(c3ncc(F)cn3)CC2)N1]
78-C
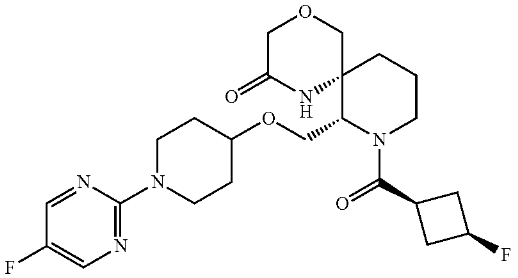 [SMILES: O=C1COC[C@]2(CCCN(C(=O)[C@H]3C[C@@H](F)C3)[C@@H]2COC2CCN(c3ncc(F)cn3)CC2)N1]
79-A
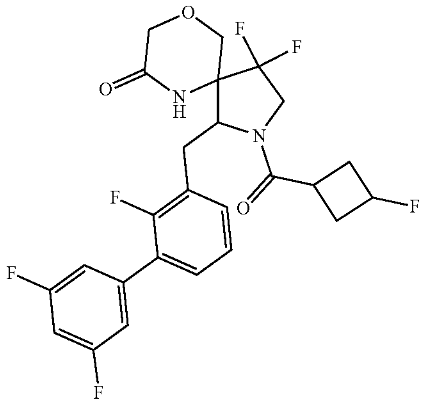 [SMILES: O=C1COCC2(N1)C(Cc1cccc(-c3cc(F)cc(F)c3)c1F)N(C(=O)C1CC(F)C1)CC2(F)F]
TABLE 1-continued
Compounds
79
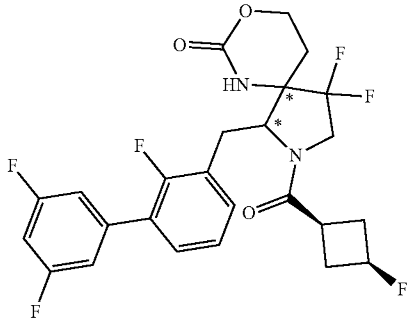
*trans-relative stereochemistry
79-B
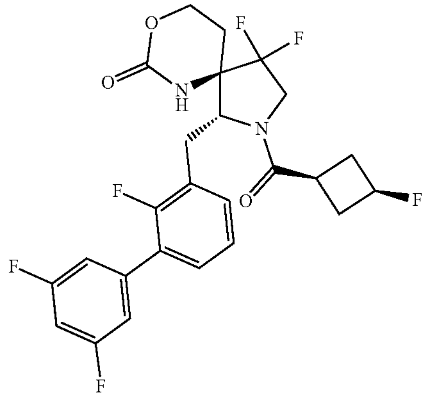 [SMILES: O=C1N[C@]2(CCO1)[C@@H](Cc1cccc(-c3cc(F)cc(F)c3)c1F)N(C(=O)[C@H]1C[C@@H](F)C1)CC2(F)F]
79-C
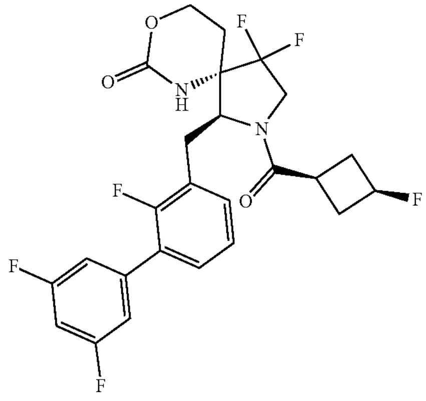 [SMILES: O=C1N[C@@]2(CCO1)[C@H](Cc1cccc(-c3cc(F)cc(F)c3)c1F)N(C(=O)[C@H]1C[C@@H](F)C1)CC2(F)F]
79-D
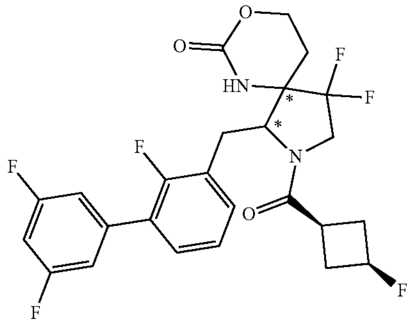
*cis-relative stereochemistry TABLE 1-continued
Compounds
79-E
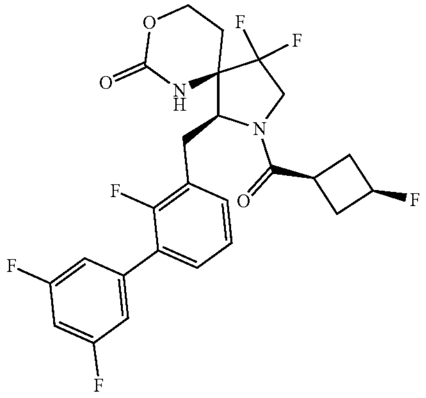 [SMILES: O=C1N[C@]2(CCO1)[C@H](Cc1cccc(-c3cc(F)cc(F)c3)c1F)N(C(=O)[C@H]1C[C@@H](F)C1)CC2(F)F]
79-F
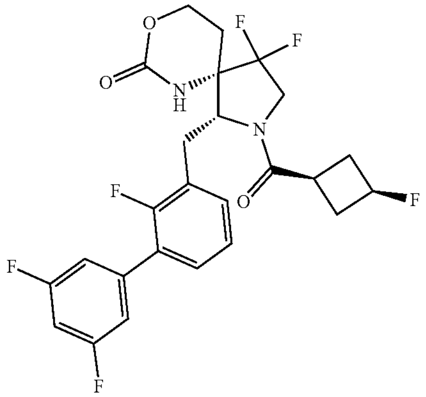 [SMILES: O=C1N[C@@]2(CCO1)[C@@H](Cc1cccc(-c3cc(F)cc(F)c3)c1F)N(C(=O)[C@H]1C[C@@H](F)C1)CC2(F)F]
80-A
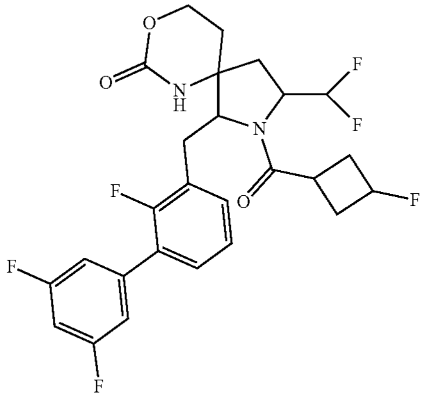 [SMILES: O=C1NC2(CCO1)CC(C(F)F)N(C(=O)C1CC(F)C1)C2Cc1cccc(-c2cc(F)cc(F)c2)c1F]
80
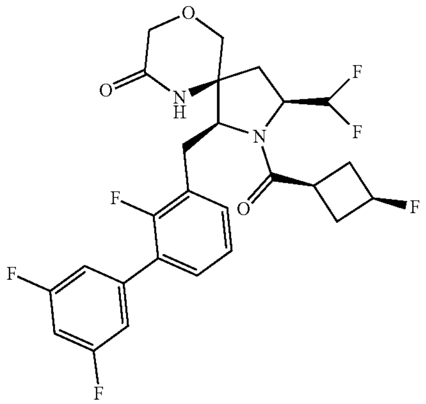 [SMILES: O=C1COC[C@@]2(C[C@@H](C(F)F)N(C(=O)[C@H]3C[C@@H](F)C3)[C@H]2Cc2cccc(-c3cc(F)cc(F)c3)c2F)N1]
TABLE 1-continued
Compounds
81-A
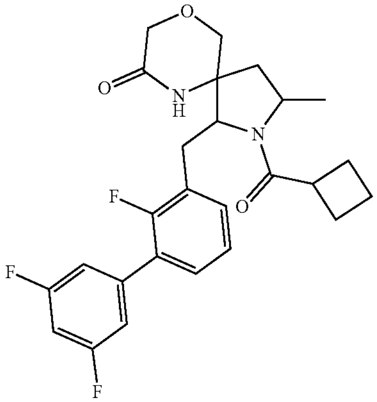 [SMILES: CC1CC2(COCC(=O)N2)C(Cc2cccc(-c3cc(F)cc(F)c3)c2F)N1C(=O)C1CCC1]
81
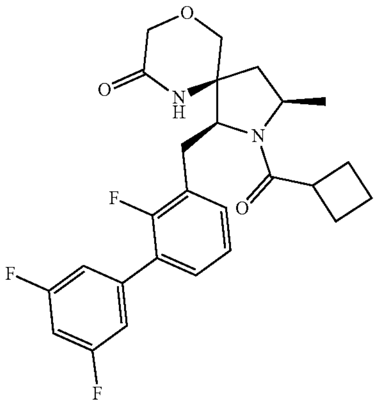 [SMILES: C[C@@H]1C[C@@]2(COCC(=O)N2)[C@H](Cc2cccc(-c3cc(F)cc(F)c3)c2F)N1C(=O)C1CCC1]
82-A
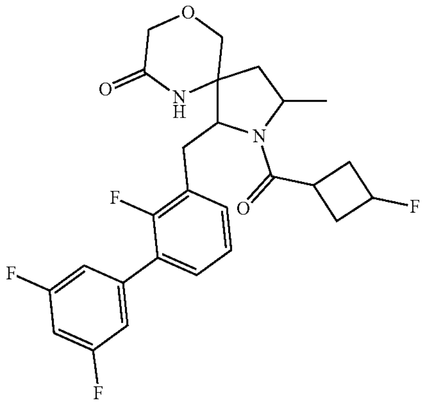 [SMILES: CC1CC2(COCC(=O)N2)C(Cc2cccc(-c3cc(F)cc(F)c3)c2F)N1C(=O)C1CC(F)C1]

TABLE 1-continued
| Compounds |
|---|
| 82 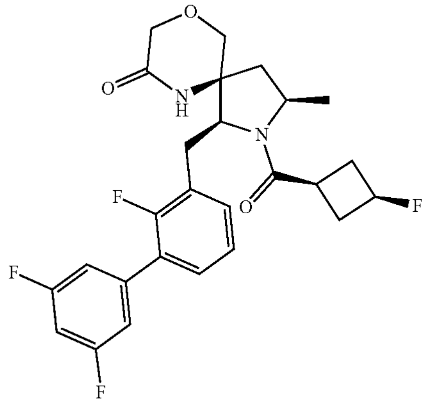 [SMILES: C[C@@H]1C[C@@]2(COCC(=O)N2)[C@H](Cc2cccc(-c3cc(F)cc(F)c3)c2F)N1C(=O)[C@H]1C[C@@H](F)C1] |
| 83-A 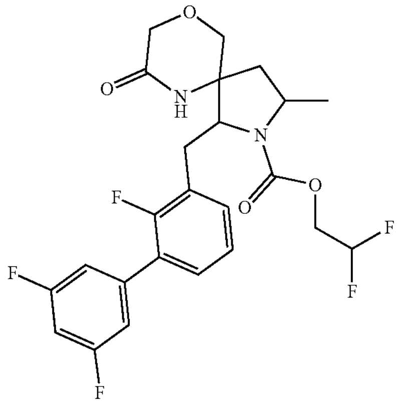 [SMILES: CC1CC2(COCC(=O)N2)C(Cc2cccc(-c3cc(F)cc(F)c3)c2F)N1C(=O)OCC(F)F] |
| 83 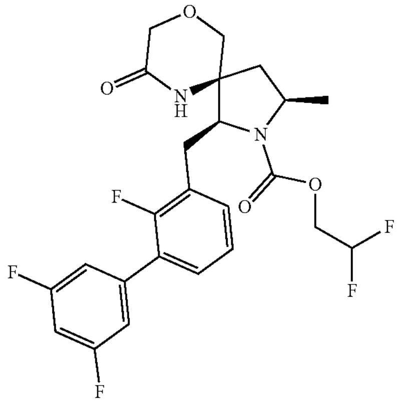 [SMILES: C[C@@H]1C[C@@]2(COCC(=O)N2)[C@H](Cc2cccc(-c3cc(F)cc(F)c3)c2F)N1C(=O)OCC(F)F] |
| 84-A 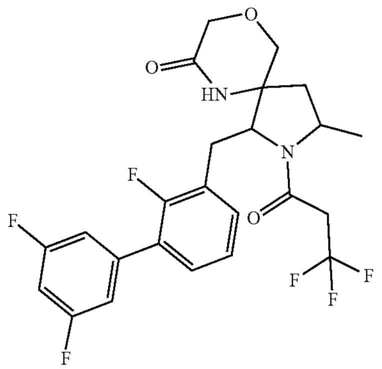 [SMILES: CC1CC2(COCC(=O)N2)C(Cc2cccc(-c3cc(F)cc(F)c3)c2F)N1C(=O)CC(F)(F)F] |
TABLE 1-continued
| Compounds |
|---|
| 84 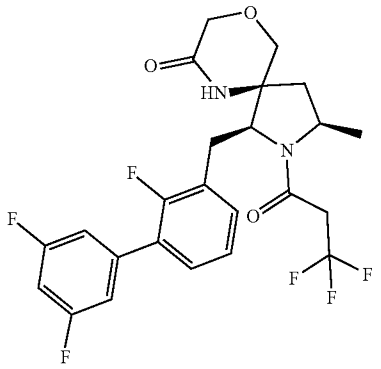 [SMILES: C[C@@H]1C[C@@]2(COCC(=O)N2)[C@H](Cc2cccc(-c3cc(F)cc(F)c3)c2F)N1C(=O)CC(F)(F)F] |
| 85-A 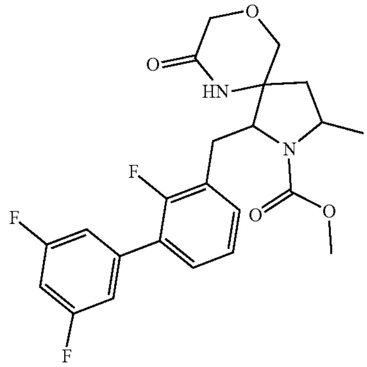 [SMILES: COC(=O)N1C(C)CC2(COCC(=O)N2)C1Cc1cccc(-c2cc(F)cc(F)c2)c1F] |
| 85 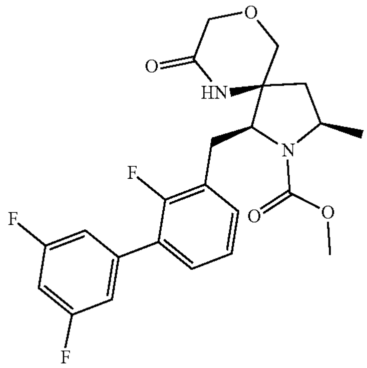 [SMILES: COC(=O)N1[C@H](C)C[C@@]2(COCC(=O)N2)[C@@H]1Cc1cccc(-c2cc(F)cc(F)c2)c1F] |
| 86-A 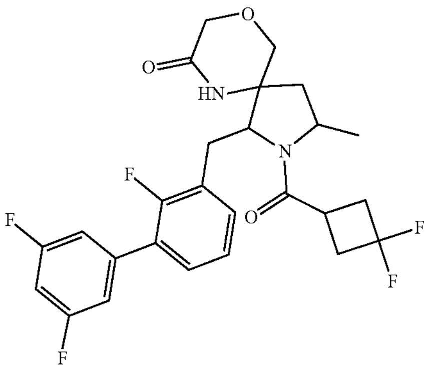 [SMILES: CC1CC2(COCC(=O)N2)C(Cc2cccc(-c3cc(F)cc(F)c3)c2F)N1C(=O)C1CC(F)(F)C1] |

TABLE 1-continued
Compounds
86
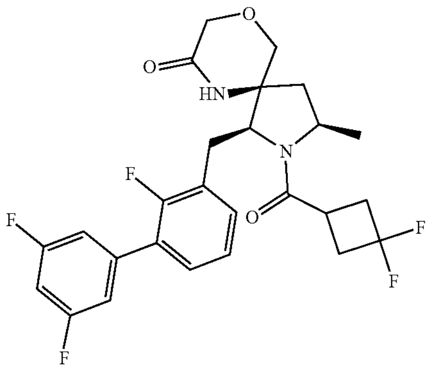 [SMILES: C[C@@H]1C[C@@]2(COCC(=O)N2)[C@H](Cc2cccc(-c3cc(F)cc(F)c3)c2F)N1C(=O)C1CC(F)(F)C1]
87-A
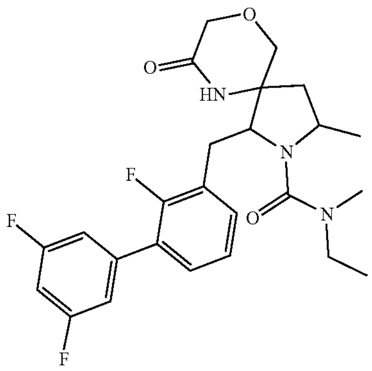 [SMILES: CCN(C)C(=O)N1C(C)CC2(COCC(=O)N2)C1Cc1cccc(-c2cc(F)cc(F)c2)c1F]
87
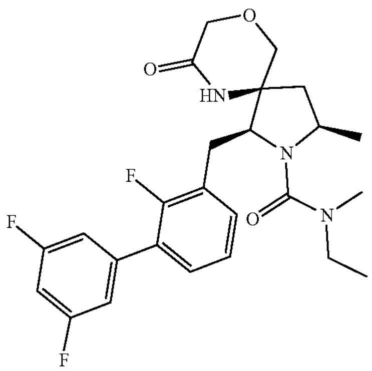 [SMILES: CCN(C)C(=O)N1[C@H](C)C[C@@]2(COCC(=O)N2)[C@@H]1Cc1cccc(-c2cc(F)cc(F)c2)c1F]
88-A
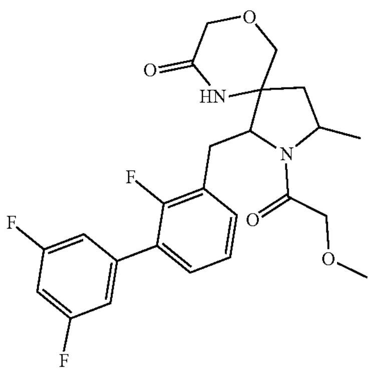 [SMILES: COCC(=O)N1C(C)CC2(COCC(=O)N2)C1Cc1cccc(-c2cc(F)cc(F)c2)c1F]
TABLE 1-continued
Compounds
88
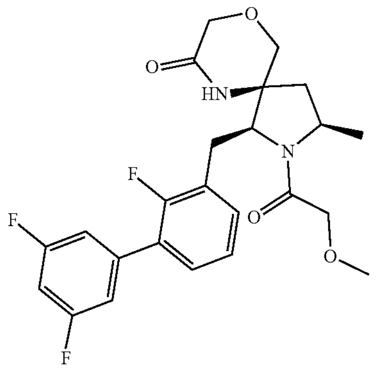 [SMILES: COCC(=O)N1[C@H](C)C[C@@]2(COCC(=O)N2)[C@@H]1Cc1cccc(-c2cc(F)cc(F)c2)c1F]
89-A
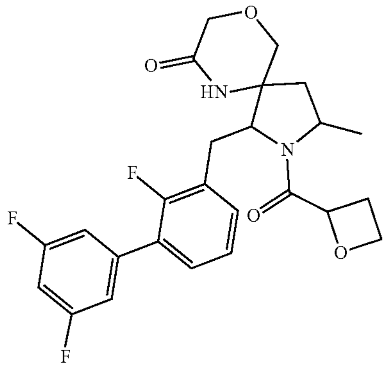 [SMILES: CC1CC2(COCC(=O)N2)C(Cc2cccc(-c3cc(F)cc(F)c3)c2F)N1C(=O)C1CCO1]
89
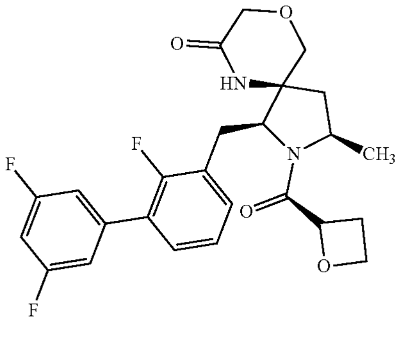
90-A
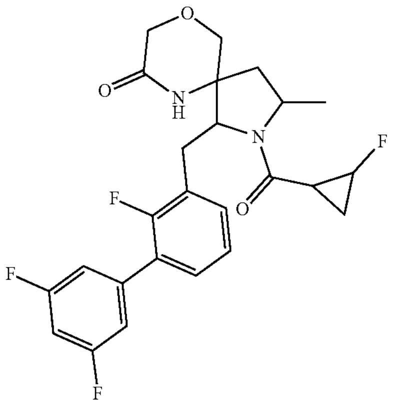 [SMILES: CC1CC2(COCC(=O)N2)C(Cc2cccc(-c3cc(F)cc(F)c3)c2F)N1C(=O)C1CC1F]

TABLE 1-continued
| Compounds |
| --- |
90-i
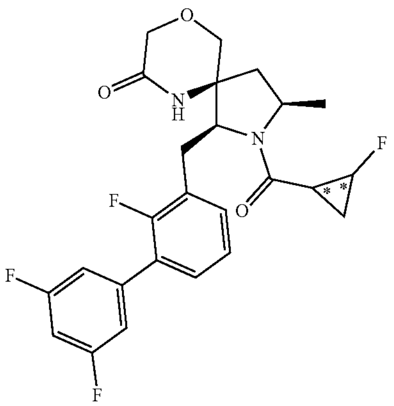
*cis-relative stereochemistry
90
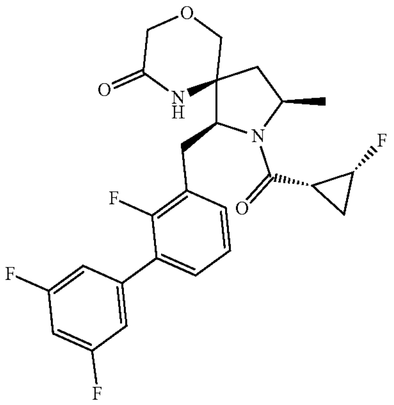 [SMILES: C[C@@H]1C[C@@]2(COCC(=O)N2)[C@H](Cc2cccc(-c3cc(F)cc(F)c3)c2F)N1C(=O)[C@H]1C[C@H]1F]
91
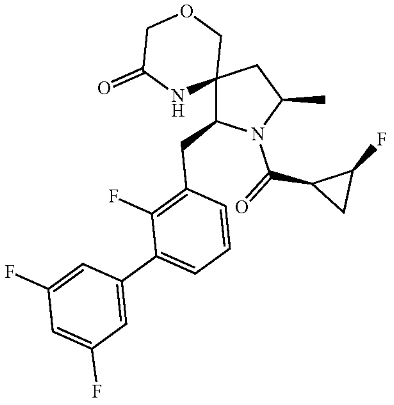 [SMILES: C[C@@H]1C[C@@]2(COCC(=O)N2)[C@H](Cc2cccc(-c3cc(F)cc(F)c3)c2F)N1C(=O)[C@@H]1C[C@@H]1F]
TABLE 1-continued
| Compounds |
| --- |
92
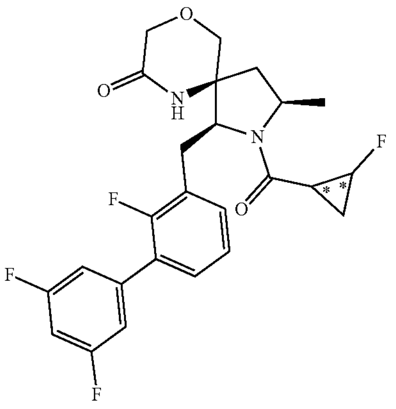
*trans-relative stereochemistry
92-B
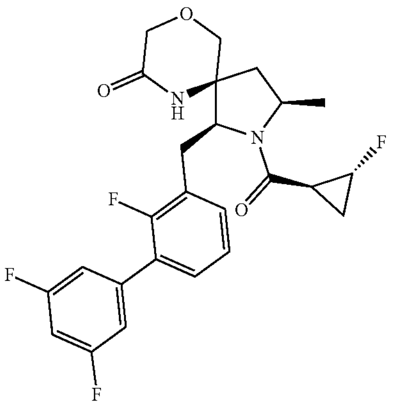 [SMILES: C[C@@H]1C[C@@]2(COCC(=O)N2)[C@H](Cc2cccc(-c3cc(F)cc(F)c3)c2F)N1C(=O)[C@@H]1C[C@H]1F]
92-C
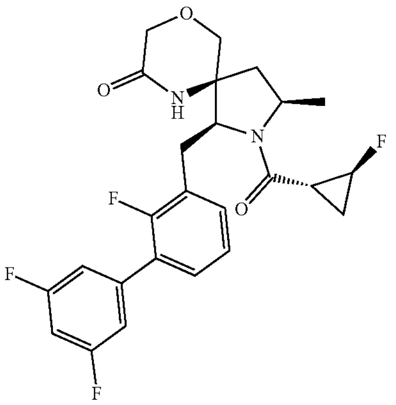 [SMILES: C[C@@H]1C[C@@]2(COCC(=O)N2)[C@H](Cc2cccc(-c3cc(F)cc(F)c3)c2F)N1C(=O)[C@H]1C[C@@H]1F]
93-A
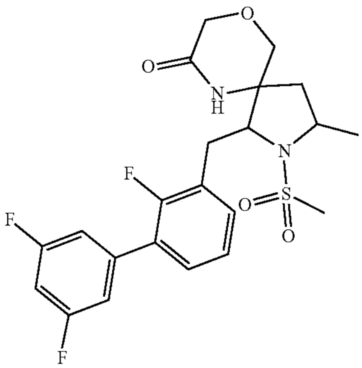 [SMILES: CC1CC2(COCC(=O)N2)C(Cc2cccc(-c3cc(F)cc(F)c3)c2F)N1S(C)(=O)=O]

TABLE 1-continued

| Compounds |
|---|
| 93 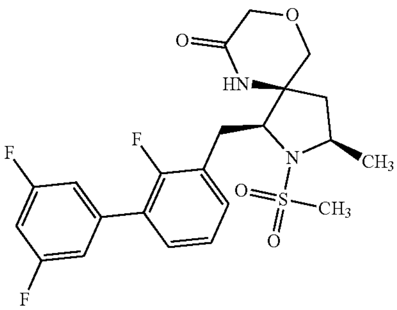 [SMILES: C[C@@H]1C[C@@]2(COCC(=O)N2)[C@H](Cc2cccc(-c3cc(F)cc(F)c3)c2F)N1S(C)(=O)=O] |

Compositions

The present disclosure provides pharmaceutical compositions for modulating orexin receptor (e.g., orexin type 2 receptor) in a subject. In some embodiments, a pharmaceutical composition comprises one or more compounds of the present disclosure ((e.g., a compound of Formula (I), (II), (III), (IV), (V-A), (V-B), (V-C), (VI-A), (VI-B), (VI-C), or Table 1) or a pharmaceutically acceptable salt thereof.

In some embodiments of the present disclosure, a pharmaceutical composition comprises a therapeutically effective amounts of one or more compounds of the present disclosure ((e.g., a compound of Formula (I), (II), (III), (IV), (V-A), (V-B), (V-C), (VI-A), (VI-B), (VI-C), or Table 1) or a pharmaceutically acceptable salt thereof.

In some embodiments, a pharmaceutical composition, as described herein, comprises one or more compounds selected from Table 1, or a pharmaceutically acceptable salt thereof or stereoisomer thereof.

In embodiments, a pharmaceutical composition, as described herein comprises one or more compounds selected from compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90-i, 90, 91, 92, or 93. In embodiments, a pharmaceutical composition, as described herein comprises one or more compounds selected from compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In some embodiments, a pharmaceutical composition, as described herein, comprises one or more compounds selected from Table 1, or a pharmaceutically acceptable salt thereof.

In embodiments, a pharmaceutical composition, as described herein comprises one or more compounds selected from compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90-i, 90, 91, 92, or 93, or a pharmaceutically acceptable salt thereof. In embodiments, a pharmaceutical composition, as described herein comprises one or more compounds selected from compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32, or a pharmaceutically acceptable salt thereof.

In some embodiments of the present disclosure, a pharmaceutical composition comprising one or more compounds of the present disclosure (e.g., a compound of Formula (I), (II), (III), (IV), (V-A), (V-B), (V-C), (VI-A), (VI-B), (VI-C), or Table 1) or a pharmaceutically acceptable salt thereof, and a pharmaceutically acceptable excipient or adjuvant is provided. The pharmaceutically acceptable excipients and adjuvants are added to the composition or formulation for a variety of purposes. In some embodiments, a pharmaceutical composition comprising one or more compounds disclosed herein, or a pharmaceutically acceptable salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

Generally, the compounds of the present disclosure are administered in a therapeutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

Methods of Treatment

The compounds of the present disclosure find use in any number of methods. For example, in some embodiments the compounds are useful in methods for modulating an orexin receptor, e.g., orexin type 2 receptor. Accordingly, in some embodiments, the present disclosure provides the use of any one of the foregoing compounds of Formula (I), (II), (III), (IV), (V-A), (V-B), (V-C), (VI-A), (VI-B), (VI-C), or Table 1 or a pharmaceutically acceptable salt thereof, for modulating orexin receptor (e.g., orexin type 2 receptor) activity. For example in some embodiments, modulating orexin receptor (e.g., orexin type 2 receptor) activity is in a mammalian cell. Modulating orexin receptor (e.g., orexin type 2 receptor) activity can be in a subject in need thereof (e.g., a mammalian subject, such as a human) and for treatment of any of the described conditions or diseases.

In some embodiments, the modulating orexin receptor (e.g., orexin type 2 receptor) activity is binding. In some embodiments, the modulating orexin receptor (e.g., orexin type 2 receptor) activity is agonizing or stimulating the orexin receptor.

In some embodiments, the present disclosure provides methods of treating a disease or disorder that is treatable by administration of an Orexin agonist, the method comprising administering a therapeutically effective amount of one or more compounds of the present disclosure (e.g., compounds of Formula (I), (II), (III), (IV), (V-A), (V-B), (V-C), (VI-A), (VI-B), (VI-C), or Table 1).

In some embodiments, the compounds of the present disclosure are used for treating, preventing, ameliorating, controlling or reducing the risk of a variety of disorders associated with orexin receptors, including one or more of the following conditions or diseases: narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, hypersomnia associated with sleep apnea, nocturnal myoclonus, disturbances of consciousness, such as coma, REM sleep interruptions, jet-lag, excessive daytime sleepiness, shift workers' sleep disturbances, dyssomnias, sleep disorders, sleep disturbances, hypersomnia associated with depression, emotional/mood disorders, drug use, Alzheimer's disease or cognitive impairment, Parkinson's disease, Guillain-Barre syndrome, Kleine Levin syndrome, and sleep disorders which accompany aging, muscular dystrophies, immune-mediated diseases; Alzheimer's sundowning; conditions associated with circadian rhythmicity as well as mental and physical disorders associated with travel across time zones and with rotating shift-work schedules; fibromyalgia; cardiac failure; diseases related to bone loss; sepsis; syndromes which are manifested by non-restorative sleep and muscle pain or sleep apnea which is associated with respiratory disturbances during sleep; conditions which result from a diminished quality of sleep; and other diseases related to general orexin system dysfunction. In some embodiments, compounds of the present invention are useful for treating, preventing, ameliorating, controlling or reducing the risk of a variety of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer, obesity, insulin resistance syndrome, cardiac failure, diseases related to bone loss, sepsis, disturbance of consciousness such as coma and the like, side effects and complications due to anesthesia, and the like, or anesthetic antagonist.

In some embodiments, a compound of the present disclosure (e.g., a compound of Formula (I), (II), (III), (IV), (V-A), (V-B), (V-C), (VI-A), (VI-B), (VI-C), or Table 1), or a pharmaceutically acceptable salt thereof, are used to treat diseases or disorders or symptoms associated with excessive sleepiness in a subject in need thereof. In some embodiments, the excessive sleepiness is caused by any one of the following: insufficient quality or quantity of night time sleep; misalignments of the body's circadian pacemaker with the environment (e.g., caused by requirement to remain awake at night for employment such as shift work or personal obligations such as caretaker for sick, young or old family members), such as jet lag, shift work and other circadian rhythm sleep disorders; another underlying sleep disorder, such as narcolepsy (e.g., narcolepsy type 1, narcolepsy type 2, probable narcolepsy), sleep apnea (e.g., obstructive sleep apnea, obstructive sleep apnea with use of continuous positive airway pressure), idiopathic hypersomnia, idiopathic excessive sleepiness, and restless legs syndrome; disorders, such as clinical depression or atypical depression; tumors; head trauma; anemia; kidney failure; hypothyroidism; injury to the central nervous system; drug abuse: genetic vitamin deficiency, such as biotin deficiency; and particular classes of prescription and over the counter medication.

In some embodiments, a compound of the present disclosure (e.g., a compound of Formula (I), (II), (III), (IV), (V-A), (V-B), (V-C), (VI-A), (VI-B), (VI-C), or Table 1), or a pharmaceutically acceptable salt thereof, are used treat any one of the following: shift work disorder; shift work sleep disorder; and jet lag syndrome. In some embodiments, the methods and uses herein are used to treat any one of the following: narcolepsy type 1, narcolepsy type 2, probable narcolepsy, idiopathic hypersomnia, idiopathic excessive sleepiness, hypersomnia, hypersomnolence, sleep apnea syndrome (e.g., obstructive sleep apnea, obstructive sleep apnea with use of continuous positive airway pressure); or disturbance of consciousness such as coma and the like; and narcolepsy syndrome accompanied by narcolepsy-like symptoms; hypersomnolence or hypersomnia syndrome accompanied by daytime hypersomnia (e.g., Parkinson's disease, Guillain-Barre syndrome and Kleine Levin syndrome); excessive daytime sleepiness in Parkinson's disease, Prader-Willi Syndrome, depressions (depression, atypical depression, major depressive disorder, treatment resistant depression), ADHD, sleep apnea syndrome (e.g., obstructive sleep apnea, obstructive sleep apnea with use of continuous positive airway pressure) and other disorders of vigilance; residual excessive daytime sleepiness in sleep apnea syndrome (e.g., obstructive sleep apnea, obstructive sleep apnea with use of continuous positive airway pressure); and the like. Narcolepsy (e.g., narcolepsy type 1, narcolepsy type 2, probable narcolepsy) may be diagnosed by diagnostic criteria generally used in the field, e.g., The third edition of the International Classification of Sleep Disorders (ICSD-3) and the fifth edition of the Diagnostic and Statistical Manual of Mental Disorders (DSM-5). In some embodiments, the excessive sleepiness is excessive daytime sleepiness or excessive sleepiness during working hours, or excessive sleepiness or reduced quantity of sleep which is caused by requirement to remain awake at night for employment (e.g., shift work) or personal obligations (e.g., caretaker for sick, young or old family members). In some embodiments, the subject suffers from the diseases or disorders or symptoms associated with excessive sleepiness. In some embodiments, the subject is sleep-deprived subject, subject with excessive sleepiness, subject with disruptive regular sleep cycle, or subject with a need to decrease sleepiness. In some embodiments, the present disclosure provides methods for decreasing or treating excessive sleepiness. In some embodiments, the excessive sleepiness is caused by narcolepsy type 1, narcolepsy type 2 or idiopathic hypersomnia. In some embodiments, the excessive sleepiness is caused by obstructive sleep apnea despite the use of continuous positive airway pressure (CPAP). In some embodiments, methods for increasing wakefulness in a subject in need thereof is provided. In some embodiments, the orexin level in the subject is not compromised or partially compromised.

In some embodiments of the present disclosure, a method for the treatment of a sleep disorder (e.g., as disclosed herein) in a subject in need thereof is provided, comprising administering a compound of the present disclosure (e.g., a compound of Formula (I), (II), (III), (IV), (V-A), (V-B), (V-C), (VI-A), (VI-B), (VI-C), or Table 1), or a pharmaceutically acceptable salt thereof, to a subject in need thereof. In some embodiments, a compound of the present disclosure (e.g., a compound of Formula (I), (II), (III), (IV), (V-A), (V-B), (V-C), (VI-A), (VI-B), (VI-C), or Table 1), or a pharmaceutically acceptable salt thereof, is used to treat a subject with a sleep disorder, to treat a sleep disorder, or to treat the symptoms of a sleep disorder.

In some embodiments of the present disclosure, a method for the treatment of narcolepsy in a subject in need thereof is provided, comprising administering a compound of the present disclosure (e.g., a compound of Formula (I), (II), (III), (IV), (V-A), (V-B), (V-C), (VI-A), (VI-B), (VI-C), or Table 1), or a pharmaceutically acceptable salt thereof, to a subject in need thereof. In some embodiments, a compound of the present disclosure (e.g., a compound of Formula (I), (II), (III), (IV), (V-A), (V-B), (V-C), (VI-A), (VI-B), (VI-C), or Table 1), or a pharmaceutically acceptable salt thereof, is used to treat a subject with narcolepsy, to treat narcolepsy, or to treat the symptoms of narcolepsy.

In some embodiments of the present disclosure, a method for the treatment of idiopathic hypersomnia (IH) in a subject in need thereof is provided, comprising administering a compound of the present disclosure (e.g., a compound of Formula (I), (II), (III), (IV), (V-A), (V-B), (V-C), (VI-A), (VI-B), (VI-C), or Table 1), or a pharmaceutically acceptable salt thereof, to a subject in need thereof. In some embodiments, a compound of the present disclosure (e.g., a compound of Formula (I), (II), (III), (IV), (V-A), (V-B), (V-C), (VI-A), (VI-B), (VI-C), or Table 1), or a pharmaceutically acceptable salt thereof, is used to treat a subject with IH, to treat IH, or to treat the symptoms of IH.

Examples

The disclosure now being generally described, it will be more readily understood by reference to the following examples which are included merely for purposes of illustration of certain aspects and embodiments of the present disclosure and are not intended to limit the invention.

The compounds of the present disclosure can be synthesized using the methods as hereinafter described below, together with synthetic methods known in the art of synthetic organic chemistry or variations thereon as appreciated by those skilled in the art.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 44th. Ed., Wiley & Sons, 2006, as well as in Jerry March, *Advanced Organic Chemistry,* $4^{th}$ edition, John Wiley & Sons, publisher, New York, 1992 which are incorporated herein by reference in their entirety.

Abbreviations

- AcOH acetic acid
- DCM dichloromethane
- DIPEA N,N-diisopropylethylamine
- DMPU N,N'-dimethylpropyleneurea
- DMSO dimethyl sulfoxide
- EtOAc ethyl acetate
- IPA isopropyl alcohol
- LDA lithium diisopropylamide
- NMO N-methylmorpholine-N-Oxide
- TEA triethylamine
- TFA trifluoroacetic acid
- TFAA trifluoroacetic anhydride
- THF tetrahydrofuran General Synthesis In embodiments, compounds of the present invention can be synthesized using the following methods. General reaction conditions are given, and reaction products can be purified by generally known methods including silica gel chromatography using various organic solvents such as hexane, dichloromethane, ethyl acetate, methanol and the like or preparative reverse phase high pressure liquid chromatography.

In some embodiments, the compounds of the present disclosure are designated as "cis-relative" or "trans-relative".

As depicted below, the term "cis-relative" as used herein refers to compounds of the present disclosure (e.g., a Compound of Formula (I) or pharmaceutically acceptable salt thereof) where the amino and $-L_2-L_1-Y—Z$ substituents on the carbons labelled with an * in the A ring are on the same face of the A ring. It should be appreciated that the "cis-relative stereochemistry" at the A ring can be depicted herein in the following equivalent ways:

(I)

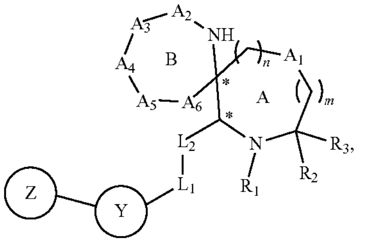

or cis-relative (I)

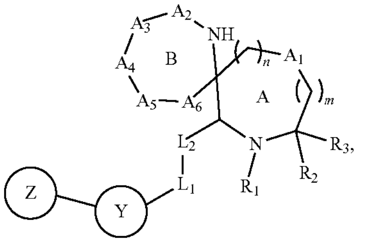

or cis-relative (I)

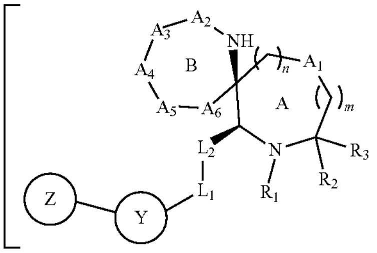

and (I)

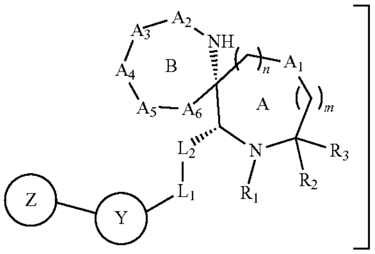

wherein n, m, $A_1$, $A_2$, $A_3$, $A_4$, $A_5$, $A_6$, $L_1$, $L_2$, $R_1$, $R_2$, $R_3$, Y and Z are defined herein.

As depicted below, the term "trans-relative" as used herein refers to compounds of the present disclosure (e.g., a Compound of Formula (I) or pharmaceutically acceptable salt thereof) where the amino and $-L_2-L_1-Y—Z$ substituents on the carbons labelled with an * in the A ring are on the opposite face of the A ring. It should be appreciated that the "trans-relative stereochemistry" at the A ring can be depicted herein in the following equivalent ways:

(I)

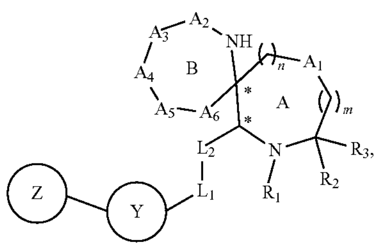

trans-relative or (I)

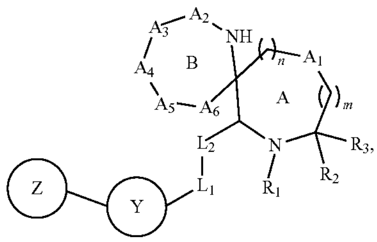

trans-relative or (I)

[

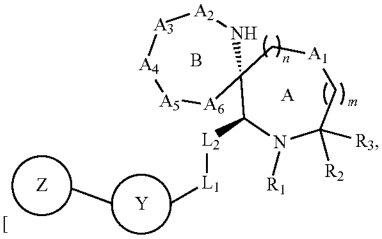

and (I)

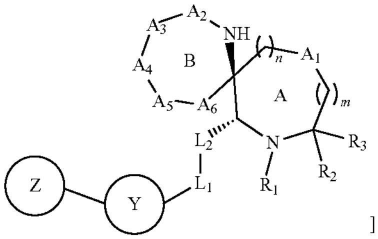

]

wherein n, m, $A_1$, $A_2$, $A_3$, $A_4$, $A_5$, $A_6$, $L_1$, $L_2$, $R_1$, $R_2$, $R_3$, Y and Z are defined herein.

Scheme 1: Representative synthesis of compounds of the disclosure

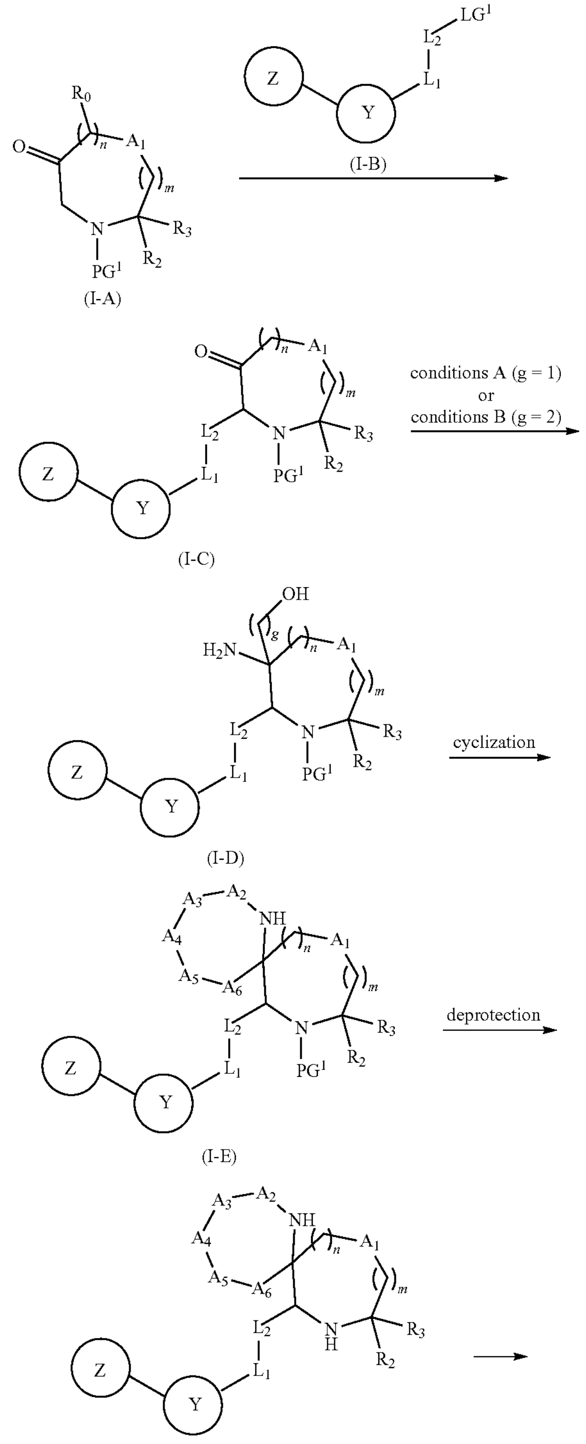

(I-A) (I-B) (I-C) (I-D) (I-E) (I-F)

-continued

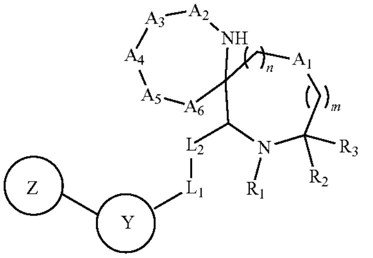

(I)

-continued

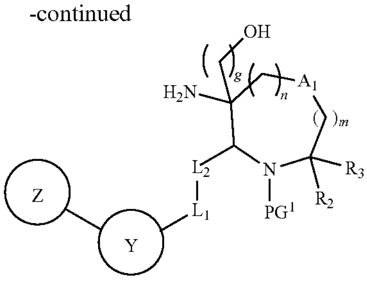

(I-D)

As shown in Scheme 1, compounds of Formula (I), wherein n, m, $A_1$, $A_2$, $A_3$, $A_4$, $A_5$, $A_6$, $L_1$, $L_2$, $R_1$, $R_2$, $R_3$, Y and Z are defined herein, can be prepared from compounds of Formula (I-A).

Compounds of Formula (I-A), wherein $R_0$ is —C(O)—O—$C_{1-6}$ alkyl, such as —C(O)—O—$CH_2CH_3$, or —C(O)—O—$CH_3$, $PG^1$ is a protecting group, such as tert-butyloxycarbonyl (Boc) or carboxybenzyl (Cbz), and n, m, $A_1$, $R_2$, and $R_3$ are defined herein, can be alkylated in a first step i) with compounds of Formula (I-B), wherein $L_1$, $L_2$, Y, and Z are defined herein and $LG^1$ is a leaving group such as —Cl, —Br, —I or a sulfonate (such as a mesylate or tosylate), in the presence of a base, such as a alkali metal amide base like LDA, and solvent (e.g., DMPU and/or an ether, such as THF) which is cooled (e.g., to about −50° C. or less, or about −78° C.). In a second step ii) the $R_0$ ester can then be saponified and decarboxylated by treating the intermediate with an alkali metal halide salt, such as sodium chloride, in the presence of an organic solvent, such as DMSO, and water and heated (e.g., at about or at least about 130° C.) to provide compounds of Formula (I-C).

Alternatively, compounds of Formula (I-A), wherein $R_0$ is H, $PG^1$ is a protecting group, such as tert-butyloxycarbonyl (Boc) or carboxybenzyl (Cbz), and n, m, $A_1$, $R_2$, and $R_3$ are defined herein, can be treated in a first step i) with a base, such as pyrrolidine in an aromatic solvent, such as toluene and heated (e.g., to reflux) and then alkylated in a second step ii) with a compound of Formula (I-B), wherein $L_1$, $L_2$, Y, and Z are defined herein and $LG^1$ is a leaving group such as —Cl, —Br, —I or a sulfonate (such as a mesylate or tosylate) and heated (e.g., to about or at least about 85° C.) to provide a compound of Formula (I-C).

Compounds of Formula (I-C) can be converted into compounds of Formula (I-D) by conditions A:

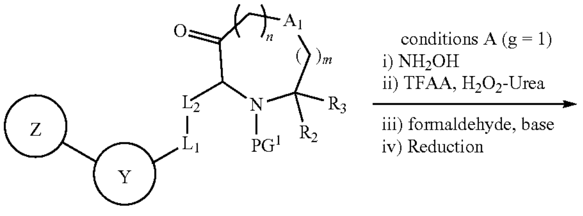

(I-C)

Compounds of Formula (I-C) can be reacted in a first step i) with hydroxylamine hydrochloride, in the presence of a tertiary amine base, such as triethylamine or diisopropylethylamine and an alcohol (such as ethanol) and heated (e.g., at about or at least about 90° C.). In a second step ii) the intermediate can then be treated with TFAA, and $H_2O_2$-urea in the presence of a base such as $NaHCO_3$ and solvent, such as acetonitrile and heated (e.g., to about or at least about 80° C.). The resulting intermediate can be reacted in a third step iii) with formaldehyde in the presence of a tertiary amine base, such as triethylamine and solvent, such as an ether solvent like THF, and heated (e.g., at about or at least about heated to 70° C.). The resulting intermediate can then undergo reduction of the nitro group in a fourth step iv) upon treatment with Zn in the presence of an acid, such as AcOH and a solvent, such as an alcohol solvent like ethanol to form compounds of Formula (I-D).

Alternatively, compounds of Formula (I-C) can be converted into compounds of Formula (I-D) by conditions B:

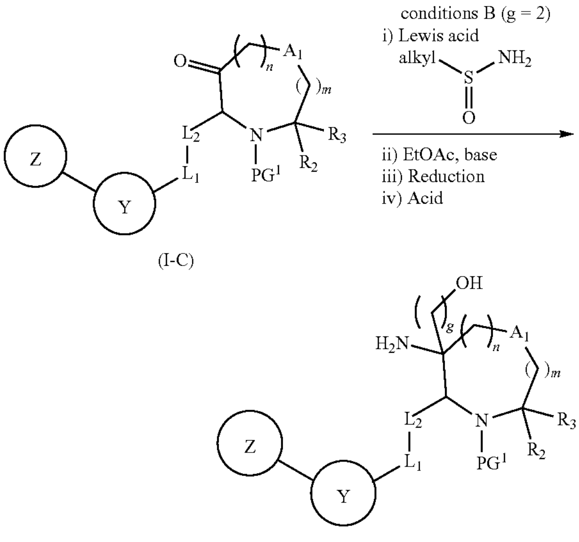

(I-C)

(I-D)

Compounds of Formula (I-C) can be reacted in a first step i) with an alkyl sulfinamide, such as (R)-2-methylpropane-2-sulfinamide in the presence of a Lewis acid, such as $Ti(OEt)_4$ and a solvent such as an ether like THF and heated (e.g., at about or at least about 60° C.). In a second step ii) the intermediate can then be treated with EtOAc, in the presence of an alkali metal amide base like LDA, and solvent, such as an ether like THF at low temperatures (e.g., about −78° C.). The resulting intermediate ester can be reduced to an alcohol in a third step iii) with a hydride reducing agent, such as $LiBH_4$ in an ether solvent like THF. The sulfinamide group can be cleaved in a fourth step iv) in the presence of an acid, such as HCl and a solvent, such as an ether solvent like dioxane to form compounds of Formula (I-D).

Compounds of Formula (I-D) can be cyclized under conditions A, by reacting Compounds of Formula (I-D) with i) a base, such as dipotassium carbonate and chloroacetyl chloride, in the presence of a solvent, such as an ether solvent like THF then ii) a base, such as an alkoxide (e.g., t-BuOK) in the presence of an alcohol solvent such as isopropyl alcohol to form compounds of Formula (I-E).

Alternatively, Compounds of Formula (I-D) can be cyclized under conditions B, by reacting Compounds of Formula (I-D) with triphosgene in the presence of a tertiary amine base such as DIPEA and solvent such as a chlorinated solvent like dichloromethane to form compounds of Formula (I-E).

Compounds of Formula (I-E) can be deprotected to form compounds of Formula (I-F). When $PG^1$ is Cbz, hydrogenation e.g., with Pd/C, and $H_2$ in an alcohol solvent, such as ethanol provides compounds of Formula (I-F). When $PG^1$ is Boc, treatment of compounds of Formula (I-E) with an acid in a solvent (such as trifluoracetic acid in dichloromethane, or HCl in methanol) gives compounds of Formula (I-F).

Compounds of Formula (I-F) can be reacted with $R_1$-$LG^2$, wherein $R_1$, is defined herein and $LG^2$ is a leaving group such as —Cl, —Br, —I or a sulfonate (such as a mesylate or tosylate), in the presence of a base such as a tertiary amine like triethylamine in a solvent such as dichloromethane form compounds of Formula (I).

Alternatively, compounds of Formula (I-F) can be reacted with an isocyanate of formula

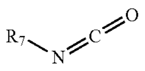

in the presence of a base, such as a tertiary amine like triethylamine to form compounds of Formula (I).

Materials and Methods

Analytical Conditions:

Method A:

Column: Waters UPLC® BEH™ C18, Part No. 186002352, 2.1×100 mm, 1.7 μm

Column Temperature: 40° C.

Mobile Phase A: 2 mM ammonia bicarbonate, buffered to pH 10

Mobile Phase B: Acetonitrile

Injection volume: 1 μL

Gradient program: Flow rate 0.6 mL/minutes

| Time | A % | B % |
|---|---|---|
| 0.00 | 95.00 | 5.00 |
| 5.30 | 0 | 100 |
| 5.80 | 0 | 100 |
| 5.82 | 95.00 | 5.00 |
| 7.00 | 95.00 | 5.00 |

UV 215 nM, PDA spectrum 200-400 nm, step: 1 nm

MSD Scan Positive: 100-1000; Scan Positive Negative: 150-850; Scan Neg: 100-1000

Method B:

Column: Phenomenex, Kinetex-XB C18, Part No. 00D-4498-AN, 2.1 mm×100 mm, 1.7 μm

Column Temperature: 40° C.

Mobile Phase A: 0.1% Formic acid in water

Mobile Phase B: 0.1% Formic acid in acetonitrile

Injection volume: 1 μL

Gradient program: Flow rate 0.6 mL/minutes

| Time | A % | B % |
|---|---|---|
| 0.00 | 95 | 5 |
| 5.30 | 0 | 100 |
| 5.80 | 0 | 100 |
| 5.82 | 95 | 5 |
| 7.00 | 95 | 5 |

UV 215 nM, PDA spectrum 200-400 nm, step: 1 nm

MSD Scan Positive: 100-1000; Scan Positive Negative: 150-850

Method C:

Column: Acquity UPLC CSH C18 (5.0 mm×2.1 mm I.d. 1.7 m) column

Column Temperature: 40° C.

Mobile Phase A: 0.1% Formic acid in water

Mobile Phase B: 0.1% Formic acid in acetonitrile

Gradient program: Flow rate 1 mL/minutes

| Time | A % | B % |
|---|---|---|
| 0.00 | 97.00 | 3.00 |
| 1.50 | 0.10 | 99.90 |
| 1.90 | 0.10 | 99.90 |
| 2.00 | 97.0 | 3.00 |

Method D:

Column: Kintex EVO $C_{18}$ (1.7 μm, 2.1×50 mm) column

Column Temperature: 40° C.

Mobile Phase A: 10 mM ammonia bicarbonate aq. solution adjusted to pH 10 with $NH_3$ Mobile Phase B: Acetonitrile Gradient program:

| Time | A % | B % |
|---|---|---|
| 0.00 | 97.00 | 3.00 |
| 1.50 | 0.10 | 99.90 |
| 1.90 | 0.10 | 99.90 |
| 2.00 | 97.0 | 3.00 |

Synthesis of (CIS)-7-({[(CIS)-4-phenylcyclohexyl]oxy}methyl)-4-oxa-1,8-diazaspiro[5.5]undecan-2-one [0001] (Intermediate 8)

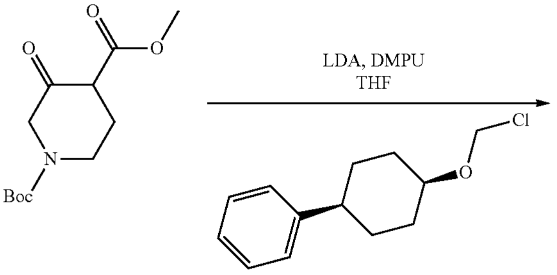

-continued
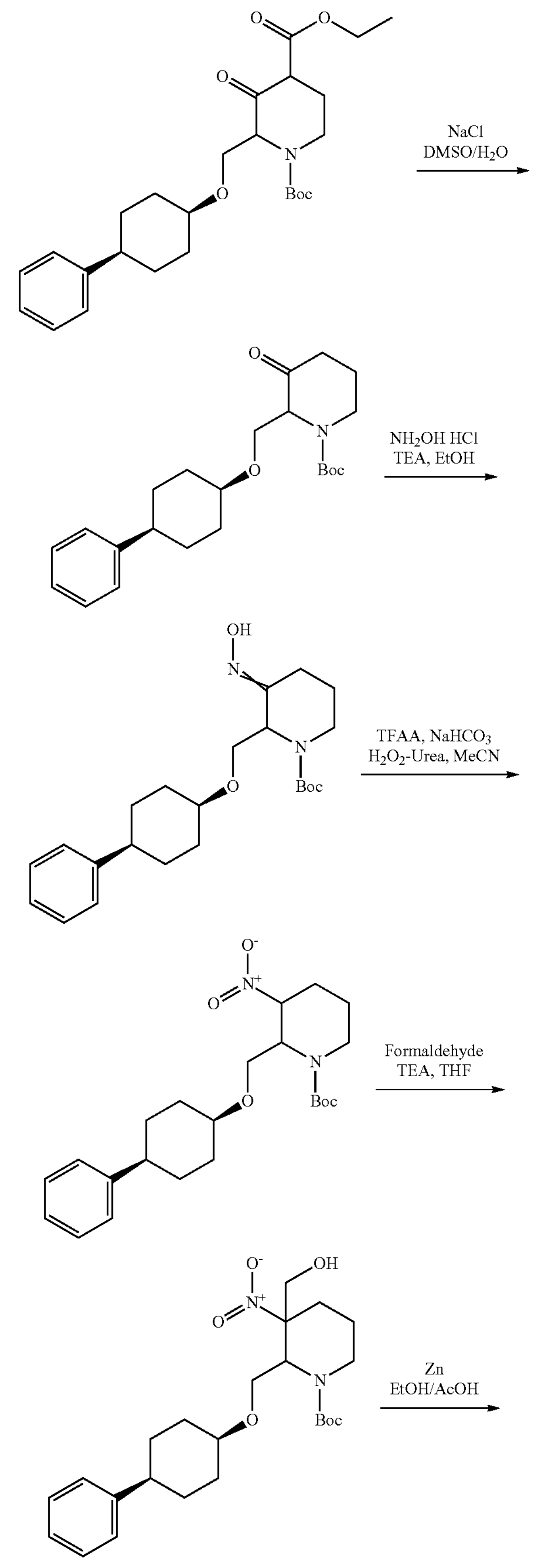
-continued
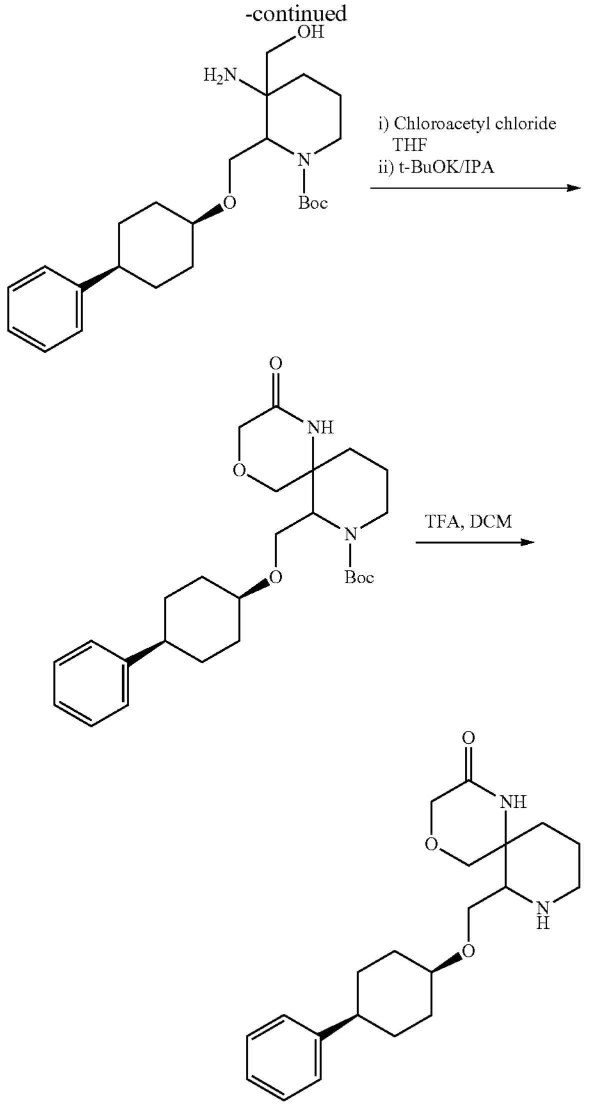
1-tert-butyl 4-ethyl 3-oxo-2-({[(CIS)-4-phenylcyclohexyl]oxy}methyl)piperidine-1,4-dicarboxylate (Intermediate 1)
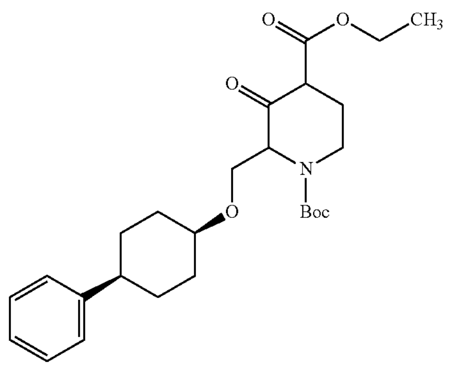 [SMILES: CCOC(=O)C1CCN(C(=O)OC(C)(C)C)C(CO[C@H]2CC[C@@H](c3ccccc3)CC2)C1=O]
To a solution of 4-phenylcyclohexanol (9.65 g, 54.8 mmol) in anhydrous DCM (97 mL) was added paraformaldehyde (1.64 g, 54.8 mmol) followed by addition of chloro (trimethyl)silane (28 mL, 21.9 mmol). The reaction was stirred for 2 h at room temperature. The reaction was filtered through a pad of $Na_2SO_4$ and concentrated in vacuo at 30° C. and gave [4-(chloromethoxy)cyclohexyl]benzene as a pale yellow oil. In a separate flask (diisopropylamino) lithium (2 M in THF) (60 mL, 12.0 mmol) was added over 30 minutes to a stirred solution of 1,3-dimethylhexahydropyrimidin-2-one (26 mL, 21.9 mmol) and 1-tert-butyl 4-ethyl 3-oxopiperidine-1,4-dicarboxylate (14.85 g, 54.8 mmol) in anhydrous THE (200 mL) at −78° C. The solution was held at this temperature for 20 minutes. The oil containing [4-(chloromethoxy)cyclohexyl]benzene was added to the reaction mixture in a solution of anhydrous THF (20 mL) over 15 minutes. The reaction mixture was stirred at −78° C. for 1 h. The reaction was quenched with a saturated aqueous solution of $NH_4Cl$ (80 mL) and extracted with EtOAc (3×100 mL). The combined organic extracts were dried over $MgSO_4$, filtered and concentrated in vacuo. The crude material was purified by silica gel column chromatography (0-20% TBME in heptane), to afford the title compound (14.3 g) as a light orange gum. $[M+H]^+$ m/z 460.5 tert-butyl 3-oxo-2-({[(CIS)-4-phenylcyclohexyl] oxy}methyl)piperidine-1-carboxylate (Intermediate 2)

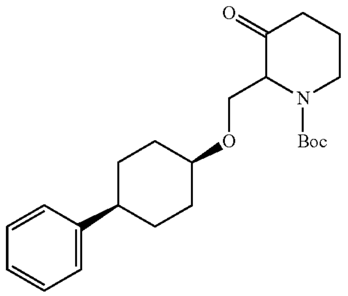 [SMILES: CC(C)(C)OC(=O)N1CCCC(=O)C1CO[C@H]1CC[C@@H](c2ccccc2)CC1]

To a solution of Intermediate 1 (14.30 g, 31.1 mmol) in DMSO (90 mL) was added sodium chloride (3.64 g, 62.2 mmol) and water (10 mL). The reaction was heated to 130° C. for 5.5 h. Additional sodium chloride (3.64 g, 62.2 mmol) was added and the reaction was stirred for 4 h at 130° C. The reaction mixture was cooled to room temperature and partitioned between $Et_2O$ (200 mL) and a 5% aqueous solution of LiCl (200 mL). The biphasic mixture was separated and the organic layer was washed with a 5% aqueous solution of LiCl (3×200 mL). The organic extracts were concentrated in vacuo and gave an orange oil (11 g). The aqueous layer was re-extracted with ether (300 mL), which was concentrated in vacuo. The crude material was purified by silica gel column chromatography (0-10% EtOAc in heptane), to afford the title compound (8.2 g) as a pale yellow oil. $[M+H]^+$ m/z 388.4 tert-butyl 3-(hydroxyimino)-2-({[(CIS)-4-phenylcyclohexyl]oxy}methyl)piperidine-1-carboxylate (Intermediate 3)

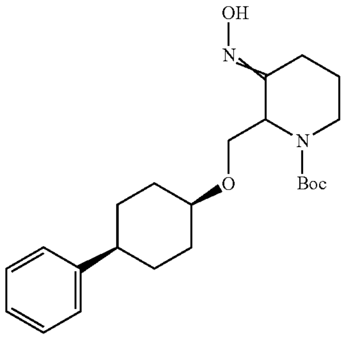 [SMILES: CC(C)(C)OC(=O)N1CCCC(=NO)C1CO[C@H]1CC[C@@H](c2ccccc2)CC1]

A solution of triethylamine (4.3 mL, 31.0 mmol), hydroxylamine hydrochloride (1:1) (2.15 g, 31.0 mmol) and Intermediate 2 (4.00 g, 10.3 mmol) in ethanol (20 mL) was heated to 90° C. for 1 h. The reaction mixture was diluted with water (50 mL) and extracted with EtOAc (3×75 mL). The organic extracts were passed through a phase separator and concentrated in vacuo, to afford the title compound (3.48 g) as a pale yellow foamy gum. $[M+H]^+$ m/z 403.4 tert-butyl 3-nitro-2-({[(CIS)-4-phenylcyclohexyl] oxy}methyl)piperidine-1-carboxylate (Intermediate 4)

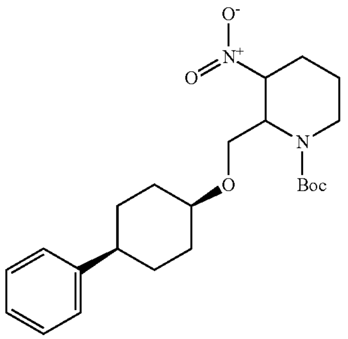 [SMILES: CC(C)(C)OC(=O)N1CCCC([N+](=O)[O-])C1CO[C@H]1CC[C@@H](c2ccccc2)CC1]

Trifluoroacetic anhydride (3.0 mL, 21.6 mmol) in anhydrous acetonitrile (14 mL) was added to a stirred solution of hydrogen peroxide-urea (1:1) (2.85 g, 30.3 mmol) in anhydrous acetonitrile (14 mL) at 0° C. The reaction was stirred at 0° C. for 2 h. The resulting solution was added dropwise to a mixture of Intermediate 3 (3.48 g, 8.65 mmol) and $NaHCO_3$ (3.63 g, 43.2 mmol) in anhydrous acetonitrile (20 mL) at 80° C., then stirred at 80° C. for 1 h. The reaction was cooled to room temperature and quenched with a saturated aqueous solution of $Na_2SO_3$, diluted with water (50 mL) and extracted with EtOAc (3×75 mL). The combined organic extracts were washed with brine (100 mL), dried over $MgSO_4$, filtered and concentrated in vacuo and gave a pale yellow gum. The crude material was purified by silica gel column chromatography (0-20% EtOAc in heptane), to afford the title compound (1.78 g) as a colourless gum which precipitate to a white solid. $[M+H]^+$ m/z 419.4 tert-butyl (CIS) 3-(hydroxymethyl)-3-nitro-2-({[(CIS)-4-phenylcyclohexyl]oxy}methyl)piperidine-1-carboxylate (Intermediate 5)

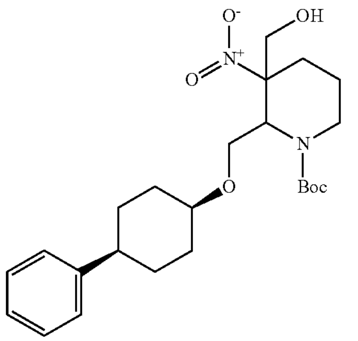 [SMILES: CC(C)(C)OC(=O)N1CCCC(CO)([N+](=O)[O-])C1CO[C@H]1CC[C@@H](c2ccccc2)CC1]

Formaldehyde (in water) (37%, 2.5 mL, 33.3 mmol) was added to Intermediate 4 (1.55 g, 3.70 mmol) and triethylamine (0.52 mL, 3.70 mmol) in THF (20 mL) at room temperature. The solution was heated to 70° C. for 18 h. The reaction mixture was diluted with water (30 mL) and extracted with EtOAc (3x50 mL). The combined organic extracts were concentrated in vacuo and the crude material was purified by silica gel column chromatography (0-40% EtOAc in heptane), to afford the title compound (1.55 g) as a colourless gum. $[M+H]^+$ m/z 449.4 tert-butyl (CIS)-3-amino-3-(hydroxymethyl)-2-({[(CIS)-4-phenylcyclohexyl]oxy}methyl)piperidine-1-carboxylatelate (Intermediate 6)

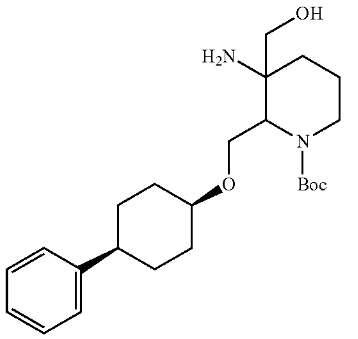 [SMILES: CC(C)(C)OC(=O)N1CCCC(N)(CO)C1CO[C@H]1CC[C@@H](c2ccccc2)CC1]

Zinc (1.90 g, 29.0 mmol) was added in three portions to a stirred solution of Intermediate 5 (1.30 g, 2.90 mmol) in ethanol (36 mL) and acetic acid (7.8 mL) at 0° C. The reaction was warmed to room temperature and stirred for 5 h. The reaction was filtered through a pad of Celite and washed with methanol. The filtrate was concentrated in vacuo, diluted with water and neutralised with a saturated aqueous solution of $NaHCO_3$ and extracted with DCM (3x25 mL). The organic extracts were concentrated in vacuo and purified by silica gel column chromatography (0-5% methanol in DCM), to afford the title compound (1.09 g) as a colourless gum. $[M+H]^+$ m/z 419.4.

tert-butyl (CIS)-2-oxo-7-({[(CIS)-4-phenylcyclohexyl]oxy}methyl)-4-oxa-1,8-diazaspiro[5.5]undecane-8-carboxylate (Intermediate 7)

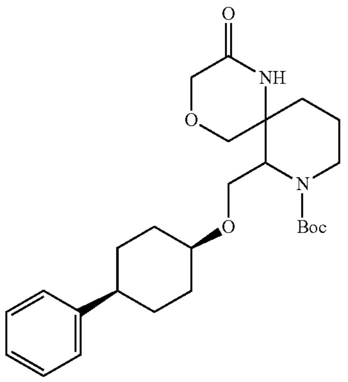 [SMILES: CC(C)(C)OC(=O)N1CCCC2(COCC(=O)N2)C1CO[C@H]1CC[C@@H](c2ccccc2)CC1]

To a solution of Intermediate 6 (800 mg, 1.91 mmol) in THE (9 mL) was added dipotassium carbonate (792 mg, 5.73 mmol) in water (8.6 mL) at 0° C. To this mixture chloroacetyl chloride (0.17 mL, 2.13 mmol) was added dropwise at 0° C. The reaction was stirred for 1 h at 0° C. Additional 2-chloroacetyl chloride (46 μL, 0.578 mmol) was added and reaction was stirred for 1 h. The mixture was quenched with water and extracted with DCM (2x20 mL), passed through a phase separator and concentrated in vacuo. The intermediate was dissolved in DCM (17 mL) and potassium 2-methylpropan-2-olate (858 mg, 7.65 mmol) in IPA (17 mL) was added at 0° C. The reaction was warmed to room temperature and stirred for 16 h. The solution was neutralised with 2 M HCl and adjusted to pH 8 with a saturated aqueous solution of $NaHCO_3$, diluted with water and extracted with DCM (3x50 mL). The organic extracts were passed through a phase separator and concentrated in vacuo. The crude material was purified by silica gel column chromatography (0-20% methanol in EtOAc), to afford the title compound (550 mg) as a colourless gum. $[M-H]^-$ m/z 457.5.

(CIS)-7-({[(CIS)-4-phenylcyclohexyl]oxy}methyl)-4-oxa-1,8-diazaspiro[5.5]undecan-2-one (Intermediate 8)

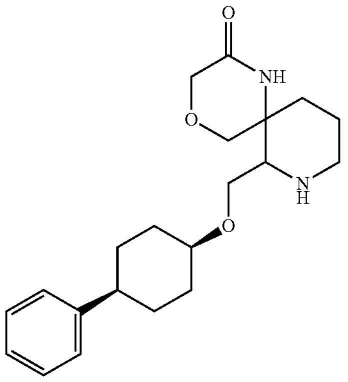 [SMILES: O=C1COCC2(CCCNC2CO[C@H]2CC[C@@H](c3ccccc3)CC2)N1]

TFA (1.3 mL) was added to a solution of Intermediate 7 (550 mg, 1.20 mmol) in DCM (2.6 mL) and mixture was stirred at room temperature for 1 h. The reaction was quenched with a saturated aqueous solution of $NaHCO_3$ solution (10 mL) and extracted with DCM (2×10 mL). The organic layers were combined, passed through a phase separator, concentrated in vacuo, to afford the title compound (400 mg) as a white solid. $[M-H]^-$ m/z 357.5

Example 1: (CIS)—N-ethyl-2-oxo-7-({[(CIS)-4-phenylcyclohexyl]oxy}methyl)-4-oxa-1,8-diazaspiro[5.5]undecane-8-carboxamide (1)

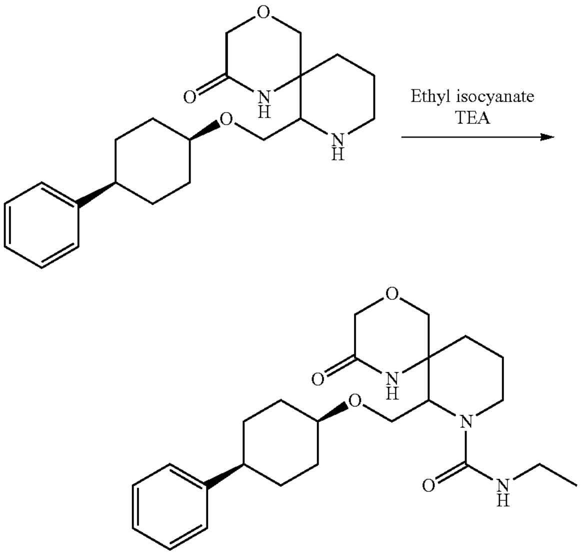

1

To a stirred solution of triethylamine (0.23 mL, 1.67 mmol) and Intermediate 8 (300 mg, 0.837 mmol) in DCM (12 mL) was added ethyl isocyanate (0.13 mL, 1.67 mmol) at room temperature. The reaction was stirred for 2 h and was quenched with 2 M NaOH (10 mL). The mixture was extracted with DCM, the organic extracts were passed through a phase separator and concentrated in vacuo. The crude material was purified by reverse phase column chromatography (10-70% MeCN in water (0.1% $NH_3$)), to afford the title compound (228 mg) as a white solid. [0203] $^1H$ NMR (400 MHz, $CDCl_3$) δ 7.34-7.27 (m, 2H), 7.23-7.15 (m, 3H), 6.32 (brs, 1H), 4.43-4.37 (m, 1H), 4.27 (d, J=16.8 Hz, 1H), 4.17-4.02 (m, 3H), 3.87-3.74 (m, 2H), 3.69-3.61 (m, 1H), 3.34 (d, J=11.8 Hz, 1H), 3.25 (q, J=7.2 Hz, 2H), 3.01 (td, J=13.0, 3.1 Hz, 1H), 2.61-2.49 (m, 1H), 2.08-1.97 (m, 2H), 1.90 (td, J=13.5, 4.9 Hz, 1H), 1.85-1.50 (m, 9H), 1.13 (t, J=7.2 Hz, 3H). 1 NH not observed. LCMS (Method A): $[M+H]^+$ m/z 430.4, RT 3.19 minutes.

Example 2: (6R,7S)—N-ethyl-2-oxo-7-({[(CIS)-4-phenylcyclohexyl]oxy}methyl)-4-oxa-1,8-diazaspiro[5.5]undecane-8-carboxamide (2) & Example 3: (6S,7R)—N-ethyl-2-oxo-7-({[(CIS)-4-phenylcyclohexyl]oxy}methyl)-4-oxa-1,8-diazaspiro[5.5]undecane-8-carboxamide (3)

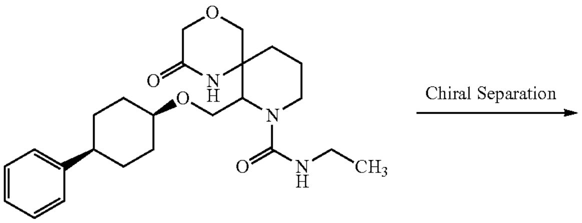

1

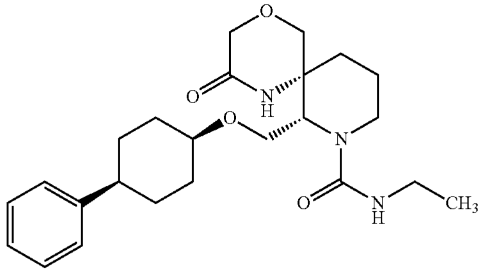

+

2

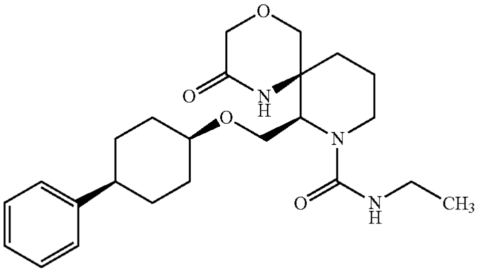

3

Example 1 (209 mg) was subjected to chiral preparative purification using Waters 600 eluting with 80/20% v/v n-Hexane/Ethanol, Chiralpak AS-H (25×2.0 cm), 5 μm, flow rate 17 mL/minutes to afford the title compounds (Peak 1, 94.4 mg, 100% ee; and Peak 2, 87 mg, 100% ee). The absolute stereochemistry of each separated compound 2 and 3 was not conclusively determined but assigned as shown below.

Peak 1 (was assigned 6R,7S at piperidine); $^1H$ NMR (400 MHz, $CDCl_3$) δ 7.30 (dd, J=8.2, 7.0 Hz, 2H), 7.23-7.14 (m, 3H), 6.26 (s, 1H), 4.78 (s, 1H), 4.41 (t, J=5.4 Hz, 1H), 4.27 (d, J=16.9 Hz, 1H), 4.16-4.03 (m, 3H), 3.86-3.72 (m, 2H), 3.65 (t, J=3.0 Hz, 1H), 3.35 (d, J=11.8 Hz, 1H), 3.25 (qd, J=7.2, 5.2 Hz, 2H), 3.01 (td, J=13.1, 3.5 Hz, 1H), 2.54 (tt, J=10.5, 5.2 Hz, 1H), 2.06-1.98 (m, 2H), 1.91 (td, J=13.6, 4.9 Hz, 1H), 1.85-1.76 (m, 1H), 1.76-1.64 (m, 4H), 1.64-1.49 (m, 4H), 1.12 (t, J=7.2 Hz, 3H). LCMS (Method C): $[M+H]^+$ m/z 430.3, RT 0.95 minutes. Chiral analysis (Chiralpak AS-H, 25×0.46 cm, 5 μm, 80:20 n-Hexane:Ethanol): RT 8.3 minutes Peak 2 (was assigned 6S,7R at piperidine): $^1H$ NMR (400 MHz, $CDCl_3$) δ 7.29 (dd, J=8.2, 6.9 Hz, 2H), 7.20 (dt, J=8.2, 2.0 Hz, 3H), 6.48 (s, 1H), 4.81 (t, J=5.4 Hz, 1H), 4.40 (dd, J=7.1, 3.6 Hz, 1H), 4.27 (d, J=16.8 Hz, 1H), 4.19-4.05 (m, 3H), 3.80 (qd, J=9.8, 5.3 Hz, 2H), 3.64 (p, J=2.9 Hz, 1H), 3.34 (d, J=11.8 Hz, 1H), 3.25 (qd, J=7.2, 5.3 Hz, 2H), 2.99 (td, J=13.1, 3.5 Hz, 1H), 2.54 (tt, J=10.6, 5.0 Hz, 1H), 2.01 (dq, J=14.9, 2.9 Hz, 2H), 1.90 (td, J=13.5, 5.0 Hz, 1H), 1.83-1.75 (m, 1H), 1.75-1.49 (m, 8H), 1.12 (t, J=7.2 Hz, 3H). LCMS (Method C): $[M+H]^+$ m/z 430.3, RT 0.95 minutes. Chiral analysis (Chiralpak AS-H, 25×0.46 cm, 5 μm, 80:20 n-Hexane:Ethanol): RT 13.7 minutes Example 4: Methyl (CIS)-2-oxo-7-({[(CIS)-4-phenylcyclohexyl]oxy}methyl)-4-oxa-1,8-diazaspiro[5.5]undecane-8-carboxylate (4)

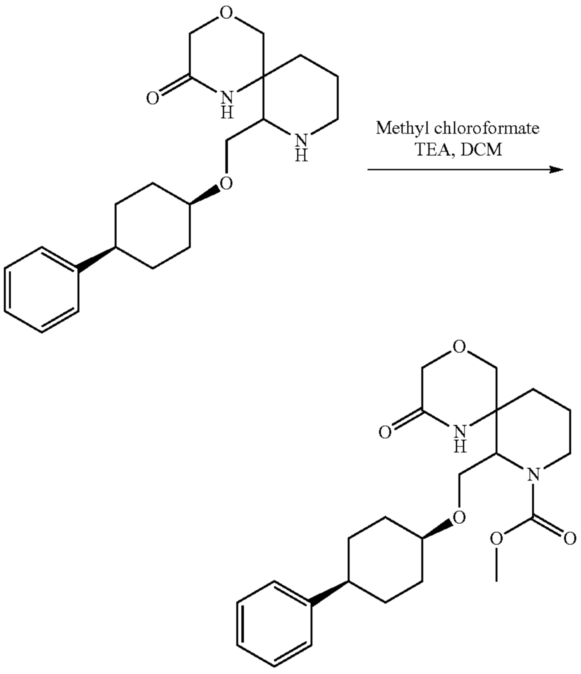

4

Methyl carbonochloridate (22 μL, 0.279 mmol) was added to a stirred solution of Intermediate 8 (50 mg, 0.139 mmol) and triethylamine (39 μL, 0.279 mmol) in DCM (2 mL) at room temperature and stirred for 1.5 h. The reaction was cooled to 0° C. and additional triethylamine (78 μL, 0.558 mmol) and methyl carbonochloridate (86 μL, 1.12 mmol) were added then the reaction was stirred for 18 h. The reaction was quenched with a saturated aqueous solution of $NaHCO_3$ and extracted with DCM (3×5 mL). The combined organic extracts were passed through a phase separator and concentrated in vacuo. The crude material was purified by silica gel column chromatography (50-100% EtOAc in heptane followed by 0-10% methanol in EtOAc), to afford the title compound (21 mg) as a white solid.

$^1H$ NMR (500 MHz, $CDCl_3$) δ 7.28-7.20 (m, 2H), 7.17-7.07 (m, 3H), 6.24-5.97 (m, 1H), 4.69-4.41 (m, 1H), 4.25-3.84 (m, 4H), 3.76 (s, 2H), 3.66 (s, 3H), 3.56 (s, 1H), 3.33 (s, 1H), 3.10 (s, 1H), 2.58-2.44 (m, 1H), 2.08 (s, 1H), 2.02-1.90 (m, 2H), 1.76 (s, 1H), 1.73-1.58 (m, 5H), 1.58-1.40 (m, 3H). Rotamers observed. LCMS (Method A): $[M+H]^+$ m/z 417.3, RT 3.50 minutes.

Example 5: Methyl (6R,7S)-2-oxo-7-({[(CIS)-4-phenylcyclohexyl]oxy}methyl)-4-oxa-1,8-diazaspiro[5.5]undecane-8-carboxylate (5) & Example 6: Methyl (6S,7R)-2-oxo-7-({[(CIS)-4-phenylcyclohexyl]oxy}methyl)-4-oxa-1,8-diazaspiro[5.5]undecane-8-carboxylate (6)

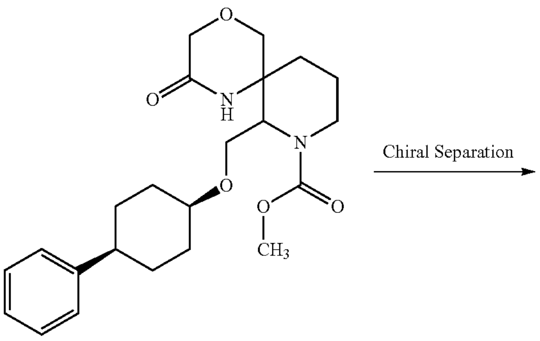

4

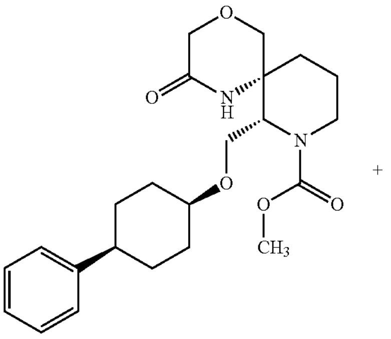

5

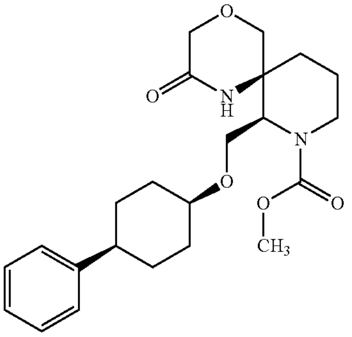

6

Example 4 (16 mg) was subjected to chiral preparative purification using Waters 600 eluting with 65/35% v/v n-Hexane/Ethanol, Chiralpak AS-H (25×2.0 cm), 5 μm, flow rate 17 mL/minutes to afford the title compounds (Peak 1, 4.9 mg, 100% ee; and Peak 2, 4.6 mg, 100% cc). The absolute stereochemistry of each separated compound 5 and 6 was not conclusively determined but assigned as shown below.

Peak 1 (was assigned 6R,7S at piperidine): 1H NMR (400 MHz, $CDCl_3$) δ 7.36-7.29 (m, 2H), 7.25-7.17 (m, 3H), 6.11 (brs, 1H), 4.58 (brs, 1H), 4.33-4.07 (m, 3H), 4.01 (brs, 1H), 3.84 (brs, 2H), 3.74 (s, 3H), 3.65 (brs, 1H), 3.42 (brs, 1H), 3.21 (brs, 1H), 2.62-2.53 (m, 1H), 2.16 (brs, 1H), 2.11-2.00 (m, 2H), 1.85 (d, J=9.46 Hz, 1H), 1.80-1.68 (m, 5H), 1.67-1.58 (m, 2H). LCMS (Method C): $[M+H]^+$ m/z 417.3, RT 1.04 minutes. Chiral analysis (Chiralpak AS-H, 25×0.46 cm, 5 μm, 80:20 n-Hexane:Ethanol): RT 7.5 minutes.

Peak 2 (was assigned 6S,7R at piperidine): 1H NMR (400 MHz, $CDCl_3$) δ 7.36-7.29 (m, 2H), 7.25-7.17 (m, 3H), 6.11 (brs, 1H), 4.58 (brs, 1H), 4.33-4.07 (m, 3H), 4.01 (brs, 1H), 3.84 (brs, 2H), 3.74 (s, 3H), 3.65 (brs, 1H), 3.42 (brs. 1H), 3.21 (brs, 1H), 2.62-2.53 (m, 1H), 2.16 (brs, 1H), 2.11-2.00 (m, 2H), 1.85 (d, J=9.46 Hz, 1H), 1.80-1.68 (m, 5H), 1.67-1.58 (m, 2H). LCMS (Method C): $[M+H]^+$ m/z 417.3, RT 1.04 minutes. Chiral analysis (Chiralpak AS-H, 25×0.46 cm, 5 μm, 80:20 n-Hexane:Ethanol): RT 11.2 minutes.

Example 7: (CIS)-8-cyclopropanecarbonyl-7-({[(CIS)-4-phenylcyclohexyl]oxy}methyl)-4-oxa-1,8-diazaspiro[5.5]undecan-2-one (7)

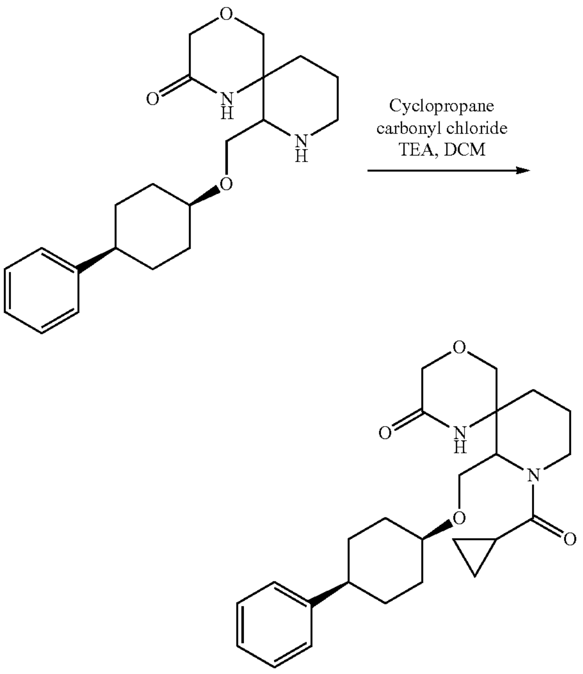

7

Cyclopropanecarbonyl chloride (25 μL, 0.279 mmol) was added to a stirred solution of Intermediate 8 (50 mg, 0.139 mmol) and triethylamine (39 μL, 0.279 mmol) in DCM (2 mL) at room temperature and stirred for 1.5 h. The reaction was quenched with a saturated aqueous solution of $NaHCO_3$ (2 mL) and extracted with DCM (3×5 mL). The combined organic extracts were passed through a phase separator and concentrated in vacuo. The crude material was purified by silica gel column chromatography (100% EtOAc), to afford the title compound (40 mg) as a white solid.

$^1H$ NMR (400 MHz, $CDCl_3$) δ 7.34-7.27 (m, 2H), 7.24-7.14 (m, 3H), 6.45-6.09 (m, 1H), 5.11-4.75 (m, 1H), 4.61 (d, J=11.1 Hz, 0.5H), 4.26 (t, J=18.4 Hz, 1H), 4.20-4.04 (m, 2H), 3.95-3.77 (m, 2.5H), 3.70-3.51 (m, 1.5H), 3.39 (dd, J=36.2, 12.0 Hz, 1H), 3.00-2.83 (m, 0.5H), 2.54 (s, 1H), 2.32-1.89 (m, 3H), 1.89-1.39 (m, 9H), 1.11-0.92 (m, 2H), 0.86-0.69 (m, 2H). 1H exchanged with solvent. LCMS (Method A): $[M+H]^+$ m/z 427.3, RT 3.43 minutes Example 8: (6R,7S)-8-cyclopropanecarbonyl-7-({[(CIS)-4-phenylcyclohexyl]oxy}methyl)-4-oxa-1,8-diazaspiro[5.5]undecan-2-one (8) & Example 9: (6S,7R)-8-cyclopropanecarbonyl-7-({[(CIS)-4-phenylcyclohexyl]oxy}methyl)-4-oxa-1,8-diazaspiro[5.5]undecan-2-one (9)

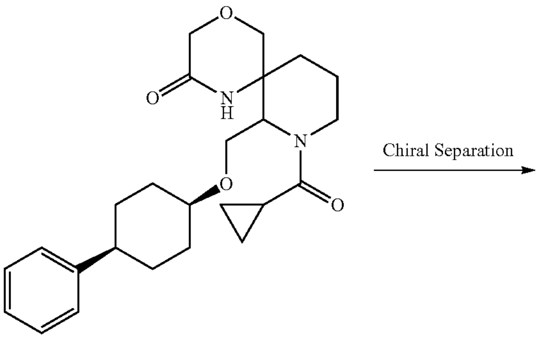

7

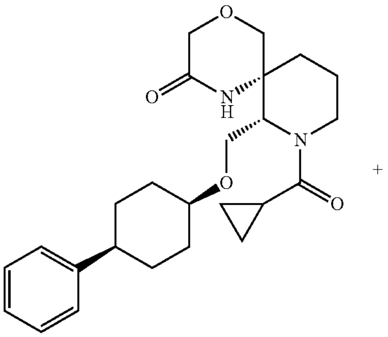

8

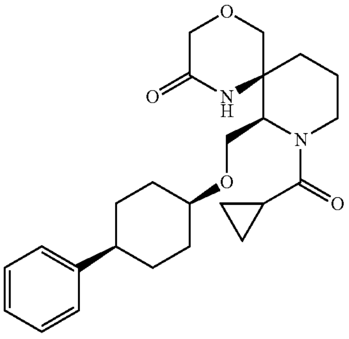

9

Example 7 (28 mg) was subjected to chiral preparative purification using Waters 600 eluting with 80/20% v/v n-Hexane/Ethanol, Chiralpak AS-H (25×2.0 cm), 5 μm, flow rate 17 mL/minutes, to afford the title compounds (Peak 1, 10.5 mg, 100% ee; and Peak 2, 10.3 mg, 100% ee). The absolute stereochemistry of each separated compound 8 and 9 was not conclusively determined but assigned as shown below.

Peak 1 (was assigned 6R,7S at piperidine): $^1H$ NMR (400 MHz, $CDCl_3$) δ 7.44-7.30 (m, 2H), 7.26-7.15 (m, 3H), 6.17 (d, J=118.2 Hz, 1H), 4.95 (d, J=117.3 Hz, 1H), 4.69-2.87 (m, 9H), 2.58 (s, 1H), 2.37-1.66 (m, 13H), 1.16-0.95 (m, 2H), 0.91-0.68 (m, 2H). LCMS (Method C): $[M+H]^+$ m/z 427.3, RT 1.02 minutes. Chiral analysis (Chiralpak AS-H, 25×0.46 cm, 5 m, 80:20 n-Hexane:Ethanol): RT 11.0 minutes Peak 2 (was assigned 6S,7R at piperidine): $^1$H NMR (500 MHz, $CDCl_3$) δ 7.36-7.30 (m, 2H), 7.26-7.17 (m, 3H), 6.17 (d, J=119.9 Hz, 1H), 4.95 (d, J=117.5 Hz, 1H), 4.68-2.86 (m, 9H), 2.58 (s, 1H), 2.37-1.61 (m, 13H), 1.10-0.95 (m, 2H), 0.92-0.71 (m, 2H). LCMS (Method C): $[M+H]^+$ m/z 427.3, RT 1.02 minutes. Chiral analysis (Chiralpak AS-H, 25×0.46 cm, 5 m, 80:20 n-Hexane:Ethanol): RT 18.9 minutes.

Example 10: (CIS)—N-ethyl-2-oxo-7-({[(CIS)-4-phenylcyclohexyl]oxy}methyl)-3-oxa-1,8-diazaspiro[5.5]undecane-8-carboxamide (10)

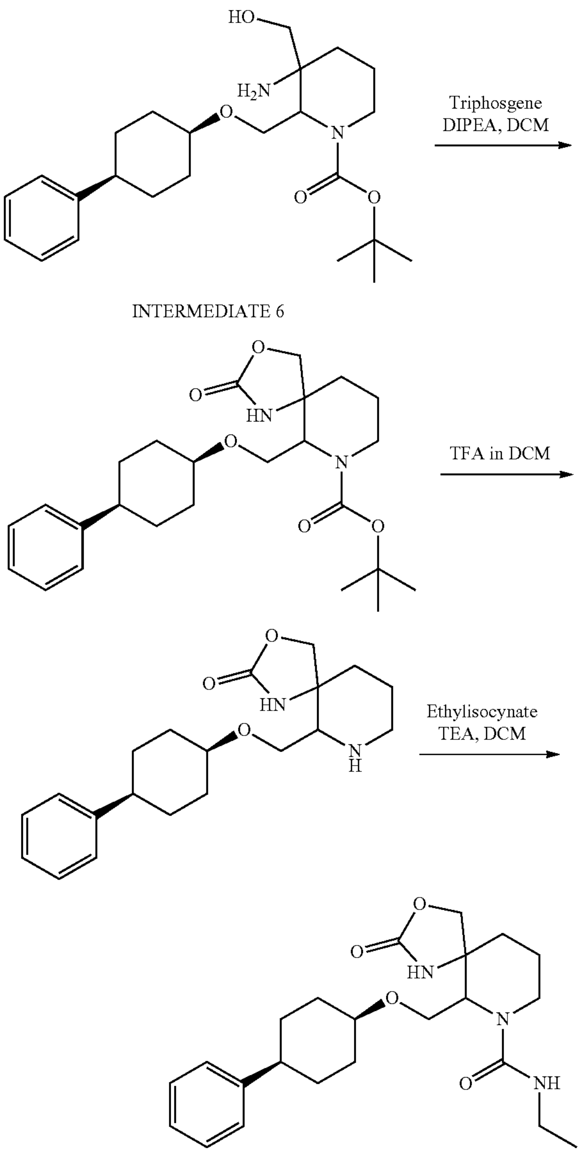

INTERMEDIATE 6

10 tert-butyl (CIS)-2-oxo-6-({[(CIS)-4-phenylcyclohexyl]oxy}methyl)-3-oxa-1,7-diazaspiro[4.5]decane-7-carboxylate (Intermediate 9)

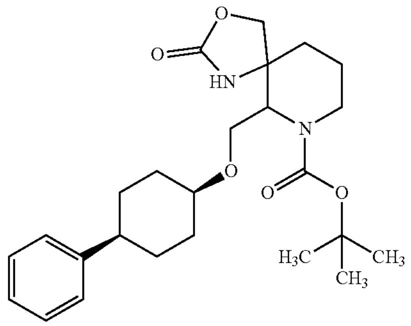 [SMILES: CC(C)(C)OC(=O)N1CCCC2(COC(=O)N2)C1CO[C@H]1CC[C@@H](c2ccccc2)CC1]

N-ethyl-N-(propan-2-yl)propan-2-amine (68 μL, 0.392 mmol) was added to a stirred solution of Intermediate 6 (164 mg, 0.392 mmol) and bis(trichloromethyl) carbonate (116 mg, 0.392 mmol) in anhydrous DCM (5 mL) at 0° C. The reaction mixture was stirred at 0° C. for 1 h then quenched with a saturated aqueous solution of $NaHCO_3$ (1 mL) and purged with $N_2$(g) for 30 min using 20% NaOH scrubber to quench excess of phosgene gas. The solution was extracted with DCM (2×5 mL), passed through a phase separator, concentrated in vacuo, to afford the title compound (219 mg) as a white gum. $[M+NH_4]^+$ m/z 462.4

(CIS)-6-({[(CIS)-4-phenylcyclohexyl]oxy}methyl)-3-oxa-1,7-diazaspiro[4.5]decan-2-one (Intermediate 10)

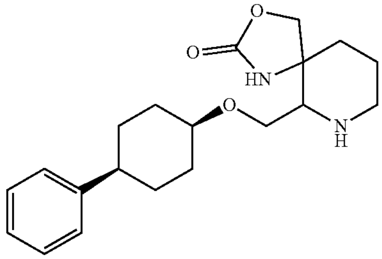 [SMILES: O=C1NC2(CCCNC2CO[C@H]2CC[C@@H](c3ccccc3)CC2)CO1]

Trifluoroacetic acid (1.0 mL, 13.1 mmol) was added to a stirred solution of Intermediate 9 (174 mg, 0.391 mmol) in DCM (1 mL) at room temperature and stirred for 1 h. The reaction was neutralised with a saturated aqueous solution of $NaHCO_3$ and extracted with DCM (3×5 mL). The combined organic extracts were passed through a phase separator, concentrated in vacuo, to afford the title compound (207 mg) as a white solid. $[M+H]^+$ m/z 345.3.

(CIS)—N-ethyl-2-oxo-7-({[(CIS)-4-phenylcyclohexyl]oxy}methyl)-3-oxa-1,8-diazaspiro[5.5]undecane-8-carboxamide (10)

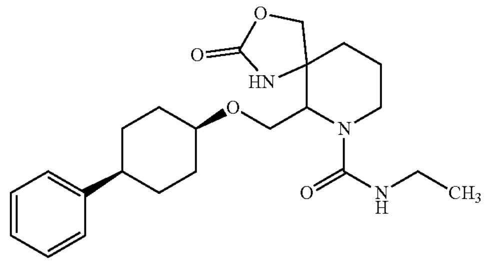 [SMILES: CCNC(=O)N1CCCC2(COC(=O)N2)C1CO[C@H]1CC[C@@H](c2ccccc2)CC1]

Ethyl isocyanate (0.24 mL, 3.00 mmol) was added to a stirred solution of triethylamine (0.25 mL, 1.80 mmol) and Intermediate 10 (207 mg, 0.601 mmol) in DCM (8 mL) at room temperature and was stirred for 30 minutes. The reaction was quenched with aq. 2 M NaOH, stirred for 20 minutes then extracted with DCM (3x5 mL). The organic extracts were passed through a phase separator and concentrated in vacuo. The crude material was purified by reverse phase column chromatography (10-100% MeCN in water (0.1% $NH_3$)), to afford the title compound (55 mg) as a white solid.

$^1$H NMR (500 MHz, $CDCl_3$) δ 7.33-7.27 (m, 2H), 7.23-7.16 (m, 3H), 6.10 (s, 1H), 4.93 (brs, 1H), 4.32 (d, J=8.9 Hz, 1H), 4.20 (t, J=5.8 Hz, 1H), 4.11 (d, J=8.9 Hz, 1H), 3.98 (dd, J=13.5, 3.9 Hz, 1H), 3.77-3.69 (m, 2H), 3.66 (p, J=3.0 Hz, 1H), 3.24 (qd, J=7.2, 3.0 Hz, 2H), 2.87 (td, J=13.1, 2.8 Hz, 1H), 2.58-2.50 (m, 1H), 2.08-1.90 (m, 3H), 1.85-1.63 (m, 7H), 1.62-1.44 (m, 2H), 1.12 (t, J=7.2 Hz, 3H). LCMS (Method A): $[M+H]^+$ m/z 416.3, RT 3.31 minutes.

Example 11: (CIS)—N-ethyl-2-oxo-7-({[(CIS)-4-phenylcyclohexyl]oxy}methyl)-3-oxa-1,8-diazaspiro[5.5]undecane-8-carboxamide (Example 11) & Example 12: (Trans)-N-ethyl-2-oxo-7-({[(CIS)-4-phenylcyclohexyl]oxy}methyl)-3-oxa-1,8-diazaspiro[5.5]undecane-8-carboxamide (Example 12)

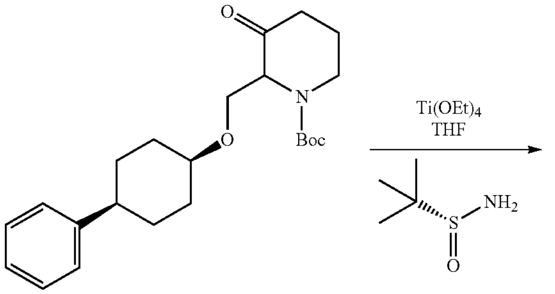

INTERMEDIATE 2

-continued

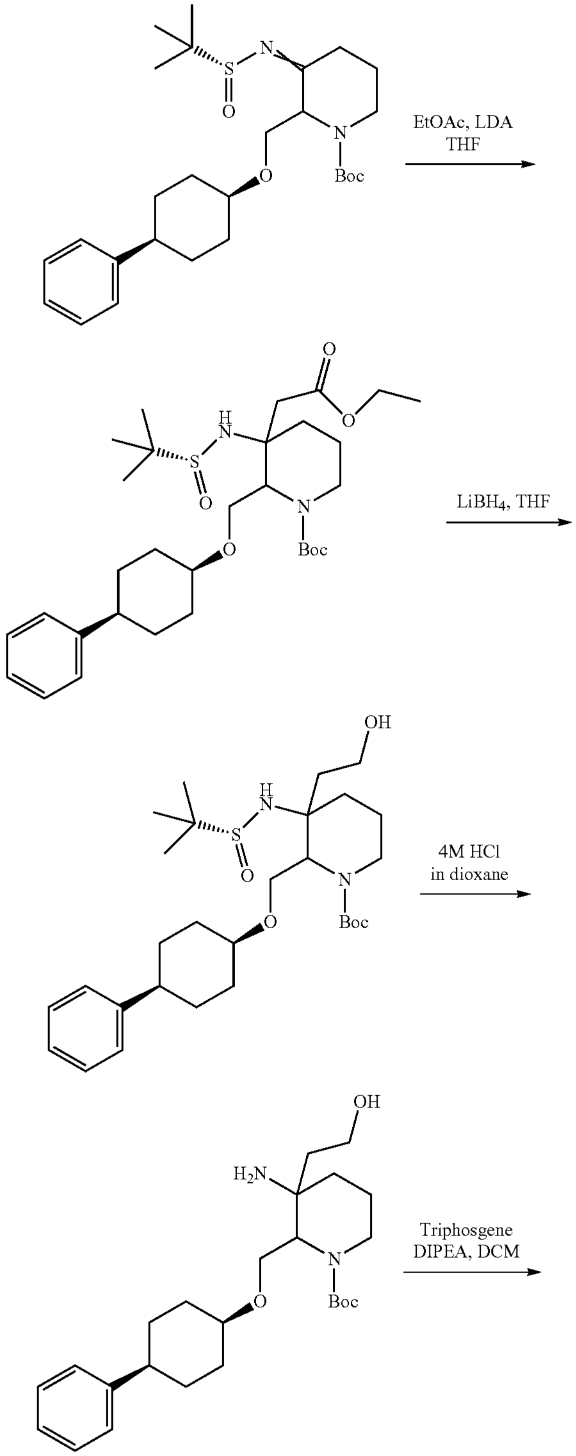

-continued

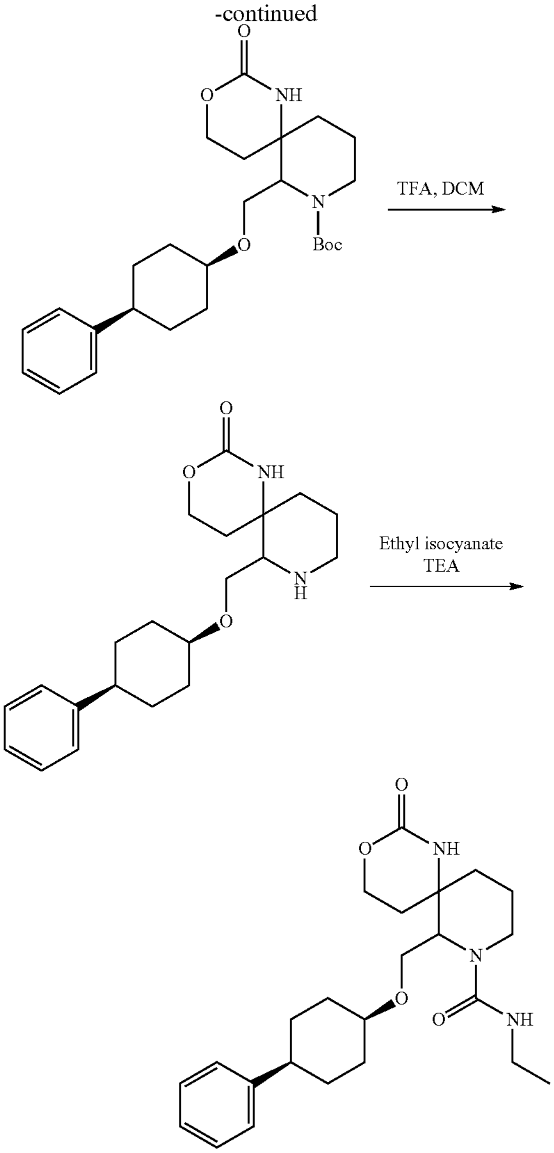

11 & 12 tert-butyl-3-{[(R)-2-methylpropane-2-sulfinyl]imino}-2-({[(CIS)-4-phenylcyclohexyl]oxy}methyl)piperidine-1-carboxylate (Intermediate 11)

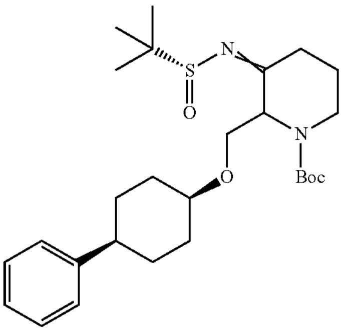 [SMILES: CC(C)(C)OC(=O)N1CCCC(=N[S@](=O)C(C)(C)C)C1CO[C@H]1CC[C@@H](c2ccccc2)CC1]

Titanium(4+) tetraethanolate (4.1 mL, 19.7 mmol) was added to a stirred solution of Intermediate 2 (3.82 g, 9.86 mmol) and (R)-2-methylpropane-2-sulfinamide (1.19 g, 9.86 mmol) in THF (62 mL) at room temperature, then the solution was heated at 60° C. for 2 h. The reaction was cooled to room temperature and poured into a saturated aqueous solution of $NaHCO_3$ solution (100 mL), filtered through a pad of Celite which was washed with DCM (2×50 mL). The organic layer was separated and the aqueous layer was extracted with DCM (100 mL). The combined organic layers were concentrated in vacuo and purified by silica gel column chromatography (0-60% EtOAc in heptane), to afford the title compound (2.47 g) as an orange gum. $[M+H]^+$ m/z 491.5 tert-butyl 3-(2-ethoxy-2-oxoethyl)-3-{[(R)-2-methylpropane-2-sulfinyl]amino}-2-({[(CIS)-4-phenylcyclohexyl]oxy}methyl)piperidine-1-carboxylate (Intermediate 12)

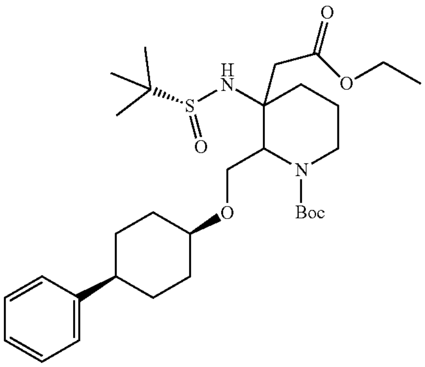 [SMILES: CCOC(=O)CC1(N[S@](=O)C(C)(C)C)CCCN(C(=O)OC(C)(C)C)C1CO[C@H]1CC[C@@H](c2ccccc2)CC1]

A solution of lithium diisopropylamide (2M in THF) (24 mL, 48.3 mmol) was added to the stirred solution of EtOAc (4.7 mL, 48.3 mmol) in anhydrous THF (24 mL) at −78° C. and mixture was stirred for 30 minutes. A solution of Intermediate 11 (2.37 g, 4.83 mmol) in anhydrous THF (2×10 mL) was added dropwise to above mixture at −78° C. and stirred for 1 h. The reaction mixture was quenched with a saturated aqueous solution of $NH_4Cl$ (20 mL), extracted with EtOAc (3×25 ml) and the organic layers were passed through a phase separator. The organic extracts were concentrated in vacuo and purified by silica gel column chromatography (0-100% EtOAc in heptane), to afford the title compound (1.43 g) as a solid gum. $[M+H]^+$ m/z 579.6.

tert-butyl 3-(2-hydroxyethyl)-3-{[(R)-2-methylpropane-2-sulfinyl]amino}-2-({[(CIS)-4-phenylcyclohexyl]oxy}methyl)piperidine-1-carboxylate (INTERMEDIATE 13)

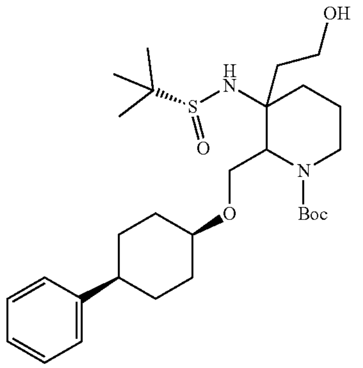 [SMILES: CC(C)(C)OC(=O)N1CCCC(CCO)(N[S@](=O)C(C)(C)C)C1CO[C@H]1CC[C@@H](c2ccccc2)CC1]

A solution of lithium tetrahydroborate (2M in THF) (6 mL, 12.6 mmol) was added drop wise to the stirred solution of Intermediate 12 (1.46 g, 2.51 mmol) in THF (23 mL) at 0° C. The reaction mixture was warmed up to room temperature and stirred for 16 h. The reaction was heated at 50° C. for 2 h, then cooled back to room temperature. Additional lithium tetrahydroborate (2 M in THF) (2.5 mL, 5.03 mmol) was added and the solution of heated at 50° C. for 2 h followed by 1 h at 60° C. The reaction was cooled to room temperature and was carefully quenched with water (25 mL), followed by a saturated aqueous solution of $NH_4Cl$ (25 mL) and extracted with EtOAc (3×50 mL). The combined organic layers were washed with brine (50 mL), dried over $MgSO_4$, filtered and concentrated in vacuo to afford the crude material. The crude material was purified by column chromatography (40-100% EtOAc in heptane then 0-10% methanol in EtOAc), to afford the title compound (755 mg) as a yellow gum. $[M+H]^+$ m/z 537.5 tert-butyl 3-amino-3-(2-hydroxyethyl)-2-({[(CIS)-4-phenylcyclohexyl]oxy}methyl)piperidine-1-carboxylate (Intermediate 14)

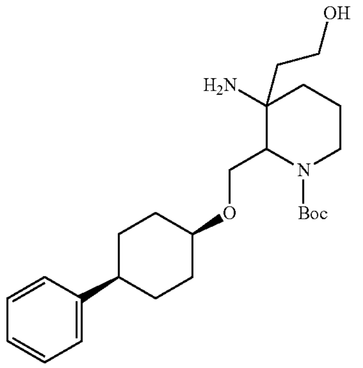 [SMILES: CC(C)(C)OC(=O)N1CCCC(N)(CCO)C1CO[C@H]1CC[C@@H](c2ccccc2)CC1]

Hydrogen chloride (4M in dioxane) (1.0 mL, 4.05 mmol) was added dropwise to a stirred solution of Intermediate 13 (725 mg, 1.35 mmol) in methanol (34 mL) at 0° C. and stirred for 4 h at 0° C. The reaction was placed in the fridge overnight and was quenched at 0° C. with a saturated aqueous solution of $NaHCO_3$ and then the methanol was removed in vacuo. The aqueous solution was then extracted with DCM:methanol (9:1; 3×25 mL). The combined organic extracts were passed through a phase separator and concentrated in vacuo to afford the crude material. The crude material was purified by silica gel column chromatography (0-2% methanol in DCM), to afford the title compound as a mixture of 4:1 cis and trans diastereomers (529 mg) as a pale yellow gum. $[M+H]^+$ m/z 433.7 tert-butyl-2-oxo-7-({[(CIS)-4-phenylcyclohexyl]oxy}methyl)-3-oxa-1,8-diazaspiro[5.5]undecane-8-carboxylate (Intermediate 15)

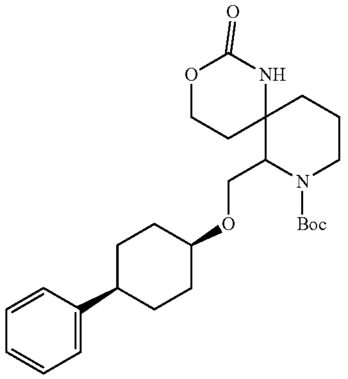 [SMILES: CC(C)(C)OC(=O)N1CCCC2(CCOC(=O)N2)C1CO[C@H]1CC[C@@H](c2ccccc2)CC1]

N-ethyl-N-(propan-2-yl)propan-2-amine (0.21 mL, 1.22 mmol) was added to a stirred solution of Intermediate 14 (529 mg, 1.22 mmol) and bis(trichloromethyl) carbonate (363 mg, 1.22 mmol) in anhydrous DCM (16 mL) at 0° C. The reaction was stirred at 0° C. for 1.5 h then quenched with a saturated aqueous solution of $NaHCO_3$ solution (1 mL) and purged with $N_2$(g) for 30 min using 20% NaOH scrubber to quench excess of phosgene gas. The solution was extracted with DCM (3×10 mL) and passed through a phase separator and concentrated in vacuo to afford the crude material. The crude material was purified by silica gel column chromatography (50-100% EtOAc in heptane), to afford the title compound as a mixture of diastereomers (326 mg) as a colourless gum. $[M+H]^+$ m/z 459.4

7-({[(CIS)-4-phenylcyclohexyl]oxy}methyl)-3-oxa-1,8-diazaspiro[5.5]undecan-2-one (Intermediate 16)

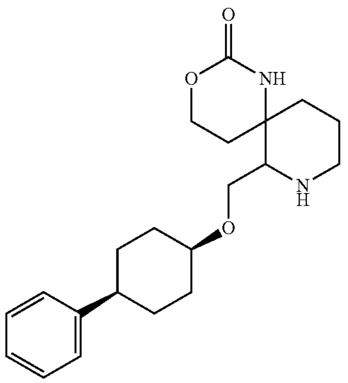 [SMILES: O=C1NC2(CCCNC2CO[C@H]2CC[C@@H](c3ccccc3)CC2)CCO1]

A solution of trifluoroacetic acid (1.5 mL, 19.6 mmol) and Intermediate 15 (163 mg, 0.355 mmol) in DCM (3 mL) was stirred at room temperature for 1 h. The reaction was quenched with a saturated aqueous solution of $NaHCO_3$ and extracted with DCM (3×5 mL), the organic extracts were passed through a phase separator, concentrated in vacuo, to afford the title compound in quantitative yield (mix of diastereomers) as a colourless gum $[M+H]^+$ m/z 359.3

(CIS)—N-ethyl-2-oxo-7-({[(CIS)-4-phenylcyclohexyl]oxy}methyl)-3-oxa-1,8-diazaspiro[5.5]undecane-8-carboxamide (11) & (Trans)-N-ethyl-2-oxo-7-({[(CIS)-4-phenylcyclohexyl]oxy}methyl)-3-oxa-1,8-diazaspiro[5.5]undecane-8-carboxamide (12)

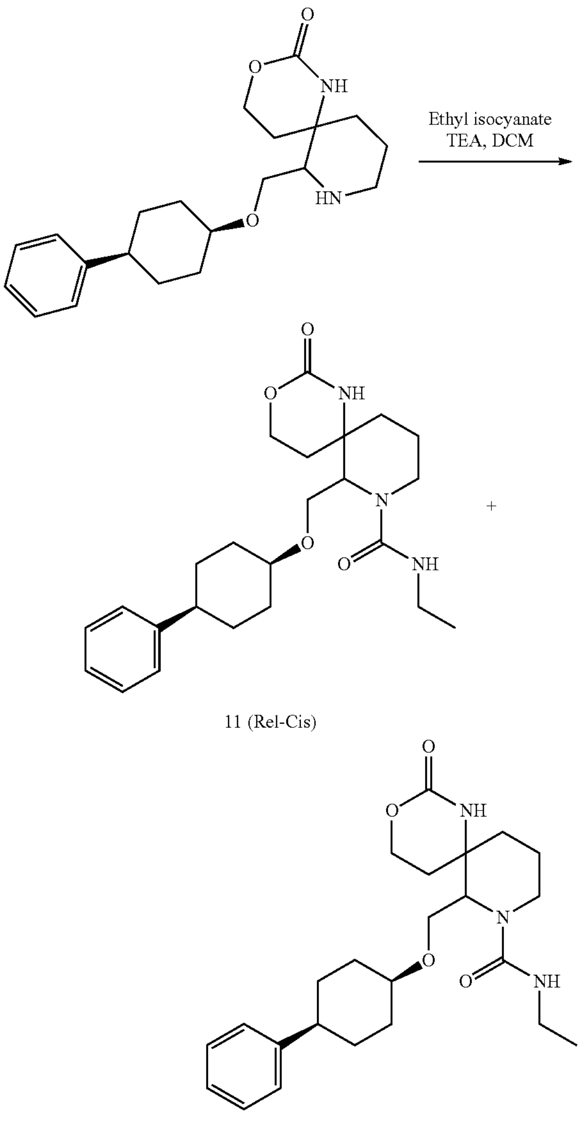

11 (Rel-Cis)

12 (Rel-Trans)

Intermediate 16 was dissolved in DCM (3 mL), and triethylamine (99 μL, 0.711 mmol) then ethyl isocyanate (56 μL, 0.711 mmol) were added sequentially at room temperature. The reaction was stirred for 2 h, quenched with 2 M NaOH and extracted with DCM. The organic extracts were passed through a phase separator and concentrated in vacuo. The crude material was purified by reverse column chromatography (10-60% MeCN in water (0.1% $NH_3$)), to afford the title compound (Example 11) 128 mg as a white solid and (Example 12) 18 mg as a pale yellow solid.

$^1H$ NMR (400 MHz, $CDCl_3$) δ 7.33-7.27 (m, 2H), 7.23-7.14 (m, 3H), 6.02 (s, 1H), 4.42-4.19 (m, 3H), 3.91 (d, J=11.9 Hz, 1H), 3.87-3.73 (m, 2H), 3.69-3.61 (m, 1H), 3.31-3.13 (m, 2H), 3.08-2.94 (m, 1H), 2.60-2.46 (m, 1H), 2.30-2.20 (m, 1H), 2.07-1.91 (m, 3H), 1.77-1.61 (m, 8H), 1.61-1.47 (m, 2H), 1.10 (t, J=7.2 Hz, 3H). 1H exchanged with solvent. LCMS (Method A): $[M+H]^+$ m/z 430.4, RT 3.15 minutes (example 11)

$^1H$ NMR (400 MHz, $CDCl_3$) δ 7.34-7.27 (m, 2H), 7.22-7.15 (m, 3H), 5.88-5.80 (m, 1H), 4.40-4.27 (m, 2H), 4.14 (dd, J=13.1, 4.2 Hz, 1H), 3.96-3.89 (m, 1H), 3.75-3.54 (m, 3H), 3.23 (q, J=7.2 Hz, 2H), 2.90 (td, J=13.2, 3.3 Hz, 1H), 2.61-2.46 (m, 1H), 2.14-2.01 (m, 1H), 2.01-1.73 (m, 6H), 1.72-1.64 (m, 5H), 1.63-1.44 (m, 2H), 1.12 (t, J=7.2 Hz, 3H). $^1H$ exchanged with solvent. LCMS (Method A): $[M+H]^+$ m/z 430.4, RT 3.40 minutes (example 12)

Example 13: (6S,7S)—N-ethyl-2-oxo-7-({[(CIS)-4-phenylcyclohexyl]oxy}methyl)-3-oxa-1,8-diazaspiro[5.5]undecane-8-carboxamide (13)

Example 14: (6R,7R)—N-ethyl-2-oxo-7-({[(CIS)-4-phenylcyclohexyl]oxy}methyl)-3-oxa-1,8-diazaspiro[5.5]undecane-8-carboxamide (14)

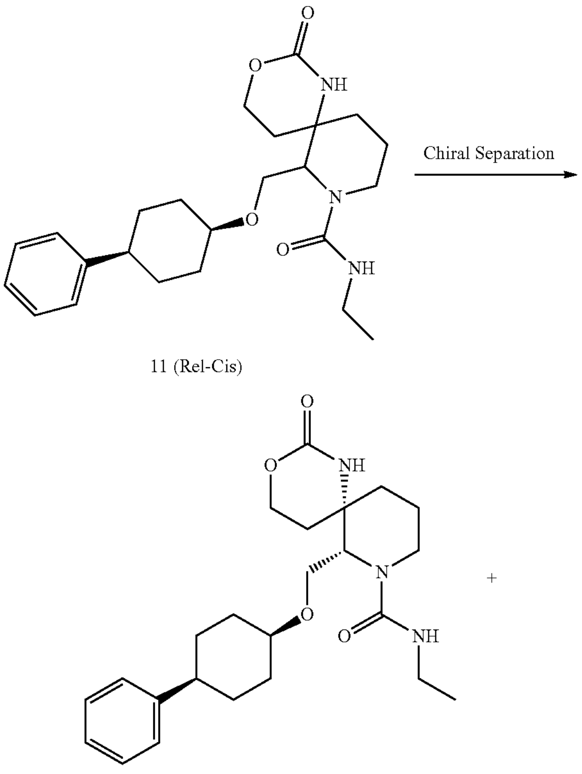

11 (Rel-Cis)

13

-continued

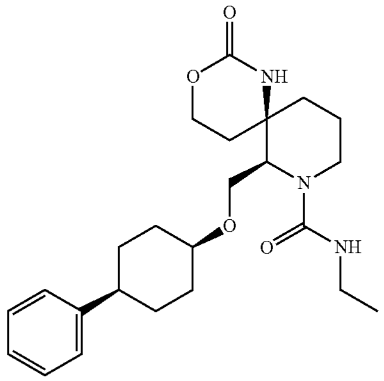

14

Example 11 (109 mg) was subjected to chiral preparative purification using Waters 600 eluting with 70/30% v/v n-Hexane/Ethanol, Chiralpak AS-H (25×2.0 cm), 5 μm, flow rate 17 mL/minutes to afford the title compounds (Peak 1, 70.2 mg, 100% ee; and Peak 2, 26.4 mg, 100% ee). The absolute stereochemistry of each separated compound 13 and 14 was not conclusively determined but assigned as shown below.

Peak 1 (was assigned 6S,7S at piperidine); $^1$H NMR (400 MHz, $CDCl_3$) δ 7.30 (d, J=7.0 Hz, 2H), 7.21 (d, J=7.5 Hz, 3H), 5.54-5.35 (m, 1H), 4.74 (brs., 1H), 4.34 (dd, J=4.9, 3.6 Hz, 3H), 3.78 (d, J=3.5 Hz, 1H), 3.91-3.77 (m, 3H), 3.66 (brs., 1H), 3.31-3.18 (m, 2H), 3.17-3.06 (m, 1H), 2.56 (t, J=7.6 Hz, 1H), 2.24 (d, J=13.9 Hz, 1H), 1.97-2.09 (m, 3H), 1.71 (brs., 8H), 1.59 (d, J=2.4 Hz, 1H), 1.13 (t, J=7.1 Hz, 3H). LCMS (Method C): $[M+H]^+$ m/z 430.3, RT 0.96 minutes. Chiral analysis (Chiralpak AS-H, 25×0.46 cm, 5 m, 70:30 n-Hexane:Ethanol): RT 6.4 minutes.

Peak 2 (was assigned 6R,7R at piperidine): $^1$H NMR (400 MHz, $CDCl_3$) δ 7.30 (d, J=7.0 Hz, 2H), 7.21 (d, J=7.5 Hz, 3H), 5.35 (s, 1H), 4.78-4.68 (m, 1H), 4.46-4.26 (m, 3H), 3.82-3.77 (m, 1H), 3.91-3.76 (m, 3H), 3.66 (t, J=2.6 Hz, 1H), 3.32-3.18 (m, 2H), 3.18-3.06 (m, 1H), 2.56 (dt, J=15.7, 7.7 Hz, 1H), 2.24 (d, J=13.9 Hz, 1H), 2.08-1.97 (m, 3H), 1.78-1.68 (m, 8H), 1.65-1.59 (m, 1H), 1.13 (t, J=7.2 Hz, 3H). LCMS (Method C): $[M+H]^+$ m/z 430.3, RT 0.96 minutes. Chiral analysis (Chiralpak AS-H, 25×0.46 cm, 5 dm, 70:30 n-Hexane:Ethanol): RT 11.7 minutes.

Example 15: (CIS)—N-ethyl-7-oxo-1-({[(CIS)-4-phenylcyclohexyl]oxy}methyl)-9-oxa-2,6-diazaspiro[4.5]decane-2-carboxamide (15)

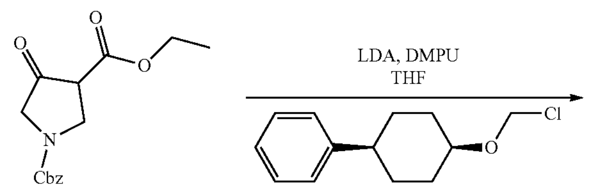

-continued

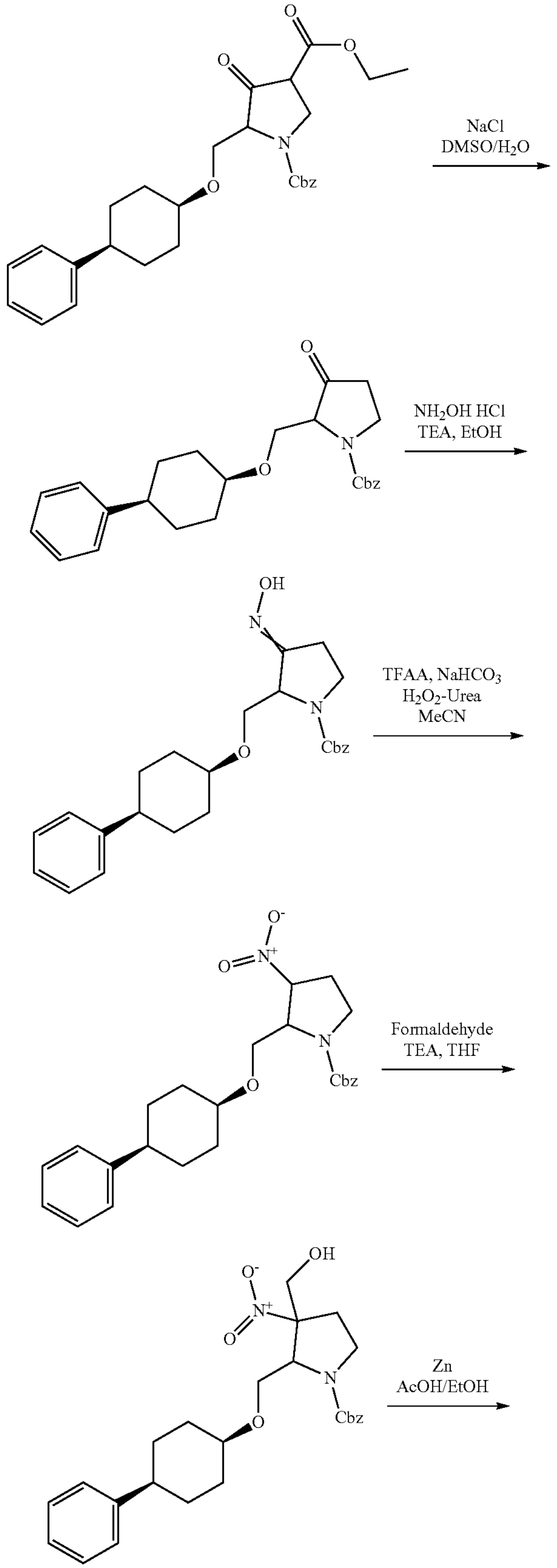

-continued

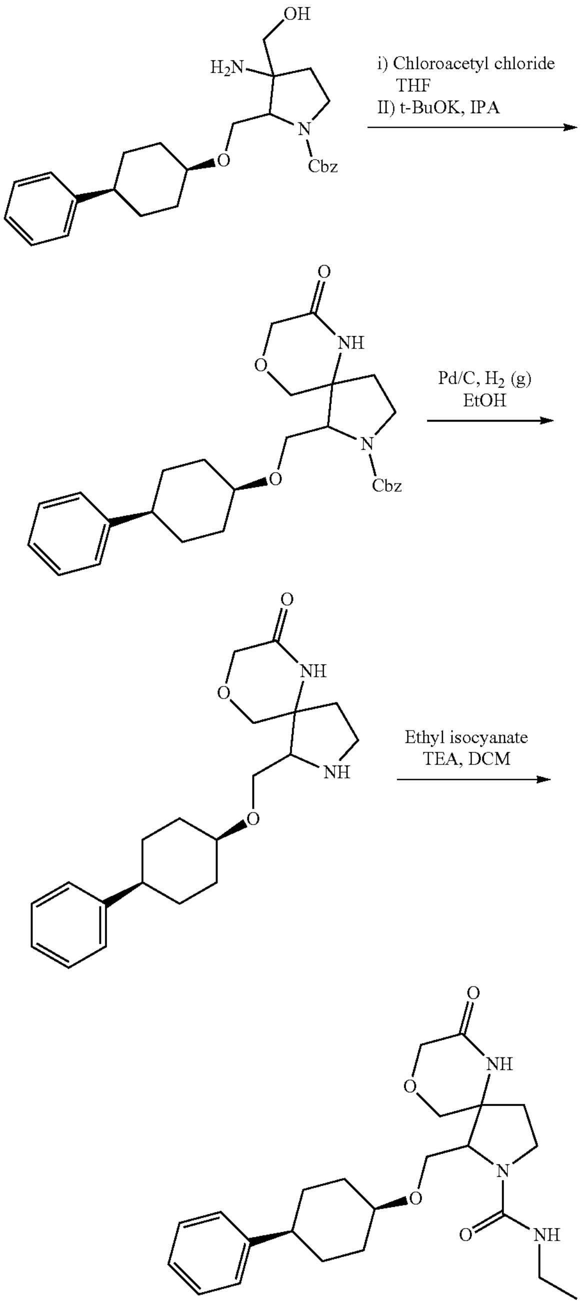

15

1-benzyl 3-ethyl 4-oxo-5-({[(CIS)-4-phenylcyclohexyl]oxy}methyl)pyrrolidine-1,3-dicarboxylate (Intermediate 17)

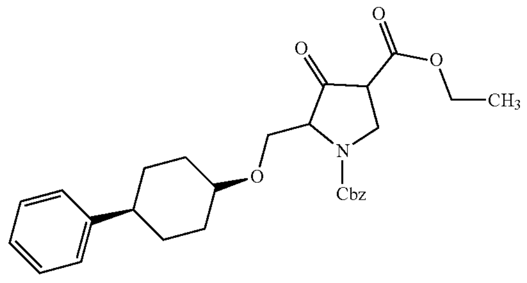

To a solution of 4-phenylcyclohexanol (5.00 g, 28.4 mmol) in anhydrous DCM (67 mL) was added paraformaldehyde (0.85 g, 28.4 mmol) followed by chloro(trimethyl) silane (14 mL, 0.113 mol) and mixture was stirred for 2 h at room temperature. The reaction was filtered through sodium sulfate, concentrated in vacuo at 30° C. and gave a colourless oil of 4-(chloromethoxy)cyclohexyl]benzene. In a separate flask 2 M (diisopropylamino)lithium (2 M in THF) (31 mL, 62.4 mmol) was added to a stirred solution of 1-benzyl 3-ethyl 4-oxopyrrolidine-1,3-dicarboxylate (8.26 g, 28.4 mmol) in anhydrous THF (50 mL) and DMPU (14 mL, 0.113 mol) at −78° C. The reaction mixture was stirred at this temperature for 20 minutes. The oil containing [4-(chloromethoxy)cyclohexyl]benzene in anhydrous THF (15 mL) was added to the reaction mixture at −78° C. and mixture was stirred for 1 h. The reaction mixture was quenched with a saturated aqueous solution of $NH_4Cl$ (50 mL) followed by water (50 mL) then extracted with EtOAc (3×50 mL). The combined organic layers were washed with brine (50 mL), dried over $Na_2SO_4$ and concentrated in vacuo to afford the crude material. The crude material was purified by silica gel column chromatography (0-100% EtOAc in heptane), to afford the title compound (5.2 μm) as a pale yellow oil. $[M+H]^+$ m/z 480.2

Benzyl 3-oxo-2-({[(CIS)-4-phenylcyclohexyl]oxy}methyl)pyrrolidine-1-carboxylate (Intermediate 18)

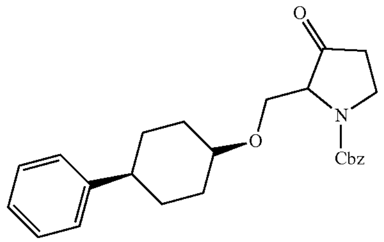

To a solution of Intermediate 17 (30%, 5.00 g, 3.13 mmol) in DMSO (15 mL) was added sodium chloride (362 mg, 6.20 mmol) and water (1.5 mL) and reaction mixture was heated to 130° C. for 2 h. The reaction mixture was cooled to room temperature, quenched with water (50 mL) and extracted with TBME (2×50 mL). The combined organic layers were washed with water (3×25 mL), brine (50 mL), dried over $Na_2SO_4$ and concentrated in vacuo to afford the crude material. The crude material was purified by silica gel column chromatography (0-100% EtOAc in heptane), to afford the title compound (1.96 g) as a pale yellow oil. $[M+H]^+$ m/z 408.2

Benzyl-3-(hydroxyimino)-2-({[(CIS)-4-phenylcyclohexyl]oxy}methyl)pyrrolidine-1-carboxylate (Intermediate 19)

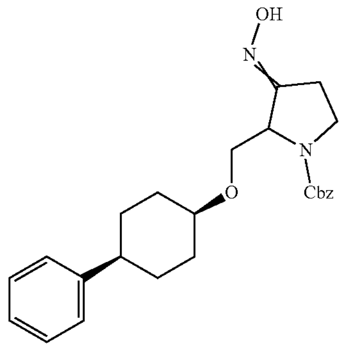 [SMILES: O=C(OCc1ccccc1)N1CCC(=NO)C1CO[C@H]1CC[C@@H](c2ccccc2)CC1]

A solution of triethylamine (2.0 mL, 14.4 mmol), hydroxylamine hydrochloride (1:1) (1.00 g, 14.4 mmol) and Intermediate 18 (1.96 g, 4.81 mmol) in ethanol (9.3193 mL) was heated to 90° C. for 1 h. The reaction mixture was cooled to room temperature, diluted with water (50 mL) and extracted with EtOAc (3×40 mL). The combined organic extracts were washed with brine (40 mL), dried over $MgSO_4$, filtered and concentrated in vacuo, to afford the title compound (2 g) as a pale yellow sticky oil. $[M+H]^+$ m/z 423.2

Benzyl 3-nitro-2-({[(CIS)-4-phenylcyclohexyl]oxy}methyl)pyrrolidine-1-carboxylate (Intermediate 20)

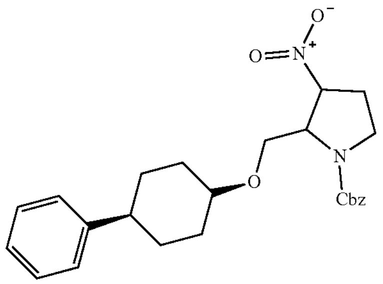

Trifluoroacetic anhydride (1.6 mL, 11.8 mmol) in anhydrous acetonitrile (8 mL) was added to a stirred solution of hydrogen peroxide-urea (1:1) (1.56 g, 16.6 mmol) in anhydrous acetonitrile (8 mL) at 0° C. The reaction was stirred at 0° C. for 2 h. The resulting solution was added dropwise to a mixture of Intermediate 19 (2.00 g, 4.73 mmol) and $NaHCO_3$ (1.99 g, 23.7 mmol) in anhydrous acetonitrile (11 mL) at room temperature. The mixture was then heated to 80° C., then stirred at 80° C. for 1 h. The reaction was cooled to room temperature and quenched with a saturated aqueous solution of $Na_2SO_3$, diluted with water (50 mL) and extracted with EtOAc (3×40 mL). The combined organic extracts were washed with brine (40 mL), dried over $MgSO_4$, filtered and concentrated in vacuo and gave a pale yellow gum. The crude material was purified by silica gel column chromatography (0-60% EtOAc in heptane), to afford the title compound (1.27 g) as a colourless oil. $[M+H]^+$ m/z 439.3

Benzyl (CIS)-3-(hydroxymethyl)-3-nitro-2-({[(CIS)-4-phenylcyclohexyl]oxy}methyl)pyrrolidine-1-carboxylate (Intermediate 21)

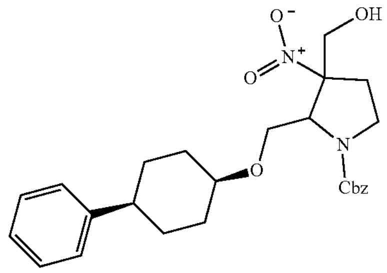 [SMILES: O=C(OCc1ccccc1)N1CCC(CO)([N+](=O)[O-])C1CO[C@H]1CC[C@@H](c2ccccc2)CC1]

Formaldehyde (in water) (37%, 1.9 mL, 26.1 mmol) was added to Intermediate 20 (1.27 g, 2.90 mmol) and triethylamine (0.48 mL, 3.48 mmol) in THF (16 mL) at room temperature. The solution was heated to 70° C. for 3.5 h. The reaction mixture was cooled to room temperature, diluted with water (30 mL) and extracted with EtOAc (3×30 mL). The combined organic extracts were washed with brine (40 mL), dried over $MgSO_4$, filtered and concentrated in vacuo. The crude material was purified by silica gel column chromatography (7-70% EtOAc in heptane), to afford the title compound (510 mg) as a sticky colourless oil. $[M+H]^+$ m/z 469.1

Benzyl (CIS) 3-amino-3-(hydroxymethyl)-2-({[(CIS)-4-phenylcyclohexyl]oxy}methyl)pyrrolidine-1-carboxylate (Intermediate 22)

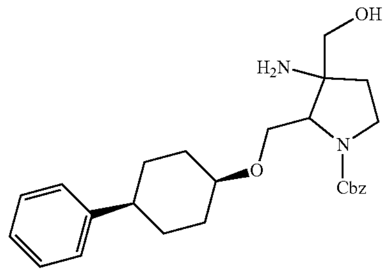 [SMILES: NC1(CO)CCN(C(=O)OCc2ccccc2)C1CO[C@H]1CC[C@@H](c2ccccc2)CC1]

A solution of Intermediate 21 (500 mg, 1.07 mmol) and zinc (698 mg, 10.7 mmol) in acetic acid (5 mL) and ethanol (35 mL) was stirred for 18 h at room temperature. The reaction was filtered through a pad of Celite and washed with Methanol. The filtrate was concentrated in vacuo, neutralized with a saturated aqueous solution of $NaHCO_3$ and extracted with DCM (3×30 mL). The combined organic extracts were washed with brine (30 mL), dried over $MgSO_4$, filtered and concentrated, to afford the title compound in quantitative yield as sticky brown foam. $[M+H]^+$ m/z 439.1.

Benzyl (CIS)-7-oxo-1-({[(CIS)-4-phenylcyclohexyl]oxy}methyl)-9-oxa-2,6-diazaspiro[4.5]decane-2-carboxylate (Intermediate 23)

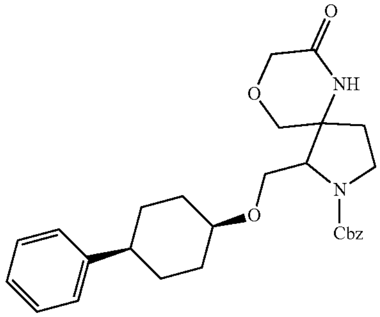 [SMILES: O=C1COCC2(CCN(C(=O)OCc3ccccc3)C2CO[C@H]2CC[C@@H](c3ccccc3)CC2)N1]

To a solution of Intermediate 22 (300 mg, 0.684 mmol) in THF (3 mL) at 0° C. was added dipotassium carbonate (284 mg, 2.05 mmol) then water (3 mL). To this mixture chloroacetyl chloride (76 μL, 0.958 mmol) was added dropwise at 0° C. The reaction was stirred for 1 h at 0° C. The mixture was quenched with water and extracted with DCM (3×20 mL). The combined organic extracts were washed with brine (20 mL), dried over $MgSO_4$, filtered and concentrated to give an oily residue. The intermediate was dissolved in DCM (6 mL) and IPA (6 mL), cooled to 0° C., potassium 2-methylpropan-2-olate (307 mg, 2.74 mmol) was added and the reaction was stirred at 0° C. for 1 h. The mixture was quenched with water (10 mL), left to stand at room temperature for 40 h. The mixture was poured onto a saturated aqueous solution of $NaHCO_3$ (20 ml). After extraction with DCM (3×20 mL), the combined organic extracts were washed with brine (20 mL), dried over $MgSO_4$, filtered and concentrated to give a pale yellow oil. The residue was purified by silica gel column chromatography (10-100% EtOAc in heptane), to afford the title compound (170 mg) as colourless oil. $[M+H]^+$ m/z 479.1

(CIS)-1-({[(CIS)-4-phenylcyclohexyl]oxy}methyl)-9-oxa-2,6-diazaspiro[4.5]decan-7-one (Intermediate 24)

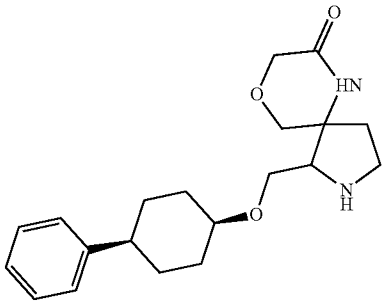 [SMILES: O=C1COCC2(CCNC2CO[C@H]2CC[C@@H](c3ccccc3)CC2)N1]

Intermediate 23 (150 mg, 0.313 mmol) was dissolved in ethanol (15 mL) and the atmosphere was evacuated and backfilled with nitrogen three times. Palladium on carbon (10%, 15 mg, 0.313 mmol) was added and the atmosphere was evacuated and backfilled with hydrogen 3 times. The reaction was stirred for 2 h and then filtered through Celite, washed with EtOAc and concentrated in vacuo, to afford the title compound (75 mg) as a light brown gum. $[M+H]^+$ m/z 345.33

(CIS)—N-ethyl-7-oxo-1-({[(CIS)-4-phenylcyclohexyl]oxy}methyl)-9-oxa-2,6-diazaspiro[4.5]decane-2-carboxamide (Example 15)

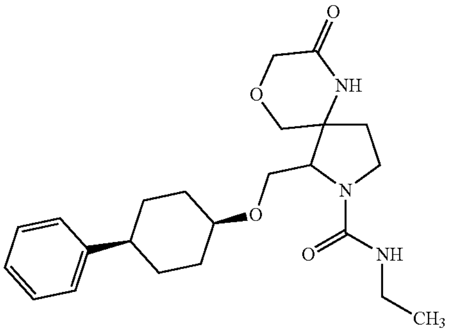 [SMILES: CCNC(=O)N1CCC2(COCC(=O)N2)C1CO[C@H]1CC[C@@H](c2ccccc2)CC1]

Ethyl isocyanate (18 μL, 0.232 mmol) was added to a solution of triethylamine (32 μL, 0.232 mmol) and Intermediate 24 (40 mg, 0.116 mmol) in anhydrous DCM (0.8 mL) at room temperature. The reaction was stirred for 1 h and was then quenched with aq. 2 M NaOH and extracted with DCM (3×10 mL). The organic layers were combined, washed with brine (25 mL), passed through a phase separator and concentrated in vacuo. The crude material was purified by reverse phase column chromatography (10-60% MeCN in water (0.1% $NH_3$)), to afford the title compound (29 mg) as a white solid.

$^1$H NMR (400 MHz, $CDCl_3$) δ 7.35-7.28 (m, 2H), 7.24-7.17 (m, 3H), 6.41 (s, 1H), 4.45 (s, 1H), 4.25 (d, J=16.7 Hz, 1H), 4.18 (d, J=16.7 Hz, 1H), 4.09 (t, J=2.3 Hz, 1H), 3.99 (dd, J=10.3, 2.1 Hz, 1H), 3.73 (d, J=11.7 Hz, 1H), 3.69-3.64 (m, 1H), 3.61 (dd, J=10.3, 3.0 Hz, 1H), 3.55 (d, J=11.7 Hz, 1H), 3.51-3.42 (m, 1H), 3.38-3.18 (m, 3H), 2.56 (tt, J=10.9, 5.3 Hz, 1H), 2.44-2.30 (m, 1H), 2.28-2.15 (m, 1H), 2.12-1.95 (m, 2H), 1.80-1.44 (m, 6H), 1.13 (t, J=7.2 Hz, 3H). LCMS (Method A): $[M+H]^+$ m/z 416.4, RT 3.07 minutes.

Example 16: (1R,5S)—N-ethyl-7-oxo-1-({[(CIS)-4-phenylcyclohexyl]oxy}methyl)-9-oxa-2,6-diazaspiro[4.5]decane-2-carboxamide (16)

Example 17: (1S,5R)—N-ethyl-7-oxo-1-({[(CIS)-4-phenylcyclohexyl]oxy}methyl)-9-oxa-2,6-diazaspiro[4.5]decane-2-carboxamide (17)

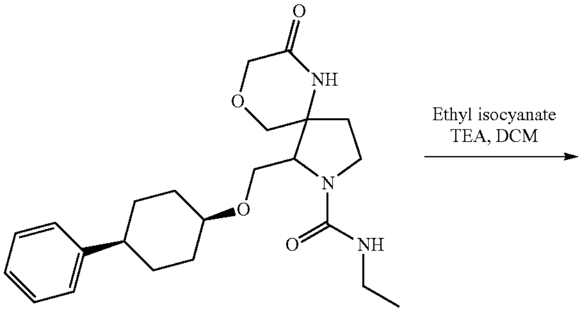

15

-continued

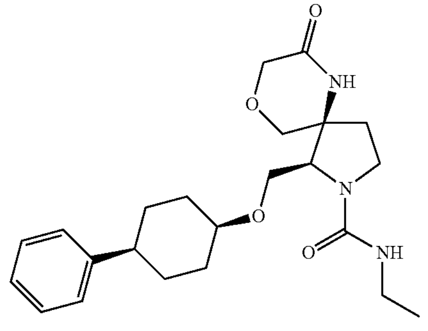

16

+

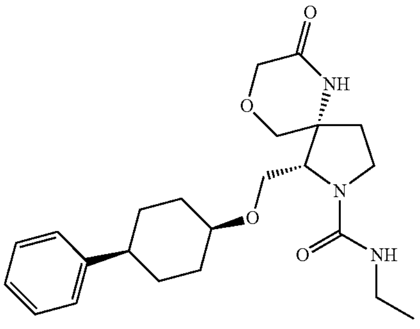

17

Example 15 (22 mg) was subjected to chiral preparative purification using Waters 600 eluting with 80/20% v/v n-Hexane/Ethanol, Chiralpak AD-H (25×2.0 cm), 5 μm, flow rate 17 mL/minutes to afford the title compounds (Peak 1, 9.4 mg, 100% ee; and Peak 2, 9.1 mg, 100% ee). The absolute stereochemistry of each separated compound 16 and 17 was not conclusively determined but assigned as shown below.

Peak 1 (was assigned 1R,5S at pyrrolidine); $^1H$ NMR (400 MHz, $CDCl_3$) δ 7.30 (dd, J=8.1, 6.9 Hz, 2H), 7.24-7.16 (m, 3H), 6.37 (s, 1H), 4.42 (s, 1H), 4.30-4.13 (m, 2H), 4.07 (t, J=2.6 Hz, 1H), 3.98 (dd, J=10.4, 2.3 Hz, 1H), 3.72 (d, J=11.7 Hz, 1H), 3.65 (q, J=2.9 Hz, 1H), 3.60 (dd, J=10.3, 3.0 Hz, 1H), 3.54 (d, J=11.7 Hz, 1H), 3.45 (td, J=9.5, 1.9 Hz, 1H), 3.36-3.17 (m, 3H), 2.61-2.49 (m, 1H), 2.42-2.29 (m, 1H), 2.24-2.15 (m, 1H), 2.07-1.98 (m, 2H), 1.77-1.45 (m, 6H), 1.12 (t, J=7.2 Hz, 3H). LCMS (Method C): $[M+H]^+$ m/z 416.3, RT 0.94 minutes. Chiral analysis (Chiralpak AD-H, 25×0.46 cm, 5 μm, 80:20 n-Hexane:Ethanol): RT 9.5 minutes.

Peak 2 (was assigned 1S,5R at pyrrolidine): $^1H$ NMR (400 MHz, $CDCl_3$) δ 7.34-7.27 (m, 2H), 7.24-7.16 (m, 3H), 6.37 (s, 1H), 4.42 (s, 1H), 4.28-4.12 (m, 2H), 4.07 (t, J=2.5 Hz, 1H), 3.98 (dd, J=10.4, 2.3 Hz, 1H), 3.72 (d, J=11.7 Hz, 1H), 3.65 (t, J=2.9 Hz, 1H), 3.60 (dd, J=10.3, 3.0 Hz, 1H), 3.54 (d, J=11.7 Hz, 1H), 3.45 (td, J=9.6, 2.0 Hz, 1H), 3.37-3.17 (m, 3H), 2.63-2.50 (m, 1H), 2.43-2.31 (m, 1H), 2.24-2.15 (m, 1H), 2.07-1.98 (m, 2H), 1.78-1.44 (m, 6H), 1.12 (t, J=7.2 Hz, 3H). LCMS (Method C): $[M+H]^+$ m/z 416.3, RT 0.94 minutes. Chiral analysis (Chiralpak AD-H, 25×0.46 cm, 5 μm, 80:20 n-Hexane:Ethanol): RT 14.7 minutes.

Example 18: (CIS)—N-ethyl-2-oxo-6-({[(CIS)-4-phenylcyclohexyl]oxy}methyl)-3-oxa-1,7-diazaspiro[4.4]nonane-7-carboxamide (18)

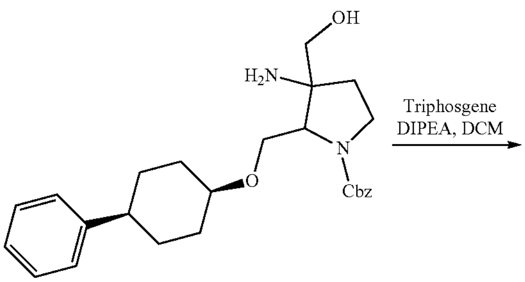

INTERMEDIATE 22

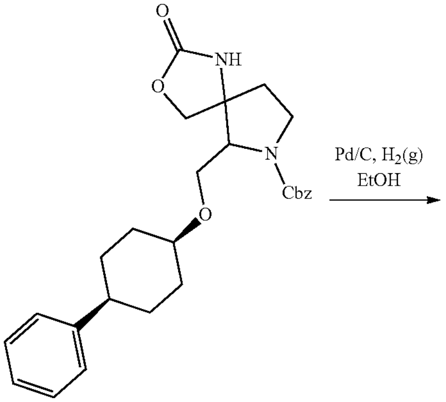

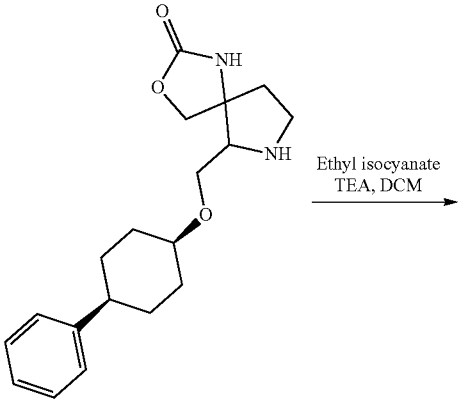

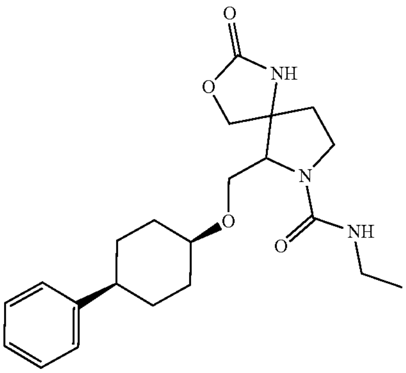

18

Benzyl (CIS)-2-oxo-6-({[(CIS)-4-phenylcyclohexyl]oxy}methyl)-3-oxa-1,7-diazaspiro[4.4]nonane-7-carboxylate (Intermediate 25)

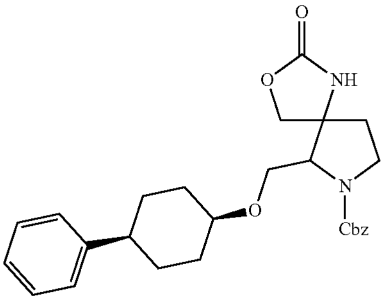 [SMILES: O=C1NC2(CCN(C(=O)OCc3ccccc3)C2CO[C@H]2CC[C@@H](c3ccccc3)CC2)CO1]

N-ethyl-N-(propan-2-yl)propan-2-amine (50 μL, 0.286 mmol) was added to a stirred solution of Intermediate 22 (110 mg, 0.251 mmol) and bis(trichloromethyl) carbonate (74 mg, 0.251 mmol) in anhydrous DCM (3 mL) at 0° C. Reaction was stirred at 0° C. for 1 h, then quenched with a saturated aqueous solution of $NaHCO_3$ solution (1 mL) and purged with $N_2$(g) for 30 min using 20% NaOH scrubber to quench excess of phosgene gas. The solution was extracted with DCM (3×3 mL) and passed through a phase separator and concentrated in vacuo to give a gum. The crude material was purified by silica gel column chromatography (0-50% EtOAc in heptane), to afford the title compound (57 mg) as a white gum. $[M+H]^+$ m/z 465.4

(CIS)-6-({[(CIS)-4-phenylcyclohexyl]oxy}methyl)-3-oxa-1,7-diazaspiro[4.4]nonan-2-one (Intermediate 26)

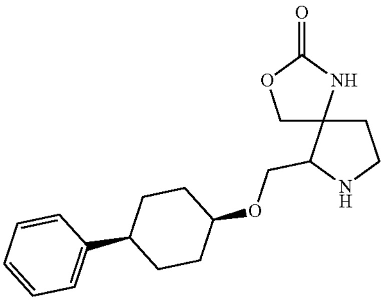 [SMILES: O=C1NC2(CCNC2CO[C@H]2CC[C@@H](c3ccccc3)CC2)CO1]

A stirred solution of Intermediate 25 (57 mg, 0.123 mmol) and palladium on carbon (10%, 13 mg, 0.123 mmol) in ethanol (6 mL) was stirred at room temperature under an atmosphere of hydrogen. The reaction was stirred for 2 h then filtered through a pad of Celite, washed with methanol and concentrated in vacuo, to afford the title compound (39 mg) as a white residue. $[M+H]^+$ m/z 331.3

(CIS)—N-ethyl-2-oxo-6-({[(CIS)-4-phenylcyclohexyl]oxy}methyl)-3-oxa-1,7-diazaspiro[4.4]nonane-7-carboxamide (18)

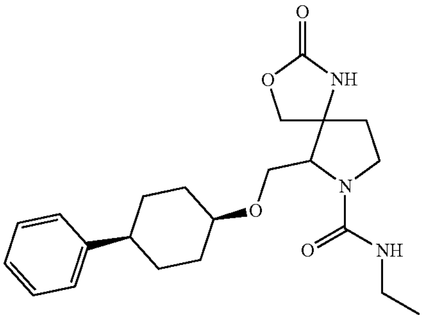 [SMILES: CCNC(=O)N1CCC2(COC(=O)N2)C1CO[C@H]1CC[C@@H](c2ccccc2)CC1]

To a stirred solution of triethylamine (28 μL, 0.201 mmol) and Intermediate 26 (33 mg, 0.100 mmol) in DCM (1.5 mL) was added ethyl isocyanate (16 μL, 0.202 mmol) at room temperature. The reaction was stirred for 1 h and was quenched with aq. 2 M NaOH (3 mL). The mixture was extracted with DCM (3×3 mL), the organic extracts were passed through a phase separator and concentrated in vacuo. The crude material was purified by reverse phase column chromatography (10-60% MeCN in water (0.1% $NH_3$), to afford the title compound (17 mg) as a white solid.

$^1$H NMR (400 MHz, $CDCl_3$) δ 7.34-7.27 (m, 2H), 7.22-7.15 (m, 3H), 5.51 (s, 1H), 4.59 (s, 1H), 4.32 (d, J=8.6 Hz, 1H), 4.23 (d, J=8.6 Hz, 1H), 3.97-3.90 (m, 2H), 3.66-3.63 (m, 1H), 3.61 (dd, J=11.0, 4.2 Hz, 1H), 3.43 (td, J=9.3, 2.2 Hz, 1H), 3.36-3.18 (m, 3H), 2.61-2.45 (m, 2H), 2.14 (ddd, J=12.3, 7.2, 2.1 Hz, 1H), 2.06-1.93 (m, 2H), 1.77-1.44 (m, 6H), 1.12 (t, J=7.2 Hz, 3H). LCMS (Method A): $[M+H]^+$ m/z 402.5, RT 3.02 minutes Example 19: Methyl 7-({[1,1'-biphenyl]-3-yl}methyl)-2-oxo-3-oxa-1,8-diazaspiro[5.5]undecane-8-carboxylate

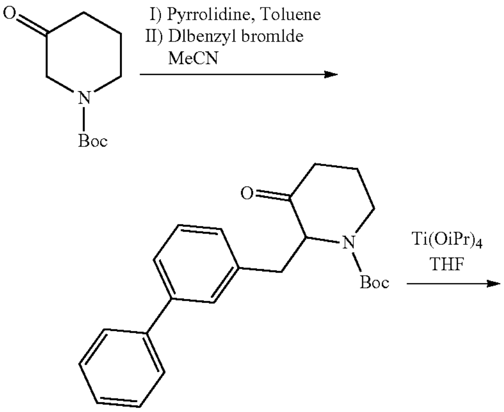

-continued

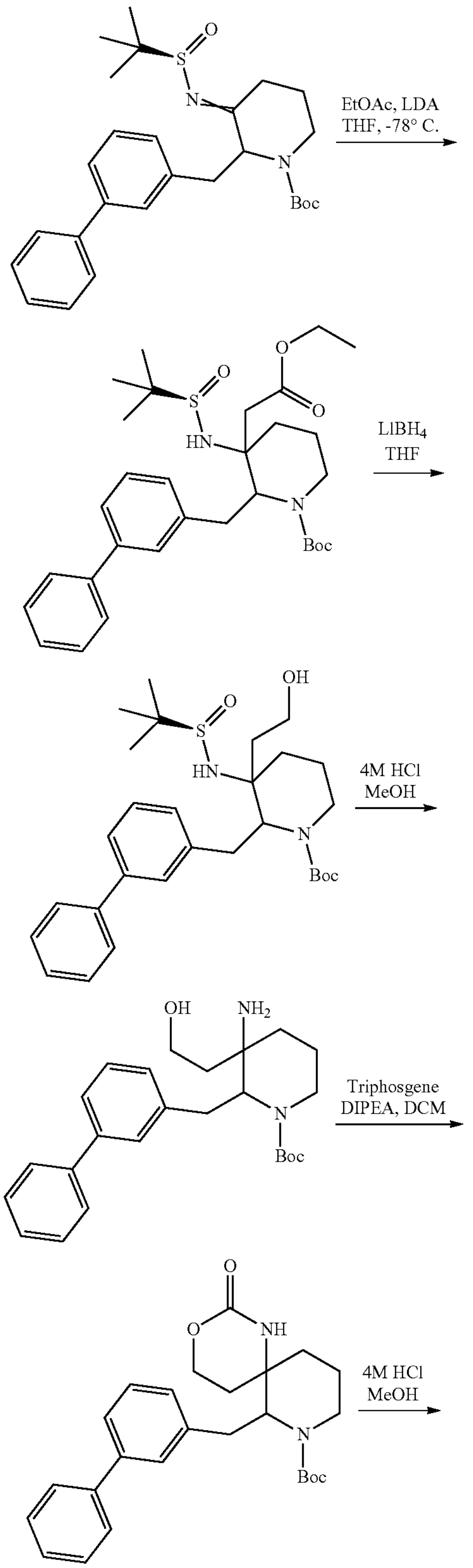

-continued

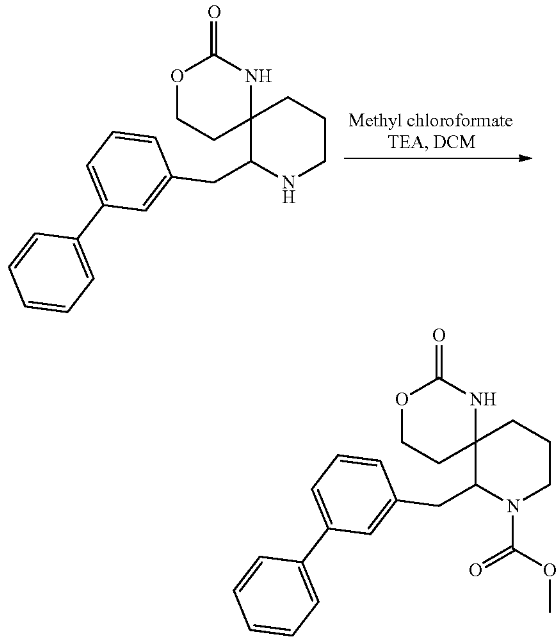

19 tert-butyl 2-({[1,1'-biphenyl]-3-yl}methyl)-3-oxopiperidine-1-carboxylate (Intermediate 27)

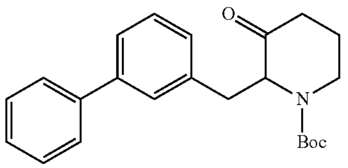 [SMILES: CC(C)(C)OC(=O)N1CCCC(=O)C1Cc1cccc(-c2ccccc2)c1]

A solution of pyrrolidine (6.3 mL, 75.3 mmol) and tert-butyl 3-oxopiperidine-1-carboxylate (10 g, 50.2 mmol) in toluene (150 mL) were heated to reflux using a Dean-Stark trap for 1.5 h. The reaction mixture was cooled to room temperature, evaporated to dryness to afford the crude material. This was dissolved in acetonitrile (100 mL) and treated with 3-(bromomethyl)biphenyl (14.88 g, 60.2 mmol) in acetonitrile (50 mL) at room temperature and mixture was heated at 85° C. for 16 h. The reaction mixture cooled to room temperature, evaporated to afford the crude material. This was dissolved in water (100 mL) then extracted with EtOAc (2×100 mL). The combined organic layers were washed with brine (100 mL), dried over $Na_2SO_4$, filtered and evaporated to dryness to afford the crude material. The crude material was purified by silica gel column chromatography (0-20% EtOAc) in heptane, to afford the title compound (14 g) as an orange oil. $[M+Na]^+$ m/z 388.2 tert-butyl-2-({[1,1'-biphenyl]-3-yl}methyl)-3-{[(R)-2-methylpropane-2-sulfinyl]imino}piperidine-1-carboxylate (Intermediate 28)

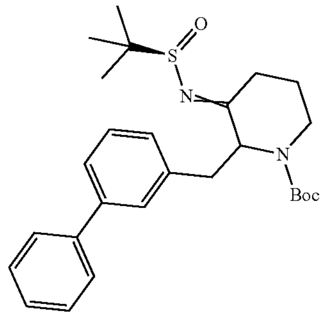 [SMILES: CC(C)(C)OC(=O)N1CCCC(=N[S@](=O)C(C)(C)C)C1Cc1cccc(-c2ccccc2)c1]

Intermediate 27 (2.50 g, 6.84 mmol), 2-methylpropane-2-sulfinamide (0.83 g, 6.84 mmol), and titanium(4+) tetraethanolate (2.9 mL, 13.7 mmol) were dissolved in THF (50 mL). The solution was heated at 60° C. for 3 h under $N_2$(g) atmosphere. The reaction was cooled to room temperature and poured into a saturated aqueous solution of $NaHCO_3$ solution (25 mL), filtered through a pad of Celite which was washed with DCM (2×25 mL). The organic layer was separated and the aqueous layer extracted with DCM (2×25 mL) and combined organic layers were dried over $MgSO_4$ and concentrated in vacuo. The crude material was purified by silica gel column chromatography (0-60% EtOAc in heptane), to afford the title compound (2.35 g) as a yellow oil. $[M+H]^+$ m/z 469.5.

tert-butyl 2-({[1,1'-biphenyl]-3-yl}methyl)-3-(2-ethoxy-2-oxoethyl)-3-{[(R)-2-methylpropane-2-sulfinyl]amino}piperidine-1-carboxylate (Intermediate 29)

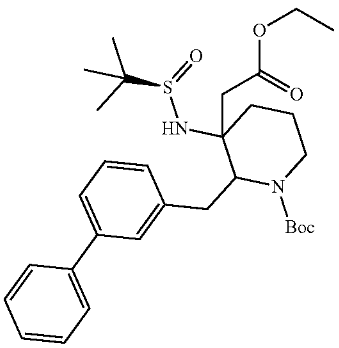 [SMILES: CCOC(=O)CC1(N[S@](=O)C(C)(C)C)CCCN(C(=O)OC(C)(C)C)C1Cc1cccc(-c2ccccc2)c1]

A solution of 2 M lithium dipropan-2-ylazanide (21 mL, 42.7 mmol) was added to the stirred solution of EtOAc (4.2 mL, 42.7 mmol) in THF (20 mL) at −78° C. and mixture was stirred for 30 minutes. A drop wise solution of Intermediate 28 (2.00 g, 4.27 mmol) in anhydrous THF (10 mL) was added to the above mixture at −78° C. and stirred for 1 h. The reaction mixture was quenched with a saturated aqueous solution of $NH_4C_1$ (20 mL) followed by water (20 mL) at −78° C., warmed up to room temperature and extracted with EtOAc (3×50 mL). The combined organic layers were washed with brine (50 mL), dried over $Na_2SO_4$, filtered and evaporated to dryness to afford the crude material. The crude material was purified by silica gel column chromatography (0-100% EtOAc in heptane), to afford the title compound (1.4 g) as a pale orange oil. $[M+H]^+$ m/z 557.6 tert-butyl 2-({[1,1'-biphenyl]-3-yl}methyl)-3-(2-hydroxyethyl)-3-{[(R)-2-methylpropane-2-sulfinyl]amino}piperidine-1-carboxylate (Intermediate 30)

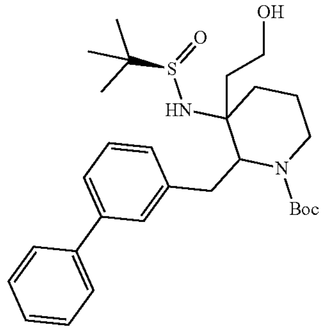 [SMILES: CC(C)(C)OC(=O)N1CCCC(CCO)(N[S@](=O)C(C)(C)C)C1Cc1cccc(-c2ccccc2)c1]

A solution of lithium tetrahydroborate (4M in THF) (900 μL, 3.60 mmol) was added dropwise to the stirred solution of Intermediate 29 (1.26 g, 2.26 mmol) in anhydrous THF (18 mL) at 0° C. and stirred for 15 minutes. The reaction mixture warmed up to room temperature and stirred for 3 h. Additional lithium tetrahydroborate (4M in THF) (2.0 mL, 8.00 mmol) was added and stirred at room temperature for 18 h. Additional 4 M lithium tetrahydroborate in THF (2.0 mL, 8.00 mmol) was added and stirred at room temperature for 2 h. The reaction mixture was further treated with lithium tetrahydroborate (4M in THF) (4.0 mL, 16.00 mmol) and stirred at room temperature for 18 h. The reaction mixture was carefully quenched with water (25 mL), followed by a saturated aqueous solution of $NH_4Cl$ (25 mL) and extracted with EtOAc (3×50 mL). The combined organic layers were washed with brine (50 mL), dried over $Na_2SO_4$, filtered and evaporated to dryness to afford the crude material. The crude material was purified by silica gel column chromatography (0-100% EtOAc in heptane), to afford the title compound (1 g) as an off white solid. $[M+H]^+$ m/z 515.6 tert-butyl 3-amino-2-({[1,1'-biphenyl]-3-yl}methyl)-3-(2-hydroxyethyl)piperidine-1-carboxylate (Intermediate 31)

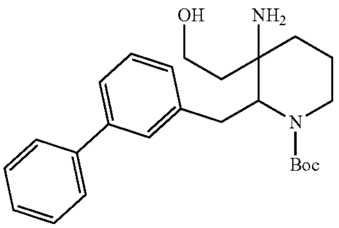 [SMILES: CC(C)(C)OC(=O)N1CCCC(N)(CCO)C1Cc1cccc(-c2ccccc2)c1]

Intermediate 30 (900 mg, 1.75 mmol) was dissolved in methanol (15 mL) and cooled to 0° C. Hydrogen chloride (4M in dioxane) (450 μL, 1.80 mmol) was added dropwise and the reaction was stirred at 0° C. for 3 h. Additional Hydrogen chloride (4M in dioxane) (50 μL, 0.200 mmol)

was added and mixture was stirred for 2 h. The reaction was quenched at 0° C. by the dropwise addition of a saturated aqueous solution of $NaHCO_3$ (10 mL) and extracted with 10% methanol in DCM (3×5 mL). The combined organic layers were filtered through phase separator, evaporated to dryness to afford the crude. The crude material was purified by silica gel column chromatography (0-100% EtOAc in heptane followed by 0-10% methanol in DCM), to afford the title compound (700 mg) as an off white solid. $[M+H]^+$ m/z 411.4 tert-butyl 7-({[1,1'-biphenyl]-3-yl}methyl)-2-oxo-3-oxa-1,8-diazaspiro[5.5]undecane-8-carboxylate (Intermediate 32)

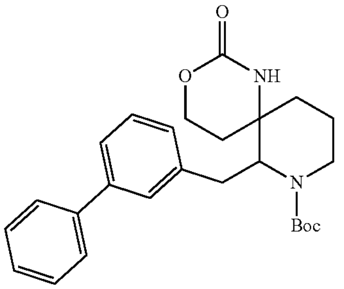 [SMILES: CC(C)(C)OC(=O)N1CCCC2(CCOC(=O)N2)C1Cc1cccc(-c2ccccc2)c1]

N-ethyl-N-(propan-2-yl)propan-2-amine (360 µL, 2.07 mmol) was added dropwise to the stirred solution of Intermediate 32 (700 mg, 1.71 mmol) and bis(trichloromethyl) carbonate (600 mg, 2.02 mmol) in DCM (10 mL) at 0-10° C. and stirred for 2 h. The reaction mixture was carefully quenched with a saturated aqueous solution of $NaHCO_3$ (5 mL) and purged with $N_2$(g) for 30 min using 20% NaOH scrubber to quench phosgene gas then extracted with DCM (2×25 mL). The combined organic layers were dried over $Na_2SO_4$, filtered, concentrated in vacuo to afford the crude material. The crude material was purified by silica gel column chromatography (0-100% EtOAc in heptane), to afford the title compound (587 mg) as an off white solid. $[M+H]^+$ m/z 437.5.

7-({[1,1'-biphenyl]-3-yl}methyl)-3-oxa-1,8-diazaspiro[5.5]undecan-2-one (Intermediate 33)

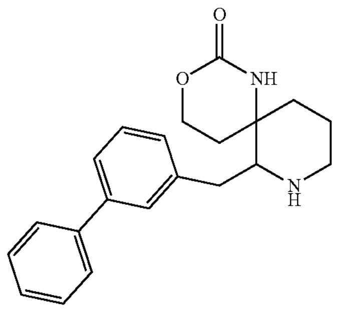 [SMILES: O=C1NC2(CCCNC2Cc2cccc(-c3ccccc3)c2)CCO1]

Intermediate 32 (200 mg, 0.458 mmol) was dissolved in DCM (2 mL) then dropwise solution of TFA (1 mL) was added and mixture was stirred at room temperature for 1 h. The reaction was quenched with a saturated aqueous solution of $Na_2CO_3$ solution (10 mL) and the extracted with DCM (2×10 mL). The organic layers were combined, passed through a phase separator, evaporated to dryness, to afford the title compound (150 mg) as an off white solid. $[M+H+MeCN]^+$ m/z 378.6

Methyl 7-({[1,1'-biphenyl]-3-yl}methyl)-2-oxo-3-oxa-1,8-diazaspiro[5.5]undecane-8-carboxylate (19)

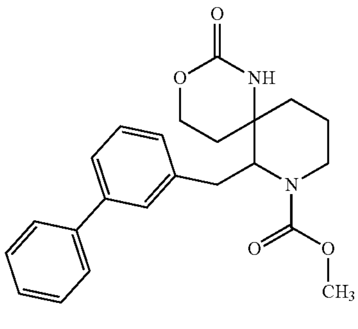 [SMILES: COC(=O)N1CCCC2(CCOC(=O)N2)C1Cc1cccc(-c2ccccc2)c1]

Methyl carbonochloridate (200 µL, 2.59 mmol) was added dropwise to the stirred solution of Intermediate 33 (151 mg, 0.448 mmol) and triethylamine (370 µL, 2.65 mmol) in DCM (3 mL) at room temperature and stirred for 30 minutes. The reaction mixture was quenched with water (10 mL) then extracted with DCM (2×10 mL). The combined organic layers were washed with brine (10 mL), dried over $Na_2SO_4$, filtered and evaporated to dryness to afford the crude material. The crude material was purified by silica gel column chromatography (0-100% EtOAc in heptane), to afford the title compound (154 mg) as an off white solid.

$^1H$ NMR (500 MHz, $CDCl_3$) δ 7.64-7.52 (m, 2H), 7.48-7.39 (m, 3H), 7.39-7.30 (m, 3H), 7.23-7.07 (m, 1H), 6.18 (brs, 1H), 4.82-3.84 (m, 5H), 3.14 (d, J=5.1 Hz, 2H), 3.07-2.89 (m, 2H), 2.22-2.13 (m, 1H), 2.09-1.89 (m, 2H), 1.87-1.62 (m, 4H). LCMS (Method A): $[M+H]^+$ m/z 395.2, RT 2.95 & 3.08 minutes Example 20: Methyl (6R,7S)-7-({[1,1'-biphenyl]-3-yl}methyl)-2-oxo-3-oxa-1,8-diazaspiro[5.5]undecane-8-carboxylate Example 21: Methyl (6S,7R)-7-({[1,1'-biphenyl]-3-yl}methyl)-2-oxo-3-oxa-1,8-diazaspiro[5.5]undecane-8-carboxylate Example 22: Methyl (6R,7R)-7-({[1,1'-biphenyl]-3-yl}methyl)-2-oxo-3-oxa-1,8-diazaspiro[5.5]undecane-8-carboxylate Example 23: Methyl (6S,7S)-7-({[1,1'-biphenyl]-3-yl}methyl)-2-oxo-3-oxa-1,8-diazaspiro[5.5]undecane-8-carboxylate

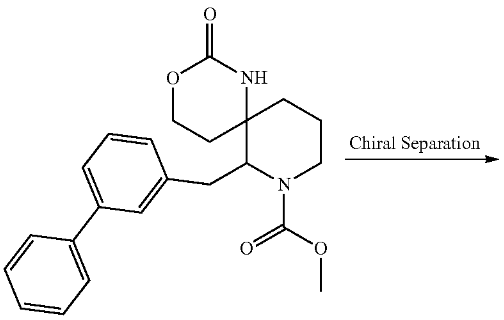

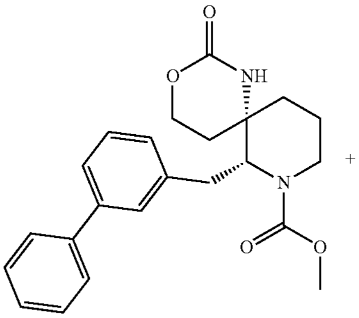

Dlastereomer 1
20

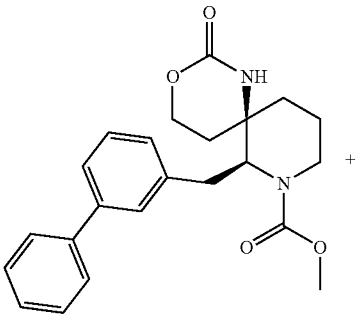

Dlastereomer 2
21

-continued

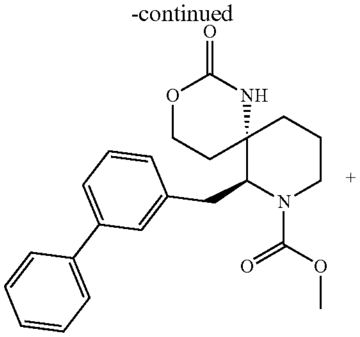

Dlastereomer 3
22

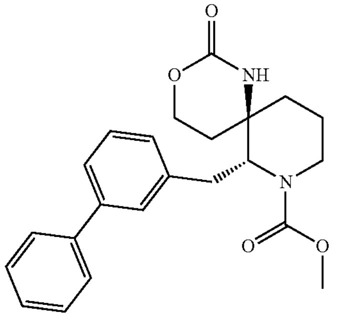

Dlastereomer 4
23

Example 19 (150 mg) was subjected to chiral SFC using Waters Prep SFC80 with a gradient of 20% ethanol, 80% $C_{02}$, Chiralpak AD-H, 10×250 mm, 5 μm, flow rate 15 mL/minutes, to afford the title compounds (Peak 1, 42 mg, 100% ee; and Peak 2, 34 mg, 100% ee, Peak 3, 5 mg, 100% ee, Peak 4, 12 mg, 100% ee as an off white solids. The absolute stereochemistry of compounds 10, 21, 22, and 23 was not conclusively determined but assigned as shown below.

Peak 1 (stereochemistry was assigned 6R,7S at piperidine); $^1H$ NMR (500 MHz, $CDCl_3$) δ 7.62-7.51 (m, 2H), 7.45-7.37 (m, 3H), 7.37-7.28 (m, 3H), 7.22-7.06 (m, 1H), 6.60 (s, 1H), 4.78 (d, J=8.4 Hz, 0.5H), 4.57-4.46 (m, 0.5H), 4.35-4.27 (m, 2H), 4.12 (d, J=11.8 Hz, 0.5H), 3.89 (d, J=12.1 Hz, 0.5H), 3.44 (s, 1H), 3.14 (s, 2H), 3.09-2.87 (m, 3H), 2.24-2.13 (m, 1H), 2.13-1.94 (m, 1H), 1.81-1.51 (m, 4H). LCMS (Method B): $[M+H]^+$ m/z 395.3, RT 2.93 minutes. Chiral analysis (Chiralpak AD-H, 4.6×250 mm, 5 μm, 80:20 $CO_2$: Ethanol): RT 5.68 minutes.

Peak 2 (stereochemistry was assigned 6S,7R at piperidine): $^1H$ NMR (500 MHz, $CDCl_3$) δ 7.63-7.51 (m, 2H), 7.46-7.38 (m, 3H), 7.38-7.29 (m, 3H), 7.22-7.06 (m, 1H), 6.15 (s, 1H), 4.78 (d, J=8.3 Hz, 0.5H), 4.60-4.37 (m, 0.5H), 4.36-4.29 (m, 2H), 4.13 (d, J=11.4 Hz, 0.5H), 3.90 (d, J=11.5 Hz, 0.5H), 3.45 (s, 1H), 3.14 (s, 2H), 3.06-2.92 (m, 3H), 2.22-2.15 (m, 1H), 2.08-1.90 (m, 1H), 1.72-1.66 (m, 4H). LCMS (Method B): $[M+H]^+$ m/z 395.3, RT 2.93 minutes. Chiral analysis (Chiralcel AD-H, 4.6×250 mm, 5 μm, 80:20 $CO_2$: Ethanol): RT 8.24 minutes.

Peak 3 (stereochemistry was assigned 6R,7R at piperidine); $^1H$ NMR (500 MHz, $CDCl_3$) δ 7.62-7.51 (m, 2H), 7.48-7.39 (m, 3H), 7.38-7.31 (m, 3H), 7.09 (d, J=7.4 Hz, 1H), 5.84 (s, 1H), 4.42-4.28 (m, 2H), 4.23 (t, J=11.2 Hz, 2H), 3.47 (s, 1H), 3.12 (s, 2H), 3.09-3.05 (m, 1H), 2.96 (d, J=11.7 Hz, 1H), 2.82 (dd, J=13.7, 3.3 Hz, 1H), 2.08-1.97 (m, 1H), 1.97-1.84 (m, 2H), 1.84-1.73 (m, 3H). LCMS (Method B): $[M+H]^+$ m/z 395.3, RT 3.07 minutes. Chiral analysis (Chiralcel AD-H, 4.6×250 mm, 5 μm, 80:20 $CO_2$: Ethanol): RT 9.93 minutes.

Peak 4 (stereochemistry was assigned 6S,7S at piperidine); $^1H$ NMR (500 MHz, $CDCl_3$) δ 7.56 (d, J=7.5 Hz, 2H), 7.44 (q, J=11.1, 9.4 Hz, 3H), 7.35 (dd, J=15.4, 7.8 Hz, 3H), 7.09 (d, J=7.4 Hz, 1H), 5.62 (s, 1H), 4.36 (s, 2H), 4.22 (t, J=13.7 Hz, 2H), 3.47 (s, 1H), 3.14 (s, 2H), 3.09-3.04 (m, 1H), 3.01-2.93 (m, 1H), 2.82 (dd, J=13.6, 2.9 Hz, 1H), 2.09-1.99 (m, 1H), 1.93 (d, J=11.8 Hz, 1H), 1.86 (d, J=13.8 Hz, 1H), 1.85-1.70 (m, 3H). Comment: mixture of rotamers. LCMS (Method B): $[M+H]^+$ m/z 395.3, RT 3.07 minutes. Chiral analysis (Chiralcel AD-H, 4.6×250 mm, 5 μm, 80:20 $CO_2$: Ethanol): RT 10.77 minutes.

Example 24: (CIS)-7-({[1,1'-biphenyl]-3-yl}methyl)-N-ethyl-2-oxo-3-oxa-1,8-diazaspiro[5.5]undecane-8-carboxamide (24)

Example 25: (Trans)-7-({[1,1'-biphenyl]-3-yl}methyl)-N-ethyl-2-oxo-3-oxa-1,8-diazaspiro[5.5]undecane-8-carboxamide (25)

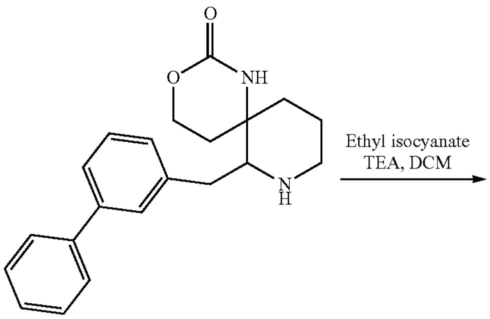

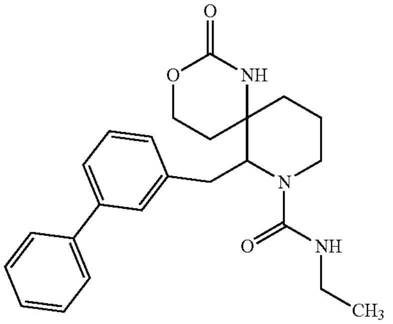

+

24 (Rel-Cis)

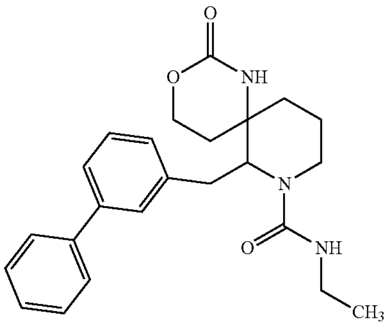

25 (Rel-trans)

Ethyl isocyanate (71 μL, 0.892 mmol) was added to a stirred solution of triethylamine (0.19 mL, 1.34 mmol) and Intermediate 33 (150 mg, 0.446 mmol) in DCM (2 mL) at room temperature and stirred for 1 h. The reaction mixture was quenched with 2 M NaOH (5 mL) and extracted with DCM (3×5 mL). The organic layer dried over $Na_2SO_4$, filtered and evaporated to dryness to afford the crude. The crude material was purified by prep HPLC Standard Method Column: XBridge™ Prep. C18 10 um OBD™, 30×100 mm, Mobile Phase: 30-95% Acetonitrile (0.2% ammonium hydroxide) in Water (0.2% ammonium hydroxide) over 10 minutes, Flow Rate: 40 mL/min, UV: 215 and 254 nm, to afford the title compounds example 24 (80 mg) and example 25 (15 mg) as an off white solid.

Example 24: $^1H$ NMR (400 MHz, $CDCl_3$) δ 7.61-7.50 (m, 2H), 7.47-7.37 (m, 4H), 7.37-7.24 (m, 3H), 7.16 (d, J=7.4 Hz, 1H), 4.61-4.37 (m, 2H), 4.37-4.24 (m, 1H), 3.73 (brs, 1H), 3.20-3.05 (m, 2H), 3.05-2.93 (m, 1H), 2.93-2.78 (m, 2H), 2.23 (d, J=14.1 Hz, 1H), 2.17-2.01 (m, 1H), 1.80-1.58 (m, 4H), 0.70 (td, J=7.1, 2.6 Hz, 3H). Comments: 1H exchanged with solvent. LCMS (Method A): $[M+H]^+$ m/z 408.5, RT 2.86 minutes.

Example 25: $^1H$ NMR (400 MHz, $CDCl_3$) δ 7.59-7.53 (m, 2H), 7.49-7.40 (m, 3H), 7.40-7.32 (m, 3H), 7.21-7.11 (m, 1H), 5.90 (s, 1H), 4.40-4.26 (m, 2H), 4.12 (dd, J=13.4, 4.5 Hz, 1H), 4.06-3.94 (m, 1H), 3.12-2.97 (m, 2H), 2.90-2.76 (m, 3H), 2.09-1.97 (m, 1H), 1.97-1.89 (m, 1H), 1.89-1.79 (m, 2H), 1.79-1.68 (m, 2H), 0.69 (t, J=7.2 Hz, 3H). Comments: 1H missing may be exchanged with solvent. LCMS (Method B): $[M+H]^+$ m/z 408.5, RT 3.07 minutes.

Example 26: (6S,7R)-7-({[1,1'-biphenyl]-3-yl}methyl)-N-ethyl-2-oxo-3-oxa-1,8-diazaspiro[5.5]undecane-8-carboxamide (26)

Example 27: (6R,7S)-7-({[1,1'-biphenyl]-3-yl}methyl)-N-ethyl-2-oxo-3-oxa-1,8-diazaspiro[5.5]undecane-8-carboxamide (27)

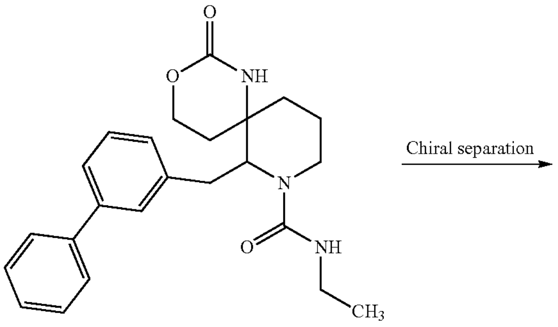

24 (Rel-Cis)

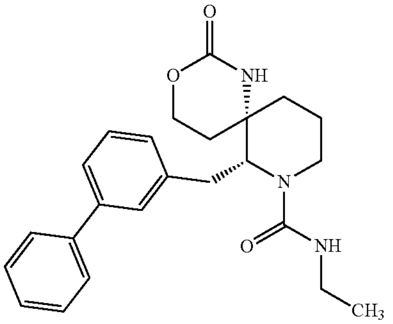

+

26

-continued

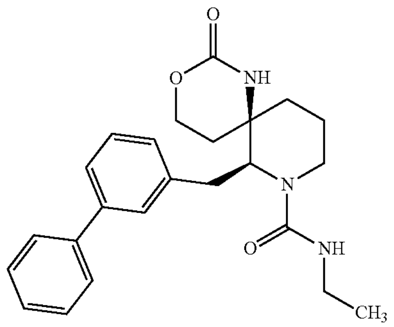

27

Example 24 (81 mg) was subjected to chiral preparative purification using Waters 600 eluting with 40/60% v/v n-Hexane/Ethanol, Chiralpak IC (25×2.0 cm), 5 μm, flow rate 17 mL/minutes, to afford the title compounds (Peak 1, 38 mg, 100% ee; and Peak 2, 28 mg, 100% ee). The absolute stereochemistry of each separated compound 26 and 27 was not conclusively determined but assigned as shown below.

Peak 1 (was assigned 6R,7S at piperidine); $^{1}$H NMR (400 MHz, $CDCl_3$) δ 7.57-7.51 (m, 2H), 7.45-7.40 (m, 3H), 7.39 (d, J=1.8 Hz, 1H), 7.33 (t, J=7.4 Hz, 2H), 7.16 (dt, J=7.5, 1.5 Hz, 1H), 6.21 (s, 1H), 4.45 (td, J=12.1, 2.5 Hz, 2H), 4.33 (ddd, J=11.9, 4.7, 2.6 Hz, 1H), 3.78 (d, J=12.5 Hz, 1H), 3.47 (d, J=9.7 Hz, 1H), 3.15-2.94 (m, 3H), 2.92-2.77 (m, 2H), 2.29-2.20 (m, 1H), 2.07-1.94 (m, 1H), 1.77-1.64 (m, 4H), 0.70 (t, J=7.2 Hz, 3H). LCMS (Method C): $[M+H]^+$ m/z 408.3, RT 0.9 minutes. Chiral analysis (Chiralcelpak IC, 25×0.46 cm, 5 m, 40:60 n-Hexane:Ethanol): RT 6.7 minutes.

Peak 2 (was assigned 6R,7S at piperidine): $^{1}$H NMR (400 MHz, $CDCl_3$) δ 7.57-7.51 (m, 2H), 7.45-7.40 (m, 3H), 7.39 (d, J=1.8 Hz, 1H), 7.35 (s, 2H), 7.16 (dt, J=7.6, 1.4 Hz, 1H), 6.29-6.24 (m, 1H), 4.45 (td, J=12.1, 2.5 Hz, 2H), 4.32 (ddd, J=11.9, 4.8, 2.6 Hz, 1H), 3.78 (d, J=12.8 Hz, 1H), 3.48 (d, J=14.1 Hz, 1H), 3.17-2.94 (m, 3H), 2.92-2.77 (m, 2H), 2.29-2.20 (m, 1H), 2.08-1.95 (m, 1H), 1.77-1.64 (m, 4H), 0.70 (t, J=7.2 Hz, 3H). LCMS (Method C): $[M+H]^+$ m/z 408.3, RT 0.9 minutes. Chiral analysis (Chiralcelpak IC, 25×0.46 cm, 5 m, 40:60 n-Hexane:Ethanol): RT 13.6 minutes.

Example 28: Methyl 6-({[1,1'-biphenyl]-3-yl}methyl)-2-oxo-1,7-diazaspiro[4.5]decane-7-carboxylate

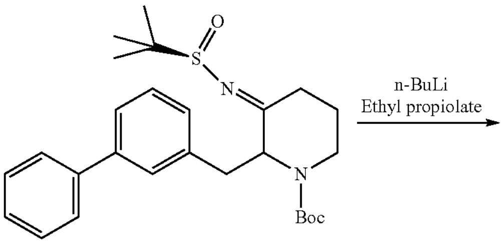

INTERMEDIATE 28

-continued

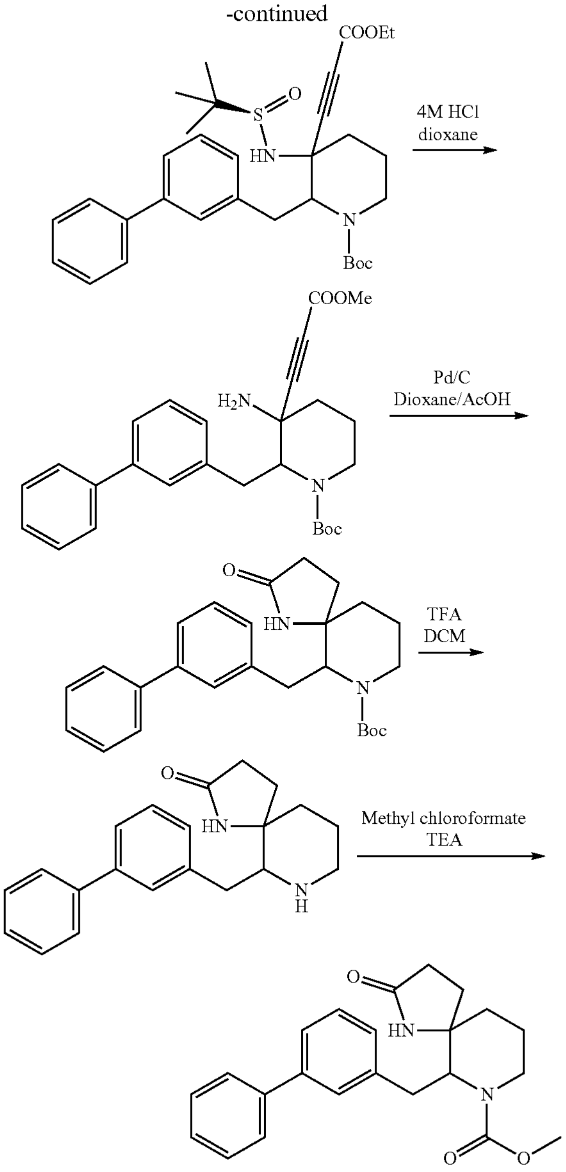

28 tert-butyl 2-({[1,1'-biphenyl]-3-yl}methyl)-3-(3-ethoxy-3-oxoprop-1-yn-1-yl)-3-{[(R)-2-methylpropane-2-sulfinyl]amino}piperidine-1-carboxylate (Intermediate 34)

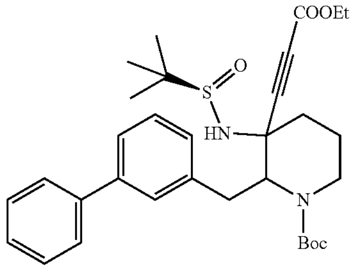 [SMILES: CCOC(=O)C#CC1(N[S@](=O)C(C)(C)C)CCCN(C(=O)OC(C)(C)C)C1Cc1cccc(-c2ccccc2)c1]

A solution of n-butyllithium (2.5 M in cyclohexanes) (1.2 mL, 2.99 mmol) was added dropwise to a solution of ethyl prop-2-ynoate (0.32 mL, 3.20 mmol) in THF (20 mL) at −78° C. under nitrogen. The reaction mixture was stirred for 10 minutes at −78° C. before a solution of Intermediate 28 (1.00 g, 2.13 mmol) in THF (10 mL) was added dropwise at −78° C. The reaction was stirred for another 10 minutes at −78° C. and then the reaction was quenched at −78° C. with 4:1 solution of heptane:acetic acid (1 mL). The reaction was allowed to warm up to room temperature for 1 h and then the reaction was partitioned between water (10 mL), a saturated aqueous solution of $NH_4Cl$ (10 mL), and EtOAc (20 mL). The aqueous layer was further extracted with EtOAc (20 mL) and the organic layers were combined, washed with brine (20 mL), dried over $MgSO_4$ and concentrated to give the crude material. The crude material was purified by silica gel column chromatography (0-60% EtOAc in heptane), to afford the title compound (600 mg) as an orange solid. $[M+NH_4]^+$ m/z 584.6 tert-butyl 3-amino-2-({[1,1'-biphenyl]-3-yl}methyl)-3-(3-methoxy-3-oxoprop-1-yn-1-yl)piperidine-1-carboxylate (Intermediate 35)

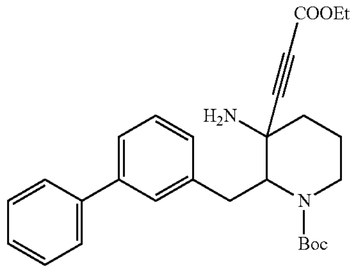 [SMILES: CCOC(=O)C#CC1(N)CCCN(C(=O)OC(C)(C)C)C1Cc1cccc(-c2ccccc2)c1]

Intermediate 34 (450 mg, 0.794 mmol) was dissolved in methanol (7.2 mL) and cooled to 0° C. Hydrogen chloride (4M in dioxane) (0.30 mL, 1.19 mmol) was added dropwise and the reaction was stirred at 0° C. for 3 h. The reaction was quenched at 0° C. by the dropwise addition of aq. 2M NaOH solution (2 mL) and diluted in EtOAc (10 mL) and water (10 mL). The solution was separated and the aqueous layer was further extracted with EtOAc (2×10 mL). The organic layers were combined and dried over $MgSO_4$ and concentrated in vacuo. The crude material was purified by silica gel column chromatography (0-80% EtOAc in hexane), to afford the title compound (80 mg) as a yellow oil. $[M+H]^+$ m/z 449.4 tert-butyl 6-({[1,1'-biphenyl]-3-yl}methyl)-2-oxo-1,7-diazaspiro[4.5]decane-7-carboxylate (Intermediate 36)

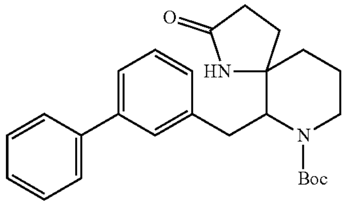 [SMILES: CC(C)(C)OC(=O)N1CCCC2(CCC(=O)N2)C1Cc1cccc(-c2ccccc2)c1]

Intermediate 35 (100 mg, 0.216 mmol) and 1,4-dioxane (2 mL) and acetic acid (25 μL, 0.432 mmol) were put under vacuum and the atmosphere was changed to $N_2$(g), re-evacuated and repeated two times and palladium on carbon (10%, 46 mg, 0.0432 mmol) was added. The flask was evacuated and refilled with $H_2$(g) and pressured to 4 bar and the solution as stirred for 3 h at room temperature. The reaction was filtered through Celite and concentrated in vacuo. The crude material was purified by silica gel column chromatography (20-100% EtOAc in heptane), to afford the title compound (55 mg) as a white solid. $[M+H]^+$ m/z 421.4

6-({[1,1'-biphenyl]-3-yl}methyl)-1,7-diazaspiro[4.5]decan-2-one (Intermediate 37)

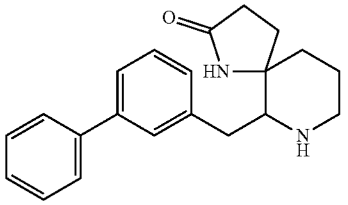 [SMILES: O=C1CCC2(CCCNC2Cc2cccc(-c3ccccc3)c2)N1]

Intermediate 36 (45 mg, 0.107 mmol) was dissolved in DCM (0.5 mL) and TFA (0.5 mL) and stirred for 2 h at room temperature. The reaction was quenched with a saturated aqueous solution of $Na_2CO_3$ solution (10 mL) and the extracted with DCM (2×10 mL). The organic layers were combined, passed through a phase separator, concentrated in vacuo, to afford the title compound (30 mg) as a yellow solid which was used without further purification. $[M+H]^+$ m/z 321.4.

Methyl 6-({[1,1'-biphenyl]-3-yl}methyl)-2-oxo-1,7-diazaspiro[4.5]decane-7-carboxylate (Example 28)

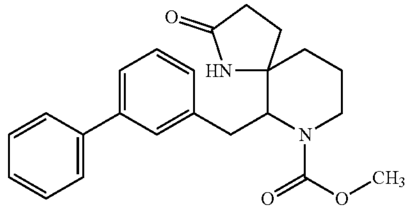 [SMILES: COC(=O)N1CCCC2(CCC(=O)N2)C1Cc1cccc(-c2ccccc2)c1]

Intermediate 37 (30 mg, 0.0936 mmol) was dissolved in DCM (1 mL) and triethylamine (78 μL, 0.562 mmol) and methyl carbonochloridate (10 μL, 0.131 mmol) were added. The solution was stirred for 1 h, then additional methyl carbonochloridate (10 μL, 0.131 mmol) was added. The reaction was stirred for 30 minutes and methyl carbonochloridate (10 μL, 0.131 mmol) was added and the reaction was stirred for 30 minutes then diluted with DCM (10 mL) and water (10 mL), separated and the aqueous layer was extracted with DCM (2×10 mL). The organic layers were combined, dried, and concentrated in vacuo to afford the crude product. The crude material was purified by silica gel column chromatography (0-8% Methanol in DCM), to afford the title compound (15 mg) as a white solid.

$^1H$ NMR (500 MHz, $CDCl_3$) δ 7.62-7.52 (m, 2H), 7.46-7.39 (m, 3H), 7.39-7.32 (m, 3H), 7.22-7.08 (m, 1H), 6.98 (s, 1H), 4.25 (m, 1H), 4.20-4.07 (m, 1H), 3.17 (s, 3H), 3.09-

2.94 (m, 2H), 2.69-2.48 (m, 1H), 2.36 (d, J=16.6 Hz, 1H), 2.29-2.00 (m, 3H), 1.98-1.87 (m, 1H), 1.84-1.57 (m, 3H). LCMS (Method B): $[M+H]^+$ m/z 379.4, RT 3.12 & 3.26 minutes.

Example 29: Methyl (5S,6S)-6-({[1,1'-biphenyl]-3-yl}methyl)-2-oxo-3-oxa-1,7-diazaspiro[4.5]decane-7-carboxylate

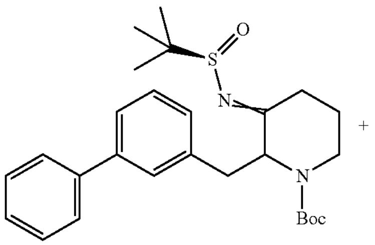

INTERMEDIATE 28

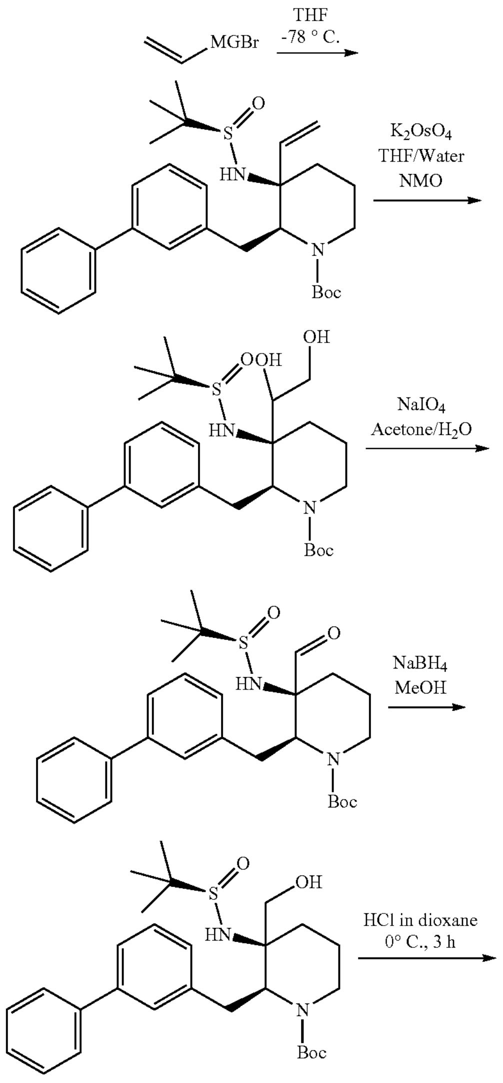

-continued

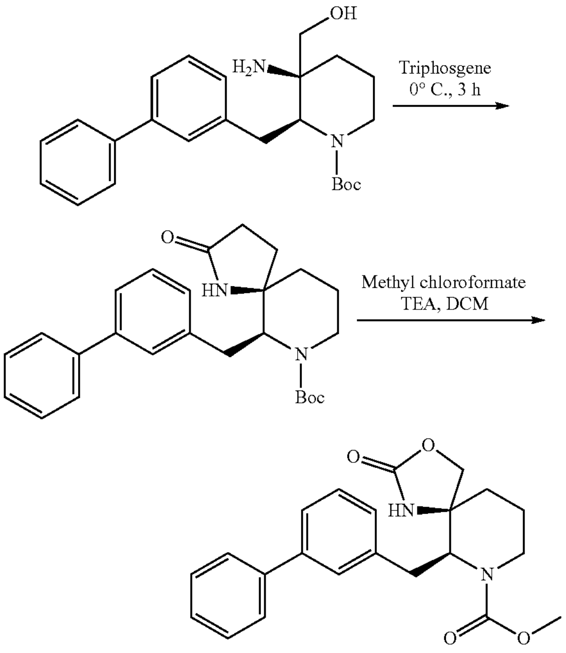

29 tert-butyl (2S,3R)-2-({[1,1'-biphenyl]-3-yl}methyl)-3-ethenyl-3-{[(R)-2-methylpropane-2-sulfinyl]amino}piperidine-1-carboxylate (INTERMEDIATE 38)

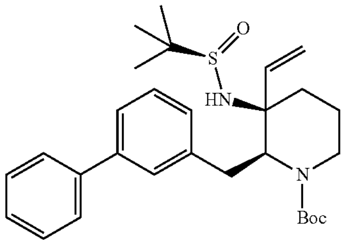 [SMILES: C=C[C@]1(N[S@](=O)C(C)(C)C)CCCN(C(=O)OC(C)(C)C)[C@H]1Cc1cccc(-c2ccccc2)c1]

Intermediate 28 (1.40 g, 2.99 mmol) in anhydrous THF (14 mL) was added to a stirred solution of bromo(ethenyl) magnesium (1 M in THF) (9.0 mL, 8.96 mmol) at −78° C. The reaction was stirred at −78° C. for 1 h. The reaction mixture was warmed to 0° C. and stirred for 30 minutes then quenched with a saturated aqueous solution of $NH_4Cl$ (20 mL) and extracted with EtOAc (3×50 mL). The combined organic extracts were dried over $MgSO_4$, filtered and concentrated in vacuo. The crude material was purified by silica gel column chromatography (20-100% EtOAc in heptane), to afford the title compound (148 mg) as a white residue/gum. $[M+H]^+$ m/z=497.5 tert-butyl (2S,3S)-2-({[1,1'-biphenyl]-3-yl}methyl)-3-(1,2-dihydroxyethyl)-3-{[(R)-2-methylpropane-2-sulfinyl]amino}piperidine-1-carboxylate (Intermediate 39)

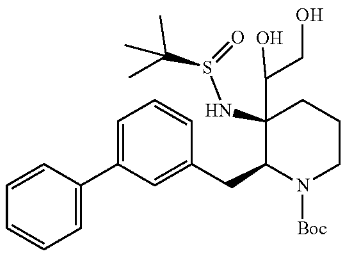 [SMILES: CC(C)(C)OC(=O)N1CCC[C@@](N[S@](=O)C(C)(C)C)(C(O)CO)[C@@H]1Cc1cccc(-c2ccccc2)c1]

To a stirred solution of potassium dioxido(dioxo)osmium hydrate (2:1:2) (5.2 mg, 0.0141 mmol) and Intermediate 38 (140 mg, 0.282 mmol) in water (0.28 mL) and THE (0.7 mL) was added 4-methyl-4-oxido-morpholin-4-ium (58 mg, 0.493 mmol) at room temperature, the reaction was then heated to 50° C. for 2 h. The reaction was quenched with a saturated aqueous solution of $Na_2SO_3$ and extracted with EtOAc (3x5 mL). The organic extracts were passed through a phase separator and concentrated in vacuo. The crude material was purified by silica gel column chromatography (30-100% EtOAc in heptane), to afford the title compound (103 mg) as a colourless solid. $[M+H]^+$ m/z=531.5 tert-butyl (2S,3S)-2-({[1,1'-biphenyl]-3-yl}methyl)-3-formyl-3-{[(R)-2-methylpropane-2-sulfinyl]amino}piperidine-1-carboxylate (Intermediate 40)

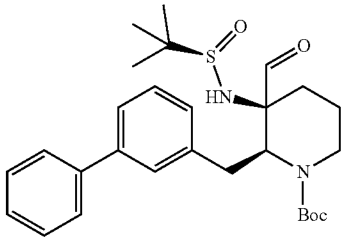 [SMILES: CC(C)(C)OC(=O)N1CCC[C@](C=O)(N[S@](=O)C(C)(C)C)[C@@H]1Cc1cccc(-c2ccccc2)c1]

To a stirred solution of Intermediate 39 (91 mg, 0.171 mmol) in acetone (2.4 mL) at 0° C. was added sodium periodate (58 mg, 0.273 mmol) in water (0.7 mL). The reaction was stirred at 0° C. for 1 h then warmed to room temperature for 16 h. The reaction was quenched with water and extracted with EtOAc (3x5 mL). The organic extracts were passed through a phase separator and concentrated in vacuo, to afford the title compound (66 mg) as a colourless residue. $[M+H]^+$ m/z=499.5 tert-butyl (2S,3S)-2-({[1,1'-biphenyl]-3-yl}methyl)-3-(hydroxymethyl)-3-{[(R)-2-methylpropane-2-sulfinyl]amino}piperidine-1-carboxylate (Intermediate 41)

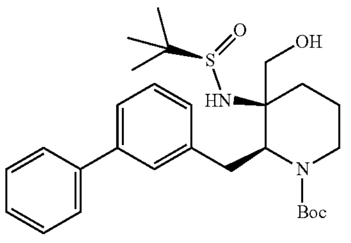 [SMILES: CC(C)(C)OC(=O)N1CCC[C@](CO)(N[S@](=O)C(C)(C)C)[C@@H]1Cc1cccc(-c2ccccc2)c1]

Sodium tetrahydroborate (11 mg, 0.291 mmol) was added to a stirred solution of Intermediate 40 (66 mg, 0.132 mmol) in methanol (2 mL) at room temperature. The reaction was stirred for 30 minutes then quenched with water and extracted with DCM (3x5 mL). The organic extracts were passed through a phase separator and concentrated in vacuo, to afford the title compound (59 mg) as a colourless residue. $[M+H]^+$ m/z=501.5 tert-butyl (2S,3S)-3-amino-2-({[1,1'-biphenyl]-3-yl}methyl)-3-(hydroxymethyl)piperidine-1-carboxylate (Intermediate 42)

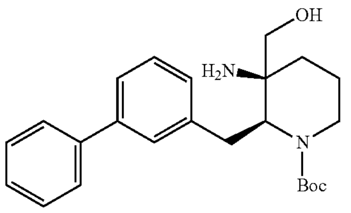 [SMILES: CC(C)(C)OC(=O)N1CCC[C@@](N)(CO)[C@@H]1Cc1cccc(-c2ccccc2)c1]

Hydrogen chloride (4M in dioxane) (26 μL, 0.104 mmol) was added dropwise to a stirred solution of Intermediate 41 (50 mg, 0.0990 mmol) in methanol (2 mL) at 0° C. and stirred for 1 h. Additional hydrogen chloride (4M in dioxane) (49 μL, 0.198 mmol) was added and the reaction was stirred for a further 2 h. The reaction was quenched at 0° C. with a saturated aqueous solution of $NaHCO_3$ and then the methanol was removed in vacuo. The aqueous solution was then extracted with DCM:Methanol (9:1, 3x5 mL). The combined organic extracts were passed through a phase separator and concentrated in vacuo. The crude material was purified by silica gel column chromatography (0-2% Methanol in DCM), to afford the title compound (39 mg) as a colourless gum. $[M+H]^+$ m/z=397.4 tert-butyl (5S,6S)-6-({[1,1'-biphenyl]-3-yl}methyl)-2-oxo-3-oxa-1,7-diazaspiro[4.5]decane-7-carboxylate (Intermediate 43)

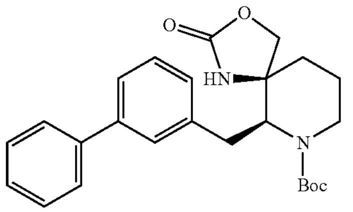 [SMILES: CC(C)(C)OC(=O)N1CCC[C@@]2(COC(=O)N2)[C@@H]1Cc1cccc(-c2ccccc2)c1]

N-ethyl-N-isopropyl-propan-2-amine (20 μL, 0.114 mmol) was added to a stirred solution of Intermediate 42 (38 mg, 0.0954 mmol) and bis(trichloromethyl) carbonate (34 mg, 0.114 mmol) in anhydrous DCM (2 mL) at 0° C. The reaction mixture was stirred at 0° C. for 1 h. The reaction was quenched with 20% NaOH and extracted with DCM (3x3 mL). The combined organic extracts were passed through a phase separator and concentrated in vacuo. The crude material was purified by silica gel column chromatography (0-5% Methanol in DCM), to afford the title compound (35 mg) as a white solid. $[M+NH_4]^+$ m/z=440.6

(5S,6S)-6-({[1,1'-biphenyl]-3-yl}methyl)-3-oxa-1,7-diazaspiro[4.5]decan-2-one (Intermediate 44)

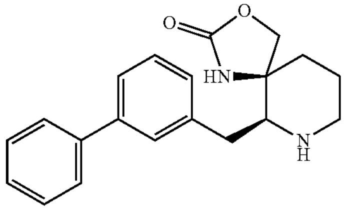 [SMILES: O=C1N[C@]2(CCCN[C@H]2Cc2cccc(-c3ccccc3)c2)CO1]

A solution of Intermediate 43 (30 mg, 0.0710 mmol) in TFA (0.18 mL) and DCM (2 mL) was stirred at room temperature for 2 h. The reaction was quenched with a saturated aqueous solution of $NaHCO_3$ and extracted with DCM (3x3 mL). The combined organic extracts were passed through a phase separator and concentrated in vacuo, to afford the title compound (28 mg) as a pale yellow gum. $[M+H+MeCN]^+$ m/z=364.5

Methyl (5S,6S)-6-({[1,1'-biphenyl]-3-yl}methyl)-2-oxo-3-oxa-1,7-diazaspiro[4.5]decane-7-carboxylate (29)

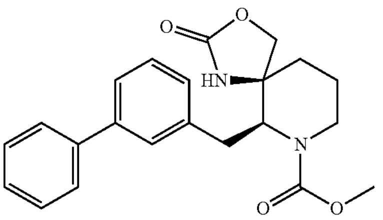 [SMILES: COC(=O)N1CCC[C@@]2(COC(=O)N2)[C@@H]1Cc1cccc(-c2ccccc2)c1]

Methyl carbonochloridate (67 μL, 0.868 mmol) was added to a stirred solution of Intermediate 44 (28 mg, 0.0868 mmol) and triethylamine (73 μL, 0.521 mmol) in DCM (2 mL) at 0° C. The reaction was then warmed to room temperature for 30 minutes. The reaction was quenched with a saturated aqueous solution of $NaHCO_3$ and extracted with DCM (3x3 mL). The combined organic extracts were passed through a phase separator and concentrated in vacuo. The crude material was purified by reverse phase column chromatography (10-100% MeCN in water (0.1% $NH_3$)), to afford the title compound (19 mg) as a white solid.

$^1H$ NMR (500 MHz, CDCl3) δ 7.57 (d, J=7.4 Hz, 2H), 7.48-7.40 (m, 3H), 7.39-7.31 (m, 3H), 7.21-7.08 (m, 1H), 5.96-5.72 (m, 1H), 4.48 (d, J=8.9 Hz, 1H), 4.38-4.23 (m, 1H), 4.19 (d, J=8.9 Hz, 1H), 4.16-4.06 (m, 1H), 3.17 (s, 3H), 3.06-2.93 (m, 2H), 2.89 (s, 1H), 2.09-2.01 (m, 1H), 1.89-1.75 (m, 2H), 1.54-1.43 (m, 1H). LCMS (Method A): $[M+NH_4]^+$ m/z 398.5, RT 2.98 minutes.

Example 30: (CIS)-6-({[1,1'-biphenyl]-3-yl}methyl)-N-ethyl-2,2-dioxo-2λ$^6$-thia-1,3,7-triazaspiro[4.5]decane-7-carboxamide

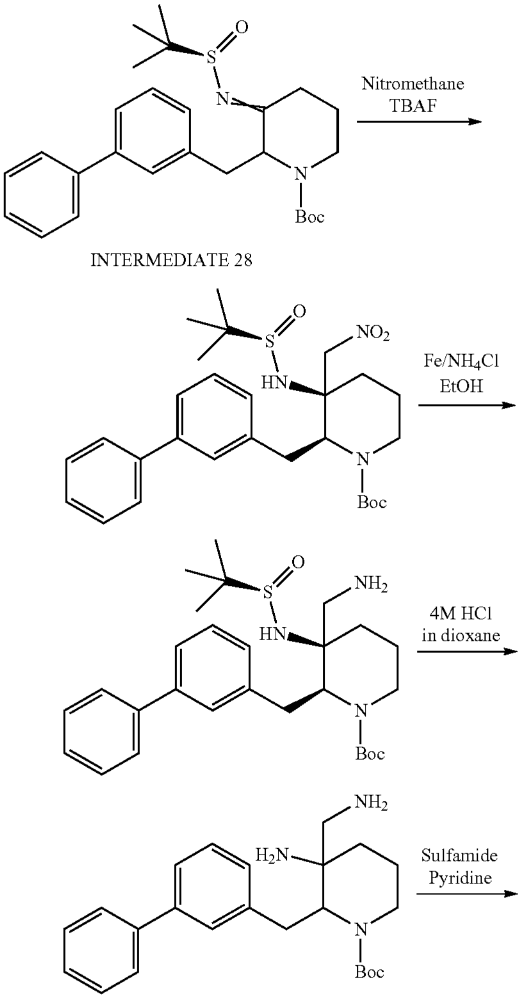

-continued

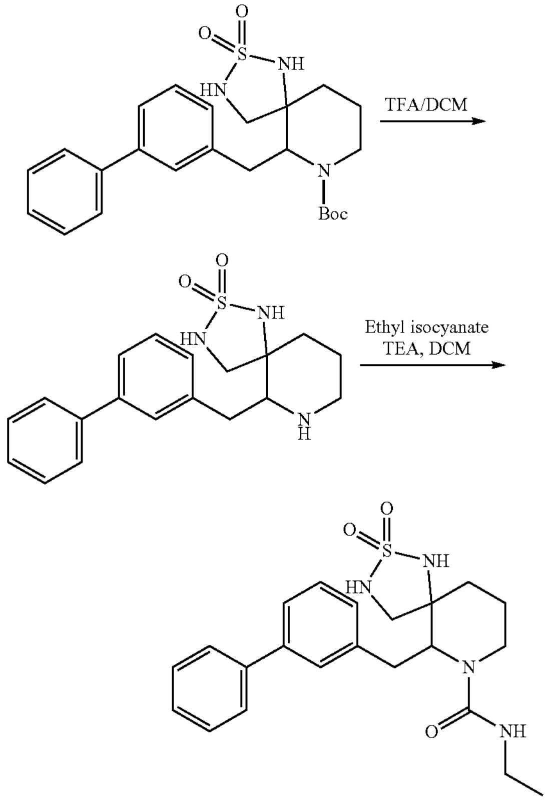

30 tert-butyl (CIS)—2-({[1,1'-biphenyl]-3-yl}methyl)-3-{[(R)-2-methylpropane-2-sulfinyl]amino}-3-(nitromethyl) piperidine-1-carboxylate (Intermediate 45)

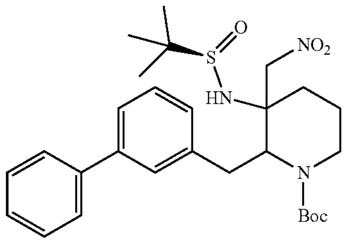 [SMILES: CC(C)(C)OC(=O)N1CCCC(C[N+](=O)[O-])(N[S@](=O)C(C)(C)C)C1Cc1cccc(-c2ccccc2)c1]

A heterogeneous solution of N,N,N-tributylbutan-1-aminium fluoride (1M in THF) (1.5 mL, 1.54 mmol) and Intermediate 28 (1.50 g, 3.07 mmol) in nitromethane (15 mL) was heated at 23° C. for 2 h. The reaction was diluted with EtOAc (25 mL) and water (25 mL) and separated. The aqueous layer was extracted with EtOAc (2x10 mL) and the organic layers were combined, dried over $MgSO_4$ and concentrated in vacuo to furnish the crude material. The crude material was purified by silica gel column chromatography (0-70% EtOAc in heptane), to afford the title compound (1.1 g) as a light yellow solid. $[M+H]^+$ m/z=530.5 tert-butyl-(CIS)-3-(aminomethyl)-2-({[1,1'-biphenyl]-3-yl}methyl)-3-{[(R)-2-methylpropane-2-sulfinyl]amino}piperidine-1-carboxylate (Intermediate 46)

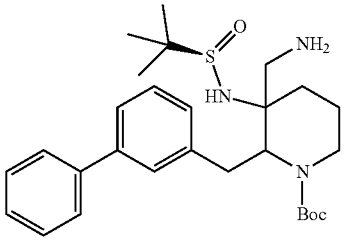

A solution of Intermediate 45 (1.00 g, 1.89 mmol), iron (527 mg, 9.44 mmol) and ammonium hydrochloride (505 mg, 9.44 mmol) were dissolved in ethanol (10 mL) and water (10 mL) then heated at 80° C. for 2 h. The mixture was poured into water (20 mL) and extracted with EtOAc (3x25 mL). The organic phases were combined, passed through a phase separator and concentrated in vacuo. The crude material was purified by silica gel column chromatography (0-10% Methanol in DCM), to afford the title compound (814 mg) as a white solid. $[M+H]^+$ m/z=500.5 tert-butyl (CIS)-3-amino-3-(aminomethyl)-2-({[1,1'-biphenyl]-3-yl}methyl)piperidine-1-carboxylate (Intermediate 47)

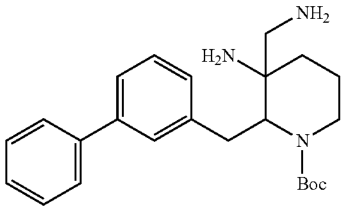 [SMILES: CC(C)(C)OC(=O)N1CCCC(N)(CN)C1Cc1cccc(-c2ccccc2)c1]

Intermediate 46 (800 mg, 1.60 mmol) was dissolved in methanol (20 mL) and cooled to 0° C. Hydrogen chloride (4M in dioxane) (1.2 mL, 4.80 mmol) was added dropwise and the solution was stirred for 5 h at 0° C. The reaction was quenched by the addition of a saturated aqueous solution of $NaHCO_3$ solution (10 mL) and EtOAc (10 mL). The solution was separated and the aqueous layer was extracted with EtOAc (2x10 mL). The organic layers were combined, washed with brine (20 mL), passed through a phase separator and concentrated in vacuo, to afford the title compound (650 mg) as a colourless oil. $[M+H]^+$ m/z=396.4 tert-butyl (CIS)-6-({[1,1'-biphenyl]-3-yl}methyl)-2,2-dioxo-2λ$^6$-thia-1,3,7-triazaspiro[4.5]decane-7-carboxylate (Intermediate 48)

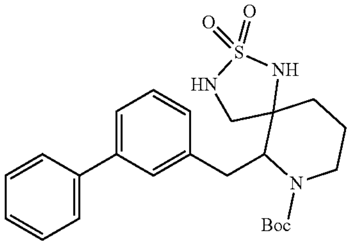 [SMILES: CC(C)(C)OC(=O)N1CCCC2(CNS(=O)(=O)N2)C1Cc1cccc(-c2ccccc2)c1]

Intermediate 47 (450 mg, 1.14 mmol) and sulfamide (131 mg, 1.37 mmol) was dissolved in pyridine (15 mL) and the reaction stirred at 110° C. for 16 h. The reaction mixture was cooled to room temperature and diluted with water (25 mL) and EtOAc (25 mL). The mixture was separated and the aqueous layer was extracted with EtOAc (2×25 mL). The organic layers were combined, washed with 2M HCl (50 mL) and brine (50 mL), dried over $MgSO_4$ and concentrated in vacuo. The crude material was purified by silica gel column chromatography (20-100% EtOAc in heptane), to afford the title compound (122 mg) as a cream solid. $[M+NH_4]^+$ m/z=475.4

(CIS)-6-({[1,1'-biphenyl]-3-yl}methyl)-2λ$^6$-thia-1,3,7-triazaspiro[4.5]decane-2,2-dione (Intermediate 49)

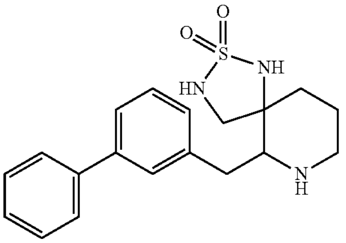 [SMILES: O=S1(=O)NCC2(CCCNC2Cc2cccc(-c3ccccc3)c2)N1]

Intermediate 48 (100 mg, 0.219 mmol) was dissolved in DCM (0.5 mL) and TFA (0.5 mL) and stirred for 1 h at room temperature. The reaction was quenched by the addition of a saturated aqueous solution of $NaHCO_3$ solution (5 mL) and extracted with DCM (3×10 mL). The organic layers were combined, passed through a phase separator and concentrated in vacuo, to afford the title compound (60 mg) as a cream solid. $[M+H]^+$ m/z=358.3

(CIS)-6-({[1,1'-biphenyl]-3-yl}methyl)-N-ethyl-2,2-dioxo-2λ$^6$-thia-1,3,7-triazaspiro[4.5]decane-7-carboxamide (30)

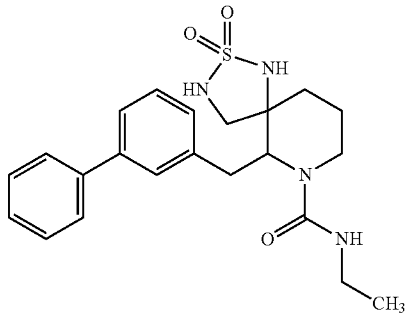 [SMILES: CCNC(=O)N1CCCC2(CNS(=O)(=O)N2)C1Cc1cccc(-c2ccccc2)c1]

To a solution of Intermediate 49 (50 mg, 0.140 mmol) and triethylamine (58 μL, 0.420 mmol) in DCM (1 mL) at room temperature was added ethyl isocyanate (22 μL, 0.280 mmol) and the solution was stirred for 30 minutes at room temperature. The solution was quenched by the addition of aq. 2M NaOH solution (5 mL) and extracted with DCM (3×10 mL). The organic layers were combined, passed through a phase separator and concentrated. The crude material was purified by silica gel column chromatography (0-100% EtOAc in heptane), to afford the title compound (47 mg) as a white solid.

$^1H$ NMR (400 MHz, $CDCl_3$) δ 7.59-7.53 (m, 2H), 7.49-7.40 (m, 4H), 7.41-7.29 (m, 2H), 7.21 (d, J=7.5 Hz, 1H), 4.41 (d, J=10.0 Hz, 1H), 4.27-4.14 (m, 1H), 4.02 (d, J=10.9 Hz, 1H), 3.69 (d, J=11.9 Hz, 1H), 3.58 (s, 1H), 3.31 (dd, J=13.7, 2.7 Hz, 1H), 3.24 (d, J=11.9 Hz, 1H), 3.05 (td, J=13.3, 2.6 Hz, 1H), 2.95 (dd, J=13.6, 11.8 Hz, 1H), 2.83 (ddt, J=19.8, 13.0, 6.9 Hz, 2H), 2.16-2.05 (m, 1H), 1.85-1.73 (m, 2H), 1.66-1.55 (m, 1H), 0.68 (t, J=7.2 Hz, 3H). NH missing may exchanged with solvent. LCMS (Method A): $[M+NH_4]^+$ m/z 446.4, RT 3.09 minutes.

Example 31: (5R,6S)-6-({[1,1'-biphenyl]-3-yl}methyl)-N-ethyl-2,2-dioxo-2λ$^6$-thia-1,3,7-triazaspiro[4.5]decane-7-carboxamide & Example 32: (5S,6R)-6-({[1,1'-biphenyl]-3-yl}methyl)-N-ethyl-2,2-dioxo-2λ$^6$-thia-1,3,7-triazaspiro[4.5]decane-7-carboxamide

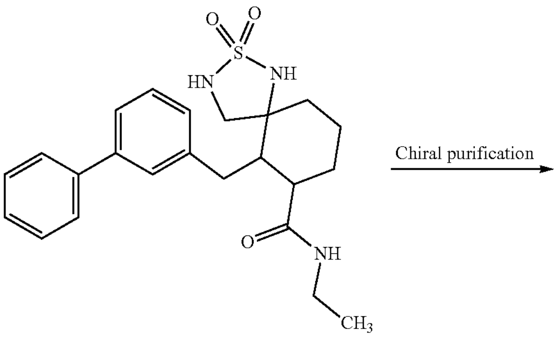

30

-continued

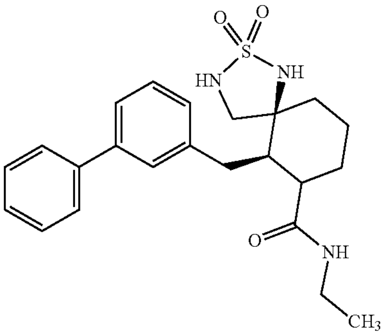

31

+

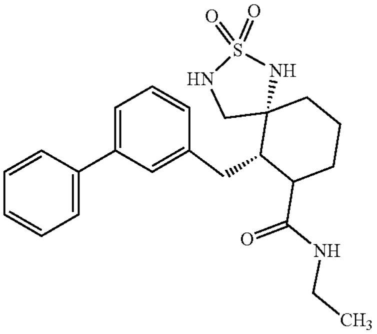

32

Example 30 (35 mg) was subjected to chiral HPLC with a gradient of 85 heptane, 15% ethanol, Chiralcel OD-H, 4.6×250 mm, 5 m, flow rate 18 mL/minutes to afford the title compounds (Peak 1, 12 mg, 100% ee; and Peak 2, 6 mg, 100% ee). The absolute stereochemistry of each separated compound 31 and 32 was not conclusively determined but assigned as shown below.

Peak 1 (was assigned 5R,6S at piperidine); $^1$H NMR (400 MHz, $CDCl_3$) δ 7.59-7.53 (m, 2H), 7.48-7.40 (m, 4H), 7.40-7.31 (m, 2H), 7.20 (dt, J=7.5, 1.2 Hz, 1H), 5.08 (s, 1H), 4.38 (d, J=9.9 Hz, 1H), 4.30 (s, 1H), 4.02 (d, J=11.2 Hz, 1H), 3.67 (d, J=11.8 Hz, 2H), 3.29 (dd, J=13.7, 2.7 Hz, 1H), 3.23 (d, J=11.9 Hz, 1H), 3.03 (td, J=13.3, 2.8 Hz, 1H), 2.94 (dd, J=13.6, 11.8 Hz, 1H), 2.82 (ddt, J=20.6, 13.2, 6.9 Hz, 2H), 2.09 (td, J=13.5, 4.6 Hz, 1H), 1.83-1.70 (m, 2H), 1.59 (ddt, J=17.9, 9.1, 4.6 Hz, 1H), 0.66 (t, J=7.2 Hz, 3H). LCMS (Method A): $[M+NH_4]^+$ m/z 446.4, RT 2.96 minutes. Chiral analysis (Chiralcel OD-H, 4.6×250 mm, 5 μm, 85:15 Heptane: Ethanol): RT 8.97 minutes.

Peak 2 (was assigned 5S,6R at piperidine): $^1$H NMR (400 MHz, $CDCl_3$) δ 7.60-7.52 (m, 2H), 7.48-7.40 (m, 4H), 7.39-7.31 (m, 2H), 7.20 (d, J=7.5 Hz, 1H), 5.08 (s, 1H), 4.39 (d, J=10.0 Hz, 1H), 4.29 (s, 1H), 4.01 (d, J=9.8 Hz, 1H), 3.67 (d, J=11.8 Hz, 2H), 3.29 (dd, J=13.7, 2.4 Hz, 1H), 3.23 (d, J=11.9 Hz, 1H), 3.03 (t, J=12.0 Hz, 1H), 2.99-2.90 (m, 1H), 2.82 (ddt, J=20.3, 13.1, 6.7 Hz, 2H), 2.15-2.04 (m, 1H), 1.87-1.70 (m, 2H), 1.65-1.51 (m, 1H), 0.67 (t, J=7.2 Hz, 3H). LCMS (Method A): $[M+NH_4]^+$ m/z 446.4, RT 2.97 minutes. Chiral analysis (Chiralcel OD-H, 4.6×250 mm, 5 m, 85:15 Heptane:Ethanol): RT 29.24 minutes.

Example 33: rel-(6S,7R)—N-ethyl-2-oxo-7-({[(CIS)-4-phenylcyclohexyl]oxy}methyl)-1,8-diazaspiro[5.5]undecane-8-carboxamide

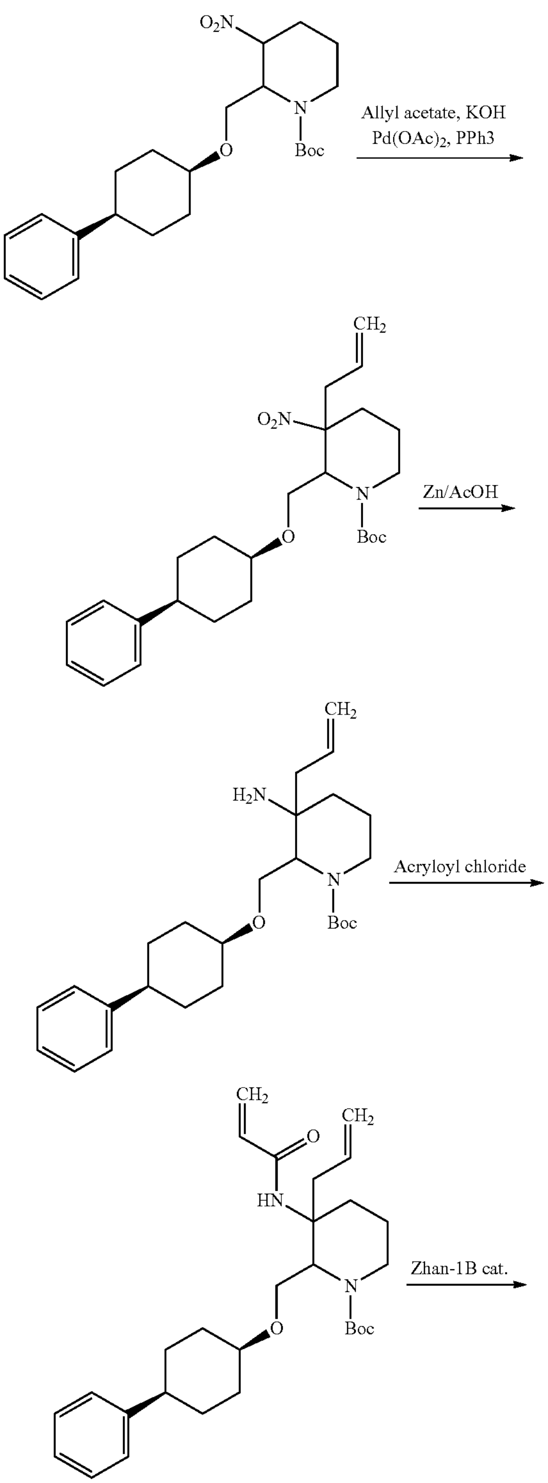

-continued

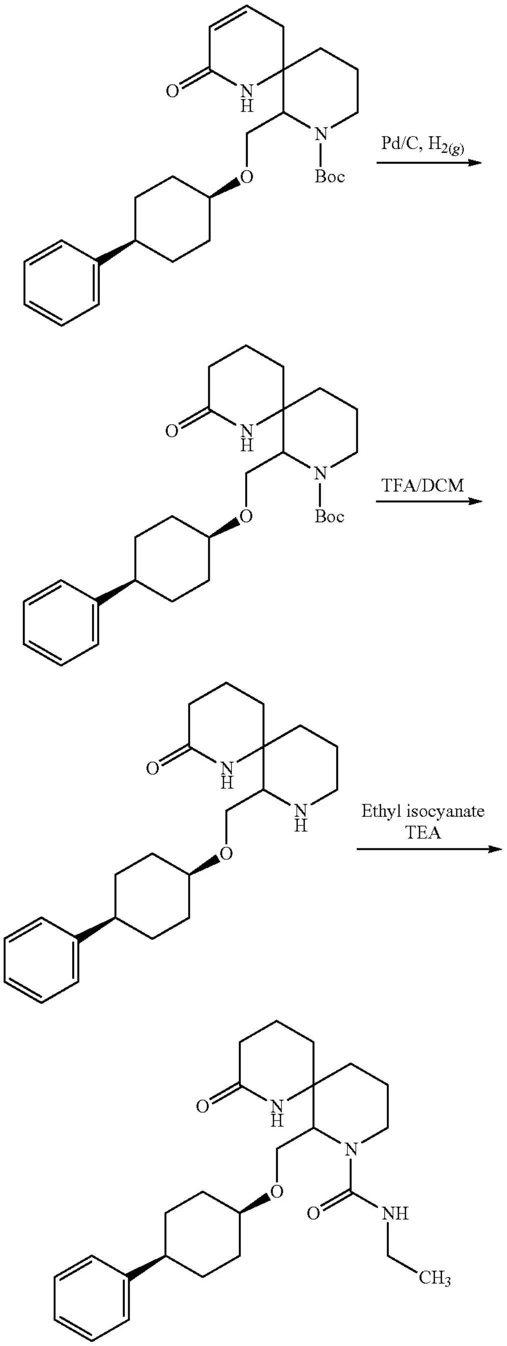

tert-butyl-rel-(2R,3R)-3-nitro-3-(prop-2-en-1-yl)-2-({[(CIS)-4-phenylcyclohexyl]oxy}methyl)piperidine-1-carboxylate (Intermediate 50)

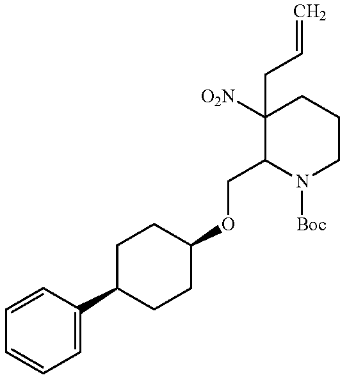 [SMILES: C=CCC1([N+](=O)[O-])CCCN(C(=O)OC(C)(C)C)C1CO[C@H]1CC[C@@H](c2ccccc2)CC1]

Potassium hydroxide (235 mg, 4.18 mmol) was dissolved in IPA (17 mL) and methanol (17 mL), this solution was stirred for 30 minutes. Intermediate 4 (92%, 1.73 g, 3.80 mmol) in methanol (20 mL) was added, the solution was then degassed. Palladium diacetate (43 mg, 0.190 mmol) was added followed by triphenylphosphine (150 mg, 0.570 mmol). The solution was heated to 45° C. stirred for 5 minutes before prop-2-en-1-yl acetate (0.45 mL, 4.18 mmol) was added. The reaction mixture was heated to 55° C. for 3 h then cooled to room temperature. Additional palladium diacetate (43 mg, 0.190 mmol), triphenylphosphine (150 mg, 0.570 mmol) and prop-2-en-1-yl acetate (0.45 mL, 4.18 mmol) were added in this order. The reaction was heated to 55° C. for 1 h then concentrated in vacuo to afford the crude material. The crude material was purified by silica gel column chromatography (0-20% TBME in heptane), to afford the title compound (1.44 g) as an oil. $[M+H]^+$ m/z 459.4.

tert-butyl-rel-(2R,3R)-3-amino-3-(prop-2-en-1-yl)-2-({[(CIS)-4-phenylcyclohexyl]oxy}methyl)piperidine-1-carboxylate (Intermediate 51)

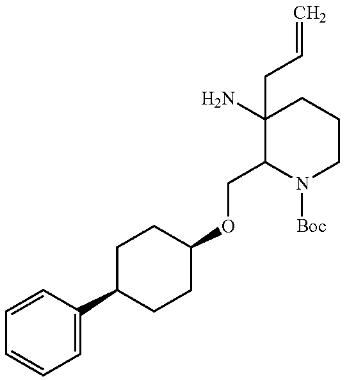

Zinc (1.9 g, 28.6 mmol) was added to a stirred solution of Intermediate 50 (1.31 g, 2.86 mmol) in ethanol (36 mL) and acetic acid (8 mL) at room temperature and the mixture was stirred for 7 h. The reaction mixture was filtered through a pad of celite and washed with methanol. The solution was reduced in volume by roughly half then neutralised with saturated aqueous $NaHCO_3$ (100 mL) and extracted with DCM (2×100 mL). The organic layers were dried over $MgSO_4$, filtered, and concentrated in vacuo to afford the crude material. The crude material was purified by basic silica gel column chromatography (0-100% EtOAc in DCM) to afford the title compound (924 mg) as an oil. $[M+H]^+$ m/z 429.8 tert-butyl-rel-(2R,3R)-3-(prop-2-en-1-yl)-3-(prop-2-enamido)-2-({[(CIS)-4-phenylcyclohexyl]oxy}methyl) piperidine-1-carboxylate (Intermediate 52)

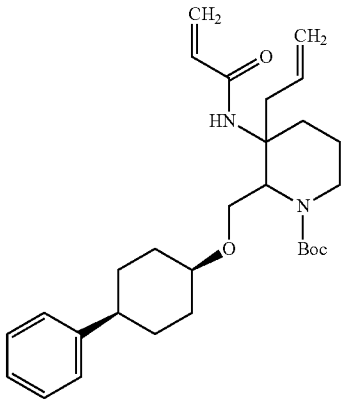 [SMILES: C=CCC1(NC(=O)C=C)CCCN(C(=O)OC(C)(C)C)C1CO[C@H]1CC[C@@H](c2ccccc2)CC1]

A solution of prop-2-enoyl chloride (0.16 mL, 1.94 mmol) was added to a stirred solution of Intermediate 51 (416 mg, 0.971 mmol) and triethylamine (0.27 mL, 1.94 mmol) in DCM (2 mL) at room temperature and the mixture was stirred for 1 h. The reaction mixture was quenched with aqueous 2 M NaOH (10 mL) and extracted with ethyl acetate (2×10 mL). The combined organic layers were passed through a phase separator and concentrated in vacuo to afford the title compound (500 mg) as an orange gum. $[M+H]^+$ m/z 483.5 tert-butyl-rel-(6R,7R)-2-oxo-7-({[(CIS)-4-phenylcyclohexyl]oxy}methyl)-1,8-diazaspiro[5.5]undec-3-ene-8-carboxylate (Intermediate 53)

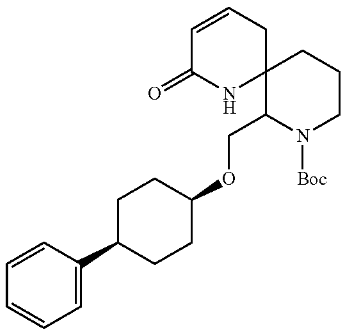 [SMILES: CC(C)(C)OC(=O)N1CCCC2(CC=CC(=O)N2)C1CO[C@H]1CC[C@@H](c2ccccc2)CC1]

A solution of Intermediate 52 (400 mg, 0.829 mmol) in anhydrous toluene (800 mL) was degassed with $N_2$(g) for 15 minutes, heated to 65° C. and [1,3-bis(2,4,6-trimethylphenyl)imidazolidin-2-ylidene]dichloro{[5-(dimethylsulfamoyl)-2-(propan-2-yloxy)phenyl]methylidene}ruthenium (30 mg, 0.0414 mmol) was then added and the reaction mixture was heated at 65° C. for 2 h with nitrogen bubbling through the solution for 2 h. Additional [1,3-bis(2,4,6-trimethylphenyl)imidazolidin-2-ylidene]dichloro{[5-(dimethylsulfamoyl)-2-(propan-2-yloxy)phenyl] methylidene}ruthenium (30 mg, 0.0414 mmol) was added and the mixture was heated at 65° C. for 2 h. Additional [1,3-bis(2,4,6-trimethylphenyl)imidazolidin-2-ylidene]dichloro{[5-(dimethylsulfamoyl)-2-(propan-2-yloxy)phenyl] methylidene}ruthenium (30 mg, 0.0414 mmol) was added and the mixture was heated at 65° C. for 4 h. The reaction mixture was concentrated in vacuo and was purified by silica gel column chromatography (0-100% EtOAc in heptane), to afford the title compound (134 mg). $[M+H]^+$ m/z 455.4 tert-butyl-rel-(6S,7R)-2-oxo-7-({[(CIS)-4-phenylcyclohexyl]oxy}methyl)-1,8-diazaspiro[5.5]undecane-8-carboxylate (Intermediate 54)

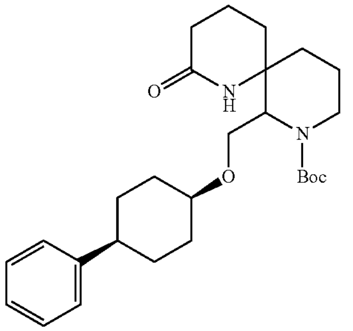

A suspension of Intermediate 53 (50 mg, 0.110 mmol) and 10% Pd/C (50% wet) (12 mg, 0.0055 mmol) in ethanol (5 mL) was stirred under a hydrogen atmosphere at room for 16 h. The reaction mixture was filtered through a pad of celite and washed with methanol. The combined organic layers were concentrated in vacuo to afford the title compound (21 mg). $[M+H]^+$ m/z=457.4.

rel-(6S,7R)—N-ethyl-2-oxo-7-({[(CIS)-4-phenylcyclohexyl]oxy}methyl)-1,8-diazaspiro[5.5]undecane-8-carboxamide (33)

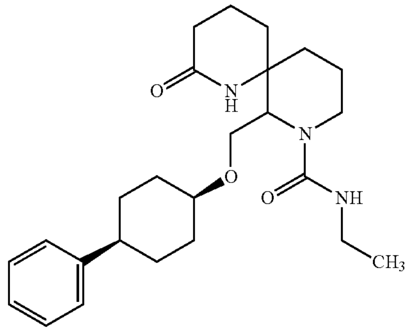 [SMILES: CCNC(=O)N1CCCC2(CCCC(=O)N2)C1CO[C@H]1CC[C@@H](c2ccccc2)CC1]

A solution of trifluoro acetic acid (1.0 mL, 13.1 mmol) and Intermediate 54 (21 mg, 0.046 mmol) in DCM (1 mL) was stirred at room temperature for 4 h. The reaction was quenched with saturated $NaHCO_3$ (2 mL) and extracted with DCM (3×2 mL). The combined organic layers were passed through a phase separator and concentrated in vacuo to afford the crude material. The crude material was dissolved in DCM (1 mL) and cooled to 0° C. Triethylamine (26 µL, 0.184 mmol) then isocyanatoethane (7.3 µL, 0.092 mmol) were added sequentially at 0° C. and the mixture was stirred for 30 minutes at room temperature. The reaction mixture was quenched with 2 M aqueous NaOH (2 mL) and extracted with DCM (3×5 mL), The combined organic layers were passed through a phase separator and concentrated in vacuo to afford the crude material. The crude material was purified by reverse column chromatography (10-60% MeCN in water (0.1% $NH_3$)), to afford the title compound (10.4 mg) as a solid.

$^1$H NMR (400 MHz, $CDCl_3$) δ 7.34-7.27 (m, 2H), 7.23-7.15 (m, 3H), 6.16 (s, 1H), 4.34-4.22 (m, 1H), 3.90 (d, J=12.5 Hz, 1H), 3.81 (dd, J=9.7, 7.1 Hz, 1H), 3.74 (dd, J=9.7, 3.3 Hz, 1H), 3.65 (p, J=3.0 Hz, 1H), 3.30-3.16 (m, 2H), 3.11-3.02 (m, 1H), 2.59-2.49 (m, 1H), 2.45 (dt, J=17.8, 4.3 Hz, 1H), 2.37-2.26 (m, 1H), 2.21 (dt, J=13.7, 4.0 Hz, 1H), 2.08-1.97 (m, 2H), 1.97-1.49 (m, 12H), 1.45-1.35 (m, 1H), 1.12 (t, J=7.2 Hz, 3H). 1 NH exchanged.

LCMS (Method A): $[M+H]^+$ m/z 428.4, RT 3.21 minutes.

Example 34: (6R,7S)—N-ethyl-2-oxo-7-({[(CIS)-4-phenylcyclohexyl]oxy}methyl)-1,8-diazaspiro[5.5]undecane-8-carboxamide Example 35: (6S,7R)—N-ethyl-2-oxo-7-({[(CIS)-4-phenylcyclohexyl]oxy}methyl)-1,8-diazaspiro[5.5]undecane-8-carboxamide

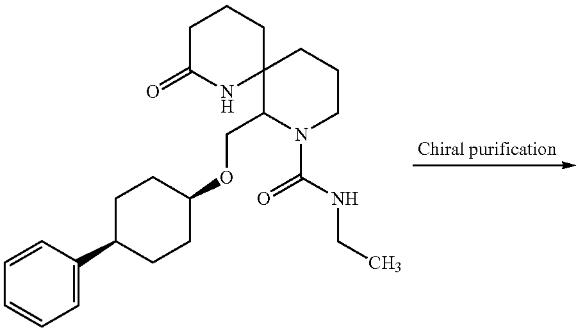

33

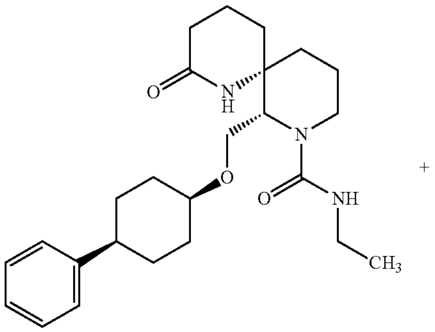

34

-continued

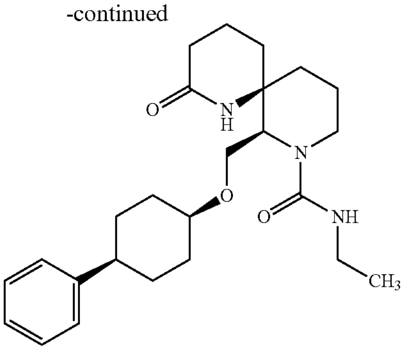

35

Example 33 (5.3 mg) was subjected to chiral preparative purification using Waters 600 eluting with 70/30% v/v n-Hexane/ethanol, Chiralpak AS-H (25×2.0 cm), 5 µm, flow rate 17 mL/minutes, to afford the title compounds (Peak 1, 2.5 mg, 100% cc; and Peak 2, 2.6 mg, 100% ee). The absolute stereochemistry of each separated compound 34 and 35 was not conclusively determined but assigned as shown below.

Example 34: Peak 1 (was assigned 6R,7S at piperidine); $^1$H NMR (400 MHz, $CDCl_3$) δ 7.36-7.28 (m, 2H), 7.25-7.14 (m, 3H), 5.96 (s, 1H), 4.76 (br s, 1H), 4.28 (br d, J=4.4 Hz, 1H), 3.93 (br d, J=12.8 Hz, 1H), 3.86-3.77 (m, 1H), 3.76-3.68 (m, 1H), 3.67-3.59 (m, 1H), 3.35-3.17 (m, 2H), 3.05 (br t, J=12.6 Hz, 1H), 2.63-2.50 (m, 1H), 2.49-2.39 (m, 1H), 2.37-2.26 (m, 1H), 2.25-2.16 (m, 1H), 2.02 (br d, J=14.0 Hz, 2H), 1.98-1.49 (m, 12H), 1.40 (ddd, J=13.8, 10.5, 5.3 Hz, 1H), 1.12 (t, J=7.2 Hz, 3H).

LCMS (Method C): $[M+H]^+$ m/z 428.5, RT 0.96 minutes.

Chiral analysis (Chiralpak AS-H, 25×0.46 cm, 5 m, 70/30 n-Hexane:ethanol): RT 5.0 minutes.

Example 35: Peak 2 (was assigned 6R,7S at piperidine): $^1$H NMR (400 MHz, $CDCl_3$) δ 7.36-7.28 (m, 2H), 7.25-7.14 (m, 3H), 5.96 (s, 1H), 4.76 (br s, 1H), 4.28 (br d, J=4.4 Hz, 1H), 3.93 (br d, J=12.8 Hz, 1H), 3.86-3.77 (m, 1H), 3.76-3.68 (m, 1H), 3.67-3.59 (m, 1H), 3.35-3.17 (m, 2H), 3.05 (br t, J=12.6 Hz, 1H), 2.63-2.50 (m, 1H), 2.49-2.39 (m, 1H), 2.37-2.26 (m, 1H), 2.25-2.16 (m, 1H), 2.02 (br d, J=14.0 Hz, 2H), 1.98-1.49 (m, 12H), 1.40 (ddd, J=13.8, 10.5, 5.3 Hz, 1H), 1.12 (t, J=7.2 Hz, 3H).

CMS (Method C): $[M+H]^+$ m/z 428.5, RT 0.96 minutes.

Chiral analysis (Chiralpak AS-H, 25×0.46 cm, 5 µm, 70/30 n-Hexane:ethanol): RT 9.4 minutes.

Example 36: rel-(6S,7R)—N-ethyl-2,2-dioxo-7-({[(CIS)-4-phenylcyclohexyl]oxy}methyl)-4-oxa-2λ$^6$-thia-1,8-diazaspiro[5.5]undecane-8-carboxamide

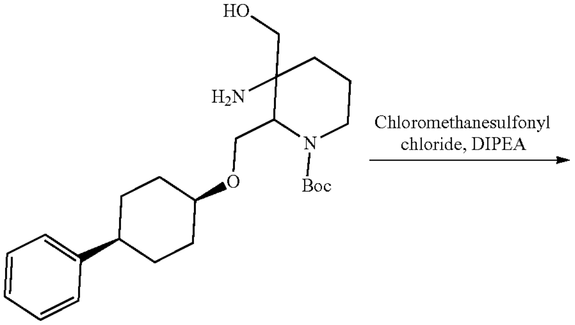

-continued

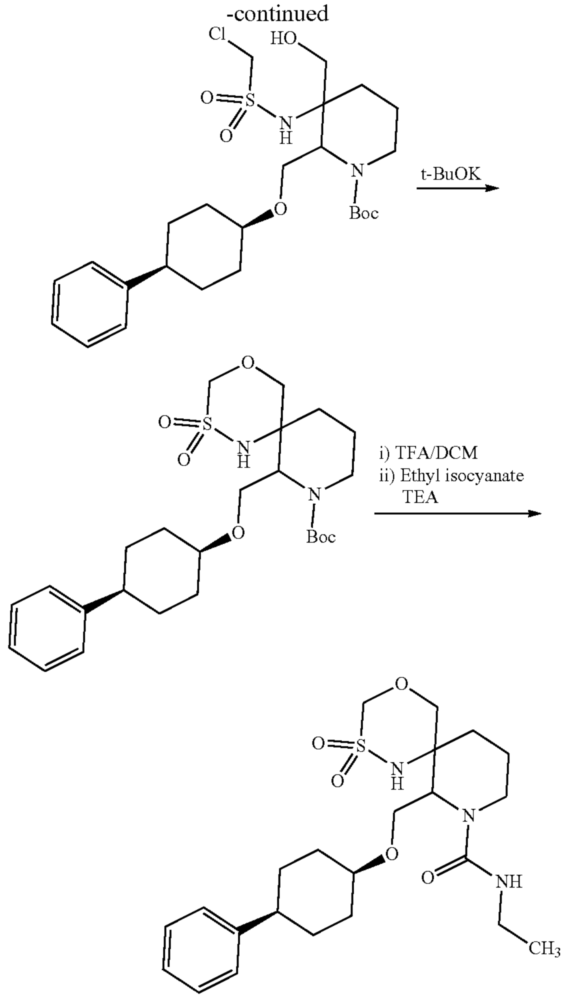

36 tert-butyl-rel-(2R,3S)-3-(chloromethanesulfonamido)-3-(hydroxymethyl)-2-({[(CIS)-4-phenylcyclohexyl]oxy}methyl)piperidine-1-carboxylate (Intermediate 55)

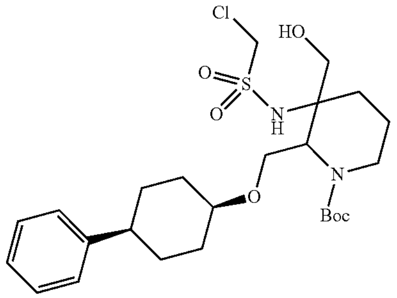 [SMILES: CC(C)(C)OC(=O)N1CCCC(CO)(NS(=O)(=O)CCl)C1CO[C@H]1CC[C@@H](c2ccccc2)CC1]

Chloromethanesulfonyl chloride (65 μL, 0.717 mmol) was added to a solution of Intermediate 6 (150 mg, 0.358 mmol) and N-ethyl-N-(propan-2-yl)propan-2-amine (0.19 mL, 1.08 mmol) in anhydrous DCM (5 mL) at 0° C. The reaction was stirred for 30 min and then diluted with DCM (5 mL) and water (5 mL). The reaction was separated, and the aqueous phase was extracted with DCM (2×5 mL). The organic phases were combined, passed through a phase separator, and concentrated in vacuo to afford to the title compound (190 mg) as a yellow gum. $[M+Na]^+$ m/z 553.2 tert-butyl-rel-(6S,7R)-2,2-dioxo-7-({[(CIS)-4-phenylcyclohexyl]oxy}methyl)-4-oxa-2$\lambda^6$-thia-1,8-diazaspiro[5.5]undecane-8-carboxylate (Intermediate 56)

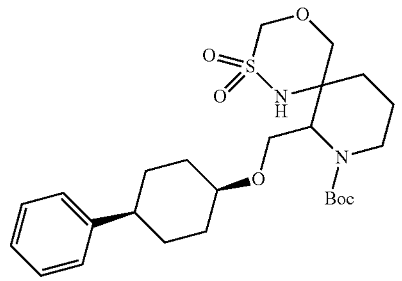 [SMILES: CC(C)(C)OC(=O)N1CCCC2(COCS(=O)(=O)N2)C1CO[C@H]1CC[C@@H](c2ccccc2)CC1]

Intermediate 55 (190 mg, 0.358 mmol) was dissolved in THF (5 mL) and potassium 2-methylpropan-2-olate (100 mg, 0.894 mmol) was added. The reaction mixture was stirred at room temperature for 2 h. The reaction was quenched with water (10 mL) and EtOAc (10 mL). The pH was adjusted to 7 with saturated aqueous $NH_4Cl$ solution (ca. 5 ml) and extracted with DCM (2×10 mL). The combined organic layers were washed with brine (15 mL), passed through a phase separator, and concentrated in vacuo to afford the crude material. The crude material was purified by silica gel column chromatography (0-100% EtOAc in heptane), to afford the title compound (45 mg) as a solid. $[M+Na]^+$ m/z 517.3.

rel-(6S,7R)—N-ethyl-2,2-dioxo-7-({[(CIS)-4-phenylcyclohexyl]oxy}methyl)-4-oxa-2$\lambda^6$-thia-1,8-diazaspiro[5.5]undecane-8-carboxamide (36)

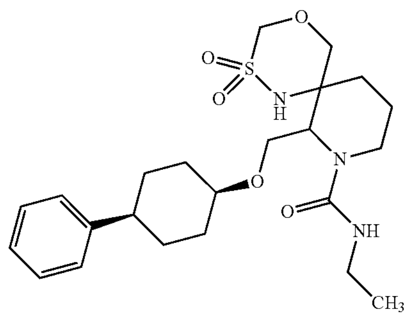 [SMILES: CCNC(=O)N1CCCC2(COCS(=O)(=O)N2)C1CO[C@H]1CC[C@@H](c2ccccc2)CC1]

Intermediate 56 (45 mg, 0.0910 mmol) was dissolved in anhydrous DCM (0.5 mL) and TFA (0.5 mL) and stirred for 30 min at room temperature. The reaction was evaporated and dissolved in anhydrous DCM (0.5 mL) and cooled to 0° C. triethylamine (51 μL, 0.364 mmol) was added followed by isocyanatoethane (14 μL, 0.182 mmol) and the reaction was stirred for 30 min at room temperature. The reaction was diluted with water (5 mL) and DCM (5 mL) and separated. The aqueous layer was further extracted with DCM (2×5 mL) and the organic layers were combined, washed with brine, passed through a phase separator, and concentrated in vacuo to afford the crude material. The crude material was purified by reverse phase column chromatography (10-100% MeCN in water (0.1% $NH_3$)) to afford the title compound (15 mg) as a solid.

$^1H$ NMR (400 MHz, $CDCl_3$) δ 7.33-7.28 (m, 2H), 7.23-7.15 (m, 3H), 5.11 (s, 1H), 4.79 (d, J=11.4 Hz, 1H), 4.73 (dd, J=8.2, 4.1 Hz, 1H), 4.56 (s, 1H), 4.53 (d, J=11.4 Hz, 1H), 4.29 (d, J=12.2 Hz, 1H), 4.22 (d, J=11.7 Hz, 1H), 4.06 (dd, J=9.4, 4.2 Hz, 1H), 3.79 (t, J=8.8 Hz, 1H), 3.74-3.67 (m, 1H), 3.40 (d, J=12.1 Hz, 1H), 3.27 (q, J=5.6 Hz, 2H), 2.91 (t, J=11.4 Hz, 1H), 2.53 (ddd, J=15.2, 7.9, 3.8 Hz, 1H), 2.10-1.97 (m, 2H), 1.88-1.48 (m, 10H), 1.13 (t, J=7.1 Hz, 3H).

LCMS (Method A): $[M+H]^+$ 466.4, RT=3.43 min

Example 37: rel-(6R,7R)—N-ethyl-2,2-dioxo-7-({[(CIS)-4-phenylcyclohexyl]oxy}methyl)-2λ$^6$-thia-1,8-diazaspiro[5.5]undecane-8-carboxamide

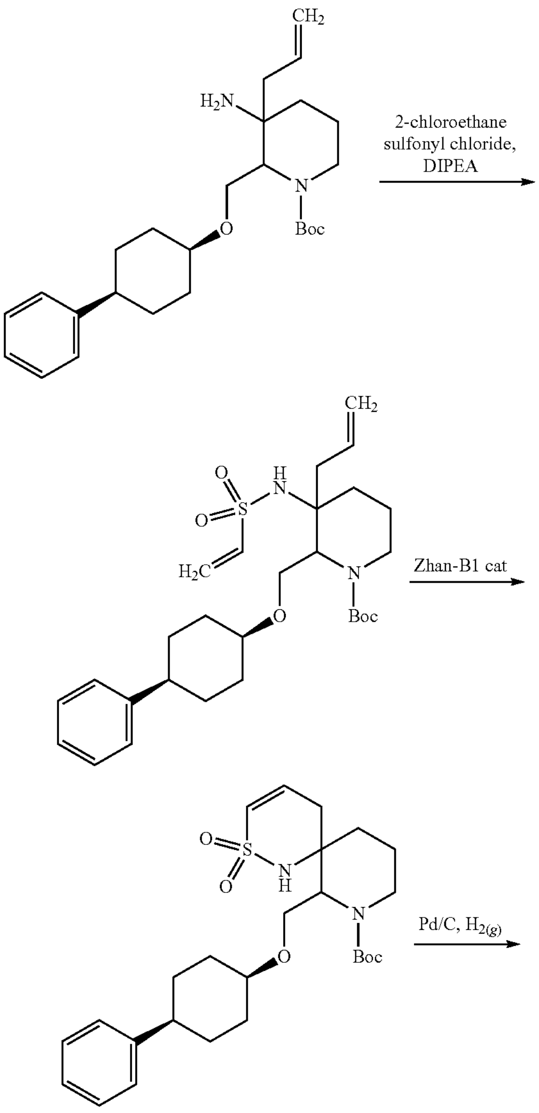

-continued

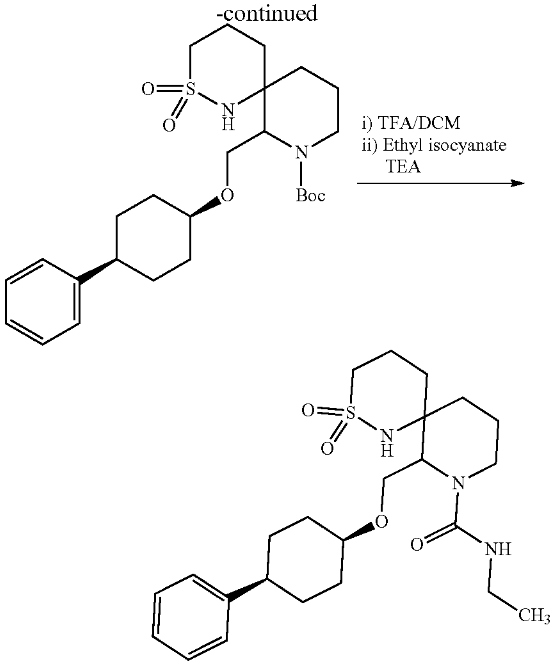

37 tert-butyl-rel-(2R,3R)-3-ethenesulfonamido-3-(prop-2-en-1-yl)-2-({[(CIS)-4-phenylcyclohexyl]oxy}methyl) piperidine-1-carboxylate (Intermediate 57)

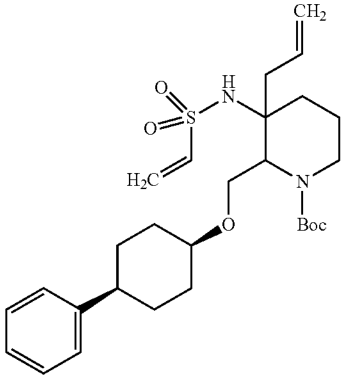 [SMILES: C=CCC1(NS(=O)(=O)C=C)CCCN(C(=O)OC(C)(C)C)C1CO[C@H]1CC[C@@H](c2ccccc2)CC1]

To a stirred solution of Intermediate 51 (200 mg, 0.467 mmol) and N-ethyl-N-(propan-2-yl)propan-2-amine (0.24 mL, 1.40 mmol) in anhydrous DCM (5 mL) was added 2-chloroethanesulfonyl chloride (93 μL, 0.933 mmol) at 0° C. and the mixture was stirred for 30 minutes. The reaction mixture was cooled to room temperature, quenched with a solution of saturated aqueous $NH_4Cl$ (10 mL), water (10 mL) and extracted with DCM (3×15 mL). The combined organic layers were washed with brine (30 mL), passed through a phase separator, and concentrated in vacuo to afford the crude material. The crude material was purified by silica gel column chromatography (0-100% EtOAc in heptane), to afford the title compound (130 mg) as a colourless gum. $[M+Na]^+$ m/z 541.3.

tert-butyl-rel-(6R,7R)-2,2-dioxo-7-({[(CIS)-4-phenylcyclohexyl]oxy}methyl)-2λ$^6$-thia-1,8-diazaspiro[5.5]undec-3-ene-8-carboxylate (Intermediate 58)

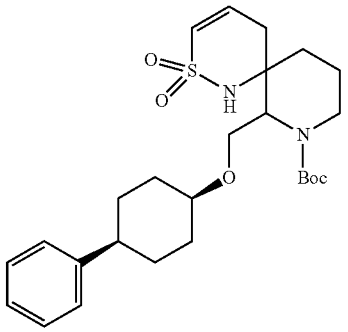 [SMILES: CC(C)(C)OC(=O)N1CCCC2(CC=CS(=O)(=O)N2)C1CO[C@H]1CC[C@@H](c2ccccc2)CC1]

A solution of Intermediate 57 (120 mg, 0.231 mmol) in anhydrous toluene (200 mL) was heated to 65° C. and degassed with $N_2$(g) for 15 min. [1,3-bis(2,4,6-trimethylphenyl)imidazolidin-2-ylidene]dichloro{[5-(dimethylsulfamoyl)-2-(propan-2-yloxy)phenyl]methylidene}ruthenium (8.5 mg, 0.0116 mmol) was added and the reaction mixture was held at 65° C. with a nitrogen bubbling through the solution for 4 h. Additional [1,3-bis(2,4,6-trimethylphenyl) imidazolidin-2-ylidene]dichloro{[5-(dimethylsulfamoyl)-2-(propan-2-yloxy)phenyl]methylidene}ruthenium (8.5 mg, 0.0116 mmol) was added and the mixture was heated for 4 h. The reaction mixture was cooled to room temperature, stirred for 16 h then additional [1,3-bis(2,4,6-trimethylphenyl) imidazolidin-2-ylidene]dichloro{[5-(dimethylsulfamoyl)-2-(propan-2-yloxy)phenyl]methylidene}ruthenium (8.5 mg, 0.0116 mmol) was added and the reaction mixture was heated for 4 h. Additional [1,3-bis(2,4,6-trimethylphenyl)imidazolidin-2-ylidene]dichloro{[5-(dimethylsulfamoyl)-2-(propan-2-yloxy)phenyl]methylidene}ruthenium (8.5 mg, 0.0116 mmol) was added and the mixture was heated for 4 h. The reaction mixture was concentrated in vacuo and the crude material was purified by reverse column chromatography (10-100% MeCN in water (0.1% $NH_3$)), to afford the title compound (56 mg) as an oil. $[M+Na]^+$ m/z 513.1 tert-butyl-rel-(6R,7R)-2,2-dioxo-7-({[(CIS)-4-phenylcyclohexyl]oxy}methyl)-2λ$^6$-thia-1,8-diazaspiro[5.5]undecane-8-carboxylate (Intermediate 59)

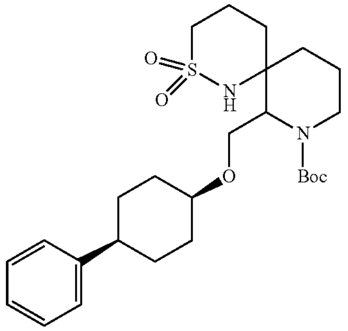 [SMILES: CC(C)(C)OC(=O)N1CCCC2(CCCS(=O)(=O)N2)C1CO[C@H]1CC[C@@H](c2ccccc2)CC1]

Intermediate 58 (55 mg, 0.112 mmol) was dissolved in ethanol (10 mL) and evacuated and back filled 3 times with nitrogen. Palladium on carbon (10% w/w) (10%, 5.9 mg, 5.60 μmol) was added and the reaction was evacuated and back filled three times with hydrogen. The reaction was stirred for 16 h, evacuated, backfilled three times with nitrogen and filtered over celite eluting with ethanol (10 mL) and EtOAc (20 mL). The solution was concentrated in vacuo, to afford the title compound (55 mg) as a colourless gum which was taken on without any further purification. $[M+Na]^+$ m/z 515.1.

rel-(6R,7R)—N-ethyl-2,2-dioxo-7-({[(CIS)-4-phenylcyclohexyl]oxy}methyl)-2λ$^6$-thia-1,8-diazaspiro[5.5]undecane-8-carboxamide (37)

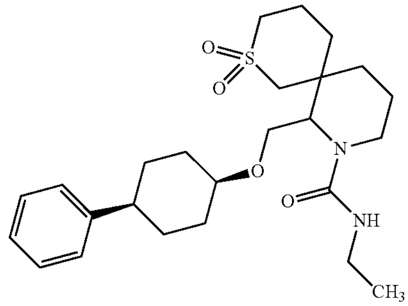 [SMILES: CCNC(=O)N1CCCC2(CCCS(=O)(=O)C2)C1CO[C@H]1CC[C@@H](c2ccccc2)CC1]

Intermediate 59 (55 mg, 0.112 mmol) was dissolved in anhydrous DCM (0.5 mL) and TFA (0.5 mL) and stirred for 30 minutes at room temperature. The mixture was evaporated and dissolved in anhydrous DCM (0.5 mL) and cooled to 0° C. Triethylamine (62 μL, 0.447 mmol) was added followed by isocyanatoethane (18 μL, 0.223 mmol) and the mixture was stirred for 30 min. The reaction mixture was diluted with water (5 mL) and DCM (5 mL) and separated. The aqueous layer was further extracted with DCM (2×5 mL). The combined organic layers were washed with brine, passed through a phase separator, and concentrated in vacuo to afford the crude material. The crude material was purified by reverse phase column chromatography (10-100% MeCN in water (0.1% $NH_3$)), to afford the title compound (43 mg) as a white solid.

$^1$H NMR (500 MHz, $CDCl_3$) δ 7.34-7.25 (m, 2H), 7.25-7.13 (m, 3H), 5.13 (s, 1H), 4.58 (dd, J=8.6, 3.5 Hz, 1H), 4.31 (s, 1H), 4.20 (d, J=11.9 Hz, 1H), 4.08 (dd, J=9.4, 3.9 Hz, 1H), 3.78 (t, J=9.1 Hz, 1H), 3.74-3.67 (m, 1H), 3.29-3.14 (m, 3H), 2.98-2.82 (m, 2H), 2.52 (tt, J=11.6, 3.8 Hz, 1H), 2.39 (tdd, J=15.0, 7.6, 3.3 Hz, 1H), 2.31 (dt, J=14.1, 3.9 Hz, 1H), 2.23 (dp, J=14.2, 4.5 Hz, 1H), 2.10-1.97 (m, 2H), 1.78 (pd, J=14.2, 13.7, 3.6 Hz, 3H), 1.72-1.59 (m, 5H), 1.59-1.48 (m, 2H), 1.37-1.28 (m, 1H), 1.11 (t, J=7.2 Hz, 3H).

LCMS (Method A): $[M+H]^+$ m/z 464.4, RT 3.57 minutes.

Example 38: rel-(1R,6S)—N-ethyl-8,8-dioxo-1-({[(CIS)-4-phenylcyclohexyl]oxy}methyl)-11-oxa-8λ$^6$-thia-2,7-diazaspiro[5.6]dodecane-2-carboxamide

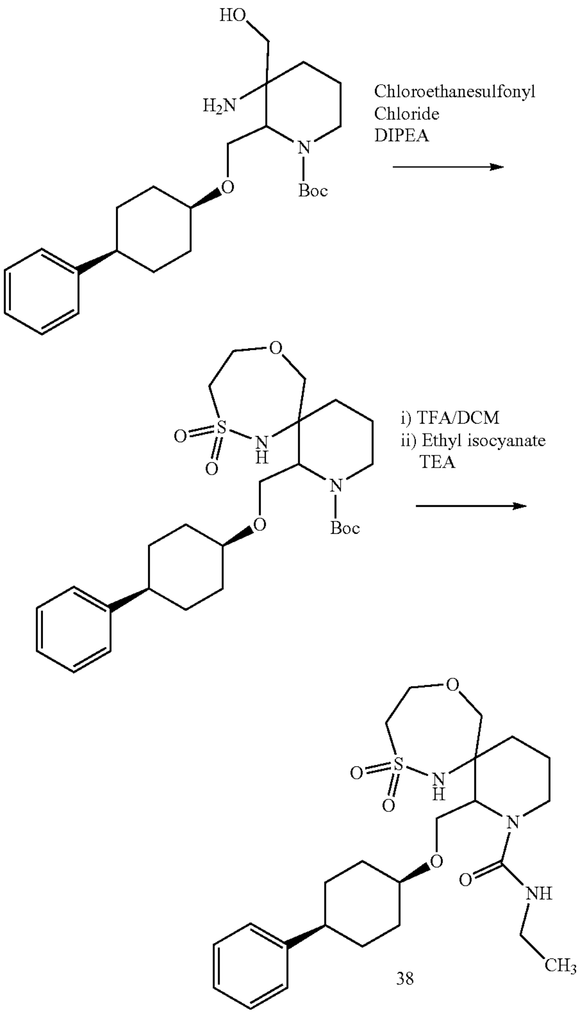

38 tert-butyl-rel-(1R,6S)-8,8-dioxo-1-({[(CIS)-4-phenylcyclohexyl]oxy}methyl)-11-oxa-8lambda6-thia-2,7-diazaspiro[5.6]dodecane-2-carboxylate (Intermediate 60)

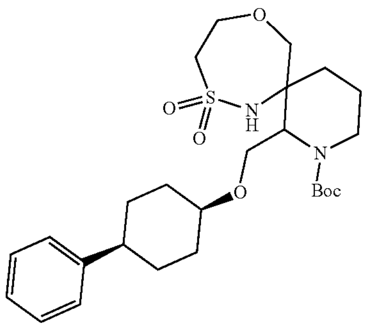 [SMILES: CC(C)(C)OC(=O)N1CCCC2(COCCS(=O)(=O)N2)C1CO[C@H]1CC[C@@H](c2ccccc2)CC1]

To a stirred solution of intermediate 6 (150 mg, 0.358 mmol) and N-ethyl-N-(propan-2-yl)propan-2-amine (0.19 mL, 1.08 mmol) in anhydrous DCM (3.75 mL) was added 2-chloroethanesulfonyl chloride (71 μL, 0.717 mmol) at 0° C. and the mixture was stirred for 30 minutes. The reaction mixture was warmed to room temperature, quenched with a solution of saturated aqueous $NH_4C_1$ (10 mL), water (10 mL) and extracted with DCM (3×15 mL). The combined organic layers were washed with brine (30 mL), passed through a phase separator, and concentrated in vacuo, to afford the title compound (110 mg) as a colourless oil which was taken through to the next step without further purification. $[M+H]^+$ m/z 509.3.

rel-(1R,6S)—N-ethyl-8,8-dioxo-1-({[(CIS)-4-phenylcyclohexyl]oxy}methyl)-11-oxa-8)$^6$-thia-2,7-diazaspiro[5.6]dodecane-2-carboxamide (38)

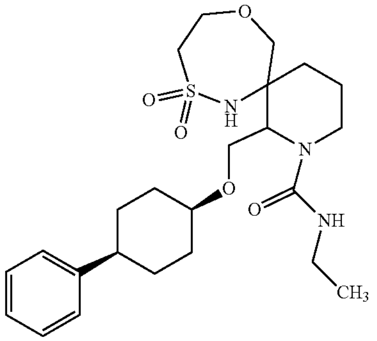 [SMILES: CCNC(=O)N1CCCC2(COCCS(=O)(=O)N2)C1CO[C@H]1CC[C@@H](c2ccccc2)CC1]

Intermediate 60 (100 mg, 0.197 mmol) was dissolved in anhydrous DCM (1.1 mL) and TFA (1.1 mL) and stirred for 30 min. The reaction was evaporated and dissolved in anhydrous DCM (1.1 mL) and cooled to 0° C. Triethyl amine (110 μL, 0.786 mmol) was added followed by isocyanatoethane (31 μL, 0.393 mmol) and the reaction was stirred for 30 min. The reaction was diluted with water (5 mL) and DCM (5 mL) and separated. The aqueous layer was further extracted with DCM (2×5 mL). The combined organic layers were washed with brine, passed through a phase separator, and concentrated in vacuo to afford the crude material. The crude material was purified by reverse phase column chromatography (10-100% MeCN in water (0.1% $NH_3$)), to afford the title compound (26 mg) as a solid.

$^1$H NMR (400 MHz, $CDCl_3$) δ 7.35-7.29 (m, 2H), 7.24-7.14 (m, 3H), 4.91 (s, 1H), 4.57 (d, J=13.2 Hz, 1H), 4.46-4.35 (m, 1H), 4.15 (d, J=15.9 Hz, 2H), 3.83 (s, 1H), 3.79-3.70 (m, 1H), 3.67 (s, 1H), 3.56-3.15 (m, 6H), 2.86 (t, J=11.5 Hz, 1H), 2.55 (tt, J=10.9, 5.1 Hz, 1H), 2.01 (dd, J=10.0, 4.1 Hz, 2H), 1.89 (s, 1H), 1.79-1.44 (m, 9H), 1.13 (t, J=7.2 Hz, 3H). NH proton obscured LCMS (Method A): $[M+H]^+$ m/z 480.4, RT 3.60 minutes.

Example 39: (6R,7S)—N-ethyl-3-methyl-2-oxo-7-({[(CIS)-4-phenylcyclohexyl]oxy}methyl)-4-oxa-1,8-diazaspiro[5.5]undecane-8-carboxamide & Example 40: (6S,7R)—N-ethyl-3-methyl-2-oxo-7-({[(CIS)-4-phenylcyclohexyl]oxy}methyl)-4-oxa-1,8-diazaspiro[5.5]undecane-8-carboxamide

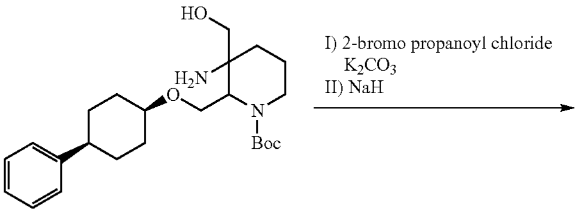

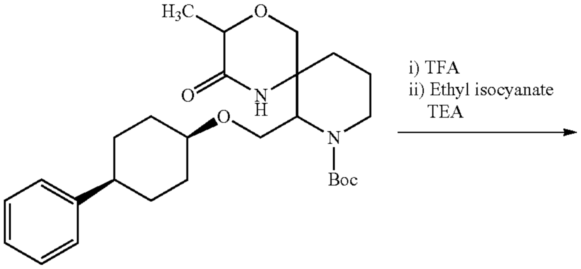

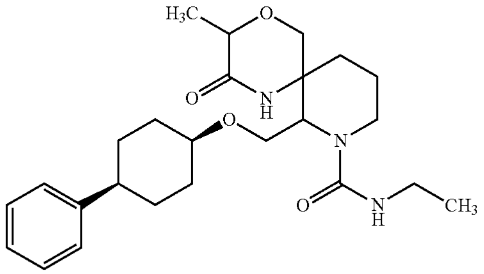

+

39

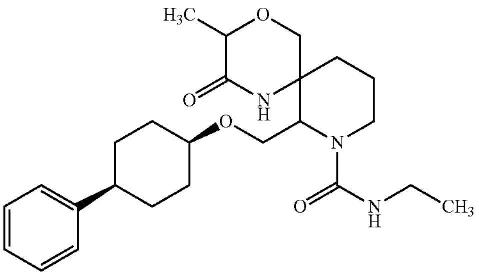

40 tert-butyl-rel-(6S,7R)-3-methyl-2-oxo-7-({[(CIS)-4-phenylcyclohexyl]oxy}methyl)-4-oxa-1,8-diazaspiro[5.5]undecane-8-carboxylate (Intermediate 61)

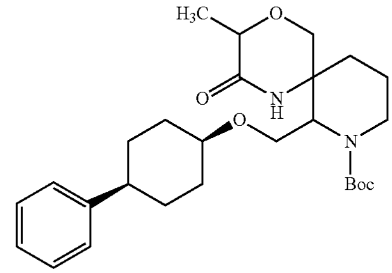 [SMILES: CC1OCC2(CCCN(C(=O)OC(C)(C)C)C2CO[C@H]2CC[C@@H](c3ccccc3)CC2)NC1=O]

A solution of $K_2CO_3$ (99 mg, 0.717 mmol) in water (2 mL) was added to a stirred solution of Intermediate 6 (100 mg, 0.239 mmol) in THF (2 mL) at 0° C. 2-bromopropanoyl chloride (48 μL, 0.476 mmol) was added and the mixture was stirred at 0° C. for 1 h. The reaction mixture was quenched with water (2 mL) and extracted with DCM (3×5 mL). The combined organic layers were concentrated in vacuo to afford the crude material. The residue was dissolved in anhydrous DMF (2 mL) then sodium hydride (8.6 mg, 0.358 mmol) was added at room temperature and the mixture was stirred for 1 h. The reaction mixture was quenched with water (5 mL), the pH was adjusted to pH 7 with 1 M aqueous HCl and saturated aqueous $NaHCO_3$ then extracted with ethyl acetate (2×50 mL) and DCM (3×50 mL). The combined organic layers were passed through a phase separator and concentrated in vacuo to afford the crude material. The crude material was purified by silica gel column chromatography (0-100% EtOAc in heptane then 0-20% methanol in EtOAc), to afford the title compound (41 mg) as a colourless residue. The material was taken through with no further purification. $[M-H]^-$ m/z 471.5.

(6R,7S)—N-ethyl-3-methyl-2-oxo-7-({[(CIS)-4-phenylcyclohexyl]oxy}methyl)-4-oxa-1,8-diazaspiro[5.5]undecane-8-carboxamide (39) & (6S,7R)—N-ethyl-3-methyl-2-oxo-7-({[(CIS)-4-phenylcyclohexyl]oxy}methyl)-4-oxa-1,8-diazaspiro[5.5]undecane-8-carboxamide (40)

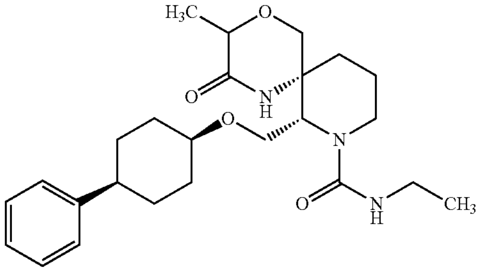

-continued

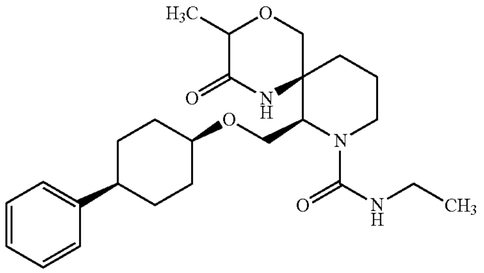

A solution of trifluoro acetic acid (1.0 mL, 13.1 mmol) and Intermediate 61 (41 mg, 0.0868 mmol) in DCM (2 mL) was stirred at room temperature for 1 h. The reaction was quenched with saturated $NaHCO_3$ (2 mL) and extracted with DCM (3x2 mL). The combined organic layers were passed through a phase separator and concentrated in vacuo to afford the crude material. The residue was dissolved in DCM (2 mL), and triethylamine (24 μL, 0.174 mmol) then isocyanatoethane (14 μL, 0.174 mmol) were added sequentially at room temperature and the mixture was stirred for 0.5 h. The reaction mixture was quenched with 2 M aqueous NaOH (2 mL) and extracted with DCM (3x5 mL). The combined organic layers were passed through a phase separator and concentrated in vacuo to afford the crude material. Attempted purification of the crude material was performed by reverse phase column chromatography (10-100% acetonitrile in water (0.1% $NH_3$)), afforded a white solid. This was purified by chiral preparative purification using Waters 600 eluting with 75/25% v/v n-Hexane/ethanol+0.1% isopropylamine, Chiralpak AS-H (25x2.0 cm), 5 μm, flow rate 17 mL/minutes, to afford the title compounds (Peak 1, 2.8 mg, 100% ee; and Peak 2, 4.9 mg, 100% ee). The absolute stereochemistry of each separated compound 39 and 40 was not conclusively determined but assigned as shown below.

Example 39: Peak 1 (was assigned 6R,7S at piperidine); $^1$H NMR (500 MHz, $CDCl_3$) δ 7.34-7.28 (m, 2H), 7.25-7.16 (m, 3H), 6.42-5.74 (m, 1H), 4.88-4.60 (m, 1H), 4.48-4.35 (m, 1H), 4.34-4.12 (m, 1H), 4.11-3.88 (m, 1H), 3.88-3.73 (m, 4H), 3.70-3.62 (m, 1H), 3.33-3.21 (m, 2H), 3.13-2.96 (m, 1H), 2.55 (tt, J=11.3, 4.2 Hz, 1H), 2.09-1.85 (m, 4H), 1.82-1.53 (m, 8H), 1.53-1.45 (m, 3H), 1.14 (t, J=7.2 Hz, 3H).

LCMS (Method C): $[M+H]^+$ m/z 444.3, RT 1.00 minutes.

Chiral analysis (Chiralcelpak AS-H, 25x0.46 cm, 5 μm, 75/25 n-Hexane/ethanol+0.1% isopropylamine): RT 5.0 minutes.

Example 40: Peak 2 (was assigned 6S, 7R at piperidine): $^1$H NMR (500 MHz, $CDCl_3$) δ 7.34-7.28 (m, 2H), 7.25-7.16 (m, 3H), 6.42-5.74 (m, 1H), 4.88-4.60 (m, 1H), 4.48-4.35 (m, 1H), 4.34-4.12 (m, 1H), 4.11-3.88 (m, 1H), 3.88-3.73 (m, 4H), 3.70-3.62 (m, 1H), 3.33-3.21 (m, 2H), 3.13-2.96 (m, 1H), 2.55 (tt, J=11.3, 4.2 Hz, 1H), 2.09-1.85 (m, 4H), 1.82-1.53 (m, 8H), 1.53-1.45 (m, 3H), 1.14 (t, J=7.2 Hz, 3H).

LCMS (Method C): $[M+H]^+$ m/z 444.3, RT 1.00 minutes.

Chiral analysis (Chiralcelpak AS-H, 25x0.46 cm, 5 μm, 75/25 n-Hexane/ethanol+0.1% isopropylamine): RT 8.0 minutes.

Example 41: rel-(6S,7R)—N-ethyl-3-fluoro-2-oxo-7-({[(CIS)-4-phenylcyclohexyl]oxy}methyl)-4-oxa-1,8-diazaspiro[5.5]undecane-8-carboxamide

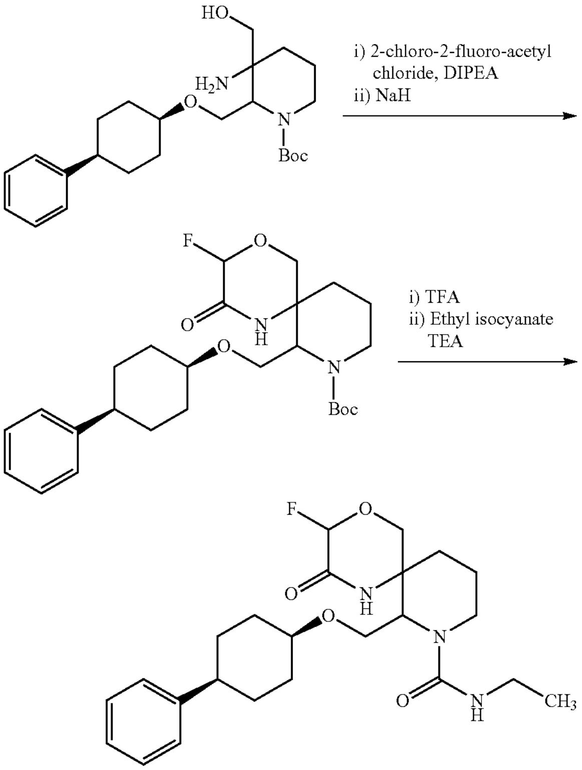

41 rel-(6S,7R)-tert-butyl-3-fluoro-2-oxo-7-({[(CIS)-4-phenylcyclohexyl]oxy}methyl)-4-oxa-1,8-diazaspiro[5.5]undecane-8-carboxylate (Intermediate 62)

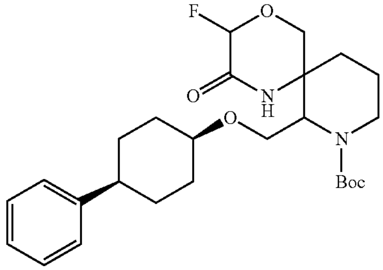 [SMILES: CC(C)(C)OC(=O)N1CCCC2(COC(F)C(=O)N2)C1CO[C@H]1CC[C@@H](c2ccccc2)CC1]

A solution of 2-chloro-2-fluoro-acetyl chloride (282 mg, 2.15 mmol) in DCM (11 mL) was added to a stirred solution of Intermediate 6 (450 mg, 1.08 mmol) and N-ethyl-N-(propan-2-yl)propan-2-amine (0.56 mL, 3.23 mmol) in DCM (11 mL) at 0° C. and the mixture was stirred for 0.5 h. The reaction mixture was quenched with water (5 mL) and extracted with DCM (3x5 mL). The combined organic layers were passed through a phase separator and concentrated in vacuo to afford the crude material. The residue was dissolved in anhydrous THF (11 mL) and added to sodium hydride (60%, 82 mg, 2.04 mmol) at room temperature, the mixture was stirred 50° C. for 0.5 h. Additional sodium hydride (60%, 82 mg, 2.04 mmol) was added at room temperature and the reaction was stirred at 50° C. for 0.5 h. More sodium hydride (60%, 82 mg, 2.04 mmol) was added at room temperature and the reaction was stirred at 50° C. for 0.5 h. The reaction mixture was cooled to room temperature, quenched with water (20 mL) and extracted with ethyl acetate (3×40 mL). The combined organic layers were dried over $MgSO_4$, filtered, and concentrated in vacuo to afford the title compound (450 mg). $[M-H]^-$ m/z 457.4.

rel-(6S,7R)—N-ethyl-3-fluoro-2-oxo-7-({[(CIS)-4-phenylcyclohexyl]oxy}methyl)-4-oxa-1,8-diazaspiro[5.5]undecane-8-carboxamide (41)

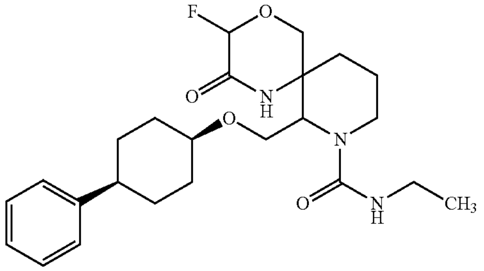 [SMILES: CCNC(=O)N1CCCC2(COC(F)C(=O)N2)C1CO[C@H]1CC[C@@H](c2ccccc2)CC1]

A solution of trifluoro acetic acid (24 mL, 0.311 mol) and Intermediate 62 (521 mg, 1.09 mmol) in DCM (23 mL) was stirred at room temperature for 1 h. The reaction was quenched with saturated $NaHCO_3$ (20 mL) and extracted with DCM (3×20 mL). The combined organic layers were passed through a phase separator and concentrated in vacuo to afford the crude material. The crude mixture was dissolved in DCM (22 mL) and triethylamine (609 μL, 4.37 mmol) then isocyanatoethane (173 μL, 2.19 mmol) were added sequentially at room temperature and the mixture was stirred for 0.5 h at room temperature. The reaction mixture was quenched with 2 M aqueous NaOH (15 mL) and extracted with DCM (3×20 mL). The combined organic layers were passed through a phase separator and concentrated in vacuo to afford the crude material. The crude material was purified by reverse column chromatography (10-60% MeCN in water (0.1% $NH_3$)), to afford the title compound (43 mg) as a white solid.

$^1$H NMR (400 MHz, $CDCl_3$) δ 7.33-7.27 (m, 2H), 7.23-7.16 (m, 3H), 6.49 (s, 1H), 5.57 (d, J=51.8 Hz, 1H), 4.78 (t, J=5.3 Hz, 1H), 4.51-4.46 (m, 1H), 4.17 (d, J=11.9 Hz, 1H), 4.07-3.99 (m, 1H), 3.87-3.70 (m, 3H), 3.64 (p, J=2.9 Hz, 1H), 3.31-3.21 (m, 2H), 3.05 (td, J=13.2, 3.0 Hz, 1H), 2.63-2.48 (m, 1H), 2.09-1.92 (m, 3H), 1.80-1.47 (m, 9H), 1.13 (t, J=7.2 Hz, 3H).

LCMS (Method A): $[M+H]^+$ m/z 448.4, RT 3.39 minutes.

Example 42: (6R,7S)—N-ethyl-3-fluoro-2-oxo-7-({[(CIS)-4-phenylcyclohexyl]oxy}methyl)-4-oxa-1,8-diazaspiro[5.5]undecane-8-carboxamide (42) & Example 43: (6S,7R)—N-ethyl-3-fluoro-2-oxo-7-({[(CIS)-4-phenylcyclohexyl]oxy}methyl)-4-oxa-1,8-diazaspiro[5.5]undecane-8-carboxamide (43)

42

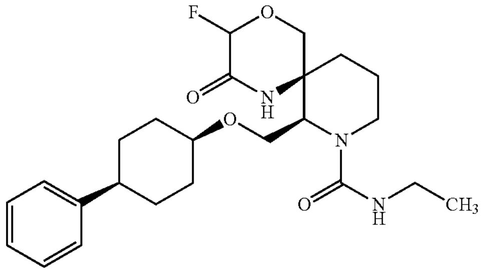

43

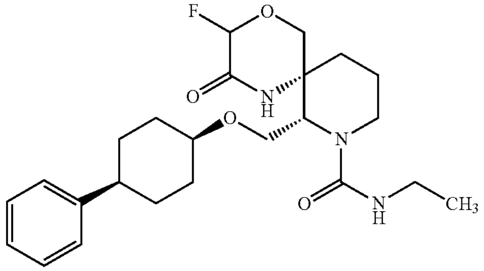

Example 41 (39 mg) was subjected to chiral preparative purification using Waters 600 eluting with 80/20% v/v n-Hexane/ethanol, Chiralpak AS-H (25×2.0 cm), 5 μm, flow rate 17 mL/minutes, to afford the title compounds (Peak 1, 15.5 mg, 100% ee; and Peak 2, 15.2 mg, 99.6% ee). The absolute stereochemistry of each separated compound 42 and 43 was not conclusively determined but assigned as shown below.

Example 42: Peak 1 (was assigned 6R,7S at piperidine); $^1$H NMR (500 MHz, $CDCl_3$) δ 7.34-7.29 (m, 2H), 7.23-7.17 (m, 3H), 5.94 (br s, 1H), 5.59 (d, J=51.9 Hz, 1H), 4.72 (br t, J=4.9 Hz, 1H), 4.53 (br d, J=3.4 Hz, 1H), 4.17 (br d, J=11.8 Hz, 1H), 4.00 (br d, J=10.6 Hz, 1H), 3.87-3.78 (m, 2H), 3.75 (dd, J=9.9, 2.7 Hz, 1H), 3.67-3.61 (m, 1H), 3.32-3.22 (m, 2H), 3.18-3.04 (m, 1H), 2.64-2.48 (m, 1H), 2.09-1.96 (m, 3H), 1.80 (br d, J=12.6 Hz, 1H), 1.77-1.66 (m, 5H), 1.64-1.56 (m, 3H), 1.14 (t, J=7.3 Hz, 3H).

LCMS (Method C): $[M+H]^+$ m/z 448.3, RT 1.01 minutes.

Chiral analysis (Chiralcelpak AS-H, 25×0.46 cm, 5 m, 80/20 n-Hexane:ethanol): RT 6.3 minutes.

Example 43: Peak 2 (was assigned 6S,7R at piperidine); $^1$H NMR (500 MHz, $CDCl_3$) δ 7.34-7.28 (m, 2H), 7.24-7.16 (m, 3H), 6.07 (br s, 1H), 5.59 (d, J=51.9 Hz, 1H), 4.74 (br t, J=5.1 Hz, 1H), 4.52 (br d, J=4.0 Hz, 1H), 4.17 (br d, J=11.9 Hz, 1H), 4.01 (br d, J=11.8 Hz, 1H), 3.90-3.79 (m, 2H), 3.75 (dd, J=9.9, 2.7 Hz, 1H), 3.69-3.59 (m, 1H), 3.35-3.20 (m, 2H), 3.19-3.05 (m, 1H), 2.63-2.49 (m, 1H), 2.12-1.95 (m, 3H), 1.80 (br d, J=13.0 Hz, 1H), 1.76-1.66 (m, 5H), 1.66-1.58 (m, 3H), 1.14 (t, J=7.2 Hz, 3H).

LCMS (Method C): $[M+H]^+$ m/z 448.3, RT 1.01 minutes.

Chiral analysis (Chiralcelpak AS-H, 25×0.46 cm, 5 μm, 80/20 n-Hexane:ethanol): RT 9.4 minutes.

Example 44: N-ethyl-8-oxo-1-({[(CIS)-4-phenylcyclohexyl]oxy}methyl)-11-oxa-2,7-diazaspiro[5.6]dodecane-2-carboxamide (44)

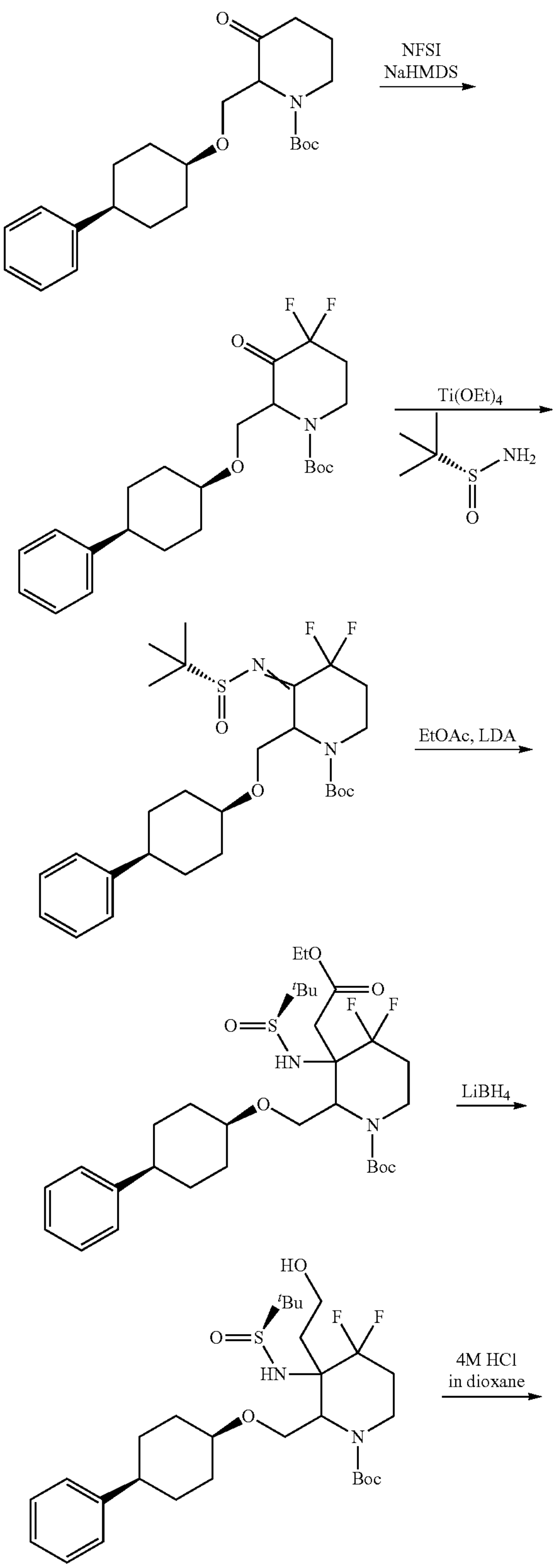

-continued

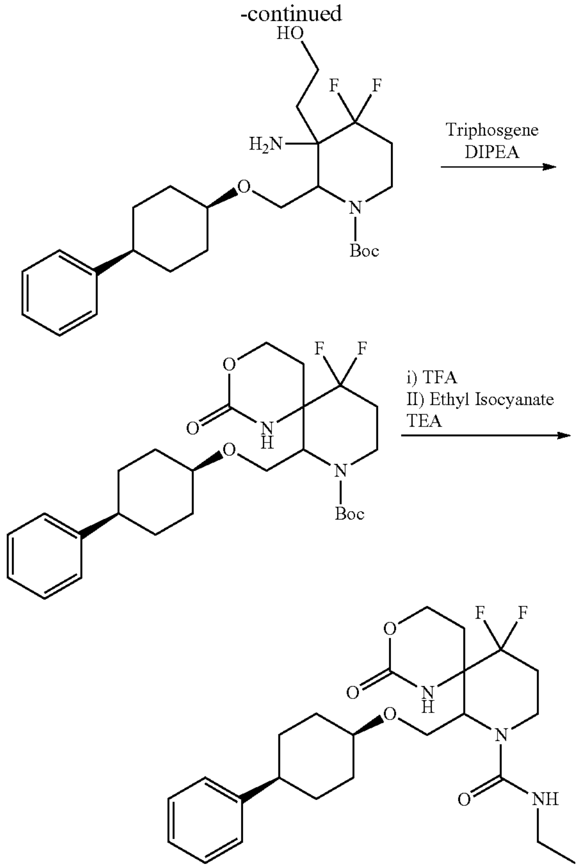

tert-butyl 4,4-difluoro-3-oxo-2-({[(CIS)-4-phenylcyclohexyl]oxy}methyl)piperidine-1-carboxylate (Intermediate 63)

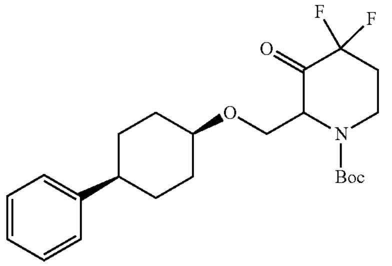 [SMILES: CC(C)(C)OC(=O)N1CCC(F)(F)C(=O)C1CO[C@H]1CC[C@@H](c2ccccc2)CC1]

Intermediate 2 (1.63 g, 4.21 mmol) in anhydrous THF (10 mL) was added dropwise to a solution of 2 M sodium 1,1,1,3,3,3-hexamethyldisilazan-2-ide (2.5 mL, 5.05 mmol) in anhydrous THF (10 mL) at −78° C. and stirred for 30 min, before N-(benzenesulfonyl)-N-fluoro-benzenesulfonamide (1592 mg, 5.05 mmol) in anhydrous THE (10 mL) were added and the mixture was stirred at this temperature for 3 h. The mixture was quenched with saturated aqueous $NaHCO_3$ (20 mL), diluted with water (20 mL), extracted with DCM (3×50 mL). The combined organic layers were dried over $Na_2SO_4$, filtered, and concentrated in vacuo to afford the title compound (2.43 g) as a crude. $[M+Na]^+$ m/z 446.1 tert-butyl(3E/Z)-4,4-difluoro-3-{[(R)-2-methylpropane-2-sulfinyl]imino}-2-({[(CIS)-4-phenylcyclohexyl]oxy}methyl)piperidine-1-carboxylate (Intermediate 64)

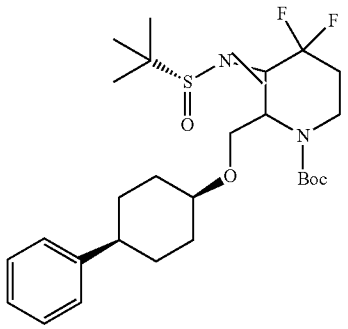

Intermediate 63 (2.43 g, 5.74 mmol), (R)-2-methylpropane-2-sulfinamide (509 mg, 4.20 mmol) and titanium(4+) tetra ethanolate (1.8 mL, 8.41 mmol) were dissolved in anhydrous THF (35 mL) and stirred at 60° C. overnight. The mixture was concentrated in vacuo and the crude material was purified by silica gel column (0-60% TBME in heptane), to afford title compound (729 mg, 50% pure) as a yellow gum. $[M+Na]^+$ m/z 549.2 tert-butyl 3-(2-ethoxy-2-oxoethyl)-4,4-difluoro-3-{[(S)-2-methylpropane-2-sulfinyl]amino}-2-({[(CIS)-4-phenyl cyclohexyl]oxy}methyl)piperidine-1-carboxylate (Intermediate 65)

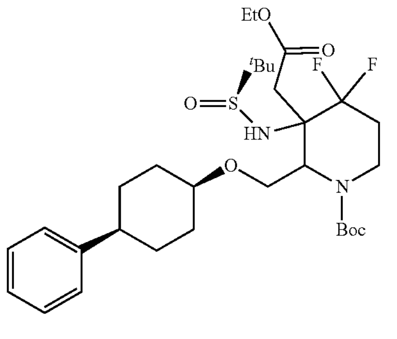 [SMILES: CCOC(=O)CC1(N[S@@](=O)C(C)(C)C)C(CO[C@H]2CC[C@@H](c3ccccc3)CC2)N(C(=O)OC(C)(C)C)CCC1(F)F]

A dropwise solution of anhydrous ethyl acetate (0.68 mL, 6.92 mmol) was added to the stirred solution of 2 M lithium dipropan-2-ylazanide (3.5 mL, 6.92 mmol) in THF (3 mL) at −78° C. and mixture was stirred for 30 min then a dropwise solution of Intermediate 64 (365 mg, 0.692 mmol) in dry THF (5 mL) was added and mixture was stirred at −78° C. for 1 h. The reaction mixture was cooled to room temperature, quenched with a solution of saturated aqueous $NH_4Cl$ (10 mL), water (10 mL) and extracted with ethyl acetate (3×25 mL). The combined organic layers were washed with brine (25 mL), dried over $MgSO_4$, filtered and concentrated in vacuo to afford the crude material. The crude material was purified by column chromatography (0-100% EtOAc in heptane), to afford the title compound (200 mg) as a beige solid. $[M+H]^+$ m/z 615.3 tert-butyl 4,4-difluoro-3-(2-hydroxyethyl)-3-{[(S)-2-methylpropane-2-sulfinyl]amino}-2-({[(CIS)-4-phenylcyclohexyl]oxy}methyl)piperidine-1-carboxylate (Intermediate 66)

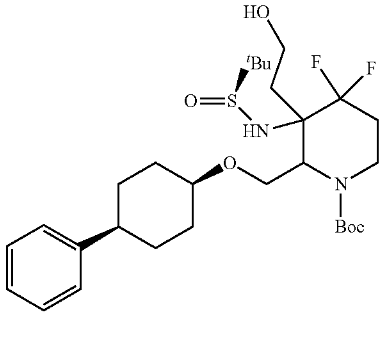 [SMILES: CC(C)(C)OC(=O)N1CCC(F)(F)C(CCO)(N[S@@](=O)C(C)(C)C)C1CO[C@H]1CC[C@@H](c2ccccc2)CC1]

A solution of 4 M lithium tetrahydroborate (0.13 mL, 0.517 mmol) was added dropwise to the stirred solution of Intermediate 65 (200 mg, 0.325 mmol) in THE (2.6 mL) at 0° C. and stirred for 1 h. The reaction mixture warmed up to room temperature and stirred for 3 h. The reaction mixture was quenched with water (5 mL, extracted with EtOAc (3×5 mL), washed with brine (5 mL), dried over $MgSO_4$, and concentrated in vacuo to afford the title compound (155 mg) as a yellow gum. $[M+H]^+$ m/z 573.5 tert-butyl 3-amino-4,4-difluoro-3-(2-hydroxyethyl)-2-({[(CIS)-4-phenylcyclohexyl]oxy}methyl)piperidine-1-carboxylate (Intermediate 67)

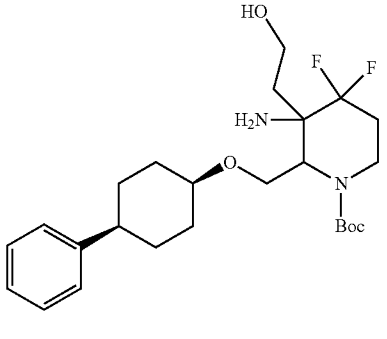 [SMILES: CC(C)(C)OC(=O)N1CCC(F)(F)C(N)(CCO)C1CO[C@H]1CC[C@@H](c2ccccc2)CC1]

Intermediate 66 (155 mg, 0.271 mmol) was dissolved in methanol (2.3 mL) and cooled to 0° C. 4M HCL in dioxane (0.070 mL, 0.279 mmol) was added dropwise and the reaction was stirred at 0° C. for 3 h. Additional 4M HCL in dioxane (7.7 μL, 0.0310 mmol) was added and the reaction mixture was stirred overnight at room temperature. The reaction was quenched at 0° C. by the dropwise addition of saturated aqueous $NaHCO_3$ (5 mL) and extracted with 10% methanol in DCM (3×5 mL). The combined organic layers were filtered through a phase separator concentrated in vacuo to afford the title compound (150 mg) as a pale-yellow oil, which was taken onto the next step without purification. $[M+H]^+$ m/z 469.5 tert-butyl 11,11-difluoro-2-oxo-7-({[(CIS)-4-phenylcyclohexyl]oxy}methyl)-3-oxa-1,8-diazaspiro[5.5]undecane-8-carboxylate (Intermediate 68)

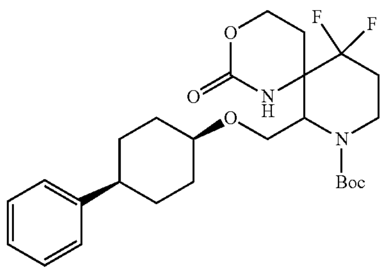 [SMILES: CC(C)(C)OC(=O)N1CCC(F)(F)C2(CCOC(=O)N2)C1CO[C@H]1CC[C@@H](c2ccccc2)CC1]

N-ethyl-N-(propan-2-yl)propan-2-amine (0.036 mL, 0.208 mmol) was added to a stirred solution of Intermediate 67 (65%, 150 mg, 0.208 mmol) and bis(trichloromethyl) carbonate (62 mg, 0.208 mmol) in at 0° C. The reaction mixture was stirred at 0° C. for 1.5 h then quenched with saturated aqueous $NaHCO_3$ solution (1 mL) and purged with $N_2$(g) for 30 min using 20% NaOH scrubber to quench excess of phosgene gas. The solution was extracted with DCM (3×1 mL) and passed through a phase separator and concentrated in vacuo to afford the crude material. The crude material was purified by silica gel column chromatography (0-100% EtOAc), to afford the title compound (60 mg) as a colourless gum. $[M+H]^+$ m/z 469.5

N-ethyl-8-oxo-1-({[(CIS)-4-phenylcyclohexyl]oxy}methyl)-11-oxa-2,7-diazaspiro[5.6]dodecane-2-carboxamide (44)

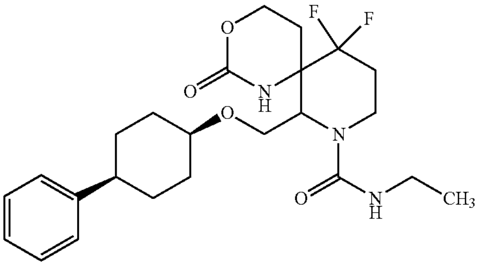 [SMILES: CCNC(=O)N1CCC(F)(F)C2(CCOC(=O)N2)C1CO[C@H]1CC[C@@H](c2ccccc2)CC1]

A solution of trifluoro acetic acid (2.6 mL, 34.5 mmol) and intermediate 68 (60 mg, 0.121 mmol) in DCM (2.6 mL) was stirred at room temperature for 1 h. The mixture was concentrated in vacuo. The residue was dissolved in DCM (1 mL) and cooled to 0° C. Triethylamine (68 μL, 0.485 mmol) then isocyanatoethane (19 μL, 0.243 mmol) were added sequentially at 0° C. and the mixture was stirred for 2 h at room temperature. The reaction mixture was quenched with 2 M aqueous NaOH (2 mL) and extracted with DCM (3×5 mL), The combined organic layers were passed through a phase separator and concentrated in vacuo to afford the crude material. The crude material was purified by reverse column chromatography (10-60% MeCN in water (0.1% $NH_3$)) to afford the title compound (8.0 mg) as a white solid.

$^1$H NMR (400 MHz, $CDCl_3$) δ 7.27-7.19 (m, 2H), 7.14-7.06 (m, 3H), 5.27 (s, 2H), 4.38 (d, J=12.6 Hz, 1H), 4.34-4.18 (m, 2H), 4.12 (d, J=9.3 Hz, 1H), 3.75-3.58 (m, 3H), 3.17-3.05 (m, 2H), 2.94 (td, J=14.0, 3.8 Hz, 1H), 2.53-2.41 (m, 1H), 1.97 (td, J=31.5, 28.3, 12.3 Hz, 6H), 1.68-1.54 (m, 6H), 1.01 (t, J=7.2 Hz, 3H).

LCMS (Method A): $[M+H]^+$ m/z 466.4, RT 3.44 minutes

Example 45: (6R,7R)—N-ethyl-11,11-difluoro-2-oxo-7-({[(CIS)-4-phenylcyclohexyl]oxy}methyl)-3-oxa-1,8-diazaspiro[5.5]undecane-8-carboxamide Example 46: (6S,7S)—N-ethyl-11,11-difluoro-2-oxo-7-({[(CIS)-4-phenylcyclohexyl]oxy}methyl)-3-oxa-1,8-diazaspiro[5.5]undecane-8-carboxamide

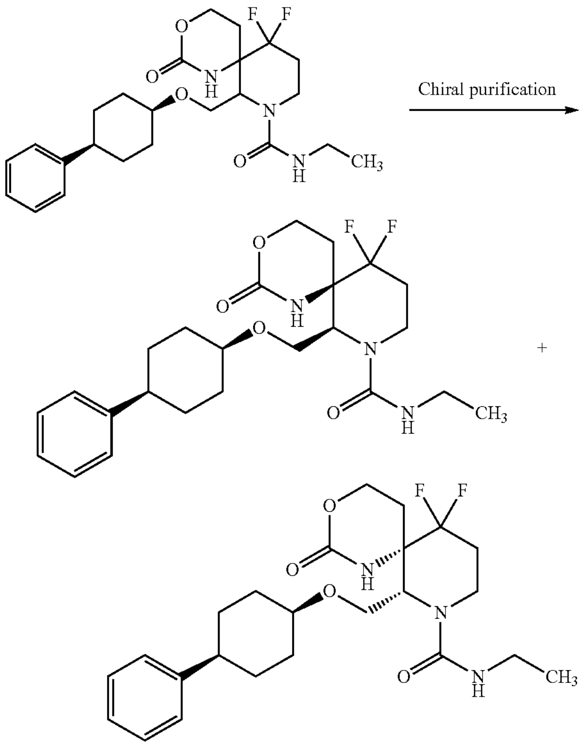

Example 44 (4.3 mg) was subjected to chiral preparative purification using Waters 600 eluting with 80/20% v/v n-Hexane/ethanol, Chiralpak AD-H (25×2.0 cm), 5 μm, flow rate 17 mL/minutes, to afford the title compounds (Peak 1, 2.1 mg, 100% ee; and Peak 2, 1.7 mg, 100% ee). The absolute stereochemistry of each separated compound 45 and 46 was not conclusively determined but assigned as shown below.

Example 45: Peak 1 (was assigned 6R,7R at piperidine); $^1$H NMR (400 MHz, $CDCl_3$) δ 7.34-7.28 (m, 2H), 7.23-7.17 (m, 3H), 5.38 (s, 1H), 5.33 (br t, J=5.1 Hz, 1H), 4.52-4.43 (m, 1H), 4.43-4.28 (m, 2H), 4.26-4.17 (m, 1H), 3.82-3.71 (m, 2H), 3.72-3.67 (m, 1H), 3.29-3.13 (m, 2H), 3.09-2.98 (m, 1H), 2.61-2.51 (m, 1H), 2.17-1.95 (m, 6H), 1.75-1.59 (m, 6H), 1.10 (t, J=7.3 Hz, 3H).

LCMS (Method C): $[M+H]^+$ m/z 466.2, RT 1.03 minutes.

Chiral analysis (Chiralcelpak AD-H, 25×0.46 cm, 5 m, 80:20 n-Hexane:ethanol): RT 4.6 minutes.

Example 46: Peak 2 (was assigned 6S, 7S at piperidine): $^1$H NMR (400 MHz, $CDCl_3$) δ 7.34-7.28 (m, 2H), 7.23-7.17 (m, 3H), 5.38 (s, 1H), 5.33 (br t, J=5.1 Hz, 1H), 4.52-4.43 (m, 1H), 4.43-4.28 (m, 2H), 4.26-4.17 (m, 1H), 3.82-3.71 (m, 2H), 3.72-3.67 (m, 1H), 3.29-3.13 (m, 2H), 3.09-2.98

(m, 1H), 2.61-2.51 (m, 1H), 2.17-1.95 (m, 6H), 1.75-1.59 (m, 6H), 1.10 (t, J=7.3 Hz, 3H).
LCMS (Method C): $[M+H]^+$ m/z 466.1, RT 1.03 minutes.
Chiral analysis (Chiralcelpak AD-H, 25×0.46 cm, 5 μm, 80:20 n-Hexane:ethanol): RT 8.5 minutes.
Example 47: (1R,3R,5S)—N-ethyl-3-methyl-7-oxo-1-({[(CIS)-4-phenylcyclohexyl]oxy}methyl)-9-oxa-2,6-diazaspiro[4.5]decane-2-carboxamide
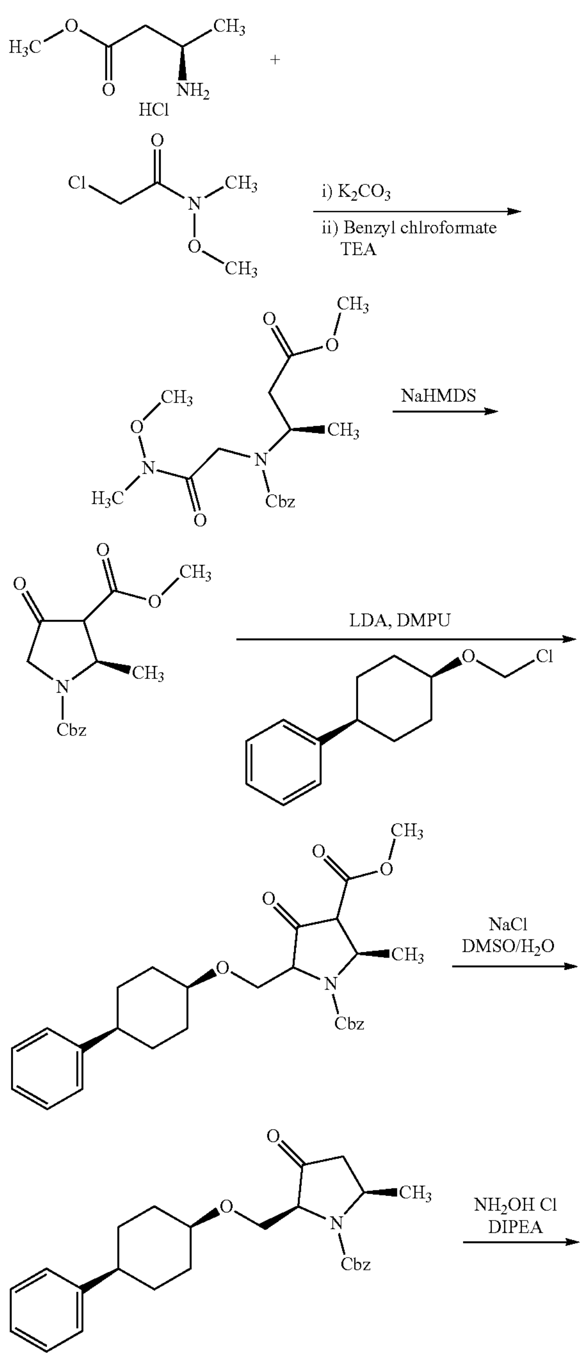
-continued
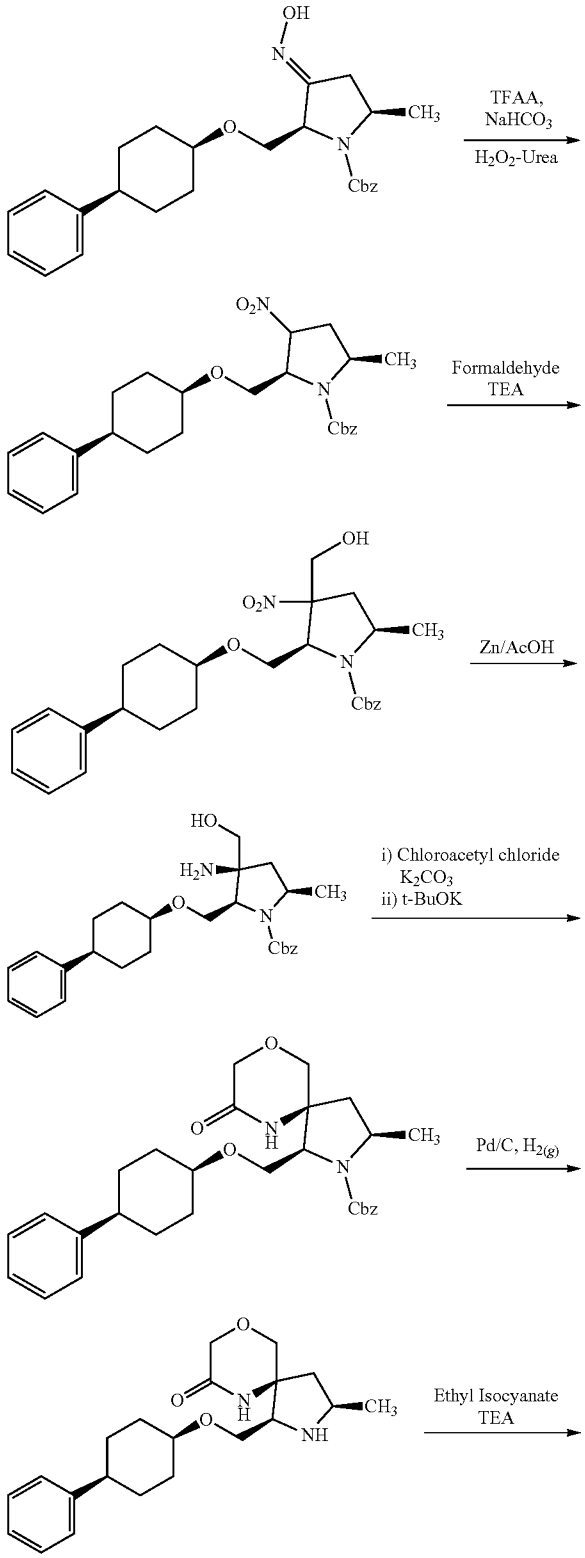

-continued

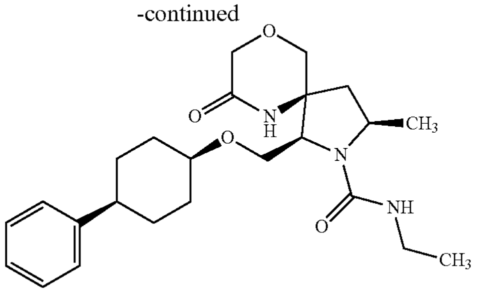

47

Intermediate 69

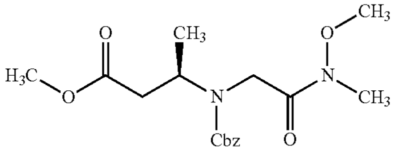

Methyl (3R)-3-{[(benzyloxy)carbonyl]({[methoxy (methyl)carbamoyl]methyl})amino}butanoate To a solution of methyl (3R)-3-aminobutanoate;hydrochloride (36.0 g, 0.234 mol) in acetonitrile (500 mL) was added dipotassium carbonate (71.3 g, 0.516 mol) followed by portion wise addition of 2-chloro-N-methoxy-N-methylacetamide (32.2 g, 0.234 mol). The reaction mixture was heated to 40° C. and stirred for 7 days. The reaction mixture was filtered and washed with ethyl acetate. The filtrate was concentrated in vacuo and the crude material was dissolved in DCM (500 mL), cooled to 0° C., then triethylamine (33 mL, 0.234 mol) and benzyl carbonochloridate (43 mL, 0.305 mol) were added dropwise and the mixture was stirred at room temperature for 24 h. The solution was diluted with DCM (500 mL), washed with $NaHCO_3$ (300 mL), passed through a phase separator, and concentrated in vacuo to afford the crude material. The crude material was purified (0-100% EtOAc in heptane) to afford the title compound methyl (39.5 g) as a pale-yellow oil. $[M+H]^+$ m/z 353.3

Intermediate 70

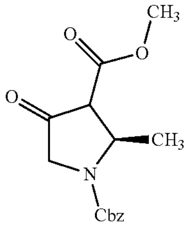 [SMILES: COC(=O)C1C(=O)CN(C(=O)OCc2ccccc2)[C@@H]1C]

1-benzyl 3-methyl (2R)-2-methyl-4-oxopyrrolidine-1,3-dicarboxylate

To a stirred solution of Intermediate 69 (7.60 g, 21.6 mmol) in anhydrous THF (150 mL) was added dropwise 2 M sodium 1,1,1,3,3,3-hexamethyldisilazan-2-ide (11 mL, 21.6 mmol) at −78° C. After the solution was stirred for 10 min at the same temperature, the reaction was quenched with 1M aqueous HCl (22 mL) and water (100 mL) and extracted with EtOAc (3×50 mL). The combined organic layers were washed with brine (50 mL) and dried over $MgSO_4$, filtered, and concentrated in vacuo to afford the crude material. The crude material was purified by silica gel column chromatography (0-80% methanol in DCM), to afford the title compound (4.40 g) as a yellow oil. $[M+H]^+$ m/z 292.2

Intermediate 71

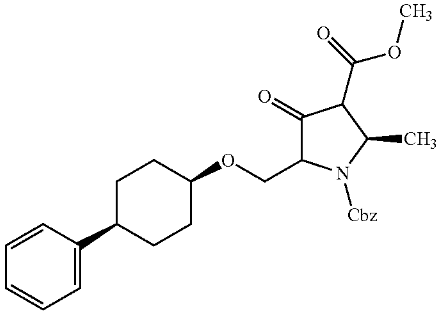 [SMILES: COC(=O)C1C(=O)C(CO[C@H]2CC[C@@H](c3ccccc3)CC2)N(C(=O)OCc2ccccc2)[C@@H]1C]

1-benzyl-3-methyl(2R)-2-methyl-4-oxo-5-({[(CIS)-4-phenylcyclohexyl]oxy}methyl)pyrrolidine-1,3-dicarboxylate To a solution of 4-phenylcyclohexanol (5.99 g, 34.0 mmol) in anhydrous DCM (50 mL) was added paraformaldehyde (1.02 g, 34.0 mmol) followed by addition of chloro (trimethyl)silane (17 mL, 0.136 mol). The reaction was stirred for 2 h at room temperature and the solution was concentrated in vacuo at 30° C. to afford a pale yellow oil of [4-(chloromethoxy)cyclohexyl]benzene. In a separate flask, 2.4 M butyllithium (34 mL, 81.6 mmol) was added to a stirred solution of N-(propan-2-yl)propan-2-amine (11 mL, 81.6 mmol) in anhydrous THF (37.438 mL) at 0° C. The reaction was held at this temperature for 0.5 h. In a third flask the freshly made LDA was added to a stirred solution of 1,3-dimethylhexahydropyrimidin-2-one (16 mL, 0.136 mol) and Intermediate 70 (9.90 g, 34.0 mmol) in anhydrous THF (100 mL) at −78° C. and the solution was held at this temperature for 20 min. [4-(chloromethoxy)cyclohexyl]benzene was added to the reaction mixture in a solution of anhydrous THF (24 mL). The reaction mixture was stirred at −78° C. for 1 h. The reaction mixture was quenched with $NH_4Cl$ (50 mL) and extracted with EtOAc (3×50 mL). The combined organic extracts were washed with brine (1×50 mL), dried over $MgSO_4$, filtered, and concentrated in vacuo to afford the crude material. The crude material was purified by silica gel column chromatography (0-40% methanol in DCM), to afford the title compound (9.90 g) as a colourless oil. $[M+H]^+$ m/z 480.3

Intermediate 72a & 72b

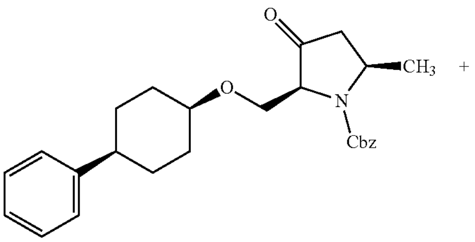

-continued

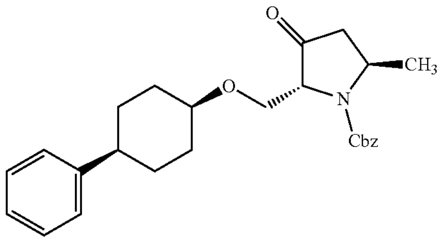

Intermediate 72a: Benzyl (2S,5R)-5-methyl-3-oxo-2-({[(CIS)-4-phenylcyclohexyl]oxy}methyl)pyrrolidine-1-carboxylate & Intermediate 72b: Benzyl (2R,5R)-5-methyl-3-oxo-2-({[(CIS)-4-phenylcyclohexyl]oxy}methyl)pyrrolidine-1-carboxylate A suspension of Intermediate 71 (7.80 g, 16.3 mmol) and sodium chloride (1.78 g, 30.5 mmol) in DMSO (78 mL) and water (7.8 mL) was heated to 130° C. for 2.5 h. The reaction mixture was cooled to room temperature, quenched water (50 mL) and extracted with EtOAc (3×30 mL). The combined organic layers were washed with water (3×30 mL), brine (20 mL), dried over $Na_2SO_4$, filtered, and concentrated in vacuo to afford the crude material. The crude material was purified by silica gel column chromatography column chromatography (0-70% EtOAc in heptane), to afford the title compounds 72a (2.4 g) and 72b (3.60 g) as a pale-yellow oil. $[M+H]^+$ m/z 422.3

Intermediate 73

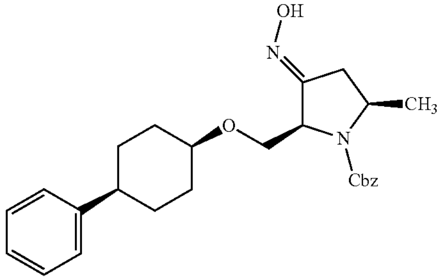 [SMILES: C[C@@H]1C/C(=N\O)[C@H](CO[C@H]2CC[C@@H](c3ccccc3)CC2)N1C(=O)OCc1ccccc1]

Benzyl-(2R,5R)-3-(hydroxyimino)-5-methyl-2-({[(CIS)-4-phenylcyclohexyl]oxy}methyl)pyrrolidine-1-carboxylate A solution of triethylamine (3.4 mL, 24.2 mmol), hydroxylamine hydrochloride (1:1) (1.68 g, 24.2 mmol) and intermediate 72a (3.40 g, 8.07 mmol) in ethanol (15 mL) was heated to 90° C. for 1 h. After cooling, the reaction mixture was diluted with water (50 mL) and extracted with EtOAc (3×40 mL). The combined organic extracts were washed with brine (40 mL), dried over $MgSO_4$, filtered, and concentrated in vacuo, to afford the title compound (3.30 g) as a colourless oil. $[M+H]^+$ m/z=437.3

Intermediate 74

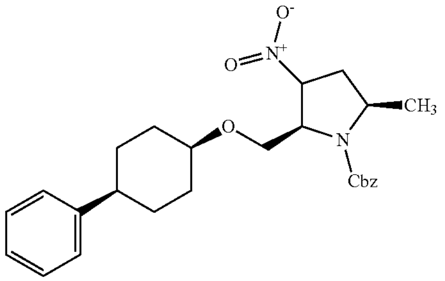 [SMILES: C[C@@H]1CC([N+](=O)[O-])[C@H](CO[C@H]2CC[C@@H](c3ccccc3)CC2)N1C(=O)OCc1ccccc1]

Benzyl(2R,5R)-5-methyl-3-nitro-2-({[(CIS)-4-phenylcyclohexyl]oxy}methyl)pyrrolidine-1-carboxylate Trifluoroacetic anhydride (1.4 mL, 10.4 mmol) in anhydrous acetonitrile (6.7 mL) was added to a stirred solution of hydrogen peroxide-urea (1:1) (1.37 g, 14.6 mmol) in anhydrous acetonitrile (6.7 mL) at 0° C. The reaction was stirred at 0° C. for 2 h. The resulting solution was added dropwise to a mixture of Intermediate 73 (2.49 g, 4.16 mmol) and sodium hydrogen carbonate (1.75 g, 20.8 mmol) in anhydrous acetonitrile (9.6184 mL) at 80° C. and the mixture was stirred at 80° C. for 1 h. The reaction was cooled to room temperature and quenched with saturated aqueous $Na_2SO_3$, diluted with water (20 mL) and extracted with EtOAc (3×20 mL). The combined organic extracts were washed with brine (20 mL), dried over $MgSO_4$, filtered, and concentrated in vacuo to afford the crude material. The crude material was purified by silica gel column chromatography (0-100% EtOAc in heptane), to afford the title (1.20 g) as a white solid. [M+H]+m/z=453.3

Intermediate 75

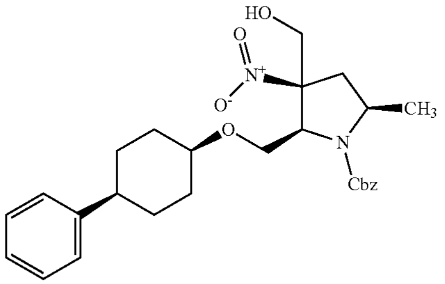 [SMILES: C[C@@H]1C[C@](CO)([N+](=O)[O-])[C@H](CO[C@H]2CC[C@@H](c3ccccc3)CC2)N1C(=O)OCc1ccccc1]

Benzyl (2R,3S,5R)-3-(hydroxymethyl)-5-methyl-3-nitro-2-({[(CIS)-4-phenylcyclohexyl]oxy}methyl)pyrrolidine-1-carboxylate Formaldehyde (37% in water, 1.9 mL, 26.1 mmol) was added to Intermediate 74 (1.27 g, 2.90 mmol) and triethylamine (0.48 mL, 3.48 mmol) in THF (13 mL) at room temperature and the solution was heated to 70° C. for 18 h. After cooling the reaction mixture was diluted with water (20 mL) and extracted with EtOAc (3×20 mL). The combined organic extracts were washed with brine (10 mL), dried over $MgSO_4$, filtered, and concentrated in vacuo to afford the title compound (1.42 g) as a colourless oil. $[M+H]^+$ m/z 483.3

Intermediate 76

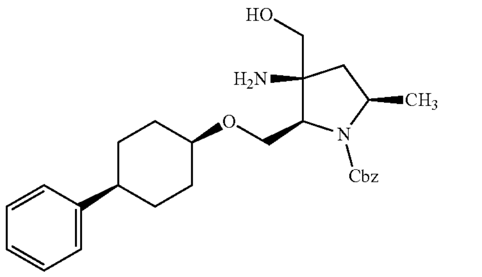 [SMILES: C[C@@H]1C[C@@](N)(CO)[C@H](CO[C@H]2CC[C@@H](c3ccccc3)CC2)N1C(=O)OCc1ccccc1]

Benzyl(2R,3S,5R)-3-amino-3-(hydroxymethyl)-5-methyl-2-({[(CIS)-4-phenylcyclohexyl]oxy}methyl)pyrrolidine-1-carboxylate A suspension of Intermediate 75 (1.16 g, 2.40 mmol) and zinc (1.6 g, 24.0 mmol) in acetic acid (11.2 mL) and ethanol (83 mL) was stirred for 2 h at room temperature. Additional zinc (1.55 g, 24.0 mmol) was added to the reaction mixture was stirred overnight at room temperature. The reaction mixture was filtered through a pad of celite and washed with methanol. The filtrate was neutralised with saturated aqueous $NaHCO_3$ and extracted with DCM (3×50 mL). The combined organic extracts were passed through a phase separator and concentrated in vacuo to afford the title compound (1.22 μm) as a white solid. $[M+H]^+$ m/z 453.4

Intermediate 77

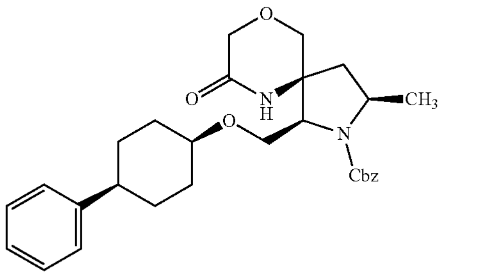 [SMILES: C[C@@H]1C[C@@]2(COCC(=O)N2)[C@H](CO[C@H]2CC[C@@H](c3ccccc3)CC2)N1C(=O)OCc1ccccc1]

Benzyl(1R,3R,5S)-3-methyl-7-oxo-1-({[(CIS)-4-phenylcyclohexyl]oxy}methyl)-9-oxa-2,6-diazaspiro[4.5]decane-2-carboxylate To a solution of Intermediate 76 (200 mg, 0.442 mmol) in THE (2 mL) at 0° C. was added dipotassium carbonate (183 mg, 1.33 mmol) then water (2 mL). To this mixture chloroacetyl chloride (49 μL, 0.619 mmol) was added dropwise at 0° C. The reaction was stirred for 2 h at 0° C. The mixture was quenched with water and extracted with DCM (3×5 mL). The combined organic extracts were washed with brine (5 mL), dried over $MgSO_4$, filtered, and concentrated in vacuo. The intermediate was dissolved in DCM (4 mL) and IPA (4 mL), cooled to 0° C. potassium 2-methylpropan-2-olate (198 mg, 1.77 mmol) was added and the reaction was stirred at 0° C. for 1 h followed by warming to room temperature and stirring overnight. The reaction mixture was quenched with water (5 mL). The mixture was poured onto saturated aqueous $NaHCO_3$ (10 ml) and extracted with DCM (3×10 mL). The combined organic extracts were washed with brine (10 mL), dried over $MgSO_4$, filtered, and concentrated in vacuo to afford the crude material. The crude material was purified by silica gel column chromatography (0-100% EtOAc in heptane), to afford the title compound (80 mg) as a colourless oil. $[M+H]^+$ m/z 493.2

Intermediate 78

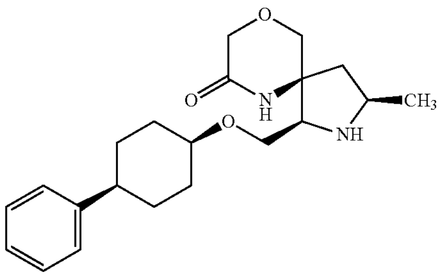 [SMILES: C[C@@H]1C[C@@]2(COCC(=O)N2)[C@H](CO[C@H]2CC[C@@H](c3ccccc3)CC2)N1]

(1R,3R,5S)-3-methyl-1-({[(CIS)-4-phenylcyclohexyl]oxy}methyl)-9-oxa-2,6-diazaspiro[4.5]decan-7-one Intermediate 77 (80 mg, 0.162 mmol) was dissolved in ethanol (8 mL) and the atmosphere was evacuated and backfilled with nitrogen 3 times. Palladium on carbon (10%) (20 mg, 0.162 mmol) was added and the atmosphere was evacuated and backfilled with hydrogen 3 times. The reaction was stirred for 2 h and then filtered through a pad of celite and washed with EtOAc. The filtrated was concentrated in vacuo to afford the title compound (58 mg) as a white gum. $[M+H]^+$ m/z 359.3

(1R,3R,5S)—N-ethyl-3-methyl-7-oxo-1-({[(CIS)-4-phenylcyclohexyl]oxy}methyl)-9-oxa-2,6-diazaspiro[4.5]decane-2-carboxamide (47)

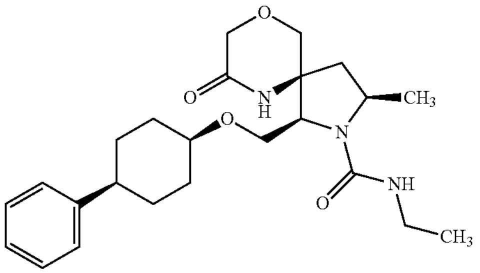 [SMILES: CCNC(=O)N1[C@H](C)C[C@@]2(COCC(=O)N2)[C@@H]1CO[C@H]1CC[C@@H](c2ccccc2)CC1]

Isocyanatoethane (26 □L, 0.324 mmol) was added to a solution of triethylamine (45 □L, 0.324 mmol) and Intermediate 78 in anhydrous DCM (1.2 mL) at room temperature. The reaction was stirred for 1 h. The reaction mixture was quenched with 2 M aqueous NaOH and extracted with DCM (3×10 mL). The organic layers were combined, washed with brine (25 mL), passed through a phase separator, and concentrated in vacuo. The crude material was purified by reverse phase flash column chromatography (10-100% MeCN in $H_2O$ (0.1% $NH_3$)), to afford the title compound (24 mg) as a white powder.

$^1H$ NMR (400 MHz, $CDCl_3$) δ 7.34-7.27 (m, 2H), 7.24-7.15 (m, 3H), 6.36 (s, 1H), 5.14 (s, 1H), 4.24 (d, J=16.8 Hz, 1H), 4.17-4.07 (m, 2H), 3.94-3.83 (m, 1H), 3.78-3.68 (m, 3H), 3.49 (dd, J=9.4, 6.9 Hz, 1H), 3.43 (d, J=11.7 Hz, 1H), 3.33-3.18 (m, 2H), 2.57 (tt, J=10.6, 4.9 Hz, 1H), 2.27 (dd, J=13.0, 7.4 Hz, 1H), 2.12-2.00 (m, 2H), 1.81 (dd, J=13.0, 9.6

Hz, 1H), 1.73 (td, J=9.0, 8.1, 3.5 Hz, 4H), 1.65-1.55 (m, 2H), 1.37 (d, J=5.9 Hz, 3H), 1.13 (t, J=7.3 Hz, 3H).

LCMS (Method A): $[M+H]^+$ m/z 430.4, RT 3.35 minutes

Example 48: (1S,3R,5R)—N-ethyl-3-methyl-7-oxo-1-({[(CIS)-4-phenylcyclohexyl]oxy}methyl)-9-oxa-2,6-diazaspiro[4.5]decane-2-carboxamide

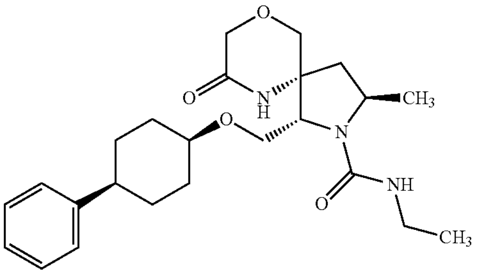 [SMILES: CCNC(=O)N1[C@H](C)C[C@]2(COCC(=O)N2)[C@H]1CO[C@H]1CC[C@@H](c2ccccc2)CC1]

Example 48 was synthesised using intermediate 72b following the same procedures used to synthesised Example 47. The material was purified by silica gel column chromatography (0-100% EtOAc in heptane), to afford Example 48 (44 mg) as a white powder. $[M+H]^+$ m/z 430.3

$^1$H NMR (500 MHz, $CDCl_3$) δ 7.31 (t, J=7.6 Hz, 2H), 7.20 (dd, J=13.4, 7.1 Hz, 3H), 6.27 (s, 1H), 4.24 (d, J=16.7 Hz, 2H), 4.12-4.05 (m, 3H), 4.03-3.90 (m, 2H), 3.65-3.59 (m, 1H), 3.56 (d, J=11.6 Hz, 1H), 3.52 (dd, J=10.5, 1.7 Hz, 1H), 3.34-3.21 (m, 2H), 2.65-2.48 (m, 2H), 2.04-1.95 (m, 2H), 1.81 (d, J=13.1 Hz, 1H), 1.72 (td, J=10.9, 10.0, 3.0 Hz, 2H), 1.69-1.42 (m, 5H), 1.29 (d, J=6.4 Hz, 3H), 1.11 (t, J=7.2 Hz, 3H).

LCMS (Method A): $[M+H]^+$ m/z 430.3, RT 3.28 minutes.

Example 49: (1R,3R,5S)-2-(2-hydroxy-2-methylpropanoyl)-3-methyl-1-({[(CIS)-4-phenylcyclohexyl]oxy}methyl)-9-oxa-2,6-diazaspiro[4.5]decan-7-one

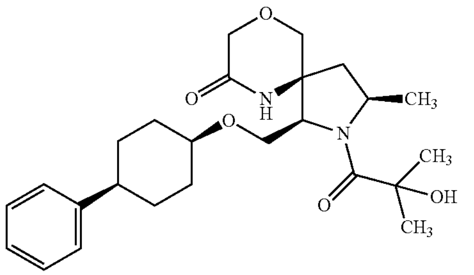 [SMILES: C[C@@H]1C[C@@]2(COCC(=O)N2)[C@H](CO[C@H]2CC[C@@H](c3ccccc3)CC2)N1C(=O)C(C)(C)O]

A solution of Intermediate 78 in anhydrous DMF (0.2 mL) was added to a stirred solution of 2-hydroxy-2-methylpropanoic acid (19 mg, 0.181 mmol), HATU (80 mg, 0.209 mmol) and DIPEA (49 µL, 0.279 mmol) in anhydrous DMF (1 mL) at room temperature and mixture was stirred for 18 h. The reaction mixture was quenched with water (2 mL) and extracted with ethyl acetate (3×2 mL). The combined organic layers were passed through a phase separator and concentrated in vacuo to afford the crude material. The crude material was purified by reverse phase column chromatography (10-100% acetonitrile in water (0.1% $NH_3$)), to afford the title compound (8.3 mg) as a beige solid.

$^1$H NMR (400 MHz, $CDCl_3$) δ 7.32 (t, J=7.4 Hz, 2H), 7.27-7.18 (m, 3H), 6.34 (s, 1H), 4.95-4.84 (m, 1H), 4.29 (d, J=16.8 Hz, 1H), 4.23-4.14 (m, 2H), 3.86 (dd, J=10.0, 3.1 Hz, 1H), 3.77-3.73 (m, 1H), 3.71-3.62 (m, 2H), 3.43 (d, J=11.8 Hz, 1H), 2.60 (tt, J=10.8, 5.0 Hz, 1H), 2.21 (dd, J=13.1, 8.5 Hz, 1H), 2.11 (d, J=12.0 Hz, 2H), 1.87 (dd, J=12.9, 9.0 Hz, 1H), 1.77 (dd, J=7.6, 4.5 Hz, 4H), 1.70-1.55 (m, 4H), 1.55 (s, 3H), 1.49 (s, 3H), 1.44 (d, J=6.2 Hz, 3H).

LCMS (Method A): $[M+H]^+$ m/z 445.4, RT 3.46 minutes.

Example 50: (1R,3R,5S)—N-(2,2-difluoroethyl)-3-methyl-7-oxo-1-({[(CIS)-4-phenylcyclohexyl]oxy}methyl)-9-oxa-2,6-diazaspiro[4.5]decane-2-carboxamide

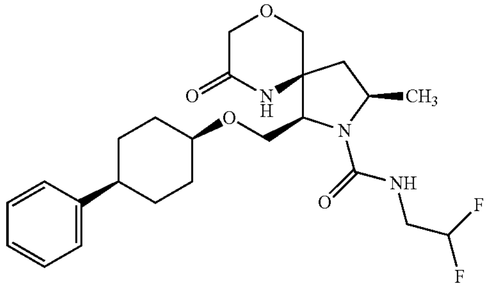 [SMILES: C[C@@H]1C[C@@]2(COCC(=O)N2)[C@H](CO[C@H]2CC[C@@H](c3ccccc3)CC2)N1C(=O)NCC(F)F]

A dropwise solution of 2,2-difluoroethanamine (22 µL, 0.307 mmol) and N-ethyl-N-isopropyl-propan-2-amine (78 µL, 0.446 mmol) in anhydrous DCM (1.7 mL) was added to a stirred solution of carbonyl dichloride (20%, 0.15 mL, 0.279 mmol) and stirred at room temperature for 2 h. This mixture was added to a solution of Intermediate 78 (50 mg, 0.139 mmol) in anhydrous DCM (1.7 mL) and the reaction was stirred at room temperature for 3 hours. Additional carbonyl dichloride (20%, 0.15 mL, 0.279 mmol) was added and the reaction was stirred at room temperature for 15 minutes. Additional 2,2-difluorocthanamine (22 µL, 0.307 mmol) was added and the reaction was stirred overnight at room temperature. The reaction mixture was quenched with a solution of saturated aqueous $NaHCO_3$ (5 mL) and purged with $N_2$(g) (20% aq. NaOH solution as scrubber) for 30 minutes. The reaction mixture was extracted with DCM (3×3 mL), the combined organic layers were passed through a phase separator and concentrated in vacuo to afford the crude material. The crude material was purified by reverse phase column chromatography (10-100% acetonitrile in water (0.1% $NH_3$)), to afford the title compound (23 mg) as a white powder.

$^1$H NMR (400 MHz, $CDCl_3$) δ 7.33-7.27 (m, 2H), 7.23-7.14 (m, 3H), 6.41 (s, 1H), 6.06-5.63 (m, 2H), 4.25 (d, J=16.9 Hz, 1H), 4.18-4.10 (m, 2H), 3.92 (dt, J=9.6, 7.0 Hz, 1H), 3.82-3.59 (m, 4H), 3.55-3.36 (m, 3H), 2.57 (p, J=8.7, 8.2 Hz, 1H), 2.27 (dd, J=13.1, 7.4 Hz, 1H), 2.11-1.99 (m, 2H), 1.79 (dd, J=13.1, 9.8 Hz, 1H), 1.76-1.66 (m, 4H), 1.64 (s, 2H), 1.37 (d, J=6.0 Hz, 3H)

LCMS (Method A): $[M+H]^+$ m/z 466.4, RT 3.34 minutes.

Example 51: (1R,3R,5S)—N-(2-methoxyethyl)-3-methyl-7-oxo-1-({[(CIS)-4-phenylcyclohexyl]oxy}methyl)-9-oxa-2,6-diazaspiro[4.5]decane-2-carboxamide

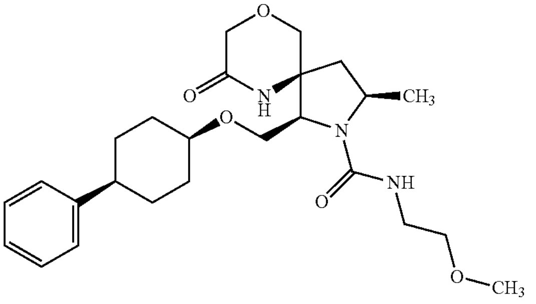 [SMILES: COCCNC(=O)N1[C@H](C)C[C@@]2(COCC(=O)N2)[C@@H]1CO[C@H]1CC[C@@H](c2ccccc2)CC1]

A dropwise solution of 1-isocyanato-2-methoxyethane (12 μL, 0.112 mmol) was added to a stirred solution of Intermediate 78 (20 mg, 0.0558 mmol) and triethylamine (16 μL, 0.112 mmol) in anhydrous DCM (0.5 mL) at room temperature and mixture was stirred for 1 h. The reaction mixture was quenched with 2 M aqueous NaOH (1 mL) and extracted with DCM (3×2 mL). The combined organic layers were passed through a phase separator and concentrated in vacuo to afford the crude material. The crude material was purified by reverse phase column chromatography (10-100% acetonitrile in water (0.1% $NH_3$)), to afford the title compound (17 mg) as a white solid.

$^1$H NMR (500 MHz, $CDCl_3$) δ 7.35-7.29 (m, 2H), 7.26-7.18 (m, 3H), 6.29 (s, 1H), 5.24 (s, 1H), 4.26 (d, J=16.8 Hz, 1H), 4.19-4.13 (m, 2H), 3.90-3.81 (m, 1H), 3.79 (dd, J=9.7, 2.3 Hz, 1H), 3.75-3.65 (m, 1H), 3.57 (dd, J=9.7, 5.2 Hz, 1H), 3.51-3.37 (m, 5H), 3.35 (s, 3H), 2.59 (tt, J=11.5, 4.0 Hz, 1H), 2.32 (dd, J=13.0, 7.5 Hz, 1H), 2.16-2.03 (m, 2H), 1.91 (dd, J=13.0, 9.5 Hz, 1H), 1.86-1.68 (m, 4H), 1.68-1.63 (m, 2H), 1.41 (d, J=6.0 Hz, 3H).

LCMS (Method B): $[M+H]^+$ m/z 460.4, RT 2.96 minutes.

Example 52: (1R,3R,5S)-2-(3,3-difluoroazetidine-1-carbonyl)-3-methyl-1-({[(CIS)-4-phenylcyclohexyl]oxy}methyl)-9-oxa-2,6-diazaspiro[4.5]decan-7-one

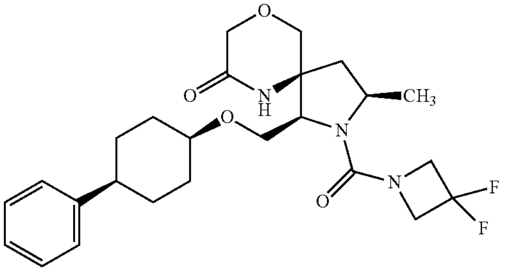 [SMILES: C[C@@H]1C[C@@]2(COCC(=O)N2)[C@H](CO[C@H]2CC[C@@H](c3ccccc3)CC2)N1C(=O)N1CC(F)(F)C1]

A dropwise solution of Intermediate 78 (40 mg, 0.112 mmol) in anhydrous DCM (0.7 mL) was added to a stirred solution of carbonyl dichloride (20%, 0.12 mL, 0.223 mmol) and N-ethyl-N-isopropyl-propan-2-amine (31 μL, 0.179 mmol) in anhydrous DCM (1.4 mL) at room temperature and mixture was stirred for 3 h. A dropwise solution of 3,3-difluoroazetidin-1-ium;chloride (22 μL, 0.245 mmol) in anhydrous DCM (1.4 mL) and N-ethyl-N-isopropyl-propan-2-amine (31 μL, 0.179 mmol) was added to the reaction mixture at room temperature and the reaction was stirred for 18 h. The reaction mixture was quenched with a solution of saturated aqueous $NaHCO_3$ (5 mL) and purged with $N_2$ (20% aq NaOH solution as scrubber) for 30 minutes. The reaction mixture was extracted with DCM (3×3 mL), the combined organic layers were passed through a phase separator and concentrated in vacuo to afford the crude material. The crude material was purified by reverse phase column chromatography (10-100% acetonitrile in water (0.1% $NH_3$)), to afford the title compound (16 mg) as a white powder.

$^1$H NMR (400 MHz, $CDCl_3$) δ 7.38-7.28 (m, 2H), 7.25-7.15 (m, 3H), 6.32 (s, 1H), 4.46-4.35 (m, 2H), 4.24 (d, J=16.7 Hz, 1H), 4.21-4.11 (m, 3H), 4.00 (s, 1H), 3.93 (dd, J=10.5, 2.2 Hz, 1H), 3.82-3.72 (m, 1H), 3.72-3.64 (m, 3H), 3.47 (d, J=11.7 Hz, 1H), 2.64-2.52 (m, 1H), 2.27 (dd, J=12.8, 7.8 Hz, 1H), 2.13-2.00 (m, 3H), 1.83-1.70 (m, 4H), 1.68-1.57 (m, 2H), 1.41 (d, J=6.1 Hz, 3H).

LCMS (Method B): $[M+H]^+$ m/z 478.4, RT 3.50 minutes.

Example 53: (1S,3R,5S)—N-ethyl-3-methyl-7-oxo-1-({2,3',5'-trifluoro-[1,1'-biphenyl]-3-yl}methyl)-9-oxa-2,6-diazaspiro[4.5]decane-2-carboxamide

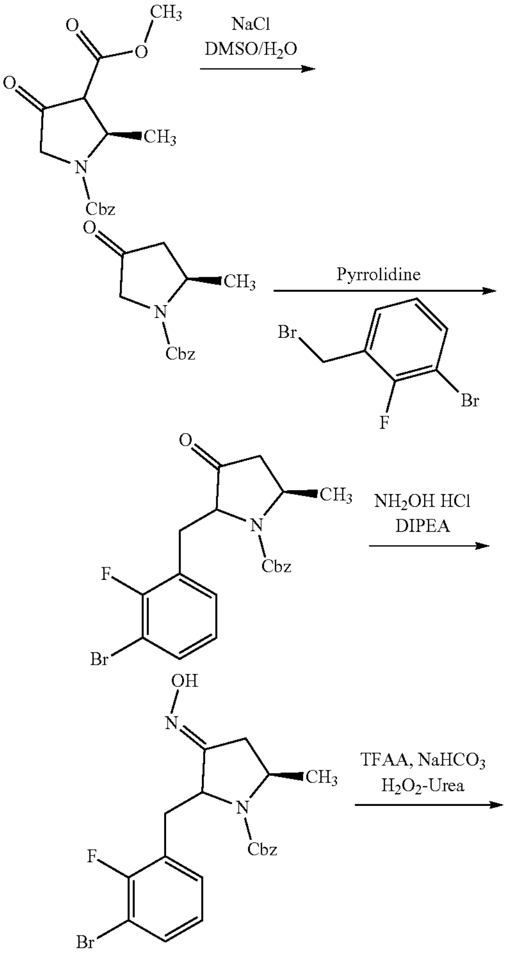

-continued

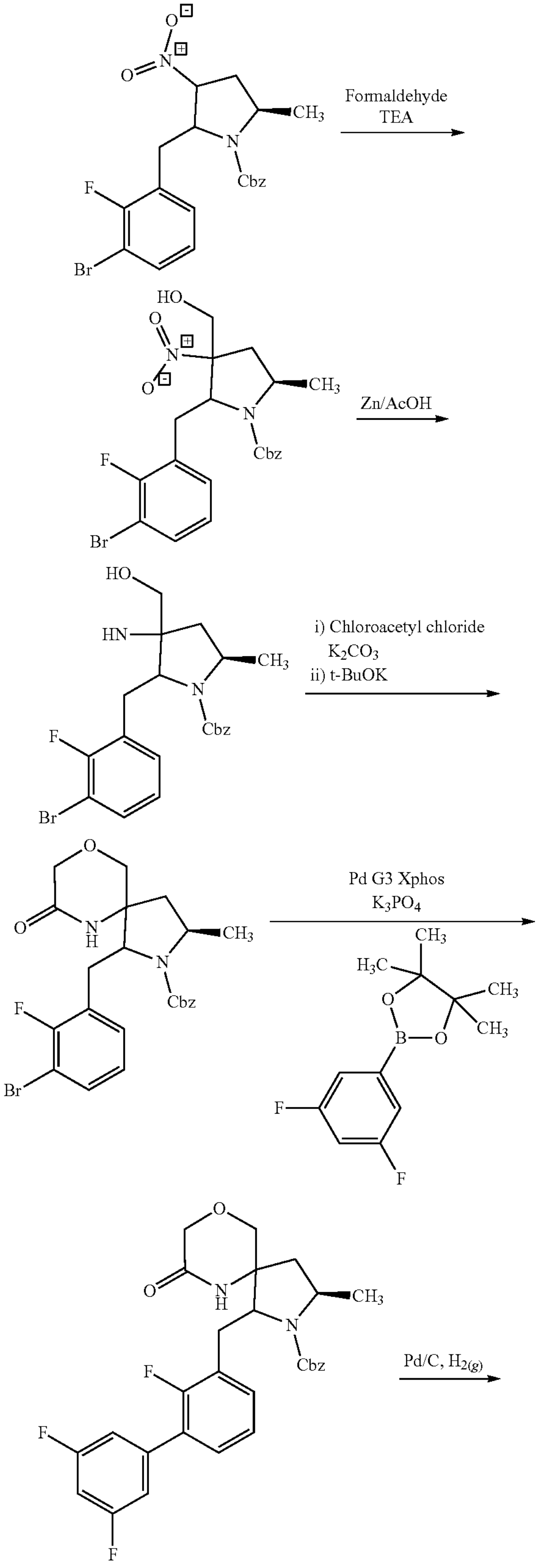

-continued

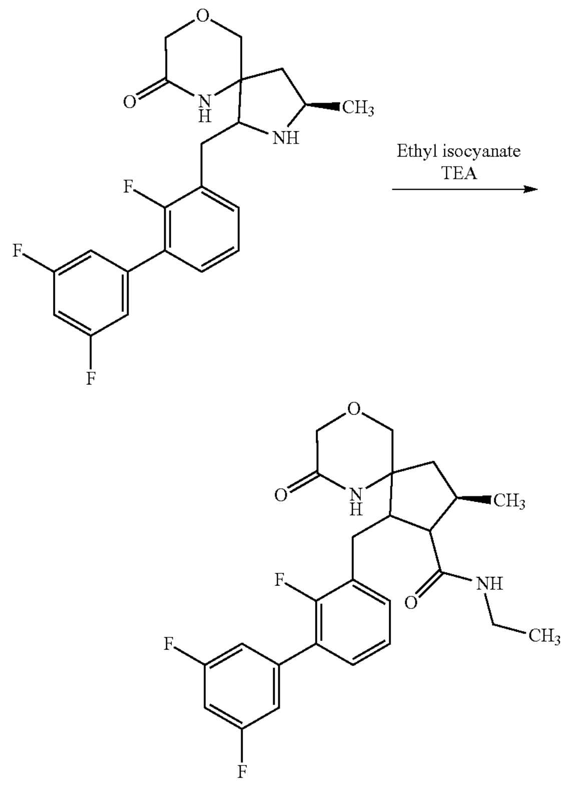

Intermediate 79

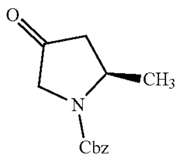 [SMILES: C[C@@H]1CC(=O)CN1C(=O)OCc1ccccc1]

Benzyl (2R)-2-methyl-4-oxopyrrolidine-1-carboxylate

Intermediate 70 (3.10 g, 10.6 mmol) in DMSO (55 mL) was added sodium chloride (1.18 g, 20.3 mmol) and water (5.5 mL) and reaction mixture was heated to 130° C. for 2.5 h. The reaction mixture was cooled to room temperature, quenched water (25 mL) and extracted with EtOAc (3×10 mL). The combined organic layers were washed with water (3×10 mL), brine (10 mL), dried over sodium sulfate, filtered, and evaporated to dryness to afford the title compound (2.31 g) as a brown oil. $[M+H]^+$ m/z 234.2

Intermediate 80

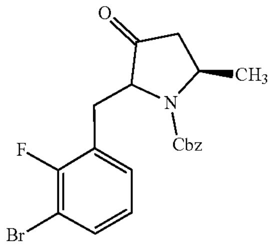 [SMILES: C[C@@H]1CC(=O)C(Cc2cccc(Br)c2F)N1C(=O)OCc1ccccc1]

Benzyl (5R)-2-[(3-bromo-2-fluorophenyl)methyl]-5-methyl-3-oxopyrrolidine-1-carboxylate A solution of pyrrolidine (1.1 mL, 13.3 mmol) and Intermediate 79 (90%, 2.30 g, 8.87 mmol) in toluene (26 mL) were heated to reflux using a Dean-Stark trap for 1.5 h. The reaction mixture was cooled to room temperature and evaporated to dryness to afford the crude material. This was dissolved in acetonitrile (18 mL) and treated with 1-bromo-3-(bromomethyl)-2-fluoro-benzene (2.85 g, 10.6 mmol) in acetonitrile (9 mL) at room temperature and mixture was heated at 85° C. for 16 h. The reaction mixture cooled to room temperature and evaporated to afford the crude material. This was dissolved in water (20 mL) then extracted with ethyl acetate (3x20 mL). The combined organic layers were washed with brine (20 mL), dried over sodium sulfate, filtered, and evaporated to dryness to afford the crude material. The crude material was purified by silica gel column chromatography (0-85% EtOAc in heptane), to afford the title compound (2.8 g) as an orange oil. $[M+H]^+$ m/z 420.2/422.1

Intermediate 81

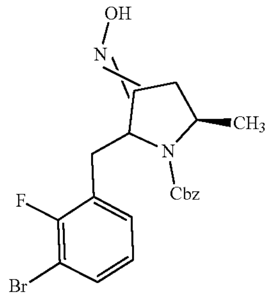

Benzyl (5R)-2-[(3-bromo-2-fluorophenyl)methyl]-3-(hydroxyimino)-5-methylpyrrolidine-1-carboxylate A solution of triethylamine (0.60 mL, 4.32 mmol), hydroxylamine hydrochloride (1:1) (0.30 g, 4.32 mmol) and Intermediate 80 (55%, 1.10 g, 1.44 mmol) in ethanol (4 mL) was heated to 90° C. for 1 h. After cooling, the reaction mixture was diluted with water (10 mL) and extracted with EtOAc (3x10 mL). The combined organic extracts were washed with brine (10 mL), dried over $MgSO_4$, filtered, and concentrated in vacuo to afford the title compound (1.1 g) as a yellow oil. $[M+H]^+$ m/z 435.1/437.1

Intermediate 82

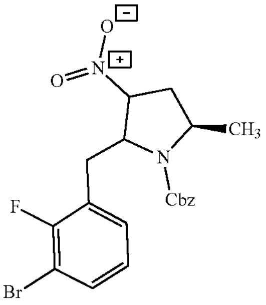 [SMILES: C[C@@H]1CC([N+](=O)[O-])C(Cc2cccc(Br)c2F)N1C(=O)OCc1ccccc1]

Benzyl (5R)-2-[(3-bromo-2-fluorophenyl)methyl]-5-methyl-3-nitropyrrolidine-1-carboxylate Trifluoroacetic anhydride (1.6 mL, 11.3 mmol) in anhydrous acetonitrile (7.2916 mL) was added to a stirred solution of hydrogen peroxide-urea (1:1) (1.48 g, 15.8 mmol) in anhydrous acetonitrile (7.3 mL) at 0° C. The reaction was stirred at 0° C. for 2 h. The resulting solution was added dropwise to a mixture of Intermediate 81 (1.96 g, 4.50 mmol) and sodium hydrogen carbonate (1.89 g, 22.5 mmol) in anhydrous acetonitrile (10 mL) at room temperature. The mixture was then heated to 80° C. and stirred for 1 h. The reaction was cooled to room temperature and quenched with saturated aqueous $Na_2SO_3$, diluted with water (50 mL) and extracted with EtOAc (3x40 mL). The combined organic extracts were washed with brine (40 mL), dried over $MgSO_4$, filtered, and concentrated in vacuo to afford the crude material. The crude material was purified by silica gel column chromatography (0-97% EtOAc in heptane), to afford the title compound (0.19 g) as a colourless gum. $[M+H]^+$ m/z 451.1/453.1

Intermediate 83

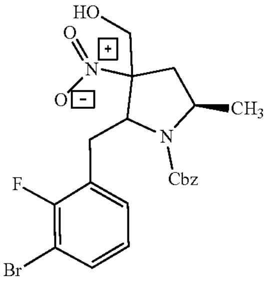 [SMILES: C[C@@H]1CC(CO)([N+](=O)[O-])C(Cc2cccc(Br)c2F)N1C(=O)OCc1ccccc1]

Benzyl (5R)-2-[(3-bromo-2-fluorophenyl)methyl]-3-(hydroxymethyl)-5-methyl-3-nitropyrrolidine-1-carboxylate Formaldehyde (37% in water, 1.9 mL, 26.1 mmol) was added to the Intermediate 82 (1.27 g, 2.90 mmol) and triethylamine (0.48 mL, 3.48 mmol) in THF (1.249 mL) at room temperature. The solution was heated to 70° C. for 6 h. After cooling, the reaction mixture was diluted with water (10 mL) and extracted with EtOAc (3x10 mL). The combined organic extracts were washed with brine (10 mL), dried over $MgSO_4$, filtered, and concentrated in vacuo to give the crude. The crude material was purified by silica gel column chromatography (0-100% EtOAc in heptane), to afford the title compound (100 mg) as a colourless oil. $[M+H]^+$ m/z 481.9/482.9

Intermediate 84

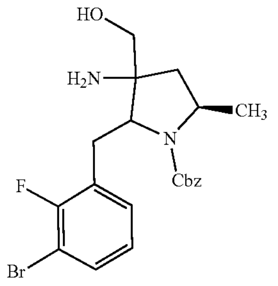 [SMILES: C[C@@H]1CC(N)(CO)C(Cc2cccc(Br)c2F)N1C(=O)OCc1ccccc1]

Benzyl (5R)-3-amino-2-[(3-bromo-2-fluorophenyl) methyl]-3-(hydroxymethyl)-5-methylpyrrolidine-1-carboxylate A suspension of Intermediate 83 (0.24 g, 0.499 mmol) and zinc (326 mg, 4.99 mmol) in acetic acid (2.3 mL) and ethanol (17 ml) was stirred for 2 h at room temperature. Additional zinc (326 mg, 4.99 mmol) was added to the reaction and the reaction mixture was stirred overnight at room temperature. The reaction mixture was filtered through a pad of celite and washed with methanol. The filtrate was neutralised with saturated aqueous $NaHCO_3$ and extracted with DCM (3×20 mL). The combined organic extracts passed through a phase separator and concentrated in vacuo to afford the title compound (220 mg) as a colourless oil. $[M+H]^+$ m/z 453.1

Intermediate 85

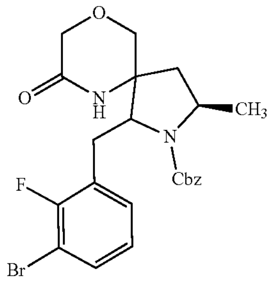 [SMILES: C[C@@H]1CC2(COCC(=O)N2)C(Cc2cccc(Br)c2F)N1C(=O)OCc1ccccc1]

Benzyl (3R)-1-[(3-bromo-2-fluorophenyl)methyl]-3-methyl-7-oxo-9-oxa-2,6-diazaspiro[4.5]decane-2-carboxylate To a solution of Intermediate 84 (220 mg, 0.487 mmol) in THF (2.2 mL) at 0° C. was added dipotassium carbonate (202 mg, 1.46 mmol) then water (2.2 mL). To this mixture chloroacetyl chloride (54 μL, 0.682 mmol) was added drop-wise at 0° C. and stirred for 1 h. The mixture was quenched with water and extracted with DCM (3×10 mL). The combined organic extracts were washed with brine (10 mL), dried over $MgSO_4$, filtered, and concentrated to give an oily residue intermediate. The intermediate was dissolved in DCM (5 mL) and IPA (5 mL) and cooled to 0° C. potassium 2-methylpropan-2-olate (219 mg, 1.95 mmol) was added and the reaction was stirred at 0° C. for 1 h. The mixture was quenched with water (10 mL). The mixture was poured onto aqueous saturated $NaHCO_3$ (5 ml) and extracted with DCM (3×10 mL). The combined organic extracts were washed with brine (5 mL), dried over $MgSO_4$, filtered, concentrated in vacuo to afford the crude material. The crude was purified by silica gel column chromatography (0-100% EtOAc in heptane), to afford the title compound (140 mg) as a colourless oil. $[M+NH_4]^+$ m/z=510.2

Intermediate 86

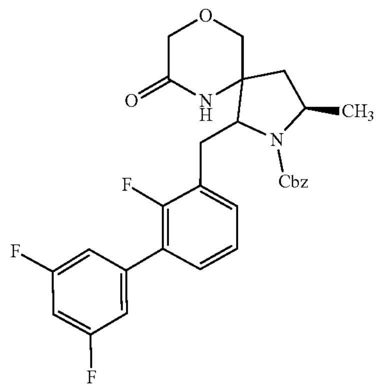 [SMILES: C[C@@H]1CC2(COCC(=O)N2)C(Cc2cccc(-c3cc(F)cc(F)c3)c2F)N1C(=O)OCc1ccccc1]

Benzyl (3R)-3-methyl-7-oxo-1-({2,3',5'-trifluoro-[1,1'-biphenyl]-3-yl}methyl)-9-oxa-2,6-diazaspiro[4.5]decane-2-carboxylate A mixture of Intermediate 85 (120 mg, 0.244 mmol), 2-(3,5-difluorophenyl)-4,4,5,5-tetramethyl-1,3,2-dioxaborolane (78 mg, 0.488 mmol), 1M aqueous tripotassium; phosphate (0.73 mL, 0.733 mmol) and THF (2.4 mL) was degassed with $N_2$(g) for 15 minutes. XPhos Pd G3 (21 mg, 0.0244 mmol) was added, and the reaction mixture was stirred under nitrogen atmosphere at 70° C. for 1 h. The reaction mixture cooled to room temperature, quenched with saturated aqueous $NaHCO_3$ (3 mL), and extracted with ethyl acetate (3×3 mL). The combined organic layers were passed through a pass separator and concentrated in vacuo to afford the crude material. The crude material was purified by silica gel column chromatography (0-100% EtOAc in heptane), to afford the title compound (90 mg) as a black oil. $[M+H]^+$ m/z 525.2

Intermediate 87

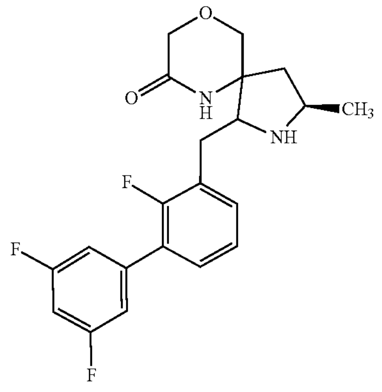 [SMILES: C[C@@H]1CC2(COCC(=O)N2)C(Cc2cccc(-c3cc(F)cc(F)c3)c2F)N1]

(3R)-3-methyl-1-({2,3',5'-trifluoro-[1,1'-biphenyl]-3-yl}methyl)-9-oxa-2,6-diazaspiro[4.5]decan-7-one Intermediate 86 (90 mg, 0.172 mmol) was dissolved in ethanol (8.2 mL) and the atmosphere was evacuated and backfilled with nitrogen 3 times. Palladium on carbon (10%) (20 mg, 0.172 mmol) was added and the atmosphere was evacuated and backfilled with hydrogen 3 times. The reaction was stirred for 2 h, filtered through a pad of celite, washed with EtOAc and concentrated in vacuo to afford the title compound (65 mg) as a pale-yellow oil. [M+H]n/z 391.2

(1S,3R,5S)—N-ethyl-3-methyl-7-oxo-1-({2,3',5'-trifluoro-[1,1'-biphenyl]-3-yl}methyl)-9-oxa-2,6-diazaspiro[4.5]decane-2-carboxamide (53)

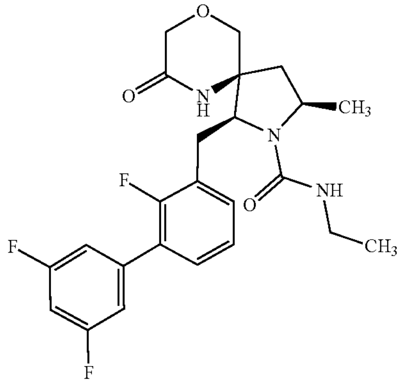 [SMILES: CCNC(=O)N1[C@H](C)C[C@@]2(COCC(=O)N2)[C@@H]1Cc1cccc(-c2cc(F)cc(F)c2)c1F]

Isocyanatoethane (26 μL, 0.333 mmol) was added to a solution triethylamine (46 μL, 0.333 mmol) and Intermediate 87 (65 mg, 0.166 mmol) in anhydrous DCM (1.3 mL) at room temperature. The reaction was stirred for 1 h and was then quenched with aqueous 2 M NaOH and extracted with DCM (3x10 mL). The organic layers were combined, washed with brine (25 mL), passed through a phase separator, and concentrated in vacuo to afford the crude material. The crude material was purified by reverse phase flash phase column chromatography (10-60% MeCN in water), to afford the title compound (12 mg) as a white solid.

$^1$H NMR (400 MHz, $CDCl_3$) δ 7.39-7.30 (m, 2H), 7.25-7.17 (m, 1H), 7.09-7.02 (m, 2H), 6.84 (tt, J=8.9, 2.3 Hz, 1H), 6.35 (s, 1H), 4.24-4.05 (m, 3H), 4.04-3.93 (m, 1H), 3.66 (d, J=11.8 Hz, 1H), 3.51 (s, 1H), 3.41 (d, J=11.8 Hz, 1H), 3.13 (dd, J=13.4, 4.8 Hz, 1H), 3.04-2.85 (m, 2H), 2.76 (dd, J=13.0, 10.1 Hz, 1H), 2.28 (dd, J=13.4, 7.6 Hz, 1H), 1.75 (dd, J=13.4, 9.8 Hz, 1H), 1.40 (d, J=6.1 Hz, 3H), 0.78 (t, J=7.2 Hz, 3H).

LCMS (Method A) $[M+H]^+$ m/z 462.3, RT 3.31 minutes

Example 54: (1S,3R,5S)-2-(2-hydroxy-2-methylpropanoyl)-3-methyl-1-({2,3',5'-trifluoro-[1,1'-biphenyl]-3-yl}methyl)-9-oxa-2,6-diazaspiro[4.5]decan-7-one

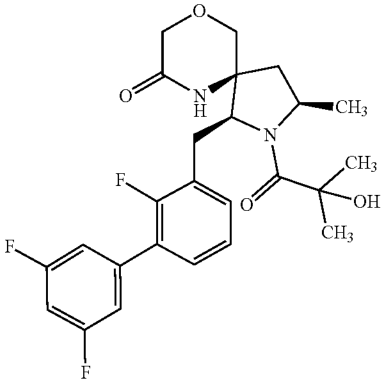 [SMILES: C[C@@H]1C[C@@]2(COCC(=O)N2)[C@H](Cc2cccc(-c3cc(F)cc(F)c3)c2F)N1C(=O)C(C)(C)O]

Intermediate 87 (40 mg, 0.102 mmol) was added to a stirred solution of 2-hydroxy-2-methylpropanoic acid (14 mg, 0.133 mmol), HATU (58 mg, 0.154 mmol) and DIPEA (36 μL, 0.205 mmol) in anhydrous DMF (0.7 mL) at room temperature and mixture was stirred for 24 h. The reaction mixture was filtered and directly purified by prep-HPLC Acidic Early Elute Method: Waters Sunfire $C_{18}$ column (30 mmx100 mm, 5 μm; temperature: room temperature). Injection volume of 1500 μL at a flow rate of 40 mL/min. 10% B (A=0.1% formic acid in water; B=0.1% formic acid in acetonitrile) for 1.90 min then a gradient of 10-95% B over 14.1 min and held for 1.9 min. A second gradient of 95-10% B was then applied over 0.3 min and held for a further 0.9 min. UV spectra were recorded at 215 nm using a Gilson detector, to afford the title compound (7.8 mg) as a beige solid.

$^1$H NMR (400 MHz, $CDCl_3$) δ 7.61-7.48 (m, 1H), 7.23-7.07 (m, 4H), 6.82 (ddd, J=11.2, 5.6, 2.3 Hz, 1H), 6.00 (s, 1H), 5.08 (d, J=8.7 Hz, 1H), 4.17 (s, 1H), 3.96 (d, J=17.0 Hz, 1H), 3.86 (d, J=17.6 Hz, 1H), 3.61 (d, J=11.7 Hz, 1H), 3.33 (d, J=11.8 Hz, 1H), 3.19 (dd, J=14.6, 10.4 Hz, 1H), 3.09 (d, J=14.3 Hz, 1H), 2.26-2.18 (m, 1H), 1.80-1.63 (m, 2H), 1.57 (s, 3H), 1.53 (s, 3H), 1.41 (d, J=6.0 Hz, 3H).

LCMS (Method A): $[M+H]^+$ m/z 477.3, RT 3.29 minutes.

Example 55: rel-(1R,6S)—N-ethyl-8-oxo-1-({[(CIS)-4-phenylcyclohexyl]oxy}methyl)-11-oxa-2,7-diazaspiro[5.6]dodecane-2-carboxamide

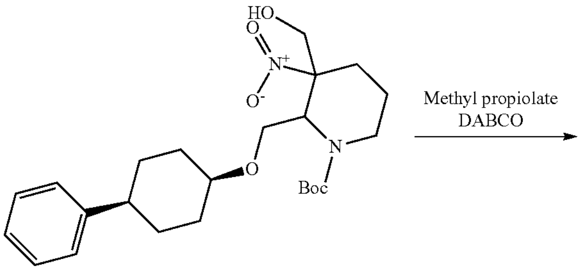

-continued

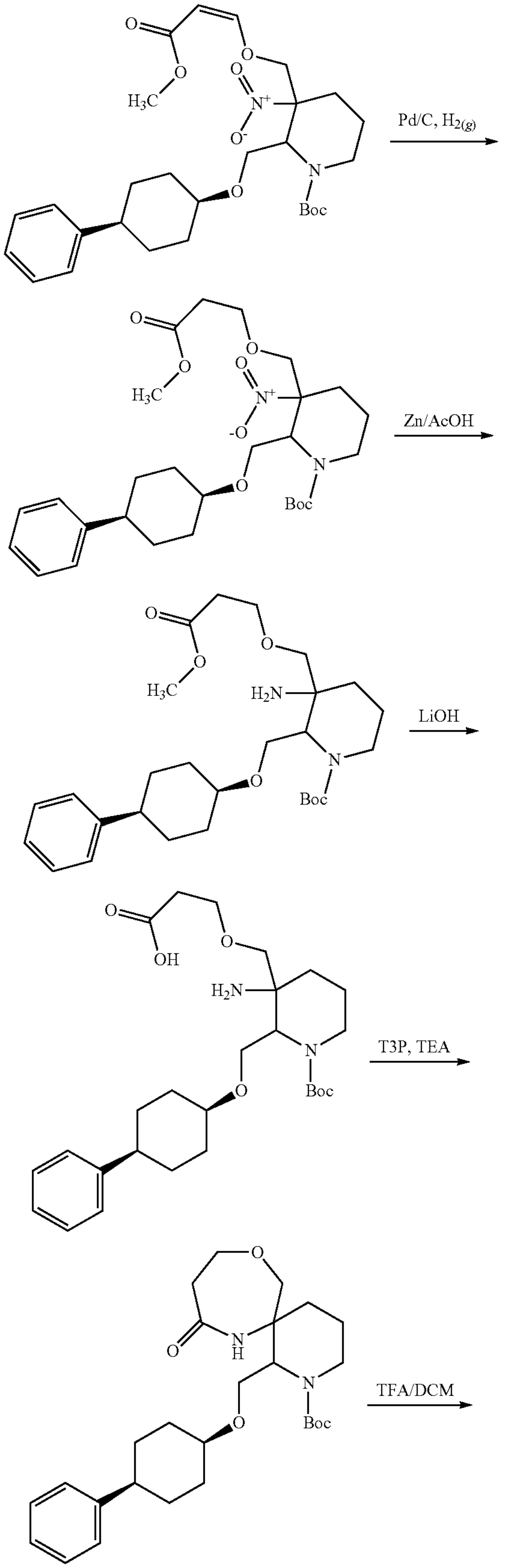

-continued

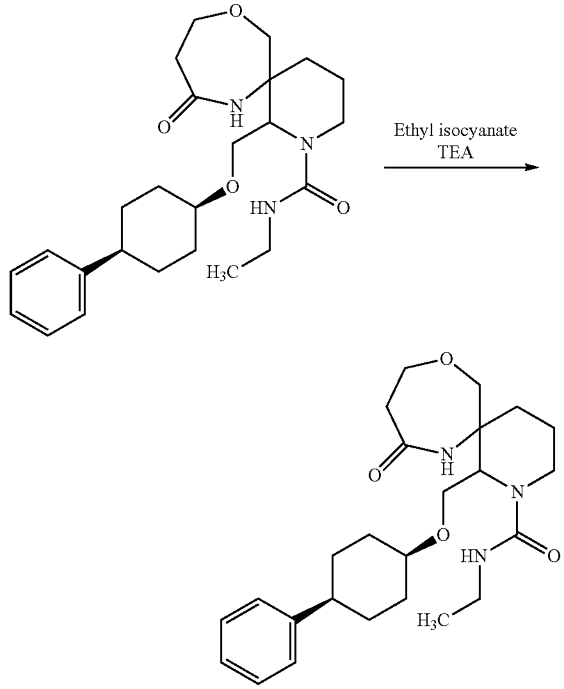

Intermediate 88

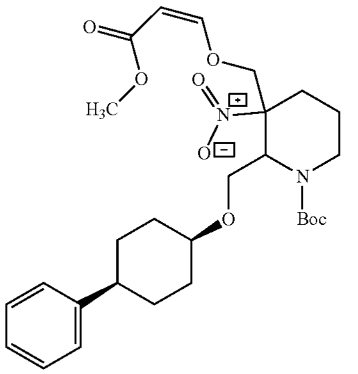 [SMILES: COC(=O)/C=C\OCC1([N+](=O)[O-])CCCN(C(=O)OC(C)(C)C)C1CO[C@H]1CC[C@@H](c2ccccc2)CC1]

tert-butyl-rel-(2R,3S)-3-({[(1E/Z)-3-methoxy-3-oxoprop-1-en-1-yl]oxy}methyl)-3-nitro-2-({[(CIS)-4-phenyl cyclohexyl]oxy}methyl)piperidine-1-carboxylate Methyl prop-2-ynoate (77 μL, 0.869 mmol) was added to a stirred solution of Intermediate 5 (300 mg, 0.669 mmol) and 1,4-diazabicyclo[2.2.2]octane (7.5 mg, 0.0669 mmol) in DCM (2.7 mL) at room temperature and stirred for 3 days. The reaction was concentrated in vacuo and the crude material was purified by silica gel column chromatography (0-100% EtOAc in heptane), to afford the title compound (257 mg) as a colourless gum. $[M+NH_4]^+$ m/z 550.4

Intermediate 89

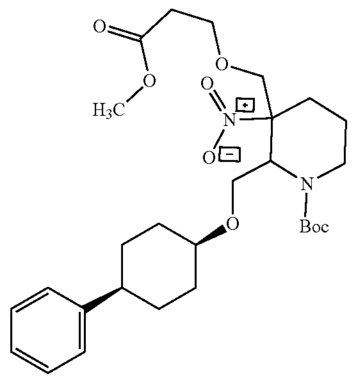 [SMILES: COC(=O)CCOCC1([N+](=O)[O-])CCCN(C(=O)OC(C)(C)C)C1CO[C@H]1CC[C@@H](c2ccccc2)CC1]

tert-butyl-rel-(2R,3S)-3-[(3-methoxy-3-oxopropoxy)methyl]-3-nitro-2-({[(CIS)-4-phenylcyclohexyl]oxy}methyl)piperidine-1-carboxylate A suspension of Intermediate 88 (257 mg, 0.483 mmol) and palladium (10% on carbon, 50% wet) (5.0%, 103 mg, 0.0483 mmol) in ethyl acetate (6 mL) was stirred at room temperature for 16 h. The reaction mixture was filtered through a pad of celite and washed with EtOAc. The filtrate was concentrated in vacuo to afford the title compound as a colourless gum (206 mg). $[M+H]^+$ m/z 535.5

Intermediate 90

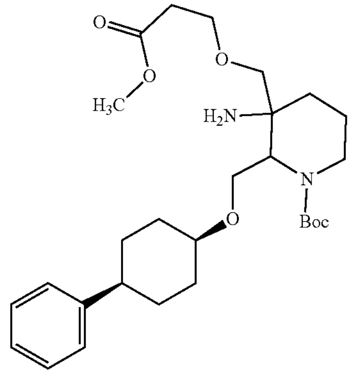 [SMILES: COC(=O)CCOCC1(N)CCCN(C(=O)OC(C)(C)C)C1CO[C@H]1CC[C@@H](c2ccccc2)CC1]

tert-butyl-rel-(2R,3S)-3-amino-3-[(3-methoxy-3-oxopropoxy)methyl]-2-({[(CIS)-4-phenylcyclohexyl]oxy}methyl)piperidine-1-carboxylate Zinc (462 mg, 7.07 mmol) was added to a stirred solution of Intermediate 89 (189 mg, 0.354 mmol) in ethanol (5 mL) and acetic acid (1.5 mL) at 0° C. The reaction was warmed to room temperature and stirred for 1 h. The reaction was heated to reflux for 1 h. The reaction mixture was filtered through a pad of celite and washed with methanol. The filtrate was concentrated in vacuo, neutralised with saturated aqueous $NaHCO_3$ (25 mL) and extracted with DCM (3×25 mL). The combined organic layers were passed through a phase separator and concentrated in vacuo to afford the title compound (179 mg) as a colourless gum. $[M+H]^+$ m/z 505.7

Intermediate 91

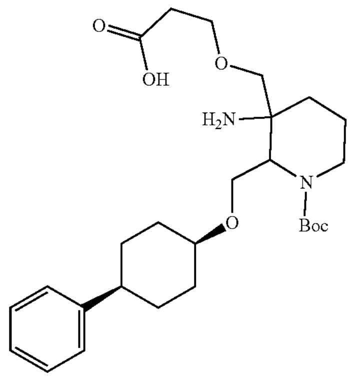 [SMILES: CC(C)(C)OC(=O)N1CCCC(N)(COCCC(=O)O)C1CO[C@H]1CC[C@@H](c2ccccc2)CC1]

3-{[rel-(2R,3S)-3-amino-1-[(tert-butoxy)carbonyl]-2-({[(CIS)-4-phenylcyclohexyl]oxy}methyl)piperidin-3-yl]methoxy}propanoic acid A solution of aqueous 2 M lithium hydroxide (1.0 mL, 2.00 mmol) was added to a stirred solution of Intermediate 90 (149 mg, 0.295 mmol) in THF (2 mL) at room temperature and stirred for 1 h. The reaction mixture was diluted with water (10 mL), brine (10 mL) and extracted with diethyl ether (2×20 mL). The aqueous layer was acidified to pH 1 with aqueous 2 M HCl and re-extracted with EtOAc (2×30 mL). The combined organic layers were dried over $MgSO_4$, filtered, and concentrated in vacuo to afford the title compound (138 mg) as a colourless glass. $[M-H]^-$ m/z 489.5.

Intermediate 92

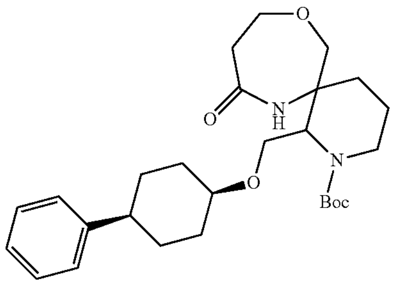 [SMILES: CC(C)(C)OC(=O)N1CCCC2(COCCC(=O)N2)C1CO[C@H]1CC[C@@H](c2ccccc2)CC1]

tert-butyl-rel-(1R,6S)-8-oxo-1-({[(CIS)-4-phenylcyclohexyl]oxy}methyl)-11-oxa-2,7-diazaspiro[5.6]dodecane-2-carboxylate A solution of T3P (50% in EtOAc) (0.38 mL, 0.637 mmol) was added to a stirred solution Intermediate 91 (125 mg, 0.255 mmol) and triethylamine (0.12 mL, 0.892 mmol) in 1,4-Dioxane (25 mL) at room temperature and the mixture was stirred for 1 h. The reaction mixture was quenched with saturated aqueous $NaHCO_3$ (25 mL) and extracted with DCM (3×50 mL). The combined organic layers were dried over $MgSO_4$, filtered, and concentrated in vacuo to afford the title compound (132 mg) as a colourless gum. $[M+Na]^+$ m/z 495.4

Intermediate 93

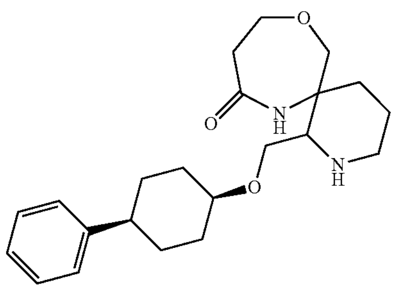 [SMILES: O=C1CCOCC2(CCCNC2CO[C@H]2CC[C@@H](c3ccccc3)CC2)N1]

rel-(1R,6S)-1-({[(CIS)-4-phenylcyclohexyl]oxy}methyl)-11-oxa-2,7-diazaspiro[5.6]dodecan-8-one A solution of Intermediate 92 (132 mg, 0.279 mmol) in TFA (0.5 mL) and DCM (1 mL) was stirred at room temperature for 2 h. The reaction was quenched with saturated aqueous $NaHCO_3$ (10 mL) and extracted with DCM (3×20 mL). The combined organic layers were passed through a phase separator and concentrated in vacuo to afford the title compound (65 mg) as a colourless gum. $[M+H]^+$ m/z 373.4 rel-(1R,6S)—N-ethyl-8-oxo-1-({[(CIS)-4-phenylcyclohexyl]oxy}methyl)-11-oxa-2,7-diazaspiro[5.6]dodecane-2-carboxamide (55)

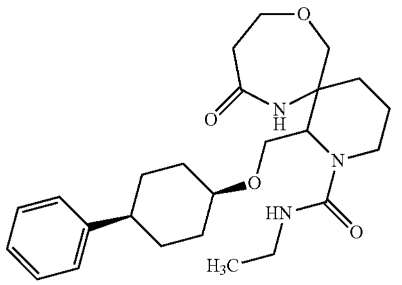 [SMILES: CCNC(=O)N1CCCC2(COCCC(=O)N2)C1CO[C@H]1CC[C@@H](c2ccccc2)CC1]

A solution of isocyanatoethane (14 μL, 0.172 mmol) was added to a stirred solution of Intermediate 93 (32 mg, 0.086 mmol) and triethylamine (24 μL, 0.172 mmol) in DCM (1 mL) at room temperature and mixture was stirred for 0.5 h. The reaction mixture was quenched with 2 M aqueous NaOH (2 mL) and the reaction mixture was passed through a phase separator and washed with DCM (3×5 mL). The combined organic layers were in vacuo to afford the crude material. The crude material was purified by reverse phase column chromatography (10-100% acetonitrile in water (0.1% $NH_3$)), to afford the title compound (20.2 mg) as a white solid.

$^1H$ NMR (500 MHz, $CDCl_3$) δ 7.32-7.27 (m, 2H), 7.25-7.22 (m, 2H), 7.20-7.15 (m, 1H), 6.20 (s, 1H), 4.56 (t, J=5.2 Hz, 1H), 4.14 (d, J=12.8 Hz, 1H), 4.08-3.97 (m, 2H), 3.83 (dd, J=9.7, 5.7 Hz, 1H), 3.75 (ddd, J=12.2, 10.3, 1.5 Hz, 1H), 3.68 (dd., J=9.7, 5.0 Hz, 1H), 3.64 (p, J=3.2 Hz, 1H), 3.51 (d, J 12.8 Hz, 1H), 3.27 (qd, J=7.2, 1.1 Hz, 2H), 2.97-2.82 (m, 2H), 2.68 (dd, J=16.3, 5.8 Hz, 1H), 2.52 (tt, J 11.9, 3.5 Hz, 1H), 2.07-1.98 (m, 2H), 1.94-1.87 (m, 1H), 1.82-1.48 (m, 10H), 1.14 (t, J=7.2 Hz, 3H). NH proton obscured LCMS (Method B): $[M+H]^+$ m/z 444.4, RT 2.95 minutes.

Example 56: 2,2-difluoroethyl-rel-(6R,7R)-4-methyl-2-oxo-7-({[(CIS)-4-phenylcyclohexyl]oxy}methyl)-1,4,8-triazaspiro[5.5]undecane-8-carboxylate

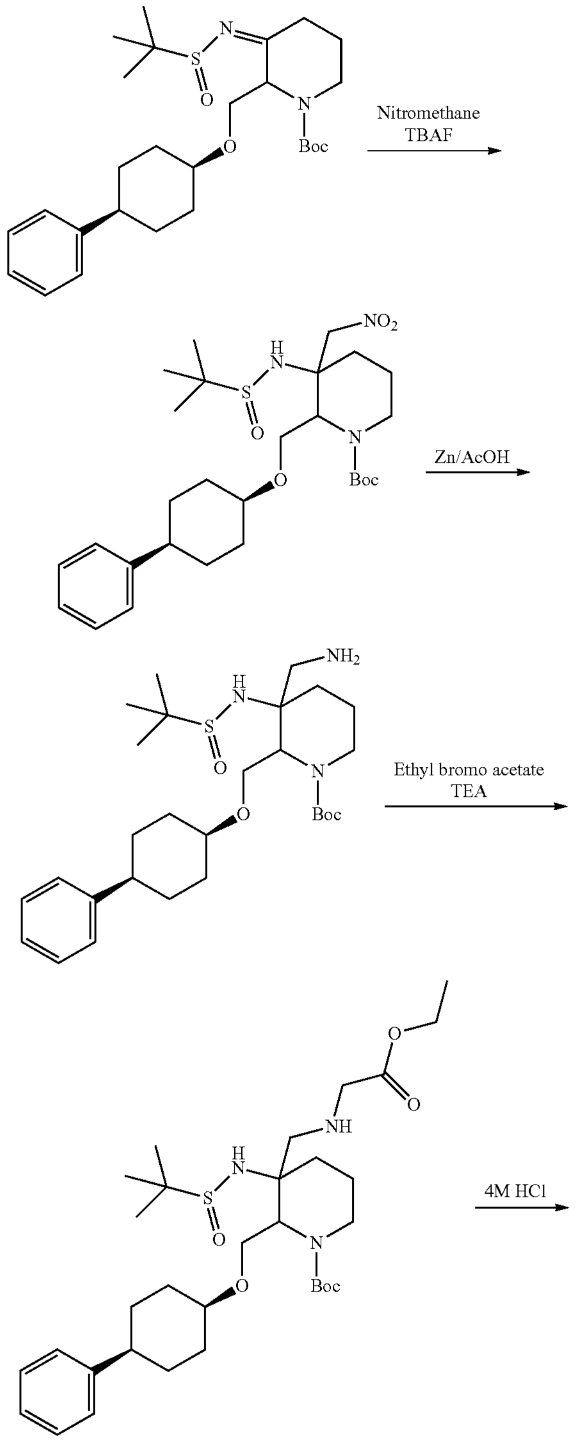

-continued

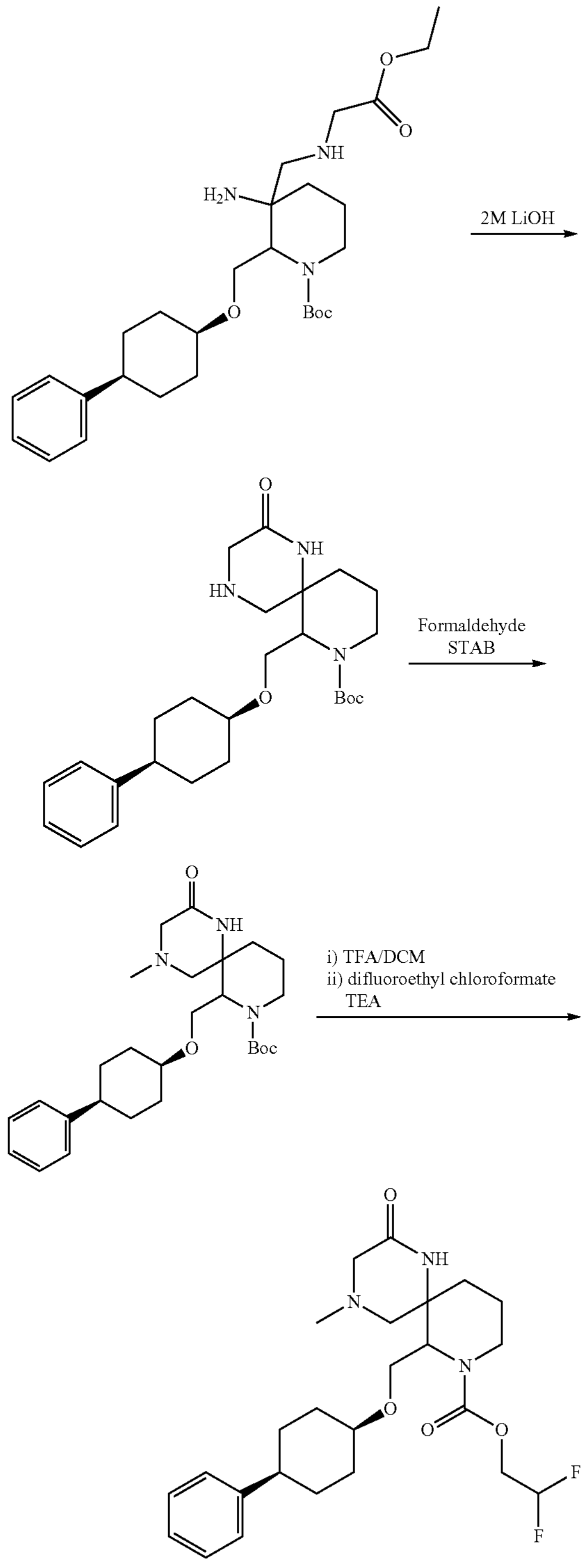

Intermediate 94

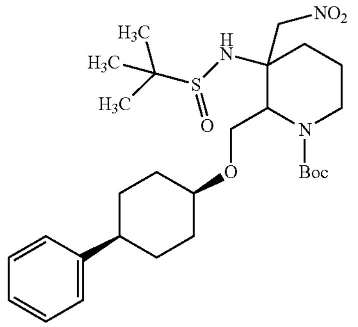

tert-butyl-rel-(2R,3R)-3-[(2-methylpropane-2-sulfinyl)amino]-3-(nitromethyl)-2-({[(CIS)-4-phenylcyclohexyl]oxy}methyl)piperidine-1-carboxylate A dropwise solution of 1 M N,N,N-tributylbutan-1-aminium fluoride in THE (1.9 mL, 1.94 mmol) was added to a stirred solution of Intermediate 11 (1.90 g, 3.87 mmol) in nitromethane (20 mL) at room temperature and the mixture was stirred for 4 h. The reaction mixture was concentrated in vacuo and then diluted with water (50 mL) and extracted with ethyl acetate (3x50 mL). The combined organic layers were washed with brine (100 mL), dried over $MgSO_4$, filtered, and concentrated in vacuo to afford the crude material. The crude material was purified by silica gel column chromatography (0-100% EtOAc in heptane), to afford the title compound (1.25 g) as a white solid. $[M+H]^+$ m/z 552.5

Intermediate 95

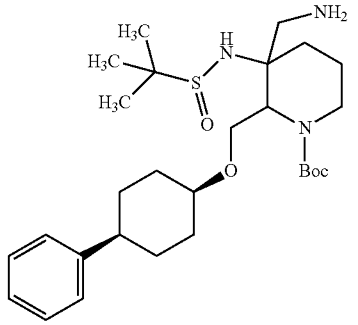 [SMILES: CC(C)(C)OC(=O)N1CCCC(C[N+](=O)[O-])(NS(=O)C(C)(C)C)C1CO[C@H]1CC[C@@H](c2ccccc2)CC1]

tert-butyl-rel-(2R,3R)-3-[(2-methylpropane-2-sulfinyl)amino]-3-(nitromethyl)-2-({[(CIS)-4-phenylcyclohexyl]oxy}methyl)piperidine-1-carboxylate Zinc (1.48 g, 22.7 mmol) was added to a stirred solution of Intermediate 94 (1.25 g, 2.27 mmol) in acetic acid (7 mL) and ethanol (25 mL) at room temperature and the mixture was stirred for 16 h. The reaction mixture was quenched and neutralised with a solution of saturated aqueous $NaHCO_3$ (30 mL), filtered through celite (washing with EtOAc) and extracted with ethyl acetate (3x30 mL). The combined organic layers were dried over $MgSO_4$, filtered, and concentrated in vacuo to afford the title compound (1.03 g). $[M+H]^+$ m/z 522.4

Intermediate 96

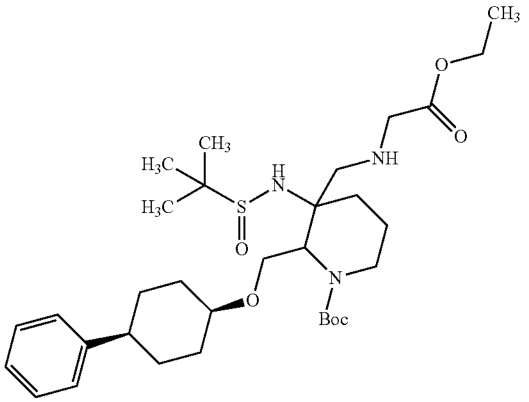 [SMILES: CCOC(=O)CNCC1(NS(=O)C(C)(C)C)CCCN(C(=O)OC(C)(C)C)C1CO[C@H]1CC[C@@H](c2ccccc2)CC1]

tert-butyl-rel-(2R,3R)-3-(aminomethyl)-3-[(2-methylpropane-2-sulfinyl)amino]-2-({[(CIS)-4-phenylcyclohexyl]oxy}methyl)piperidine-1-carboxylate A dropwise solution of ethyl bromoacetate (255 μL, 2.30 mmol) was added to a stirred solution of triethylamine (534 μL, 3.83 mmol) and Intermediate 95 (1.00 g, 1.92 mmol) in anhydrous THF (25 mL) at room temperature and the mixture was stirred for 16 h. The reaction mixture was quenched with water (25 mL) and extracted with ethyl acetate (3×30 mL). The combined organic layers were washed with brine (50 mL), dried over $MgSO_4$, filtered, and concentrated in vacuo to afford the crude material. The crude material was purified by silica gel column chromatography (0-100% EtOAc in heptane then 0-20% methanol in DCM), to afford the title compound (1 g) as a colourless oil. $[M+H]^+$ m/z 608.4

Intermediate 97

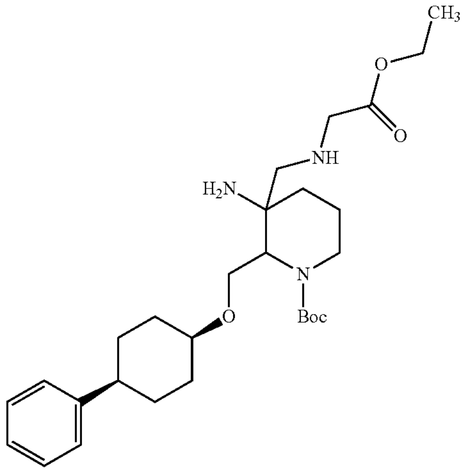 [SMILES: CCOC(=O)CNCC1(N)CCCN(C(=O)OC(C)(C)C)C1CO[C@H]1CC[C@@H](c2ccccc2)CC1]

tert-butyl-rel-(2R,3R)-3-{[(2-ethoxy-2-oxoethyl)amino]methyl}-3-[(2-methylpropane-2-sulfinyl)amino]-2-({[(CIS)-4-phenylcyclohexyl]oxy}methyl)piperidine-1-carboxylate A dropwise solution of 4 M hydrogen chloride (4M in dioxane) (1.1 mL, 4.44 mmol) was added to a stirred solution of Intermediate 96 (900 mg, 1.48 mmol) in methanol (5 mL) at 0° C. and the mixture was stirred for 16 h. The reaction mixture was warmed to room temperature, quenched with a solution of saturated aqueous $NaHCO_3$ (25 mL) and extracted with ethyl acetate (3×25 mL). The combined organic layers were washed with brine (50 mL), dried over $MgSO_4$, filtered, and concentrated in vacuo to afford the crude material (600 mg) as a yellow oil which was taken on without further purification. $[M+H]^+$ m/z 504.5

Intermediate 98

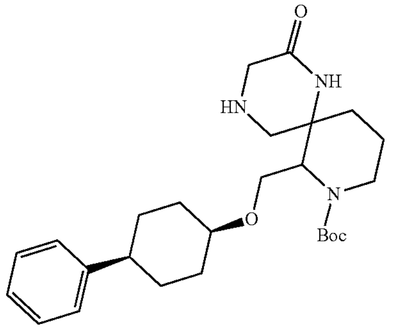 [SMILES: CC(C)(C)OC(=O)N1CCCC2(CNCC(=O)N2)C1CO[C@H]1CC[C@@H](c2ccccc2)CC1]

tert-butyl-rel-(6R,7R)-2-oxo-7-({[(CIS)-4-phenylcyclohexyl]oxy}methyl)-1,4,8-triazaspiro[5.5]undecane-8-carboxylate A solution of lithium hydroxide (2 M in water) (1.5 mL, 3.0 mmol) was added to a stirred solution of Intermediate 97 (600 mg, 1.49 mmol) in THF (10 mL) at room temperature and the mixture was stirred for 1 h. The reaction mixture was quenched with water (25 mL) and extracted with ethyl acetate (3×25 mL). The crude material was purified by reverse phase column chromatography (10-100% acetonitrile in water (0.1% $NH_3$)), to afford the title compound (48 mg) as a white solid. $[M+H]^+$ m/z 458.4

Intermediate 99

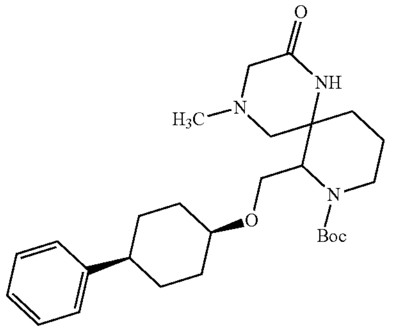 [SMILES: CN1CC(=O)NC2(CCCN(C(=O)OC(C)(C)C)C2CO[C@H]2CC[C@@H](c3ccccc3)CC2)C1]

tert-butyl-rel-(6R,7R)-4-methyl-2-oxo-7-({[(CIS)-4-phenylcyclohexyl]oxy}methyl)-1,4,8-triazaspiro[5.5]undecane-8-carboxylate A dropwise solution of formaldehyde (37% in water) (37%, 32 μL, 0.393 mmol) was added to a stirred solution of tert-butyl Intermediate 98 (15 mg, 0.0328 mmol) in DCM (0.6 mL) at room temperature and the mixture was stirred for 1 h. Sodium triacetoxyborohydride (28 mg, 0.131 mmol) was added and the reaction was stirred for a further hour.

The reaction mixture was diluted with water (5 mL) and extracted with DCM (3×5 mL). The combined organic layers were washed with brine (10 mL), dried over $MgSO_4$, filtered, and concentrated in vacuo to afford the title compound (15 mg) as a colourless oil. $[M+H]^+$ m/z 472.5

2,2-difluoroethyl-rel-(6R,7R)-4-methyl-2-oxo-7-({[(CIS)-4-phenylcyclohexyl]oxy}methyl)-1,4,8-triazaspiro[5.5]undecane-8-carboxylate (56)

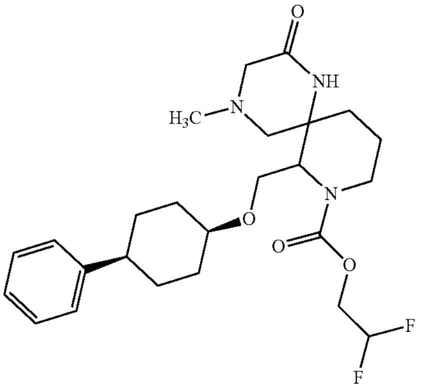 [SMILES: CN1CC(=O)NC2(CCCN(C(=O)OCC(F)F)C2CO[C@H]2CC[C@@H](c3ccccc3)CC2)C1]

Intermediate 99 (20 mg, 0.0424 mmol) was stirred in a mixture of anhydrous DCM (0.25 mL) and TFA (0.25 mL) for 30 minutes at room temperature. The reaction mixture was quenched with $NaHCO_3$ solution (5 mL) and extracted with DCM (3×5 mL). The combined organic layers were dried over $MgSO_4$, filtered, and concentrated in vacuo to afford the crude material. A dropwise solution of 2,2-difluoroethyl chloroformate (5.3 µL, 0.0509 mmol) was added to a stirred solution of crude material and triethylamine (14 µL, 0.102 mmol) in anhydrous DCM (0.5 mL) at 0° C. and the mixture was stirred for 30 minutes. An additional 2,2-difluoroethyl chloroformate (5.3 µL, 0.0509 mmol) was added and the reaction stirred for 30 more minutes. The reaction mixture was quenched with water (5 mL) and extracted with DCM (3×5 mL). The combined organic layers were washed with brine (10 mL), dried over $MgSO_4$, filtered, and concentrated in vacuo to afford the crude material. The crude material was purified by reverse phase column chromatography (10-100% acetonitrile in water (0.1% ammonia), to afford the title compound (8.6 mg) as a white solid.

$^1H$ NMR (400 MHz, DMSO) δ 7.75 (s, 1H), 7.27 (dd, J=8.0, 7.0 Hz, 2H), 7.22-7.12 (m, 3H), 6.17 (tdd, J=54.8, 7.4, 3.8 Hz, 1H), 4.81-4.73 (m, 1H), 4.48-4.05 (m, 3H), 3.95-3.84 (m, 1H), 3.72 (t, J=10.3 Hz, 1H), 3.59 (s, 1H), 3.48 (dd, J=10.3, 4.3 Hz, 1H), 3.18 (d, J=16.3 Hz, 1H), 2.97 (d, J=11.7 Hz, 1H), 2.86 (d, J=11.4 Hz, 1H), 2.58 (dd, J=16.3, 3.5 Hz, 1H), 2.50-2.44 (m, 1H), 2.22 (s, 3H), 2.02-1.77 (m, 4H), 1.71-1.41 (m, 8H). 2 Rotamers, and peak at 2.44-2.50 obscured by DMSO peak.

LCMS (Method B): $[M+H]^+$ m/z 480.1, RT 3.11 minutes.

Example 57: 2,2-difluoroethyl-rel-(6R,7R)-3-methyl-2-oxo-7-({[(CIS)-4-phenylcyclohexyl]oxy}methyl)-1,3,8-triazaspiro[5.5]undecane-8-carboxylate

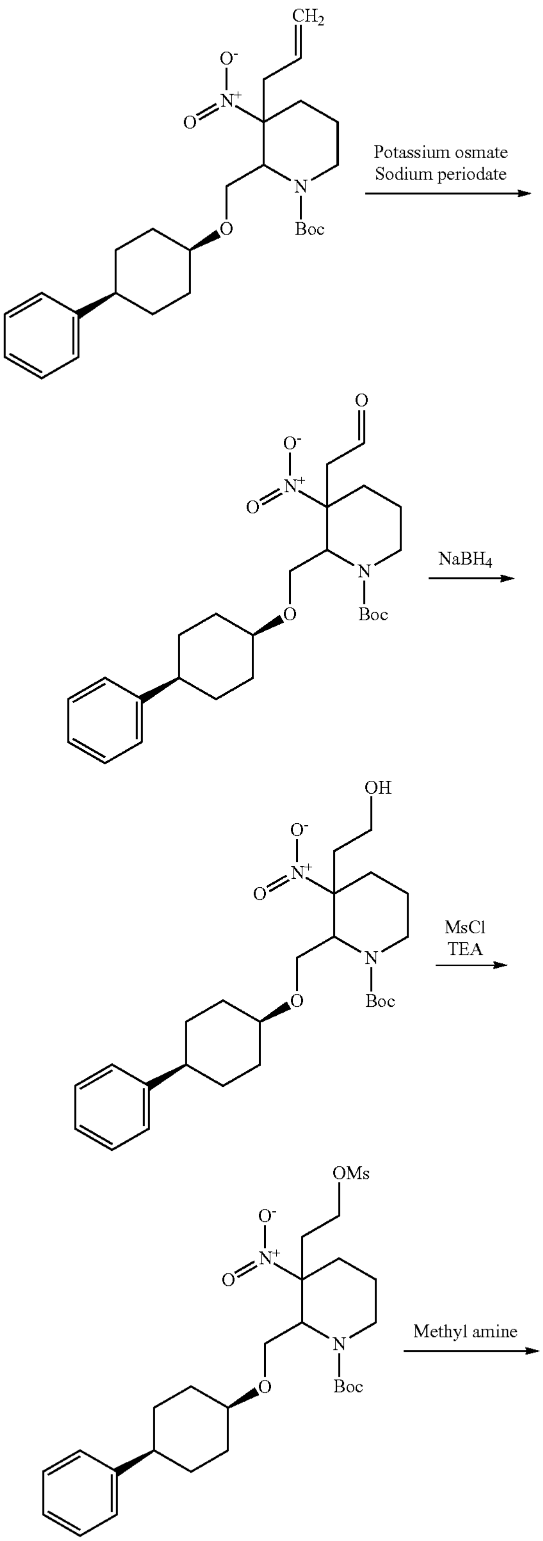

-continued

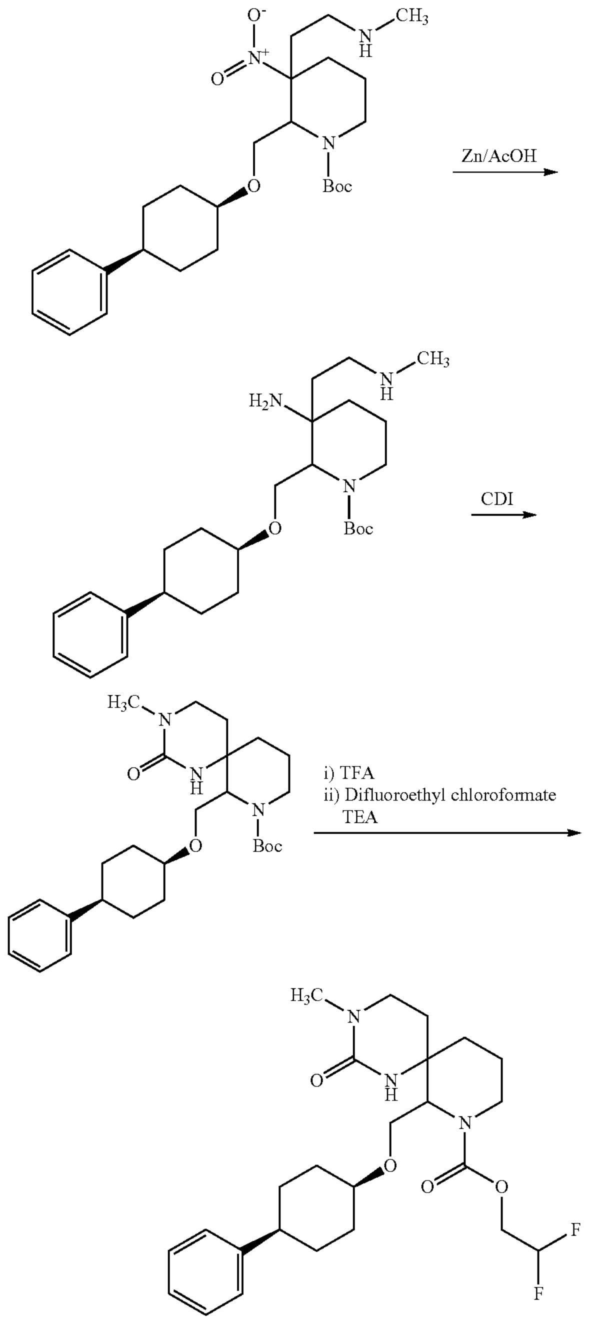

Intermediate 100

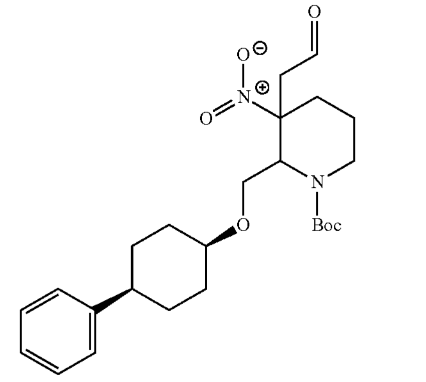 [SMILES: CC(C)(C)OC(=O)N1CCCC(CC=O)([N+](=O)[O-])C1CO[C@H]1CC[C@@H](c2ccccc2)CC1]

tert-butyl-rel-(2R,3R)-3-nitro-3-(2-oxoethyl)-2-({[(CIS)-4-henylcyclohexyl]oxy}methyl)piperidine-1-carboxylate To Intermediate 50 (1.00 g, 2.18 mmol) in THF (25 mL) and water (6.25 mL) was added potassium dioxido(dioxo) osmium hydrate (2:1:2) (40 mg, 0.109 mmol) and stirred for 10 minutes at room temperature. Sodium periodate (1.40 g, 6.54 mmol) was added, and the reaction was stirred for 20 hours. Additional sodium periodate (1.40 g, 6.54 mmol) was added, and the reaction was stirred for 4 hours. The reaction was quenched by the addition of sodium sulfite solution (20 mL) and water (50 mL) and extracted with ethyl acetate (3×50 mL). The organic phases were combined, dried ($MgSO_4$), filtered and concentrated in vacuo. The crude material was purified by silica gel column chromatography (0-60% EtOAc in heptane), to afford the title compound (660 mg) as a colourless oil. $[M+H-Boc]^+$ m/z 361.3

Intermediate 101

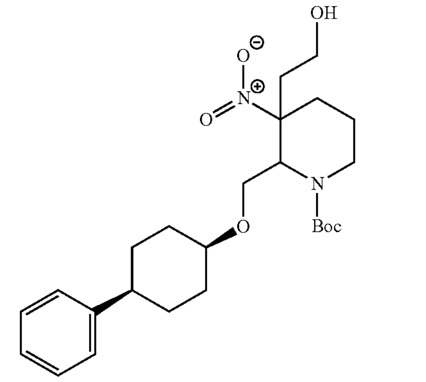 [SMILES: CC(C)(C)OC(=O)N1CCCC(CCO)([N+](=O)[O-])C1CO[C@H]1CC[C@@H](c2ccccc2)CC1]

tert-butyl-rel-(2R,3R)-3-(2-hydroxyethyl)-3-nitro-2-({[(CIS)-4-phenylcyclohexyl]oxy}methyl)piperidine-1-carboxylate Sodium tetrahydroborate (80 mg, 2.12 mmol) was added to a stirred solution of Intermediate 100 (650 mg, 1.41 mmol) in anhydrous methanol (15 mL) at 0° C. and the mixture was stirred for 1 h. The reaction mixture was concentrated in vacuo then diluted with water (10 mL) and extracted with ethyl acetate (3×10 mL). The combined organic layers were washed with brine (20 mL), dried over $MgSO_4$, filtered, and concentrated in vacuo to afford the crude material. The crude material was purified by silica gel column chromatography (0-100% EtOAc in heptane), to afford the title compound (615 mg) as a white solid. [M+H-Boc]$^+$ m/z 363.3

Intermediate 102

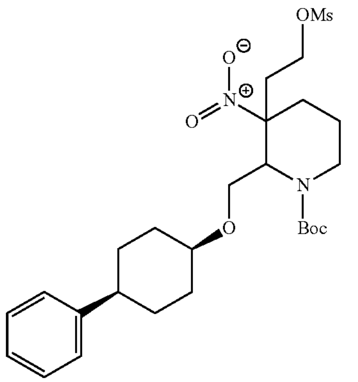 [SMILES: CC(C)(C)OC(=O)N1CCCC(CCOS(C)(=O)=O)([N+](=O)[O-])C1CO[C@H]1CC[C@@H](c2ccccc2)CC1]

tert-butyl-rel-(2R,3R)-3-[2-(methanesulfonyloxy) ethyl]-3-nitro-2-({[(CIS)-4-phenylcyclohexyl] oxy}methyl) piperidine-1-carboxylate A dropwise solution of methanesulfonyl chloride (125 μL, 1.62 mmol) was added to a stirred solution of Intermediate 101 (600 mg, 1.30 mmol) and triethylamine (226 μL, 1.62 mmol) in anhydrous DCM (10 mL) at 0° C. and the mixture was stirred for 3 h. The reaction mixture was warmed to room temperature, quenched with water (25 mL) and extracted with DCM (3x25 mL). The combined organic layers were dried over $MgSO_4$, filtered, and concentrated in vacuo to afford the crude material. The crude material was purified by silica gel column chromatography (0-50% EtOAc in heptane), to afford the title compound (560 mg) as a colourless gum. [M+Na]$^+$ m/z 563.3

Intermediate 103

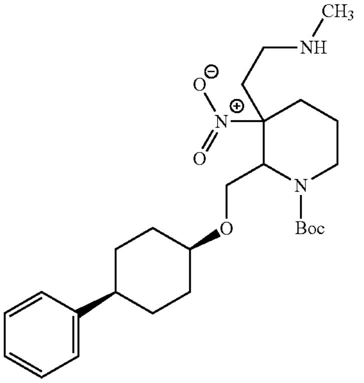 [SMILES: CNCCC1([N+](=O)[O-])CCCN(C(=O)OC(C)(C)C)C1CO[C@H]1CC[C@@H](c2ccccc2)CC1]

tert-buty-rel-(2R,3R)-3-[2-(methylamino)ethyl]-3-nitro-2-({[(CIS)-4-phenylcyclohexyl]oxy}methyl) piperidine-1-carboxylate A dropwise solution of methanamine (33% in EtOH) (33%, 5.0 mL, 40.2 mmol) was added to a stirred solution of tert-butyl Intermediate 102 (550 mg, 1.02 mmol) in THF (15 mL) at room temperature and the mixture was heated at 65° C. for 16 h. The reaction mixture was cooled to room temperature, concentrated in vacuo then diluted with a solution of saturated aqueous $NaHCO_3$ (10 mL) and extracted with ethyl acetate (3x10 mL). The combined organic layers were dried over $MgSO_4$, filtered, and concentrated in vacuo to afford the crude material. The crude material was taken on without further purification to afford the title compound (430 mg) as a yellow oil. [M+H]$^+$ m/z 476.8

Intermediate 104

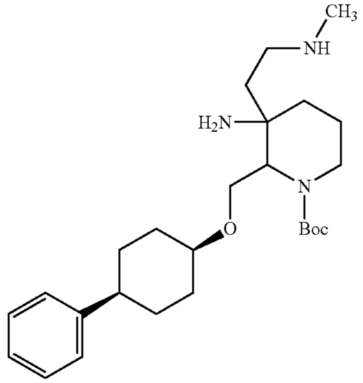 [SMILES: CNCCC1(N)CCCN(C(=O)OC(C)(C)C)C1CO[C@H]1CC[C@@H](c2ccccc2)CC1]

tert-butyl-rel-(2R,3R)-3-amino-3-[2-(methylamino) ethyl]-2-({[(CIS)-4-phenylcyclohexyl]oxy}methyl) piperidine-1-carboxylate Zinc (591 mg, 9.04 mmol) was added to a stirred solution of Intermediate 103 (430 mg, 0.904 mmol) in acetic acid (3 mL) and ethanol (11 mL) at room temperature and the mixture was stirred for 16 h. The reaction mixture was quenched with a solution of saturated aqueous $NaHCO_3$ (10 mL), filtered through celite (washing with EtOAc) and extracted with ethyl acetate (3x10 mL). The combined organic layers were dried over MgSO4, filtered, and concentrated in vacuo to afford the crude material. Crude material (135 mg) was taken on without further purification. [M+H]$^+$ m/z 446.3

Intermediate 105

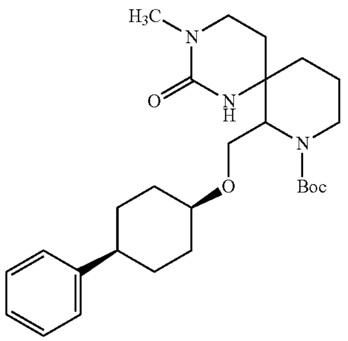 [SMILES: CN1CCC2(CCCN(C(=O)OC(C)(C)C)C2CO[C@H]2CC[C@@H](c3ccccc3)CC2)NC1=O]

tert-butyl-rel-(6R,7R)-3-methyl-2-oxo-7-({[(CIS)-4-phenylcyclohexyl]oxy}methyl)-1,3,8-triazaspiro[5.5] undecane-8-carboxylate CDI (18 mg, 0.112 mmol) was added to a stirred solution of Intermediate 104 (100 mg, 0.224 mmol) in anhydrous DMF (2.5 mL) at room temperature and the mixture was stirred for 30 minutes. A further di-1H-imidazol-1-ylmethanone (18 mg, 0.112 mmol) was added and the reaction was stirred for 30 minutes. The reaction mixture was quenched with water (5 mL) and extracted with DCM (3×5 mL). The combined organic layers were washed with brine (10 mL), dried over $MgSO_4$, filtered, and concentrated in vacuo to afford the crude material. The crude material was purified by reverse phase column chromatography (10-100% acetonitrile in water (0.1% formic acid)), to afford the title compound (41 mg) as a white solid. $[M+H]^+$ m/z 472.4

2,2-difluoroethyl-rel-(6R,7R)-3-methyl-2-oxo-7-({[(CIS)-4-phenylcyclohexyl]oxy}methyl)-1,3,8-triazaspiro[5.5]undecane-8-carboxylate (57)

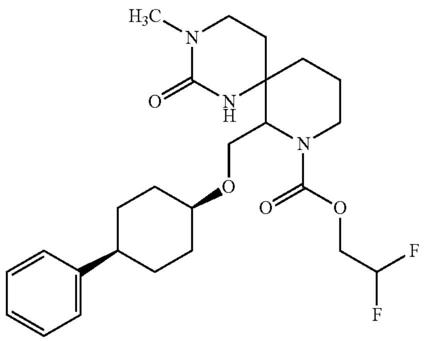 [SMILES: CN1CCC2(CCCN(C(=O)OCC(F)F)C2CO[C@H]2CC[C@@H](c3ccccc3)CC2)NC1=O]

Intermediate 105 (40 mg, 0.0848 mmol) was stirred in a mixture of anhydrous DCM (0.5 mL) and TFA (0.5 mL) for 30 minutes at room temperature. The reaction mixture was quenched with $NaHCO_3$ solution (1 mL) and extracted with DCM (3×5 mL). The combined organic layers were dried over $MgSO_4$, filtered, and concentrated in vacuo to afford the crude material. A dropwise solution of 2,2-difluoroethyl chloroformate (8.8 µL, 0.0848 mmol) was added to a stirred solution of crude material and triethylamine (28 µL, 0.204 mmol) in anhydrous DCM (1 mL) at 0° C. and the mixture was stirred for 30 minutes. The reaction mixture was quenched with methanol (0.5 mL) then water (5 mL) and extracted with DCM (3×5 mL). The combined organic layers were washed with brine (10 mL), dried over $MgSO_4$, filtered, and concentrated in vacuo to afford the crude material. The crude material was purified by reverse phase column chromatography (10-100% acetonitrile in water (0.1% formic acid)), to afford the title compound (23 mg) as a white solid.

$^1H$ NMR (400 MHz, DMSO) δ 7.29-7.23 (m, 2H), 7.22-7.18 (m, 2H), 7.18-7.12 (m, 1H), 6.17 (tt, J=54.7, 3.4 Hz, 1H), 5.88 (s, 1H), 4.32 (s, 3H), 3.90 (d, J=12.9 Hz, 1H), 3.76 (dd, J=10.5, 8.8 Hz, 1H), 3.66 (dd, J=10.6, 4.7 Hz, 1H), 3.60 (s, 1H), 3.33 (td, J=11.9, 4.4 Hz, 1H), 3.14 (ddd, J=12.5, 5.7, 3.3 Hz, 1H), 2.95 (d, J=15.1 Hz, 1H), 2.80 (s, 3H), 2.59-2.52 (m, 1H), 2.05 (d, J=14.4 Hz, 1H), 2.01-1.83 (m, 3H), 1.81-1.40 (m, 10H).

LCMS (Method B): $[M+H]^+$ m/z 480.4, RT 3.64 minutes.

Example 58: (1R,3R,5S)-2-cyclobutanecarbonyl-3-methyl-1-({[(CIS)-4-phenylcyclohexyl]oxy}methyl)-9-oxa-2,6-diazaspiro[4.5]decan-7-one

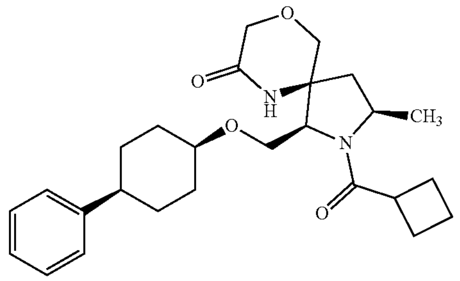 [SMILES: C[C@@H]1C[C@@]2(COCC(=O)N2)[C@H](CO[C@H]2CC[C@@H](c3ccccc3)CC2)N1C(=O)C1CCC1]

A solution of Intermediate 78 (69%, 15 mg, 0.0289 mmol) in anhydrous DMF (0.1 mL) was added to a stirred solution of cyclobutanecarboxylic acid (4.8 µL, 0.0499 mmol), HATU (24 mg, 0.0631 mmol) and DIPEA (15 µL, 0.0859 mmol) in anhydrous DMF (0.3 mL) at room temperature and mixture was stirred for 18 h. The reaction mixture was, quenched with water (2 mL) and extracted with ethyl acetate (3×2 mL). The combined organic layers were passed through a phase separator and concentrated in vacuo to afford the crude material. The crude material was purified by reverse phase column chromatography (10-100% acetonitrile in water (0.1% Formic acid)), to afford the title compound (1.8 mg) as a colourless gum.

$^1H$ NMR (400 MHz, $CDCl_3$) δ 7.30 (t, J=7.6 Hz, 2H), 7.25-7.15 (m, 3H), 6.51-6.11 (m, 1H), 4.40-4.10 (m, 3H), 4.06-3.94 (m, 1H), 3.92-3.76 (m, 1H), 3.72-3.66 (m, 1H), 3.65-3.55 (m, 1H), 3.49-3.35 (m, 1H), 3.33-3.11 (m, 1H), 2.65-2.25 (m, 3H), 2.26-2.14 (m, 2H), 2.11-2.03 (m, 2H), 2.01-1.86 (m, 2H), 1.80-1.66 (m, 6H), 1.65-1.53 (m, 2H), 1.43 (d, J=6.1 Hz, 3H)

LCMS (Method B): $[M+H]^+$ m/z 441.4, RT 3.58 minutes.

Example 59: (1R,3R,5S)-3-methyl-2-[(1s,3s)-3-fluorocyclobutanecarbonyl]-1-({[(CIS)-4-phenylcyclohexyl]oxy}methyl)-9-oxa-2,6-diazaspiro[4.5]decan-7-one

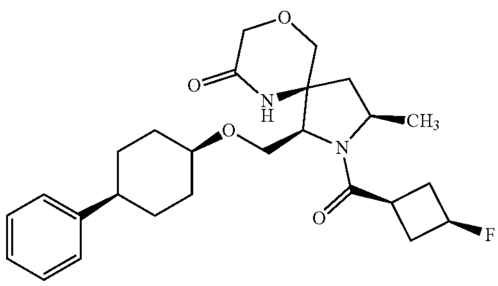 [SMILES: C[C@@H]1C[C@@]2(COCC(=O)N2)[C@H](CO[C@H]2CC[C@@H](c3ccccc3)CC2)N1C(=O)[C@H]1C[C@@H](F)C1]

A solution of Intermediate 78 (20 mg, 0.0558 mmol) in anhydrous DMF (0.1 mL) was added to a stirred solution of 3-fluorocyclobutanecarboxylic acid (9.0 mg, 0.0762 mmol), HATU (32 mg, 0.0842 mmol) and DIPEA (20 µL, 0.115 mmol) in anhydrous DMF (0.4 mL) at room temperature and mixture was stirred for 18 h. The reaction mixture was, quenched with water (2 mL) and extracted with ethyl acetate (3×2 mL). The combined organic layers were passed through a phase separator and concentrated in vacuo to afford the crude material. The crude material was purified by reverse phase column chromatography (10-100% acetonitrile in water (0.1% $NH_3$)), to afford the title compound (5.1 mg) as a beige solid.

$^1$H NMR (400 MHz, $CDCl_3$) δ 7.30 (t, J=7.6 Hz, 2H), 7.25-7.16 (m, 3H), 6.40 (s, 0.5H), 6.12 (s, 0.5H), 4.93 (ddd, J=55.5, 15.3, 8.3 Hz, 1H), 4.36 (s, 0.5H), 4.28-4.08 (m, 2H), 4.02 (d, J=3.1 Hz, 1H), 3.92-3.79 (m, 1H), 3.67 (dd, J=8.4, 4.1 Hz, 2.5H), 3.59 (d, J=11.7 Hz, 1H), 3.43 (dd, J=22.9, 11.8 Hz, 1H), 2.80-2.34 (m, 6H), 2.19 (dd, J=12.9, 8.1 Hz, 1H), 2.10-2.01 (m, 2H), 1.94 (dd, J=13.0, 9.5 Hz, 1H), 1.83-1.60 (m, 6H), 1.43 (dd, J=6.1, 1.8 Hz, 3H).

LCMS (Method A): $[M+H]^+$ m/z 459.5, RT 3.65 minutes.

Example 60: (1R,3R,5S)-2-{bicyclo[1.1.1]pentane-1-carbonyl}-3-methyl-1-({[(CIS)-4-phenylcyclohexyl]oxy}methyl)-9-oxa-2,6-diazaspiro[4.5]decan-7-one Example 60

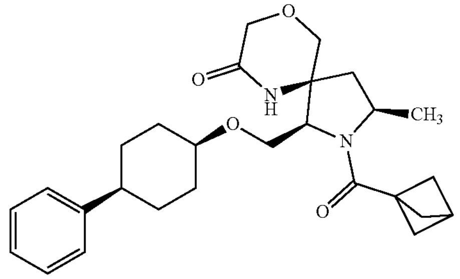 [SMILES: C[C@@H]1C[C@@]2(COCC(=O)N2)[C@H](CO[C@H]2CC[C@@H](c3ccccc3)CC2)N1C(=O)C12CC(C1)C2]

A solution of Intermediate 78 (20 mg, 0.0558 mmol) in anhydrous DMF (0.1 mL) was added to a stirred solution of bicyclo[1.1.1]pentane-1-carboxylic acid (8.1 mg, 0.0725 mmol), HATU (32 mg, 0.0837 mmol) and DIPEA (19 μL, 0.112 mmol) in anhydrous DMF (0.4 mL) at room temperature and mixture was stirred for 18 h. The reaction mixture was, quenched with water (2 mL) and extracted with ethyl acetate (3×2 mL). The combined organic layers were passed through a phase separator and concentrated in vacuo to afford the crude material. The crude material was purified by reverse phase column chromatography (10-100% acetonitrile in water (0.1% $NH_3$)), to afford the title compound (10 mg) as a white powder.

$^1$H NMR (400 MHz, $CDCl_3$) δ 7.35-7.28 (m, 2H), 7.24-7.16 (m, 3H), 6.25 (s, 1H), 4.37 (s, 1H), 4.26 (d, J=16.7 Hz, 1H), 4.21-4.10 (m, 1H), 4.05-3.87 (m, 1H), 3.75 (dd, J=10.1, 2.6 Hz, 1H), 3.72-3.64 (m, 2H), 3.60 (d, J 11.6 Hz, 1H), 3.43 (d, J=11.6 Hz, 1H), 2.63-2.52 (m, 1H), 2.50 (s, 1H), 2.26-2.03 (m, 9H), 1.92 (dd, J=12.9, 9.3 Hz, 1H), 1.84-1.69 (m, 4H), 1.61 (s, 2H), 1.52-1.36 (m, 3H).

LCMS (Method A): $[M+H]^+$ m/z 453.4, RT 3.62 minutes.

Example 61: 2,2-difluoroethyl (1R,3R,5S)-3-methyl-7-oxo-1-({[(CIS)-4-phenylcyclohexyl]oxy}methyl)-9-oxa-2,6-diazaspiro[4.5]decane-2-carboxylate

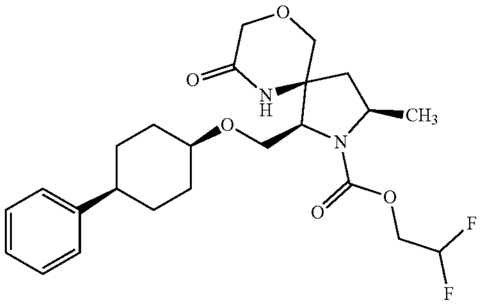 [SMILES: C[C@@H]1C[C@@]2(COCC(=O)N2)[C@H](CO[C@H]2CC[C@@H](c3ccccc3)CC2)N1C(=O)OCC(F)F]

A dropwise solution of 2,2-difluoroethyl chloroformate (8.6 μL, 0.0837 mmol) was added to a stirred solution of Intermediate 78 (20 mg, 0.0558 mmol) and triethylamine (19 μL, 0.134 mmol) in anhydrous DCM (0.5 mL) at 0° C. and mixture was stirred for 1 h. The reaction mixture was, quenched with methanol (1 mL) and concentrated in vacuo to afford the crude material. The crude material was purified by reverse phase column chromatography (10-100% acetonitrile in water (0.1% $NH_3$)), to afford the title compound (11 mg) as a white solid.

$^1$H NMR (400 MHz, $CDCl_3$) δ 7.30 (t, J=7.4 Hz, 2H), 7.25-7.16 (m, 3H), 6.29 (d, J=26.4 Hz, 1H), 5.96 (t, J=54.7 Hz, 1H), 4.47-4.31 (m, 1H), 4.31-4.02 (m, 4H), 3.87-3.74 (m, 2H), 3.74-3.67 (m, 2H), 3.63 (d, J=10.4 Hz, 1H), 3.49 (dd, J=11.6, 4.0 Hz, 1H), 2.67-2.49 (m, 1H), 2.40-2.15 (m, 1H), 2.11-1.95 (m, 3H), 1.84-1.68 (m, 4H), 1.68-1.59 (m, 2H), 1.43 (dd, J=11.4, 5.9 Hz, 3H).

LCMS (Method B): $[M+H]^+$ m/z 467.3, RT 3.69 minutes.

Example 62: (1R,3R,5S)-3-methyl-7-oxo-1-({[(CIS)-4-phenylcyclohexyl]oxy}methyl)-N-(2,2,2-trifluoroethyl)-9-oxa-2,6-diazaspiro[4.5]decane-2-carboxamide

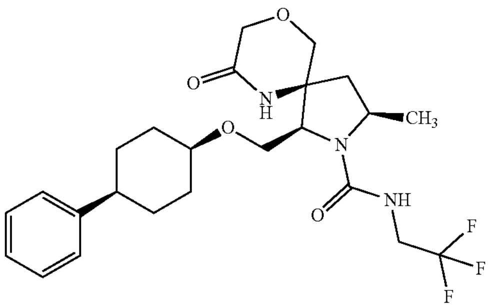 [SMILES: C[C@@H]1C[C@@]2(COCC(=O)N2)[C@H](CO[C@H]2CC[C@@H](c3ccccc3)CC2)N1C(=O)NCC(F)(F)F]

A dropwise solution of Intermediate 78 (40 mg, 0.112 mmol) in anhydrous DCM (1.4 mL) was added to a stirred solution of carbonyl dichloride (20%, 0.12 mL, 0.223 mmol) and N-ethyl-N-isopropyl-propan-2-amine (62 μL, 0.357 mmol) in N-ethyl-N-isopropyl-propan-2-amine (62 μL, 0.357 mmol) at room temperature and mixture was stirred for 3 h. A dropwise solution of 2,2,2-trifluoroethanamine (24 mg, 0.245 mmol) was added to the reaction mixture at room temperature and the reaction was stirred for 18 h. The reaction mixture was quenched with a solution of saturated aqueous $NaHCO_3$ (5 mL) and purged with $N_2$(g) (20% aq. NaOH solution as scrubber) for 30 minutes. The reaction mixture was extracted with DCM (3×3 mL), the combined organic layers were passed through a phase separator and concentrated in vacuo to afford the crude material. The crude material was purified by reverse phase column chromatography (10-100% acetonitrile in water (0.1% $NH_3$)), to afford the title compound (10 mg) as a white powder.

$^1$H NMR (400 MHz, $CDCl_3$) δ 7.34-7.26 (m, 2H), 7.19 (dd, J=7.3, 4.2 Hz, 3H), 6.23 (s, 1H), 5.91 (s, 1H), 4.27 (d, J=16.9 Hz, 1H), 4.19-4.10 (m, 2H), 4.10-4.02 (m, 1H), 3.96 (dt, J=9.8, 7.0 Hz, 1H), 3.79-3.69 (m, 3H), 3.63 (ddd, J=14.9, 9.0, 5.8 Hz, 1H), 3.49-3.41 (m, 2H), 2.61-2.51 (m, 1H), 2.28 (dd, J=13.1, 7.4 Hz, 1H), 2.09-2.00 (m, 2H), 1.82-1.58 (m, 7H), 1.37 (d, J=6.0 Hz, 3H).

LCMS (Method B): $[M+H]^+$ m/z 484.4, RT 3.36 minutes.

Example 63: (1R,3R,5S)-2-(3-methoxypyridin-2-yl)-3-methyl-1-({[(CIS)-4-phenylcyclohexyl]oxy}methyl)-9-oxa-2,6-diazaspiro[4.5]decan-7-one

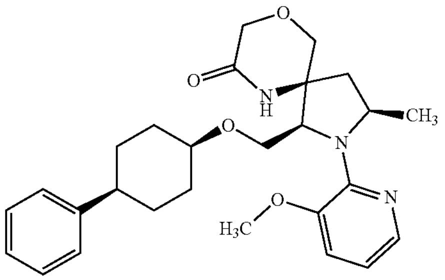 [SMILES: COc1cccnc1N1[C@H](C)C[C@@]2(COCC(=O)N2)[C@@H]1CO[C@H]1CC[C@@H](c2ccccc2)CC1]

A solution of Intermediate 78 (20 mg, 0.0558 mmol), 2-fluoro-3-methoxypyridine (8 μL, 0.0725 mmol), cesium carbonate (36 mg, 0.112 mmol) in DMF (0.6 mL) was heated in at 140° C. for 3 days. The reaction mixture was cooled to room temperature, quenched with water (1 mL) and extracted with ethyl acetate (3×1 mL). The combined organic layers were passed through a phase separator and concentrated in vacuo to afford the crude material. The crude material was purified by reverse phase column chromatography (10-100% acetonitrile in water (0.1% $NH_3$)), followed by reverse phase column chromatography (10-100% acetonitrile in water (0.1% Formic acid)), to afford impure title product (5 mg, 50%). This material was purified by prep HPLC Standard Method Column: XBridge™ Prep. C18 10 um OBD™, 30×100 mm, Mobile Phase: 5-95% Acetonitrile (0.2% ammonium hydroxide) in Water (0.2% ammonium hydroxide) over 10 minutes, Flow Rate: 40 mL/min, UV: 215 and 254 nm, to afford the title compound (0.5 mg) as a colourless oil.

$^1$H NMR (500 MHz, $CDCl_3$) δ 8.04-7.88 (m, 1H), 7.26-7.21 (m, 3H), 7.17-7.08 (m, 3H), 7.04-6.97 (m, 1H), 6.41-6.27 (m, 1H), 4.72 (s, 1H), 4.24-4.13 (m, 1H), 4.08 (dd, J=16.7, 4.6 Hz, 1H), 3.98-3.90 (m, 1H), 3.87-3.81 (m, 4H), 3.65 (d, J=2.7 Hz, 1H), 3.59-3.49 (m, 1H), 3.42-3.34 (m, 1H), 2.52 (dt, J=15.4, 8.7 Hz, 1H), 2.34-2.25 (m, 1H), 2.22-2.13 (m, 1H), 2.07-1.96 (m, 2H), 1.76-1.70 (m, 3H), 1.69-1.62 (m, 3H), 1.27 (d, J=3.6 Hz, 3H).

LCMS (Method A): $[M+H]^+$ m/z 466.4, RT 4.30 minutes.

Example 64: (1R,3R,5S)-3-methyl-2-(1-methyl-1H-1,2,3,4-tetrazol-5-yl)-1-({[(CIS)-4-phenylcyclohexyl]oxy}methyl)-9-oxa-2,6-diazaspiro[4.5]decan-7-one

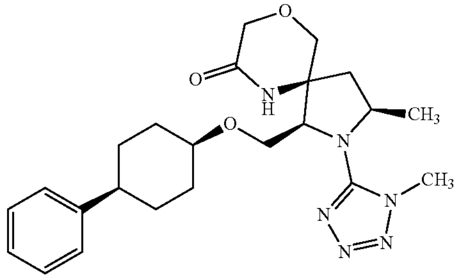 [SMILES: C[C@@H]1C[C@@]2(COCC(=O)N2)[C@H](CO[C@H]2CC[C@@H](c3ccccc3)CC2)N1c1nnnn1C]

5-chloro-1-methyl-tetrazole (21 mg, 0.181 mmol) was added to a stirred solution of Intermediate 78 (50 mg, 0.139 mmol) and triethylamine (58 μL, 0.418 mmol) in DMF (1.4 mL) at room temperature and the stirred mixture was heated at 140° C. for 48 hours. The reaction mixture was cooled to room temperature, quenched with water (1 mL) and extracted with ethyl acetate (3×2 mL). The combined organic layers were passed through a phase separator and concentrated in vacuo to afford the crude material. The crude material was purified by reverse phase column chromatography (10-100% acetonitrile in water (0.1% $NH_3$)), to afford a mixture of compounds, which was further purified by acidic preparative HPLC (Waters CSH C18 column (19 mm×100 mm, 5 m; temperature: room temperature). Injection volume of 1500 L at a flow rate of 20 mL/min. 5% B (A=0.2% Formic acid in water; B=acetonitrile) for 2.0 min then a gradient of 5-95% B over 18.0 min and held for 2.0 min. A second gradient of 95-10% B was then applied over 0.2 min and held for 0.9 min. UV spectra were recorded at 215 nm using a Gilson detector), to afford the title compound (4 mg) as a white powder.

$^1$H NMR (400 MHz, $CDCl_3$) δ 7.36-7.27 (m, 2H), 7.23-7.15 (m, 3H), 6.65 (s, 1H), 4.31-4.12 (m, 2H), 4.15-4.08 (m, 1H), 4.04-3.97 (m, 4H), 3.90 (dd, J=10.4, 2.8 Hz, 1H), 3.80-3.67 (m, 3H), 3.56 (d, J=11.9 Hz, 1H), 2.57 (p, J=7.7 Hz, 1H), 2.37 (dd, J=12.9, 7.4 Hz, 1H), 2.13-1.98 (m, 3H), 1.78-1.55 (m, 6H), 1.37 (d, J=6.0 Hz, 3H).

LCMS (Method B): $[M+H]^+$ m/z 441.3, RT 3.05 minutes.

Example 65: 2,2-difluoroethyl-rel-(6R,7R)-2-oxo-7-({[(CIS)-4-phenylcyclohexyl]oxy}methyl)-3-oxa-1,8-diazaspiro[5.5]undecane-8-carboxylate

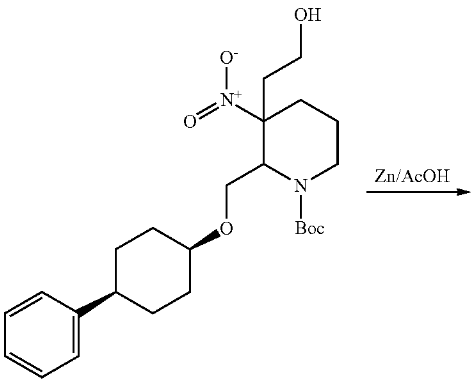

-continued

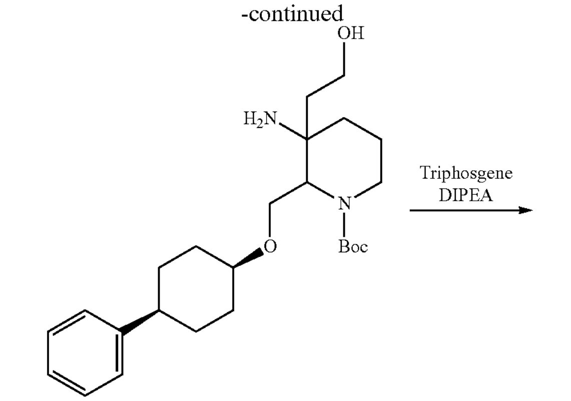

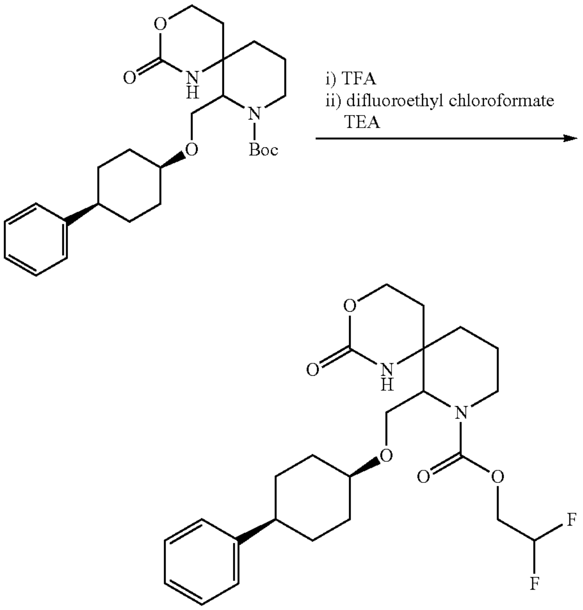

Intermediate 106

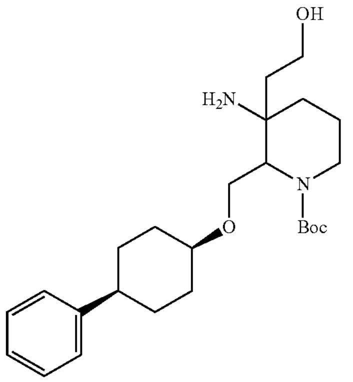 [SMILES: CC(C)(C)OC(=O)N1CCCC(N)(CCO)C1CO[C@H]1CC[C@@H](c2ccccc2)CC1]

tert-butyl-rel-(2R,3R)-3-amino-3-(2-hydroxyethyl)-2-({[(CIS)-4-phenylcyclohexyl]oxy}methyl)piperidine-1-carboxylate Zinc (1.84 g, 28.1 mmol) was added to a stirred solution of Intermediate 101 (650 mg, 1.41 mmol) in ethanol (19.5 mL) and acetic acid (5 mL) at 0° C. and the mixture was stirred for 2 h while warming to room temperature. The reaction was filtered through a pad of celite, washing the methanol (2×10 mL) and concentrated in vacuo. The reaction was neutralised with $NaHCO_3$ solution and extracted with DCM (3×10 mL). The combined organic layers were washed with brine (20 mL), dried over $MgSO_4$, filtered, and concentrated in vacuo to afford the title compound (605 mg) as a colourless gum. $[M+H]^+$ m/z 433.5

Intermediate 107

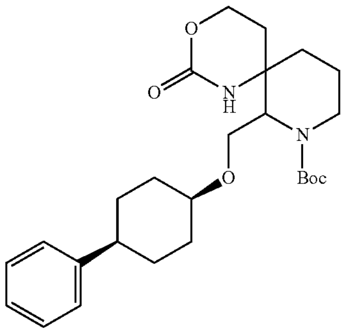 [SMILES: CC(C)(C)OC(=O)N1CCCC2(CCOC(=O)N2)C1CO[C@H]1CC[C@@H](c2ccccc2)CC1]

tert-butyl-rel-(6R,7R)-2-oxo-7-({[(CIS)-4-phenylcyclohexyl]oxy}methyl)-3-oxa-1,8-diazaspiro[5.5]undecane-8-carboxylate A dropwise solution of N-ethyl-N-(propan-2-yl)propan-2-amine (0.36 mL, 2.08 mmol) was added to a stirred solution of bis(trichloromethyl) carbonate (535 mg, 1.80 mmol) and Intermediate 106 (600 mg, 1.39 mmol) in anhydrous DCM (20 mL) at 0° C. and the mixture was stirred for 30 mins. The reaction mixture was warmed to room temperature and purged for 30 mins with a stream of N2 through a 5N NaOH solution (to quench any excess phosgene). The reaction was then quenched with water (20 mL) and extracted with DCM (3×20 mL). The combined organic layers were washed with brine (30 mL), dried over $MgSO_4$, filtered, and concentrated in vacuo to afford the crude material. The crude material was purified by reverse phase column chromatography (10-100% acetonitrile in water (0.1% $NH_3$)), to afford the title compound (524 mg) as a white solid. $[M+H]^+$ m/z 459.5

Intermediate 108

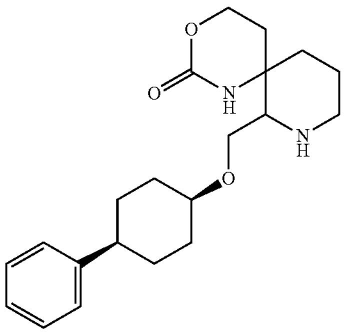 [SMILES: O=C1NC2(CCCNC2CO[C@H]2CC[C@@H](c3ccccc3)CC2)CCO1]

rel-(6R,7R)-7-({[(CIS)-4-phenylcyclohexyl]oxy}methyl)-3-oxa-1,8-diazaspiro[5.5]undecan-2-one Intermediate 107 (100 mg, 0.218 mmol) was dissolved in DCM (0.5 mL) then dropwise solution of TFA (0.5 mL) was added and mixture was stirred at room temperature for 1 h. The reaction was evaporated to dryness to afford the title compound (80 mg) as a colourless sticky solid. $[M+H]^+$ m/z 359.3

Example 65

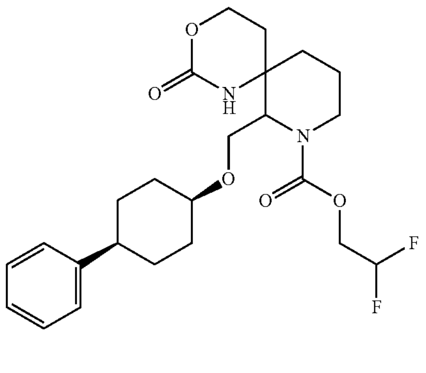 [SMILES: O=C1NC2(CCCN(C(=O)OCC(F)F)C2CO[C@H]2CC[C@@H](c3ccccc3)CC2)CCO1]

2,2-difluoroethyl-rel-(6R,7R)-2-oxo-7-({[(CIS)-4-phenylcyclohexyl]oxy}methyl)-3-oxa-1,8-diazaspiro[5.5]undecane-8-carboxylate A dropwise solution of 2,2-difluoroethyl chloroformate (8.6 μL, 0.0837 mmol) was added to a stirred solution of Intermediate 108 (20 mg, 0.0558 mmol) and triethylamine (19 μL, 0.134 mmol) in anhydrous DCM (0.5 mL) at 0° C. and mixture was stirred for 1 h at 0° C. The reaction mixture was, quenched with methanol (1 mL) and concentrated in vacuo to afford the crude material. The crude material was purified by reverse phase column chromatography (10-100% acetonitrile in water (0.1% $NH_3$)), to afford the title compound (10 mg) as a white solid.

$^1H$ NMR (400 MHz, $CDCl_3$) δ 7.34-7.27 (m, 2H), 7.23-7.15 (m, 3H), 5.93 (tt, J=55.1, 3.8 Hz, 1H), 5.55-5.42 (s, 1H), 4.49-3.96 (m, 6H), 3.91-3.74 (m, 2H), 3.68-3.61 (m, 1H), 3.30-3.04 (m, 1H), 2.63-2.46 (m, 1H), 2.26-1.93 (m, 4H), 1.77-1.65 (m, 7H), 1.60-1.47 (m, 3H).

LCMS (Method A): $[M+H]^+$ m/z 467.4, RT 3.60 minutes.

Example 66: (6R,7R)-8-[(CIS)-3-fluorocyclobutanecarbonyl]-7-({[(CIS)-4-phenylcyclohexyl]oxy}methyl)-3-oxa-1,8-diazaspiro[5.5]undecan-2-one & Example 67: (6S,7S)-8-[(CIS)-3-fluorocyclobutanecarbonyl]-7-({[(CIS)-4-phenylcyclohexyl]oxy}methyl)-3-oxa-1,8-diazaspiro[5.5]undecan-2-one

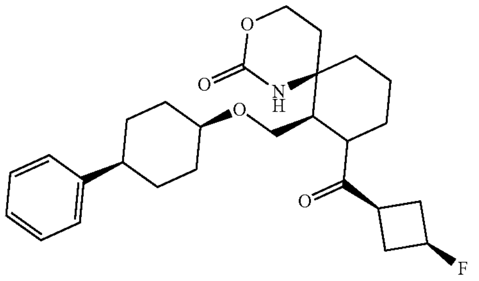

-continued

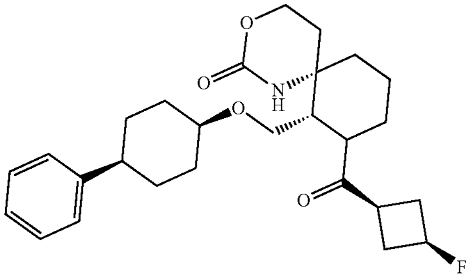

A solution of Intermediate 108 (45 mg, 0.126 mmol) in anhydrous DMF (0.23 mL) was added to a stirred solution of 3-fluorocyclobutanecarboxylic acid (20 mg, 0.169 mmol), HATU (72 mg, 0.189 mmol) and DIPEA (65 μL, 0.372 mmol) in anhydrous DMF (0.9 mL) at room temperature and mixture was stirred for 18 h. The reaction mixture was, quenched with water (2 mL) and extracted with ethyl acetate (3×2 mL). The combined organic layers were passed through a phase separator and concentrated in vacuo to afford the crude material. The crude material was purified by reverse phase column chromatography (10-100% acetonitrile in water (0.1% $NH_3$)), to afford the compound (47 mg) as an off white solid. This was purified by basic preparative HPLC (Waters XSelect CSH column (30 mm×100 mm, 3 μm; temperature: room temperature). Injection volume of 1000 μL at a flow rate of 40 mL/min. [$A_1$: Waters+0.1% $NH_3OH$]; [B1: MeCN+0.1% $NH_3OH$]. Gradient: from 3% B1 to 99.9% B1 in 1.5 min (flow: 1.00 mL/min)), then by chiral preparative purification using Waters 600 eluting with 65/35% v/v n-Hexane/ethanol, Chiralpak AS-H (25×2.0 cm), 5 μm, flow rate 17 mL/minutes, to afford the title compounds (Peak 1, 14.1 mg, 100% ee; and Peak 2, 14.3 mg, 100% ee). The absolute stereochemistry of each separated compound 66 and 67 was not conclusively determined but assigned as shown below.

Example 66: Peak 1 (was assigned 6R,7R at piperidine); $^1H$ NMR (400 MHz, $CDCl_3$) δ 7.34-7.28 (m, 2H), 7.24-7.15 (m, 3H), 5.31 (br s, 1H), 5.15-4.73 (m, 2H), 4.46-4.23 (m, 2H), 3.96-3.70 (m, 2H), 3.69-3.38 (m, 3H), 2.86-2.67 (m, 1H), 2.65-2.40 (m, 5H), 2.38-2.22 (m, 1H), 2.12-1.92 (m, 3H), 1.88-1.46 (m, 10H).

LCMS (Method C): $[M+H]^+$ m/z 459.4, RT 1.07 minutes.

Chiral analysis (Chiralcelpak AS-H, 25×0.46 cm, 5 μm, 40:60 n-Hexane:ethanol): RT 8.5 minutes.

Example 67: Peak 2 (was assigned 6S, 7S at piperidine): $^1H$ NMR (400 MHz, $CDCl_3$) δ 7.34-7.28 (m, 2H), 7.24-7.15 (m, 3H), 5.31 (br s, 1H), 5.15-4.73 (m, 2H), 4.46-4.23 (m, 2H), 3.96-3.70 (m, 2H), 3.69-3.38 (m, 3H), 2.86-2.67 (m, 1H), 2.65-2.40 (m, 5H), 2.38-2.22 (m, 1H), 2.12-1.92 (m, 3H), 1.88-1.46 (m, 10H).

LCMS (Method C): $[M+H]^+$ m/z 459.4, RT 1.07 minutes.

Chiral analysis (Chiralcelpak AS-H, 25×0.46 cm, 5 μm, 40:60 n-Hexane:ethanol): RT 13.9 minutes.

Example 68: rel-(6R,7R)-7-({[(CIS)-4-phenylcyclohexyl]oxy}methyl)-8-(2,2,2-trifluoroethyl)-3-oxa-1,8-diazaspiro[5.5]undecan-2-one

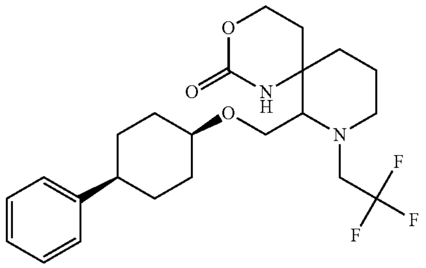 [SMILES: O=C1NC2(CCCN(CC(F)(F)F)C2CO[C@H]2CC[C@@H](c3ccccc3)CC2)CCO1]

rel-(6R,7R)-7-({[(CIS)-4-phenylcyclohexyl]oxy}methyl)-8-(2,2,2-trifluoroethyl)-3-oxa-1,8-diazaspiro[5.5]undecan-2-one A solution of 2,2,2-trifluoroethyl trifluoromethanesulfonate (24 μL, 0.167 mmol) was added to a stirred solution of Intermediate 108 (41 mg, 0.110 mmol) and DIPEA (45 μL, 0.258 mmol) in anhydrous THF (1 mL) at room temperature and mixture was stirred for 60 h. The reaction mixture was, quenched with water (2 mL) and extracted with ethyl acetate (3×2 mL). The combined organic layers were passed through a phase separator and concentrated in vacuo to afford the crude material. The crude material was purified by reverse phase column chromatography (10-100% acetonitrile in water (0.1% $NH_3$)), to afford the title compound (13 mg) as a white powder.

LCMS (Method A): $[M+H]^+$ m/z 441.5, RT 4.30 minutes.

1H NMR (400 MHz, $CDCl_3$) δ 7.35-7.27 (m, 2H), 7.23-7.16 (m, 3H), 5.61 (s, 1H), 4.38-4.27 (m, 2H), 3.82 (dd, J=10.3, 6.9 Hz, 1H), 3.72 (dd, J=10.3, 3.4 Hz, 1H), 3.62 (s, 1H), 3.43 (dq, J=19.2, 9.4 Hz, 1H), 3.30 (dq, J=18.1, 9.1 Hz, 1H), 3.05-2.92 (m, 2H), 2.76-2.66 (m, 1H), 2.60-2.47 (m, 2H), 2.03 (d, J=14.3 Hz, 2H), 1.87-1.64 (m, 8H), 1.62-1.52 (m, 3H).

Example 69: rel-(1S,5S)-(4R)—N-ethyl-4-methyl-7-oxo-1-({2,3',5'-trifluoro-[1,1'-biphenyl]-3-yl}methyl)-9-oxa-2,6-diazaspiro[4.5]decane-2-carboxamide; & Example 70: rel-(1S,5S)-(4S)—N-ethyl-4-methyl-7-oxo-1-({2,3',5'-trifluoro-[1,1'-biphenyl]-3-yl}methyl)-9-oxa-2,6-diazaspiro[4.5]decane-2-carboxamide

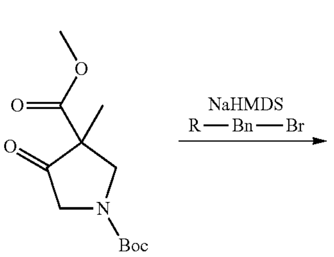

-continued

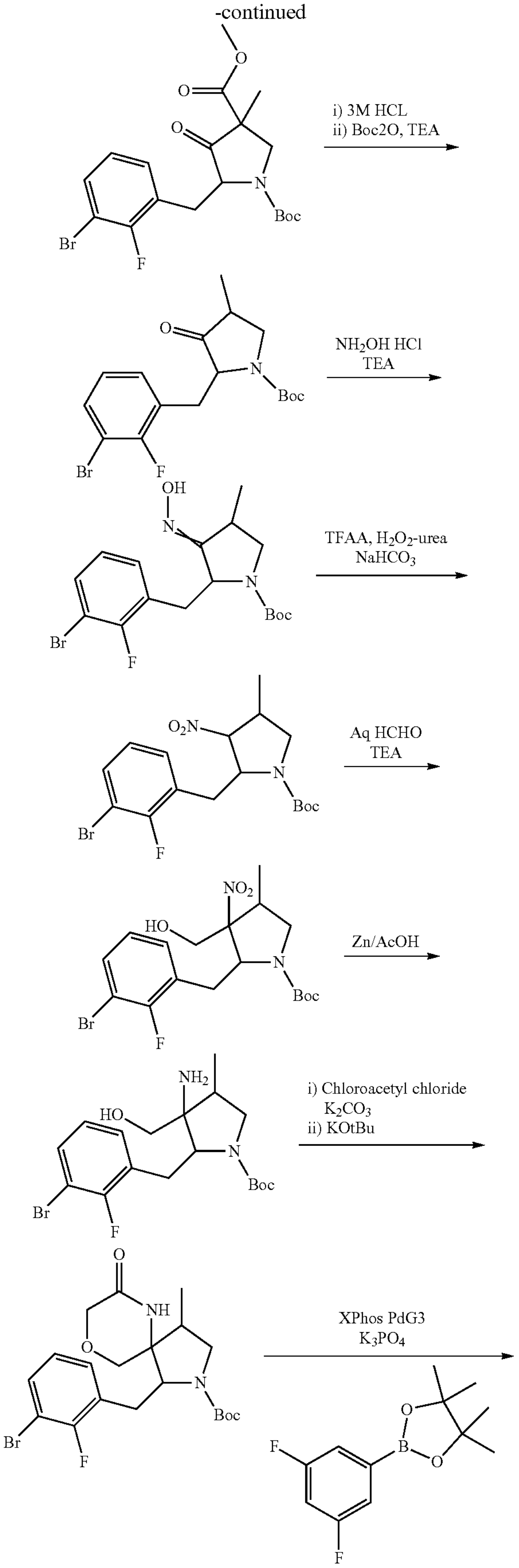

-continued

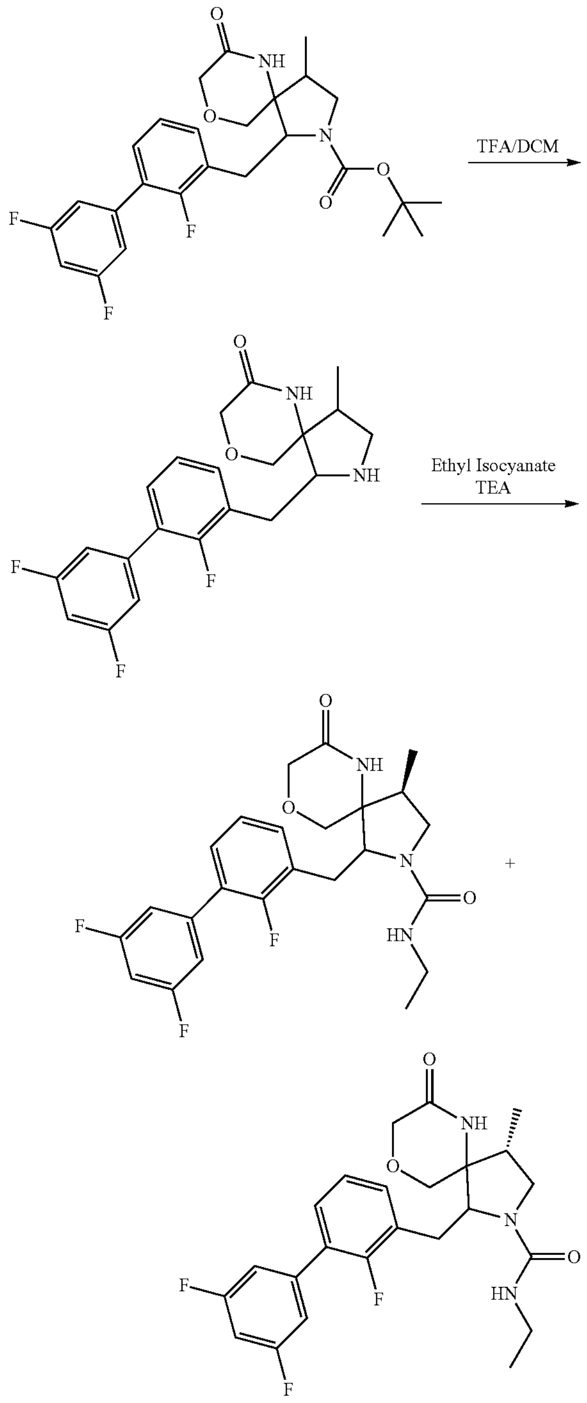

Intermediate 109

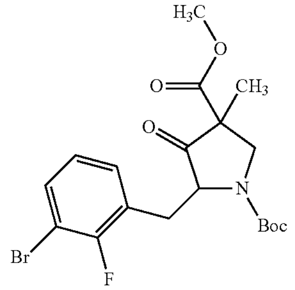 [SMILES: COC(=O)C1(C)CN(C(=O)OC(C)(C)C)C(Cc2cccc(Br)c2F)C1=O]

1-tert-butyl 3-methyl 5-[(3-bromo-2-fluorophenyl)methyl]-3-methyl-4-oxopyrrolidine-1,3-dicarboxylate A solution of 0.6 M sodium 1,1,1,3,3,3-hexamethyldisilazan-2-ide (14 mL, 8.11 mmol) was added to a stirred solution of 1-tert-butyl 3-ethyl 3-methyl-4-oxopyrrolidine-1,3-dicarboxylate (2.00 g, 7.37 mmol) in anhydrous THF (28 mL) at −78° C. and the mixture was stirred for 15 min. 1-bromo-3-(bromomethyl)-2-fluoro-benzene (2.17 g, 8.11 mmol) in anhydrous THF (9 mL) was added, the reaction mixture was allowed to warm to room temperature and stirred for 1 h. The reaction mixture was quenched with saturated aqueous $NH_4Cl$ (20 mL) and extracted with DCM (3×50 mL). The combined organic layers were passed through a phase separator and concentrated in vacuo to afford the crude material. The crude material was purified by silica gel column chromatography (0-10% EtOAc in heptane), to afford the title compounds (2:1 ratio of diastereomers) (1.8 g) as a pale-yellow oil. $[M\text{-}Boc+H]^+$ m/z 358.0 and 360.0

Intermediate 110

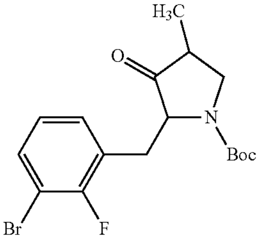 [SMILES: CC1CN(C(=O)OC(C)(C)C)C(Cc2cccc(Br)c2F)C1=O]

tert-butyl 2-[(3-bromo-2-fluorophenyl)methyl]-4-methyl-3-oxopyrrolidine-1-carboxylate A suspension of Intermediate 109 (99%, 2.89 g, 6.24 mmol) in 3M hydrogen chloride (42 mL, 0.125 mol) was heated to 105° C. for 6 h. The reaction was quenched with saturate aqueous $Na_2CO_3$ (20 mL) and extracted with DCM (3×50 ml). The combined organic layers were dried over $MgSO_4$, filtered, and concentrated in vacuo to afford the crude material as a brown liquid. The crude was dissolved in DCM (25 mL) and methanol (25 mL) and triethylamine (2.6 mL, 18.7 mmol) and di-tert-butyl dicarbonate (2.04 g, 9.34 mmol) were added. The mixture was stirred at room temperature for 16 h, then concentrated. 0.5 M NaOH (50 ml) was added, and the mixture extracted with DCM (3×50 ml). The combined organic extracts were dried ($MgSO_4$), filtered, and concentrated. The crude was purified by silica gel column chromatography (0-40% EtOAc in heptane), to afford the title compound (1.13 g) as a yellow oil. (M-tBu+H)+ m/z 330.3 & 332.3

Intermediate 111

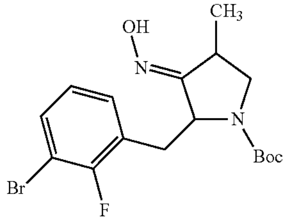 [SMILES: CC1CN(C(=O)OC(C)(C)C)C(Cc2cccc(Br)c2F)/C1=N/O]

tert-butyl-2-[(3-bromo-2-fluorophenyl)methyl]-3-(hydroxyimino)-4-methylpyrrolidine-1-carboxylate A solution of triethylamine (2.1 mL, 15.2 mmol), hydroxylamine hydrochloride (1:1) (1.06 g, 15.3 mmol) and Intermediate 110 (99%, 1.98 g, 5.07 mmol) in ethanol (10.3 mL) was heated to 90° C. for 1 h. The reaction mixture was diluted with water (50 mL) and extracted with EtOAc (3×75 mL). The organic extracts were dried over magnesium sulfate and concentrated in vacuo. The crude material was purified by silica gel column chromatography (0-100% EtOAc in heptane), to afford the title compound (2 g) as a colourless gum. $[M\text{-tButyl+H}]^+$ m/z 345.0 & 347.0

Intermediate 112

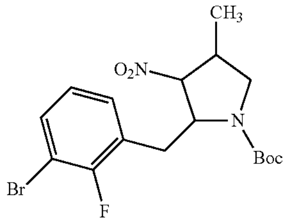 [SMILES: CC1CN(C(=O)OC(C)(C)C)C(Cc2cccc(Br)c2F)C1[N+](=O)[O-]]

tert-butyl 2-[(3-bromo-2-fluorophenyl)methyl]-4-methyl-3-nitropyrrolidine-1-carboxylate A solution of trifluoroacetic anhydride (1.8 mL, 13.0 mmol) in acetonitrile (9.45 mL) was added to a stirred solution of hydrogen peroxide-urea (1:1) (1.70 g, 18.1 mmol) in acetonitrile (9.45 mL) at 0° C. and the mixture was stirred at 0° C. for 2 h. The resulting solution was added dropwise to a mixture of Intermediate 111 (2.10 g, 5.18 mmol) and sodium hydrogen carbonate (2.18 g, 25.9 mmol) in acetonitrile (9.45 mL) at 80° C. for 1 h. The reaction mixture was cooled to room temperature, quenched with saturated aqueous $Na_2SO_3$ (10 mL) and stirred for 10 min then extracted with EtOAc (2×25 mL). The combined organic extracts were dried over $MgSO_4$, filtered, and concentrated in vacuo to afford the crude material. The crude material was purified by silica gel column chromatography (0-100% EtOAc in heptane), to afford the title compounds (1.24 g) as a pale-yellow oil. $[M\text{-tButyl+H}]^+$ m/z 361.2 & 363.1

Intermediate 113

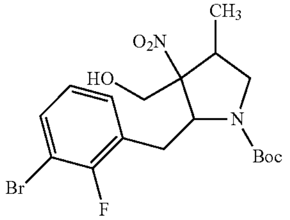 [SMILES: CC1CN(C(=O)OC(C)(C)C)C(Cc2cccc(Br)c2F)C1(CO)[N+](=O)[O-]]

tert-butyl-rel-(2S,3S)-2-[(3-bromo-2-fluorophenyl)methyl]-3-(hydroxymethyl)-4-methyl-3-nitropyrrolidine-1-carboxylate Formaldehyde (in water) (37%, 1.8 mL, 24.2 mmol) was added to Intermediate 112 (90%, 1.24 g, 2.67 mmol) and triethylamine (0.45 mL, 3.22 mmol) in THF (13.551 mL) at room temperature. The solution was heated to 70° C. for 18 h. After cooling the reaction mixture was diluted with water (20 mL) and extracted with EtOAc (3×25 mL). The combined organic extracts were washed with brine (40 mL), dried over $MgSO_4$, filtered, and concentrated in vacuo and silica gel column chromatography (0-90% EtOAc in heptane), to afford the title compound (1.03 g) as a yellow oil. $[M\text{-tBu+H}]^+$ m/z 393.1 & 391.1

Intermediate 114

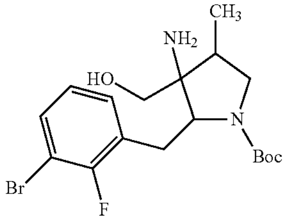 [SMILES: CC1CN(C(=O)OC(C)(C)C)C(Cc2cccc(Br)c2F)C1(N)CO]

tert-butyl-rel-(2S,3S)-3-amino-2-[(3-bromo-2-fluorophenyl)methyl]-3-(hydroxymethyl)-4-methylpyrrolidine-1-carboxylate A suspension of Intermediate 113 (100%, 1.03 g, 2.30 mmol) and zinc (1.50 g, 22.9 mmol) in acetic acid (11 mL) and ethanol (79 mL) was stirred for 2 h at room temperature. The reaction mixture was filtered through a pad of celite and washed with methanol. The filtrate was neutralised with $NaHCO_3$, extracted with DCM (3×25 mL), organic layer was dried over $MgSO_4$ and concentrated under vacuum to afford the title compound (850 mg) as a colourless oil. $[M+H]^+$ m/z=417.2 & 419.2

Intermediate 115

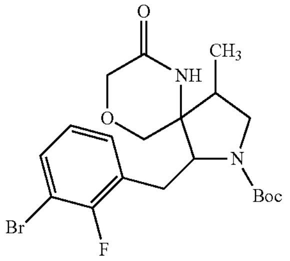 [SMILES: CC1CN(C(=O)OC(C)(C)C)C(Cc2cccc(Br)c2F)C12COCC(=O)N2]

tert-butyl-rel-(1S,5S)-1-[(3-bromo-2-fluorophenyl) methyl]-4-methyl-7-oxo-9-oxa-2,6-diazaspiro[4.5] decane-2-carboxylate To a solution of Intermediate 114 (77%, 425 mg, 0.784 mmol) in THF (3.3 mL) at 0° C. was added dipotassium carbonate (325 mg, 2.35 mmol) then water (3.3 mL). To this mixture chloroacetyl chloride (0.087 mL, 1.10 mmol) was added dropwise at 0° C. The reaction was stirred for 1 h at 0° C. The mixture was quenched with water and extracted with DCM (3×15 mL) The combined organic extracts were washed with brine (10 mL), dried over $MgSO_4$, filtered, and concentrated to give an oily residue. The crude material was dissolved in DCM (7 mL) and IPA (11 mL), cooled to 0° C. Potassium 2-methylpropan-2-olate (351 mg, 3.13 mmol) was added and the reaction was stirred at 0° C. for 1 h. The reaction was quenched by addition of water (2 mL). The mixture was poured onto saturated aqueous $NaHCO_3$ (10 ml). After extraction with DCM (3×15 mL), the combined organic extracts were washed with brine (20 mL), dried over $MgSO_4$, filtered, and concentrated to give a pale-yellow oil. The crude material was purified by silica gel column chromatography (0-100% EtOAc in heptane), to afford the title compound (274 mg) as a white solid. $[M-H]^-$ m/z 455.3 & 457.3

Intermediate 116

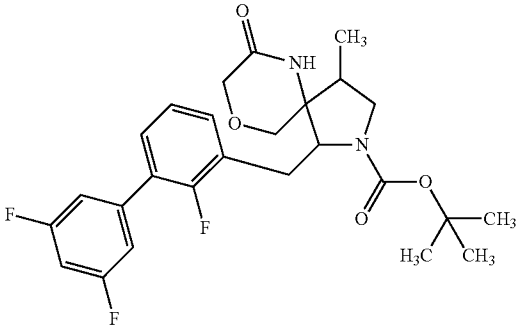 [SMILES: CC1CN(C(=O)OC(C)(C)C)C(Cc2cccc(-c3cc(F)cc(F)c3)c2F)C12COCC(=O)N2]

tert-butyl-rel-(1S,5S)-4-methyl-7-oxo-1-({2,3',5'-trifluoro-[1,1'-biphenyl]-3-yl}methyl)-9-oxa-2,6-diazaspiro[4.5]decane-2-carboxylate A mixture of Intermediate 115 (95%, 260 mg, 0.541 mmol), 2-(3,5-difluorophenyl)-4,4,5,5-tetramethyl-1,3,2-dioxaborolane (259 mg, 1.08 mmol), 1 M tripotassium;phosphate (1M in H2O) (1.6 mL, 1.62 mmol) and THF (5.3 mL) was degassed for 15 mins ($N_2$ purge). XPhos Pd G3 (46 mg, 0.0548 mmol) was added, and the reaction mixture was stirred under nitrogen atmosphere at 70° C. for 1 h. The reaction mixture was poured into saturated aqueous $NaHCO_3$ (10 mL), and the mixture was extracted with ethyl acetate (3×25 mL). The organic layer was passed through a pass separator and concentrated under reduced pressure. The crude material was purified by silica gel column chromatography (0-100% EtOAc in heptane) to afford the title compound (172 mg) as a yellow oil. $[M-H]^-$ m/z 489.4

Intermediate 117

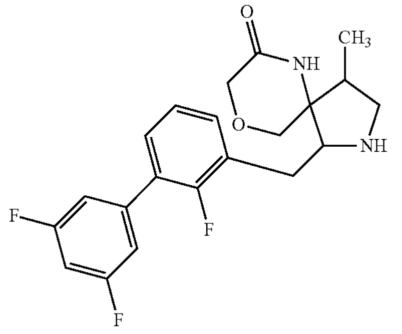 [SMILES: CC1CNC(Cc2cccc(-c3cc(F)cc(F)c3)c2F)C12COCC(=O)N2]

rel-(1S,5S)-4-methyl-1-({2,3',5'-trifluoro-[1,1'-biphenyl]-3-yl}methyl)-9-oxa-2,6-diazaspiro[4.5]decan-7-one tert-butyl Intermediate 116 (97%, 177 mg, 0.350 mmol) was stirred in a mixture of TFA (0.4 mL) and anhydrous DCM (0.4 mL) for 30 minutes at room temperature. The reaction mixture was quenched with $NaHCO_3$ solution (5 mL) and extracted with DCM (3×5 mL). The combined organic layers were dried over $MgSO_4$, filtered, and concentrated in vacuo to afford the title compound (129 mg) as a white solid. $[M+H]^+$ m/z 391.3 rel-(1S,5S)-(4R)—N-ethyl-4-methyl-7-oxo-1-({2,3',5'-trifluoro-[1,1'-biphenyl]-3-yl}methyl)-9-oxa-2,6-diazaspiro[4.5]decane-2-carboxamide (69); & rel-(1S,5S)-(4S)—N-ethyl-4-methyl-7-oxo-1-({2,3',5'-trifluoro-[1,1'-biphenyl]-3-yl}methyl)-9-oxa-2,6-diazaspiro[4.5]decane-2-carboxamide (70)

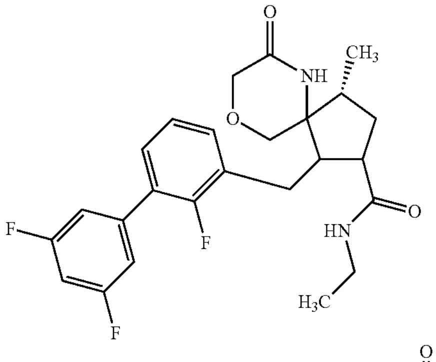

+

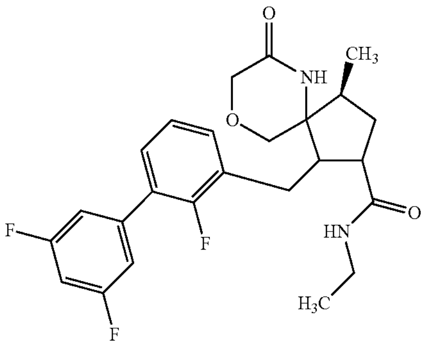

Isocyanatoethane (23 μL, 0.287 mmol) was added to a solution of triethylamine (40 μL, 0.288 mmol) and Intermediate 117 (56 mg, 0.144 mmol) in anhydrous DCM (1.1 mL) at room temperature. The reaction was stirred for 1 hour and was then quenched with 2 M NaOH and extracted with DCM (3×10 mL). The organic layers were combined, washed with brine (25 mL), passed through a phase separator, and concentrated in vacuo. The crude material was purified by using basic preparative HPLC (Waters Sunfire C18 column (30 mm×100 mm, 5 μm; temperature: room temperature) to afford the title compounds example 69 (14 mg) and example 70 (17 mg)

Example 69: $^{1}$H NMR (400 MHz, $CDCl_3$) δ 7.41 (t, J=6.3 Hz, 1H), 7.35-7.30 (m, 1H), 7.20 (t, J=7.6 Hz, 1H), 7.11 (d, J=7.5 Hz, 2H), 6.84 (tt, J=8.9, 2.3 Hz, 1H), 6.63 (s, 1H), 4.27 (dd, J=8.7, 5.3 Hz, 1H), 4.14 (t, J=5.3 Hz, 1H), 4.07 (d, J=16.7 Hz, 1H), 3.86-3.71 (m, 2H), 3.52 (d, J=11.9 Hz, 1H), 3.41-3.32 (m, 2H), 3.23 (ddd, J=12.9, 7.3, 5.7 Hz, 2H), 3.08 (dd, J=10.4, 8.7 Hz, 1H), 3.00 (dd, J=14.0, 8.8 Hz, 1H), 2.23 (q, J=7.9 Hz, 1H), 1.19 (d, J=7.0 Hz, 3H), 1.09 (t, J=7.2 Hz, 3H). LCMS (method A) (ESI+) $(M+H)^+$: 462.3, rt=3.09

LCMS (Method A): $[M-H]^-$ m/z 462.3, RT 3.09 minutes.

Example 70: $^{1}$H NMR (400 MHz, $CDCl_3$) δ 7.43 (t, J=6.3 Hz, 1H), 7.28-7.25 (m, 1H), 7.24-7.19 (m, 1H), 7.12 (d, J=7.5 Hz, 2H), 6.84 (tt, J=8.9, 2.3 Hz, 1H), 6.30 (s, 1H), 4.45 (t, J=6.9 Hz, 1H), 4.06-3.88 (m, 3H), 3.66-3.51 (m, 3H), 3.23-3.11 (m, 2H), 3.05 (t, J=10.2 Hz, 1H), 3.00 (d, J=6.7 Hz, 2H), 2.49-2.37 (m, 1H), 1.12 (d, J=7.0 Hz, 3H), 1.01 (t, J=7.2 Hz, 3H). LCMS (Method A) (ESI+) (M+H)+: 462.3, rt=3.00.

LCMS (Method A): $[M-H]^-$ m/z 462.3, RT 3.0 minutes.

Example 71: rel-(1S,5S)-2-[(1s,3s)-3-fluorocyclobutanecarbonyl]-1-({2,3',5'-trifluoro-[1,1'-biphenyl]-3-yl}methyl)-9-oxa-2,6-diazaspiro[4.5]decan-7-one

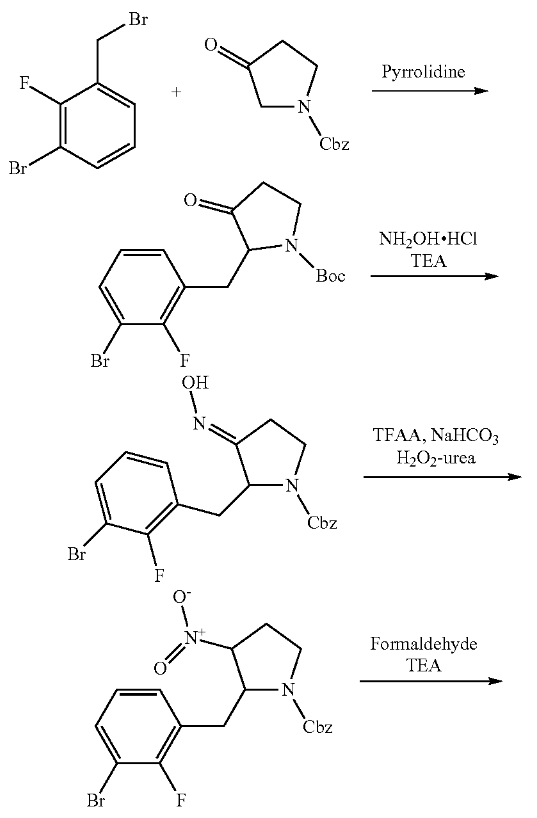

-continued

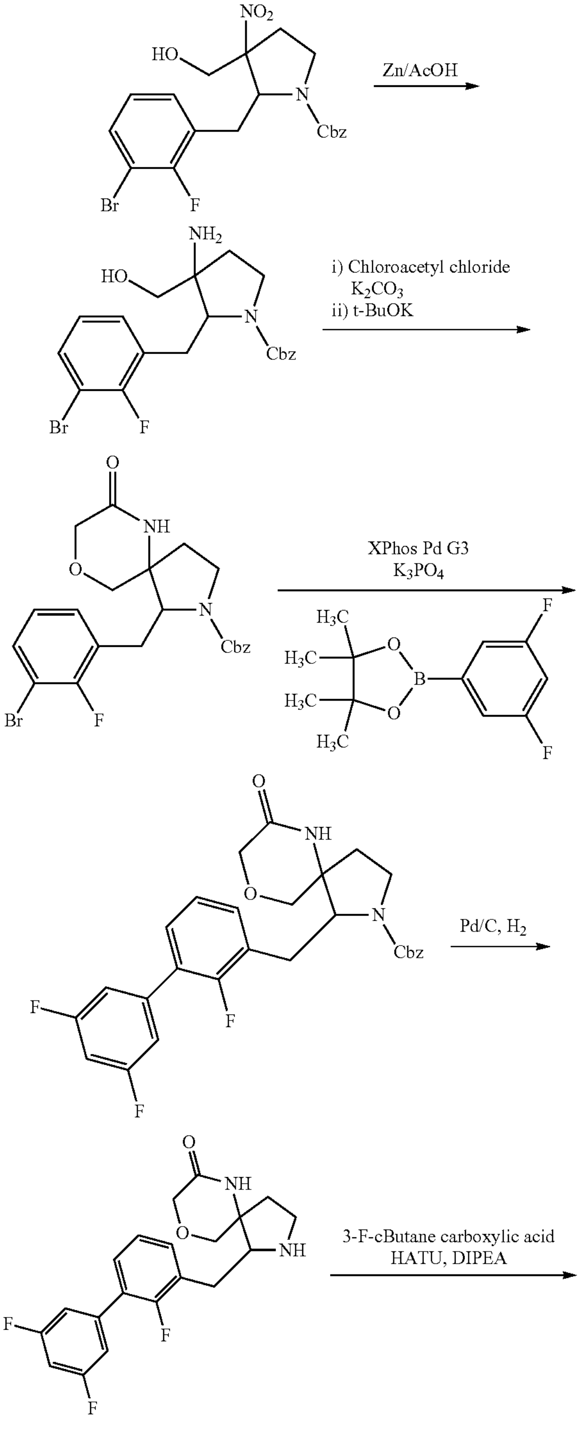

-continued

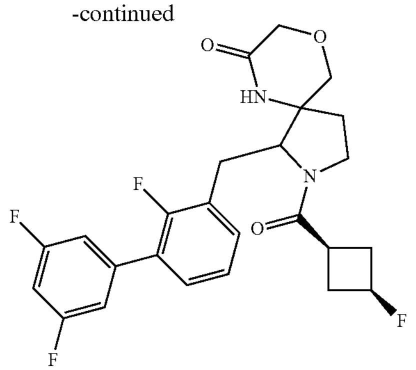

Intermediate 118

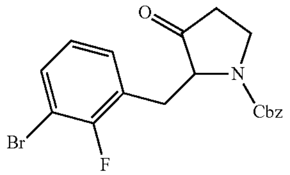 [SMILES: O=C1CCN(C(=O)OCc2ccccc2)C1Cc1cccc(Br)c1F]

Benzyl 2-[(3-bromo-2-fluorophenyl)methyl]-3-oxopyrrolidine-1-carboxylate

Pyrrolidine (4.8 mL, 57.6 mmol) was added to the stirred solution of benzyl 3-oxopyrrolidine-1-carboxylate (8.42 g, 38.4 mmol) in toluene (118 mL) at room temperature and mixture was heated at 140° C. (external temperature) using a Dean-Stark trap for 1.5 h. The reaction mixture was cooled to room temperature, evaporated to dryness to afford the crude material. This was dissolved in anhydrous acetonitrile (67 mL) and treated with 1-bromo-3-(bromomethyl)-2-fluoro-benzene (12.34 g, 46.1 mmol) in acetonitrile (34 mL) at room temperature and mixture was heated at 80° C. for 16 h. The reaction mixture cooled to room temperature, concentrated in vacuo to afford the crude material. This was dissolved in water (50 mL) and acidified with 1M HCl to pH 1 then extracted with ethyl acetate (3×50 mL). The combined organic layers were washed with brine (50 mL), dried over sodium sulfate, filtered, and evaporated to dryness to afford the crude material. The crude material was purified by silica gel column chromatography (0-40% EtOAc in heptane), to afford the title compound (6.74 g) as a pale-yellow thick oil. $[M+H]^+$ m/z 406.1 and 408.1

Intermediate 119

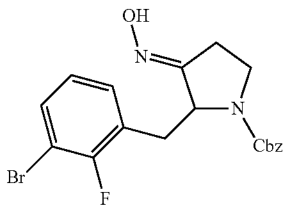 [SMILES: O=C(OCc1ccccc1)N1CC/C(=N\O)C1Cc1cccc(Br)c1F]

Benzyl-2-[(3-bromo-2-fluorophenyl)methyl]-3-(hydroxyimino)pyrrolidine-1-carboxylate A solution of triethylamine (5.1 mL, 36.3 mmol), hydroxylamine hydrochloride (1:1) (2.52 g, 36.3 mmol) and Intermediate 118 (73%, 6.74 g, 12.1 mmol) in ethanol (24.5 mL) was heated to 90° C. for 1 h. The reaction mixture was diluted with water (50 mL) and extracted with EtOAc (3×75 mL). The organic extracts were dried over magnesium sulfate and concentrated in vacuo. The crude material was purified by column chromatography (0-100% EtOAc in heptane), to afford the title compound (6.60 g) as a colourless gum. $[M+H]^+$ m/z=421.1/423.1

Intermediate 120

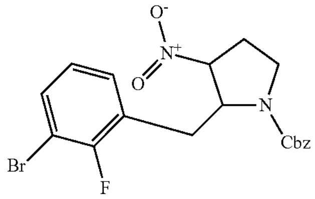 [SMILES: O=C(OCc1ccccc1)N1CCC([N+](=O)[O-])C1Cc1cccc(Br)c1F]

Benzyl 2-[(3-bromo-2-fluorophenyl)methyl]-3-nitropyrrolidine-1-carboxylate

A solution of trifluoroacetic anhydride (3.9 mL, 27.8 mmol) in acetonitrile (20 mL) was added to a stirred solution of hydrogen peroxide-urea (1:1) (3.66 g, 38.9 mmol) in acetonitrile (20 mL) at 0° C. and the mixture was stirred at 0° C. for 2 h. The resulting solution was added dropwise to a mixture of Intermediate 119 (71%, 6.60 g, 11.1 mmol) and sodium hydrogen carbonate (4.67 g, 55.6 mmol) in acetonitrile (20 mL) at 80° C. for 1 h. The reaction mixture was cooled to room temperature, quenched with saturated aqueous $Na_2SO_3$ (10 mL) and stirred for 10 min then extracted with EtOAc (2×25 mL). The combined organic extracts were dried over $MgSO_4$, filtered, and concentrated in vacuo to afford the crude material. The crude material was purified by silica gel column chromatography (0-100% EtOAc in heptane), to afford the title compound (5.20 g) as a pale-yellow oil. $[M+H]^+$ m/z 437.2/440.2

Intermediate 121

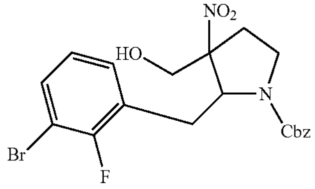

Benzyl-rel-(2S,3S)-2-[(3-bromo-2-fluorophenyl)methyl]-3-(hydroxymethyl)-3-nitropyrrolidine-1-carboxylate Formaldehyde (in water) (37%, 6.2 mL, 83.8 mmol) was added to Intermediate 120 (78%, 5.20 g, 9.28 mmol) and triethylamine (1.6 mL, 11.2 mmol) in THF (47 mL) at RT. The solution was heated to 70° C. for 18 h. After cooling the reaction mixture was diluted with water (20 mL) and extracted with EtOAc (3×50 mL). The combined organic extracts were washed with brine (40 mL), dried over $MgSO_4$, filtered, and concentrated in vacuo to afford the crude material. The crude material was purified by silica gel column chromatography (EtOAc in heptane), to afford the title compound (4.67 g) as a yellow oil. $[M+H]^+$ m/z 467.1 & 469.1

Intermediate 122

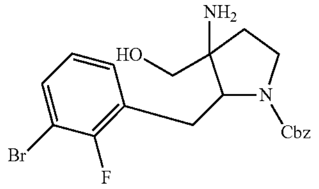 [SMILES: O=C(OCc1ccccc1)N1CCC(CO)([N+](=O)[O-])C1Cc1cccc(Br)c1F]

Benzyl rel-(2S,3S)-3-amino-2-[(3-bromo-2-fluorophenyl)methyl]-3-(hydroxymethyl)pyrrolidine-1-carboxylate A suspension of benzyl Intermediate 121 (78%, 4.67 g, 7.80 mmol) and zinc (5.10 g, 78.0 mmol) in acetic acid (36 mL) and ethanol (269 mL) was stirred for 2 h at room temperature. The reaction mixture was filtered through a pad of celite and washed with methanol. The filtrate was neutralised with $NaHCO_3$, extracted with DCM (3×75 mL), organic layer was dried ($MgSO_4$) and concentrated under vacuum to the title compound (4.30 g) as a colourless oil. $[M+H]^+$ m/z 437.2 & 439.2

Intermediate 123

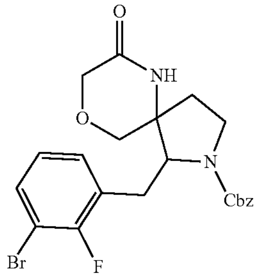 [SMILES: O=C1COCC2(CCN(C(=O)OCc3ccccc3)C2Cc2cccc(Br)c2F)N1]

Benzyl rel-(1S,5S)-1-[(3-bromo-2-fluorophenyl)methyl]-7-oxo-9-oxa-2,6-diazaspiro[4.5]decane-2-carboxylate To a solution of Intermediate 122 (0.87 g, 1.99 mmol) in THF (8.5 mL) at 0° C. was added dipotassium carbonate (825 mg, 5.97 mmol) then water (8.5 mL). To this mixture chloroacetyl chloride (0.22 mL, 2.78 mmol) was added dropwise at 0° C. The reaction was stirred for 1 h at 0° C. The mixture was quenched with water and extracted with DCM (3×25 mL). The combined organic extracts were washed with brine (20 mL), dried over $MgSO_4$, filtered, and concentrated to give an oily residue. The intermediate was dissolved in DCM (18 mL) and IPA (28 mL), cooled to 0° C. Potassium 2-methylpropan-2-olate (893 mg, 7.96 mmol) was added and the reaction was stirred at 0° C. for 1 h. The reaction was quenched by addition of water (20 mL). The mixture was poured onto aqueous saturated $NaHCO_3$ (30 ml). After extraction with DCM (3×25 mL), the combined organic extracts were washed with brine (20 mL), dried over $MgSO_4$, filtered, and concentrated to give a pale-yellow oil. The crude material was purified by silica gel column chromatography (0-100% EtOAc in heptane), to afford the title compound (430 mg) as a white solid. $[M+H]^+$ m/z 475.2 & 477.2

Intermediate 124

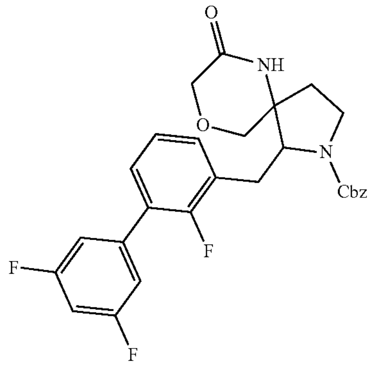 [SMILES: O=C1COCC2(CCN(C(=O)OCc3ccccc3)C2Cc2cccc(-c3cc(F)cc(F)c3)c2F)N1]

Benzyl-rel-(1S,5S)-7-oxo-1-({2,3',5'-trifluoro-[1,1'-biphenyl]-3-yl}methyl)-9-oxa-2,6-diazaspiro[4.5]decane-2-carboxylate A mixture of Intermediate 123 (250 mg, 0.524 mmol), 2-(3,5-difluorophenyl)-4,4,5,5-tetramethyl-1,3,2-dioxaborolane (251 mg, 1.05 mmol), aqueous 1M tripotassium; phosphate (1.6 mL, 1.57 mmol) and THF (5.1 mL) was degassed for 15 mins (N2 purge). XPhos Pd G3 (45 mg, 0.0531 mmol) was added, and the reaction mixture was stirred under nitrogen atmosphere at 70° C. for 1 h. The reaction mixture was poured into saturated aqueous $NaHCO_3$ (10 mL), and the mixture was extracted with ethyl acetate (3×25 mL). The organic layer was passed through a pass separator and concentrated under reduced pressure. The crude was purified by silica gel column chromatography (0-100% EtOAc in heptane), to afford the title compound (180 mg) as a yellow oil. $[M+H]^+$ m/z 511.3

Intermediate 125

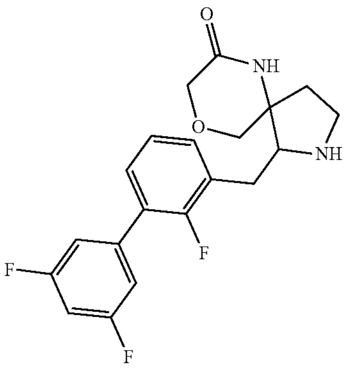 [SMILES: O=C1COCC2(CCNC2Cc2cccc(-c3cc(F)cc(F)c3)c2F)N1]

rel-(1S,5S)-1-({2,3',5'-trifluoro-[1,1'-biphenyl]-3-yl}methyl)-9-oxa-2,6-diazaspiro[4.5]decan-7-one Intermediate 124 (240 mg, 0.465 mmol) was dissolved in ethanol (22 mL) and the atmosphere was evacuated and backfilled with nitrogen 3 times. palladium on carbon (10%) (5.0%, 99 mg, 0.0465 mmol) was added and the atmosphere was evacuated and backfilled with hydrogen 3 times. The reaction was stirred for 2 hours and then filtered through celite, washing with EtOAc, and concentrated in vacuo to afford the title compound (163 mg) as an orange solid. $[M+H]^+$ m/z 377.2 rel-(1S,5S)-2-[(1s,3s)-3-fluorocyclobutanecarbonyl]-1-({2,3',5'-trifluoro-[1,1'-biphenyl]-3-yl}methyl)-9-oxa-2,6-diazaspiro[4.5]decan-7-one (71)

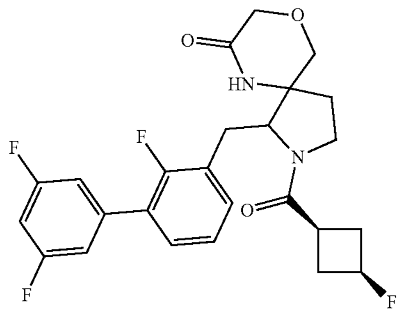 [SMILES: O=C1COCC2(CCN(C(=O)[C@H]3C[C@@H](F)C3)C2Cc2cccc(-c3cc(F)cc(F)c3)c2F)N1]

A solution of Intermediate 125 (48 mg, 0.128 mmol) in anhydrous DMF (0.23 mL) was added to a stirred solution of 3-fluorocyclobutanecarboxylic acid (20 mg, 0.172 mmol), HATU (73 mg, 0.193 mmol) and DIPEA (66 μL, 0.379 mmol) in anhydrous DMF (0.9162 mL) at room temperature and mixture was stirred for 2 h. The reaction mixture was filtered. The crude material was purified by prep HPLC Standard Method Column: XBridge™ Prep. C18 10 um OBD™, 30×100 mm, Mobile Phase: 30-95% acetonitrile (0.2% ammonium hydroxide) in water (0.2% ammonium hydroxide) over 10 minutes, Flow Rate: 40 mL/min, UV: 215 and 254 nm, to afford the title compounds (9.5 mg) as a white solid.

$^1H$ NMR (400 MHz, $CDCl_3$) δ 7.49-7.29 (m, 1H), 7.25-7.15 (m, 2H), 7.13-6.99 (m, 2H), 6.89-6.77 (m, 1H), 6.57 (s, 1H), 5.07-4.25 (m, 2H), 4.24-4.07 (m, 1H), 4.06-3.87 (m, 1H), 3.80-3.28 (m, 4H), 3.15-2.66 (m, 2H), 2.63-2.15 (m, 4H), 2.14-1.98 (m, 2H), 1.97-1.70 (m, 1H).

LCMS (Method B): $[M+H]^+$ m/z 477.2, RT 3.07 minutes.

Example 72: (1S,5S)-2-[(CIS)-3-fluorocyclobutanecarbonyl]-1-({2,3',5'-trifluoro-[1,1'-biphenyl]-3-yl}methyl)-9-oxa-2,6-diazaspiro[4.5]decan-7-one (Example 72) & Example 73: (1R,5R)-2-[(CIS)-3-fluorocyclobutanecarbonyl]-1-({2,3',5'-trifluoro-[1,1'-biphenyl]-3-yl}methyl)-9-oxa-2,6-diazaspiro[4.5]decan-7-one (Example 73)

Example 72 & 73

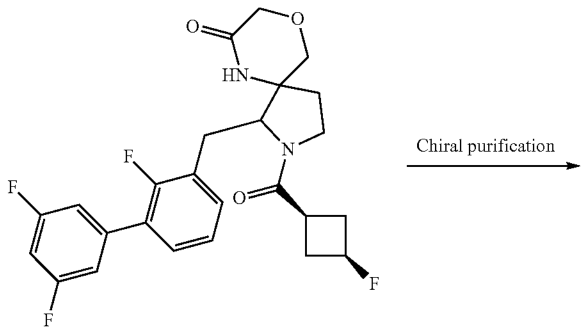

71

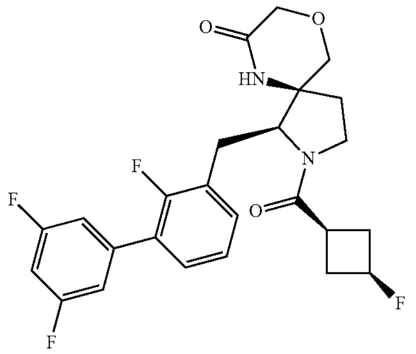

+

72

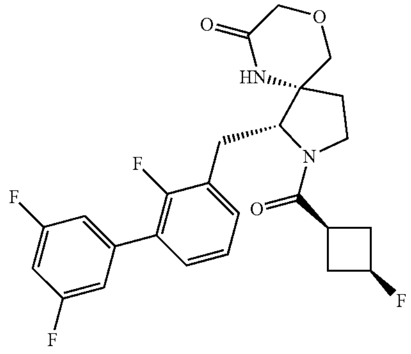

73

Example 71 (6 mg) was subjected to chiral preparative purification using Waters 600 eluting with 75/25% v/v n-Hexane/(ethanol+0.1% isopropylamine), Chiralpak IC (25×2.0 cm), 5 μm, flow rate 17 mL/minutes, to afford the title compounds (Peak 1, 2.2 mg, 100% ee; and Peak 2, 2.7 mg, 99.1% ee). The absolute stereochemistry of compound 72 and 73 was not conclusively determined but assigned as shown below.

Example 72: Peak 1 (was assigned 1S, 5S at pyrrolidine); $^1H$ NMR (500 MHz, $CDCl_3$) δ 7.45-7.16 (m, 3H), 7.23-7.10

(m, 2H), 7.04-6.91 (m, 1H), 4.96-4.49 (m, 1H), 4.81-4.32 (m, 1H), 4.24-3.86 (m, 2H), 3.77-3.40 (m, 4H), 3.09-2.82 (m, 2H), 2.75-1.82 (m, 1H), 2.56-1.50 (m, 6H).

LCMS (Method C): $[M+H]^+$ m/z 477.3, RT 0.98 minutes.

Chiral analysis (Chiralpak IC, 25×0.46 cm, 5 μm, 75:25 n-Hexane/(ethanol+0.1% isopropylamine)): RT 10.0 minutes.

Example 73: Peak 2 (was assigned 1R,5R at pyrrolidine): $^1$H NMR (500 MHz, $CDCl_3$) δ 7.45-7.16 (m, 3H), 7.23-7.10 (m, 2H), 7.04-6.91 (m, 1H), 4.96-4.49 (m, 1H), 4.81-4.32 (m, 1H), 4.24-3.86 (m, 2H), 3.77-3.40 (m, 4H), 3.09-2.82 (m, 2H), 2.75-1.82 (m, 1H), 2.56-1.50 (m, 6H).

LCMS (Method C): $[M+H]^+$ m/z 477.3, RT 0.98 minutes.

Chiral analysis (Chiralpak IC, 25×0.46 cm, 5 μm, 75:25 n-Hexane/(ethanol+0.1% isopropylamine)): RT 12.1 minutes.

Example 74: 2,2-difluoroethyl (1S,5S)-8-fluoro-7-oxo-1-({2,3',5'-trifluoro-[1,1'-biphenyl]-3-yl}methyl)-9-oxa-2,6-diazaspiro[4.5]decane-2-carboxylate & Example 75: 2,2-difluoroethyl (1R,5R)-8-fluoro-7-oxo-1-({2,3',5'-trifluoro-[1,1'-biphenyl]-3-yl}methyl)-9-oxa-2,6-diazaspiro[4.5]decane-2-carboxylate

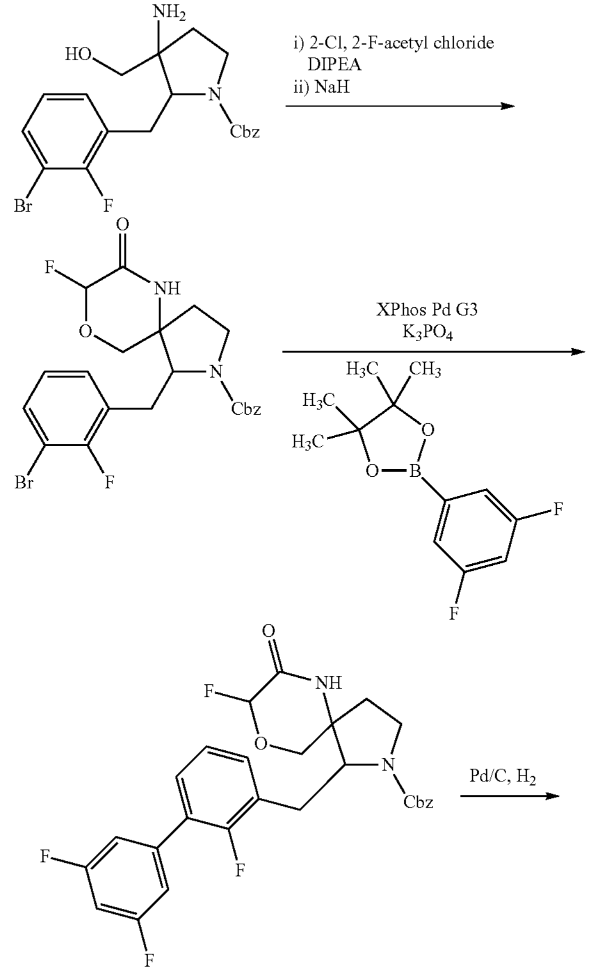

-continued

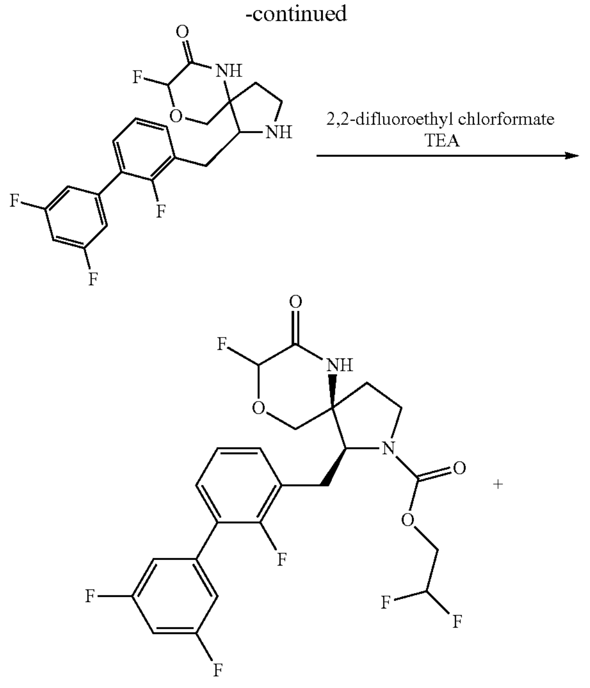

74

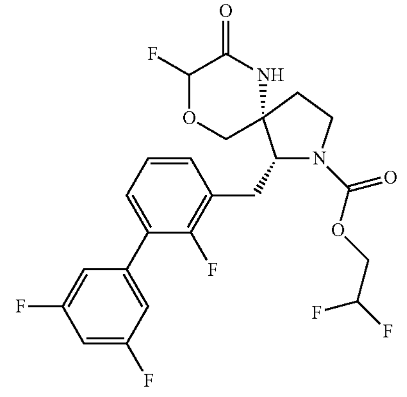

75

Intermediate 126

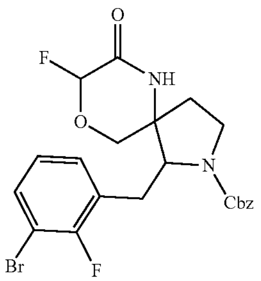 [SMILES: O=C1NC2(CCN(C(=O)OCc3ccccc3)C2Cc2cccc(Br)c2F)COC1F]

Benzyl-rel-(1S,5S)-1-[(3-bromo-2-fluorophenyl)methyl]-8-fluoro-7-oxo-9-oxa-2,6-diazaspiro[4.5]decane-2-carboxylate A solution of 2-chloro-2-fluoro-acetyl chloride (125 mg, 0.956 mmol) in DCM (5 mL) was added to a stirred solution of Intermediate 122 (200 mg, 0.478 mmol) and N-ethyl-N-(propan-2-yl)propan-2-amine (250 μL, 1.44 mmol) in DCM (5 mL) at 0° C. and the mixture was stirred for 0.5 h. The reaction mixture was quenched with water (10 mL) and extracted with DCM (20 mL×3). The combined organic layers were passed through a phase separator and concentrated in vacuo to afford the crude material. The residue was dissolved in anhydrous THF (21 mL) and slowly added to sodium hydride (60%, 0.16 g, 4.00 mmol) in anhydrous THF (11.5 mL) at 0° C., the mixture was stirred for 30 min at this temperature and then heated at 50° C. for 5 h, and then at room temperature for 16 hours. The crude was purified by silica gel chromatography (0-100% EtOAc in heptane), to afford the title compound (150 mg) as a colourless oil. $[M+H]^+$ m/z 495.2 & 497.2

Intermediate 127

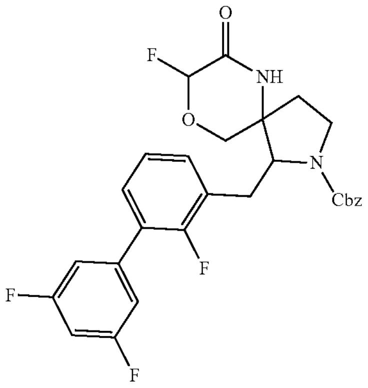 [SMILES: O=C1NC2(CCN(C(=O)OCc3ccccc3)C2Cc2cccc(-c3cc(F)cc(F)c3)c2F)COC1F]

Benzyl-rel-(1S,5S)-8-fluoro-7-oxo-1-({2,3',5'-trifluoro-[1,1'-biphenyl]-3-yl}methyl)-9-oxa-2,6-diazaspiro[4.5]decane-2-carboxylate A mixture of Intermediate 126 (46%, 150 mg, 0.139 mmol), 2-(3,5-difluorophenyl)-4,4,5,5-tetramethyl-1,3,2-dioxaborolane (66 mg, 0.275 mmol), 1 M tripotassium;phosphate (1M in $H_2O$) (0.42 mL, 0.420 mmol) and THF (1.35 mL) was degassed for 15 minutes ($N_2$ purge). XPhos Pd G3 (5.9 mg, 6.96 μmol) was added, and the reaction mixture was stirred under nitrogen atmosphere at 50° C. for 1 h. The reaction mixture was poured into saturated aqueous $NaHCO_3$ (5 mL), and the mixture was extracted with ethyl acetate (3x5 mL). The organic layer was passed through a pass separator and concentrated under reduced pressure. The crude was purified by silica gel chromatography (0-100% EtOAc in heptane), to afford the title compound (148 mg) as a yellow oil. $[M+H]^+$ m/z 529.4

Intermediate 128

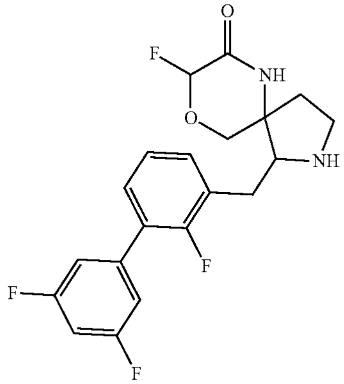 [SMILES: O=C1NC2(CCNC2Cc2cccc(-c3cc(F)cc(F)c3)c2F)COC1F]

rel-(1S,5S)-8-fluoro-1-({2,3',5'-trifluoro-[1,1'-biphenyl]-3-yl}methyl)-9-oxa-2,6-diazaspiro[4.5]decan-7-one Intermediate 127 (49%, 148 mg, 0.137 mmol) was dissolved in ethanol (6.5 mL) and the atmosphere was evacuated and backfilled with nitrogen 3 times. Palladium on carbon (10%) (5.0%, 29 mg, 0.0137 mmol) was added and the atmosphere was evacuated and backfilled with hydrogen 3 times. The reaction was stirred for 3 hours and then filtered through celite, washing with EtOAc, and concentrated in vacuo to afford the title compound (80 mg) as a yellow oil. $[M+H]^+$ m/z 395.2

2,2-difluoroethyl (1S,5S)-8-fluoro-7-oxo-1-({2,3',5'-trifluoro-[1,1'-biphenyl]-3-yl}methyl)-9-oxa-2,6-diazaspiro[4.5]decane-2-carboxylate (74) & 2,2-difluoroethyl (1R,5R)-8-fluoro-7-oxo-1-({2,3',5'-trifluoro-[1,1'-biphenyl]-3-yl}methyl)-9-oxa-2,6-diazaspiro[4.5]decane-2-carboxylate (75)

74

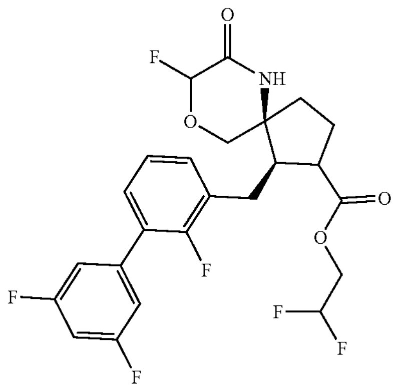

-continued

75

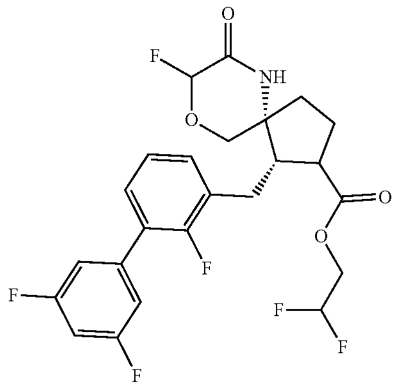

A dropwise solution of 2,2-difluoroethyl chloroformate (16 μL, 0.155 mmol) in anhydrous DCM (0.45 mL) was added to a stirred solution of Intermediate 128 (50%, 80 mg, 0.101 mmol) and triethylamine (34 μL, 0.244 mmol) in anhydrous DCM (0.45 mL) at 0° C. and mixture was stirred for 1 h at 0° C. The reaction mixture was, quenched with methanol (1 mL) and concentrated in vacuo to afford the crude material. The crude material was purified by reverse phase column chromatography (10-100% acetonitrile in water (0.1% $NH_3$)), to afford the mixture of products (16 mg) as a white solid. $[M-H]^-$ m/z 501.3. The latter was subjected to chiral preparative purification using Waters 600 eluting with 75/25% v/v n-Hexane/ethanol, Chiralcel OD-H (25×2.0 cm), 5 μm, flow rate 17 mL/minutes, to afford the title compounds (Peak 1+2, 3.7 mg, 28.2% ee+71.8% ee, respectively; and Peak 3+4, 3.5 mg, 28.7% ee+70.6% ee, respectively). The absolute stereochemistry of compounds 74 and 75 in each peak was not conclusively determined but assigned as shown below.

Example 74: Peak 1+2 (was assigned 1S, 5S at pyrrolidine, racemic at morpholinone); $^1H$ NMR (400 MHz, $CDCl_3$) δ 7.38-7.28 (m, 1H), 7.20 (q, J=7.6 Hz, 2H), 7.07 (d, J=8.6 Hz, 2H), 6.83 (d, J=9.7 Hz, 1H), 6.23 (d, J=34.9 Hz, 1H), 5.95-5.06 (m, 2H), 4.55 (d, J=28.3 Hz, 1H), 4.37-4.03 (m, 2H), 3.97 (s, 1H), 3.70 (t, J=13.7 Hz, 1H), 3.49 (d, J=45.0 Hz, 2H), 3.13-2.77 (m, 2H), 2.49-1.94 (m, 2H).

LCMS (Method C): $[M+H]^+$ m/z 503.2, RT 1.09-1.10 minutes.

Chiral analysis (Chiralcel OD-H, 25×0.46 cm, 5 μm, 75:25 n-Hexane:ethanol): RT Peak 1 6.9 minutes, Peak 2 7.7 minutes.

Example 75: Peak 3+4 (was assigned 1R,5R at pyrrolidine, racemic at morpholinone): $^1H$ NMR (400 MHz, $CDCl_3$) δ 7.38-7.28 (m, 1H), 7.19 (q, J=7.5 Hz, 2H), 7.14-7.03 (m, 2H), 6.83 (d, J=9.5 Hz, 1H), 6.34 (t, J=36.0 Hz, 1H), 6.06-5.08 (m, 2H), 4.55 (d, J=29.1 Hz, 1H), 4.35-4.03 (m, 2H), 3.98 (d, J=12.6 Hz, 1H), 3.69 (t, J=13.8 Hz, 1H), 3.62-3.33 (m, 2H), 3.14-2.78 (m, 2H), 2.48-1.96 (m, 2H).

LCMS (Method C): $[M+H]^+$ m/z 503.2, RT 1.09-1.10 minutes.

Chiral analysis (Chiralcel OD-H, 25×0.46 cm, 5 μm, 75:25 n-Hexane:ethanol): RT Peak 3 10.7 minutes, Peak 4 12.1 minutes.

Example 76: rel-(6S,7R)—N-ethyl-7-({[1-(5-fluoropyrimidin-2-yl)piperidin-4-yl]oxy}methyl)-2-oxo-4-oxa-1,8-diazaspiro[5.5]undecane-8-carboxamide

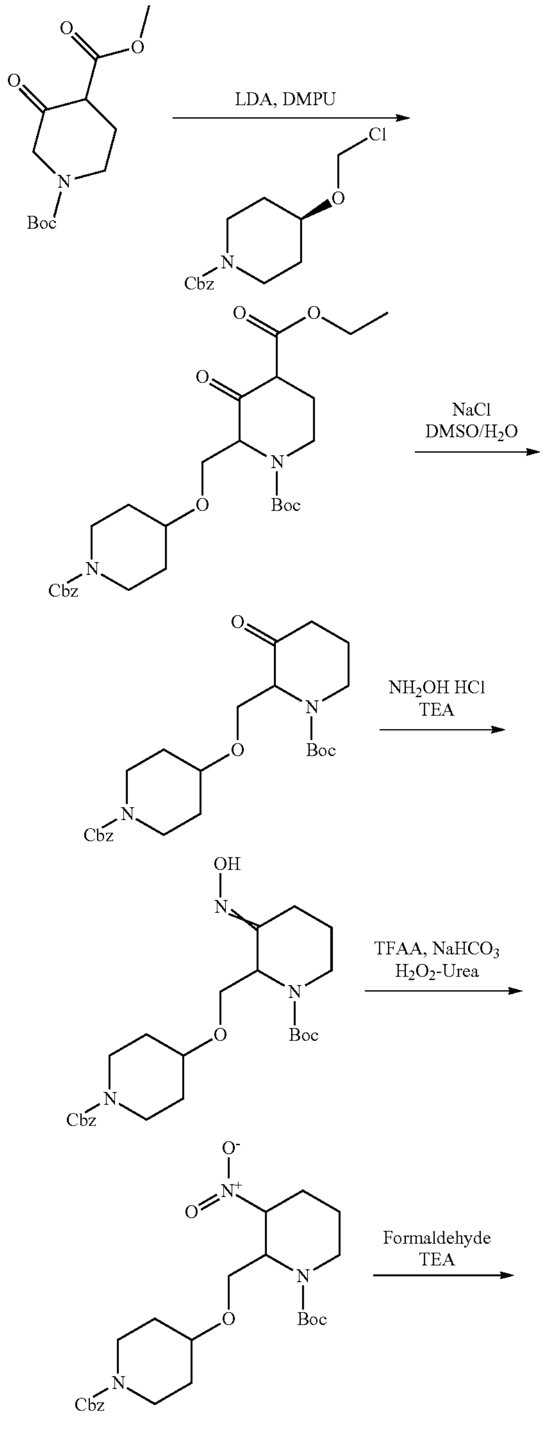

-continued

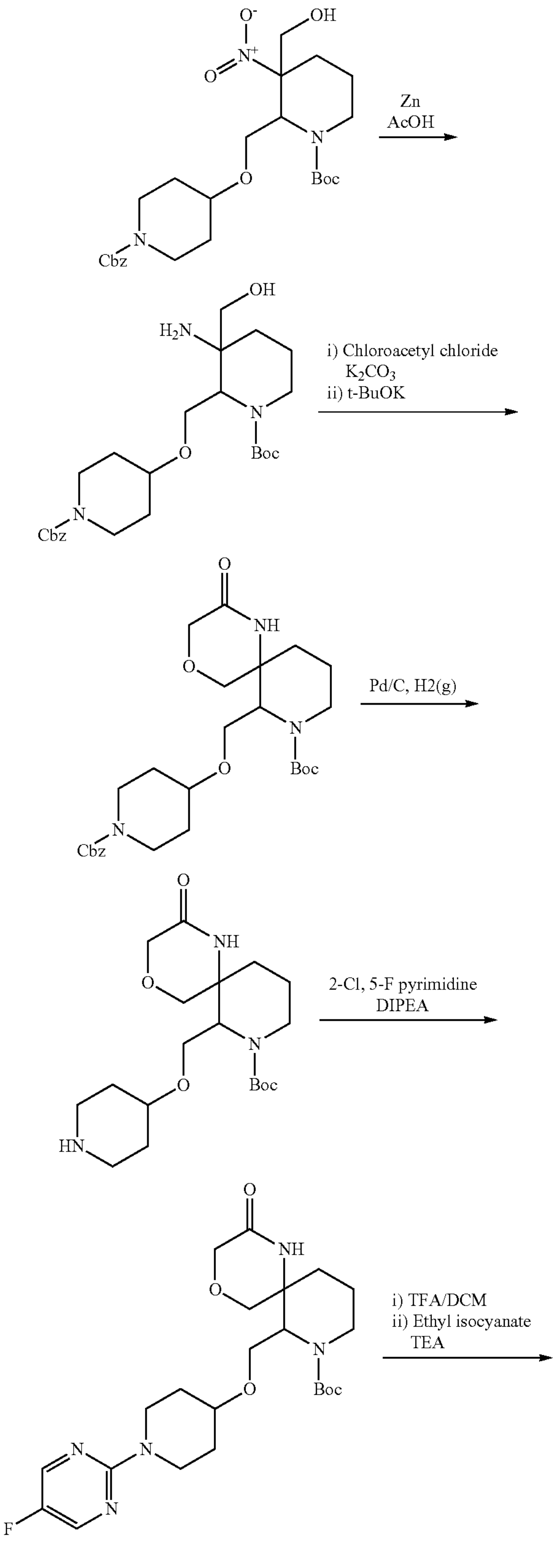

-continued

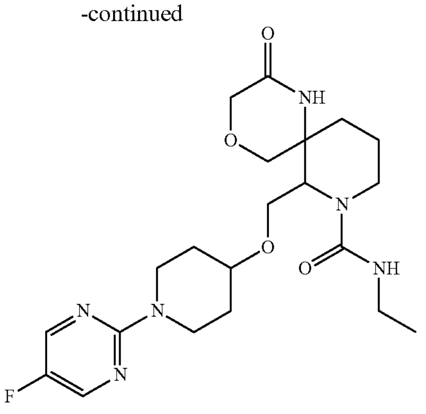

76

Intermediate 129

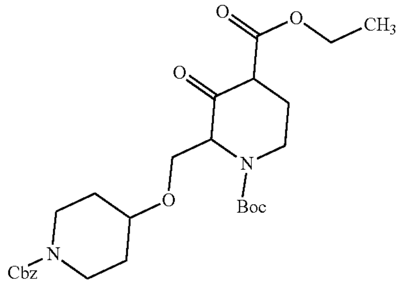 [SMILES: CCOC(=O)C1CCN(C(=O)OC(C)(C)C)C(COC2CCN(C(=O)OCc3ccccc3)CC2)C1=O]

1-tert-butyl-4-ethyl-2-[({1-[(benzyloxy)carbonyl]piperidin-4-yl}oxy)methyl]-3-oxopiperidine-1,4-dicarboxylate A 500 mL RBF equipped with stir bar, rubber septum, and attached via needle line to vacuum/nitrogen ramp was charged with a solution of diisopropylamine (23.74 mL, 169.4 mmol) in anhydrous THF (70 mL) under nitrogen. The mixture was cooled at −5° C. and a 2.5 M solution of nBuLi in hexane (67.76 mL, 169.4 mmol) was added dropwise while keeping the internal temperature below 0° C. The mixture was stirred over 20 minutes at this temperature. In a separate three-necked 1 L RBF equipped with stir bar, rubber septum, vacuum/nitrogen stopcock and thermometer were charged with a solution of ethyl 1-N-boc-3-oxo-piperidine-4-carboxylate (20.89 g, 77 mmol) and 1,3-dimethyl-1,3-diazinan-2-one (37.1 mL, 308 mmol) in anhydrous THF (160 mL). The mixture was cooled below −65° C. with an acetone/dry ice bath and the previously prepared solution of LDA was added dropwise to the substrate mixture over 20 minutes, while keeping the internal temperature below −65° C. After the addition the mixture was stirred at the same temperature over 30 minutes. In a separate 25 mL RBB equipped with stir bar, rubber septum, and attached via needle line to vacuum/nitrogen ramp was charged with a solution of benzyl 4-(chloromethoxy)piperidine-1-carboxylate (24.03 g, 84.7 mmol) in anhydrous THE (70 mL). This solution was pre-cooled at 0° C. before being added dropwise to the mixture of lithiated piperidone substrate while keeping the internal temperature below −65° C. The mixture was stirred at this temperature over 1 h. The mixture was allowed to slowly warm up to 0° C., then the reaction was quenched with sat. aq. $NH_4Cl$ (250 mL) and water (150 mL). The mixture was extracted with EtOAc (200 mL), then the organic phase was separated and washed with brine (200 mL), dried over $Na_2SO_4$, filtered, and concentrated in vacuo give a yellow oil. The crude material was purified by silica gel column chromatography (0-26% EtOAc in cHex), to afford the title compound (32 g) as a colourless oil. $[M+H]^+$ m/z 419.4

Intermediate 130

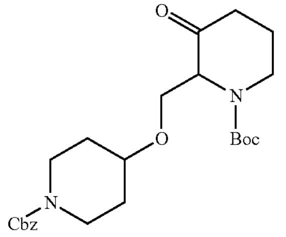 [SMILES: CC(C)(C)OC(=O)N1CCCC(=O)C1COC1CCN(C(=O)OCc2ccccc2)CC1]

tert-butyl 2-[({1-[(benzyloxy)carbonyl]piperidin-4-yl}oxy)methyl]-3-oxopiperidine-1-carboxylate A suspension of Intermediate 129 (3.85 g, 7.42 mmol) and sodium chloride (1.25 g, 21.3 mmol) in DMSO (30 mL) and water (3.5 mL) was heated to 120° C. (ext. temp) for 6 h. The reaction mixture was cooled to room temperature, diluted with water (100 mL) and extracted with diethyl ether (3×50 mL). The combined organic layers were washed with water (400 mL), brine (100 mL), dried over $MgSO_4$, filtered, and concentrated in vacuo to afford the crude material. The crude material was purified by column chromatography (0-80% EtOAc in heptane), to afford the title compound (1.75 g) as a yellow oil. $[M+H]^+$ m/z 447.4

Intermediate 131

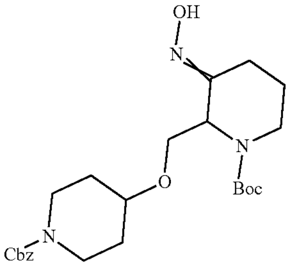 [SMILES: CC(C)(C)OC(=O)N1CCCC(=NO)C1COC1CCN(C(=O)OCc2ccccc2)CC1]

tert-butyl 2-[({1-[(benzyloxy)carbonyl]piperidin-4-yl}oxy)methyl]-3-(hydroxyimino)piperidine-1-carboxylate A dropwise solution of triethylamine (2.1 mL, 14.8 mmol) was added to a stirred solution of hydroxylamine hydrochloride (1:1) (1.03 g, 14.8 mmol) and Intermediate 130 (2.20 g, 4.93 mmol) in ethanol (15 mL) at room temperature and the mixture was heated at 80° C. for 1 h. The reaction mixture was cooled to room temperature, concentrated in vacuo, diluted with water (25 mL) and extracted with ethyl acetate (3×20 mL). The combined organic layers were washed with brine (30 mL), dried over $MgSO_4$, filtered, and concentrated in vacuo to afford the crude material. The crude material was purified by silica gel column chromatography (0-100% EtOAc in heptane), to afford the title compound (1.88 g) as a yellow oil. $[M+H]^+$ m/z 462.5

Intermediate 132

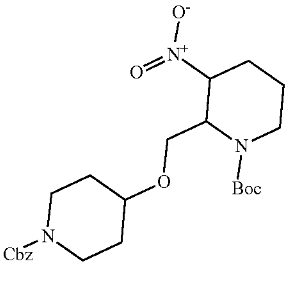 [SMILES: CC(C)(C)OC(=O)N1CCCC([N+](=O)[O-])C1COC1CCN(C(=O)OCc2ccccc2)CC1]

tert-butyl 2-[({1-[(benzyloxy)carbonyl]piperidin-4-yl}oxy)methyl]-3-nitropiperidine-1-carboxylate A solution of trifluoroacetic anhydride (1.4 mL, 9.75 mmol) was added to a stirred solution of hydrogen peroxide-urea (1:1) (1.28 g, 13.6 mmol) in acetonitrile (10 mL) at 0° C. and the mixture was stirred at 0° C. for 2 h. The resulting solution was added dropwise to a mixture of Intermediate 131 (1.80 g, 3.90 mmol) and sodium hydrogen carbonate (1.64 g, 19.5 mmol) in acetonitrile (10 mL) at 80° C. and the mixture was stirred at 80° C. for 1 h. The reaction mixture was cooled to room temperature, quenched with saturated aqueous $Na_2SO_3$ (10 mL) and stirred for 10 min then extracted with EtOAc (2×25 mL). The combined organic layers were washed with brine (25 mL), dried over $MgSO_4$, filtered, and concentrated in vacuo to afford the crude material. The crude material was purified by silica gel column chromatography (0-100% EtOAc in heptane), to afford the title compound (1.4 g) as a colourless oil. $[M+H]^+$ m/z 478.3

Intermediate 133

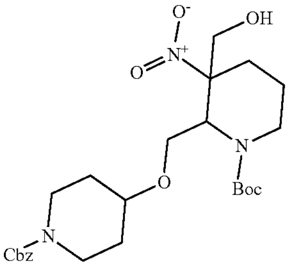 [SMILES: CC(C)(C)OC(=O)N1CCCC(CO)([N+](=O)[O-])C1COC1CCN(C(=O)OCc2ccccc2)CC1]

tert-butyl rel-(2R,3S)-2-[({1-[(benzyloxy)carbonyl]piperidin-4-yl}oxy)methyl]-3-(hydroxymethyl)-3-nitropiperidine-1-carboxylate A solution of formaldehyde (in water) (37%, 1.1 mL, 14.7 mmol) was added to a stirred solution of Intermediate 132 (1.40 g, 2.93 mmol) and triethylamine (0.41 mL, 2.93 mmol) in THF (15 mL) at room temperature and the mixture was heated at 70° C. for 16 h. The reaction mixture was cooled to room temperature, quenched with water (40 mL) and extracted with ethyl acetate (3×50 mL). The combined organic layers were washed with brine (50 mL), dried over $MgSO_4$, filtered, and concentrated in vacuo to afford the crude material. The crude material was purified by silica gel column chromatography (0-60% EtOAc in heptane), to afford the title compound (1.03 g) as a colourless oil. $[M+Na]^+$ m/z 530.3

Intermediate 134

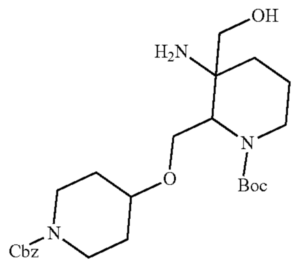 [SMILES: CC(C)(C)OC(=O)N1CCCC(N)(CO)C1COC1CCN(C(=O)OCc2ccccc2)CC1]

tert-butyl-rel-(2R,3S)-3-amino-2-[({1-[(benzyloxy) carbonyl]piperidin-4-yl}oxy)methyl]-3-(hydroxymethyl) piperidine-1-carboxylate Zinc (1.29 g, 19.7 mmol) was added to a stirred solution of Intermediate 133 (1.00 g, 1.97 mmol) in acetic acid (2.5 mL) and ethanol (10 mL) at room temperature and the mixture was stirred for 16 h. The reaction mixture was quenched with a solution of saturated aqueous $NaHCO_3$ (10 mL), filtered through celite (washing with EtOAc) and extracted with ethyl acetate (3×10 mL). The combined organic layers were dried over $MgSO_4$, filtered, and concentrated in vacuo to afford the crude material. Crude material (700 mg) was taken on without further purification as a colourless gum. $[M+H]^+$ m/z 478.4

Intermediate 135

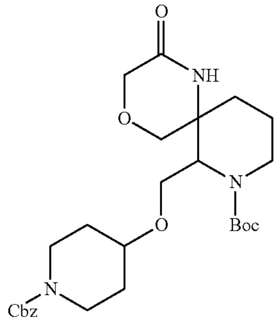 [SMILES: CC(C)(C)OC(=O)N1CCCC2(COCC(=O)N2)C1COC1CCN(C(=O)OCc2ccccc2)CC1]

tert-butyl-rel-(6S,7R)-7-[({1-[(benzyloxy)carbonyl] piperidin-4-yl}oxy)methyl]-2-oxo-4-oxa-1,8-diazaspiro[5.5]undecane-8-carboxylate A dropwise solution of chloroacetyl chloride (163 µL, 2.05 mmol) was added to a stirred solution of Intermediate 134 (700 mg, 1.47 mmol) and dipotassium carbonate (608 mg, 4.40 mmol) in THF (6 mL) and water (6 mL) at 0° C. and the mixture was stirred for 1 h. The reaction mixture was diluted with water (10 mL) and extracted with DCM (3×10 mL). The combined organic layers were dried over $MgSO_4$, filtered, and concentrated in vacuo to afford the crude intermediate. The crude intermediate was dissolved in DCM (12 mL) and IPA (20 mL), cooled to 0° C. and potassium 2-methylpropan-2-olate (658 mg, 5.86 mmol) was added and the reaction was stirred at 0° C. for 16 h. The reaction was quenched by addition of water (20 mL). The mixture was poured onto aqueous saturated $NaHCO_3$ (30 mL). After extraction with DCM (3×15 mL), the combined organic extracts were washed with brine (20 mL), dried over $MgSO_4$, filtered to afford the crude material. The crude material was purified by reverse phase column chromatography (10-100% acetonitrile in water (0.1% $NH_3$)), to afford the title compound (350 mg) as a colourless oil. $[M+Na]^+$ m/z 540.3

Intermediate 136

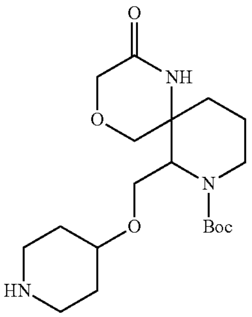 [SMILES: CC(C)(C)OC(=O)N1CCCC2(COCC(=O)N2)C1COC1CCNCC1]

tert-butyl-rel-(6S,7R)-2-oxo-7-[(piperidin-4-yloxy) methyl]-4-oxa-1,8-diazaspiro[5.5]undecane-8-carboxylate Intermediate 135 (350 mg, 0.676 mmol) was dissolved in ethanol (25 mL) and the atmosphere was evacuated and backfilled with nitrogen 3 times. Palladium on carbon (10%) (10%, 72 mg, 0.0676 mmol) was added and the atmosphere was evacuated and backfilled with hydrogen 3 times. The reaction was stirred for 2 hours and then filtered through celite, washing with EtOAc and concentrated in vacuo to furnish the title compound (250 mg) as a beige solid. $[M+H]^+$ m/z 384.4

Intermediate 137

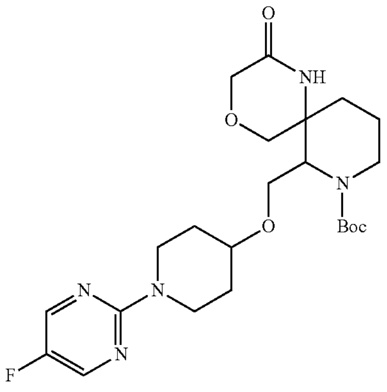 [SMILES: CC(C)(C)OC(=O)N1CCCC2(COCC(=O)N2)C1COC1CCN(c2ncc(F)cn2)CC1]

tert-butyl-rel-(6S,7R)-7-({[1-(5-fluoropyrimidin-2-yl)piperidin-4-yl]oxy}methyl)-2-oxo-4-oxa-1,8-diazaspiro[5.5]undecane-8-carboxylate 2-chloro-5-fluoropyrimidine (72 µL, 0.782 mmol) was added to a stirred solution of N-ethyl-N-(propan-2-yl)propan-2-amine (1.1 mL, 6.52 mmol) and Intermediate 136 (250 mg, 0.652 mmol) in anhydrous acetonitrile (10 mL) at room temperature and mixture was heated at 80° C. for 16 h. The reaction mixture was cooled to room temperature, quenched with water (10 mL) and extracted with ethyl acetate (3×20 mL). The combined organic layers were washed with brine (25 mL), dried over $MgSO_4$, filtered, and concentrated in vacuo to afford the crude material. The crude material was purified by reverse phase column chromatography (10-100% acetonitrile in water (0.1% $NH_3$)), to afford the title compound (180 mg) as a white solid. $[M+H]^+$ m/z 480.4 rel-(6S,7R)—N-ethyl-7-({[1-(5-fluoropyrimidin-2-yl)piperidin-4-yl]oxy}methyl)-2-oxo-4-oxa-1,8-diazaspiro[5.5]undecane-8-carboxamide (76)

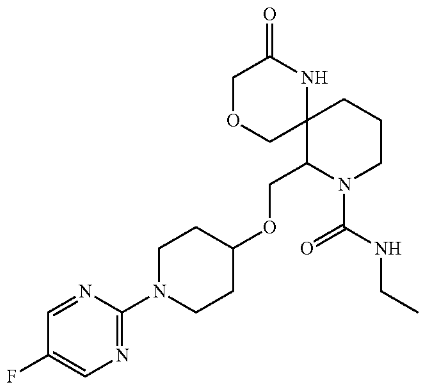 [SMILES: CCNC(=O)N1CCCC2(COCC(=O)N2)C1COC1CCN(c2ncc(F)cn2)CC1]

Intermediate 137 (40 mg, 0.0834 mmol) was dissolved in anhydrous DCM (0.3 mL) and TFA (0.3 mL) and stirred for 30 minutes. The reaction was quenched with saturated $NaHCO_3$ solution (5 mL) and extracted with DCM (3×5 mL). The combined organic layers were dried over $MgSO_4$, filtered, and concentrated in vacuo to afford the crude material. The crude materials were dissolved in anhydrous DCM (0.3 mL) and triethylamine (47 µL, 0.334 mmol) was added followed by isocyanatoethane (13 µL, 0.167 mmol) and the reaction was stirred for 30 minutes. The reaction mixture was diluted with water (5 mL) and DCM (5 mL) and separated. The aqueous layer was further extracted with DCM (2×5 mL). The combined organic layers were washed with brine (10 mL), dried over $MgSO_4$, filtered, and concentrated in vacuo to afford the crude material. The crude material was purified by basic preparative HPLC (Waters XBridge C18 column (30 mm×100 mm, 5 m; temperature: room temperature). Injection volume of 1500 L at a flow rate of 40 mL/min. 10% B (A=0.2% ammonium hydroxide in water; B=0.2% ammonium hydroxide in acetonitrile) for 2.0 min then a gradient of 10-95% B over 14.0 min and held for 2.0 min. A second gradient of 95-10% B was then applied over 0.2 min and held for 0.9 min. UV spectra were recorded at 215 nm using a Gilson detector), to afford the title compound (11 mg) as a solid.

$^1H$ NMR (400 MHz, DMSO) δ 8.42 (d, J=0.8 Hz, 2H), 7.96 (s, 1H), 6.14 (t, J=5.5 Hz, 1H), 4.47 (s, 1H), 4.02 (d, J=16.4 Hz, 1H), 3.98-3.86 (m, 4H), 3.78 (d, J=13.1 Hz, 1H), 3.74-3.63 (m, 2H), 3.60 (dt, J=7.6, 4.0 Hz, 1H), 3.52-3.40 (m, 2H), 3.24 (d, J=11.6 Hz, 1H), 3.06-2.95 (m, 2H), 2.71 (t, J=12.6 Hz, 1H), 1.78 (dd, J=13.6, 5.3 Hz, 3H), 1.53-1.29 (m, 5H), 0.95 (t, J=7.1 Hz, 3H).

LCMS (Method A): $[M+H]^+$ m/z 451.4, RT 2.31 minutes.

Example 77: 2,2-difluoroethyl-rel-(6S,7R)-7-({[1-(5-fluoropyrimidin-2-yl)piperidin-4-yl]oxy}methyl)-2-oxo-4-oxa-1,8-diazaspiro[5.5]undecane-8-carboxylate

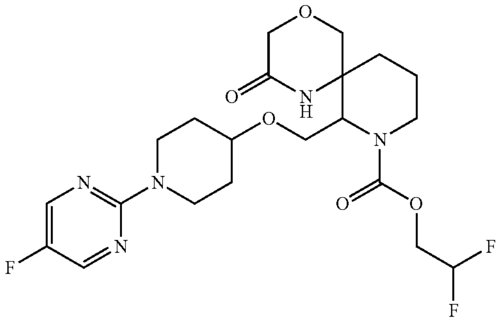 [SMILES: O=C1COCC2(CCCN(C(=O)OCC(F)F)C2COC2CCN(c3ncc(F)cn3)CC2)N1]

2,2-difluoroethyl-rel-(6S,7R)-7-({[1-(5-fluoropyrimidin-2-yl)piperidin-4-yl]oxy}methyl)-2-oxo-4-oxa-1,8-diazaspiro[5.5]undecane-8-carboxylate Intermediate 137 (40 mg, 0.0834 mmol) was stirred in a mixture of anhydrous DCM (0.3 mL) and TFA (0.3 mL) for 30 minutes at room temperature. The reaction mixture was quenched with $NaHCO_3$ solution (10 mL) and extracted with DCM (3×20 mL). The combined organic layers were dried over $MgSO_4$, filtered, and concentrated in vacuo to afford the crude material. A dropwise solution of 2,2-difluoroethyl chloroformate (13 µL, 0.125 mmol) was added to a stirred solution of crude material and triethylamine (28 µL, 0.200 mmol) in anhydrous DCM (0.6 mL) at 0° C. and the mixture was stirred for 30 minutes. The reaction mixture was concentrated in vacuo to afford the crude material. The crude material was purified by basic preparative HPLC (Waters XBridge C18 column (30 mm×100 mm, 5 µm; temperature: room temperature). Injection volume of 1500 µL at a flow rate of 40 mL/min. 10% B (A=0.2% ammonium hydroxide in water; B=0.2% ammonium hydroxide in acetonitrile) for 2.0 min then a gradient of 10-95% B over 14.0 min and held for 2.0 min. A second gradient of 95-10% B was then applied over 0.2 min and held for 0.9 min. UV spectra were recorded at 215 nm using a Gilson detector), to afford the title compound (18 mg) as a white solid $^1H$ NMR (400 MHz, DMSO) δ 8.42 (d, J=0.8 Hz, 2H), 8.07 (d, J=7.6 Hz, 1H), 6.44-5.94 (m, 1H), 4.69-4.46 (m, 1H), 4.37-4.20 (m, 2H), 4.05 (d, J=16.5 Hz, 1H), 3.99-3.88 (m, 4H), 3.87-3.80 (m, 1H), 3.75 (t, J=9.9 Hz, 1H), 3.65 (dd, J=12.3, 4.6 Hz, 1H), 3.59 (dq, J=7.8, 4.1 Hz, 1H), 3.44 (ddd. J=12.7, 8.5, 3.6 Hz, 2H), 3.26 (dd, J=11.8, 6.8 Hz, 1H), 2.85 (dt, J=35.0, 13.0 Hz, 1H), 1.85-1.69 (m, 3H), 1.52 (d, J=13.9 Hz, 2H), 1.42 (d, J=8.4 Hz, 3H).

LCMS (Method A): $[M+H]^+$ m/z 488.4, RT 2.88 minutes.

Example 78: rel-(6S,7R)-8-(3-fluorocyclobutanecarbonyl)-7-({[1-(5-fluoropyrimidin-2-yl)piperidin-4-yl]oxy}methyl)-4-oxa-1,8-diazaspiro[5.5]undecan-2-one

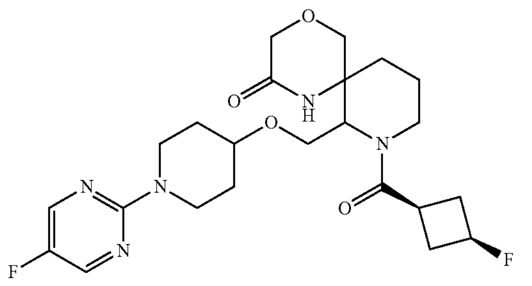 [SMILES: O=C1COCC2(CCCN(C(=O)[C@H]3C[C@@H](F)C3)C2COC2CCN(c3ncc(F)cn3)CC2)N1]

Intermediate 137 (40 mg, 0.0834 mmol) was stirred in a mixture of anhydrous DCM (0.3 mL) and TFA (0.3 mL) for 30 minutes at room temperature. The reaction mixture was quenched with $NaHCO_3$ solution (10 mL) and extracted with DCM (3×20 mL). The combined organic layers were dried over $MgSO_4$, filtered, and concentrated in vacuo to afford the crude material. This was added to a stirred solution of crude material, 3-fluorocyclobutanecarboxylic acid (14 mg, 0.117 mmol) and N-ethyl-N-(propan-2-yl)propan-2-amine (45 μL, 0.250 mmol) in anhydrous DMF (0.6 mL) at room temperature and the mixture was stirred for 30 minutes. The reaction mixture was purified by basic preparative HPLC (Waters XBridge C18 column (30 mm×100 mm, 5 μm; temperature: room temperature). Injection volume of 1500 μL at a flow rate of 40 mL/min. 10% B (A=0.2% ammonium hydroxide in water; B=0.2% ammonium hydroxide in acetonitrile) for 2.0 min then a gradient of 10-95% B over 14.0 min and held for 2.0 min. A second gradient of 95-10% B was then applied over 0.2 min and held for 0.9 min. UV spectra were recorded at 215 nm using a Gilson detector), to afford the title compound (20 mg) as a white solid.

$^1H$ NMR (400 MHz, DMSO) δ 8.42 (d, J=0.9 Hz, 2H), 8.17 (s, 1H), 5.07-4.79 (m, 1H), 4.30-4.15 (m, 1H), 4.09 (d, J=16.5 Hz, 1H), 4.04-3.81 (m, 4H), 3.83-3.53 (m, 3H), 3.55-3.37 (m, 2H), 3.22 (t, J=11.9 Hz, 1H), 2.89-2.79 (m, 1H), 2.57 (t, J=12.0 Hz, 2H), 2.41-2.08 (m, 4H), 1.78 (td, J=14.3, 5.0 Hz, 3H), 1.53 (s, 2H), 1.39 (ddd, J=26.6, 18.4, 13.3 Hz, 3H).

LCMS (Method A): $[M+H]^+$ m/z 480.4, RT 2.68 minutes.

Example 79: rel-(1S,5R)-4,4-difluoro-2-[(CIS)-3-fluorocyclobutanecarbonyl]-1-({2,3',5'-trifluoro-[1,1'-biphenyl]-3-yl}methyl)-8-oxa-2,6-diazaspiro[4.5]decan-7-one

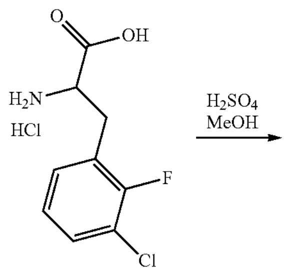

-continued

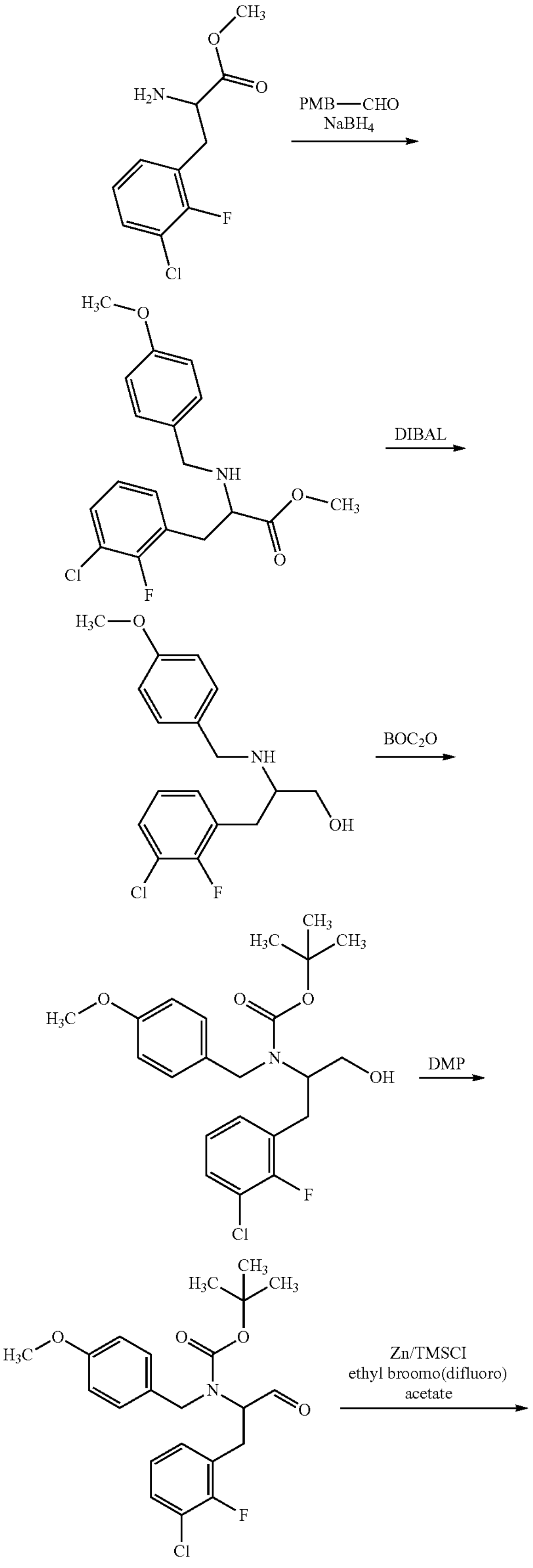

-continued
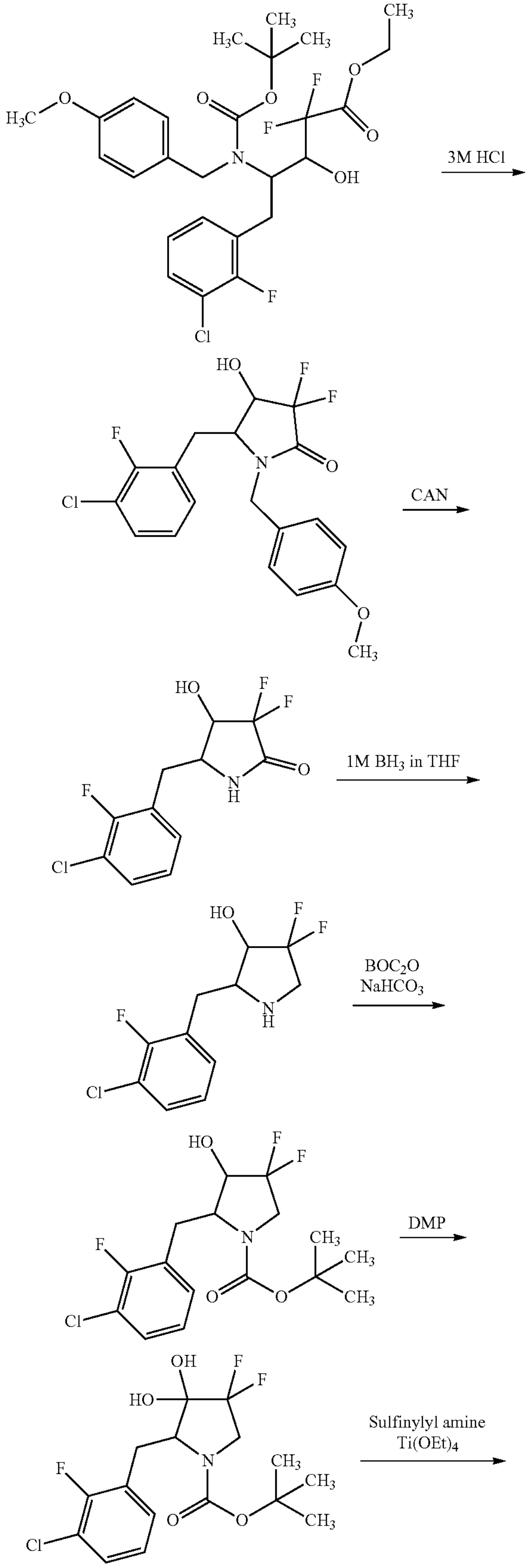
-continued
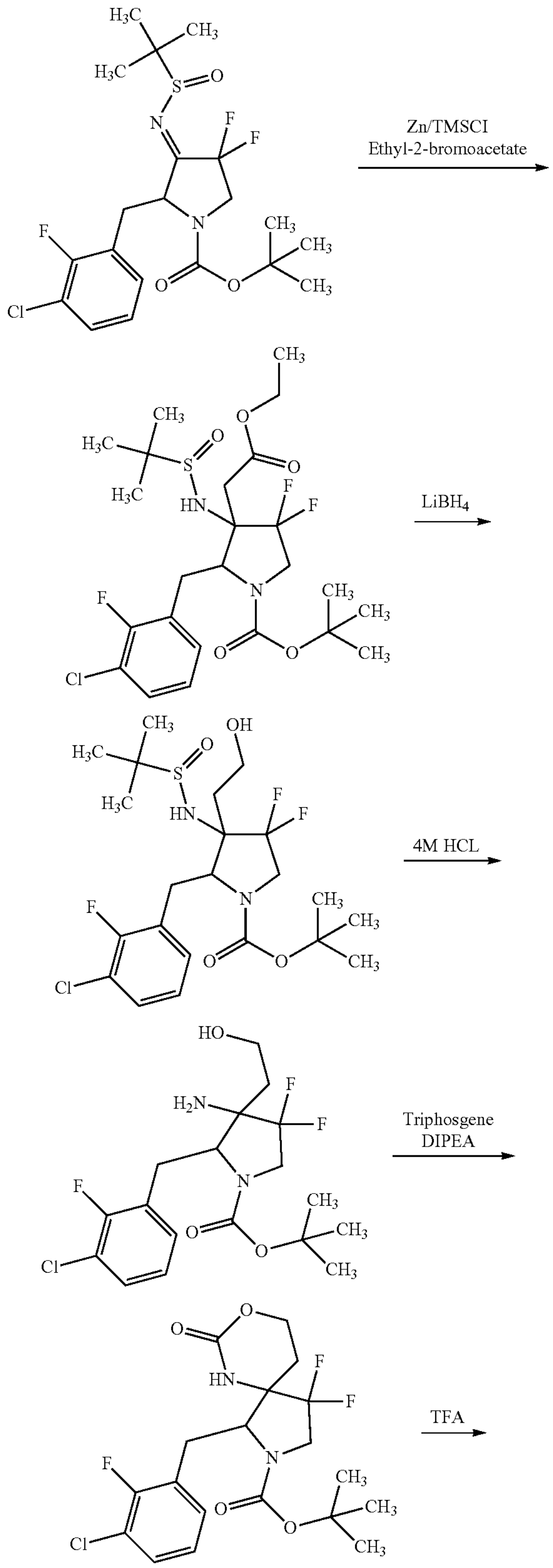

-continued

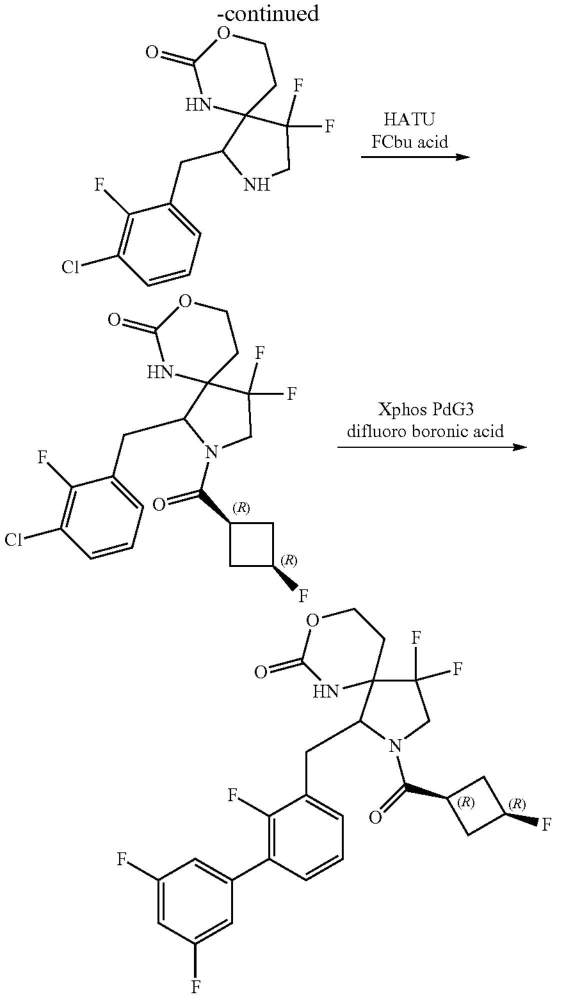

Intermediate 138

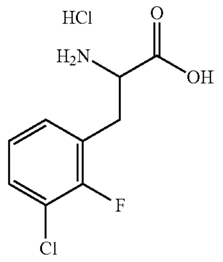 [SMILES: NC(Cc1cccc(Cl)c1F)C(=O)O ; Cl]

2-amino-3-(3-chloro-2-fluorophenyl)propanoic acid hydrochloride

Intermediate 138 (31 g, 86.2 mmol) was dissolved in 6 M HCl (400 mL, 2.40 mol) and 1,4-Dioxane (50 mL) was added to ensure the compound was dissolved and the mixture was heated at 100° C. for 16 hours. The reaction was concentrated, and the resultant solid was suspended in diethyl ether (100 mL). The solid was filtered off and washed with diethyl ether (2×50 mL) to afford the title compound (21.6 g) as a white solid. $[M+H]^+$ m/z=218.07

Intermediate 139

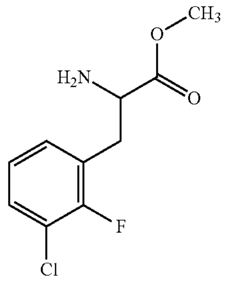

Methyl 2-amino-3-(3-chloro-2-fluorophenyl)propanoate

A dropwise solution of $H_2SO_4$ (5.0 mL) was added to a stirred solution of Intermediate 139 (21.60 g, 85.0 mmol) in methanol (200 mL) at room temperature and the mixture was heated at 65° C. for 16 h. The reaction mixture was cooled to room temperature and concentrated in vacuo. The resulting solid was dissolved in water (100 mL) and EtOAc (100 mL) and basified with $NaHCO_3$ (solid) until the pH was 7-8. The mixture was separated, and the aqueous layer was extracted with EtOAc (2×100 mL). The combined organic layers were washed with brine (100 mL), dried over $MgSO_4$, filtered, and concentrated in vacuo to afford the desired product (17.9 g) as a colourless oil. $[M+H]^+$ m/z=232.05

Intermediate 140

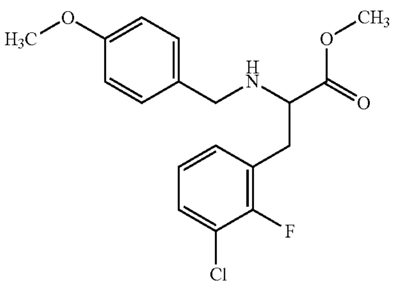

Methyl 3-(3-chloro-2-fluorophenyl)-2-{[(4-methoxyphenyl)methyl]amino}propanoate 4-methoxybenzaldehyde (5.7 mL, 46.6 mmol) was added to a stirred solution of Intermediate 140 (9.00 g, 38.9 mmol) and sodium tetrahydroborate (2.94 g, 77.7 mmol) in methanol (100 mL) 1 g of $MgSO_4$ was added at room temperature and the mixture was stirred for 16 h. sodium tetrahydroborate (2.94 g, 77.7 mmol) was added at 0 C (carefully) and the reaction was stirred for 1 hour at room temperature. The methanol was removed in vacuo and the residue was dissolved in water (50 mL) and extracted with EtOAc (3×50 mL). The combined organic layers were washed with brine (50 mL), dried over $MgSO_4$, filtered, and concentrated in vacuo to afford the crude material. The crude material was purified by silica gel column chromatography (0-50% EtOAc in heptane), to afford the title compound (7.25 g) as a colourless oil. $[M+H]^+$ m/z=352.22

Intermediate 141

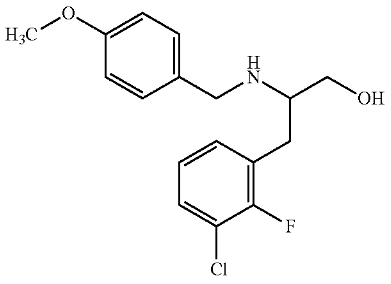 [SMILES: COc1ccc(CNC(CO)Cc2cccc(Cl)c2F)cc1]

3-(3-chloro-2-fluorophenyl)-2-{[(4-methoxyphenyl) methyl]amino}propan-1-ol

A dropwise solution of 1 M hydrido[bis(2-methylpropyl)] aluminum ((1M in cyclohexane) (96 mL, 95.5 mmol) was added to a stirred solution of Intermediate 141 (14.00 g, 39.8 mmol) in THF-Anhydrous (150 mL) at 0 C and mixture was stirred for 3 h. The reaction mixture was warmed to room temperature, quenched dropwise with water (50 mL) followed by saturated potassium sodium tartrate solution (150 mL) and EtOAc (150 mL) and the mixture was stirred for 16 hours. The mixture was separated, and the aqueous layer was extracted with EtOAc (2×100 mL). The combined organic layers were washed with brine (100 mL), dried over $MgSO_4$, filtered, and concentrated in vacuo to afford the crude material as an orange oil which was taken on without further purification. $[M+H]^+$ m/z=324.22

Intermediate 142

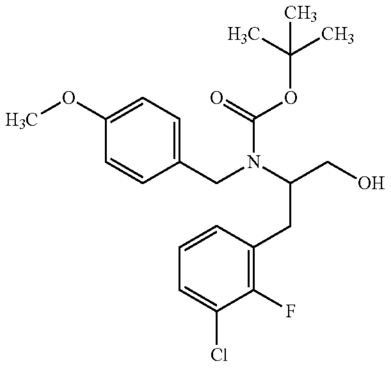 [SMILES: COc1ccc(CN(C(=O)OC(C)(C)C)C(CO)Cc2cccc(Cl)c2F)cc1]

tert-butyl N-[1-(3-chloro-2-fluorophenyl)-3-hydroxypropan-2-yl]-N-[(4-methoxyphenyl)methyl] carbamate A di-tert-butyl dicarbonate (9.71 g, 44.5 mmol) was added to a stirred solution of Intermediate 142 (12.00 g, 37.1 mmol) in 1,4-Dioxane (100 mL) at room temperature and the mixture was stirred for 18 hours. The reaction mixture was quenched with water (100 mL) and extracted with ethyl acetate (3×100 mL). The combined organic layers were washed with brine (100 mL), dried over $MgSO_4$, filtered, and concentrated in vacuo to afford the crude material. The crude material was purified by silica gel column chromatography (0-80% EtOAc in heptane), to afford the title compound (12.7 g) as an orange oil. $[M+H]^+$ m/z=424.26

Intermediate 143

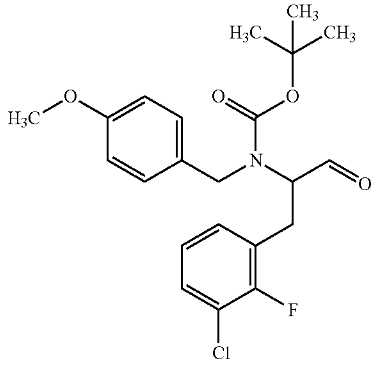 [SMILES: COc1ccc(CN(C(=O)OC(C)(C)C)C(C=O)Cc2cccc(Cl)c2F)cc1]

tert-butyl N-[1-(3-chloro-2-fluorophenyl)-3-oxopropan-2-yl]-N-[(4-methoxyphenyl)methyl]carbamate 1,1,1-tris(acetyloxy)-1lambda-~5~,2-benziodoxol-3(1H)-one (16.52 g, 38.9 mmol) was added to a stirred solution of Intermediate 143 (12.70 g, 30.0 mmol) in DCM-Anhydrous (150 mL) at 0° C. and the mixture was stirred for 3 h. The reaction mixture was warmed to room temperature, quenched with water (50 mL) and extracted with DCM (3×50 mL). The combined organic layers were washed with brine (50 mL), dried over $MgSO_4$, filtered, and concentrated in vacuo to afford the crude material. The crude material was purified by silica gel column chromatography (0-50% EtOAc in heptane), to afford the title compound (5.8 g) as an orange oil. $[M+H]^+$ m/z=422.2

Intermediate 144

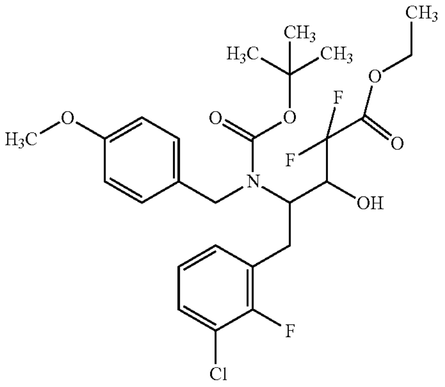 [SMILES: CCOC(=O)C(F)(F)C(O)C(Cc1cccc(Cl)c1F)N(Cc1ccc(OC)cc1)C(=O)OC(C)(C)C]

Ethyl 4-{[(tert-butoxy)carbonyl][(4-methoxyphenyl) methyl]amino}-5-(3-chloro-2-fluorophenyl)-2,2-difluoro-3-hydroxypentanoate A dropwise solution of chloro(trimethyl)silane (496 uL, 3.91 mmol) was added to a stirred solution of activated zinc (4.26 g, 65.2 mmol) in THF-Anhydrous (100 mL) at room temperature. The reaction was warmed to 40° C. and ethyl bromo(difluoro)acetate (3.3 mL, 26.1 mmol) was added dropwise, ensuring the internal temperature does not go higher than 55° C. and the reaction was stirred at 40° C. for 15 minutes. Stirring was stopped and the zinc residue was allowed to be settled and the solution was transferred via cannula to a stirred solution of tert-butyl Intermediate 144 (5.50 g, 13.0 mmol) in THF-Anhydrous (40 mL) and the mixture was heated to 40° C. for 1 hour. The reaction mixture was cooled to room temperature, quenched with water (100 mL) and extracted with ethyl acetate (3×100 mL). The combined organic layers were washed with brine (100 mL), dried over $MgSO_4$, filtered, and concentrated in vacuo to afford the crude material. The crude material was purified by silica gel column chromatography (0-50% EtOAc in heptane), to afford the title compound (3.08 g) as an orange oil. $[M+H]^+$ m/z=546.29

Intermediate 145

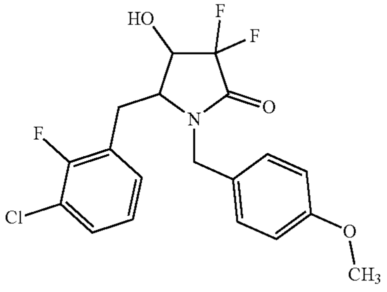 [SMILES: COc1ccc(CN2C(=O)C(F)(F)C(O)C2Cc2cccc(Cl)c2F)cc1]

5-[(3-chloro-2-fluorophenyl)methyl]-3,3-difluoro-4-hydroxy-1-[(4-methoxyphenyl)methyl]pyrrolidin-2-one A dropwise solution of 3 M HCl in cyclopentyl methyl ether (18 mL, 54.9 mmol) was added to a stirred solution of intermediate 145 (3.00 g, 5.49 mmol) in ethanol (20 mL) at room temperature and the mixture was stirred for 16 h. The reaction mixture was concentrated in vacuo then diluted with water (20 mL) and extracted with ethyl acetate (3×20 mL). The combined organic layers were washed with brine (25 mL), dried over $MgSO_4$, filtered, and concentrated in vacuo to afford the crude material. The crude material was purified by silica gel column chromatography (0-100% EtOAc in heptane), to afford the title compound (1.8 g) as a colourless oil. $[M+NH_4]^+$ m/z=417.16

Intermediate 146

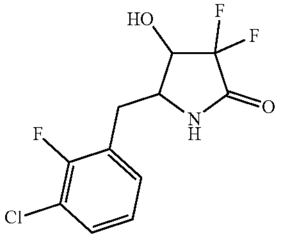 [SMILES: O=C1NC(Cc2cccc(Cl)c2F)C(O)C1(F)F]

5-[(3-chloro-2-fluorophenyl)methyl]-3,3-difluoro-4-hydroxypyrrolidin-2-one

Ammonium cerium(4+) nitrate (2:1:6) (7.38 g, 13.5 mmol) was added to a stirred solution of Intermediate 146 (1.80 g, 4.50 mmol) in Acetonitrile-Anhydrous (35 mL) at room temperature and the mixture was stirred for 16 h. The reaction mixture was quenched with water (50 mL) and extracted with ethyl acetate (3×50 mL). The combined organic layers were washed with brine (50 mL), dried over $MgSO_4$, filtered, and concentrated in vacuo to afford the crude material. The crude material was purified by silica gel column chromatography (0-80% EtOAc in heptane), to afford the title compound (1 g) as a yellow oil. $[M+NH_4]^+$ m/z=297.12

Intermediate 147

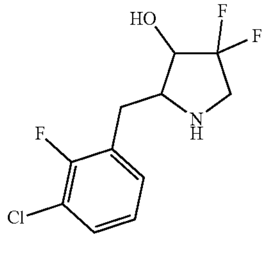 [SMILES: OC1C(Cc2cccc(Cl)c2F)NCC1(F)F]

2-[(3-chloro-2-fluorophenyl)methyl]-4,4-difluoropyrrolidin-3-ol

A dropwise solution of 1 M borane in THF (8.0 mL, 8.05 mmol) was added to a stirred solution of Intermediate 147 (900 mg, 3.22 mmol) in THF-Anhydrous (13.5 mL) at room temperature and the mixture was heated at 60° C. for 4 h. The reaction mixture was cooled to room temperature, quenched with water (0.1 mL), stirred at room temperature for 10 minutes and concentrated in vacuo. 1M HCl (1 mL) was added, and the reaction was heated at 60° C. for 1.5 hours. The reaction was cooled to room temperature, made pH 7-8 with $NaHCO_3$ solution was extracted with ethyl acetate (3×10 mL). The combined organic layers were washed with brine (10 mL), dried over $MgSO_4$, filtered, and concentrated in vacuo to afford the crude material. The crude material was purified by reverse phase column chromatography (10-100% acetonitrile in water (0.1% formic acid)), to afford the title compound (300 mg) as a white solid. $[M+H]^+$ m/z=266.07

Intermediate 148

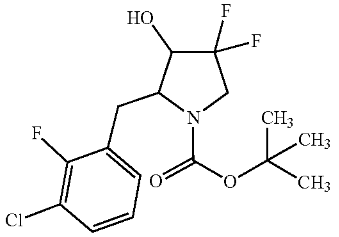 [SMILES: CC(C)(C)OC(=O)N1CC(F)(F)C(O)C1Cc1cccc(Cl)c1F]

tert-butyl 2-[(3-chloro-2-fluorophenyl)methyl]-4,4-difluoro-3-hydroxypyrrolidine-1-carboxylate Di-tert-butyl dicarbonate (288 mg, 1.32 mmol) was added to a stirred solution of sodium hydrogen carbonate (119 mg, 1.41 mmol) and Intermediate 148 (250 mg, 0.941 mmol) in Water (6.25 mL) at room temperature and the mixture was stirred for 16 h. The reaction mixture was diluted with water (10 mL) and extracted with ethyl acetate (3×10 mL). The combined organic layers were washed with brine (10 mL), dried over $MgSO_4$, filtered, and concentrated in vacuo to afford the crude material (95 mg) which was taken on without further purification. $[M+NH_4]^+$ m/z=383.15

Intermediate 149

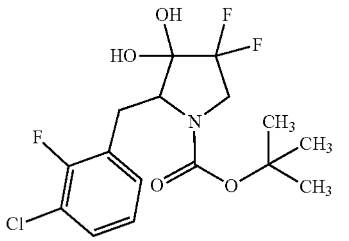 [SMILES: CC(C)(C)OC(=O)N1CC(F)(F)C(O)(O)C1Cc1cccc(Cl)c1F]

tert-butyl 2-[(3-chloro-2-fluorophenyl)methyl]-4,4-difluoro-3,3-dihydroxypyrrolidine-1-carboxylate 1,1,1-tris(acetyloxy)-1lambda~5~,2-benziodoxol-3(1H)-one (528 mg, 1.24 mmol) was added to a stirred solution of Intermediate 149 (350 mg, 0.957 mmol) in DCM-Anhydrous (10.5 mL) at room temperature and mixture was stirred for 2 h. The reaction mixture was quenched with water 10 mL) and extracted with DCM (3×10 mL). The combined organic layers were washed with brine (15 mL), dried over $MgSO_4$, filtered, and concentrated in vacuo to afford the crude material. The crude material was purified by silica gel column chromatography (0-100% EtOAc in heptane), to afford the title compound (323 mg) as a pale-yellow solid. $[M+NH_4]^+$ m/z=399.17

Intermediate 150

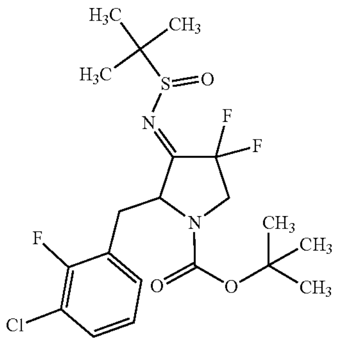 [SMILES: CC(C)(C)OC(=O)N1CC(F)(F)/C(=N\S(=O)C(C)(C)C)C1Cc1cccc(Cl)c1F]

tert-butyl 2-[(3-chloro-2-fluorophenyl)methyl]-4,4-difluoro-3-[(2-methylpropane-2-sulfinyl)imino]pyrrolidine-1-carboxylate A dropwise solution of $Ti(OEt)_4$ (362 uL, 1.73 mmol) was added to a stirred solution of 2-methylpropane-2-sulfinamide (105 mg, 0.864 mmol) and Intermediate 150 (220 mg, 0.576 mmol) in THF-Anhydrous (0.5 mL) at room temperature and the mixture was heated at 60° C. for 6 h. The reaction was concentrated in vacuo and dissolved in EtOAc (5 mL) and water (5 mL). The turbid solution was filtered through celite and separated. The aqueous layer was extracted with EtOAc (2×5 mL). The combined organic layers were washed with brine (10 mL), dried over $MgSO_4$, filtered, and concentrated in vacuo to afford the crude material which was taken on to the next step. $[M-tBu+H]^+$ m/z=411.1

Intermediate 151

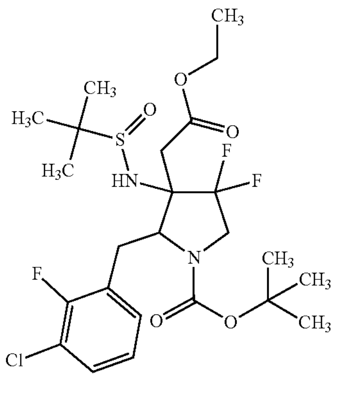 [SMILES: CCOC(=O)CC1(NS(=O)C(C)(C)C)C(Cc2cccc(Cl)c2F)N(C(=O)OC(C)(C)C)CC1(F)F]

tert-butyl 2-[(3-chloro-2-fluorophenyl)methyl]-3-(2-ethoxy-2-oxoethyl)-4,4-difluoro-3-[(2-methylpropane-2-sulfinyl)amino]pyrrolidine-1-carboxylate To a mixture of activated zinc (1.82 g, 27.8 mmol) and THF-Anhydrous (30 mL) was added chloro(trimethyl)silane (0.21 mL, 1.67 mmol) under argon atmosphere at room temperature. The mixture was warmed to 40° C. and ethyl 2-bromoacetate (1.2 mL, 11.1 mmol) was added dropwise to the mixture with vigorously stirring at 40° C. while keeping the internal temperature of about 50° C. The mixture was stirred at 50° C. for 15 min. Stirring was stopped and 10 ml of the solution was removed using a syringe and added to Intermediate 151 (260 mg, 0.557 mmol) in THF (20 mL) at 40° C. and the reaction was heated to 60° C. and stirred for 2 h. The reaction mixture was cooled to room temperature, quenched with water (20 mL) and ethyl acetate (20 mL) and passed through a celite filter. The filtrate was separated, and the aqueous layer was extracted with ethyl acetate (3×20 mL). The crude material was purified by silica gel column chromatography (0-100% EtOAc in heptane), to afford the title compound (120 mg) as an orange oil. $[M+Na]^+$ m/z=577.13

Intermediate 152

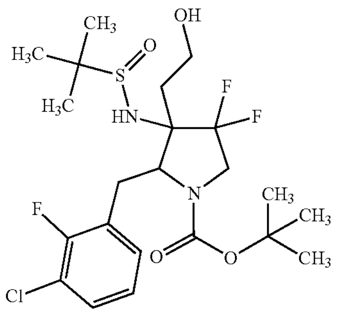 [SMILES: CC(C)(C)OC(=O)N1CC(F)(F)C(CCO)(NS(=O)C(C)(C)C)C1Cc1cccc(Cl)c1F]

tert-butyl 2-[(3-chloro-2-fluorophenyl)methyl]-4,4-difluoro-3-(2-hydroxyethyl)-3-[(2-methylpropane-2-sulfinyl)amino]pyrrolidine-1-carboxylate 2 M $LiBH_4$ (0.048 mL, 0.0951 mmol) was added dropwise to a stirred solution of Intermediate 152 (44%, 120 mg, 0.0951 mmol) in THF-Anhydrous (5 mL) at 0° C. and mixture was stirred for 20 h at room temperature. The reaction mixture was quenched with water (10 mL) and extracted with EtOAc (3×10 mL). The combined organic layers were dried (hydrophobic frit) and concentrated in vacuo to afford the title compound (107 mg) as a yellow oil. $[M+H]^+$ m/z=513.2

Intermediate 153

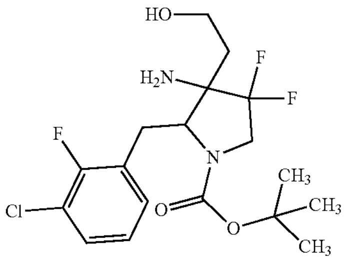 [SMILES: CC(C)(C)OC(=O)N1CC(F)(F)C(N)(CCO)C1Cc1cccc(Cl)c1F]

tert-butyl 2-[(3-chloro-2-fluorophenyl)methyl]-4,4-difluoro-3-(2-hydroxyethyl)-3-[(2-methylpropane-2-sulfinyl)amino]pyrrolidine-1-carboxylate 4 M hydrogen chloride in dioxane (0.045 mL, 0.179 mmol) was added dropwise to a stirred solution of Intermediate 153 (57%, 107 mg, 0.119 mmol) in Methanol (5 mL) at 0° C. and mixture was stirred for 6 h. The reaction mixture was quenched with 1M NaOH (1 mL), diluted with water (10 ml) and extracted with EtOAc (3×10 mL). The combined organic layers were dried over $MgSO_4$, filtered, and concentrated in vacuo to afford the title compound (104 mg) as a yellow oil. $M+H]^+$ m/z=409.2

Intermediate 154

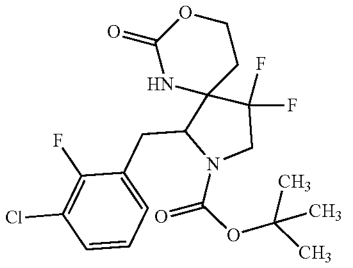 [SMILES: CC(C)(C)OC(=O)N1CC(F)(F)C2(CCOC(=O)N2)C1Cc1cccc(Cl)c1F]

tert-butyl 1-[(3-chloro-2-fluorophenyl)methyl]-4,4-difluoro-7-oxo-8-oxa-2,6-diazaspiro[4.5]decane-2-carboxylate N-ethyl-N-isopropyl-propan-2-amine (0.035 mL, 0.198 mmol) was added portion wise to a stirred solution of Intermediate 154 (39%, 104 mg, 0.0992 mmol) and bis (trichloromethyl) carbonate (44 mg, 0.149 mmol) in DCM-Anhydrous (2.6 mL) at 0° C. and mixture was stirred for 1 h. The reaction mixture was quenched with water (10 mL) and extracted with EtOAc (3×10 mL). The combined organic layers were washed with brine (20 mL), dried over $MgSO_4$, filtered, and concentrated in vacuo to afford the title compound (103 mg) as a yellow oil. $[M+H]^+$ m/z=435.1

Intermediate 155

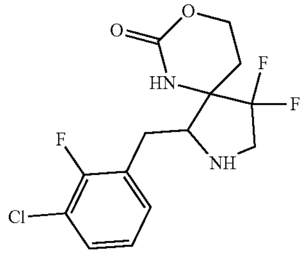 [SMILES: O=C1NC2(CCO1)C(Cc1cccc(Cl)c1F)NCC2(F)F]

1-[(3-chloro-2-fluorophenyl)methyl]-4,4-difluoro-8-oxa-2,6-diazaspiro[4.5]decan-7-one TFA (1 mL) was added dropwise to a stirred solution of Intermediate 155 (54%, 103 mg, 0.128 mmol) in DCM-Anhydrous (1 mL) at room temperature and mixture was stirred for 1 h. The reaction mixture was quenched with $NaHCO_3$ (10 mL) and extracted with EtOAc (3×10 mL). The combined organic layers were washed with brine (20 mL), dried over $MgSO_4$, filtered, and concentrated in vacuo to afford the title compound (98 mg) as a yellow oil. $[M+H]^+$ m/z=335.0

Intermediate 156

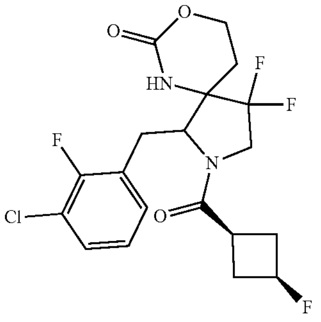 [SMILES: O=C1NC2(CCO1)C(Cc1cccc(Cl)c1F)N(C(=O)[C@H]1C[C@@H](F)C1)CC2(F)F]

1-[(3-chloro-2-fluorophenyl)methyl]-4,4-difluoro-2-[(CIS)-3-fluorocyclobutanecarbonyl]-8-oxa-2,6-diazaspiro[4.5]decan-7-one A solution of Intermediate 156 (61%, 98 mg, 0.179 mmol) in DMF-Anhydrous (1.1731 mL) was added dropwise to a stirred solution of 3-fluorocyclobutanecarboxylic acid (28 mg, 0.233 mmol), N-ethyl-N-isopropyl-propan-2-amine (0.094 mL, 0.537 mmol) and N-[(dimethylamino)(3H-[1,2,3]triazolo[4,5-b]pyridin-3-yloxy)methylidene]-N-methyl-methanaminium hexafluorophosphate (102 mg, 0.269 mmol) in DMF-Anhydrous (2.3462 mL) at room temperature and mixture was stirred for 2 h. The reaction mixture was quenched with water (10 mL) and extracted with EtOAc (3×10 mL). The combined organic layers were washed with brine (10 mL), dried over $MgSO_4$, filtered, and concentrated to afford the title compound (132 mg) as a dark yellow oil. $[M+H]^+$ m/z=435.1

4,4-difluoro-2-[(CIS)-3-fluorocyclobutanecarbonyl]-1-({2,3',5'-trifluoro-[1,1'-biphenyl]-3-yl}methyl)-8-oxa-2,6-diazaspiro[4.5]decan-7-one (79)

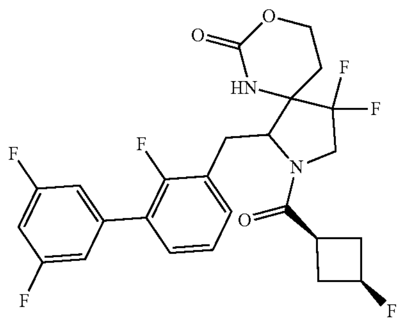 [SMILES: O=C1NC2(CCO1)C(Cc1cccc(-c3cc(F)cc(F)c3)c1F)N(C(=O)[C@H]1C[C@@H](F)C1)CC2(F)F]

A mixture of Intermediate 157 (45%, 132 mg, 0.137 mmol), 2-(3,5-difluorophenyl)-4,4,5,5-tetramethyl-1,3,2-dioxaborolane (66 mg, 0.273 mmol), 1 M $K_3PO_4$ in water (0.41 mL, 0.410 mmol) and THF-Anhydrous (3 mL) was degassed for 15 mins ($N_2$ purge). XPhos Pd G3 (12 mg, 0.0137 mmol) was added, and the reaction mixture was stirred under nitrogen atmosphere at 70° C. for 1 h. The reaction mixture cooled to room temperature, quenched with aqueous $NaHCO_3$ solution (3 mL), and the mixture was extracted with ethyl acetate (3×3 mL). The combined organic layers were passed through a phase separator and concentrated under reduced pressure. The crude material was purified by silica gel column chromatography (0-100% EtOAc in heptane), to afford the title compound (9.5 mg) as an off-white solid.

LCMS (Method A): $[M+H]^+$ m/z 381.2, RT 3.14 minutes.

$^1H$ NMR (400 MHz, $CDCl_3$) δ 7.41 (t, J=7.2 Hz, 1H), 7.33-7.25 (m, 1H), 7.22 (t, J=7.6 Hz, 1H), 7.16-7.01 (m, 2H), 6.83 (t, J=8.9 Hz, 1H), 6.15 (s, 1H), 5.08-4.82 (m, 1H), 4.60 (s, 1H), 4.33 (s, 1H), 4.16-3.96 (m, 2H), 3.88-3.72 (m, 1H), 3.14 (d, J=7.2 Hz, 2H), 2.65-2.15 (m, 7H).

Intermediate 157

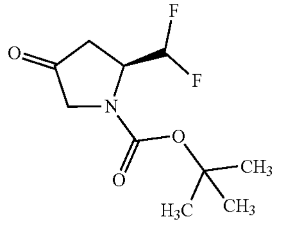 [SMILES: CC(C)(C)OC(=O)N1CC(=O)C[C@H]1C(F)F]

tert-butyl (2S)-2-(difluoromethyl)-4-oxopyrrolidine-1-carboxylate 1,1,1-tris(acetyloxy)-1lambda~5~,2-benziodoxol-3(1H)-one (3.93 g, 9.27 mmol) was added portion wise to a stirred solution of tert-butyl (2S,4S)-2-(difluoromethyl)-4-hydroxy-pyrrolidine-1-carboxylate (2.00 g, 8.43 mmol) in anhydrous DCM (20 mL) at 0° C. and the mixture was stirred for 1 h. The reaction mixture was quenched with water (10 mL) and extracted with DCM (3×10 mL). The combined organic layers were passed through a phase separator and concentrated in vacuo to afford the crude material. The crude material was purified by silica gel column chromatography (0-100% EtOAc in heptane), to afford title compound (1.84 g) as a white solid.

$^1H$ NMR (400 MHz, $CDCl_3$) δ 6.12 (t, J=55.7 Hz, 1H), 4.68-4.39 (m, 1H), 4.02-3.85 (m, 1H), 3.68 (dd, J=18.9, 1.4 Hz, 1H), 2.84-2.55 (m, 2H), 1.48 (s, 9H).

Example 80: (1S,3S,5S)-3-(difluoromethyl)-2-[(1s,3s)-3-fluorocyclobutanecarbonyl]-1-({2,3',5'-trifluoro-[1,1'-biphenyl]-3-yl}methyl)-9-oxa-2,6-diazaspiro[4.5]decan-7-one

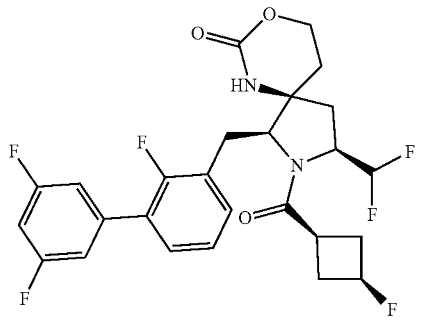 [SMILES: O=C1N[C@@]2(CCO1)C[C@@H](C(F)F)N(C(=O)[C@H]1C[C@@H](F)C1)[C@H]2Cc1cccc(-c2cc(F)cc(F)c2)c1F]

Example 80 was prepared in similar manner to procedure described for example 53 starting form intermediate 158

A solution of rel-(1S,5S),(3S)-3-(difluoromethyl)-1-({2,3',5'-trifluoro-[1,1'-biphenyl]-3-yl}methyl)-9-oxa-2,6-diazaspiro[4.5]decan-7-one (150 mg) in anhydrous DMF (0.2022 mL) was added to a stirred solution of 3-fluorocyclobutanecarboxylic acid (56 mg), HATU (201 mg) and DIPEA (66 μL) in anhydrous DMF (0.8088 mL) at room temperature and mixture was stirred for 2 h. The reaction mixture was filtered. The crude material was purified by prep HPLC early elute Method Column: XBridge™ Prep. C18 10 um OBD™, 30×100 mm, Mobile Phase: 10-95% Acetonitrile (0.2% ammonium hydroxide) in Water (0.2% ammonium hydroxide) over 10 minutes, Flow Rate: 40 mL/min, UV: 215 and 254 nm, to afford (13 mg) as a as a colourless oil.

LCMS (Method A): $[M+H]^+$ m/z 527.3, RT 3.55 minutes.

$^1H$ NMR (500 MHz, $CDCl_3$) δ 7.36-7.30 (m, 1H), 7.20-7.17 (m, 2H), 7.03 (d, J=7.2 Hz, 2H), 6.86 (tt, J=8.8, 2.3 Hz, 1H), 6.53 (s, 1H), 6.33 (dd, J=60.6, 54.8 Hz, 1H), 4.59 (dq, J=55.5, 7.0 Hz, 1H), 4.31 (dt, J=25.9, 8.2 Hz, 2H), 4.20 (d, J=17.1 Hz, 1H), 4.12 (d, J=17.1 Hz, 1H), 3.51 (d, J=12.2 Hz, 1H), 3.46 (d, J=11.9 Hz, 1H), 3.28 (dd, J=13.5, 4.3 Hz, 1H), 2.71-2.60 (m, 1H), 2.54 (dt, J=11.2, 5.3 Hz, 1H), 2.49-2.37 (m, 1H), 2.32 (dd, J=13.8, 9.7 Hz, 1H), 2.22-2.07 (m, 2H), 1.87-1.70 (m, 2H).

Example 81: (1S,3R,5S)-2-cyclobutanecarbonyl-3-methyl-1-({2,3',5'-trifluoro-[1,1'-biphenyl]-3-yl}methyl)-9-oxa-2,6-diazaspiro[4.5]decan-7-one

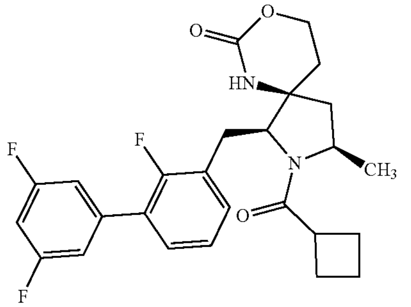 [SMILES: C[C@@H]1C[C@@]2(CCOC(=O)N2)[C@H](Cc2cccc(-c3cc(F)cc(F)c3)c2F)N1C(=O)C1CCC1]

Example 81 was prepared in similar manner to procedure described for Example 58

LCMS (Method C): $[M+H]^+$ m/z 473.2, RT 1.09 minutes.

$^1H$ NMR (400 MHz, $CDCl_3$) δ 7.59-7.18 (m, 3H), 7.17-7.01 (m, 2H), 6.91-6.75 (m, 1H), 6.46-6.14 (m, 1H), 4.84-4.23 (m, 1H), 4.20-3.83 (m, 2H), 4.09-3.77 (m, 1H), 3.63-3.34 (m, 2H), 3.32-3.02 (m, 1H), 2.99-2.59 (m, 1H), 2.53-2.37 (m, 1H), 2.37-1.91 (m, 5H), 1.85-1.47 (m, 3H), 1.49-1.27 (m, 3H).

Example 82: (1S,3R,5S)-3-methyl-2-[(1s,3s)-3-fluorocyclobutanecarbonyl]-1-({2,3',5'-trifluoro-[1,1'-biphenyl]-3-yl}methyl)-9-oxa-2,6-diazaspiro[4.5]decan-7-one

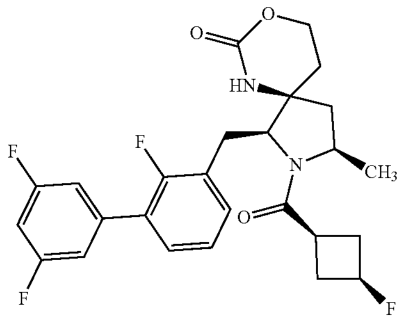 [SMILES: C[C@@H]1C[C@@]2(CCOC(=O)N2)[C@H](Cc2cccc(-c3cc(F)cc(F)c3)c2F)N1C(=O)[C@H]1C[C@@H](F)C1]

Example 82 was prepared in similar manner to procedure described for Example 58

LCMS (Method C): $[M+H]^+$ m/z 491.2, RT 1.09 minutes.

$^1H$ NMR (400 MHz, $CDCl_3$) δ 7.55-7.18 (m, 3H), 7.16-6.97 (m, 2H), 6.91 (m, 1H), 6.79-6.18 (m, 1H), 5.05-4.48 (m, 1H), 4.86-4.21 (m, 1H), 4.23-3.89 (m, 2H), 4.15-3.77 (m, 1H), 3.60-3.34 (m, 2H), 3.30-2.86 (m, 1H), 3.14-2.62 (m, 1H), 2.56-2.36 (m, 2H), 2.34-2.24 (m, 1H), 2.62-1.71 (m, 1H), 2.22-1.70 (m, 2H), 1.91-1.66 (m, 1H), 1.53-1.32 (m, 3H).

Example 83: 2,2-difluoroethyl (1S,3R,5S)-3-methyl-7-oxo-1-({2,3',5'-trifluoro-[1,1'-biphenyl]-3-yl}methyl)-9-oxa-2,6-diazaspiro[4.5]decane-2-carboxylate

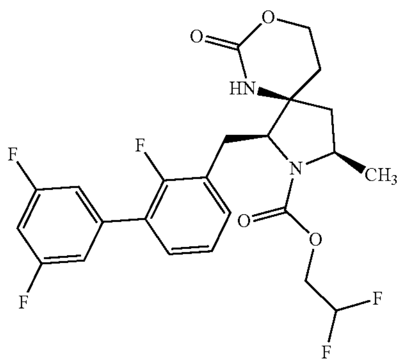 [SMILES: C[C@@H]1C[C@@]2(CCOC(=O)N2)[C@H](Cc2cccc(-c3cc(F)cc(F)c3)c2F)N1C(=O)OCC(F)F]

Example 83 was prepared in similar manner to procedure described for Example 61

LCMS (Method C): $[M+H]^+$ m/z 499.2, RT 1.10 minutes.

$^1H$ NMR (400 MHz, $CDCl_3$) δ 7.44-7.22 (m, 2H), 7.22-7.15 (m, 1H), 7.11 (br d, J=6.8 Hz, 2H), 6.89-6.74 (m, 1H), 6.52-6.15 (m, 1H), 6.06-5.35 (m, 1H), 4.47 (br s, 1H), 4.39-3.92 (m, 4H), 3.91-3.76 (m, 1H), 3.69 (d, J=11.6 Hz, 1H), 3.44 (d, J=11.8 Hz, 1H), 3.14 (br dd, J=13.3, 6.5 Hz, 1H), 2.98-2.54 (m, 1H), 2.31 (dd, J=13.5, 7.6 Hz, 1H), 1.77 (dd, J=13.6, 9.6 Hz, 1H), 1.42 (br s, 3H).

Example 84: (1S,3R,5S)-3-methyl-1-({2,3',5'-trifluoro-[1,1'-biphenyl]-3-yl}methyl)-2-(3,3,3-trifluoropropanoyl)-9-oxa-2,6-diazaspiro[4.5]decan-7-one

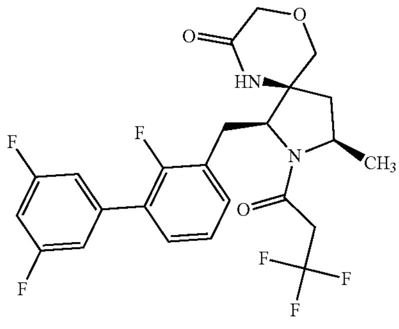 [SMILES: C[C@@H]1C[C@@]2(COCC(=O)N2)[C@H](Cc2cccc(-c3cc(F)cc(F)c3)c2F)N1C(=O)CC(F)(F)F]

Example 84 was prepared in similar manner to procedure described for Example 58

LCMS (Method C): $[M+H]^+$ m/z 501.1, RT 1.07 minutes.

$^1H$ NMR (400 MHz, $CDCl_3$) δ 7.51-7.16 (m, 3H), 7.16-6.94 (m, 2H), 6.88-6.73 (m, 1H), 6.94-6.29 (m, 1H), 4.93-4.19 (m, 1H), 4.35-3.85 (m, 3H), 3.70-3.55 (m, 1H), 3.51-3.38 (m, 1H), 3.30 (br dd, J=13.5, 3.4 Hz, 1H), 3.00-2.66 (m, 1H), 3.27-2.54 (m, 1H), 2.54-2.26 (m, 1H), 3.24-1.99 (m, 1H), 1.94-1.77 (m, 1H), 1.55-1.41 (m, 3H).

Example 85: Methyl (1S,3R,5S)-3-methyl-7-oxo-1-({2,3',5'-trifluoro-[1,1'-biphenyl]-3-yl}methyl)-9-oxa-2,6-diazaspiro[4.5]decane-2-carboxylate

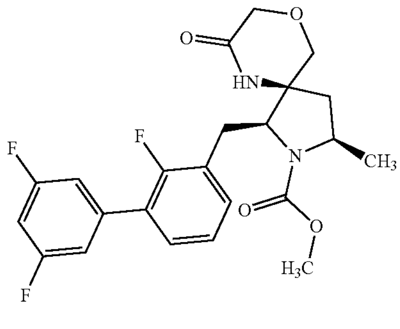 [SMILES: COC(=O)N1[C@H](C)C[C@@]2(COCC(=O)N2)[C@@H]1Cc1cccc(-c2cc(F)cc(F)c2)c1F]

Example 85 was prepared in similar manner to procedure described for Example 61

LCMS (Method C): $[M+H]^+$ m/z 449.2, RT 1.04 minutes.

$^1H$ NMR (400 MHz, $CDCl_3$) δ 7.35-7.20 (m, 2H), 7.20-7.14 (m, 1H), 7.15-7.02 (m, 2H), 6.87-6.78 (m, 1H), 6.46 (br s, 1H), 4.47 (t, J=5.6 Hz, 1H), 4.07 (br s, 2H), 3.87-3.75 (m, 1H), 3.70 (d, J=11.6 Hz, 1H), 3.43 (br d, J=11.7 Hz, 1H), 3.41 (br s, 3H), 3.13 (br dd, J=13.3, 6.0 Hz, 1H), 2.70 (br s, 1H), 2.29 (dd, J=13.5, 7.6 Hz, 1H), 1.75 (dd, J=13.4, 9.7 Hz, 1H), 1.41 (br d, J=3.5 Hz, 3H).

Example 86: (1S,3R,5S)-2-(3,3-difluorocyclobutanecarbonyl)-3-methyl-1-({2,3',5'-trifluoro-[1,1'-biphenyl]-3-yl}methyl)-9-oxa-2,6-diazaspiro[4.5]decan-7-one

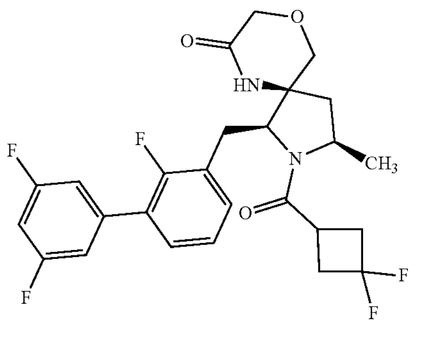 [SMILES: C[C@@H]1C[C@@]2(COCC(=O)N2)[C@H](Cc2cccc(-c3cc(F)cc(F)c3)c2F)N1C(=O)C1CC(F)(F)C1]

Example 86 was prepared in similar manner to procedure described for Example 58

LCMS (Method C): $[M+H]^+$ m/z 509.2, RT 1.09 minutes.

$^1H$ NMR (400 MHz, $CDCl_3$) δ 7.48-7.31 (m, 1H), 7.26-7.16 (m, 2H), 7.14-6.97 (m, 2H), 6.91-6.75 (m, 1H), 6.68-6.23 (m, 1H), 4.88-4.24 (m, 1H), 4.25-3.88 (m, 2H), 4.14-3.84 (m, 1H), 3.64-3.36 (m, 2H), 3.33-3.06 (m, 1H), 3.05-2.70 (m, 2H), 2.95-2.61 (m, 1H), 2.31 (dd, J=13.6, 8.1 Hz, 1H), 3.05-2.10 (m, 1H), 2.69-1.80 (m, 2H), 1.81 (dd, J=13.6, 9.6 Hz, 1H), 1.53-1.35 (m, 3H).

Example 87: (1S,3R,5S)—N-ethyl-N,3-dimethyl-7-oxo-1-({2,3',5'-trifluoro-[1,1'-biphenyl]-3-yl}methyl)-9-oxa-2,6-diazaspiro[4.5]decane-2-carboxamide

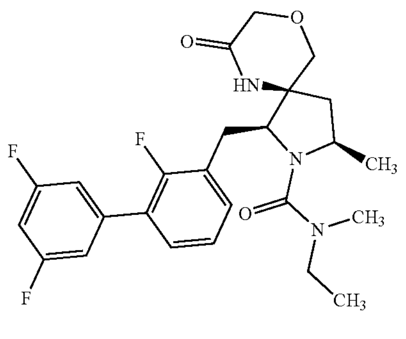 [SMILES: CCN(C)C(=O)N1[C@H](C)C[C@@]2(COCC(=O)N2)[C@@H]1Cc1cccc(-c2cc(F)cc(F)c2)c1F]

Example 87 was prepared in similar manner to procedure described for Example 58

LCMS (Method C): $[M+H]^+$ m/z 476.3, RT 1.08 minutes.

$^1H$ NMR (400 MHz, $CDCl_3$) δ 7.51-7.44 (m, 1H), 7.25-7.20 (m, 1H), 7.20-7.15 (m, 1H), 7.16-7.10 (m, 2H), 6.81 (tt, J=8.9, 2.2 Hz, 1H), 6.15 (br s, 1H), 4.29 (dd, J=9.0, 4.2 Hz, 1H), 4.02 (d, J=16.8 Hz, 1H), 3.97-3.85 (m, 2H), 3.70 (d, J=11.7 Hz, 1H), 3.46 (d, J=11.6 Hz, 1H), 3.38-3.25 (m, 1H), 3.24 (br dd, J=14.8, 3.5 Hz, 1H), 3.15 (dq, J=14.0, 7.1 Hz, 1H), 3.04 (dd, J=14.4, 9.1 Hz, 1H), 2.81 (s, 3H), 2.32 (dd, J=13.5, 8.0 Hz, 1H), 1.76 (dd, J=13.5, 7.9 Hz, 1H), 1.33 (d, J=6.4 Hz, 3H), 1.12 (t, J=7.1 Hz, 3H).

Example 88: (1S,3R,5S)-2-(2-methoxyacetyl)-3-methyl-1-({2,3',5'-trifluoro-[1,1'-biphenyl]-3-yl}methyl)-9-oxa-2,6-diazaspiro[4.5]decan-7-one

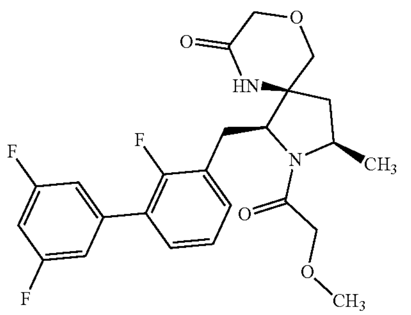 [SMILES: COCC(=O)N1[C@H](C)C[C@@]2(COCC(=O)N2)[C@@H]1Cc1cccc(-c2cc(F)cc(F)c2)c1F]

To a mixture of Intermediate 87 (50 mg, 0.130 mmol) and triethylamine (26.78 μL, 0.190 mmol) in DCM (1.7 mL) under stirring at 0° C., 2-methoxyacetyl chloride (12.88 μL, 0.140 mmol) was added. The mixture was stirred at room temperature for 16 h. MeOH/$H_2O$ (1:9) was added and the mixture was extracted with DCM. The organic layer was dried ($Na_2SO_4$) and evaporated in vacuo. The product was purified by silica gel column chromatography (0-100% EtOAc in DCM) to afford the title compound (20 mg) as a white solid.

LCMS (Method C): $[M+H]^+$ m/z 463.2, RT 0.92 minutes.

$^1H$ NMR (400 MHz, $CDCl_3$) δ 7.55-7.31 (m, 1H), 7.30-7.24 (m, 1H), 7.24-7.16 (m, 1H), 7.16-6.99 (m, 2H), 6.95-6.77 (m, 1H), 6.74-6.18 (m, 1H), 4.94-4.35 (m, 1H), 4.25-3.84 (m, 3H), 3.73-3.52 (m, 2H), 3.48-3.36 (m, 1H), 3.20 (s, 3H), 3.37-3.05 (m, 2H), 3.00-2.56 (m, 1H), 2.49-2.18 (m, 1H), 1.96-1.69 (m, 1H), 1.54-1.33 (m, 3H).

Example 89: (1S,3R,5S)-3-methyl-2-[(2R)-oxetane-2-carbonyl]-1-({2,3',5'-trifluoro-[1,1'-biphenyl]-3-yl}methyl)-9-oxa-2,6-diazaspiro[4.5]decan-7-one

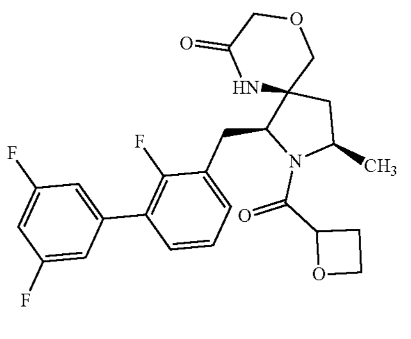 [SMILES: C[C@@H]1C[C@@]2(COCC(=O)N2)[C@H](Cc2cccc(-c3cc(F)cc(F)c3)c2F)N1C(=O)C1CCO1]

Example 89 was prepared in similar manner to procedure described for Example 58

LCMS (Method C): $[M+H]^+$ m/z 475.2, RT 0.91 minutes.

$^1H$ NMR (400 MHz, $CDCl_3$) δ 7.65-7.41 (m, 1H), 7.33-7.07 (m, 4H), 6.89-6.71 (m, 1H), 6.12-5.91 (m, 1H), 5.42-5.01 (m, 1H), 4.77-4.50 (m, 2H), 4.90-4.23 (m, 1H), 4.20-4.06 (m, 1H), 4.04-3.81 (m, 2H), 3.75-3.49 (m, 1H), 3.47-3.28 (m, 1H), 3.24-2.74 (m, 4H), 2.42-2.18 (m, 1H), 1.82-1.70 (m, 1H), 1.51-1.29 (m, 3H).

Example 90: (1S,3R,5S)-2-(2-fluorocyclopropanecarbonyl)-3-methyl-1-({2,3',5'-trifluoro-[1,1'-biphenyl]-3-yl}methyl)-9-oxa-2,6-diazaspiro[4.5]decan-7-one—Cis cPr Diastereomer 1

Example 91: (1S,3R,5S)-2-(2-fluorocyclopropanecarbonyl)-3-methyl-1-({2,3',5'-trifluoro-[1,1'-biphenyl]-3-yl}methyl)-9-oxa-2,6-diazaspiro[4.5]decan-7-one—Cis cPr Diastereomer 2

Example 92: (1S,3R,5S)-2-(2-fluorocyclopropanecarbonyl)-3-methyl-1-({2,3',5'-trifluoro-[1,1'-biphenyl]-3-yl}methyl)-9-oxa-2,6-diazaspiro[4.5]decan-7-one—trans cPr Diastereomer 3 and 4

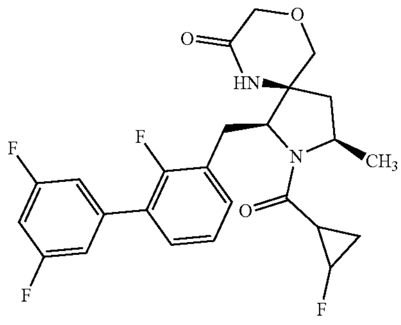

Diast. 1 (Cis on cPr)

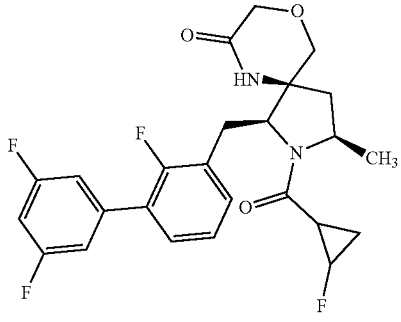

Diast. 2 (Cis on cPr)

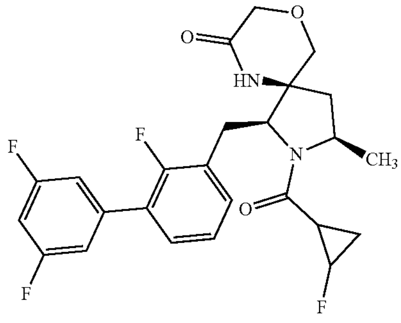

Diast. 3 + 4 (Trans on cPr)

Examples 90, 91, 92 were prepared in similar manner to procedure described for Example 58. The absolute stereochemistry of each compound 90, 91, and 92 was not conclusively determined but assigned as shown below Example 90: Peak 1 (cis isomer 1 at cyclopropyl); $^1$H NMR (400 MHz, $CDCl_3$) δ 7.52-7.14 (m, 3H), 7.16-7.00 (m, 2H), 6.91-6.74 (m, 1H), 6.85-6.47 (m, 1H), 4.97-4.55 (m, 1H), 4.28-3.86 (m, 3H), 4.98-3.74 (m, 1H), 3.76-3.53 (m, 1H), 3.48-3.34 (m, 1H), 3.32-3.05 (m, 1H), 3.01-2.79 (m, 1H), 2.62-2.23 (m, 1H), 1.50 (br d, J=6.1 Hz, 3H), 1.97-1.45 (m, 3H), 1.18-0.72 (m, 1H).

LCMS (Method C): $[M+H]^+$ m/z 476.0, RT 1.01 minutes.

Example 91: Peak 2 (cis isomer 2 at cyclopropyl); $^1$H NMR (400 MHz, $CDCl_3$) δ 7.53-7.24 (m, 2H), 7.24-7.16 (m, 1H), 7.16-6.96 (m, 2H), 6.92-6.74 (m, 1H), 6.49-6.16 (m, 1H), 4.81-4.58 (m, 1H), 4.91-4.48 (m, 1H), 4.20-4.05 (m, 1H), 4.27-3.86 (m, 2H), 3.76-3.62 (m, 1H), 3.49-3.33 (m, 1H), 3.35-3.06 (m, 1H), 3.06-2.70 (m, 1H), 2.53-2.24 (m, 1H), 1.91-1.76 (m, 1H), 2.19-1.64 (m, 1H), 1.53-1.38 (m, 3H), 1.03-0.80 (m, 1H), 1.20-0.64 (m, 1H).

LCMS (Method C): $[M+H]^+$ m/z 476.0, RT 1.02 minutes.

Example 92: Peak 3 (trans isomers 1 and 2 at cyclopropyl); LCMS (Method C): $[M+H]^+$ m/z 476.0, RT 1.05 minutes.

Example 93: (1S,3R,5S)-2-methanesulfonyl-3-methyl-1-({2,3',5'-trifluoro-[1,1'-biphenyl]-3-yl}methyl)-9-oxa-2,6-diazaspiro[4.5]decan-7-one

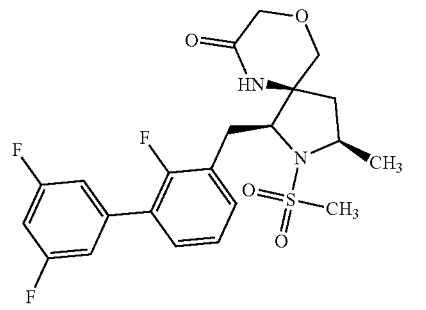 [SMILES: C[C@@H]1C[C@@]2(COCC(=O)N2)[C@H](Cc2cccc(-c3cc(F)cc(F)c3)c2F)N1S(C)(=O)=O]

A stirred solution of Intermediate 87 (50 mg, 0.13 mmol) and triethylamine (27 uL, 0.19 mmol) in dry THF (1.3 mL) was cooled to 0° C., then methanesulfonyl chloride (12 uL, 0.15 mmol) was added. The mixture was stirred for 3 h allowing the temperature to increase gradually. Then the reaction was quenched with water and the water phase was extracted with EtOAc (x3). The combined organic layers were filtered through a phase separator, then concentrated in vacuo. The product was purified by reverse phase flash phase column chromatography (0-65% MeCN in water) to afford the title compound (17 mg) as white solid.

LCMS (Method C): $[M+H]^+$ m/z 469.1, RT 1.02 minutes.

$^1$H NMR (400 MHz, $CDCl_3$) δ 7.39-7.34 (m, 1H), 7.34-7.28 (m, 1H), 7.25-7.19 (m, 1H), 7.13-7.04 (m, 2H), 6.84 (tt, J=8.9, 2.4 Hz, 1H), 6.36 (s, 1H), 4.64 (dd, J=9.4, 5.9 Hz, 1H), 4.18-4.07 (m, 2H), 4.06-3.95 (m, 1H), 3.89 (d, J=11.8 Hz, 1H), 3.50 (d, J=11.8 Hz, 1H), 3.10 (dd, J=13.6, 6.1 Hz, 1H), 2.83 (dd, J=13.6, 9.4 Hz, 1H), 2.35 (s, 3H), 2.41-2.32 (m, 1H), 1.86 (dd, J=13.2, 9.9 Hz, 1H), 1.40 (d, J=6.1 Hz, 3H).

Example 94: IP-1 Accumulation Assay

The accumulation of Inositol-1 Monophosphate (IP-1) was measured using IP-One HTRF® Terbium cryptate based assay (Cisbio) in human recombinant OX1 (hOX1) and at OX2 (hOX2) receptors expressed in CHO cells (DiscoverX) according to the manufacturer's instructions for cells tested in suspension.

hOX1-CHO and hOX2-CHO cells were seeded into white 384-well plates at a density of 20,000 cells/well in Hank's Balanced Salt Solution (HBSS) containing 20 mM HEPES pH 7.4, 50 mM, LiCl and 0.1% and Bovine Serum Albumin (BSA).

Compounds of the present disclosure were tested in a 11 points concentration response curve (CRC) serially diluted in neat DMSO at 200 fold concentrations and added by Echo acoustic liquid handling (Labcyte) to the cells (0.5% DMSO final in the assay). After 60 min of incubation at 37° C. detection reagents, IP1-d2 tracer and anti-IP1-cryptate were diluted in lysis buffer according to the manufacturer's descriptions and added to the cells.

Following 60 min incubation at room temperature, time-resolved fluorescence (HTRF) was measured at 615 nm and 665 nm by Envision Multilabel reader (Perkin Elmer) and the HTRF ratio (A665/A615×$10^4$) was calculated.

The IP-1 accumulation response was expressed as percentage of the maximal OX-A response.

Curve fitting and $EC_{50}$ estimations were carried out using a four-parameter logistic model using XLfit Software. Mean data of $EC_{50}$ are calculated from at least two independent experiments performed in duplicates.

In Table 2, below Category A corresponds to compounds displaying an IC50<100 nM, Category B between 100 nM and 1,000 nM, Category C between 1,000 nM and 10,000 nM and Category D above 10,000 nM.

TABLE 2

EC50 values of compounds at OX2R

| Ex. No. | Structure | Name | Comment | EC50_OX2R Category |
|---|---|---|---|---|
| 1 | 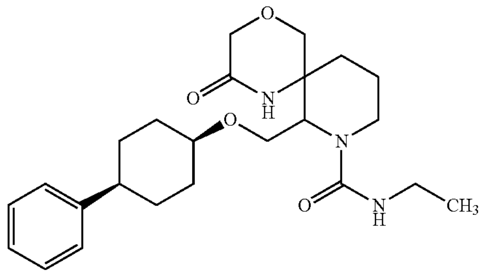 [SMILES: CCNC(=O)N1CCCC2(COCC(=O)N2)C1CO[C@H]1CC[C@@H](c2ccccc2)CC1] | (CIS)-N-ethyl-2-oxo-7-({[(CIS)-4-phenylcyclohexyl]oxy}methyl)-4-oxa-1,8-diazaspiro[5.5]undecane-8-carboxamide | Racemic-CIS | A |
| 2 | 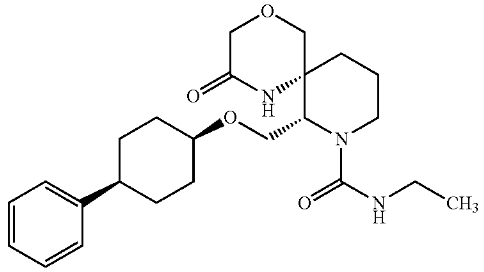 [SMILES: CCNC(=O)N1CCC[C@]2(COCC(=O)N2)[C@H]1CO[C@H]1CC[C@@H](c2ccccc2)CC1] | (6R,7S)-N-ethyl-2-oxo-7-({[(CIS)-4-phenylcyclohexyl]oxy}methyl)-4-oxa-1,8-diazaspiro[5.5]undecane-8-carboxamide | Enantiomer 1 | C |
| 3 | 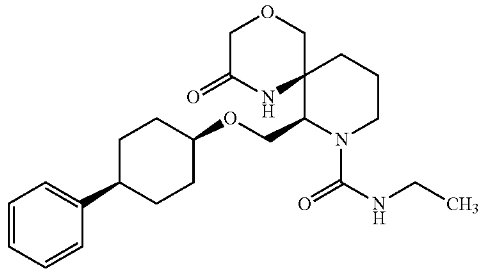 [SMILES: CCNC(=O)N1CCC[C@@]2(COCC(=O)N2)[C@@H]1CO[C@H]1CC[C@@H](c2ccccc2)CC1] | (6S,7R)-N-ethyl-2-oxo-7-({[(CIS)-4-phenylcyclohexyl]oxy}methyl)-4-oxa-1,8-diazaspiro[5.5]undecane-8-carboxamide | Enantiomer 2 | A |
| 4 | 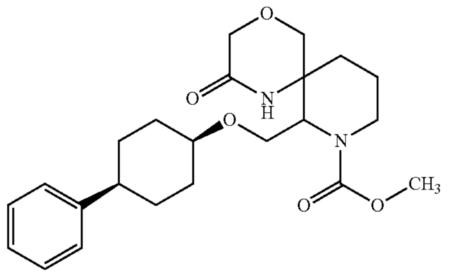 [SMILES: COC(=O)N1CCCC2(COCC(=O)N2)C1CO[C@H]1CC[C@@H](c2ccccc2)CC1] | methyl (CIS)-2-oxo-7-({[(CIS)-4-phenylcyclohexyl]oxy}methyl)-4-oxa-1,8-diazaspiro[5.5]undecane-8-carboxylate | Racemic-CIS | C |

TABLE 2-continued

| EC50 values of compounds at OX2R | | | | |
|---|---|---|---|---|
| Ex. No. | Structure | Name | Comment | EC50_OX2R Category |
| 5 | 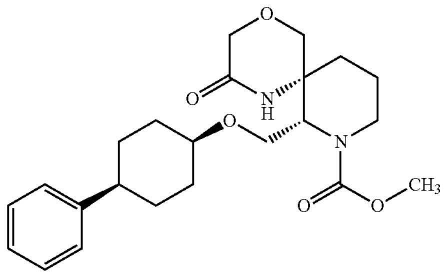 [SMILES: COC(=O)N1CCC[C@]2(COCC(=O)N2)[C@H]1CO[C@H]1CC[C@@H](c2ccccc2)CC1] | methyl (6R,7S)-2-oxo-7-({[(CIS)-4-phenylcyclohexyl]oxy}methyl)-4-oxa-1,8-diazaspiro[5.5]undecane-8-carboxylate | Enantiomer 1 | D |
| 6 | 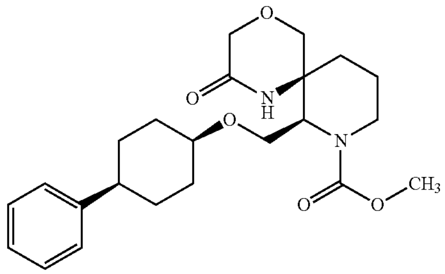 [SMILES: COC(=O)N1CCC[C@@]2(COCC(=O)N2)[C@@H]1CO[C@H]1CC[C@@H](c2ccccc2)CC1] | methyl (6S,7R)-2-oxo-7-({[(CIS)-4-phenylcyclohexyl]oxy}methyl)-4-oxa-1,8-diazaspiro[5.5]undecane-8-carboxylate | Enantiomer 2 | B |
| 7 | 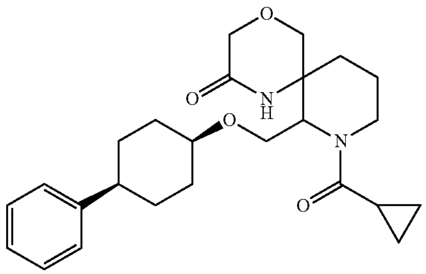 [SMILES: O=C1COCC2(CCCN(C(=O)C3CC3)C2CO[C@H]2CC[C@@H](c3ccccc3)CC2)N1] | (CIS)-8-cyclopropanecarbonyl-7-({[(CIS)-4-phenylcyclohexyl]oxy}methyl)-4-oxa-1,8-diazaspiro[5.5]undecan-2-one | Racemic-CIS | B |
| 8 | 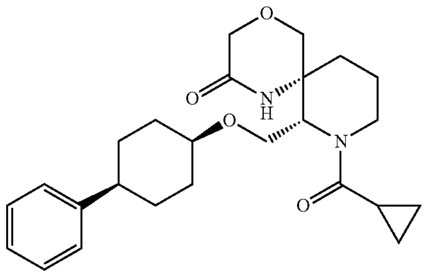 [SMILES: O=C1COC[C@]2(CCCN(C(=O)C3CC3)[C@@H]2CO[C@H]2CC[C@@H](c3ccccc3)CC2)N1] | (6R,7S)-8-cyclopropanecarbonyl-7-({[(CIS)-4-phenylcyclohexyl]oxy}methyl)-4-oxa-1,8-diazaspiro[5.5]undecan-2-one | Enantiomer 1 | D |
| 9 | 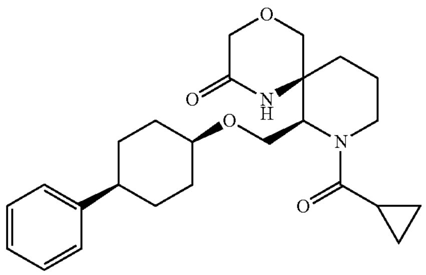 [SMILES: O=C1COC[C@@]2(CCCN(C(=O)C3CC3)[C@H]2CO[C@H]2CC[C@@H](c3ccccc3)CC2)N1] | (6S,7R)-8-cyclopropanecarbonyl-7-({[(CIS)-4-phenylcyclohexyl]oxy}methyl)-4-oxa-1,8-diazaspiro[5.5]undecan-2-one | Enantiomer 2 | B |

TABLE 2-continued

| EC50 values of compounds at OX2R | | | | |
|---|---|---|---|---|
| Ex. No. | Structure | Name | Comment | EC50_OX2R Category |
| 10 | 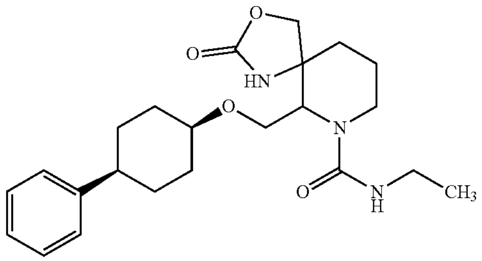 [SMILES: CCNC(=O)N1CCCC2(COC(=O)N2)C1CO[C@H]1CC[C@@H](c2ccccc2)CC1] | (CIS)-N-ethyl-2-oxo-6-({[(CIS)-4-phenylcyclohexyl]oxy}methyl)-3-oxa-1,7-diazaspiro[4.5]decane-7-carboxamide | Racemic-CIS | C |
| 11 | 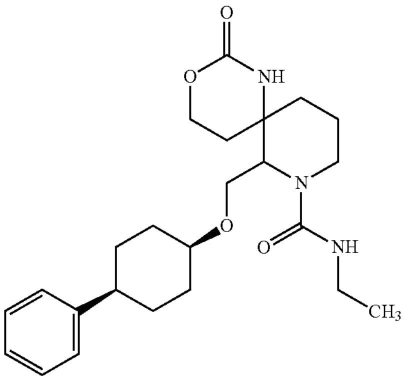 [SMILES: CCNC(=O)N1CCCC2(CCOC(=O)N2)C1CO[C@H]1CC[C@@H](c2ccccc2)CC1] | (CIS)-N-ethyl-2-oxo-7-({[(CIS)-4-phenylcyclohexyl]oxy}methyl)-3-oxa-1,8-diazaspiro[5.5]undecane-8-carboxamide | Cis relative | A |
| 12 | 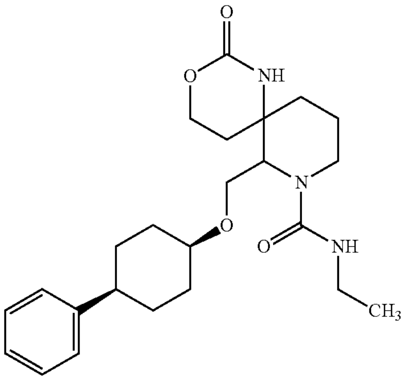 [SMILES: CCNC(=O)N1CCCC2(CCOC(=O)N2)C1CO[C@H]1CC[C@@H](c2ccccc2)CC1] | (Trans)-N-ethyl-2-oxo-7-({[(CIS)-4-phenylcyclohexyl]oxy}methyl)-3-oxa-1,8-diazaspiro[5.5]undecane-8-carboxamide | Trans relative | C |
| 13 | 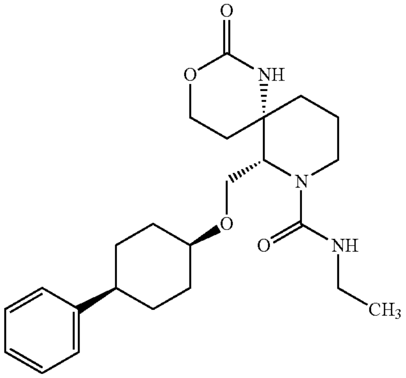 [SMILES: CCNC(=O)N1CCC[C@]2(CCOC(=O)N2)[C@H]1CO[C@H]1CC[C@@H](c2ccccc2)CC1] | (6S,7S)-N-ethyl-2-oxo-7-({[(CIS)-4-phenylcyclohexyl]oxy}methyl)-3-oxa-1,8-diazaspiro[5.5]undecane-8-carboxamide | Enantiomer 1 | D |

TABLE 2-continued

| EC50 values of compounds at OX2R | | | | |
|---|---|---|---|---|
| Ex. No. | Structure | Name | Comment | EC50_OX2R Category |
| 14 | 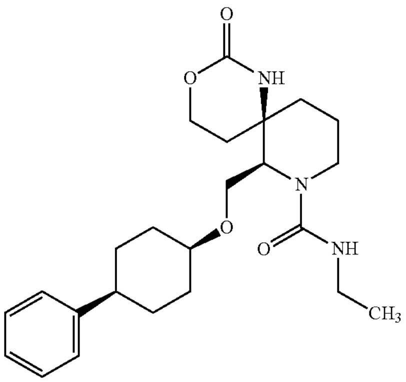 [SMILES: CCNC(=O)N1CCC[C@@]2(CCOC(=O)N2)[C@@H]1CO[C@H]1CC[C@@H](c2ccccc2)CC1] | (6R,7R)-N-ethyl-2-oxo-7-({[(CIS)-4-phenylcyclohexyl]oxy}methyl)-3-oxa-1,8-diazaspiro[5.5]undecane-8-carboxamide | Enantiomer 2 | A |
| 15 | 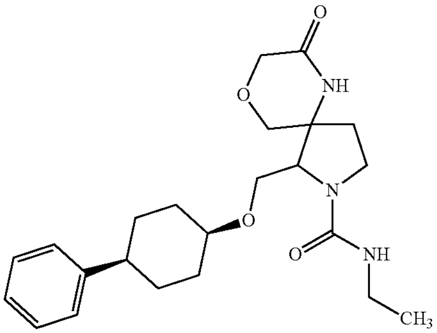 [SMILES: CCNC(=O)N1CCC2(COCC(=O)N2)C1CO[C@H]1CC[C@@H](c2ccccc2)CC1] | (CIS)-N-ethyl-7-oxo-1-({[(CIS)-4-phenylcyclohexyl]oxy}methyl)-9-oxa-2,6-diazaspiro[4.5]decane-2-carboxamide | Cis racemic | C |
| 16 | 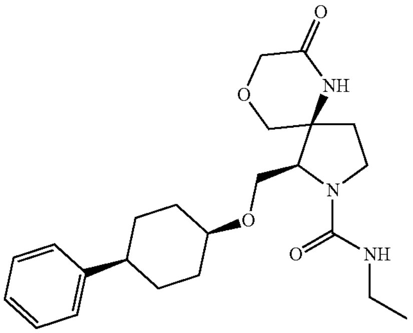 [SMILES: CCNC(=O)N1CC[C@@]2(COCC(=O)N2)[C@@H]1CO[C@H]1CC[C@@H](c2ccccc2)CC1] | (1R,5S)-N-ethyl-7-oxo-1-({[(CIS)-4-phenylcyclohexyl]oxy}methyl)-9-oxa-2,6-diazaspiro[4.5]decane-2-carboxamide | Enantiomer 1 | B |
| 17 | 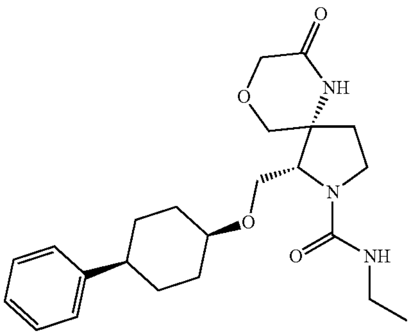 [SMILES: CCNC(=O)N1CC[C@]2(COCC(=O)N2)[C@H]1CO[C@H]1CC[C@@H](c2ccccc2)CC1] | (1R,5S)-N-ethyl-7-oxo-1-({[(CIS)-4-phenylcyclohexyl]oxy}methyl)-9-oxa-2,6-diazaspiro[4.5]decane-2-carboxamide | Enantiomer 2 | D |

TABLE 2-continued

EC50 values of compounds at OX2R

| Ex. No. | Structure | Name | Comment | EC50_OX2R Category |
|---|---|---|---|---|
| 18 | 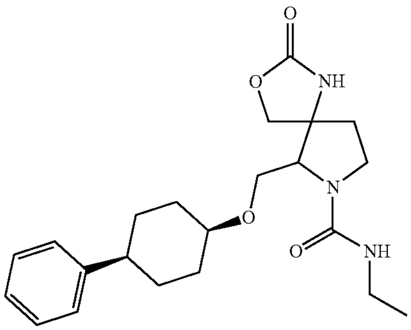 [SMILES: CCNC(=O)N1CCC2(COC(=O)N2)C1CO[C@H]1CC[C@@H](c2ccccc2)CC1] | (CIS)-N-ethyl-2-oxo-6-({[(CIS)-4-phenylcyclohexyl]oxy}methyl)-3-oxa-1,7-diazaspiro[4.4]nonane-7-carboxamide | Cis racemic | D |
| 19 | 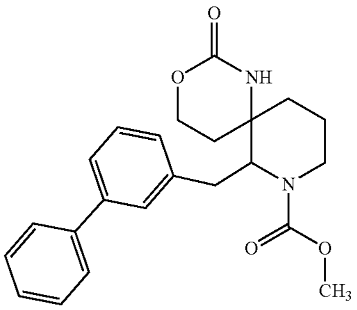 [SMILES: COC(=O)N1CCCC2(CCOC(=O)N2)C1Cc1cccc(-c2ccccc2)c1] | methyl 7-({[1,1'-biphenyl]-3-yl}methyl)-2-oxo-3-oxa-1,8-diazaspiro[5.5]undecane-8-carboxylate | mix of 4 isomers (77:22 cis:trans) | D |
| 20 | 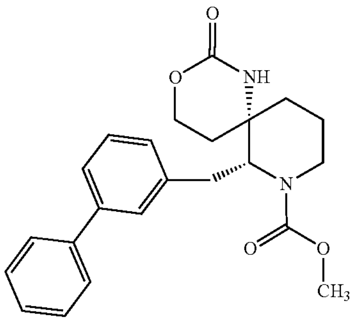 [SMILES: COC(=O)N1CCC[C@]2(CCOC(=O)N2)[C@H]1Cc1cccc(-c2ccccc2)c1] Diastereomer 1 | methyl (6R,7S)-7-({[1,1'-biphenyl]-3-yl}methyl)-2-oxo-3-oxa-1,8-diazaspiro[5.5]undecane-8-carboxylate | stereochemistry assigned as shown | D |
| 21 | 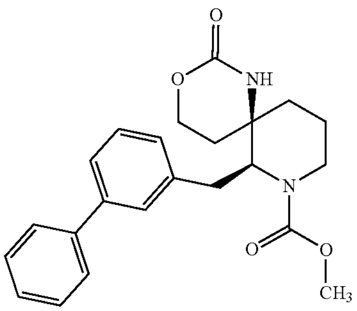 [SMILES: COC(=O)N1CCC[C@@]2(CCOC(=O)N2)[C@@H]1Cc1cccc(-c2ccccc2)c1] Diastereomer 2 | methyl (6S,7R)-7-({[1,1'-biphenyl]-3-yl }methyl)-2-oxo-3-oxa-1,8-diazaspiro[5.5]undecane-8-carboxylate | stereochemistry assigned as shown | D |

TABLE 2-continued

EC50 values of compounds at OX2R

| Ex. No. | Structure | Name | Comment | EC50_OX2R Category |
|---|---|---|---|---|
| 22 | 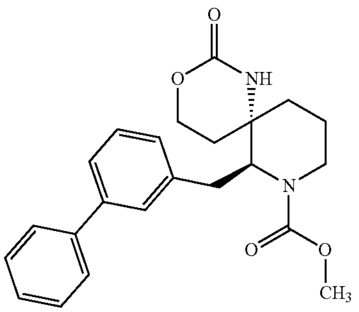 [SMILES: COC(=O)N1CCC[C@]2(CCOC(=O)N2)[C@@H]1Cc1cccc(-c2ccccc2)c1] Diastereomer 3 | methyl (6R,7R)-7-({[1,1'-biphenyl]-3-yl}methyl)-2-oxo-3-oxa-1,8-diazaspiro[5.5]undecane-8-carboxylate | stereochemistry assigned as shown | D |
| 23 | 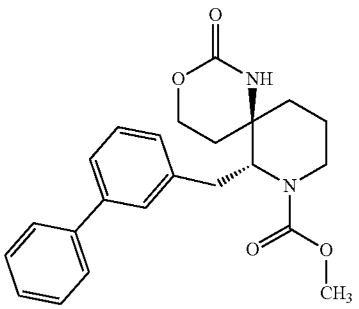 [SMILES: COC(=O)N1CCC[C@@]2(CCOC(=O)N2)[C@H]1Cc1cccc(-c2ccccc2)c1] Diastereomer 4 | methyl (6S,7S)-7-({[1,1'-biphenyl]-3-yl}methyl)-2-oxo-3-oxa-1,8-diazaspiro[5.5]undecane-8-carboxylate | stereochemistry assigned as shown | D |
| 24 | 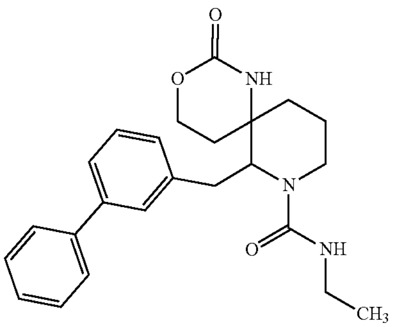 [SMILES: CCNC(=O)N1CCCC2(CCOC(=O)N2)C1Cc1cccc(-c2ccccc2)c1] | (CIS)-7-({[1,1'-biphenyl]-3-yl}methyl)-N-ethyl-2-oxo-3-oxa-1,8-diazaspiro[5.5]undecane-8-carboxamide | Racemic cis | C |
| 25 | 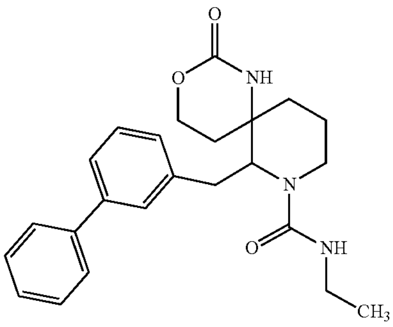 [SMILES: CCNC(=O)N1CCCC2(CCOC(=O)N2)C1Cc1cccc(-c2ccccc2)c1] | (Trans)-7-({[1,1'-biphenyl]-3-yl}methyl)-N-ethyl-2-oxo-3-oxa-1,8-diazaspiro[5.5]undecane-8-carboxamide | Racemic Trans | D |

TABLE 2-continued

EC50 values of compounds at OX2R

| Ex. No. | Structure | Name | Comment | EC50_OX2R Category |
|---|---|---|---|---|
| 26 | 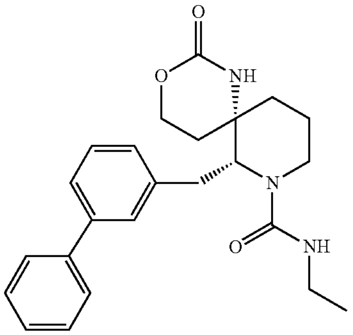 [SMILES: CCNC(=O)N1CCC[C@]2(CCOC(=O)N2)[C@H]1Cc1cccc(-c2ccccc2)c1] | (6S,7R)-7-({[1,1'-biphenyl]-3-yl}methyl)-N-ethyl-2-oxo-3-oxa-1,8-diazaspiro[5.5]undecane-8-carboxamide | stereochemistry assigned as shown-Enatiomer 1 | D |
| 27 | 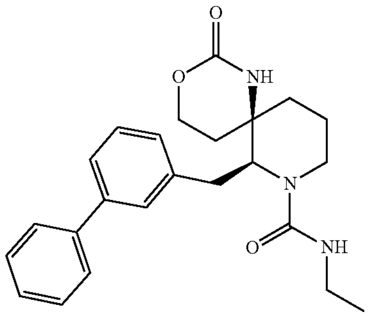 [SMILES: CCNC(=O)N1CCC[C@@]2(CCOC(=O)N2)[C@@H]1Cc1cccc(-c2ccccc2)c1] | (6R,7S)-7-({[1,1'-biphenyl]-3-yl}methyl)-N-ethyl-2-oxo-3-oxa-1,8-diazaspiro[5.5]undecane-8-carboxamide | stereochemistry assigned as shown-Enatiomer 2 | B |
| 28 | 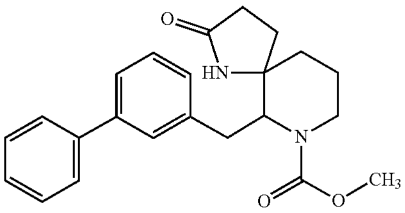 [SMILES: COC(=O)N1CCCC2(CCC(=O)N2)C1Cc1cccc(-c2ccccc2)c1] | Methyl 6-({[1,1'-biphenyl]-3-yl}methyl)-2-oxo-1,7-diazaspiro[4.5]decane-7-carboxylate | Mixture of diastereoisomers | D |
| 29 | 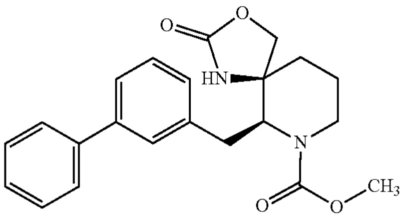 [SMILES: COC(=O)N1CCC[C@@]2(COC(=O)N2)[C@@H]1Cc1cccc(-c2ccccc2)c1] | Methyl (5S,6S)-6-({[1,1'-biphenyl]-3-yl}methyl)-2-oxo-3-oxa-1,7-diazaspiro[4.5]decane-7-carboxylate | Enantiomer | D |
| 30 | 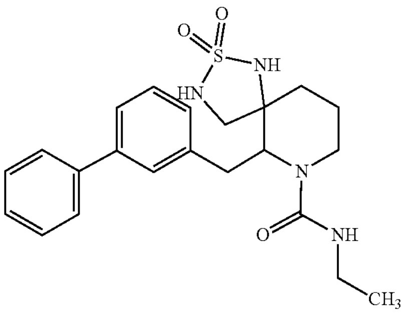 [SMILES: CCNC(=O)N1CCCC2(CNS(=O)(=O)N2)C1Cc1cccc(-c2ccccc2)c1] | (CIS)-6-({[1,1'-biphenyl]-3-yl}methyl)-N-ethyl-2,2-dioxo-2$\lambda^6$-thia-1,3,7-triazaspiro[4.5]decane-7-carboxamide | Mix of Cis enantiomers | D |

TABLE 2-continued

| EC50 values of compounds at OX2R | | | | |
|---|---|---|---|---|
| Ex. No. | Structure | Name | Comment | EC50_OX2R Category |
| 31 | 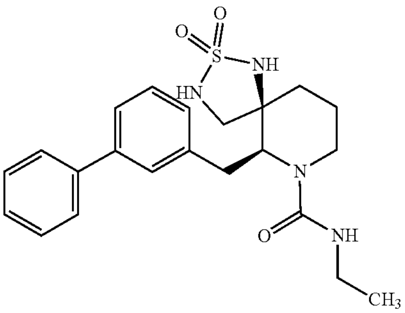 [SMILES: CCNC(=O)N1CCC[C@@]2(CNS(=O)(=O)N2)[C@@H]1Cc1cccc(-c2ccccc2)c1] | (5R,6S)-6-({[1,1'-biphenyl]-3-yl}methyl)-N-ethyl-2,2-dioxo-2λ$^6$-thia-1,3,7-triazaspiro[4.5]decane-7-carboxamide | Enatiomer 1 | D |
| 32 | 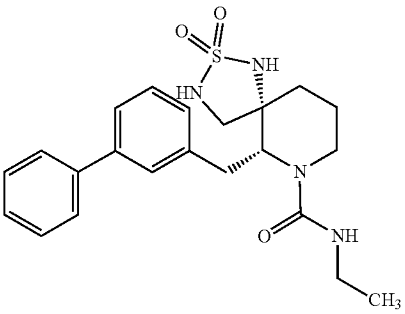 [SMILES: CCNC(=O)N1CCC[C@]2(CNS(=O)(=O)N2)[C@H]1Cc1cccc(-c2ccccc2)c1] | (5S,6R)-6-({[1,1'-biphenyl]-3-yl}methyl)-N-ethyl-2,2-dioxo-2λ$^6$-thia-1,3,7-triazaspiro[4.5]decane-7-carboxamide | Enatiomer 2 | D |
| 33 | 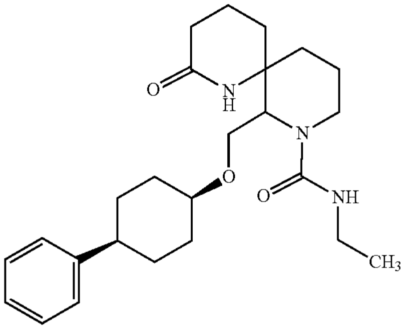 [SMILES: CCNC(=O)N1CCCC2(CCCC(=O)N2)C1CO[C@H]1CC[C@@H](c2ccccc2)CC1] | rel-(6S,7R)-N-ethyl-2-oxo-7-({[(1s,4s)-4-phenylcyclohexyl]oxy}methyl)-1,8-diazaspiro[5.5]undecane-8-carboxamide | Mix of Cis enantiomers | A |
| 34 | 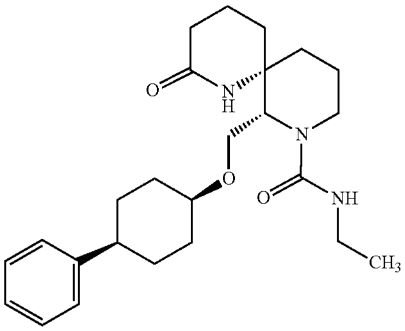 [SMILES: CCNC(=O)N1CCC[C@]2(CCCC(=O)N2)[C@H]1CO[C@H]1CC[C@@H](c2ccccc2)CC1] | (6R,7S)-N-ethyl-2-oxo-7-({[(CIS)-4-phenylcyclohexyl]oxy}methyl)-1,8-diazaspiro[5.5]undecane-8-carboxamide | Enatiomer 1 | D |

TABLE 2-continued

| EC50 values of compounds at OX2R | | | | |
|---|---|---|---|---|
| Ex. No. | Structure | Name | Comment | EC50_OX2R Category |
| 35 | 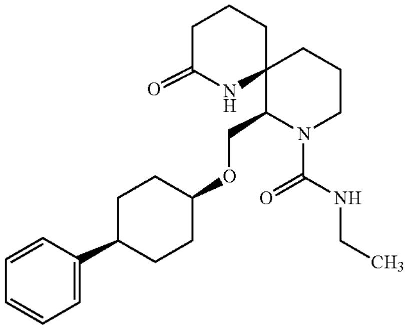 [SMILES: CCNC(=O)N1CCC[C@@]2(CCCC(=O)N2)[C@@H]1CO[C@H]1CC[C@@H](c2ccccc2)CC1] | (6S,7R)-N-ethyl-2-oxo-7-({[(CIS)-4-phenylcyclohexyl]oxy}methyl)-1,8-diazaspiro[5.5]undecane-8-carboxamide | Enatiomer 2 | A |
| 36 | 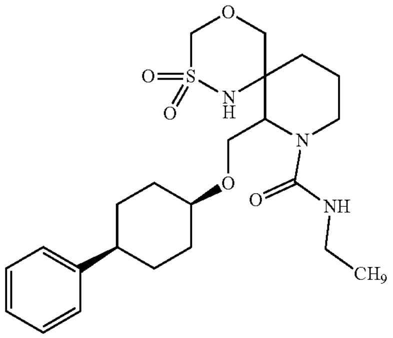 | rel-(6S,7R)-N-ethyl-2,2-dioxo-7-({[(1s,4s)-4-phenylcyclohexyl]oxy}methyl)-4-oxa-2λ$^6$-thia-1,8-diazaspiro[5.5]undecane-8-carboxamide | Mix of Cis enantiomers | B |
| 37 | 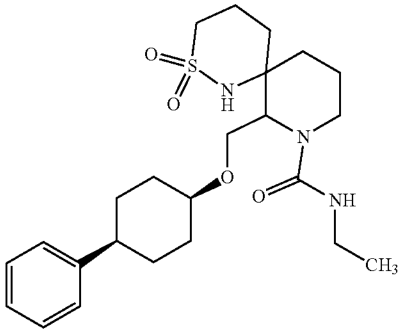 [SMILES: CCNC(=O)N1CCCC2(CCCS(=O)(=O)N2)C1CO[C@H]1CC[C@@H](c2ccccc2)CC1] | rel-(6R,7R)-N-ethyl-2,2-dioxo-7-({[(1s,4s)-4-phenylcyclohexyl]oxy}methyl)-2λ$^6$-thia-1,8-diazaspiro[5.5]undecane-8-carboxamide | Mix of Cis enantiomers | B |
| 38 | 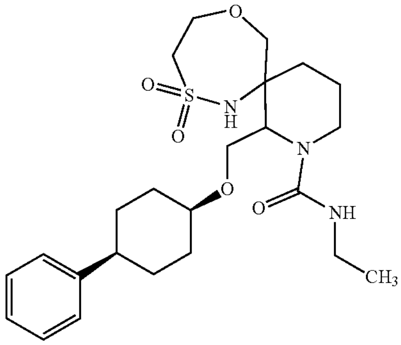 [SMILES: CCNC(=O)N1CCCC2(COCCS(=O)(=O)N2)C1CO[C@H]1CC[C@@H](c2ccccc2)CC1] | rel-(1R,6S)-N-ethyl-8,8-dioxo-1-({[(1s,4s)-4-phenylcyclohexyl]oxy}methyl)-11-oxa-8λ$^6$-thia-2,7-diazaspiro[5.6]dodecane-2-carboxamide | Mix of Cis enantiomers | B |

TABLE 2-continued

EC50 values of compounds at OX2R

| Ex. No. | Structure | Name | Comment | EC50_OX2R Category |
|---|---|---|---|---|
| 39 | 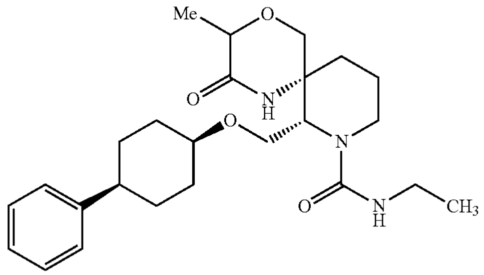 | (6S,7R)-N-ethyl-3-methyl-2-oxo-7-({[(1s,4s)-4-phenylcyclohexyl]oxy}methyl)-4-oxa-1,8-diazaspiro[5.5]undecane-8-carboxamide | Mixture of diastereomers | D |
| 40 | 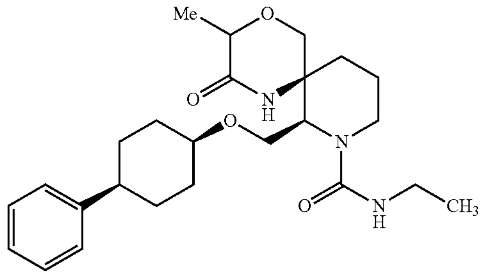 | (6R,7S)-N-ethyl-3-methyl-2-oxo-7-({[(1s,4s)-4-phenylcyclohexyl]oxy}methyl)-4-oxa-1,8-diazaspiro[5.5]undecane-8-carboxamide | Mixture of diastereomers | A |
| 41 | 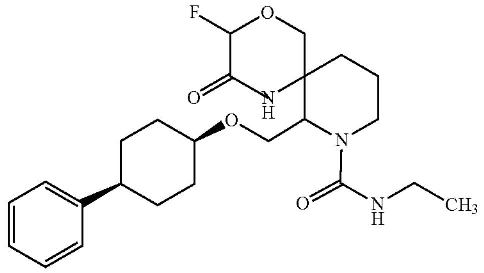 [SMILES: CCNC(=O)N1CCCC(N)(COC(F)C(C)=O)C1CO[C@H]1CC[C@@H](c2ccccc2)CC1] | rel-(6R,7S)-N-ethyl-3-fluoro-2-oxo-7-({[(CIS)-4-phenylcyclohexyl]oxy}methyl)-4-oxa-1,8-diazaspiro[5.5]undecane-8-carboxamide | Mix of diastereomers | A |
| 42 | 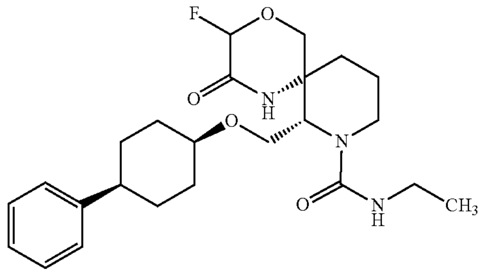 | (6R,7S)-N-ethyl-3-fluoro-2-oxo-7-({[(CIS)-4-phenylcyclohexyl]oxy}methyl)-4-oxa-1,8-diazaspiro[5.5]undecane-8-acarboxamide | Isomer 1 | C |
| 43 | 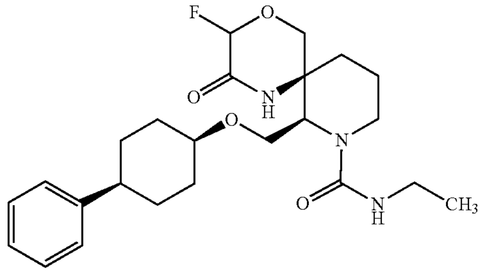 | (6S,7R)-N-ethyl-3-fluoro-2-oxo-7-({[(CIS)-4-phenylcyclohexyl]oxy}methyl)-4-oxa-1,8-diazaspiro[5.5]undecane-8-carboxamide | Isomer 2 | A |

TABLE 2-continued

| EC50 values of compounds at OX2R | | | | |
|---|---|---|---|---|
| Ex. No. | Structure | Name | Comment | EC50_OX2R Category |
| 44 | 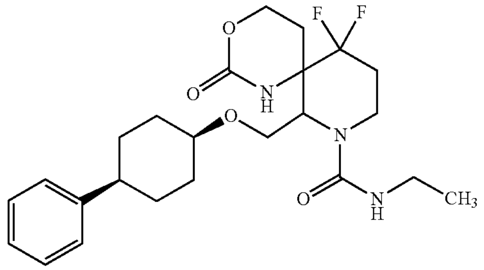 [SMILES: CCNC(=O)N1CCC(F)(F)C2(CCOC(=O)N2)C1CO[C@H]1CC[C@@H](c2ccccc2)CC1] | N-ethyl-8-oxo-1-({[(CIS)-4-phenylcyclohexyl]oxy}methyl)-11-oxa-2,7-diazaspiro[5.6]dodecane-2-carboxamide | Mix of CIS enantiomers | A |
| 45 | 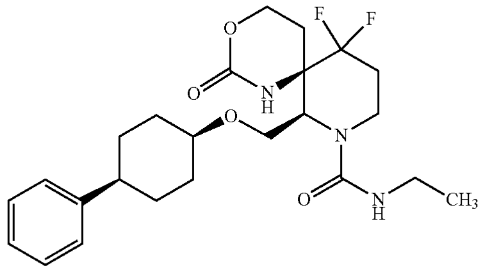 [SMILES: CCNC(=O)N1CCC(F)(F)[C@@]2(CCOC(=O)N2)[C@@H]1CO[C@H]1CC[C@@H](c2ccccc2)CC1] | (6R,7R)-N-ethyl-11,11-difluoro-2-oxo-7-({[(CIS)-4-phenylcyclohexyl]oxy}methyl)-3-oxa-1,8-diazaspiro[5.5]undecane-8-carboxamide | Enantiomer 1 | A |
| 46 | 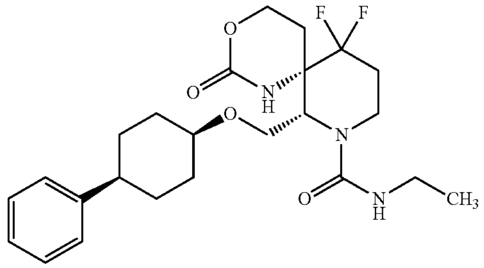 [SMILES: CCNC(=O)N1CCC(F)(F)[C@]2(CCOC(=O)N2)[C@H]1CO[C@H]1CC[C@@H](c2ccccc2)CC1] | (6S,7S)-N-ethyl-11,11-difluoro-2-oxo-7-({[(CIS)-4-phenylcyclohexyl]oxy}methyl)-3-oxa-1,8-diazaspiro[5.5]undecane-8-carboxamide | Enantiomer 2 | D |
| 47 | 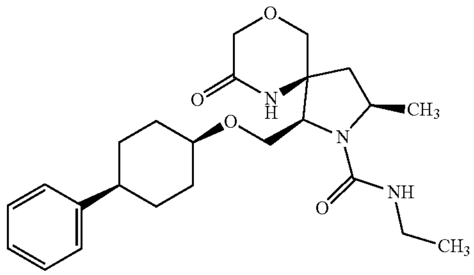 [SMILES: CCNC(=O)N1[C@H](C)C[C@@]2(COCC(=O)N2)[C@@H]1CO[C@H]1CC[C@@H](c2ccccc2)CC1] | (1R,3R,5S)-N-ethyl-3-methyl-7-oxo-1-({[(CIS)-4-phenylcyclohexyl]oxy}methyl)-9-oxa-2,6-diazaspiro[4.5]decane-2-carboxamide | | A |
| 48 | 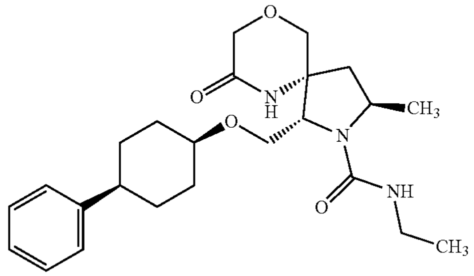 [SMILES: CCNC(=O)N1[C@H](C)C[C@]2(COCC(=O)N2)[C@H]1CO[C@H]1CC[C@@H](c2ccccc2)CC1] | (1S,3R,5R)-N-ethyl-3-methyl-7-oxo-1-({[(CIS)-4-phenylcyclohexyl]oxy}methyl)-9-oxa-2,6-diazaspiro[4.5]decane-2-carboxamide | | D |

TABLE 2-continued

EC50 values of compounds at OX2R

| Ex. No. | Structure | Name | Comment | EC50_OX2R Category |
|---|---|---|---|---|
| 49 | 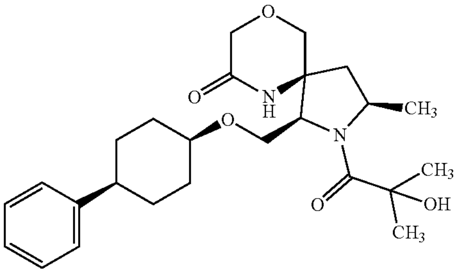 [SMILES: C[C@@H]1C[C@@]2(COCC(=O)N2)[C@H](CO[C@H]2CC[C@@H](c3ccccc3)CC2)N1C(=O)C(C)(C)O] | (1R,3R,5S)-2-(2-hydroxy-2-methylpropanoyl)-3-methyl-1-({[(CIS)-4-phenylcyclohexyl]oxy}methyl)-9-oxa-2,6-diazaspiro[4.5]decan-7-one | | C |
| 50 | 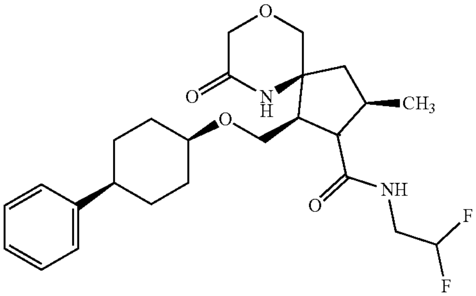 | (1R,3R,5S)-N-(2,2-difluoroethyl)-3-methyl-7-oxo-1-({[(CIS)-4-phenylcyclohexyl]oxy}methyl)-9-oxa-2,6-diazaspiro[4.5]decane-2-carboxamide | | A |
| 51 | 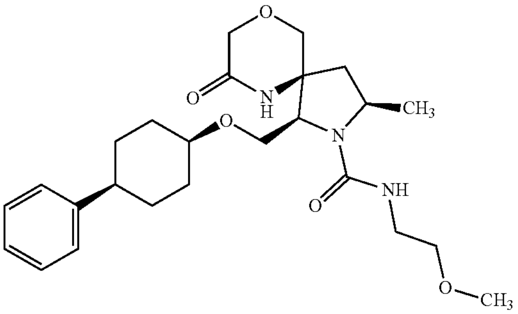 [SMILES: COCCNC(=O)N1[C@H](C)C[C@@]2(COCC(=O)N2)[C@@H]1CO[C@H]1CC[C@@H](c2ccccc2)CC1] | (1R,3R,5S)-N-(2-methoxyethyl)-3-methyl-7-oxo-1-({[(CIS)-4-phenylcyclohexyl]oxy}methyl)-9-oxa-2,6-diazaspiro[4.5]decane-2-carboxamide | | A |
| 52 | 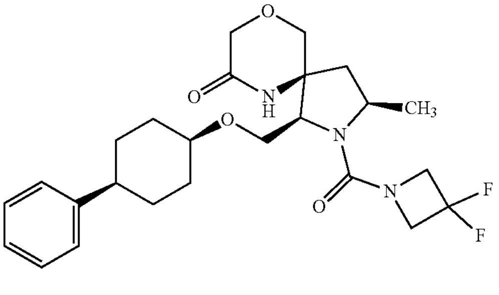 [SMILES: C[C@@H]1C[C@@]2(COCC(=O)N2)[C@H](CO[C@H]2CC[C@@H](c3ccccc3)CC2)N1C(=O)N1CC(F)(F)C1] | (1R,3R,5S)-2-(3,3-difluoroazetidine-1-carbonyl)-3-methyl-1-({[(CIS)-4-phenylcyclohexyl]oxy}methyl)-9-oxa-2,6-diazaspiro[4.5]decan-7-one | | C |

TABLE 2-continued

| EC50 values of compounds at OX2R | | | | |
|---|---|---|---|---|
| Ex. No. | Structure | Name | Comment | EC50_OX2R Category |
| 53 | 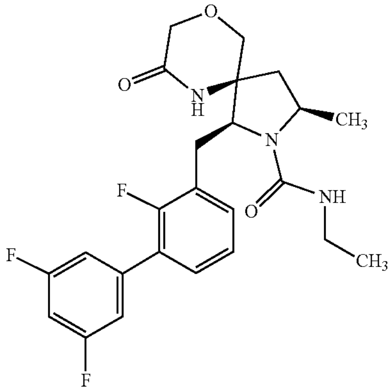 [SMILES: CCNC(=O)N1[C@H](C)C[C@@]2(COCC(=O)N2)[C@@H]1Cc1cccc(-c2cc(F)cc(F)c2)c1F] | (1S,3R,5S)-N-ethyl-3-methyl-7-oxo-1-({2,3',5'-trifluoro-[1,1'-biphenyl]-3-yl}methyl)-9-oxa-2,6-diazaspiro[4.5]decane-2-carboxamide | | A |
| 54 | 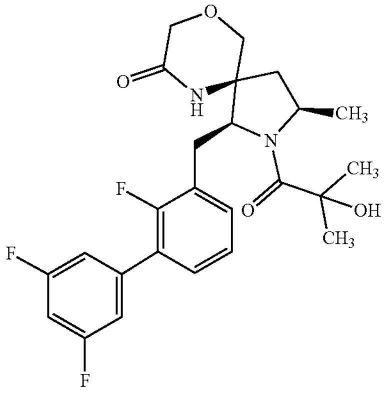 [SMILES: C[C@@H]1C[C@@]2(COCC(=O)N2)[C@H](Cc2cccc(-c3cc(F)cc(F)c3)c2F)N1C(=O)C(C)(C)O] | (1S,3R,5S)-2-(2-hydroxy-2-methylpropanoyl)-3-methyl-1-({2,3',5'-trifluoro-[1,1'-biphenyl]-3-yl}methyl)-9-oxa-2,6-diazaspiro[4.5]decan-7-one | | B |
| 55 | 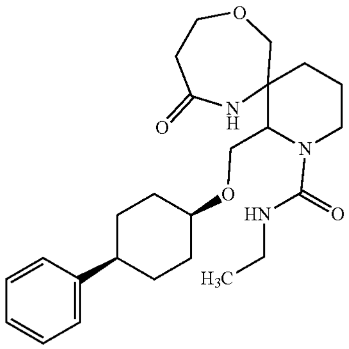 [SMILES: CCNC(=O)N1CCCC2(COCCC(=O)N2)C1CO[C@H]1CC[C@@H](c2ccccc2)CC1] | rel-(1R,6S)-N-ethyl-8-oxo-1-({[(CIS)-4-phenylcyclohexyl]oxy}methyl)-11-oxa-2,7-diazaspiro[5.6]dodecane-2-carboxamide | Mixture of enantiome | A |
| 56 | 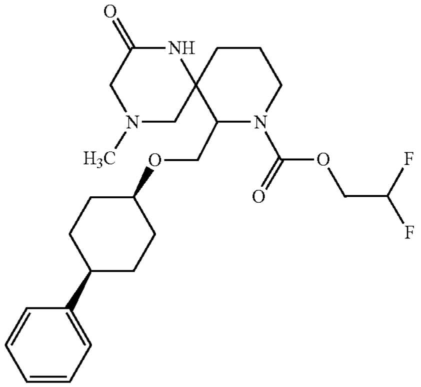 [SMILES: CN1CC(=O)NC2(CCCN(C(=O)OCC(F)F)C2CO[C@H]2CC[C@@H](c3ccccc3)CC2)C1] | 2,2-difluoroethyl-rel-(6R,7R)-4-methyl-2-oxo-7-({[(1s,4s)-4-phenylcyclohexyl]oxy}methyl)-1,4,8-triazaspiro[5.5]undecane-8-carboxylate | Mixture of enantiomers | B |

TABLE 2-continued

| EC50 values of compounds at OX2R | | | | |
|---|---|---|---|---|
| Ex. No. | Structure | Name | Comment | EC50_OX2R Category |
| 57 | 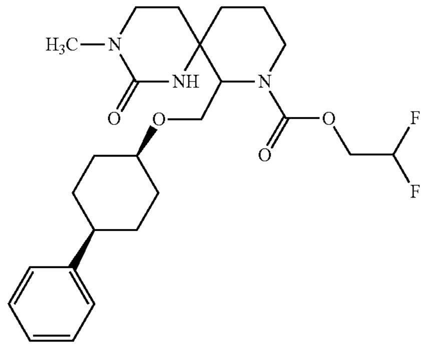 [SMILES: CN1CCC2(CCCN(C(=O)OCC(F)F)C2CO[C@H]2CC[C@@H](c3ccccc3)CC2)NC1=O] | 2,2-difluoroethyl-rel-(6R,7R)-3-methyl-2-oxo-7-({[(1s,4s)-4-phenylcyclohexyl]oxy}methyl)-1,3,8-triazaspiro[5.5]undecane-8-carboxylate | Mixture of enantiomers | D |
| 58 | 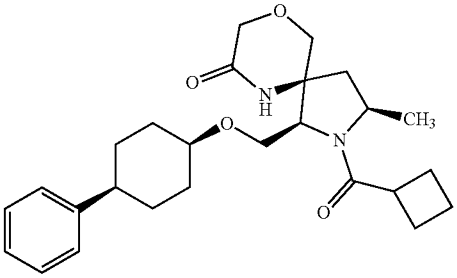 [SMILES: C[C@@H]1C[C@@]2(COCC(=O)N2)[C@H](CO[C@H]2CC[C@@H](c3ccccc3)CC2)N1C(=O)C1CCC1] | (1R,3R,5S)-2-cyclobutanecarbonyl-3-methyl-1-({[(CIS)-4-phenylcyclohexyl]oxy}methyl)-9-oxa-2,6-diazaspiro[4.5]decan-7-one | | A |
| 59 | 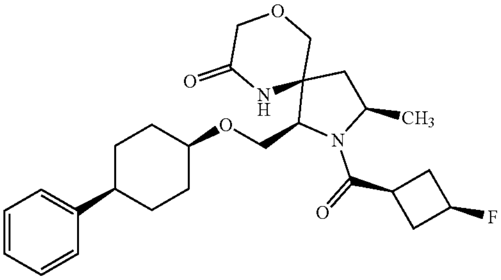 [SMILES: C[C@@H]1C[C@@]2(COCC(=O)N2)[C@H](CO[C@H]2CC[C@@H](c3ccccc3)CC2)N1C(=O)[C@H]1C[C@@H](F)C1] | (1R,3R,5S)-3-methyl-2-[(CIS)-3-fluorocyclobutanecarbonyl]-1-({[(CIS)-4-phenylcyclohexyl]oxy}methyl)-9-oxa-2,6-diazaspiro[4.5]decan-7-one | | A |
| 60 | 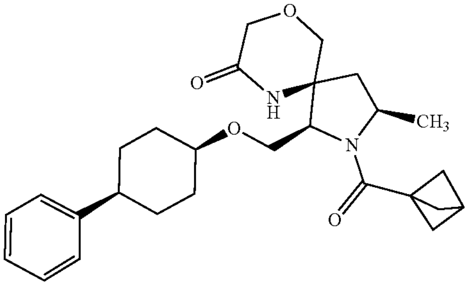 [SMILES: C[C@@H]1C[C@@]2(COCC(=O)N2)[C@H](CO[C@H]2CC[C@@H](c3ccccc3)CC2)N1C(=O)C12CC(C1)C2] | (1R,3R,5S)-2-{bicyclo[1.1.1]pentane-1-carbonyl}-3-methyl-1-({[(CIS)-4-phenylcyclohexyl]oxy}methyl)-9-oxa-2,6-diazaspiro[4.5]decan-7-one | | C |
| 61 | 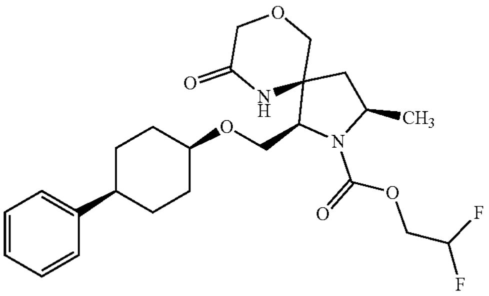 [SMILES: C[C@@H]1C[C@@]2(COCC(=O)N2)[C@H](CO[C@H]2CC[C@@H](c3ccccc3)CC2)N1C(=O)OCC(F)F] | 2,2-difluoroethyl (1R,3R,5S)-3-methyl-7-oxo-1-({[(CIS)-4-phenylcyclohexyl]oxy}methyl)-9-oxa-2,6-diazaspiro[4.5]decane-2-carboxylate | | A |

TABLE 2-continued

EC50 values of compounds at OX2R

| Ex. No. | Structure | Name | Comment | EC50_OX2R Category |
|---|---|---|---|---|
| 62 | 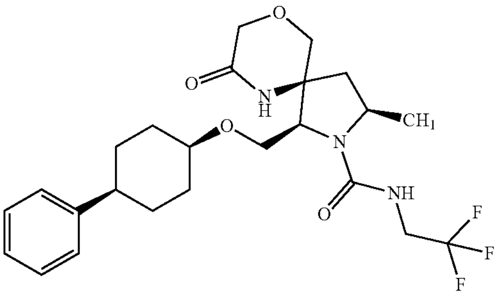 | (1R,3R,5S)-3-methyl-7-oxo-1-({[(CIS)-4-phenylcyclohexyl]oxy}methyl)-N-(2,2,2-trifluoroethyl)-9-oxa-2,6-diazaspiro[4.5]decane-2-carboxamide | | A |
| 63 | 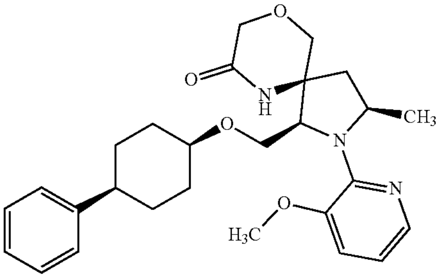 [SMILES: COc1cccnc1N1[C@H](C)C[C@@]2(COCC(=O)N2)[C@@H]1CO[C@H]1CC[C@@H](c2ccccc2)CC1] | (1R,3R,5S)-2-(3-methoxypyridin-2-yl)-3-methyl-1-({[(CIS)-4-phenylcyclohexyl]oxy}methyl)-9-oxa-2,6-diazaspiro[4.5]decan-7-one | | B |
| 64 | 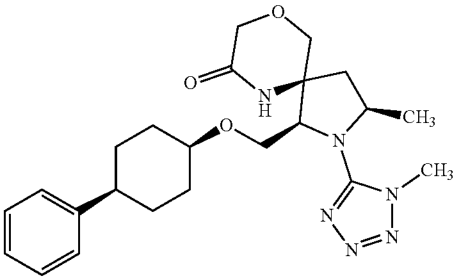 [SMILES: C[C@@H]1C[C@@]2(COCC(=O)N2)[C@H](CO[C@H]2CC[C@@H](c3ccccc3)CC2)N1c1nnnn1C] | (1R,3R,5S)-3-methyl-2-(1-methyl-1H-1,2,3,4-tetrazol-5-yl)-1-({[(CIS)-4-phenylcyclohexyl]oxy}methyl)-9-oxa-2,6-diazaspiro[4.5]decan-7-one | | A |
| 65 | 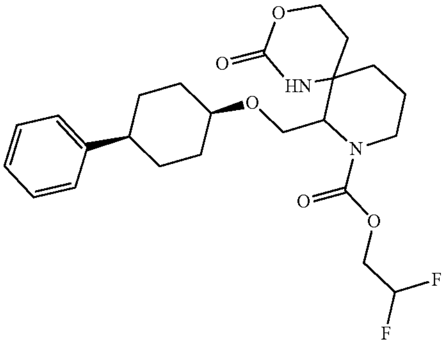 [SMILES: O=C1NC2(CCCN(C(=O)OCC(F)F)C2CO[C@H]2CC[C@@H](c3ccccc3)CC2)CCO1] | 2,2-difluoroethyl-rel-(6R,7R)-2-oxo-7-({[(CIS)-4-phenylcyclohexyl]oxy}methyl)-3-oxa-1,8-diazaspiro[5.5]undecane-8-carboxylate | Mixture of enantiomers | B |
| 66 | 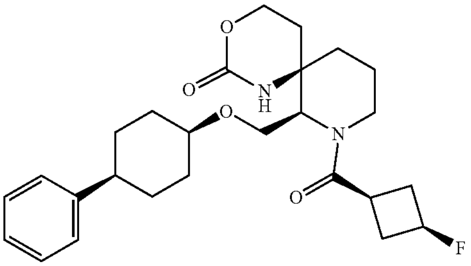 [SMILES: O=C1N[C@]2(CCCN(C(=O)[C@H]3C[C@@H](F)C3)[C@H]2CO[C@H]2CC[C@@H](c3ccccc3)CC2)CCO1] | (6R,7R)-8-[(1s,3s)-3-fluorocyclobutanecarbonyl]-7-({[(1s,4s)-4-phenylcyclohexyl]oxy}methyl)-3-oxa-1,8-diazaspiro[5.5]undecan-2-one | Enantiomer 1 | A |

TABLE 2-continued

EC50 values of compounds at OX2R

| Ex. No. | Structure | Name | Comment | EC50_OX2R Category |
|---|---|---|---|---|
| 67 | 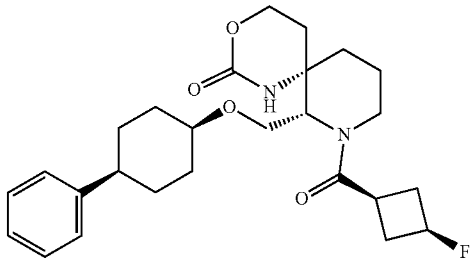 [SMILES: O=C1N[C@@]2(CCCN(C(=O)[C@H]3C[C@@H](F)C3)[C@@H]2CO[C@H]2CC[C@@H](c3ccccc3)CC2)CCO1] | (6S,7S)-8-[(1s,3s)-3-fluorocyclobutanecarbonyl]-7-({[(1s,4s)-4-phenylcyclohexyl]oxy}methyl)-3-oxa-1,8-diazaspiro[5.5]undecan-2-one | Enantiomer 2 | D |
| 68 | 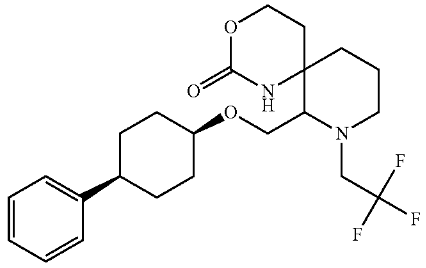 [SMILES: O=C1NC2(CCCN(CC(F)(F)F)C2CO[C@H]2CC[C@@H](c3ccccc3)CC2)CCO1] | rel-(6R,7R)-7-({[(1s,4s)-4-phenylcyclohexyl]oxy}methyl)-8-(2,2,2-trifluoroethyl)-3-oxa-1,8-diazaspiro[5.5]undecan-2-one | Mixture of enantiomers | D |
| 69 | 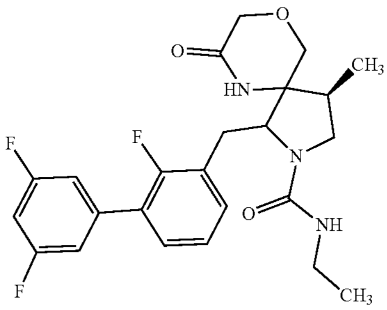 [SMILES: CCNC(=O)N1C[C@H](C)C2(COCC(=O)N2)C1Cc1cccc(-c2cc(F)cc(F)c2)c1F] | (4S)-N-ethyl-4-methyl-7-oxo-1-({2,3',5'-trifluoro-[1,1'-biphenyl]-3-yl}methyl)-9-oxa-2,6-diazaspiro[4.5]decane-2-carboxamide | Mixture of enantiomers | E |
| 70 | 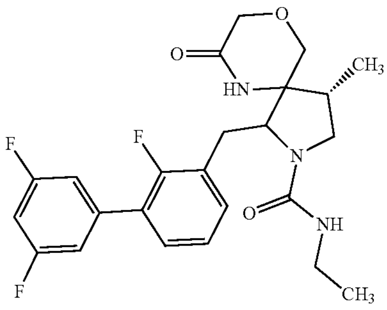 [SMILES: CCNC(=O)N1C[C@@H](C)C2(COCC(=O)N2)C1Cc1cccc(-c2cc(F)cc(F)c2)c1F] | (4R)-N-ethyl-4-methyl-7-oxo-1-({2,3',5'-trifluoro-[1,1'-biphenyl]-3-yl}methyl)-9-oxa-2,6-diazaspiro[4.5]decane-2-carboxamide | Mixture of enantiomers | C |
| 71 | 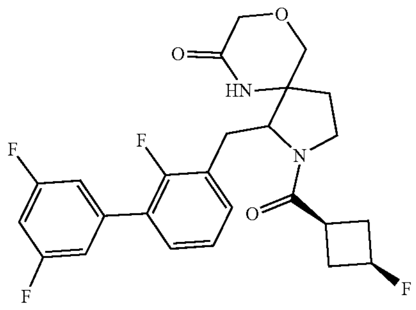 [SMILES: O=C1COCC2(CCN(C(=O)[C@H]3C[C@@H](F)C3)C2Cc2cccc(-c3cc(F)cc(F)c3)c2F)N1] | rel-(1S,5S)-2-[(1s,3s)-3-fluorocyclobutanecarbonyl]-1-({2,3',5'-trifluoro-[1,1'-biphenyl]-3-yl}methyl)-9-oxa- 2,6-diazaspiro[4.5]decan-7-one | Mixture of enantiomers | B |

TABLE 2-continued

| EC50 values of compounds at OX2R | | | | |
|---|---|---|---|---|
| Ex. No. | Structure | Name | Comment | EC50_OX2R Category |
| 72 | 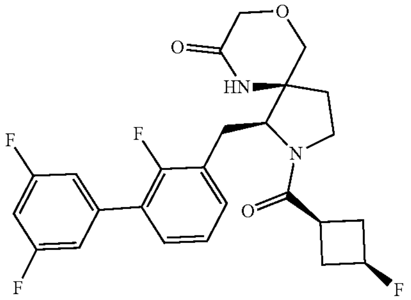 [SMILES: O=C1COC[C@@]2(CCN(C(=O)[C@H]3C[C@@H](F)C3)[C@H]2Cc2cccc(-c3cc(F)cc(F)c3)c2F)N1] | (1S,5S)-2-[(CIS)-3-fluorocyclobutanecarbonyl]-1-({2,3',5'-trifluoro-[1,1'-biphenyl]-3-yl}methyl)-9-oxa-2,6-diazaspiro[4.5]decan-7-one | Enantiomer 1 | B |
| 73 | 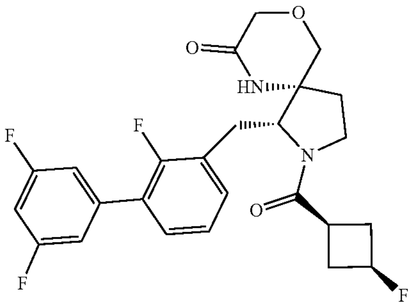 [SMILES: O=C1COC[C@]2(CCN(C(=O)[C@H]3C[C@@H](F)C3)[C@@H]2Cc2cccc(-c3cc(F)cc(F)c3)c2F)N1] | (1R,5R)-2-[(CIS)-3-fluorocyclobutanecarbonyl]-1-({2,3',5'-trifluoro-[1,1'-biphenyl]-3-yl}methyl)-9-oxa-2,6-diazaspiro[4.5]decan-7-one | Enantiomer 2 | D |
| 74 | 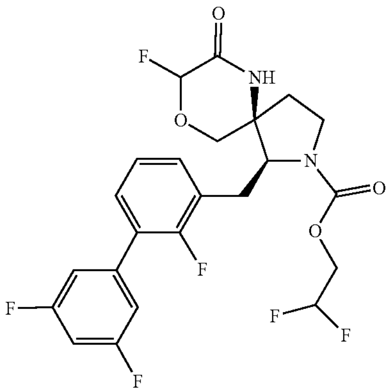 | 2,2-difluoroethyl (1S,5S)-8-fluoro-7-oxo-1-({2,3',5'-trifluoro-[1,1'-biphenyl]-3-yl }methyl)-9-oxa-2,6- | Diastereomer 1 | C |
| 75 | 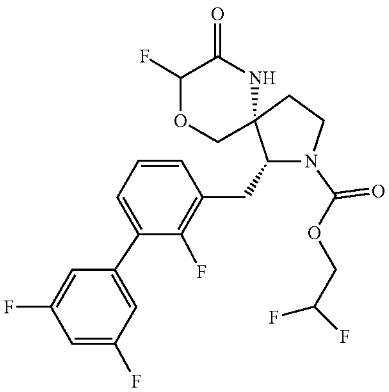 | 2,2-difluoroethyl (1R,5R)-8-fluoro-7-oxo-1-({2,3',5'-trifluoro-[1,1'-biphenyl]-3-yl}methyl)-9-oxa-2,6-diazaspiro[4.5]decane-2-carboxylate" | Diastereomer 2 | D |

TABLE 2-continued

EC50 values of compounds at OX2R

| Ex. No. | Structure | Name | Comment | EC50_OX2R Category |
|---|---|---|---|---|
| 76 | 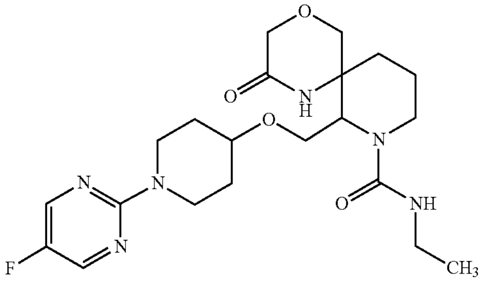 [SMILES: CCNC(=O)N1CCCC2(COCC(=O)N2)C1COC1CCN(c2ncc(F)cn2)CC1] | rel-(6S,7R)-N-ethyl-7-({[1-(5-fluoropyrimidin-2-yl)piperidin-4-yl]oxy}methyl)-2-oxo-4-oxa-1,8-diazaspiro[5.5]undecane-8-carboxamide | Mixture of enantiomers | B |
| 77 | 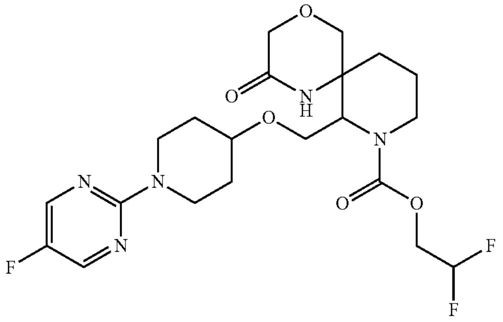 [SMILES: O=C1COCC2(CCCN(C(=O)OCC(F)F)C2COC2CCN(c3ncc(F)cn3)CC2)N1] | 2,2-difluoroethyl-rel-(6S,7R)-7-({[1-(5-fluoropyrimidin-2-yl)piperidin-4-yl]oxy}methyl)-2-oxo-4-oxa-1,8-diazaspiro[5.5]undecane-8-carboxylate | Mixture of enantiomers | C |
| 78 | 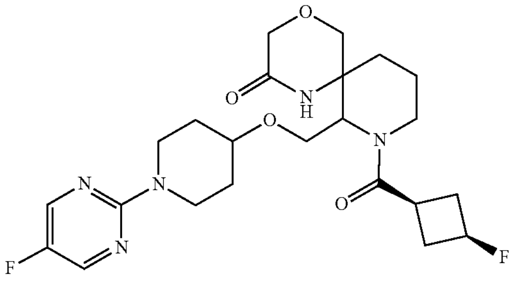 [SMILES: O=C1COCC2(CCCN(C(=O)[C@H]3C[C@@H](F)C3)C2COC2CCN(c3ncc(F)cn3)CC2)N1] | rel-(6S,7R)-7-({[1-(5-fluoropyrimidin-2-yl)piperidin-4-yl]oxy}methyl)-8-[(CIS)-3-fluorocyclobutanecarbonyl]-4-oxa-1,8-diazaspiro[5.5]undecan-2-one | Mixture of enantiomers | B |
| 79 | 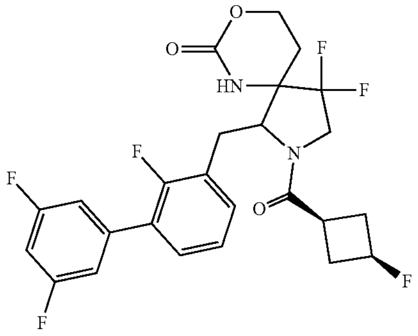 [SMILES: O=C1NC2(CCO1)C(Cc1cccc(-c3cc(F)cc(F)c3)c1F)N(C(=O)[C@H]1C[C@@H](F)C1)CC2(F)F] | 4,4-difluoro-2-[(CIS)-3-fluorocyclobutanecarbonyl]-1-({2,3',5'-trifluoro-[1,1'-biphenyl]-3-yl}methyl)-8-oxa-2,6-diazaspiro[4.5]decan-7-one | Mixture with known relative stereochemistry | B |
| 80 | 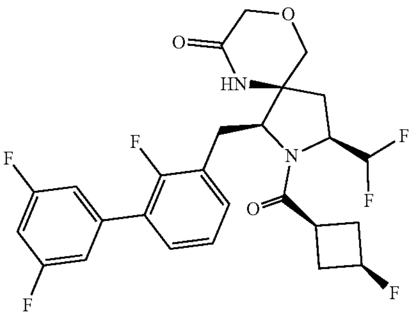 [SMILES: O=C1COC[C@@]2(C[C@@H](C(F)F)N(C(=O)[C@H]3C[C@@H](F)C3)[C@H]2Cc2cccc(-c3cc(F)cc(F)c3)c2F)N1] | (1S,3S,5S)-3-(difluoromethyl)-2-[(CIS)-3-fluorocyclobutanecarbonyl]-1-({2,3',5'-trifluoro-[1,1'-biphenyl]-3-yl}methyl)-9-oxa-2,6-diazaspiro[4.5]decan-7-one | | B |

TABLE 2-continued

| EC50 values of compounds at OX2R | | | | |
|---|---|---|---|---|
| Ex. No. | Structure | Name | Comment | EC50_OX2R Category |
| 81 | 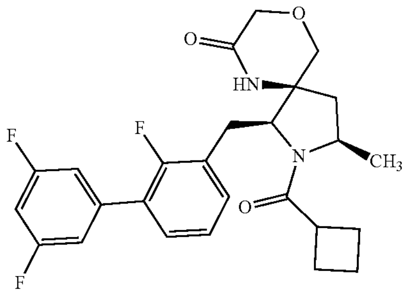 [SMILES: C[C@@H]1C[C@@]2(COCC(=O)N2)[C@H](Cc2cccc(-c3cc(F)cc(F)c3)c2F)N1C(=O)C1CCC1] | (1S,3R,5S)-2-cyclobutanecarbonyl-3-methyl-1-({2,3',5'-trifluoro-[1,1'-biphenyl]-3-yl}methyl)-9-oxa-2,6-diazaspiro[4.5]decan-7-one | | A |
| 82 | 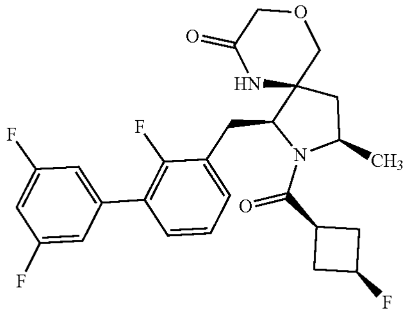 [SMILES: C[C@@H]1C[C@@]2(COCC(=O)N2)[C@H](Cc2cccc(-c3cc(F)cc(F)c3)c2F)N1C(=O)[C@H]1C[C@@H](F)C1] | (1S,3R,5S)-3-methyl-2-[(1s,3s)-3-fluorocyclobutanecarbonyl]-1-({2,3',5'-trifluoro-[1,1'-biphenyl]-3-yl}methyl)-9-oxa-2,6-diazaspiro[4.5]decan-7-one | | A |
| 83 | 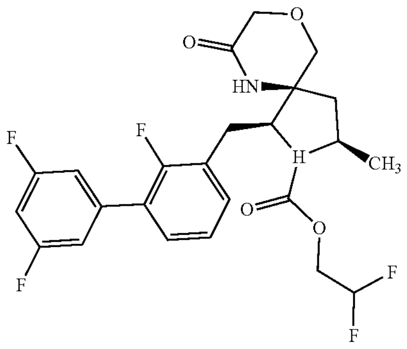 | 2,2-difluoroethyl (1S,3R,5S)-3-methyl-7-oxo-1-({2,3',5'-trifluoro-[1,1'-biphenyl]-3-yl}methyl)-9-oxa-2,6-diazaspiro[4.5]decane-2-carboxylate | | B |
| 84 | 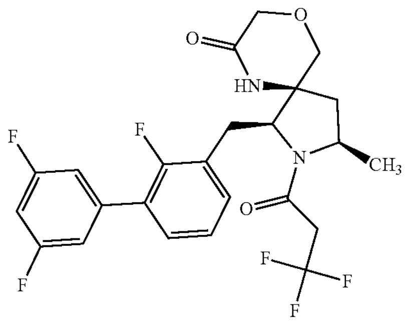 [SMILES: C[C@@H]1C[C@@]2(COCC(=O)N2)[C@H](Cc2cccc(-c3cc(F)cc(F)c3)c2F)N1C(=O)CC(F)(F)F] | (1S,3R,5S)-3-methyl-1-({2,3',5'-trifluoro-[1,1'-biphenyl]-3-yl}methyl)-2-(3,3,3-trifluoropropanoyl)-9-oxa-2,6-diazaspiro[4.5]decan-7-one | | B |

TABLE 2-continued

| EC50 values of compounds at OX2R | | | | |
|---|---|---|---|---|
| Ex. No. | Structure | Name | Comment | EC50_OX2R Category |
| 85 | 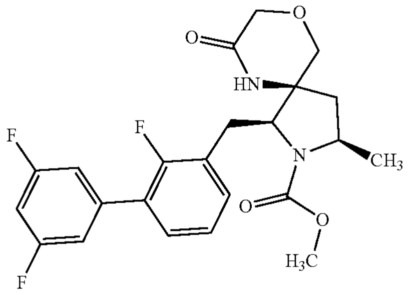 [SMILES: COC(=O)N1[C@H](C)C[C@@]2(COCC(=O)N2)[C@@H]1Cc1cccc(-c2cc(F)cc(F)c2)c1F] | methyl (1S,3R,5S)-3-methyl-7-oxo-1-({2,3',5'-trifluoro-[1,1'-biphenyl]-3-yl}methyl)-9-oxa-2,6-diazaspiro[4.5]decane-2-carboxylate | | D |
| 86 | 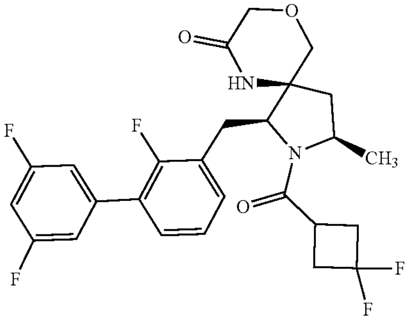 [SMILES: C[C@@H]1C[C@@]2(COCC(=O)N2)[C@H](Cc2cccc(-c3cc(F)cc(F)c3)c2F)N1C(=O)C1CC(F)(F)C1] | (1S,3R,5S)-2-(3,3-difluorocyclobutanecarbonyl)-3-methyl-1-({2,3',5'-trifluoro-[1,1'-biphenyl]-3-yl }methyl)-9-oxa-2,6-diazaspiro[4.5]decan-7-one | | B |
| 87 | 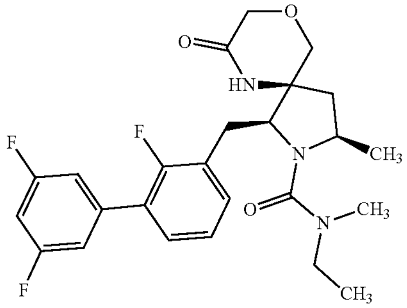 [SMILES: CCN(C)C(=O)N1[C@H](C)C[C@@]2(COCC(=O)N2)[C@@H]1Cc1cccc(-c2cc(F)cc(F)c2)c1F] | (1S,3R,5S)-N-ethyl-N,3-dimethyl-7-oxo-1-({2,3',5'-trifluoro-[1,1'-biphenyl]-3-yl }methyl)-9-oxa-2,6-diazaspiro[4.5]decane-2-carboxamide | | B |
| 88 | 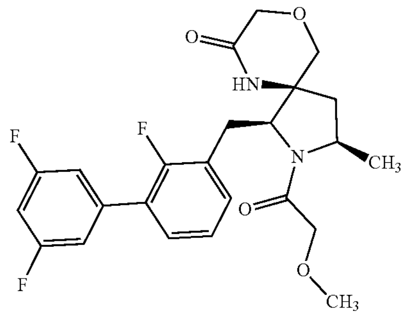 [SMILES: COCC(=O)N1[C@H](C)C[C@@]2(COCC(=O)N2)[C@@H]1Cc1cccc(-c2cc(F)cc(F)c2)c1F] | (1S,3R,5S)-2-(2-methoxyacetyl)-3-methyl-1-({2,3',5'-trifluoro-[1,1'-biphenyl]-3-yl}methyl)-9-oxa-2,6-diazaspiro[4.5]decan-7-one | | C |
| 89 | 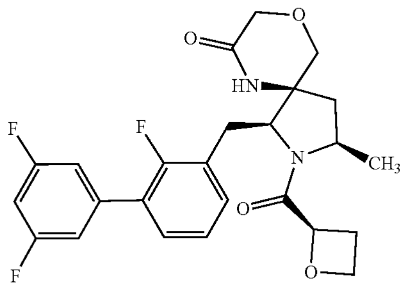 [SMILES: C[C@@H]1C[C@@]2(COCC(=O)N2)[C@H](Cc2cccc(-c3cc(F)cc(F)c3)c2F)N1C(=O)[C@H]1CCO1] | (1S,3R,5S)-3-methyl-2-[(2R)-oxetane-2-carbonyl]-1-({2,3',5'-trifluoro-[1,1'-biphenyl]-3-yl}methyl)-9-oxa-2,6-diazaspiro[4.5]decan-7-one | | B |

TABLE 2-continued

EC50 values of compounds at OX2R

| Ex. No. | Structure | Name | Comment | EC50_OX2R Category |
|---|---|---|---|---|
| 90 | 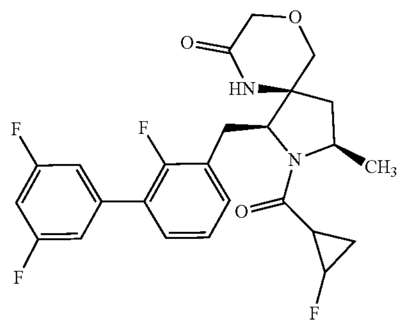 [SMILES: C[C@@H]1C[C@@]2(COCC(=O)N2)[C@H](Cc2cccc(-c3cc(F)cc(F)c3)c2F)N1C(=O)C1CC1F] | (1S,3R,5S)-2-(2-fluorocyclopropanecarbonyl)-3-methyl-1-({2,3',5'-trifluoro-[1,1'-biphenyl]-3-yl}methyl)-9-oxa-2,6-diazaspiro[4.5]decan-7-one | Cis-isomer 1 | B |
| 91 | 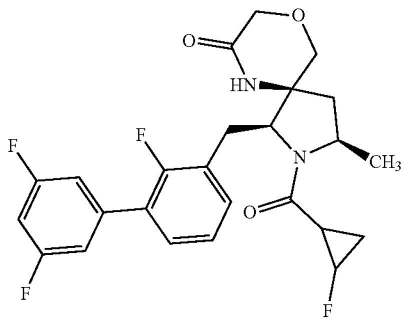 [SMILES: C[C@@H]1C[C@@]2(COCC(=O)N2)[C@H](Cc2cccc(-c3cc(F)cc(F)c3)c2F)N1C(=O)C1CC1F] | (1S,3R,5S)-2-(2-fluorocyclopropanecarbonyl)-3-methyl-1-({2,3',5'-trifluoro-[1,1'-biphenyl]-3-yl}methyl)-9-oxa-2,6-diazaspiro[4.5]decan-7-one | Cis-isomer 2 | B |
| 92 | 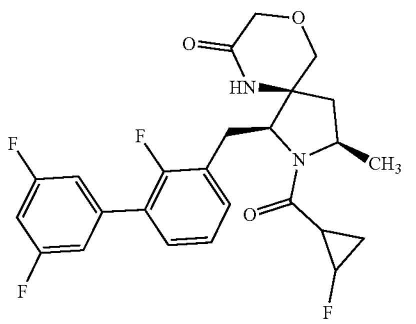 [SMILES: C[C@@H]1C[C@@]2(COCC(=O)N2)[C@H](Cc2cccc(-c3cc(F)cc(F)c3)c2F)N1C(=O)C1CC1F] | (1S,3R,5S)-2-(2-fluorocyclopropanecarbonyl)-3-methyl-1-({2,3',5'-trifluoro-[1,1'-biphenyl]-3-yl}methyl)-9-oxa-2,6-diazaspiro[4.5]decan-7-one | Trans isomer 3/4 | B |
| 93 | 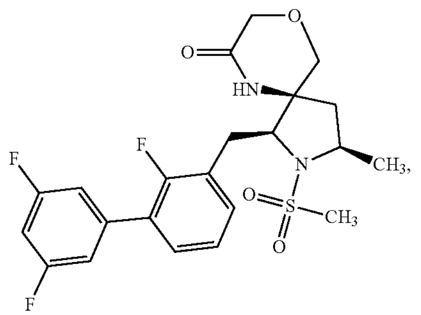 | (1S,3R,5S)-2-methanesulfonyl-3-methyl-1-({2,3',5'-trifluoro-[1,1'-biphenyl]-3-yl}methyl)-9-oxa-2,6-diazaspiro[4.5]decan-7-one | | D |

The invention claimed is:

1. A compound of Formula (I):

(I)

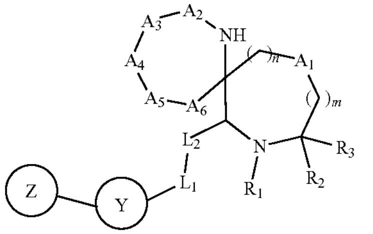

or a pharmaceutically acceptable salt thereof, wherein n and m are independently 0 or 1;

$A_1$ is —O—, —$CR_4R_5$—, —$NR_6$—, —S— or a bond;

$A_2$ is —C(O)— or —$S(O)_2$—;

$A_3$ and $A_4$, are independently —O—, —$CR_4R_5$—, —$NR_6$, —S— or a bond; or $A_3$ and $A_4$ together are —$C(R_4)$=$C(R_5)$—;

$A_5$ and $A_6$ are independently —O—, —$CR_4R_5$—, —$NR_6$, —S— or a bond; with the proviso that the ring that includes $A_2$, $A_3$, $A_4$, $A_5$ and $A_6$ does not contain —O—O—, —$NR_6$—$NR_6$— or —O—$NR_6$—;

$L_1$ is —O—, —$CR_4R_5$— or a bond;

$L_2$ is —$CR_4R_5$;

$R_1$ is a alkyl, cycloalkyl, heterocyclyl, aryl, heteroaryl, —(C=O)alkyl, —(C=O)cycloalkyl, —(C=O)heterocyclyl, —(C=O)aryl, —(C=O)heteroaryl, —(C=O)—O-alkyl, —(C=O)—O-cycloalkyl, —(C=O)—O-heterocyclyl, —(C=O)—O-aryl, —(C=O)—O-heteroaryl, —$S(O)_2$-alkyl, —$S(O)_2$-cycloalkyl, —$S(O)_2$-heterocyclyl, —$S(O)_2$-aryl, —$S(O)_2$-heteroaryl or —(C=O)$NR_7R_8$, or $R_1$ and $R_2$ together with the atom to which they are attached form a heterocycle or heteroaryl;

$R_2$ and $R_3$ are independently hydrogen, halogen, alkyl, cycloalkyl or heterocyclyl, or $R_2$ and $R_3$ together with the atom to which they are attached form a carbocycle or heterocycle;

$R_4$ and $R_5$ are independently hydrogen, alkyl, cycloalkyl, heterocyclyl, alkoxy, —O-cycloalkyl, —O-heterocyclyl or halogen, or $R_4$ and $R_5$ together with the atom to which they are attached to form a carbocycle or heterocycle;

$R_6$ is hydrogen, alkyl, cycloalkyl, heterocyclyl, aryl, heteroaryl, —(C=O)alkyl, —(C=O)cycloalkyl, —(C=O)heterocyclyl, —(C=O)aryl, —(C=O)heteroaryl, —(C=O)—O-alkyl, —(C=O)—O-cycloalkyl, —(C=O)—O-heterocyclyl, —(C=O)—O-aryl, —(C=O)—O-heteroaryl, —$S(O)_2$-alkyl, —$S(O)_2$-cycloalkyl, —$S(O)_2$-heterocyclyl, —$S(O)_2$-aryl, —$S(O)_2$-heteroaryl or —(C=O)$NR_7R_8$, $R_7$ and $R_8$ are independently hydrogen, alkyl, cycloalkyl, heterocyclyl, aryl or heteroaryl, or $R_7$ and $R_8$ together with the atom to which they are attached to form a heterocycle;

Y is cycloalkyl, heterocyclyl, heteroaryl or aryl; and

Z is absent, heteroaryl or aryl.

2. The compound of claim 1, wherein $R_1$ is $C_{1-6}$ alkyl, 5 or 6-membered heteroaryl, —(C=O)$NR_7R_8$, —(C=O)—O—$C_{1-6}$ alkyl, —(C=O) $C_{3-6}$ cycloalkyl, —(C=O) $C_{1-6}$ alkyl, —(C=O)—$C_{4-6}$ saturated heterocyclyl or —$S(O)_2$—$C_{1-6}$ alkyl;

wherein each $C_{1-6}$ alkyl, $C_{3-6}$ cycloalkyl, $C_{4-6}$ saturated heterocyclyl and heteroaryl is independently optionally substituted with one or more hydroxy, —$C_{1-6}$ alkyl, —O—$C_{1-6}$ alkyl, or fluoro.

3. The compound of claim 1, wherein $R_2$ and $R_3$ are independently hydrogen or $C_{1-5}$ alkyl; wherein $C_{1-5}$ alkyl is optionally substituted with one or more fluoro.

4. The compound of claim 1, wherein $R_4$ and $R_5$ are independently hydrogen, halogen, or $C_{1-5}$ alkyl.

5. The compound of claim 1, wherein $R_7$ and $R_8$ are independently hydrogen or $C_{1-6}$ alkyl or $R_7$ and $R_8$ together with the atom to which they are attached to form a saturated heterocycle, wherein the $C_{1-6}$ alkyl, and saturated heterocycle are independently optionally substituted with one or more fluoro or —O—$C_{1-6}$ alkyl.

6. The compound of claim 1, wherein Y is a 3-7 membered monocycloalkyl, 4-7 membered saturated heterocyclyl, or phenyl; wherein the phenyl is optionally substituted with one or more fluoro.

7. The compound of claim 1, wherein m and n are 0.

8. The compound of claim 1, wherein m is 1 and n is 0.

9. The compound of claim 1, wherein $A_1$ is —$CR_4R_5$—.

10. The compound of claim 1, wherein $A_2$ is —C(O)—.

11. The compound of claim 1, wherein $A_3$, $A_4$, $A_5$, and $A_6$ together with the atoms to which they are attached form a 6-membered heterocycle.

12. The compound of claim 1, wherein $L_1$ is a bond or —O—.

13. The compound of claim 1, wherein the compound is a compound of Formula (II):

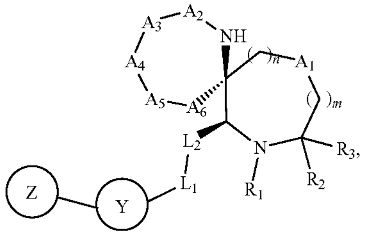

or a pharmaceutically acceptable salt thereof.

14. The compound of claim 13, wherein:

(i) Y is cyclohexyl and Z is aryl; or (ii) Y is aryl and Z is aryl.

15. The compound of claim 1, wherein the compound is a compound of Formula (III):

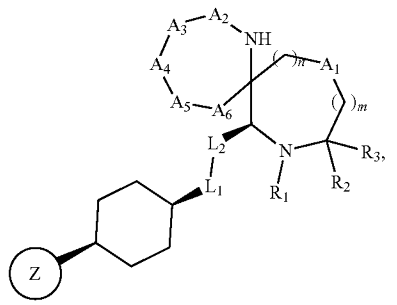

or a pharmaceutically acceptable salt thereof.

16. The compound of claim 1, wherein the compound is a compound of Formula (IV):

(IV)

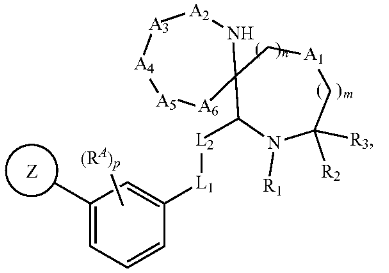

or a pharmaceutically acceptable salt thereof, wherein $R^A$ is independently, for each occurrence, selected from the group consisting of hydroxy, halogen, —$NO_2$, —CN, —$NR_7R_8$, —$CO_2R_9$, —$OC(O)R_9$, —$COR_9$, —$C(O)NR_7R_8$, —$NR_7C(O)R_8$, —$OC(O)NR_7R_8$, —$NR_7C(O)OR_9$, —$S(O)_wR_9$, wherein w is 0, 1, or 2, —$OSO_2R_9$, —$SO_3R_9$, —$S(O)_2NR_7R_8$, —$NR_7S(O)_2R_9$, —$NR_7C(O)NR_7R_8$, —$C_{1-6}$ alkyl-$NR_7R_8$, —$C_{1-6}$ alkyl-O—$C_{1-6}$ alkyl, —$C_{1-6}$ alkyl, $C_{1-6}$ alkoxy, $C_{2-6}$ alkenyl, and $C_{2-6}$ alkynyl;

$R_7$ and $R_8$ are independently hydrogen, alkyl, cycloalkyl, heterocyclyl, aryl or heteroaryl, or $R_7$ and $R_8$ together with the atom to which they are attached to form a heterocycle;

$R_9$ is independently for each occurrence, selected from the group consisting of hydrogen, $C_{1-6}$alkyl, $C_{2-6}$alkenyl, $C_{2-6}$alkynyl, aryl, cycloalkyl, heterocyclyl, and heteroaryl; and p is 0, 1, 2, 3, or 4.

17. The compound of claim 1, wherein the compound of Formula (I) is selected from the group consisting of:

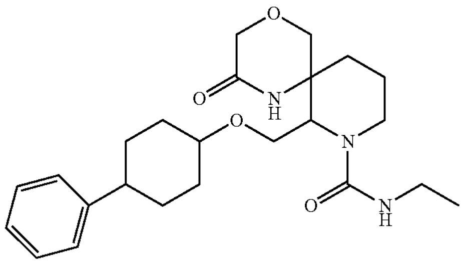

,

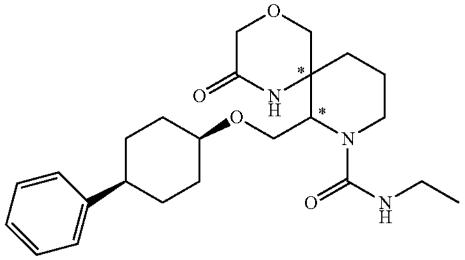

,

* cis-relative stereochemistry

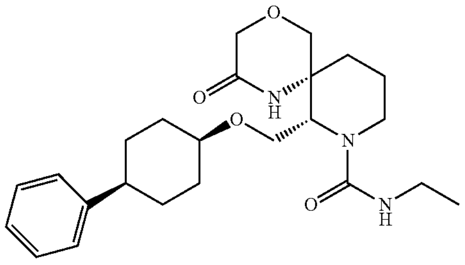

,

-continued

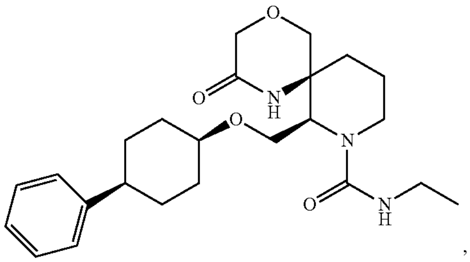

,

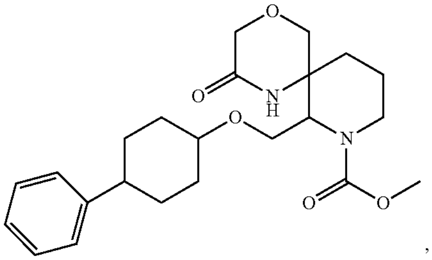

,

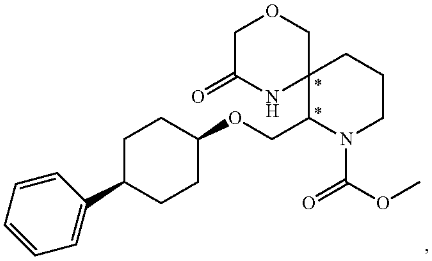

,

* cis-relative stereochemistry

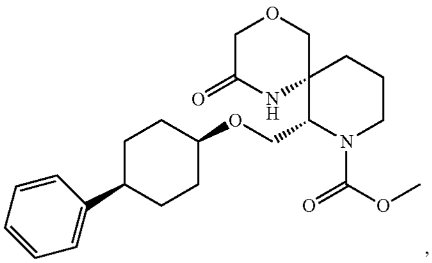

,

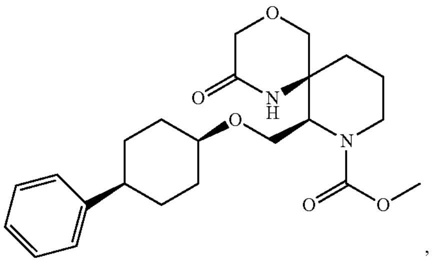

,

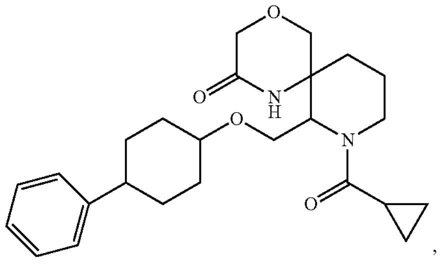

,

-continued
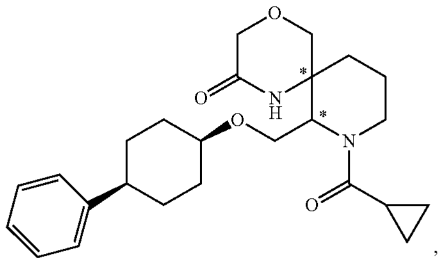
,
* cis-relative stereochemistry
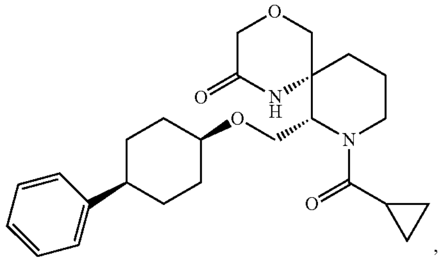
,
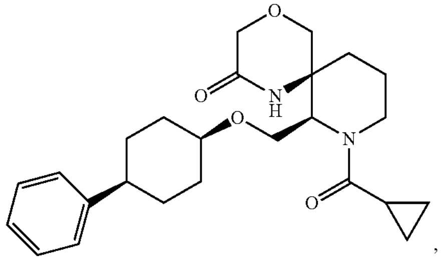
,
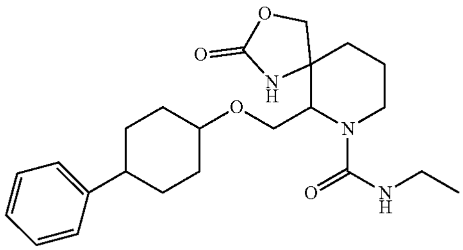
,
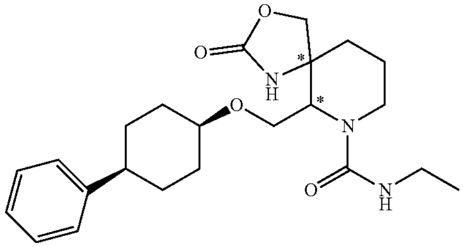
,
* cis-relative stereochemistry
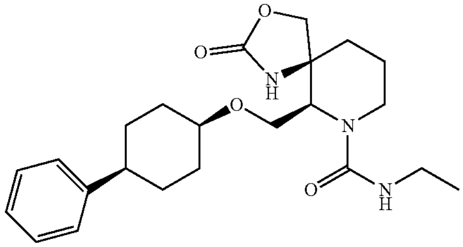
,
-continued
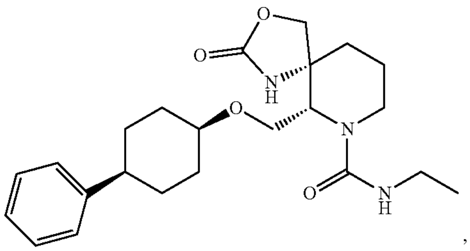
,
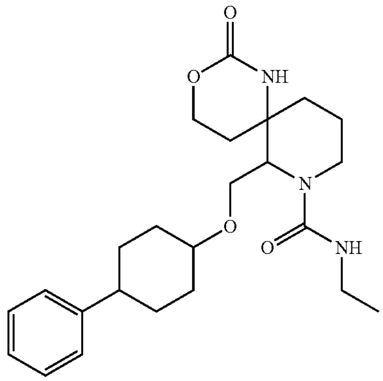
,
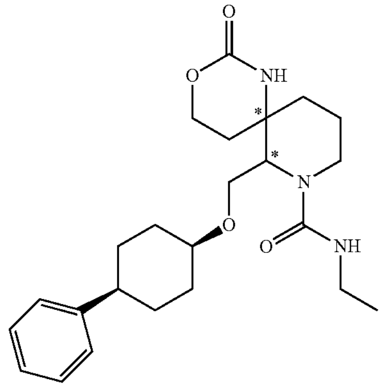
,
* cis-relative stereochemistry
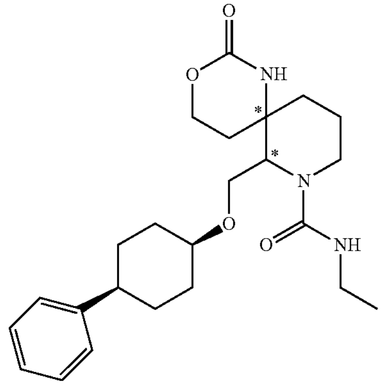
,
* trans-relative stereochemistry -continued
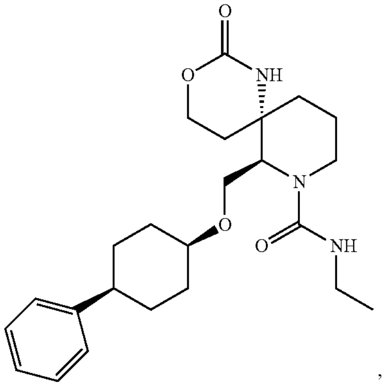
,
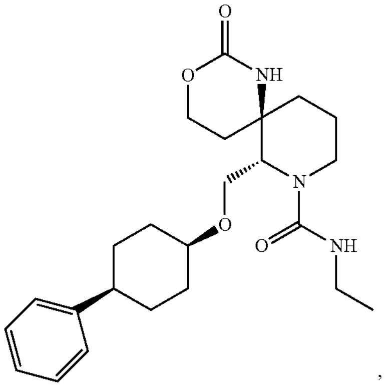
,
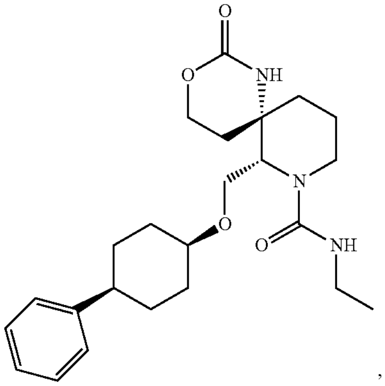
,
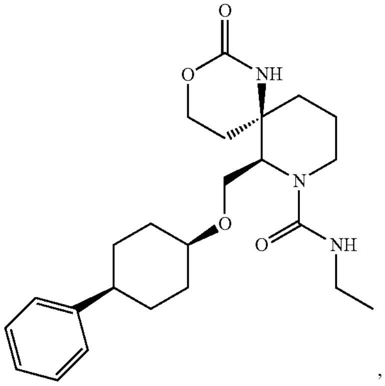
,
-continued
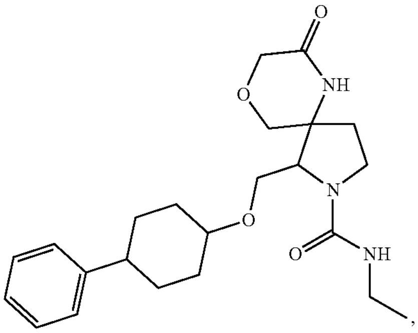
,
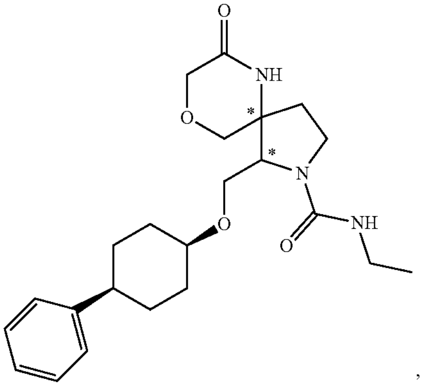
,
* cis-relative stereochemistry
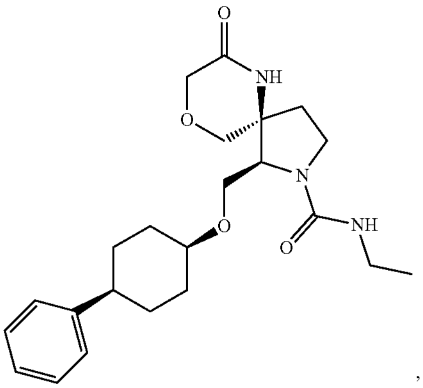 [SMILES: CCNC(=O)N1CC[C@@]2(COCC(=O)N2)[C@@H]1CO[C@H]1CC[C@@H](c2ccccc2)CC1]
,
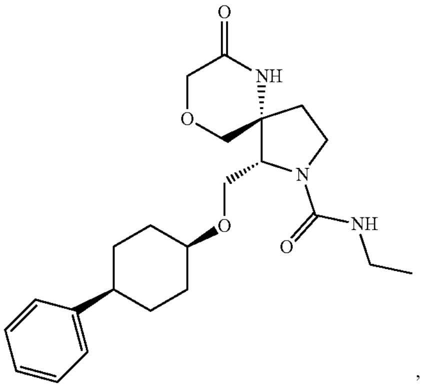
, -continued
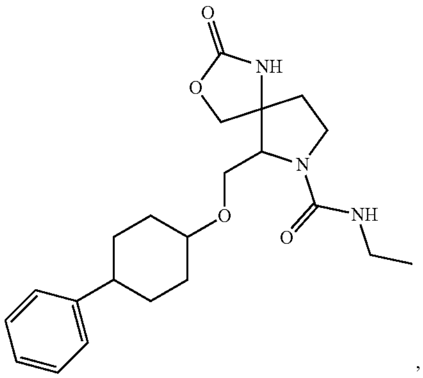
,
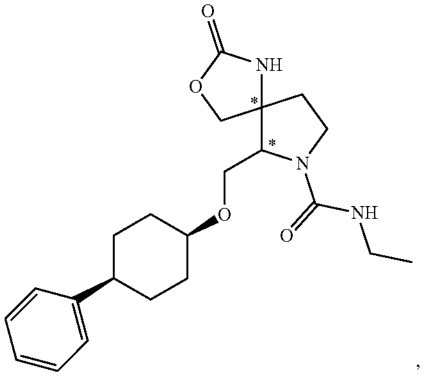
,
* cis-relative stereochemistry
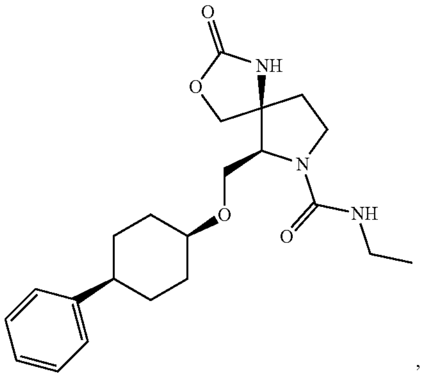
,
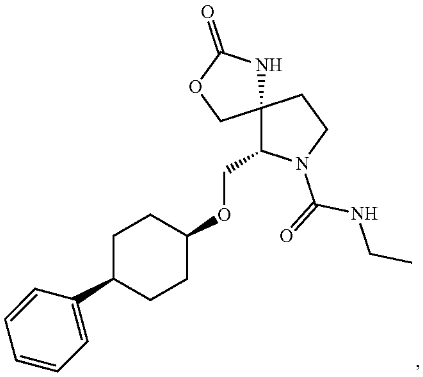
,
-continued
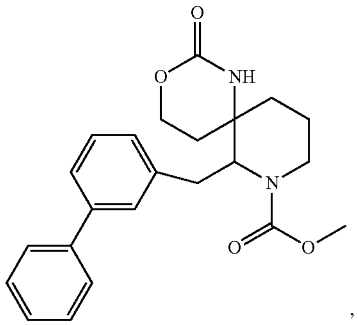
,
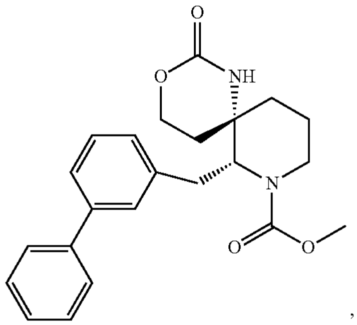
,
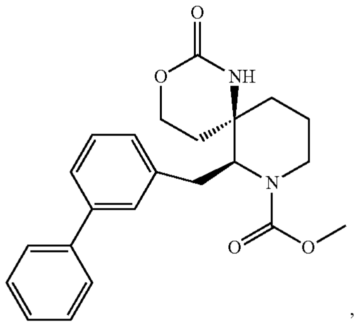
,
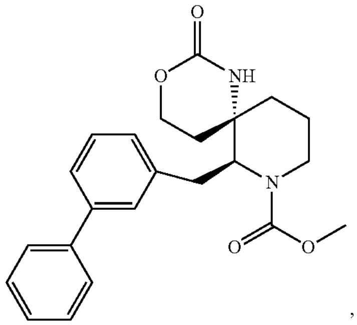
,
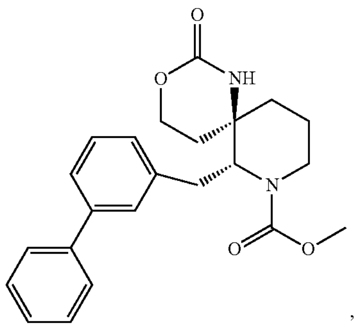
, -continued
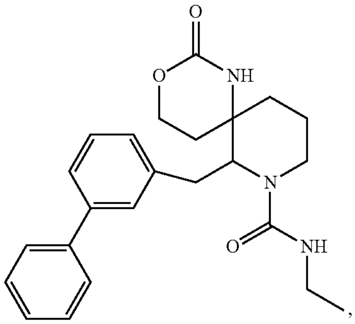
,
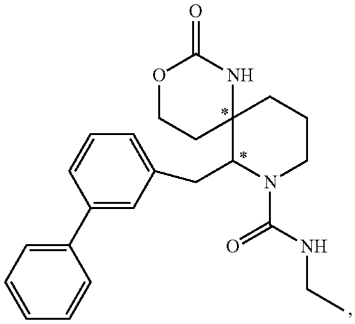
,
* cis-relative stereochemistry
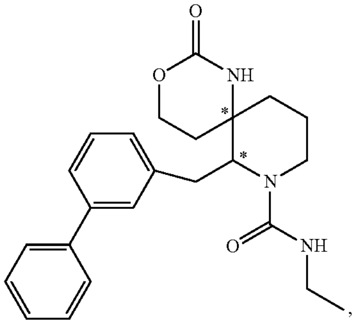
,
* trans-relative stereochemistry
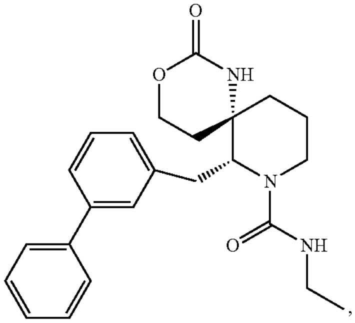
,
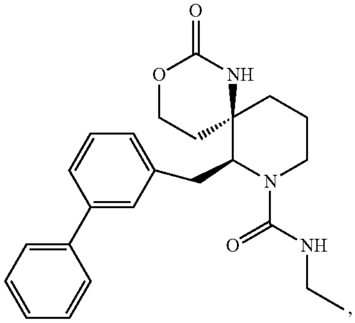
,
-continued
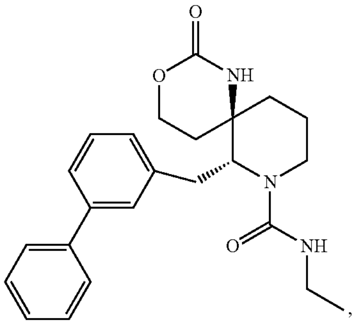
,
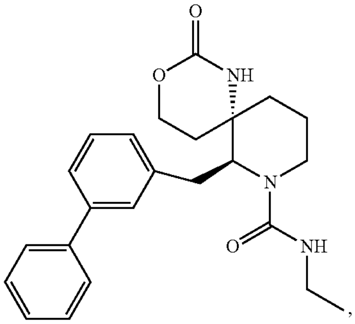
,
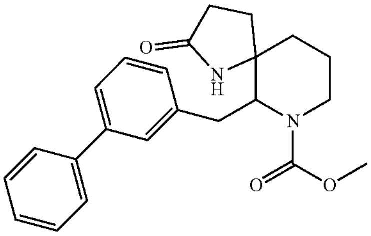
,
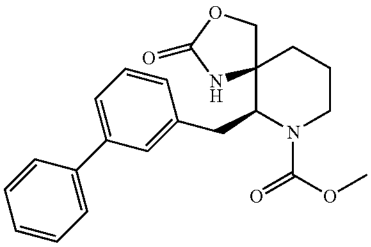
,
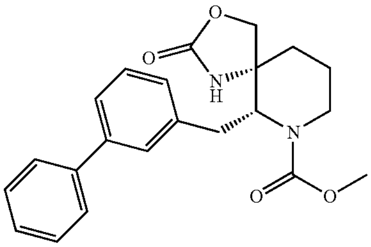
,
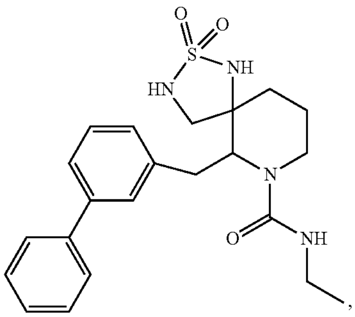
, -continued
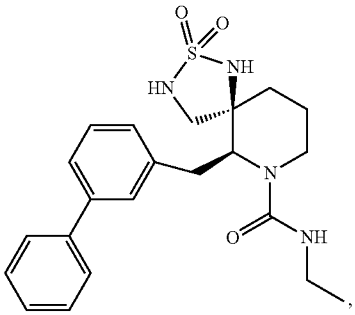
,
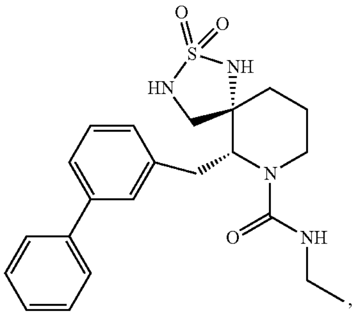
,
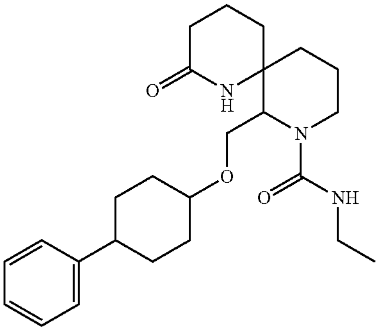
,
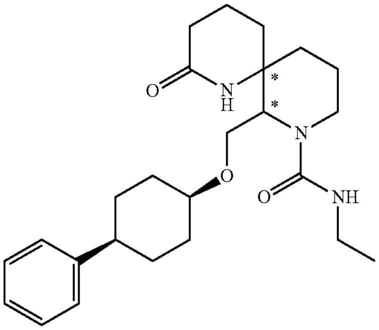
,
* cis-relative stereochemistry
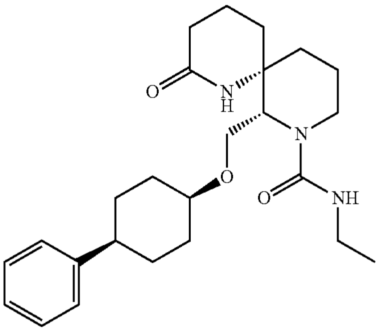
,
-continued
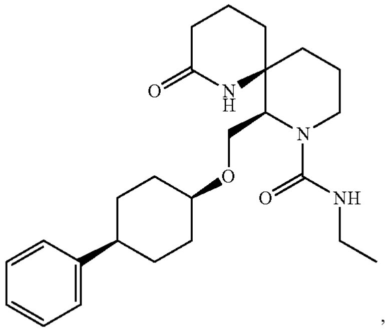
,
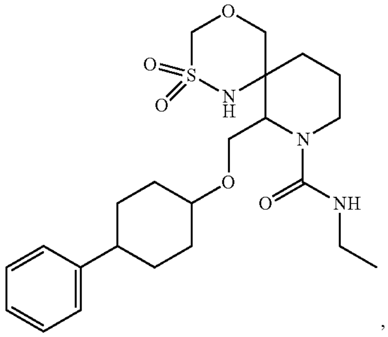
,
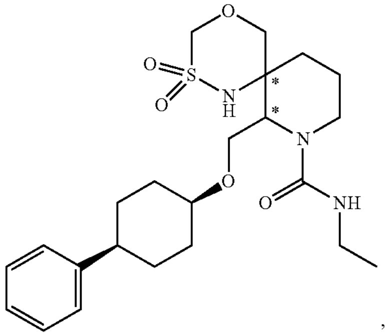
,
* cis-relative stereochemistry
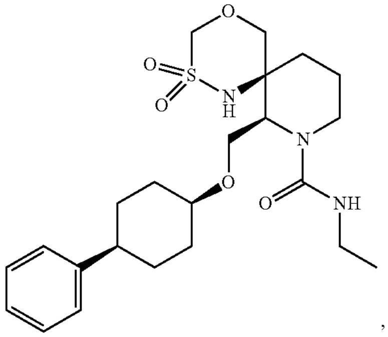
,
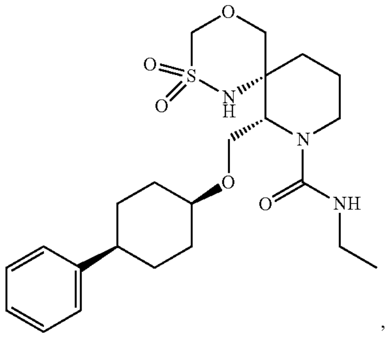
, -continued
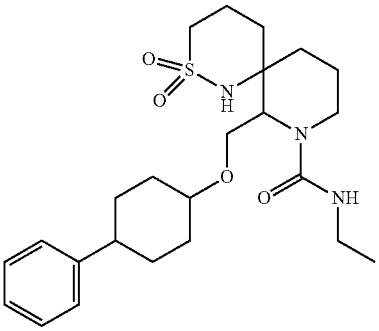
,
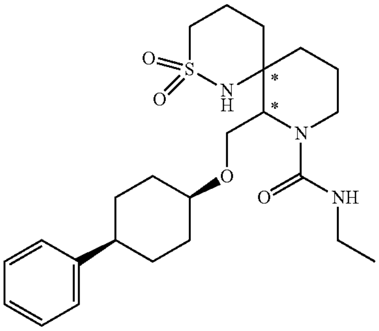
,
* cis-relative stereochemistry
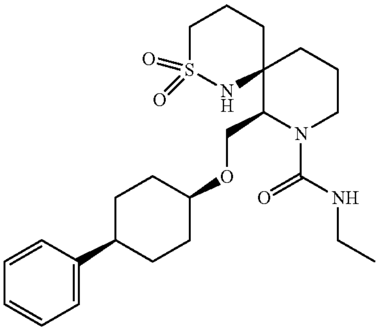
,
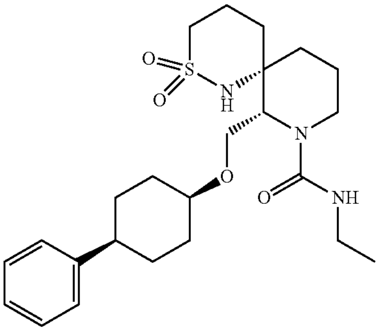
,
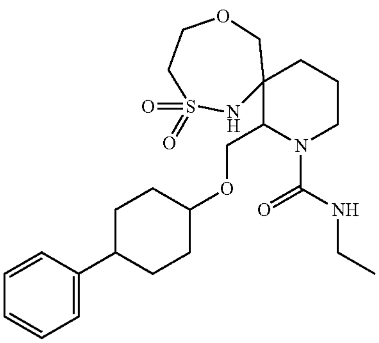
,
-continued
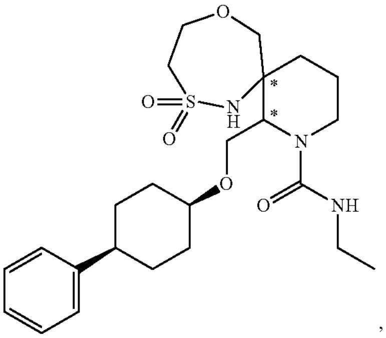
,
* cis-relative stereochemistry
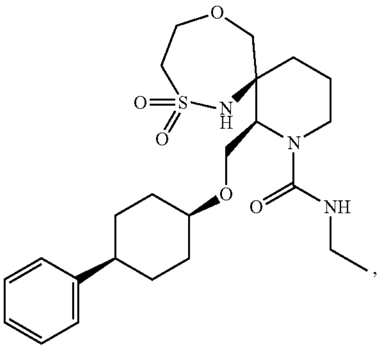
,
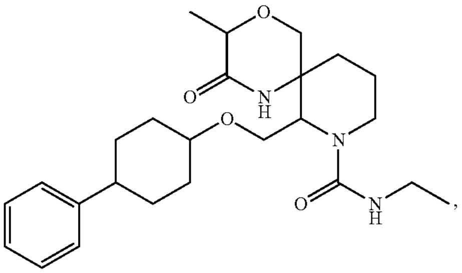
,
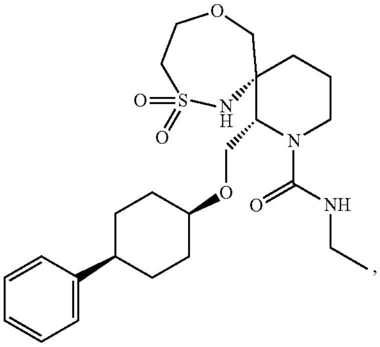
,
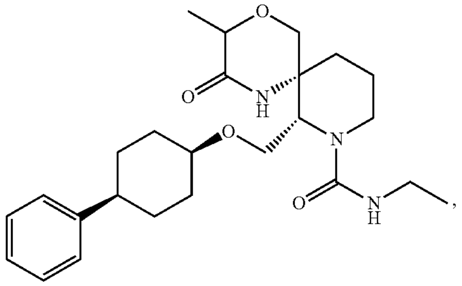
, -continued
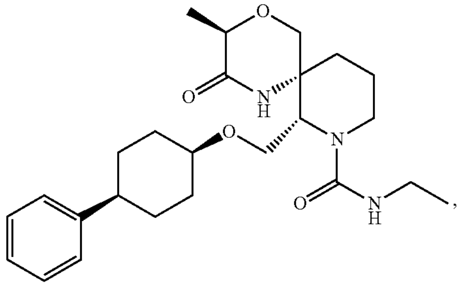
,
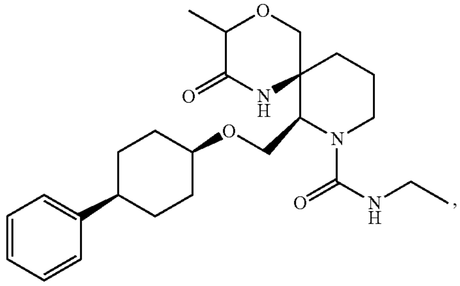
,
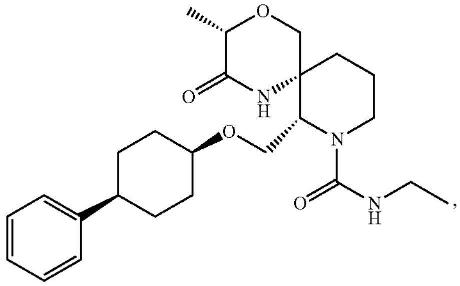
,
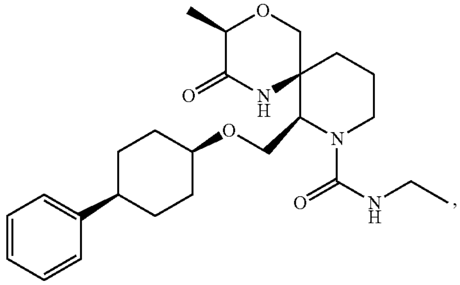
,
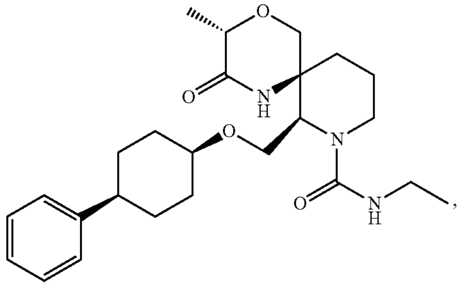
,
-continued
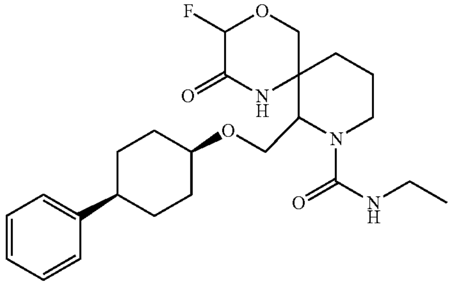
,
*cis-relative stereochemistry
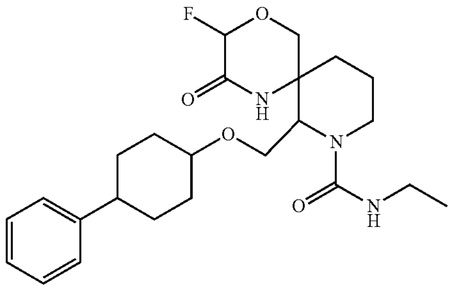
,
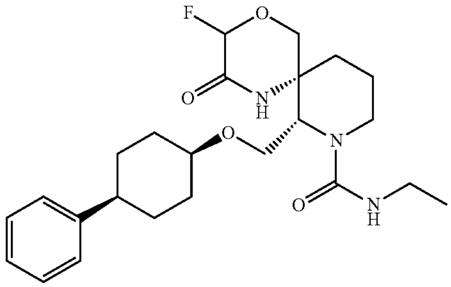
,
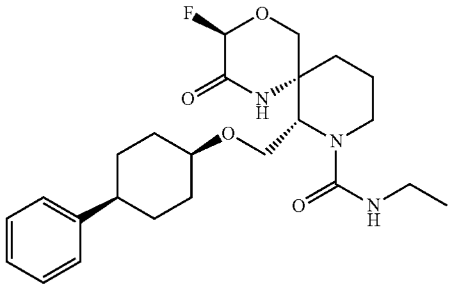
,
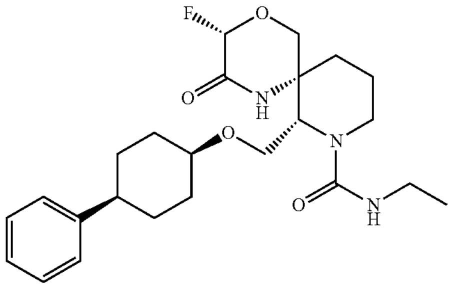
, -continued
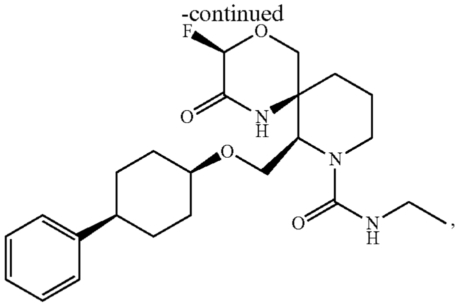,
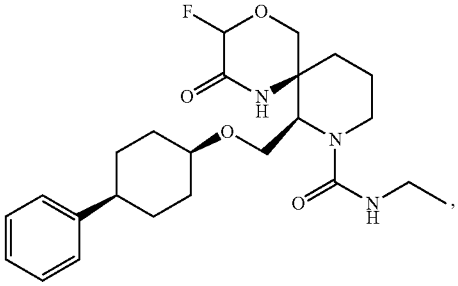,
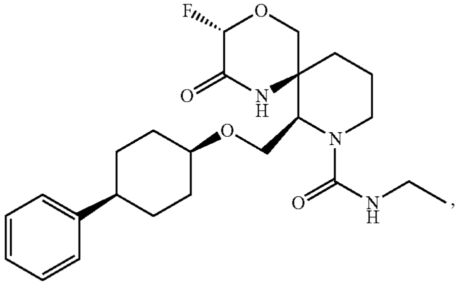,
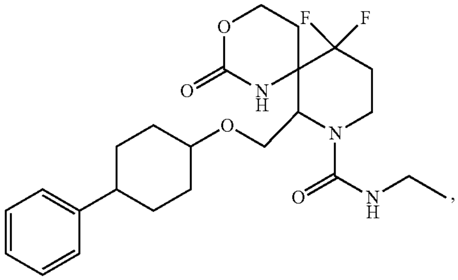,
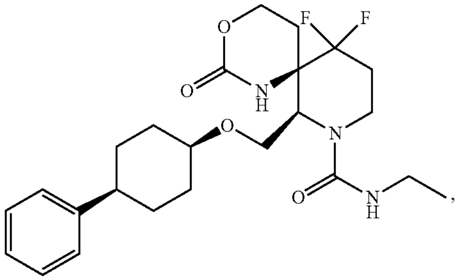,
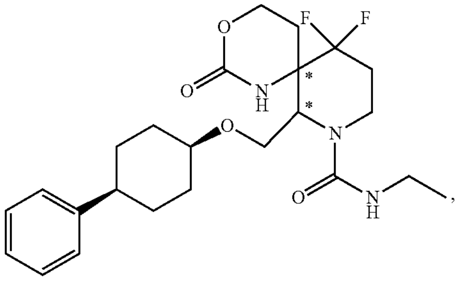,
*cis-relative stereochemistry
-continued
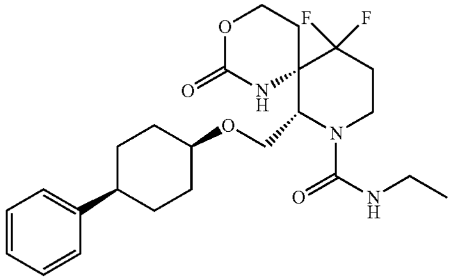,
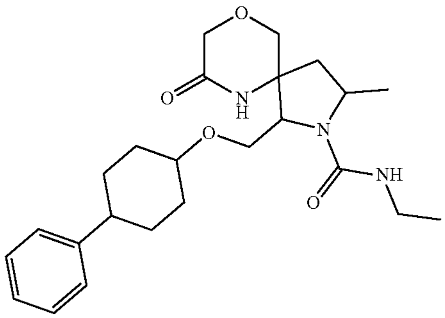,
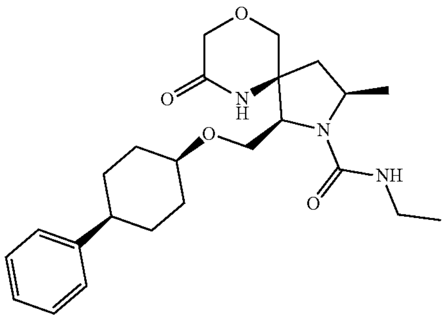,
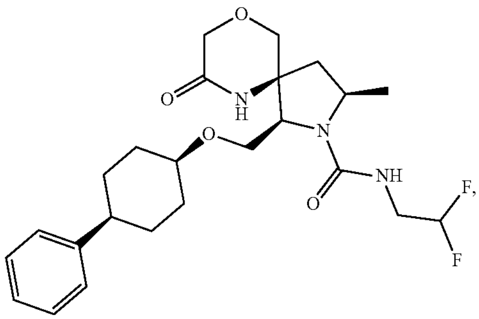
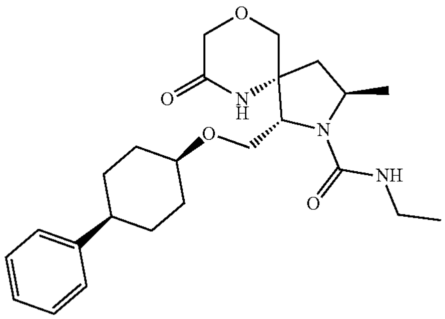, -continued
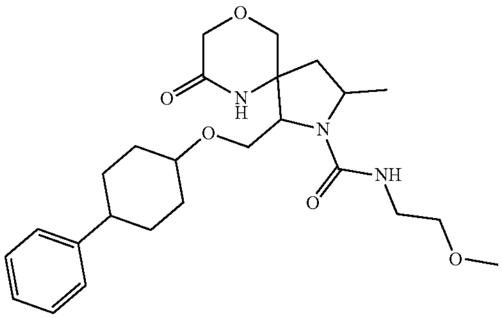
,
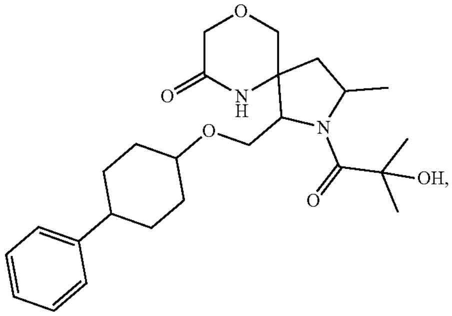
,
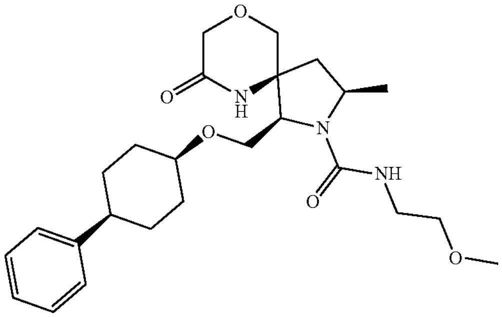
,
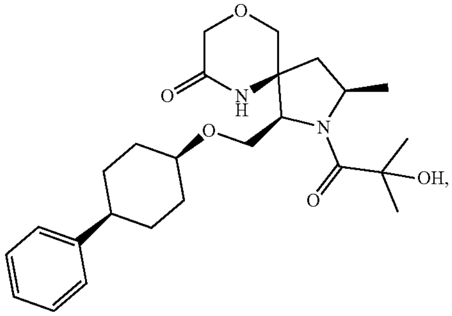
,
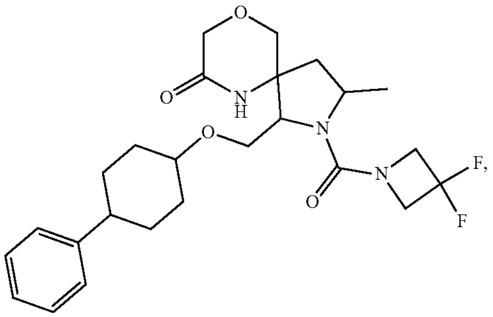
,
-continued
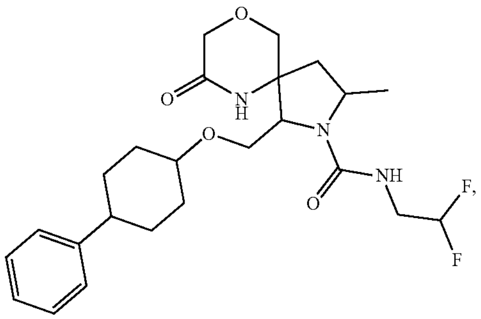
,
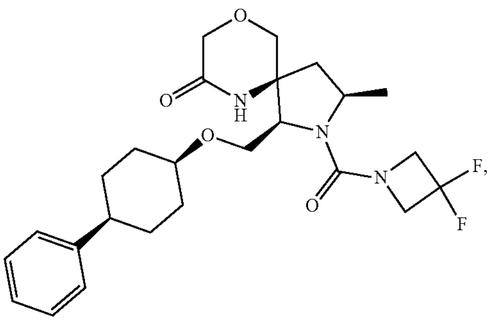 [SMILES: C[C@@H]1C[C@@]2(COCC(=O)N2)[C@H](CO[C@H]2CC[C@@H](c3ccccc3)CC2)N1C(=O)N1CC(F)(F)C1]
,
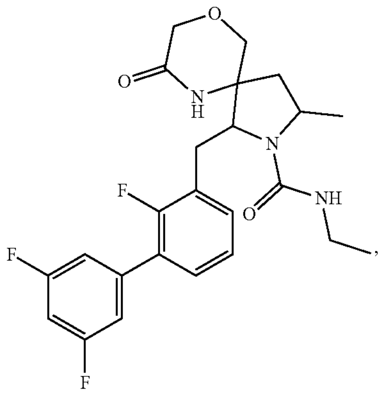
,
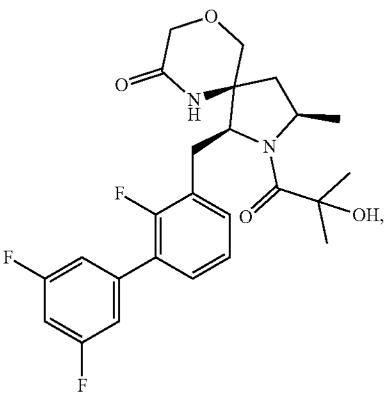
, -continued
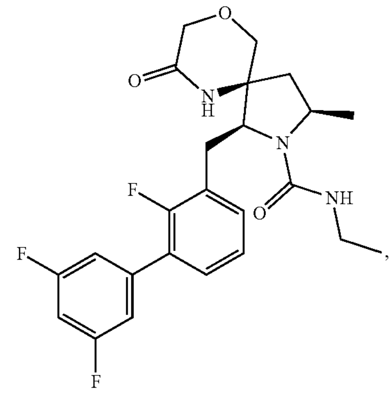
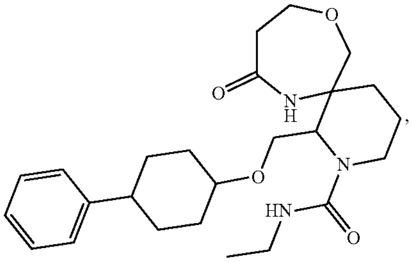
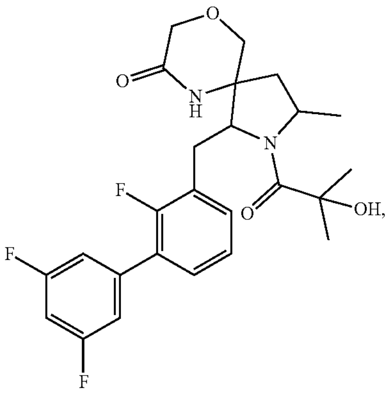
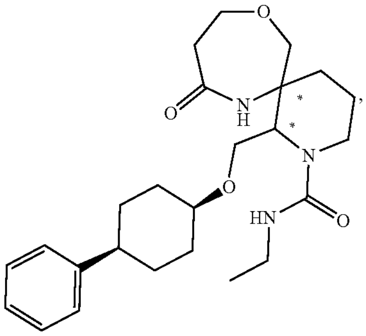
*cis-relative stereochemistry
-continued
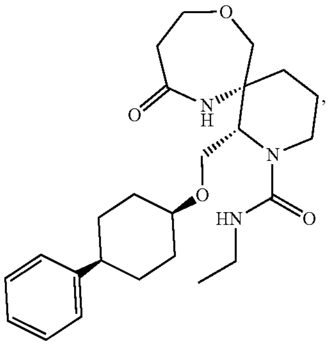
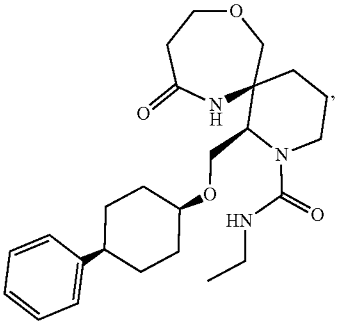
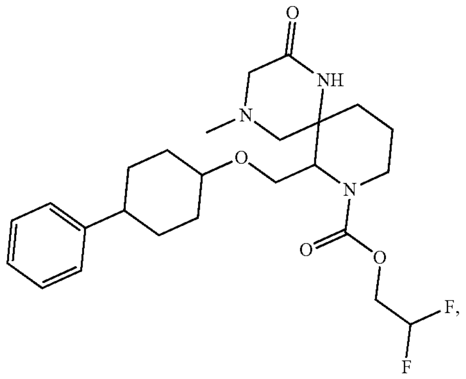
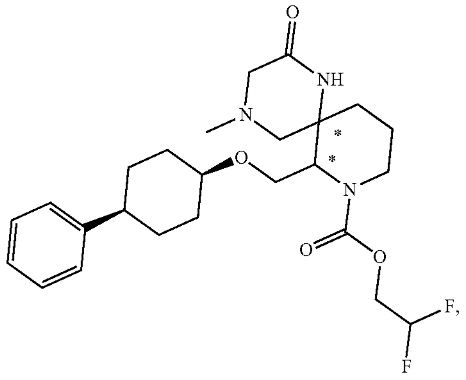
*cis-relative stereochemistry -continued
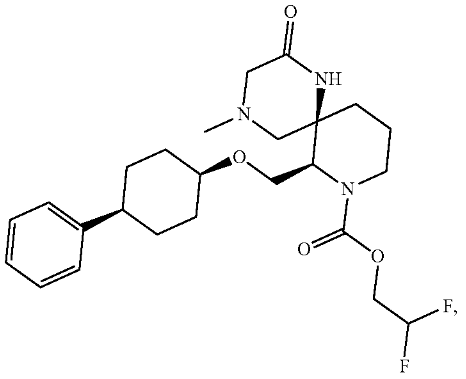
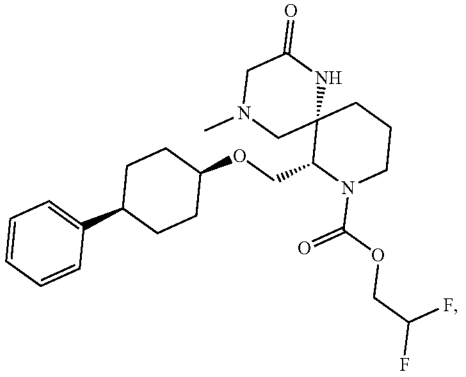
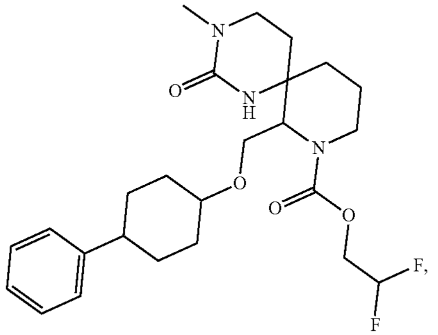
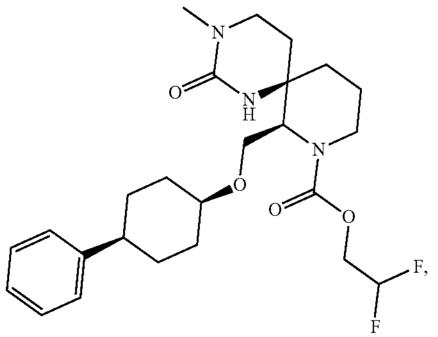
-continued
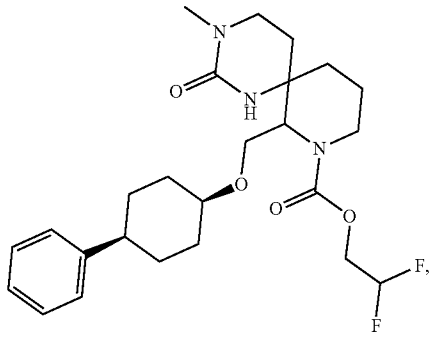
*cis-relative stereochemistry
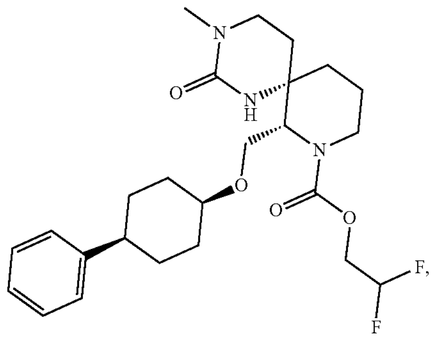
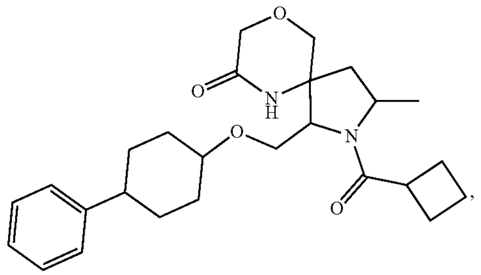
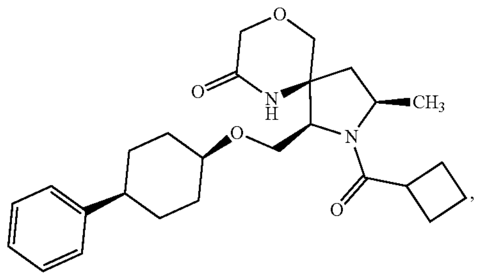
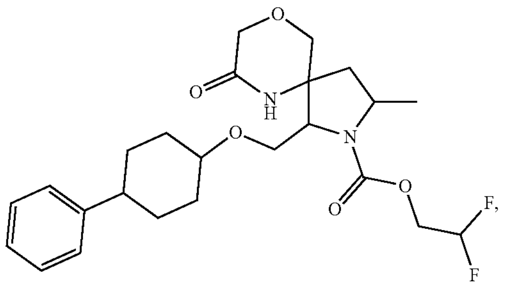

-continued
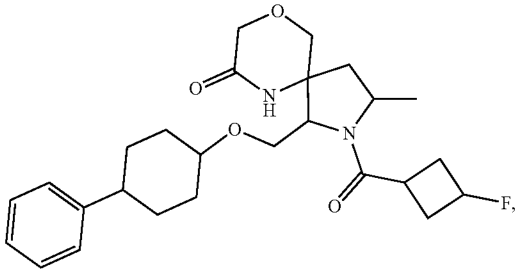
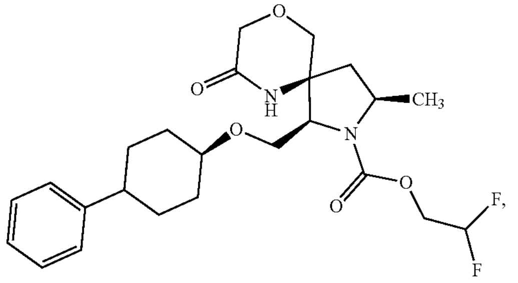
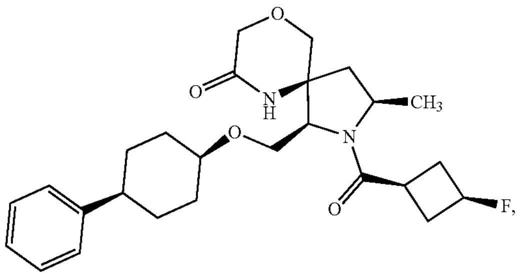
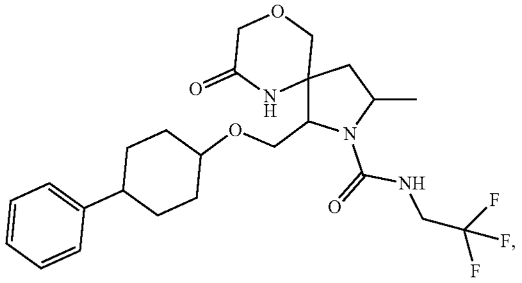
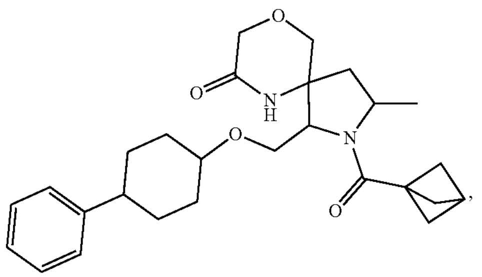
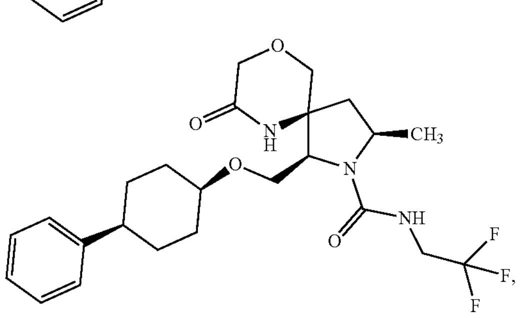
-continued
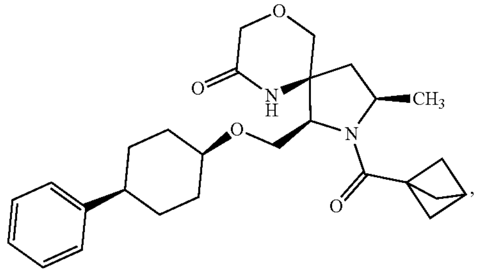
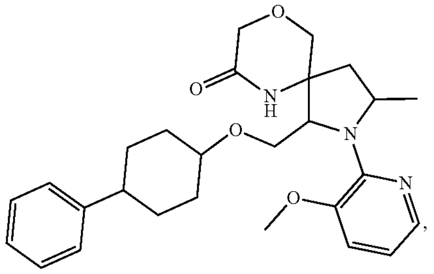
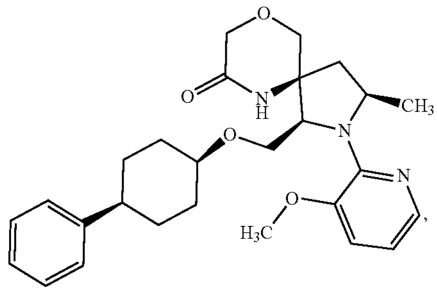
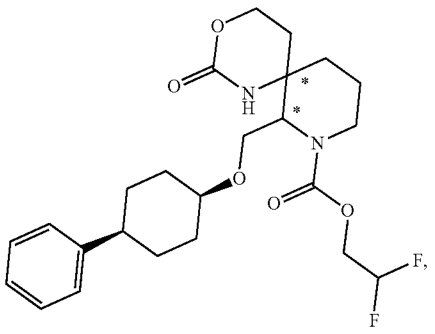
*cis-relative stereochemistry
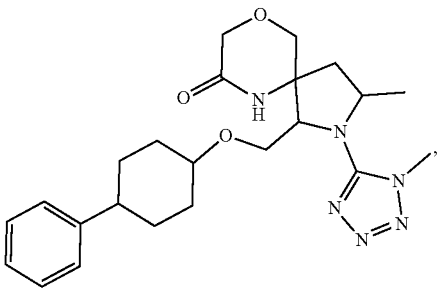

-continued
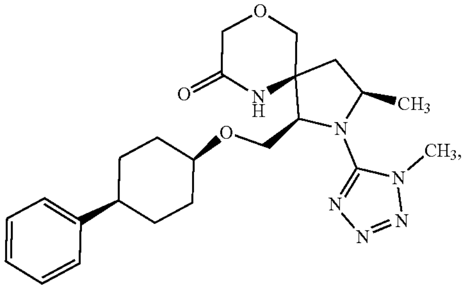
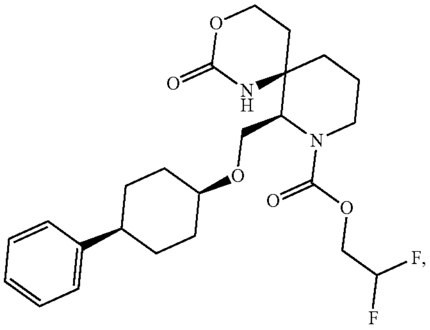
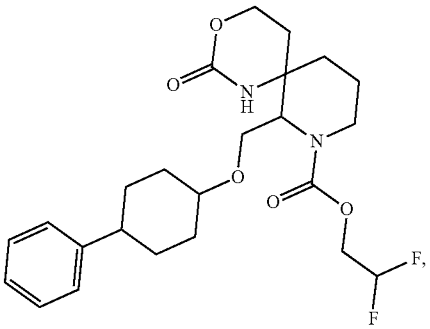
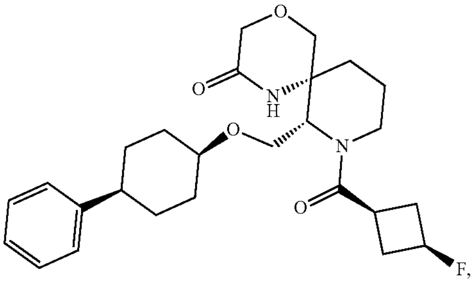
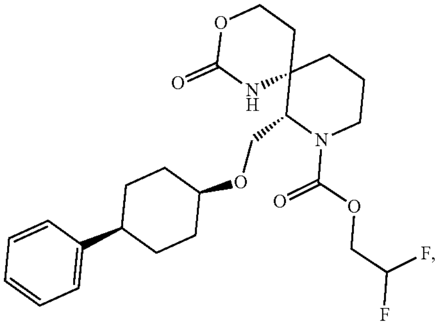
-continued
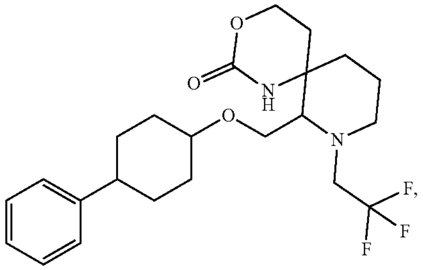
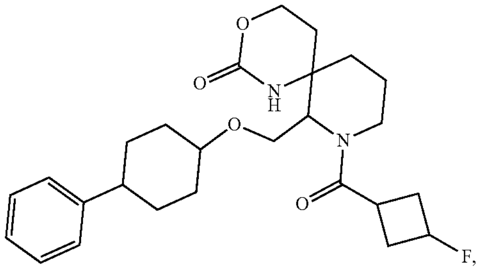
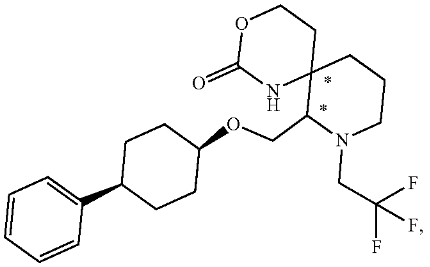
*cis-relative stereochemistry
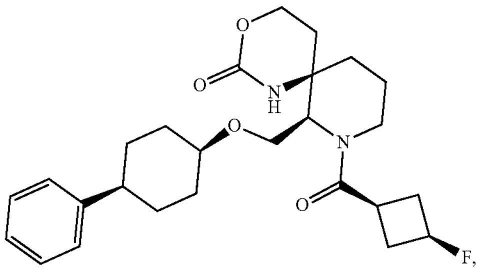
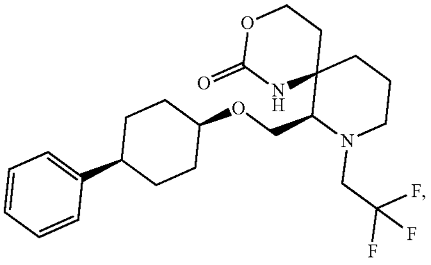

-continued
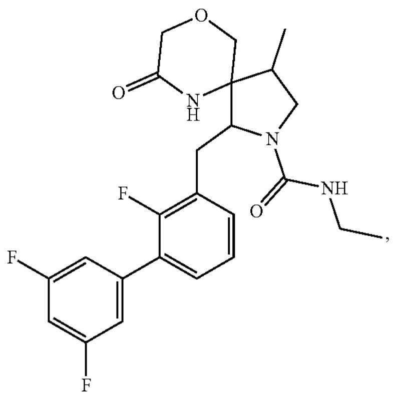
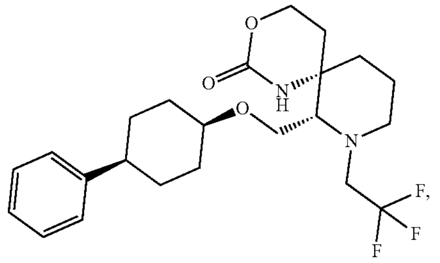
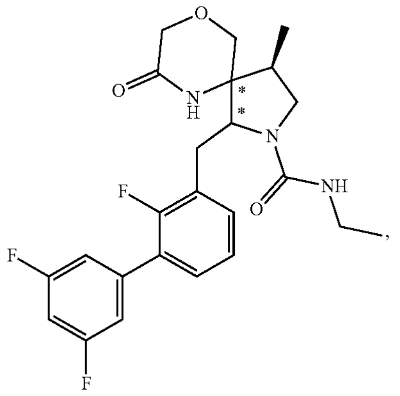
*cis-relative stereochemistry
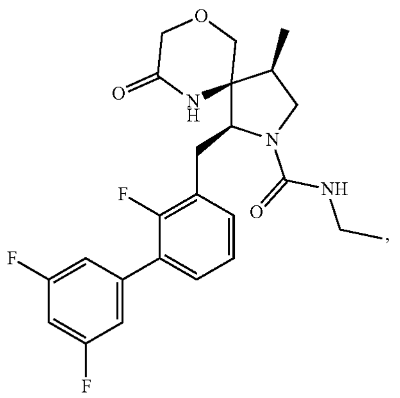
-continued
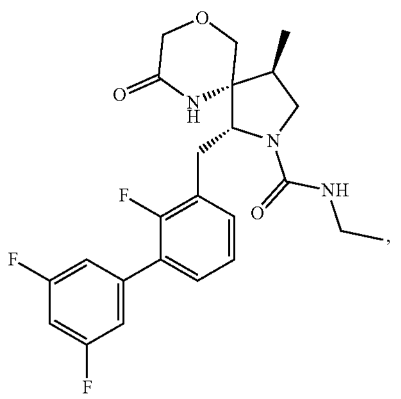
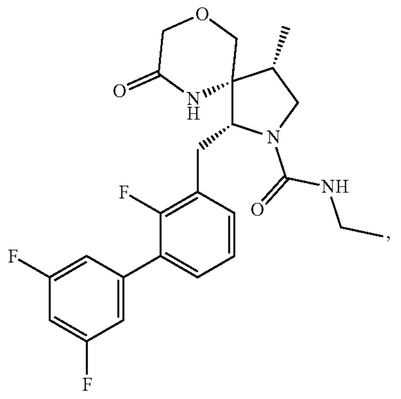
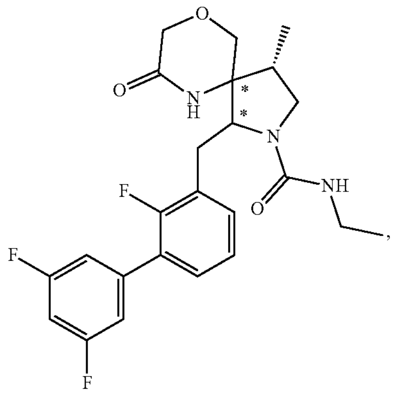
*cis-relative stereochemistry
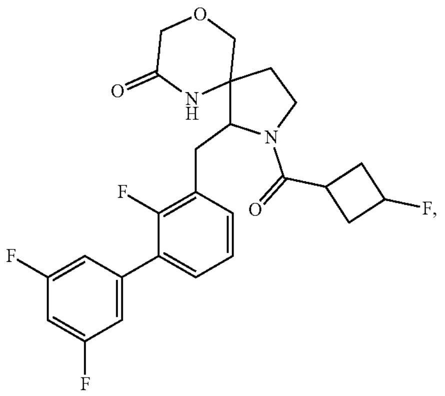

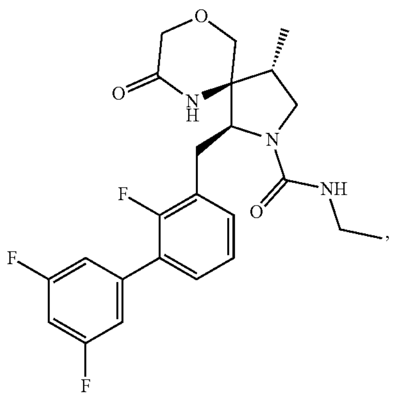
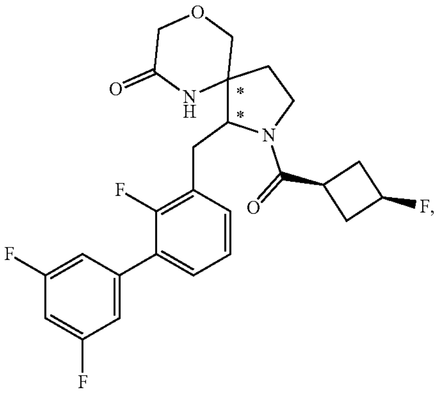
*cis-relative stereochemistry
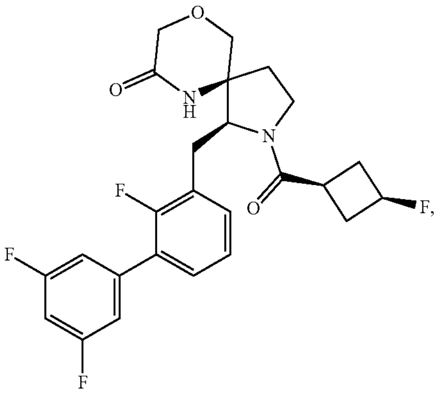
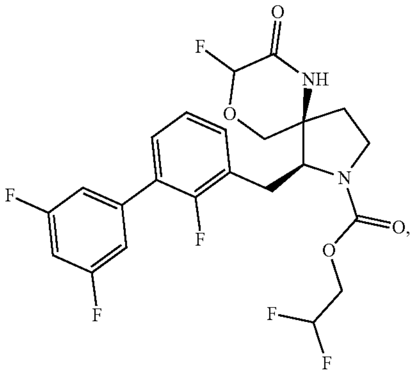
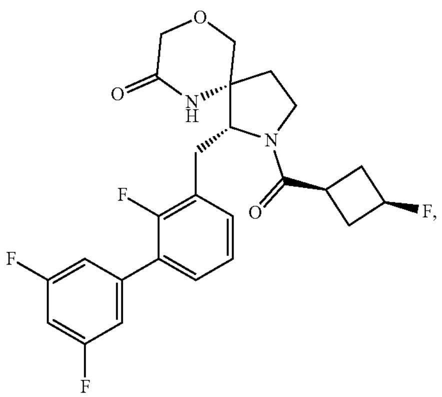
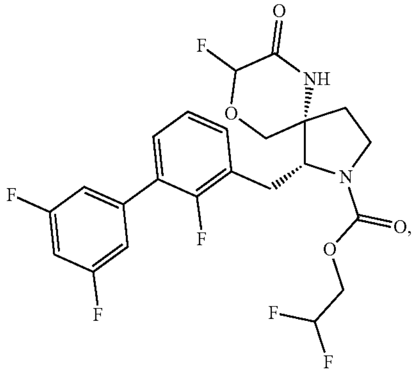
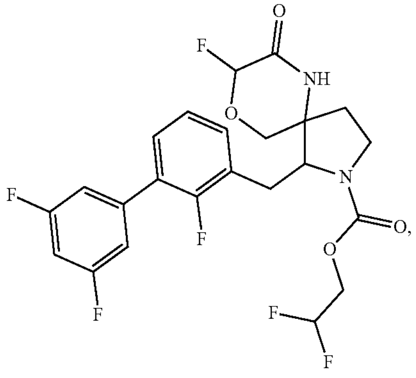
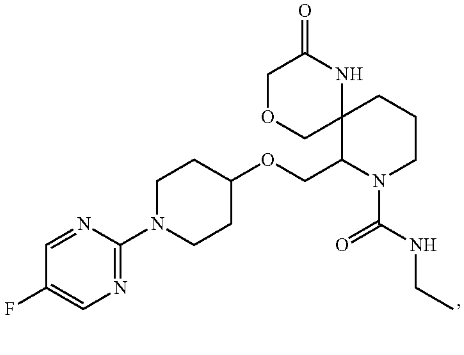

-continued
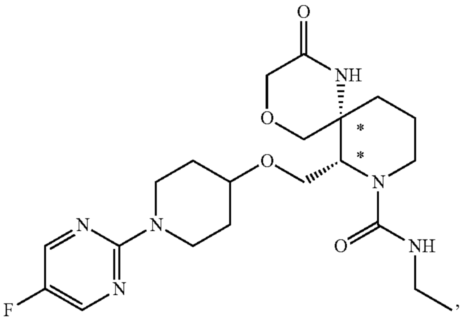
*cis-relative stereochemistry
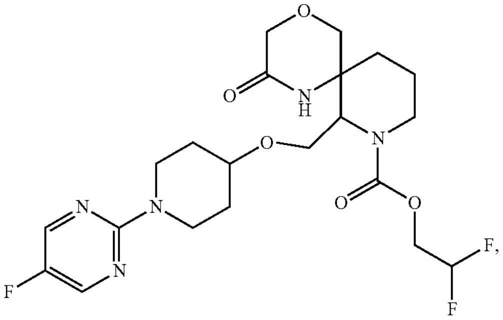
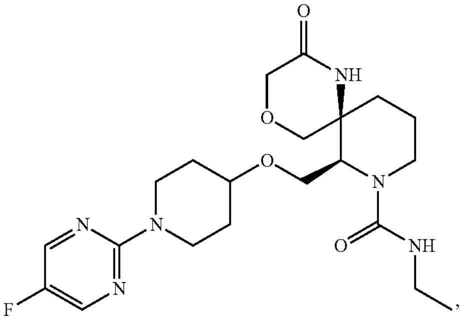
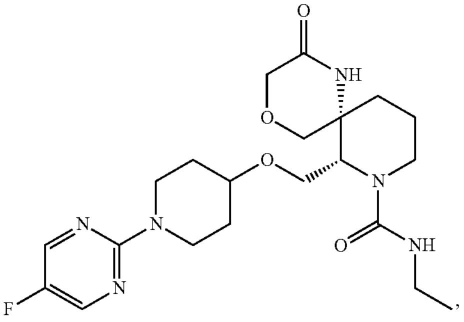
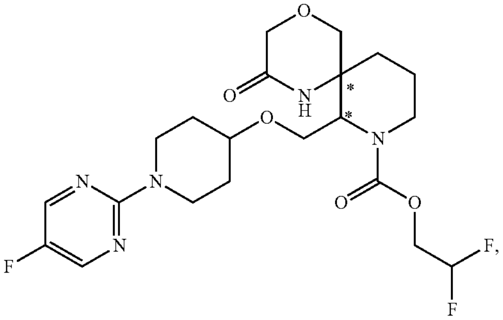
*cis-relative stereochemistry
-continued
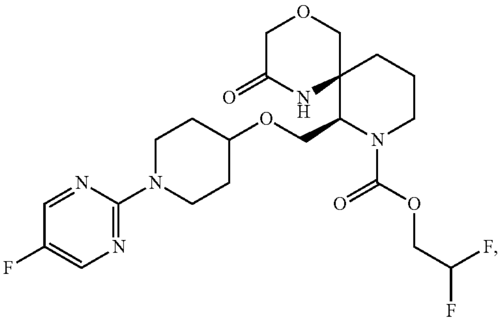
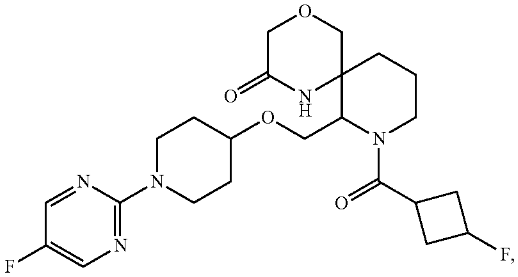
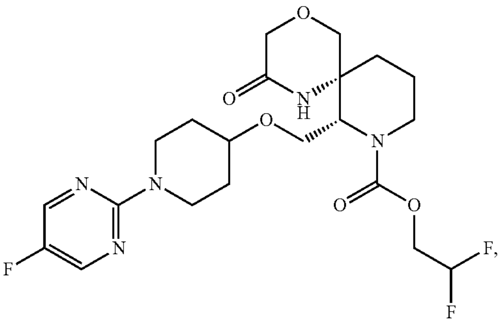
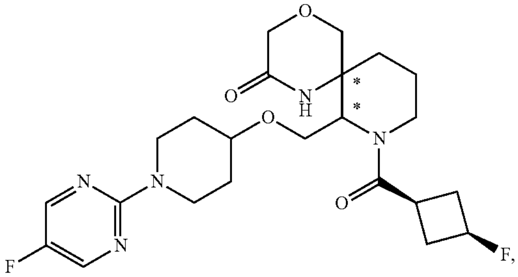
*cis-relative stereochemistry
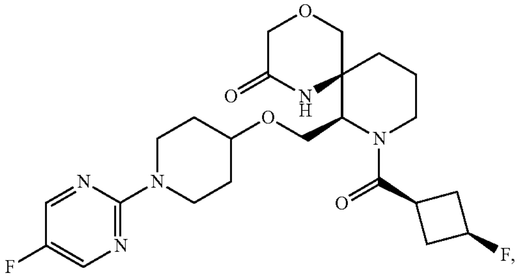

-continued
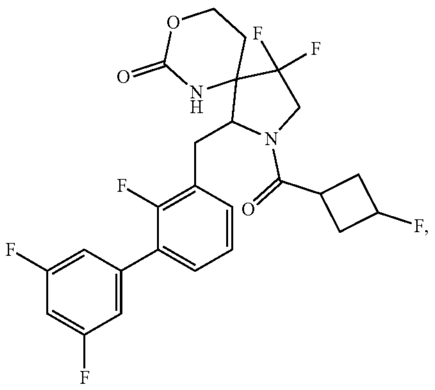
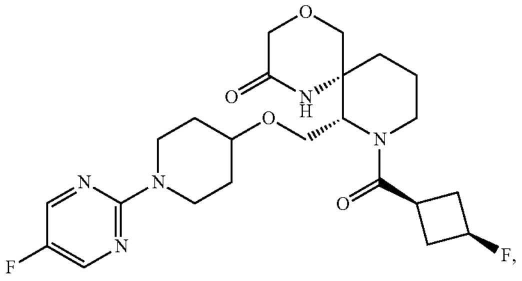
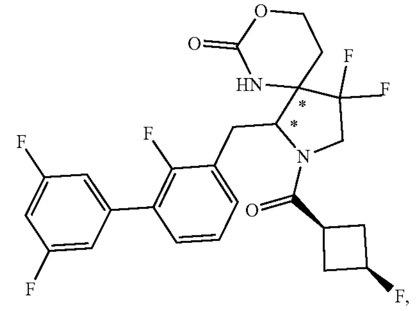
*trans-relative stereochemistry
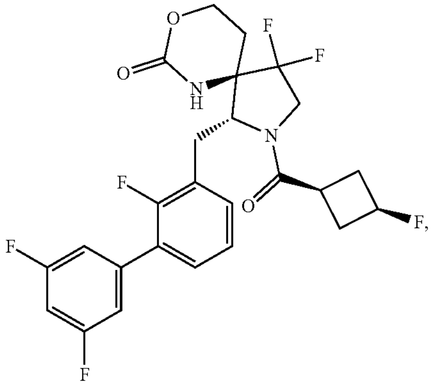
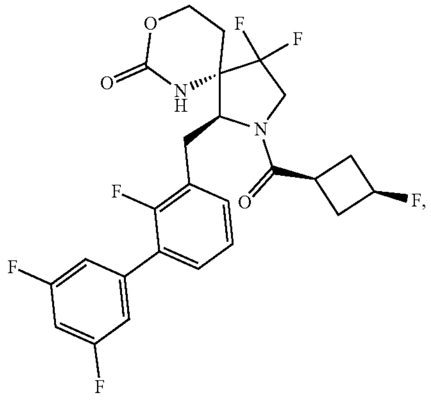
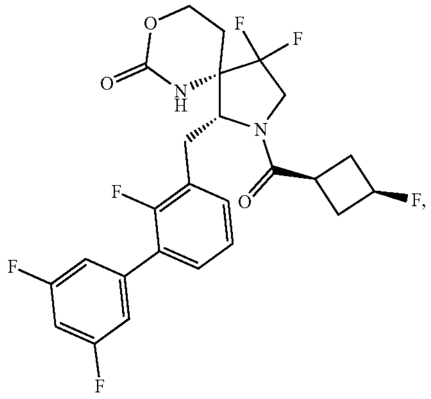
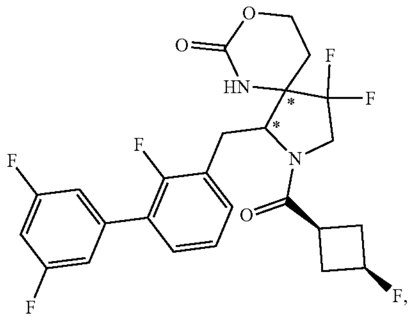
*cis-relative stereochemistry
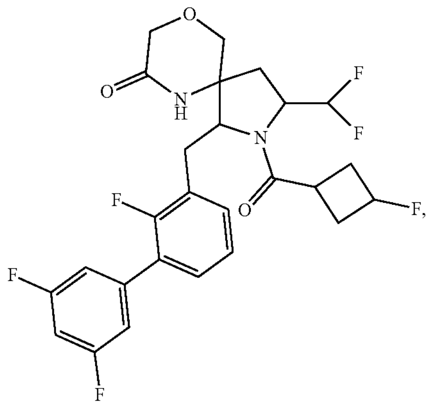

-continued
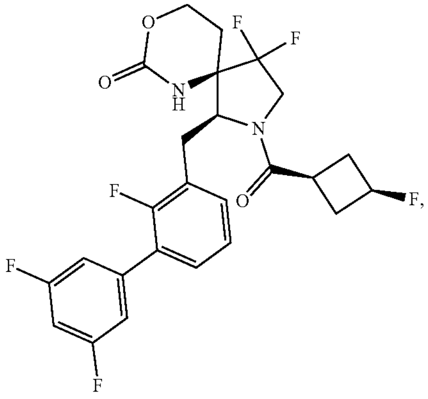
,
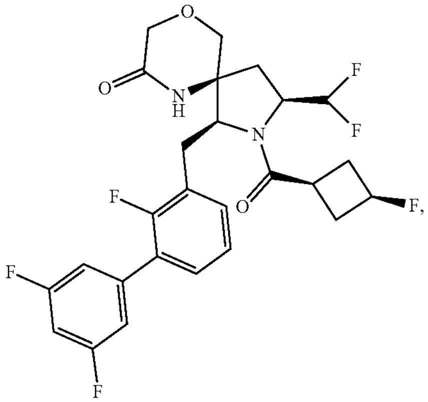
,
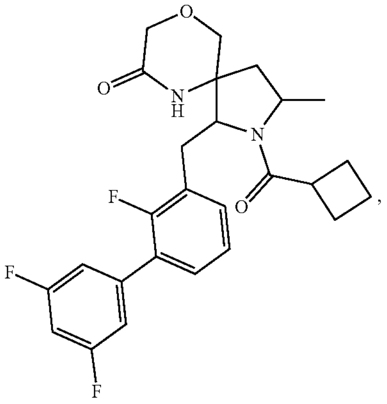
,
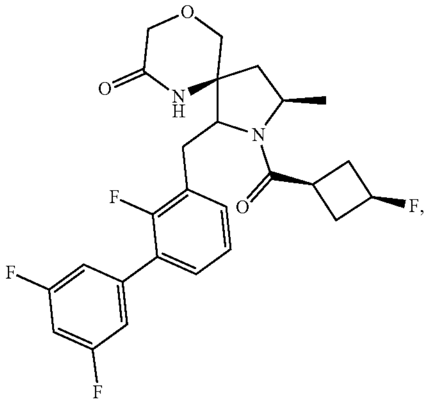
,
-continued
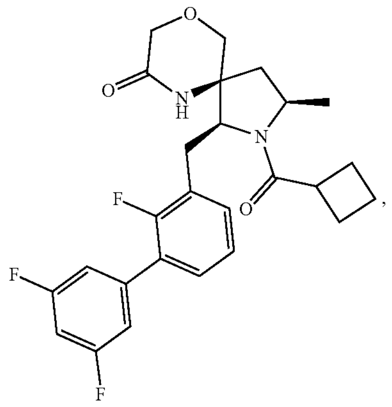
,
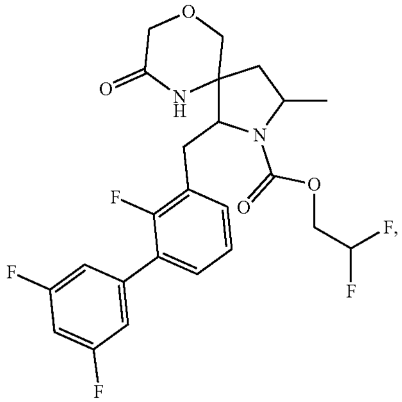
,
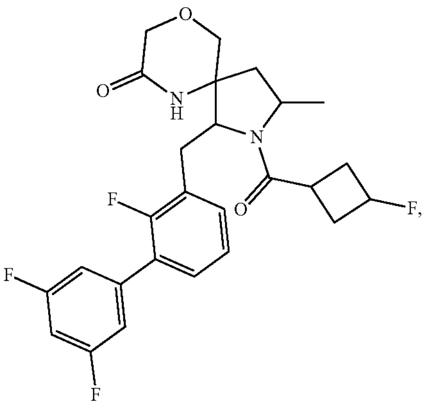
,
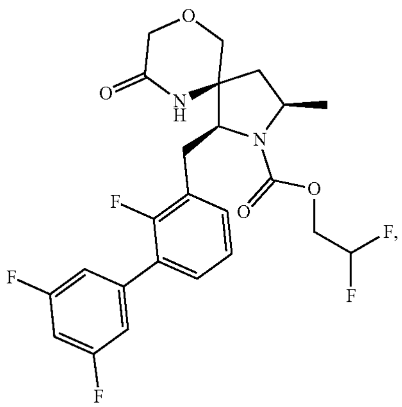
, -continued
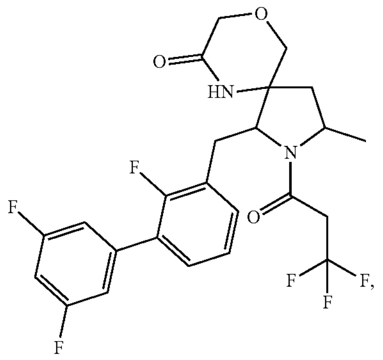
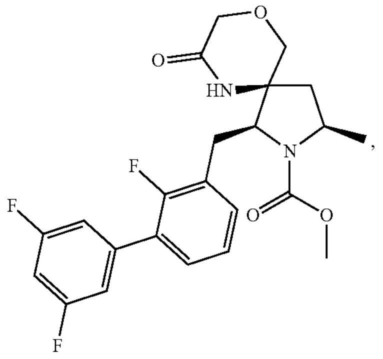
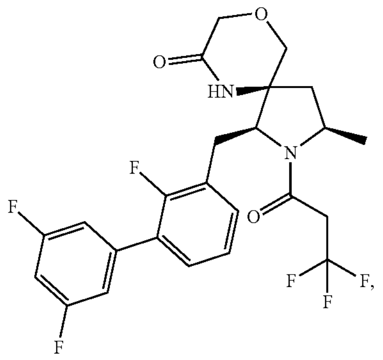
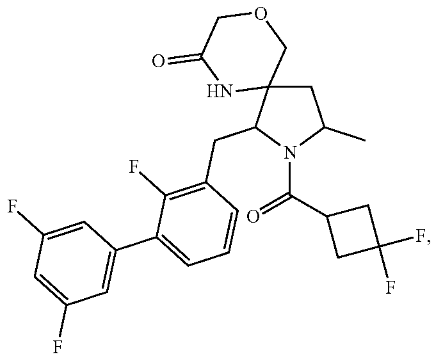
-continued
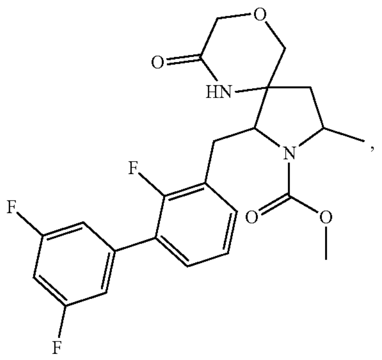
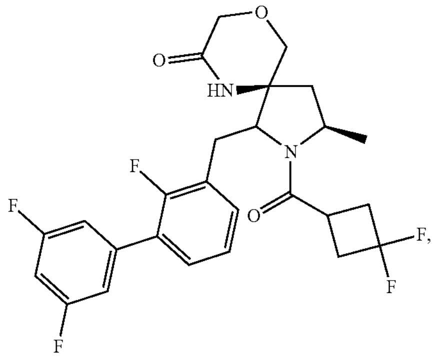
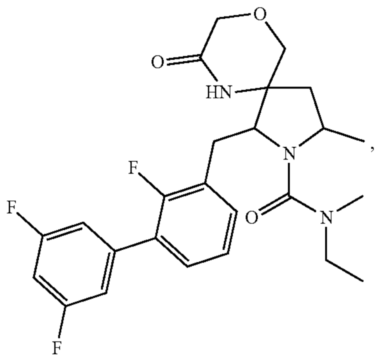
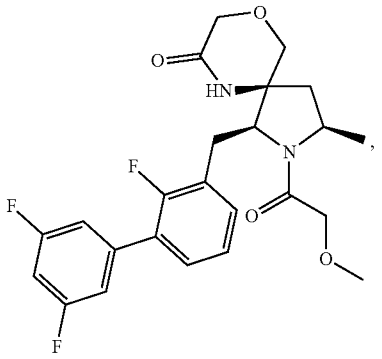

-continued
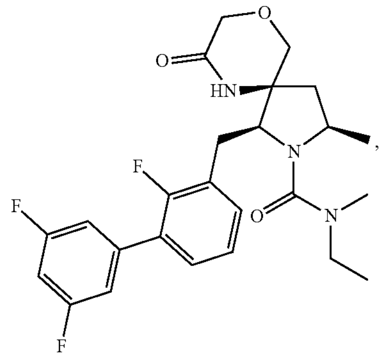
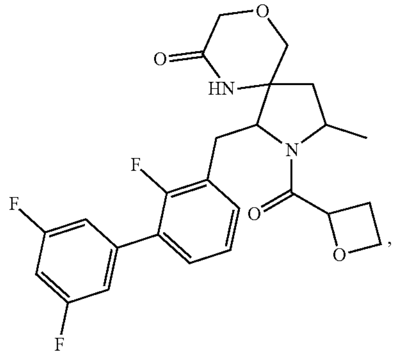
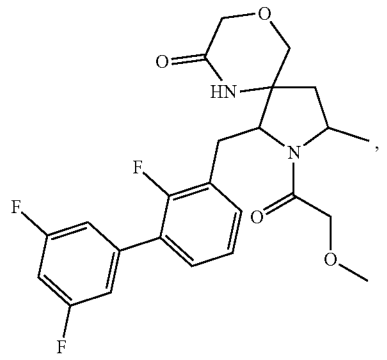
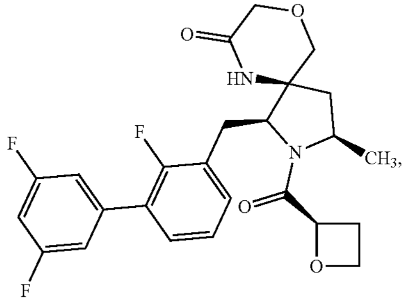
-continued
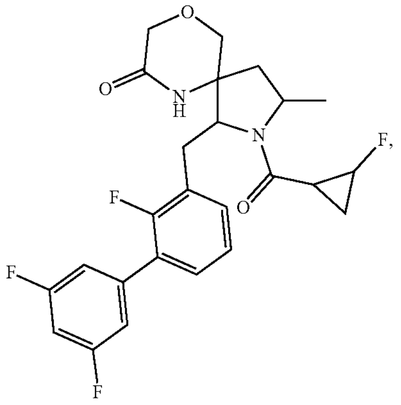
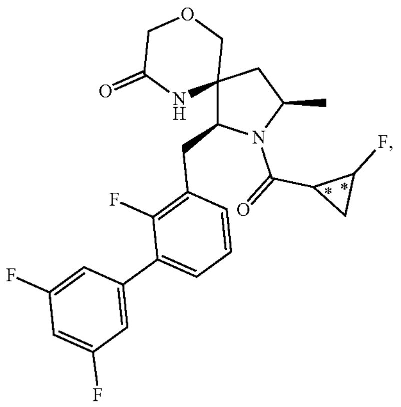
*cis-relative stereochemistry
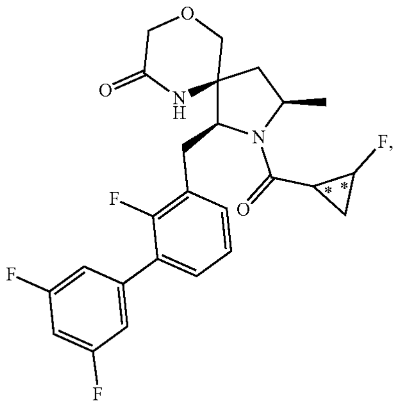
*trans-relative stereochemistry
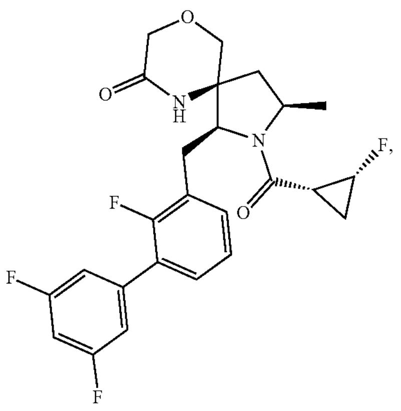

-continued

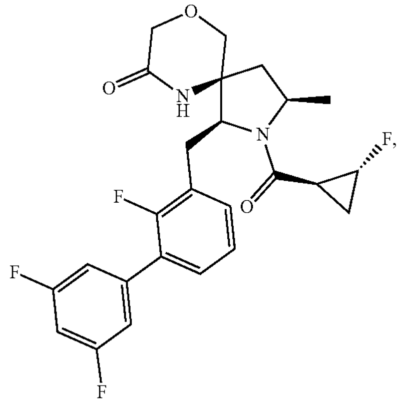

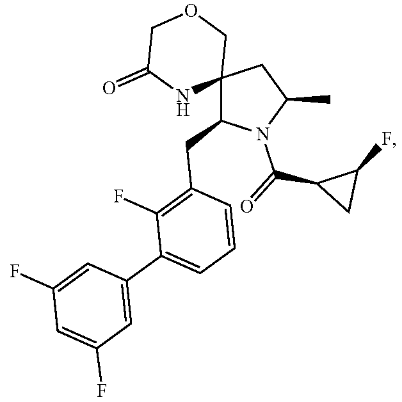

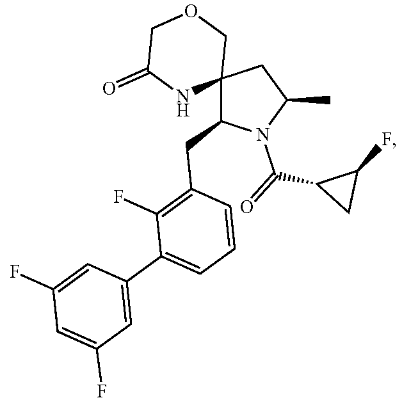

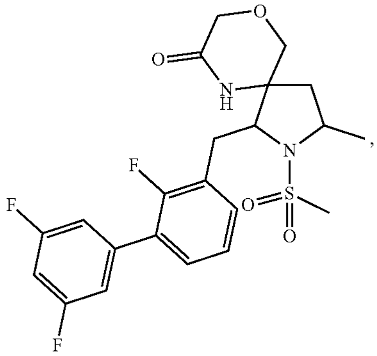

, and

-continued

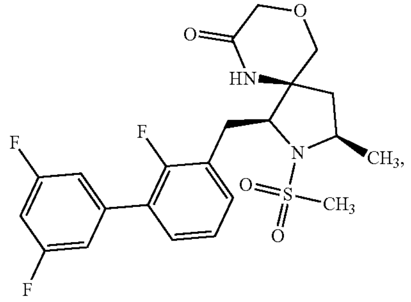 [SMILES: C[C@@H]1C[C@@]2(COCC(=O)N2)[C@H](Cc2cccc(-c3cc(F)cc(F)c3)c2F)N1S(C)(=O)=O]

or a pharmaceutically acceptable salt thereof.

18. A pharmaceutical composition comprising a compound of claim 1 and pharmaceutically acceptable excipient.

19. A method of treating:

(i) a sleep disorder; or (ii) narcolepsy; or (iii) hypersomnia; or (iv) excessive sleepiness in a subject in need thereof, comprising administering to the subject a therapeutically effective amount of the compound of claim 1.

20. The compound of claim 17, wherein the compound is selected from the group consisting of:

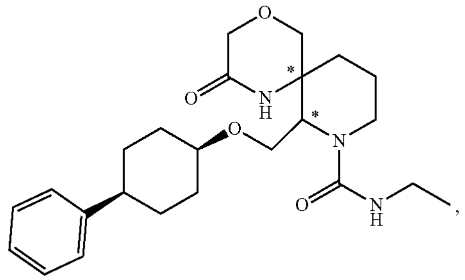

*cis-relative stereochemistry

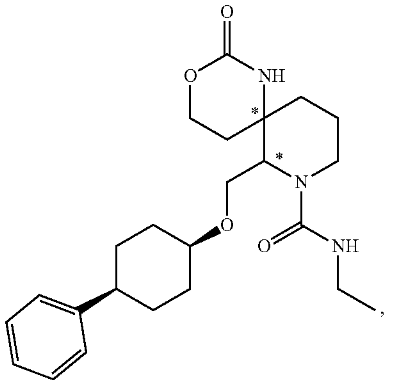

*cis-relative stereochemistry

-continued
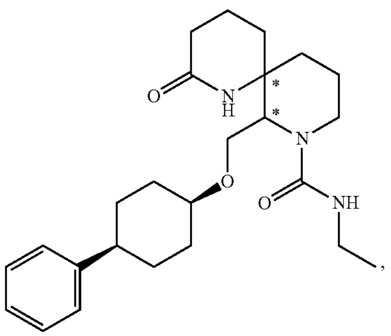
*cis-relative stereochemistry
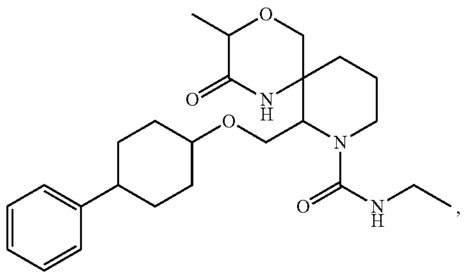
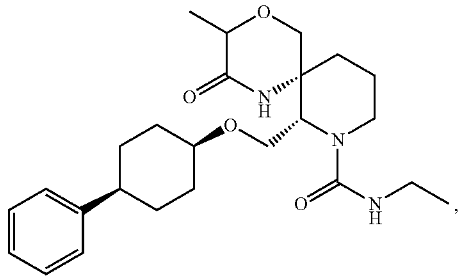
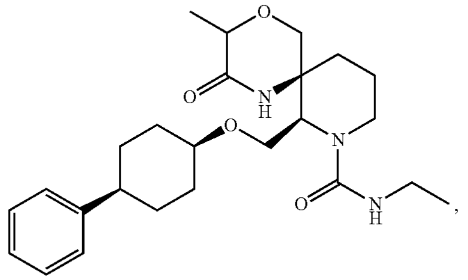
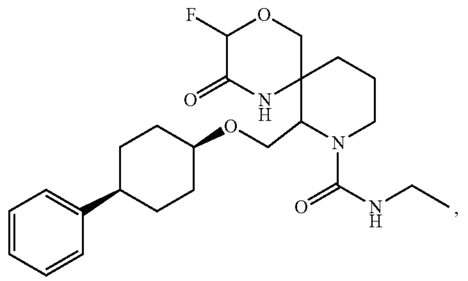
*cis-relative stereochemistry
-continued
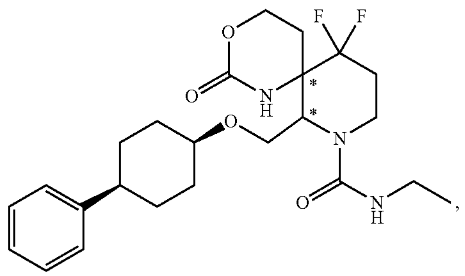
*cis-relative stereochemistry
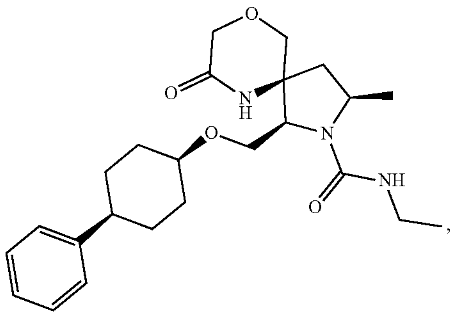
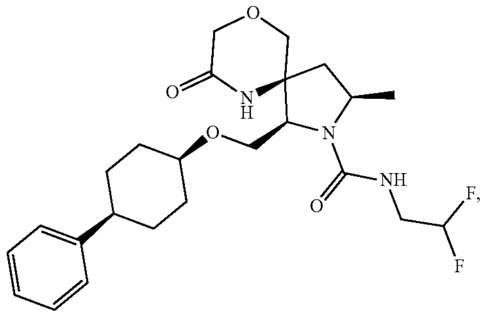
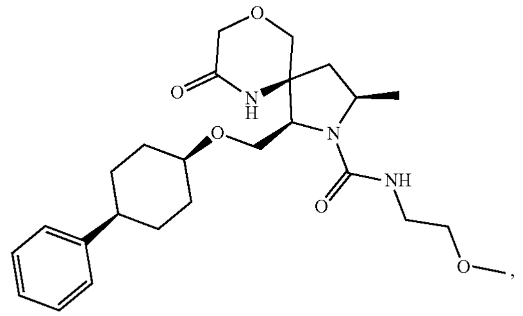
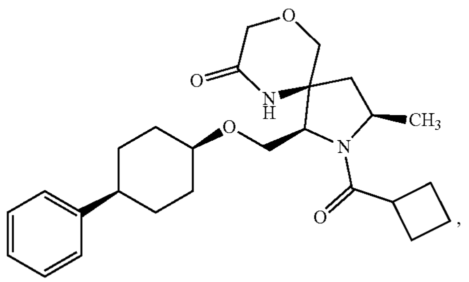

-continued
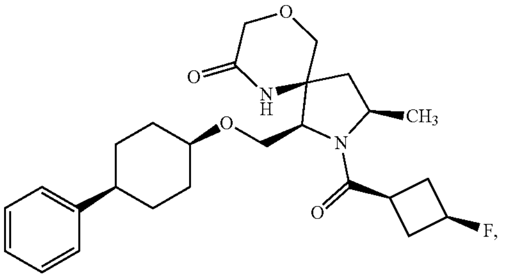
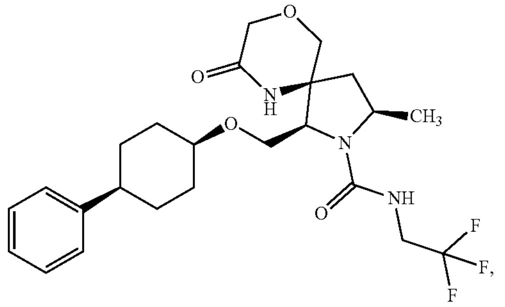
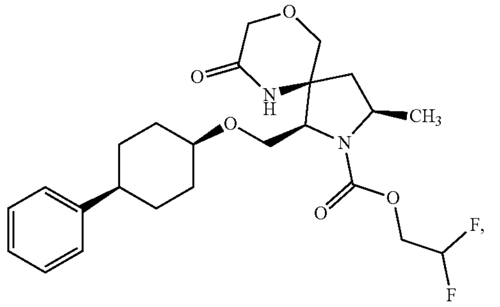
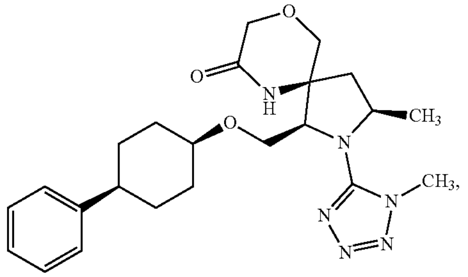
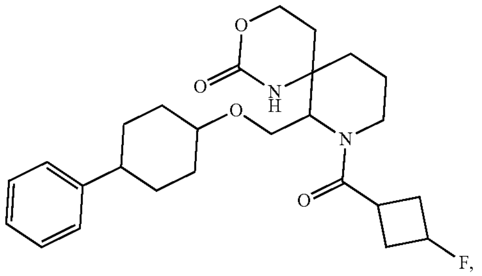
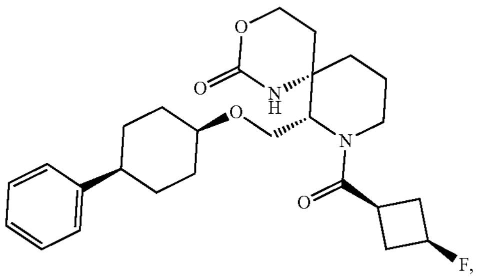
-continued
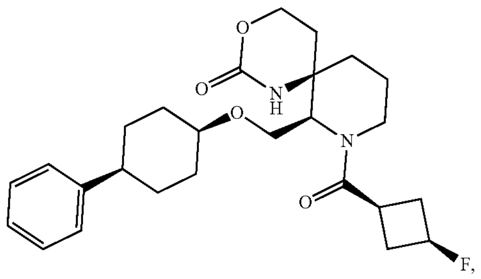
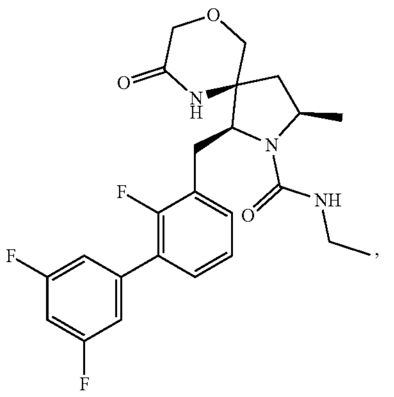
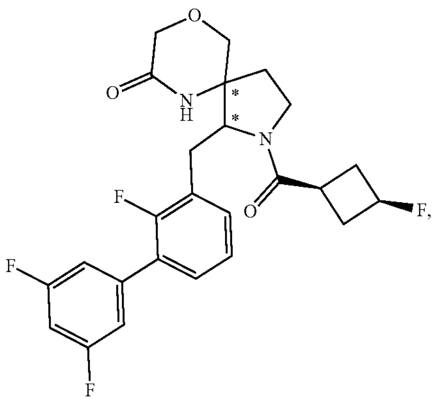
*cis-relative stereochemistry
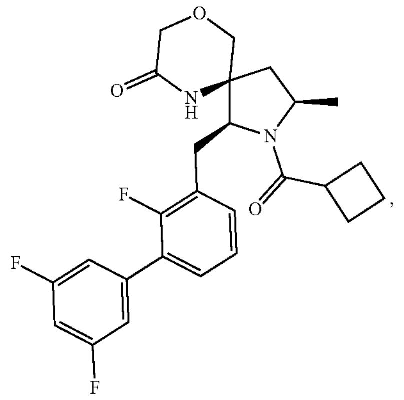

-continued
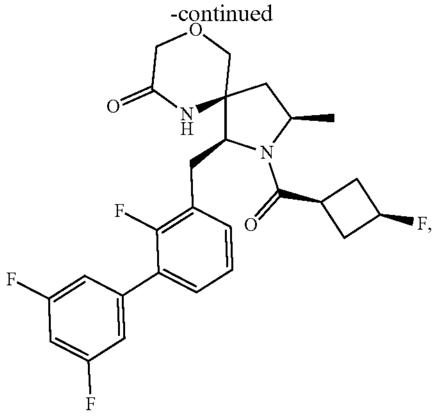
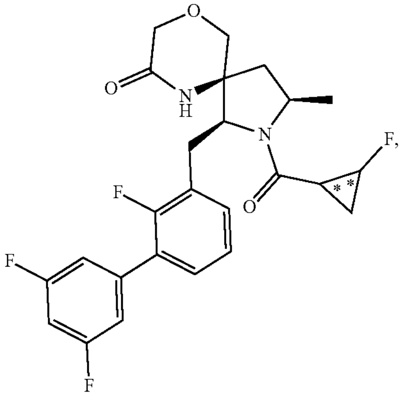
and
*cis-relative stereochemistry
-continued
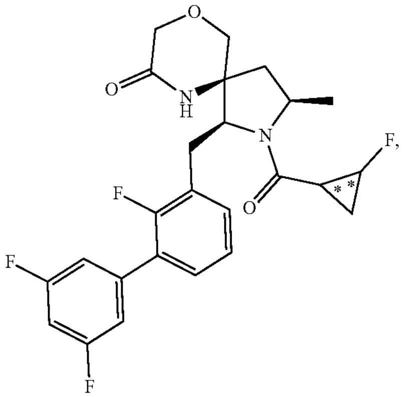
*trans-relative stereochemistry
or a pharmaceutically acceptable thereof.
* * * * *